United States Patent
Wada et al.

(10) Patent No.: US 9,980,487 B2
(45) Date of Patent: May 29, 2018

(54) FUSED 11-MEMBERED COMPOUNDS AND AGRICULTURAL/HORTICULTURAL FUNGICIDES CONTAINING THEM

(71) Applicant: SDS BIOTECH K.K., Tokyo (JP)

(72) Inventors: Hiroshi Wada, Ibaraki (JP); Daisuke Horikoshi, Ibaraki (JP); Makoto Bamba, Ibaraki (JP); Tsuyoshi Kawano, Ibaraki (JP); Takatoshi Sakaguchi, Ibaraki (JP)

(73) Assignee: SDS BIOTECH K.K., Tokyo (JP)

(*) Notice: Subject to any disclaimer, the term of this patent is extended or adjusted under 35 U.S.C. 154(b) by 0 days. days.

(21) Appl. No.: 15/503,069

(22) PCT Filed: Jun. 11, 2015

(86) PCT No.: PCT/JP2015/066841
§ 371 (c)(1),
(2) Date: Feb. 10, 2017

(87) PCT Pub. No.: WO2016/024434
PCT Pub. Date: Feb. 18, 2016

(65) Prior Publication Data
US 2017/0231226 A1 Aug. 17, 2017

(30) Foreign Application Priority Data
Aug. 13, 2014 (WO) .................. PCT/JP2014/071409

(51) Int. Cl.
*A01N 43/78* (2006.01)
*C07D 417/04* (2006.01)
*C07D 417/14* (2006.01)

(52) U.S. Cl.
CPC ........... *A01N 43/78* (2013.01); *C07D 417/04* (2013.01); *C07D 417/14* (2013.01)

(58) Field of Classification Search
CPC .. C07D 417/04; C07D 471/14; C07D 277/10; A01N 43/78
USPC .......................................... 546/209; 548/146
See application file for complete search history.

(56) References Cited

U.S. PATENT DOCUMENTS

| | | | |
|---|---|---|---|
| 4,218,464 A | 8/1980 | Bondinell et al. | |
| 2001/0051620 A1 | 12/2001 | Berger et al. | |
| 2003/0039838 A1 | 2/2003 | Chen et al. | |
| 2009/0298894 A1 | 12/2009 | Ohmori et al. | |
| 2010/0137245 A1 | 6/2010 | Cristau et al. | |
| 2010/0190828 A1 | 7/2010 | Cristau et al. | |
| 2011/0046178 A1 | 2/2011 | Cristau et al. | |
| 2011/0105429 A1 | 5/2011 | Cristau et al. | |
| 2011/0224257 A1 | 9/2011 | Cristau et al. | |
| 2011/0301197 A1 | 12/2011 | Cristau et al. | |
| 2011/0306620 A1 | 12/2011 | Cristau et al. | |
| 2011/0312999 A1 | 12/2011 | Cristau et al. | |
| 2012/0065197 A1 | 3/2012 | Cristau et al. | |
| 2012/0122928 A1 | 5/2012 | Tsuchiya et al. | |
| 2012/0245204 A1 | 9/2012 | Hoffmann et al. | |
| 2014/0005224 A1 | 1/2014 | Hillebrand et al. | |
| 2014/0228404 A1 | 8/2014 | Hillebrand et al. | |
| 2015/0024935 A1 | 1/2015 | Tsuchiya et al. | |
| 2016/0251344 A1 | 9/2016 | Olenik et al. | |

FOREIGN PATENT DOCUMENTS

| | | |
|---|---|---|
| EP | 2423210 A1 | 2/2012 |
| JP | 2001-302658 A | 10/2001 |
| JP | 2004-137255 A | 5/2004 |
| JP | 2008-529982 A | 8/2008 |
| JP | 2009-502948 A | 1/2009 |
| JP | 2010-516765 A | 5/2010 |
| JP | 2010-533716 A | 10/2010 |
| JP | 2011-021013 A | 2/2011 |
| JP | 2011-510925 A | 4/2011 |
| JP | 2012-512248 A | 5/2012 |
| JP | 2013-544761 A | 12/2013 |
| JP | 2014-501246 A | 1/2014 |
| WO | WO-1993/09113 A1 | 5/1993 |

(Continued)

OTHER PUBLICATIONS

Ahad, J. et al., Organic and Bio-organic Chemistry, 1980, No. 11, pp. 2445-2449.
Bhattacharjee, D. et al., Journal of Heterocyclic Chemistry, 1980, vol. 17, No. 2, pp. 315-320.
ISR of PCT/JP2015/066841.
Jansen, R. J. et al., Journal of Organic Chemistry, 2001, vol. 66, No. 8, pp. 2643-2653.
John E. Anthony et al., The International Society for Optical Engineering, 2005, vol. 5940,594002/1-594002/12, Scheme2.
Masanobu Suzuki et al., Agricultural and Biological Chemistry, 1987, 51(4), pp. 1121-1127, Scheme I.
Meisenheimer, P. L. et al., Drug Metabolism and Disposition, 2011, vol. 39, No. 12, pp. 2403-2410.

(Continued)

*Primary Examiner* — Rita J Desai
(74) *Attorney, Agent, or Firm* — McCarter & English, LLP; Steven G. Davis; Wei Song

(57) ABSTRACT

The invention relates to a compound or a salt thereof of formula [1],

[Chemical Formula 1]

[1]

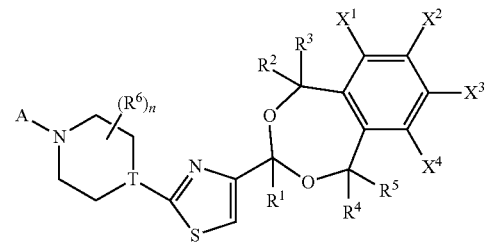

a fungicidal composition containing the compound or a salt thereof, a method for controlling plant disease occurring from phytopathogenic microorganism including the step of applying the fungicidal composition and a production method of the compound.

21 Claims, No Drawings

(56) References Cited

FOREIGN PATENT DOCUMENTS

| | | |
|---|---|---|
| WO | WO-2006/082001 A1 | 8/2006 |
| WO | WO-2007/014290 A2 | 2/2007 |
| WO | WO-2008/0013622 A2 | 1/2008 |
| WO | WO-2008/0013925 A2 | 1/2008 |
| WO | WO-2008/0091580 A2 | 7/2008 |
| WO | WO-2008/091580 A2 | 7/2008 |
| WO | WO-2008/0091594 A2 | 7/2008 |
| WO | WO-2009/014637 A2 | 1/2009 |
| WO | WO-2009/0055514 A2 | 4/2009 |
| WO | WO-2009/094407 A2 | 7/2009 |
| WO | WO-2009/0094445 A2 | 7/2009 |
| WO | WO-2009/131090 A1 | 10/2009 |
| WO | WO-2009/0132785 A1 | 11/2009 |
| WO | WO-2010/0037479 A1 | 4/2010 |
| WO | WO-2010/0065579 A2 | 6/2010 |
| WO | WO-2010/0066353 A1 | 6/2010 |
| WO | WO-2010/077752 A1 | 7/2010 |
| WO | WO-2010/0149275 A1 | 12/2010 |
| WO | WO-2011/0018401 A1 | 2/2011 |
| WO | WO-2011/0018415 A2 | 2/2011 |
| WO | 2011/051243 A1 | 5/2011 |
| WO | WO-2011/0051244 A1 | 5/2011 |
| WO | WO-2011/0076510 A1 | 6/2011 |
| WO | WO-2011/0076699 A1 | 6/2011 |
| WO | WO-2011/0085170 A1 | 7/2011 |
| WO | WO-2011/0134969 A1 | 11/2011 |
| WO | WO-2011/0144586 A1 | 11/2011 |
| WO | WO-2011/0146182 A1 | 11/2011 |
| WO | WO-2011/0147765 A1 | 12/2011 |
| WO | WO-2012/0020060 A1 | 2/2012 |
| WO | WO-2012/0025557 A1 | 3/2012 |
| WO | WO-2012/037411 A2 | 3/2012 |
| WO | WO-2012/0045798 A1 | 4/2012 |
| WO | WO-2012/0055837 A1 | 5/2012 |
| WO | WO-2012/0069633 A1 | 5/2012 |
| WO | WO-2012/082580 A2 | 6/2012 |
| WO | WO-2012/0104273 A1 | 8/2012 |
| WO | WO-2012/0107475 A1 | 8/2012 |
| WO | WO-2012/0107477 A1 | 8/2012 |
| WO | WO-2012/0168188 A1 | 12/2012 |
| WO | WO-2013/0000941 A1 | 1/2013 |
| WO | WO-2013/0000943 A1 | 1/2013 |
| WO | WO-2013/0037768 A1 | 3/2013 |
| WO | WO-2013/0056911 A1 | 4/2013 |
| WO | WO-2013/0056915 A1 | 4/2013 |
| WO | WO-2013/0098229 A2 | 7/2013 |
| WO | WO-2013/0116251 A2 | 8/2013 |
| WO | WO-2013/0127704 A1 | 9/2013 |
| WO | WO-2013/0127784 A1 | 9/2013 |
| WO | WO-2013/0127789 A1 | 9/2013 |
| WO | WO-2013/0127808 A1 | 9/2013 |
| WO | WO-2013/0191866 A1 | 12/2013 |
| WO | WO-2014/0060176 A1 | 4/2014 |
| WO | WO-2014/0075873 A1 | 5/2014 |
| WO | WO-2014/0075874 A1 | 5/2014 |
| WO | WO-2014/0118142 A1 | 8/2014 |
| WO | WO-2014/0118143 A1 | 8/2014 |
| WO | WO-2014/0154530 A1 | 10/2014 |
| WO | WO-2014/0179144 A1 | 11/2014 |
| WO | WO-2014/0206896 A1 | 12/2014 |
| WO | WO-2015/0036379 A1 | 3/2015 |
| WO | WO-2015/0055574 A1 | 4/2015 |
| WO | WO-2015/0067802 A1 | 5/2015 |

OTHER PUBLICATIONS

Santoso, H. et al., Organic & Biomolecular Chemistry, 2014, vol. 12, No. 1, pp. 171-176.

Theodora W. Greene et al., Protection for the Hydroxyl Group, Including 1,2- and 1,3- Diols, p. 198.

Vishwakarma Singh et al., Tetrahedron Letters, 2015, 56 (15), pp. 1982-1985, Scheme 1.

Supplementary European Search Report for Application No. 15832228.9, dated Jan. 8, 2018. 5 pages.

FUSED 11-MEMBERED COMPOUNDS AND AGRICULTURAL/HORTICULTURAL FUNGICIDES CONTAINING THEM

CROSS-REFERENCE TO RELATED APPLICATIONS

This application is a U.S. national stage filing under 35 U.S.C. § 371(c), of International Application No. PCT/JP2015/066841, filed on Jun. 11, 2015, which claims foreign priority of International Application No. PCT/JP2014/071409, filed on Aug. 13, 2014. The entire contents of each of the aforementioned applications are incorporated herein by reference.

TECHNICAL FIELD

The present invention relates to a new fused 11-membered compound or a salt thereof, a fungicidal composition for agricultural/horticultural use containing said salt or compound as an active component, and a method of use thereof. The present invention further relates to a method for producing a new fused 11-membered compound and a new benzenedimethanol compound and a salt thereof.

BACKGROUND ART

It has been known that piperidine derivatives substituted with specific heterocycles are available for use as fungicidal composition for protecting crops. The following patent documents may be referred to.

CITATION LIST

Patent Documents

Patent Document 1: WO 2007/014290
Patent Document 2: WO 2008/013622
Patent Document 3: WO 2008/013925
Patent Document 4: WO 2008/091580
Patent Document 5: WO 2008/091594
Patent Document 6: WO 2009/055514
Patent Document 7: WO 2009/094407
Patent Document 8: WO 2009/094445
Patent Document 9: WO 2009/132785
Patent Document 10: WO 2010/037479
Patent Document 11: WO 2010/065579
Patent Document 12: WO 2010/066353
Patent Document 13: WO 2010/149275
Patent Document 14: WO 2011/018401
Patent Document 15: WO 2011/018415
Patent Document 16: WO 2011/051244
Patent Document 17: WO 2011/076510
Patent Document 18: WO 2011/076699
Patent Document 19: WO 2011/085170
Patent Document 20: WO 2011/134969
Patent Document 21: WO 2011/144586
Patent Document 22: WO 2011/146182
Patent Document 23: WO 2011/147765
Patent Document 24: WO 2012/020060
Patent Document 25: WO 2012/025557
Patent Document 26: WO 2012/045798
Patent Document 27: WO 2012/055837
Patent Document 28: WO 2012/069633
Patent Document 29: WO 2012/082580
Patent Document 30: WO 2012/104273
Patent Document 31: WO 2012/107475
Patent Document 32: WO 2012/107477
Patent Document 33: WO 2012/168188
Patent Document 34: WO 2013/000941
Patent Document 35: WO 2013/000943
Patent Document 36: WO 2013/037768
Patent Document 37: WO 2013/056911
Patent Document 38: WO 2013/056915
Patent Document 39: WO 2013/098229
Patent Document 40: WO 2013/116251
Patent Document 41: WO 2013/127704
Patent Document 42: WO 2013/127784
Patent Document 43: WO 2013/127789
Patent Document 44: WO 2013/127808
Patent Document 45: WO 2013/191866
Patent Document 46: WO 2014/060176
Patent Document 47: WO 2014/075873
Patent Document 48: WO 2014/075874
Patent Document 49: WO 2014/118142
Patent Document 50: WO 2014/118143
Patent Document 51: WO 2014/154530
Patent Document 52: WO 2014/179144
Patent Document 53: WO 2014/206896
Patent Document 54: WO 2015/036379
Patent Document 55: WO 2015/055574
Patent Document 56: WO 2015/067802

SUMMARY OF INVENTION

Technical Problem

To achieve a high productivity in the field of agriculture/horticulture, it is quite important to effectively control plant disease that occur, and various products have been used so far. However, there is a continuous demand for agricultural/horticultural fungicides that can adapt to changes in cultivar, changes in the cultivation time, area or the like, and changes in the cultivation technique in the field of agriculture/horticulture. In addition, the problem of drug resistivity may also occur, so a development of a new compound is still in need.

Solution to Problem

The present inventors continued extensive studies to solve the above problem, and found that a new compound, which is a fused 11-membered compound, exhibits a significant agricultural/horticultural fungicidal activity, and completed the invention based on that knowledge.

The present invention encompasses disclosures of the following compounds.

[1] A compound or a salt thereof according to formula [1]:

[Formula 1]

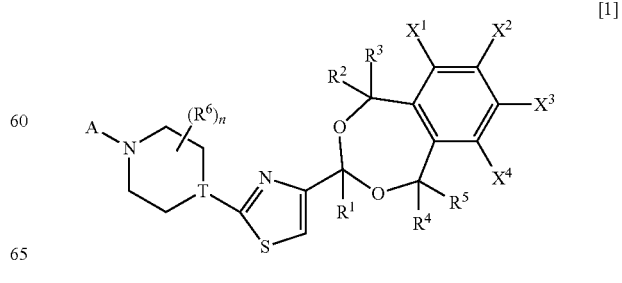

wherein, A is a group selected from

[Formula 2]

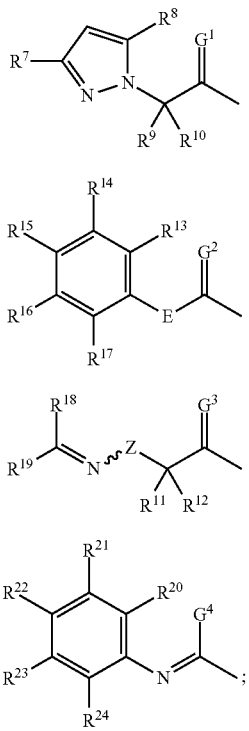

T is either CH or a nitrogen atom;

$R^1$ is a hydrogen atom, $C_1$-$C_6$ alkyl, $C_2$-$C_6$ alkenyl, $C_1$-$C_6$ haloalkyl, $C_1$-$C_6$ alkoxy, halogen, cyano or hydroxy;

each of $R^2$, $R^3$, $R^4$ and $R^5$ is independently a hydrogen atom, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen, cyano or hydroxyl, or $R^2$ together with $R^3$ and $R^4$ together with $R^5$ are independently taken together with a carbon atom to which they are attached to form a carbonyl group (C=O);

$R^6$ is oxo, $C_1$-$C_6$ alkyl, $C_2$-$C_6$ alkenyl, $C_1$-$C_6$ haloalkyl, $C_1$-$C_6$ alkoxy, halogen, cyano or hydroxy;

n is 0-2;

each of $X^1$, $X^2$, $X^3$ and $X^4$ is independently a hydrogen atom, halogen, cyano, hydroxy, nitro, formyl, mercapto, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, carboxy, carbamoyl, $C_3$-$C_6$ cycloalkyl, $C_3$-$C_8$ halocycloalkyl, $C_3$-$C_6$ cycloalkoxy, $C_3$-$C_8$ halocycloalkoxy, $C_3$-$C_6$ alkynylalkoxy, $C_3$-$C_6$ haloalkynylalkoxy, $C_2$-$C_6$ alkoxyalkyl, $C_4$-$C_{10}$ cycloalkoxyalkyl, $C_2$-$C_6$ haloalkoxyalkyl, $C_4$-$C_{10}$ halocycloalkoxyalkyl, $C_3$-$C_8$ alkoxyalkoxyalkyl, $C_2$-$C_6$ alkoxyalkoxy, $C_4$-$C_{10}$ cycloalkylalkoxy, $C_1$-$C_6$ hydroxyalkyl, $C_4$-$C_{10}$ cycloalkylalkyl, $C_4$-$C_{10}$ alkylcycloalkyl, $C_6$-$C_{14}$ cycloalkylcycloalkyl, $C_4$-$C_{10}$ halocycloalkylalkyl, $C_6$-$C_{14}$ halocycloalkylcycloalkyl, $C_4$-$C_{10}$ haloalkylcycloalkyl, $C_5$-$C_{10}$ alkylcycloalkylalkyl, $C_3$-$C_8$ cycloalkenyl, $C_3$-$C_8$ halocycloalkenyl, —$SR^{25}$, —$S(O)R^{25}$, —$S(O)_2R^{25}$, —$OS(O)_2R^{25}$, —($C_1$-$C_6$ alkyl)$S(O)_2R^{25}$, $C_2$-$C_6$ alkylthioalkyl, $C_2$-$C_6$ alkylsulfinylalkyl, $C_2$-$C_6$ alkylsulfonylalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ haloalkoxycarbonyl, $C_4$-$C_8$ cycloalkoxycarbonyl, $C_5$-$C_{10}$ cycloalkylalkoxycarbonyl, $C_2$-$C_6$ alkylcarbonyloxy, $C_2$-$C_6$ haloalkylcarbonyloxy, $C_4$-$C_8$ cycloalkylcarbonyloxy, $C_2$-$C_6$ alkoxycarbonyloxy, $C_2$-$C_6$ haloalkoxycarbonyloxy, $C_4$-$C_8$ cycloalkoxycarbonylloxy, $C_3$-$C_6$ alkylcarbonylalkoxy, —$NR^{26}R^{27}$, $C_2$-$C_6$ alkylaminoalkyl, $C_3$-$C_8$(dialkylamino)alkyl, $C_2$-$C_6$ haloalkylaminoalkyl, $C_4$-$C_{10}$ cycloalkylaminoalkyl, $C_1$-$C_6$ alkylsulfonylamino, $C_1$-$C_6$ haloalkylsulfonylamino, $C_2$-$C_6$ alkylaminocarbonyl, $C_3$-$C_{10}$(dialkylamino)carbonyl, $C_4$-$C_8$ cycloalkylaminocarbonyl, $C_2$-$C_8$ dialkylhydroxyamino, $C_2$-$C_8$(dialkylamino)hydroxy, $C_3$-$C_{10}$ trialkylhydrazinyl, $C_3$-$C_{10}$ trialkylsilyl, $C_4$-$C_{10}$ trialkylsilylalkyl, $C_5$-$C_{10}$ trialkylsilylalkynyl, $C_3$-$C_{10}$ trialkylsilyloxy, $C_4$-$C_{12}$ trialkylsilylalkyloxy, $C_5$-$C_{12}$ trialkylsilylalkoxyalkyl, $C_5$-$C_{12}$ trialkylsilylalkynyloxy, $C_2$-$C_6$ alkylsulfonyloxyalkyl, $C_2$-$C_6$ haloalkylsulfonyloxyalkyl, —$C(=NOR^{28})R^{29}$, —$C(=NR^{30})R^{29}$, $C_2$-$C_6$ cyanoalkyl, phenyl, phenoxy or benzyl, or $X^1$ together with $X^2$, $X^2$ together with $X^3$ and $X^3$ together with $X^4$ form a $C_2$-$C_6$ alkylene chain that may include an oxygen atom, a sulfur atom, a nitrogen atom, or they are taken together with a carbon atom to which they are attached to form a thiophene ring, a pyridine ring, a pyrrole ring, an imidazole ring, a benzene ring, a naphthalene ring, a pyrimidine ring, a furan ring, a pyrazine ring, a pyrazole ring or an oxazole ring;

$R^{25}$ is $C_1$-$C_8$ alkyl, $C_3$-$C_8$ cycloalkyl, $C_1$-$C_6$ haloalkyl, $C_3$-$C_8$ halocycloalkyl, $C_1$-$C_6$ alkylamino, phenyl or benzyl, and phenyl or benzyl may be substituted with at least one $R^{31}$;

$R^{31}$ is $C_1$-$C_6$ alkyl, $C_3$-$C_8$ cycloalkyl, $C_1$-$C_6$ haloalkyl, $C_1$-$C_6$ alkoxy, $C_1$-$C_6$ haloalkoxy, $C_3$-$C_8$ cycloalkoxy, $C_3$-$C_8$ halocycloalkyl, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, halogen, cyano or hydroxy;

each of $R^{26}$ and $R^{27}$ is independently a hydrogen atom, $C_1$-$C_6$ alkyl, $C_3$-$C_8$ cycloalkyl, $C_1$-$C_6$ haloalkyl, $C_3$-$C_8$ halocycloalkyl, $C_1$-$C_6$ alkoxy, $C_2$-$C_8$ dialkylamino, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ haloalkoxycarbonyl or $C_3$-$C_{10}$ (dialkylamino)carbonyl;

$R^{28}$ is a hydrogen atom, $C_1$-$C_6$ alkyl, $C_1$-$C_6$ haloalkyl or benzyl;

$R^{29}$ is a hydrogen atom, $C_1$-$C_6$ alkyl, $C_3$-$C_8$ cycloalkyl, $C_1$-$C_6$ haloalkyl, $C_3$-$C_8$ halocycloalkyl, $C_4$-$C_{10}$ cycloalkylalkyl, phenyl or benzyl;

$R^{30}$ is $C_1$-$C_6$ alkyl, $C_3$-$C_8$ cycloalkyl, $C_1$-$C_6$ haloalkyl, $C_3$-$C_8$ halocycloalkyl, phenyl or benzyl;

each of $R^7$ and $R^8$ is independently $C_1$-$C_4$ alkyl, $C_3$-$C_6$ cycloalkyl or $C_1$-$C_4$ haloalkyl; E is —$CR^{32}R^{33}$— or —$NR^{34}$—;

each of $R^9$, $R^{10}$, $R^{11}$, $R^{12}$, $R^{32}$ and $R^{33}$ is independently a hydrogen atom, halogen, cyano, hydroxy, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_1$-$C_6$ haloalkoxy, $C_3$-$C_6$ cycloalkyl, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl or $C_1$-$C_6$ haloalkylsulfonyl;

$R^{34}$ is a hydrogen atom, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_2$-$C_6$ alkoxyalkyl, $C_3$-$C_6$ cycloalkyl, $C_3$-$C_6$ halocycloalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylcarbonyl, $C_2$-$C_6$ haloalkylcarbonyl, $C_2$-$C_6$ alkoxycarbonyl, $C_3$-$C_6$ alkoxycarbonylalkyl, $C_2$-$C_6$ alkylaminocarbonyl, $C_3$-$C_6$ (dialkylamino)carbonyl, $C_1$-$C_6$ alkylsulfonyl or $C_1$-$C_6$ haloalkylsulfonyl;

$G^1$, $G^2$ and $G^3$ is an oxygen atom or a sulfur atom;

each of $R^{13}$, $R^4$, $R^{15}$, $R^{16}$, $R^{17}$, $R^{20}$, $R^{21}$, $R^{22}$, $R^{23}$ and $R^{24}$ is independently a hydrogen atom, halogen, cyano, hydroxy, amino, nitro, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_1$-$C_6$ haloalkoxy, $C_3$-$C_6$ cycloalkyl, $C_3$-$C_6$ halocycloalkyl, $C_4$-$C_{10}$ cycloalkylalkyl, $C_4$-$C_{10}$ alkylcycloalkyl, $C_5$-$C_{10}$ alkylcycloalkylalkyl, $C_2$-$C_6$ alkoxyalkyl, $C_1$-$C_6$ hydroxyalkyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_8$ dialkylamino, $C_3$-$C_6$ cycloalkylamino, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl, $C_2$-$C_6$ alkylcarbonyloxy, $C_2$-$C_6$ alkylcarbonylthio, $C_2$-$C_6$ alkylaminocarbonyl, $C_2$-$C_8$ (dialkylamino)carbonyl, or $C_3$-$C_6$ trialkylsilyl;

$R^{18}$ is a hydrogen atom, $C_1$-$C_6$ alkyl, $C_1$-$C_6$ haloalkyl, $C_1$-$C_6$ alkoxy, $C_1$-$C_6$ haloalkoxy, $C_1$-$C_3$ alkylthio, halogen, cyano or hydroxy;

$R^{19}$ is a hydrogen atom, halogen, cyano, hydroxy, formyl, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, carboxy, carbamoyl, $C_3$-$C_6$ cycloalkyl, $C_3$-$C_8$ halocycloalkyl, $C_3$-$C_6$ cycloalkoxy, $C_3$-$C_8$ halocycloalkoxy, $C_2$-$C_6$ alkoxyalkyl, $C_4$-$C_6$ cycloalkylalkyl, $C_4$-$C_6$ alkylcycloalkyl, $C_4$-$C_6$ halocycloalkylalkyl, $C_3$-$C_8$ cycloalkenyl, $C_3$-$C_8$ halocycloalkenyl, $C_1$-$C_6$ alkylthio, $C_1$-$C_6$ haloalkylthio, $C_3$-$C_6$ cycloalkylthio, $C_2$-$C_6$ alkylthioalkyl, $C_2$-$C_6$ alkylsulfinylalkyl, $C_2$-$C_6$ alkylsulfonylalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ haloalkoxycarbonyl, $C_4$-$C_6$ cycloalkoxycarbonyl, $C_5$-$C_{10}$ cycloalkylalkoxycarbonyl, $C_2$-$C_6$ alkylcarbonyloxy, $C_2$-$C_6$ haloalkylcarbonyloxy, $C_1$-$C_6$ alkylamino, $C_1$-$C_6$ dialkylamino, $C_1$-$C_6$ haloalkylamino, $C_1$-$C_6$ halodialkylamino, $C_3$-$C_6$ cycloalkylamino, $C_2$-$C_6$ alkylaminoalkyl, $C_3$-$C_6$ (dialkylamino)alkyl, $C_2$-$C_6$ haloalkylaminoalkyl, $C_1$-$C_6$ alkylsulfonylamino, $C_1$-$C_6$ haloalkylsulfonylamino, $C_2$-$C_6$ alkylcarbonylamino, $C_2$-$C_6$ haloalkylcarbonylamino, $C_2$-$C_6$ alkylaminocarbonyl or $C_3$-$C_{10}$ (dialkylamino)carbonyl; or $R^{18}$ and $R^{19}$ are taken together with a carbon atom to which they are attached to form a 3-7 membered ring containing members selected from carbon atom and at most 4 heteroatoms independently selected from at most 2 oxygen atoms, at most 2 sulfur atoms, at most 2 nitrogen atoms, and at most 2 silicon atoms, wherein at most 3 carbon atom members may be substituted with oxo or thioxo, a sulfur atom member is independently selected from $S(=O)_p$ $(=NR^{35})_q$, a silicon atom member is independently selected from $SiR^{36}R^{37}$, and a ring may be optionally substituted with at most 4 substituents independently selected from halogen, cyano, $C_1$-$C_2$ alkyl, $C_1$-$C_2$ haloalkyl, $C_1$-$C_2$ alkoxy or $C_1$-$C_2$ haloalkoxy on a carbon atom member, and cyano, $C_1$-$C_2$ alkyl or $C_1$-$C_2$ alkoxy on a nitrogen atom member;

$R^{35}$ is independently selected from a hydrogen atom, cyano, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, $C_3$-$C_8$ halocycloalkyl, $C_1$-$C_6$ alkylamino, $C_2$-$C_6$ dialkylamino, $C_1$-$C_6$ haloalkylamino or phenyl;

each of p and q is independently 0, 1 or 2, wherein a sum of p and q is 0, 1 or 2; each of $R^{36}$ and $R^{37}$ is independently $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ halocycloalkyl, $C_4$-$C_{10}$ cycloalkylalkyl, $C_4$-$C_7$ alkylcycloalkyl or $C_5$-$C_7$ alkylcycloalkylalkyl;

Z is an oxygen atom, a sulfur atom, —N($R^{38}$)—, —C($R^{39}$)$_2$—, —OC($R^{39}$)$_2$—, —SC($R^{39}$)$_2$— or —N($R^{38}$)C($R^{39}$)$_2$—, wherein a left bond is a bond with a nitrogen atom of A-3, and a right bond is a bond with a carbon atom of A-3;

$R^{38}$ is a hydrogen atom, cyano, $C_1$-$C_4$ alkyl, $C_1$-$C_4$ haloalkyl, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_5$ (dialkylamino)carbonyl, $C_1$-$C_4$ alkylsulfonyl or $C_1$-$C_4$ haloalkylsulfonyl;

$R^{18}$ and $R^{38}$ are taken together with a carbon atom and a nitrogen atom to which they are attached to form a 5-7 membered partially unsaturated ring containing members in addition to the linking atoms selected from carbon atom and at most 5 heteroatoms independently selected from at most 1 oxygen atom, at most 1 sulfur atom, at most 3 nitrogen atoms, and a ring may be optionally substituted with at most 3 substituents independently selected from halogen, cyano, nitro, $C_1$-$C_2$ alkyl, $C_1$-$C_2$ haloalkyl, $C_1$-$C_2$ alkoxy or $C_1$-$C_2$ haloalkoxy on a carbon atom member, and cyano, $C_1$-$C_2$ alkyl or $C_1$-$C_2$ alkoxy on a nitrogen atom member;

$R^{39}$ is independently a hydrogen atom, $C_1$-$C_6$ alkyl or $C_1$-$C_6$ haloalkyl, $G^4$ is —$OR^{40}$, —$SR^{41}$, —$NR^{42}R^{43}$ or $R^{44}$;

each of $R^{40}$ and $R^{41}$ is independently $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_2$-$C_6$ alkoxyalkyl, $C_4$-$C_8$ cycloalkoxyalkyl, $C_3$-$C_6$ alkoxyalkoxyalkyl, $C_3$-$C_6$ cycloalkyl, $C_3$-$C_6$ halocycloalkyl, $C_2$-$C_6$ alkylaminoalkyl, $C_3$-$C_6$ (dialkylamino)alkyl, $C_2$-$C_6$ haloalkylaminoalkyl, $C_4$-$C_8$ cycloalkylaminoalkyl, $C_4$-$C_8$ cycloalkylalkyl, $C_4$-$C_8$ alkylcycloalkyl, $C_4$-$C_8$ halocycloalkylalkyl, $C_5$-$C_8$ alkylcycloalkylalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ alkylaminocarbonyl, $C_3$-$C_6$ (dialkylamino)carbonyl or $C_4$-$C_8$ cycloalkylaminocarbonyl;

$R^{42}$ is a hydrogen atom, cyano, amino, hydroxy, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_2$-$C_6$ alkoxyalkyl, $C_1$-$C_6$ alkylamino, $C_2$-$C_8$ dialkylamino, $C_1$-$C_6$ haloalkylamino, $C_2$-$C_8$ halodialkylamino, $C_4$-$C_8$ cycloalkylalkyl, $C_1$-$C_6$ alkylsulfonyl, $C_1$-$C_6$ haloalkylsulfonyl, $C_2$-$C_6$ alkylcarbonyl or $C_2$-$C_6$ haloalkylcarbonyl;

$R^{43}$ is a hydrogen atom, $C_1$-$C_6$ alkyl, $C_2$-$C_6$ alkenyl, $C_2$-$C_6$ alkynyl, $C_1$-$C_6$ haloalkyl or $C_3$-$C_6$ cycloalkyl;

$R^{42}$ and $R^{43}$ are taken together with a nitrogen atom to which they are attached to may form a pyrrolidine ring, a piperidine ring or a morpholine ring;

$R^{44}$ is a hydrogen atom, cyano, $C_1$-$C_4$ alkyl, $C_1$-$C_4$ haloalkyl, $C_2$-$C_4$ alkoxyalkyl, $C_2$-$C_4$ alkylcarbonyl, $C_2$-$C_4$ alkoxycarbonyl, $C_2$-$C_3$ alkylaminocarbonyl, $C_3$-$C_6$ (dialkylamino)carbonyl, $C_1$-$C_6$ haloalkylamino or $C_2$-$C_8$ halodialkylamino).

[2] The compound or a salt thereof according to [1], wherein $R^1$, $R^2$ and $R^4$ are hydrogen atoms;

each of $R^3$ and $R^5$ is independently a hydrogen atom or methyl;

n is 0;

each of $X^1$, $X^2$, $X^3$ and $X^4$ is independently a hydrogen atom, halogen, cyano, hydroxy, nitro, formyl, mercapto, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_1$-$C_6$ hydroxyalkyl, $C_1$-$C_6$ alkoxy, $C_1$-$C_6$ haloalkoxy, carboxy, $C_3$-$C_6$ alkynylalkoxy, $C_2$-$C_6$ alkoxyalkyl, —$SR^{25}$, —$S(O)R^{25}$, —$S(O)_2R^{25}$, —$OS(O)_2R^{25}$, $C_2$-$C_6$ alkylthioalkyl, $C_2$-$C_6$ alkylcarbonyl, $C_2$-$C_6$ alkoxycarbonyl, $C_2$-$C_6$ alkylcarbonyloxy, $C_2$-$C_6$ alkoxycarbonyloxy, —$NR^{26}R^{27}$, $C_1$-$C_6$ alkylsulfonylamino, $C_2$-$C_6$ alkylaminoalkyl, —$C(=NOR^{28})R^{29}$, $C_2$-$C_6$ cyanoalkyl, phenyl, phenoxy or benzyl, or $X^1$ together with $X^2$, $X^2$ together with $X^3$ and $X^3$ together with $X^4$ form a $C_2$-$C_6$ alkylene chain that may contain an oxygen atom, or they are taken together with a carbon atom to which they are attached to form a benzene ring;

$R^{25}$ is $C_1$-$C_8$ alkyl, $C_3$-$C_6$ cycloalkyl, $C_1$-$C_6$ haloalkyl, or $C_1$-$C_6$ alkylamino;

each of $R^{26}$ and $R^{27}$ is independently a hydrogen atom, $C_1$-$C_6$ alkyl, $C_2$-$C_6$ alkylcarbonyl or $C_2$-$C_6$ alkoxycarbonyl;

each of $R^{28}$ and $R^{29}$ is independently a hydrogen atom or $C_1$-$C_6$ alkyl;

each of $R^7$ and $R^8$ is independently $C_1$-$C_6$ alkyl or $C_1$-$C_6$ haloalkyl;

E is —$CR^{32}R^{33}$—;

$R^9$, $R^{10}$, $R^{11}$, $R^{12}$, $R^{32}$ and $R^{33}$ are hydrogen atoms;

each of $R^{13}$, $R^{16}$, $R^{20}$ and $R^{23}$ is independently a hydrogen atom, halogen, $C_1$-$C_6$ alkyl or $C_1$-$C_6$ haloalkyl;

$R^{14}$, $R^{15}$, $R^{17}$, $R^{21}$, $R^{22}$ and $R^{24}$ are hydrogen atoms;

each of $R^{18}$ and $R^{19}$ is independently a hydrogen atom, $C_1$-$C_6$ alkyl or $C_1$-$C_6$ haloalkyl;

Z is an oxygen atom;

$G^4$ is —$OR^{40}$;

$R^{40}$ is $C_1$-$C_6$ alkyl.

[3] The compound or a salt thereof according to [1] or [2], wherein

T is CH;

$R^3$ and $R^5$ are hydrogen atoms;

each of $X^1$, $X^2$, $X^3$ and $X^4$ is independently a hydrogen atom, halogen, cyano, hydroxy, nitro, formyl, $C_1$-$C_4$ alkyl, $C_1$-$C_4$ haloalkyl, $C_1$-$C_4$ hydroxyalkyl, $C_1$-$C_4$ alkoxy, $C_1$-$C_4$ haloalkoxy, —$SR^{25}$, —$S(O)_2R^{25}$, —$OS(O)_2R^{25}$, $C_2$-$C_4$ alkylcarbonyloxy, $C_2$-$C_4$ alkoxycarbonyloxy, or —$C(=NOR^{28})R^{29}$;

$R^{25}$ is $C_1$-$C_4$ alkyl, cyclopropyl or $C_1$-$C_4$ haloalkyl;

each of $R^{28}$ and $R^{29}$ is independently a hydrogen atom or methyl;

each of $R^7$ and $R^8$ is independently $C_1$-$C_4$ alkyl or $C_1$-$C_4$ haloalkyl;

$G^1$, $G^2$ and $G^3$ are oxygen atoms;

each of $R^{13}$, $R^{16}$, $R^{20}$ and $R^{23}$ is independently a hydrogen atom, a chlorine atom, methyl or trifluoromethyl;

each of $R^{18}$ and $R^{19}$ is independently a hydrogen atom, $C_1$-$C_4$ alkyl or $C_1$-$C_4$ haloalkyl;

$R^{40}$ is methyl.

[4] The compound or a salt thereof according to any one of [1] to [3], wherein each of $X^1$, $X^2$, $X^3$ and $X^4$ is independently a hydrogen atom, nitro, a fluorine atom, methyl, trifluoromethyl, methoxy, difluoromethoxy, trifluoromethoxy or —$OS(O)_2R^{25}$;

$R^{25}$ is methyl;

$R^7$ is trifluoromethyl or difluoromethyl;

$R^8$ is methyl, trifluoromethyl or difluoromethyl;

each of $R^{13}$, $R^{16}$, $R^{20}$ and $R^{23}$ is independently a hydrogen atom or methyl;

each of $R^{18}$ and $R^{19}$ is independently a hydrogen atom, methyl or trifluoromethyl.

[5] The compound or a salt thereof according to any one of [1] to [4], wherein at least one of $X^1$, $X^2$, $X^3$, $X^4$ is —$OS(O)_2R^{25}$.

[6] The compound or a salt thereof according to [1] to [5], wherein $X^1$ is —$OS(O)_2R^{25}$.

[7] The compound or a salt thereof according to any one of [1] to [6], wherein $X^2$ and $X^3$ are hydrogen atoms.

[8] The compound or a salt thereof according to any one of [1] to [7], wherein A is A-1.

[9] The compound or a salt thereof according to any one of [1] to [8], selected from 4-[4-(1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-fluoro-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6,9-difluoro-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(7,8-dimethyl-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(7,8-dichloro-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-ethylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7-methylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(1,5-dihydro-3H-2,4-naphthodioxepin-3-yl)-2-thiazolyl]-1-[2-[5-methyl-3-(trifluoronethyl)-1H-pyrazole-1-yl]acetyl]piperidine, 4-[4-(7-fluoro-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-nitro-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-cyclopropylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methyl-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-bromo-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(7-(trifluoromethyl)-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6,7,8,9-tetrafluoro-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(1-menthyl-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-methyl-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7-methyl-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-butylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-propylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-chloro-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-bromo-9-methoxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-octylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine,

- 4-[4-(6-methoxy-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
- 4-[4-(7-nitro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
- 4-[4-(6-isopropylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine,
- 4-[4-(7-ethylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine,
- 4-[4-[6-(1,1,1-trifluoropropane-3-yl)sulfonyloxy-1,5-dihydro-3H-2,4-benzodioxepin-3-yl]-2-thiazolyl]-1-[2-[5-methyl-3-(trifluoronethyl)-1H-pyrazole-1-yl]acetyl]piperidine,
- 4-[4-(1,5,7,8,9-pentahydro-3H-2,4-indenodioxepin-3-yl)-2-thiazolyl]-1-[2-[5-methyl-3-(trifluoronethyl)-1H-pyrazole-1-yl]acetyl]piperidine,
- 4-[4-(6-methylsulfonyloxy-9-nitro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
- 4-[4-(6-hydroxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
- 4-[4-(6-cyclopropylcarbonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
- 4-[4-(6-fluoro-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-[6-(trifluoromethyl)sulfonyloxy-1,5-dihydro-3H-2,4-benzodioxepin-3-yl]-2-thiazolyl]-1-[2-[5-methyl-3-(trifluoromethyl)-1H-pyrazole-1-yl]acetyl]piperidine,
- 4-[4-(6-methoxycarbonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine,
- 4-[4-(6-methylsulfonyloxy-1,5-dihydro-3H-2,4-benzodioxepin-3-yl)-2-thiazolyl]-1-[2-(2,5-dimethylphenyl)acetyl]piperidine,
- 4-[4-(6-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-(6-fluoro-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-(6-methoxy-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-(7-chloro-1,5-dihydro-3H-2,4-benzodioxepin-3-yl)-2-thiazolyl]-1-[2-[5-methyl-3-(trifluoronethyl)-1H-pyrazole-1-yl]acetyl]piperidine,
- 4-[4-(6-fluoro-1,5-dihydro-3H-2,4-benzodioxepin-3-yl)-2-thiazolyl]-1-[2-[3,5-bis(trifluoronethyl)-1H-pyrazole-1-yl]acetyl]piperidine,
- 4-[4-(6-methylsulfonyloxy-1,5-dihydro-3H-2,4-benzodioxepin-3-yl)-2-thiazolyl]-1-[2-[3,5-bis(trifluoronethyl)-1H-pyrazole-1-yl]acetyl]piperidine,
- 4-[4-(6-methylsulfonylamino-1,5-dihydro-3H-2,4-benzodioxepin-3-yl)-2-thiazolyl]-1-[2-[5-methyl-3-(trifluoronethyl)-1H-pyrazole-1-yl]acetyl]piperidine,
- 4-[4-(6-methyl-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-(7-fluoro-6-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
- 4-[4-(6-methoxy-9-nitro-1,5-dihydro-3H-2,4-benzodioxepin-3-yl)-2-thiazolyl]-1-[2-[5-methyl-3-(trifluoronethyl)-1H-pyrazole-1-yl]acetyl]piperidine,
- 4-[4-(6-methylsulfonyl-1,5-dihydro-3H-2,4-benzodioxepin-3-yl)-2-thiazolyl]-1-[2-[5-methyl-3-(trifluoronethyl)-1H-pyrazole-1-yl]acetyl]piperidine,
- 4-[4-(6-phenylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine,
- 4-[4-(7-nitro-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-(6,9-difluoro-1,5-dihydro-3H-2,4-benzodioxepin-3-yl)-2-thiazolyl]-1-[2-[3,5-bis(trifluoronethyl)-1H-pyrazole-1-yl]acetyl]piperidine,
- 4-[4-(6,9-difluoro-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-(6-hydroxymethyl-1,5-dihydro-3H-2,4-benzodioxepin-3-yl)-2-thiazolyl]-1-[2-[5-methyl-3-(trifluoronethyl)-1H-pyrazole-1-yl]acetyl]piperidine,
- 4-[4-(6-isopropylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-(6-butylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-(6,7,8,9-tetrafluoro-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-(6-phenyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
- 4-[4-(6-bromo-9-methoxy-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-(6-chloro-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-(6-octylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine,
- 4-[4-[7-(trifluoromethyl)-1,5-dihydro-3H-2,4-benzodioxepin-3-yl]-2-thiazolyl]-1-[2-[3,5-bis(difluoromethyl)-1H-pyrazole-1-yl]acetyl]piperidine,
- 4-[4-(1,5,7,8,9-pentahydro-3H-2,4-indenodioxepin-3-yl)-2-thiazolyl]-1-[2-[3,5-bis(difluoromethyl)-1H-pyrazole-1-yl]acetyl]piperidine,
- 4-[4-[6-(methoxyimino)methyl-1,5-dihydro-3H-2,4-benzodioxepin-3-yl]-2-thiazolyl]-1-[2-[5-methyl-3-(trifluoromethyl)-1H-pyrazole-1-yl]acetyl]piperidine,
- 4-[4-(6-methylsulfonyloxy-1,5-dihydro-3H-2,4-benzodioxepin-3-yl)-2-thiazolyl]-1-[2-(2,5-dichlorophenyl)acetyl]piperidine,
- 4-[4-(6-fluoro-1,5-dihydro-3H-2,4-benzodioxepin-3-yl)-2-thiazolyl]-1-[2-(2,5-dichlorophenyl)acetyl]piperidine,
- 4-[4-(6,9-difluoro-1,5-dihydro-3H-2,4-benzodioxepin-3-yl)-2-thiazolyl]-1-[2-(2,5-dichlorophenyl)acetyl]piperidine,
- 4-[4-(6-methylsulfonyloxy-1,5-dihydro-3H-2,4-benzodioxepin-3-yl)-2-thiazolyl]-1-[N-(2,5-dimethylphenyl)carbamoyl]piperidine,
- 4-[4-(6-methylsulfonyloxy-1,5-dihydro-3H-2,4-benzodioxepin-3-yl)-2-thiazolyl]-1-[2-[(propane-2-ylideneamino)oxy]acetyl]piperidine, and 4-[4-(6-methylsulfonyloxy-1,5-dihydro-3H-2,4-benzodioxepin-3-yl)-2-thiazolyl]-1-[(Z)-[(2,5-dimethylphenyl)imino](methoxy)methyl]piperidine.

[10] The compound or a salt thereof according to any one of [1] to [9], selected from 4-[4-(6-methylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-ethylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7-methylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-cyclopropylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methyl-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-butylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-propylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-octylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-methoxy-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-isopropylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(7-ethylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-[6-(1,1,1-trifluoropropane-3-yl)sulfonyloxy-1,5-dihydro-3H-2,4-benzodioxepin-3-yl]-2-thiazolyl]-1-[2-[5-methyl-3-(trifluoronethyl)-1H-pyrazole-1-yl]acetyl]piperidine, 4-[4-(6-methylsulfonyloxy-9-nitro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-[6-(trifluoromethyl)sulfonyloxy-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-methoxy-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-methyl-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(7-fluoro-6-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-phenylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-isopropylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-butylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-octylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-methylsulfonyloxy-1,5-dihydro-3H-2,4-benzodioxepin-3-yl)-2-thiazolyl]-1-[N-(2,5-dimethylphenyl)carbamoyl]piperidine, 4-[4-(6-methylsulfonyloxy-1,5-dihydro-3H-2,4-benzodioxepin-3-yl)-2-thiazolyl]-1-[[2-(propane-2-ylideneamino)oxy]acetyl]piperidine, and 4-[4-(6-methylsulfonyloxy-1,5-dihydro-3H-2,4-benzodioxepin-3-yl)-2-thiazolyl]-1-[(Z)-[(2,5-dimethylphenyl)imino](methoxy)methyl]piperidine.

[11] A compound or a salt thereof according to any of [1] to [8] selected from

4-[4-(6,7-dimethyl-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-chloro-9-methylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-bromo-9-methylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-isopropylsulfonyloxy-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-butylsulfonyloxy-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-[6-(chloromethyl)-1,5-dihydro-3H-2,4-benzodioxepin-3-yl]-2-thiazolyl]-1-[2-[5-methyl-3-(trifluoronethyl)-1H-pyrazole-1-yl]acetyl]piperidine, 4-[4-[6-(formyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-[6-(2,2-dimethylhydrazono)methyl-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-[6-(cyanomethyl)-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-(6-phenyl-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-methoxy-9-nitro-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(1-methyl-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(1,5-dihydro-3H-2,4-naphthodioxepin-3-yl)-2-thiazolyl]-1-[2-[3,5-bis(difluoromethyl)-1H-pyrazole-1-yl]acetyl]piperidine, 4-[4-(7-tert-butyl-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(7-tert-butyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7-fluoro-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-[7-(trifluoromethyl)-1,5-dihydro-3H-2,4-benzodioxepin-3-yl]-2-thiazolyl]-1-[2-[3,5-bis(difluoromethyl)-1H-pyrazole-1-yl]acetyl]piperidine, 4-[4-(6-bromo-9-methoxy-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-methoxy-9-nitro-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6,7,8,9-tetrafluoro-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-(trifluoromethoxy)-9-methoxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(1-methyl-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(1,5-dihydro-3H-2,4-naphthodioxepin-3-yl)-2-thiazolyl]-1-[2-[3,5-bis(trifluoronethyl)-1H-pyrazole-1-yl]acetyl]piperidine, 4-[4-[6-(dimethylaminosulfonyloxy)-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-(7-fluoro-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(7-tert-butyl-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-chloro-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-[6-(difluoromethoxy)-1,5-dihydro-3H-2,4-benzodioxepin-3-yl]-2-thiazolyl]-1-[2-[5-methyl-3-(trifluoronethyl)-1H-pyrazole-1-yl]acetyl]piperidine, 4-[4-(7-nitro-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-[6-(hydroxyimino)methyl-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-[6-(difluoromethyl)-1,5-dihydro-3H-2,4-benzodioxepin-3-yl]-2-thiazolyl]-1-[2-[5-methyl-3-(trifluoronethyl)-1H-pyrazole-1-yl]acetyl]piperidine, 4-[4-(7-bromo-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7-bromo-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6,9-dibromo-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-iodo-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-chloro-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-[6,9-bis(methylsulfonyloxy)-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-(6-cyano-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[3,5-dimethyl-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[5-methyl-3-(trifluoronethyl)-1H-pyrazole-1-yl]thioacetyl]piperidine, 4-[4-(6-fluoro-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]thioacetyl]piperidine, 4-[4-(6-methoxy-9-methylsulfonyloxy-1,5-dihydro-3H-2,4-benzodioxepin-3-yl)-2-thiazolyl]-1-[2-[5-chloro-3-(trifluoromethyl)-1H-pyrazole-1-yl]acetyl]piperidine, 4-[4-(6-methoxy-9-methylsulfonyloxy-1,5-dihydro-3H-2,4-benzodioxepin-3-yl)-2-thiazolyl]-1-[2-(3,5-dichloro-1H-pyrazole-1-yl)acetyl]piperidine, 4-[4-(6-chloro-9-methoxy-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-bromo-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-chloro-9-methoxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-bromo-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-nitro-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methoxy-9-methylsulfonyloxy-1,5-dihydro-3H-2,4-benzodioxepin-3-yl)-2-thiazolyl]-1-[2-[3,5-dimethyl-1H-pyrazole-1-yl]acetyl]piperidine, 4-[4-(6-chloro-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-methoxy-9-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-chloro-9-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[3,5-bis(dichloromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[3,5-dimethyl-1H-pyrazole-1-yl]acetyl]piperidine, 4-[4-(6,7-dimethyl-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6,7-dimethyl-9-methylsulfonyloxy-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-bromo-9-methylsulfonyloxy-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-methylsulfonyloxy-9-nitro-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-bromo-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-nitro-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[5-methyl-3-(trifluoronethyl)-1H-pyrazole-1-yl]acetyl]piperazine, 4-[4-(6-methylsulfonyloxy-9-nitro-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-iodo-9-methylsulfonyloxy-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-iodo-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(7-fluoro-6-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(7-fluoro-6-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-fluoro-9-methoxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6-methoxy-9-methyl-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-methoxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-[6-(difluoromethoxy)-1,5-dihydro-3H-2,4-benzodioxepin-3-yl]-2-thiazolyl]-1-[2-[3,5-bis(difluoromethyl)-1H-pyrazole-1-yl]acetyl]piperidine, 4-[4-[6-(difluoromethoxy)-1,5-dihydro-3H-2,4-benzodioxepin-3-yl]-2-thiazolyl]-1-[2-[3,5-bis(trifluoromethyl)-1H-pyrazole-1-yl]acetyl]piperidine, 4-[4-(7-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(7-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methoxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methoxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-fluoro-9-methoxy-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-[6-(difluoromethoxy)-9-methylsulfonyloxy-1,5-dihydro-3H-2,4-benzodioxepin-3-yl]-2-thiazolyl]-1-[2-[5-methyl-3-(trifluoronethyl)-1H-pyrazole-1-yl]acetyl]piperidine, 4-[4-(6-acetoxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-[6-(hydroxyimino)methyl-1,5-dihydro-3H-2,4-benzodioxepin-3-yl]-2-thiazolyl]-1-[2-[3,5-bis(difluoromethyl)-1H-pyrazole-1-yl]acetyl]piperidine, 4-[4-[6,9-bis(methylsulfonyloxy)-1,5-dihydro-3H-2,4-benzodioxepin-3-yl]-2-thiazolyl]-1-[2-[3,5-bis(difluoromethyl)-1H-pyrazole-1-yl]acetyl]piperidine, 4-[4-[6,9-bis(methylsulfonyloxy)-1,5-dihydro-3H-2,4-benzodioxepin-3-yl]-2-thiazolyl]-1-[2-[3,5-bis(trifluoromethyl)-1H-pyrazole-1-yl]acetyl]piperidine, 4-[4-(6-cyano-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-[6-(hydroxyimino)methyl-1,5-dihydro-3H-2,4-benzodioxepin-3-yl]-2-thiazolyl]-1-[2-[3,5-bis(trifluoromethyl)-1H-pyrazole-1-yl]acetyl]piperidine, 4-[4-(6-cyano-1,5-dihydro-3H-2,4-benzodioxepin-3-yl)-2-thiazolyl]-1-[2-[3,5-bis(trifluoronethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperazine, 4-[4-(6-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]propanoyl]piperidine, 4-[4-(6-fluoro-9-methylsulfonyloxy-1,5-dihydro-3H-2,4-benzodioxepin-3-yl)-2-thiazolyl]-1-[2-[5-methyl-3-(difluoromethyl)-1H-pyrazole-1-yl]acetyl]piperidine, 4-[4-(6-fluoro-9-methylsulfonyloxy-1,5-dihydro-3-methyl-2,4-benzodioxepin-3-yl)-2-thiazolyl]-1-[2-[5-methyl-3-(trifluoromethyl)-1H-pyrazole-1-yl]acetyl]piperidine, 4-[4-(6-fluoro-9-methylsulfonyloxy-1,5-dihydro-3-methyl-2,4-benzodioxepin-3-yl)-2-thiazolyl]-1-[2,2-difluoro-2-[5-methyl-3-(trifluoronethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]propanoyl]piperidine, 4-[4-(6-fluoro-9-methylsulfonyloxy-1,5-dihydro-3H-2,4-benzodioxepin-3-yl)-2-thiazolyl]-3-methyl-1-[2-[5-methyl-3-(trifluoromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]thioacetyl]piperidine, 4-[4-(6-fluoro-9-methylsulfonyloxy-1,5-dihydro-3H-2,4-benzodioxepin-3-yl)-2-thiazolyl]-2-methyl-1-[2-[5-methyl-3-(trifluoromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]propanoyl]piperidine, 4-[4-(6-fluoro-9-hydroxy-1,5-dihydro-3H-2,4-benzodioxepin-3-yl)-2-thiazolyl]-1-[2-[5-methyl-3-(trifluoronethyl)-1H-pyrazole-1-yl]acetyl]piperidine, 4-[4-(6,9-difluoro-1,5-dihydro-3H-2,4-benzodioxepin-3-yl)-2-thiazolyl]-1-[2-(2,5-dimethylphenyl)acetyl]piperidine,
4-[4-(6-fluoro-1,5-dihydro-3H-2,4-benzodioxepin-3-yl)-2-thiazolyl]-1-[2-(2,5-dimethylphenyl)acetyl]piperidine,
4-[4-(6-fluoro-9-methylsulfonyloxy-1,5-dihydro-3H-2,4-benzodioxepin-3-yl)-2-thiazolyl]-1-[2-(2,5-dimethylphenyl)acetyl]piperidine,
4-[4-(6-methoxy-9-nitro-1,5-dihydro-3H-2,4-benzodioxepin-3-yl)-2-thiazolyl]-1-[2-(2,5-dimethylphenyl)acetyl]piperidine,
4-[4-(7-fluoro-1,5-dihydro-3H-2,4-benzodioxepin-3-yl)-2-thiazolyl]-1-[2-(2,5-dimethylphenyl)acetyl]piperidine,
4-[4-(1,5-dihydro-3H-2,4-benzodioxepin-3-yl)-2-thiazolyl]-1-[2-(2,5-dimethylphenyl)acetyl]piperidine,
4-[4-(6-butylsulfonyloxy-1,5-dihydro-3H-2,4-benzodioxepin-3-yl)-2-thiazolyl]-1-[2-(2,5-dimethylphenyl)acetyl]piperidine,
4-[4-(1-methyl-1,5-dihydro-3H-2,4-benzodioxepin-3-yl)-2-thiazolyl]-1-[2-(2,5-dimethylphenyl)acetyl]piperidine,
4-[4-(6-fluoro-9-methylsulfonyloxy-1,5-dihydro-3H-2,4-benzodioxepin-3-yl)-2-thiazolyl]-1-[N-(2,5-dimethylphenyl)carbamoyl]piperidine,
4-[4-(6,9-difluoro-1,5-dihydro-3H-2,4-benzodioxepin-3-yl)-2-thiazolyl]-1-[N-(2,5-dimethylphenyl) carbamoyl]piperidine,
4-[4-(6-fluoro-9-methylsulfonyloxy-1,5-dihydro-3H-2,4-benzodioxepin-3-yl)-2-thiazolyl]-1-[2-(2,5-dichlorophenyl)acetyl]piperidine,
4-[4-(6-bromo-1,5-dihydro-3H-2,4-benzodioxepin-3-yl)-2-thiazolyl]-1-[2-(2,5-dimethylphenyl)acetyl]piperidine,
4-[4-(7-nitro-1,5-dihydro-3H-2,4-benzodioxepin-3-yl)-2-thiazolyl]-1-[2-(2,5-dimethylphenyl)acetyl]piperidine,
4-[4-(6-bromo-1,5-dihydro-3H-2,4-benzodioxepin-3-yl)-2-thiazolyl]-1-[2-(2,5-dichlorophenyl)acetyl]piperidine,
4-[4-(6-chloro-9-methoxy-1,5-dihydro-3H-2,4-benzodioxepin-3-yl)-2-thiazolyl]-1-[2-(2,5-dimethylphenyl)acetyl]piperidine,
4-[4-(7-nitro-1,5-dihydro-3H-2,4-benzodioxepin-3-yl)-2-thiazolyl]-1-[2-(2,5-dichlorophenyl)acetyl]piperidine,
4-[4-(6-chloro-1,5-dihydro-3H-2,4-benzodioxepin-3-yl)-2-thiazolyl]-1-[2-(2,5-dichlorophenyl)acetyl]piperidine,
4-[4-(6-chloro-9-methoxy-1,5-dihydro-3H-2,4-benzodioxepin-3-yl)-2-thiazolyl]-1-[2-(2,5-dichlorophenyl)acetyl]piperidine,
4-[4-(6-bromo-9-methoxy-1,5-dihydro-3H-2,4-benzodioxepin-3-yl)-2-thiazolyl]-1-[2-(2,5-dimethylphenyl)acetyl]piperidine,
4-[4-(6-bromo-9-methoxy-1,5-dihydro-3H-2,4-benzodioxepin-3-yl)-2-thiazolyl]-1-[2-(2,5-dichlorophenyl)acetyl]piperidine,
4-[4-(6-methoxy-9-methylsulfonyloxy-1,5-dihydro-3H-2,4-benzodioxepin-3-yl)-2-thiazolyl]-1-[2-(2,5-dichlorophenyl)acetyl]piperidine,
4-[4-(6,7,8,9-tetrafluoro-1,5-dihydro-3H-2,4-benzodioxepin-3-yl)-2-thiazolyl]-1-[2-(2,5-dimethylphenyl)acetyl]piperidine,
4-[4-(6-methoxy-9-methylsulfonyloxy-1,5-dihydro-3H-2,4-benzodioxepin-3-yl)-2-thiazolyl]-1-[2-(2,5-dimethylphenyl)acetyl]piperidine,
4-[4-(6,7,8,9-tetrafluoro-1,5-dihydro-3H-2,4-benzodioxepin-3-yl)-2-thiazolyl]-1-[2-(2,5-dichlorophenyl)acetyl]piperidine,
4-[4-(6-methylsulfonyloxy-1,5-dihydro-3H-2,4-benzodioxepin-3-yl)-2-thiazolyl]-1-[2-[2,5-bis(trifluoronethyl)phenyl]acetyl]piperidine,
4-[4-(6,7-dimethyl-9-methylsulfonyloxy-1,5-dihydro-3H-2,4-benzodioxepin-3-yl)-2-thiazolyl]-1-[2-(2,5-dimethylphenyl)acetyl]piperidine,
4-[4-(6,7-dimethyl-9-methylsulfonyloxy-1,5-dihydro-3H-2,4-benzodioxepin-3-yl)-2-thiazolyl]-1-[2-(2,5-dichlorophenyl)acetyl]piperidine,
4-[4-(6-bromo-9-methylsulfonyloxy-1,5-dihydro-3H-2,4-benzodioxepin-3-yl)-2-thiazolyl]-1-[2-(2,5-dimethylphenyl)acetyl]piperidine,
4-[4-(6-methylsulfonyloxy-9-nitro-1,5-dihydro-3H-2,4-benzodioxepin-3-yl)-2-thiazolyl]-1-[2-(2,5-dichlorophenyl)acetyl]piperidine,
4-[4-(6-bromo-9-methylsulfonyloxy-1,5-dihydro-3H-2,4-benzodioxepin-3-yl)-2-thiazolyl]-1-[2-(2,5-dichlorophenyl)acetyl]piperidine,
4-[4-(6-nitro-1,5-dihydro-3H-2,4-benzodioxepin-3-yl)-2-thiazolyl]-1-[2-(2,5-dichlorophenyl)acetyl]piperidine,
4-[4-(6-methylsulfonyloxy-9-nitro-1,5-dihydro-3H-2,4-benzodioxepin-3-yl)-2-thiazolyl]-1-[2-(2,5-dimethylphenyl)acetyl]piperidine,
4-[4-(6-chloro-9-methylsulfonyloxy-1,5-dihydro-3H-2,4-benzodioxepin-3-yl)-2-thiazolyl]-1-[2-(2,5-dimethylphenyl)acetyl]piperidine,
4-[4-(6-nitro-1,5-dihydro-3H-2,4-benzodioxepin-3-yl)-2-thiazolyl]-1-[2-(2,5-dimethylphenyl)acetyl]piperidine,
4-[4-(6-iodo-9-methylsulfonyloxy-1,5-dihydro-3H-2,4-benzodioxepin-3-yl)-2-thiazolyl]-1-[2-(2,5-dimethylphenyl)acetyl]piperidine,
4-[4-(6-chloro-9-methylsulfonyloxy-1,5-dihydro-3H-2,4-benzodioxepin-3-yl)-2-thiazolyl]-1-[2-(2,5-dichlorophenyl)acetyl]piperidine,
4-[4-(7-fluoro-6-methylsulfonyloxy-1,5-dihydro-3H-2,4-benzodioxepin-3-yl)-2-thiazolyl]-1-[2-(2,5-dimethylphenyl)acetyl]piperidine,
4-[4-(7-fluoro-6-methylsulfonyloxy-1,5-dihydro-3H-2,4-benzodioxepin-3-yl)-2-thiazolyl]-1-[2-(2,5-dichlorophenyl)acetyl]piperidine,
4-[4-(6-iodo-9-methylsulfonyloxy-1,5-dihydro-3H-2,4-benzodioxepin-3-yl)-2-thiazolyl]-1-[2-(2,5-dichlorophenyl)acetyl]piperidine,
4-[4-(6-methoxy-9-methyl-1,5-dihydro-3H-2,4-benzodioxepin-3-yl)-2-thiazolyl]-1-[2-(2,5-dimethylphenyl)acetyl]piperidine,
4-[4-(6-methoxy-9-methyl-1,5-dihydro-3H-2,4-benzodioxepin-3-yl)-2-thiazolyl]-1-[2-(2,5-dichlorophenyl)acetyl]piperidine,
4-[4-[6-(difluoromethoxy)-1,5-dihydro-3H-2,4-benzodioxepin-3-yl]-2-thiazolyl]-1-[2-(2,5-dimethylphenyl)acetyl]piperidine,
4-[4-[6-(difluoromethoxy)-1,5-dihydro-3H-2,4-benzodioxepin-3-yl]-2-thiazolyl]-1-[2-(2,5-dichlorophenyl)acetyl]piperidine,
4-[4-(7-methylsulfonyloxy-1,5-dihydro-3H-2,4-benzodioxepin-3-yl)-2-thiazolyl]-1-[2-(2,5-dichlorophenyl)acetyl]piperidine,
4-[4-(6-methoxy-1,5-dihydro-3H-2,4-benzodioxepin-3-yl)-2-thiazolyl]-1-[2-(2,5-dimethylphenyl)acetyl]piperidine,
4-[4-(6-methoxy-1,5-dihydro-3H-2,4-benzodioxepin-3-yl)-2-thiazolyl]-1-[2-(2,5-dichlorophenyl)acetyl]piperidine,
4-[4-(6-fluoro-9-methoxy-1,5-dihydro-3H-2,4-benzodioxepin-3-yl)-2-thiazolyl]-1-[2-(2,5-dimethylphenyl)acetyl]piperidine,
4-[4-[6,9-bis(methylsulfonyloxy)-1,5-dihydro-3H-2,4-benzodioxepin-3-yl]-2-thiazolyl]-1-[2-(2,5-dimethylphenyl)acetyl]piperidine, 4-[4-(6-methylsulfonyloxy-1,5-dihydro-3H-2,4-benzodioxepin-3-yl)-2-thiazolyl]-1-[2-(2,5-dimethylphenyl)acetyl]piperazine, 4-[4-(6-fluoro-9-methylsulfonyloxy-1,5-dihydro-3H-2,4-benzodioxepin-3-yl)-2-thiazolyl]-1-[N-(2,5-dimethylphenyl)-N-methylcarbamoyl]piperidine, 4-[4-(6-methylsulfonyloxy-1,5-dihydro-3H-2,4-benzodioxepin-3-yl)-2-thiazolyl]-1-[N-(2,5-dimethylphenyl)-N-methylcarbamoyl]piperidine, 4-[4-(6-fluoro-9-methylsulfonyloxy-1,5-dihydro-3H-2,4-benzodioxepin-3-yl)-2-thiazolyl]-1-[2-(2,5-dimethylphenyl)thioacetyl]piperidine, 4-[4-(6-fluoro-1,5-dihydro-3H-2,4-benzodioxepin-3-yl)-2-thiazolyl]-1-[2-[(1,1,1-trifluoroethane-2-ylideneamino)oxy]acetyl]piperidine, 4-[4-(6-fluoro-9-methylsulfonyloxy-1,5-dihydro-3H-2,4-benzodioxepin-3-yl)-2-thiazolyl]-1-[2-[(1,1,1-trifluoroethane-2-ylideneamino)oxy]acetyl]piperidine, 4-[4-(6,9-difluoro-1,5-dihydro-3H-2,4-benzodioxepin-3-yl)-2-thiazolyl]-1-[2-[(1,1,1-trifluoroethane-2-ylideneamino)oxy]acetyl]piperidine, 4-[4-(6-methoxy-9-methylsulfonyloxy-1,5-dihydro-3H-2,4-benzodioxepin-3-yl)-2-thiazolyl]-1-[2-[(1,1,1-trifluoroethane-2-ylideneamino)oxy]acetyl]piperidine, and 4-[4-(6-methylsulfonyloxy-1,5-dihydro-3H-2,4-benzodioxepin-3-yl)-2-thiazolyl]-1-[2-[(1,1,1-trifluoroethane-2-ylideneamino)oxy]acetyl]piperidine.

[12] A fungicidal composition comprising a compound or a salt thereof according to any of [1]-[11].

[13] A method of controlling plant disease generated from phytopathogenic microorganism comprising steps of applying the fungicidal composition of [12] to an entire plant or a part thereof or seeds of a plant.

[14] A method of producing a compound of formula [1a] comprising a step of reacting a thiazole derivative of formula [2] and a benzene derivative of formula [3] under a presence of an acid or Lewis acid and a solvent:

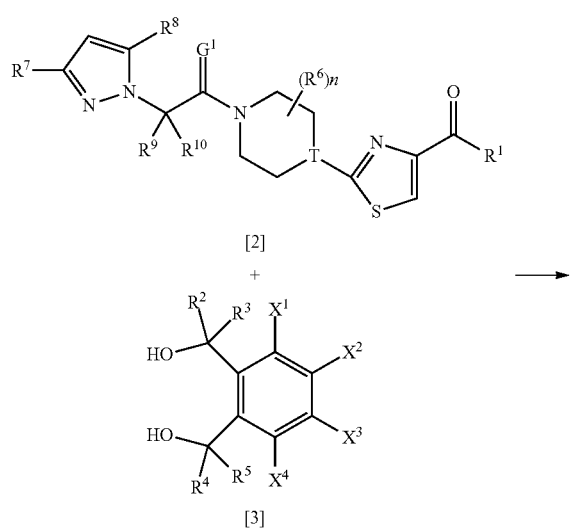

[Formula 3]

[2]

+

[3]

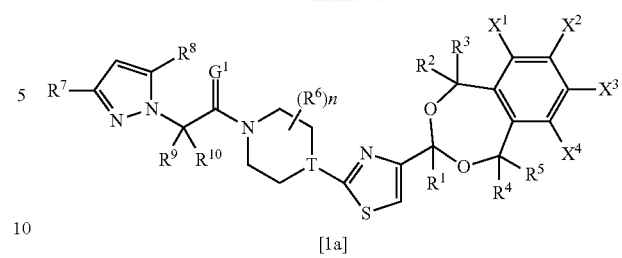

[1a]

wherein $R^1$, $R^2$, $R^3$, $R^4$, $R^5$, $R^6$, $R^7$, $R^8$, $R^9$, $R^{10}$, $G^1$, $X^1$, $X^2$, $X^3$, $X^4$, T and n are as defined in [1].

[15]

A method of producing a compound of formula [1b] comprising a step of reacting a thiazole derivative of formula [4] and a benzene derivative of formula [3] under a presence of an acid or Lewis acid and a solvent:

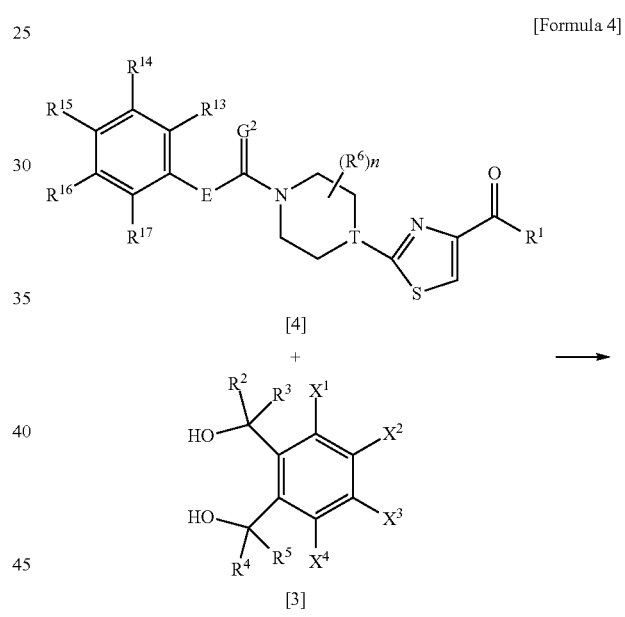

[Formula 4]

[4]

+

[3]

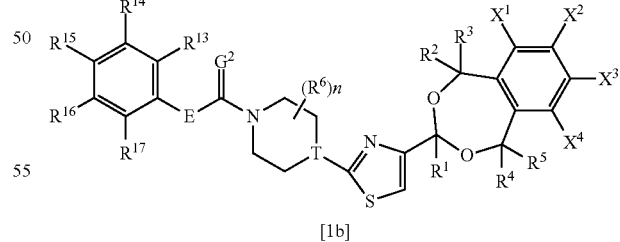

[1b]

wherein, $R^1$, $R^2$, $R^3$, $R^4$, $R^5$, $R^6$, $R^{13}$, $R^{14}$, $R^{15}$, $R^{16}$, $R^{17}$, E, $G^2$, $X^1$, $X^2$, $X^3$, $X^4$, T and n are as defined in [1].

[16] A method of producing a compound of formula [1c] comprising a step of reacting a thiazole derivative of formula [5] and a benzene derivative of formula [3] under a presence of an acid or Lewis acid and a solvent:

[Formula 5]

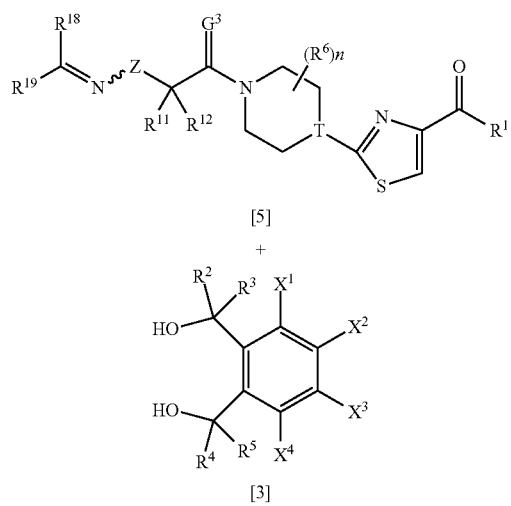

[5]

+

[3]

→

[1c]

wherein $R^1$, $R^2$, $R^3$, $R^4$, $R^5$, $R^6$, $R^{11}$, $R^{12}$, $R^{18}$, $R^{19}$, $G^3$, $X^1$, $X^2$, $X^3$, $X^4$, Z, T and n are as defined in [1].

[17]

A method of producing a compound of formula [1d] comprising a step of reacting a thiazole derivative of formula [6] and a benzene derivative of formula [3] under a presence of an acid or Lewis acid and a solvent:

[Formula 6]

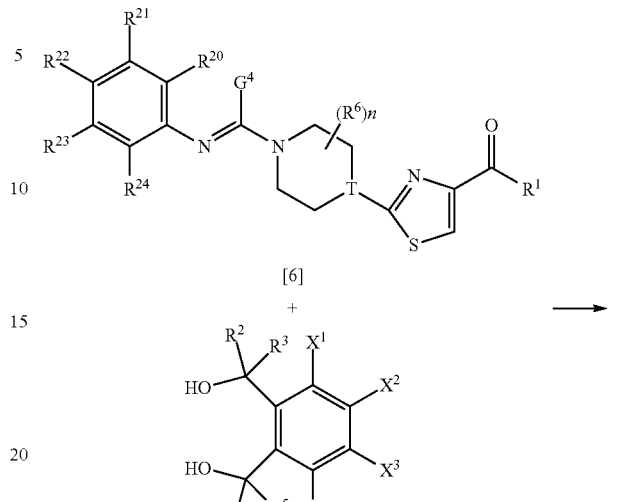

[6]

+

[3]

→

[1d]

wherein $R^1$, $R^2$, $R^3$, $R^4$, $R^5$, $R^6$, $R^{20}$, $R^{21}$, $R^{22}$, $R^{23}$, $R^{24}$, $G^4$, $X^1$, $X^2$, $X^3$, $X^4$, T and n are as defined in [1].

[18]

A method of producing a compound of formula [1a] comprising a step of reacting a piperidine derivative of formula [7] and a carboxylic acid derivative of formula [8] under a presence of a dehydration/condensation agent and a solvent (step 1) or a step of reacting a piperidine derivative of formula [7] and a carboxylic acid derivative of formula [9] under a presence of a base and a solvent (step 2):

[Chemical Formula 7]

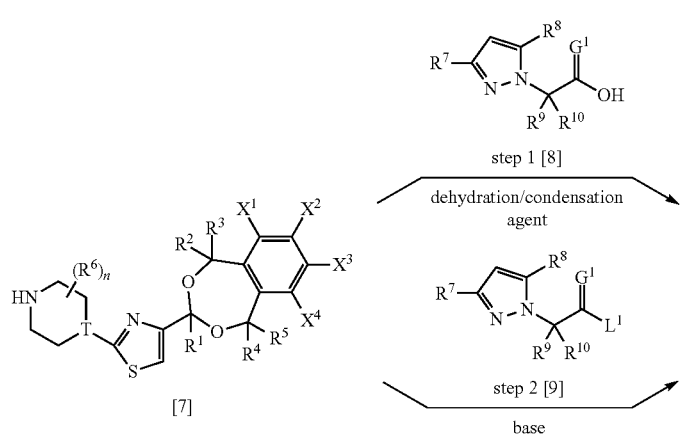

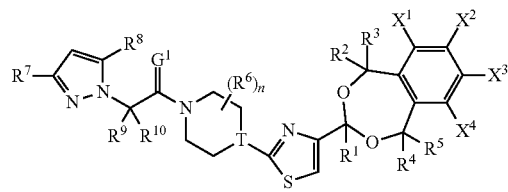

[1a]

wherein $R^1$, $R^2$, $R^3$, $R^4$, $R^5$, $R^6$, $R^7$, $R^8$, $R^9$, $R^{10}$, $G^1$, $X^1$, $X^2$, $X^3$, $X^4$, T and n are as defined in [1], and $L^1$ is a halogen such as a chlorine atom, or a bromine atom.

[19]

A method of producing a compound of formula [1b] comprising a step of reacting a piperidine derivative of formula [7] and a carboxylic acid derivative of formula [10] under a presence of a dehydration/condensation agent and a solvent (step 1), or a step of reacting a piperidine derivative of formula [7] and a carboxylic acid derivative of formula [11] under a presence of a base and a solvent (step 2):

[20]

A method of producing a compound of formula [1c] comprising a step of reacting a piperidine derivative of formula [7] and a carboxylic acid derivative of formula [12] under a presence of a dehydration/condensation agent and a solvent (step 1), or a step of reacting a piperidine derivative of formula [7] and a carboxylic acid derivative of formula [13] under a presence of a base and a solvent (step 2):

[Chemical Formula 8]

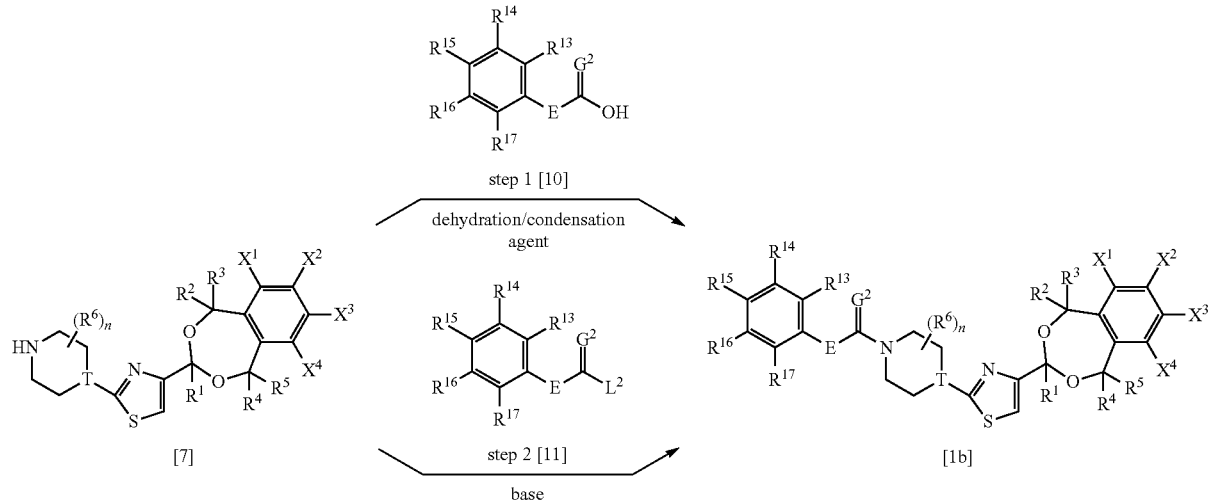

wherein $R^1$, $R^2$, $R^3$, $R^4$, $R^5$, $R^6$, $R^{13}$, $R^{14}$, $R^{15}$, $R^{16}$, $R^{17}$, E, $G^2$, $X^1$, $X^2$, $X^3$, $X^4$, T and n are as defined in [1], and $L^2$ is a halogen such as a chlorine atom, or a bromine atom.

[Formula 9]

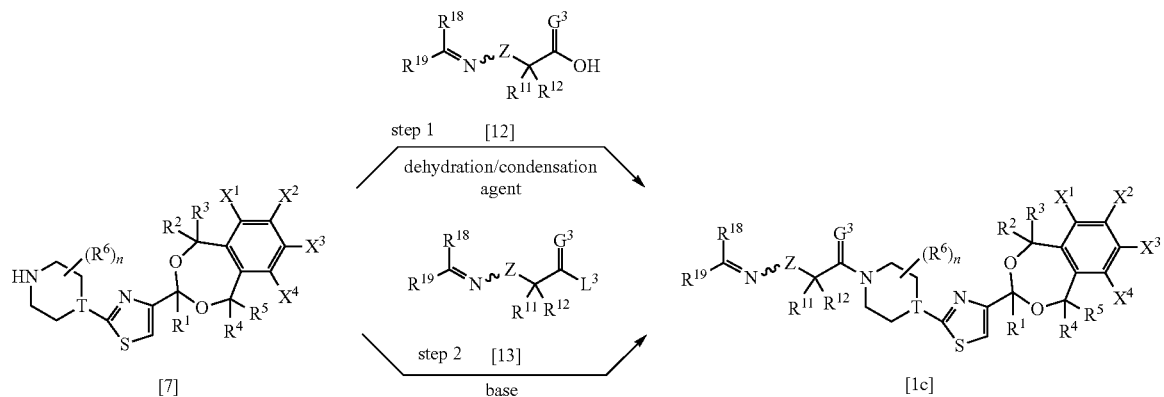

wherein $R^1, R^2, R^3, R^4, R^5, R^6, R^{11}, R^{12}, R^{18}, R^{19}, G^3, X^1, X^2, X^3, X^4$, Z, T and n are as defined in [1], and $L^3$ is a halogen such as a chlorine atom, or a bromine atom.

[21]

A method of producing a compound of formula [1d] comprising a step of reacting a substituted 11 membered compound of formula [14] and formula [15] under a presence of a base and a solvent:

[Formula 10]

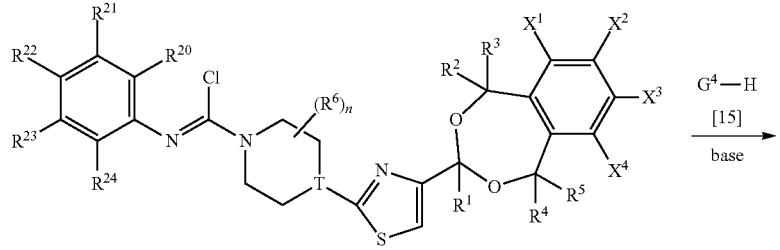

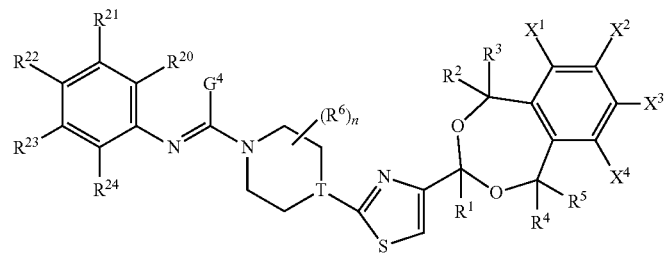

wherein $R^1, R^2, R^3, R^4, R^5, R^6, R^{20}, R^{21}, R^{22}, R^{23}, R^{24}, G^4, X^1, X^2, X^3, X^4$, T and n are as defined in [1].

[22]

A method of producing a compound of formula [1d] comprising a step of reacting a substituted 11 membered compound of formula [16] and formula [17] or formula [18] under a presence of a base and a solvent:

[Formula 11]

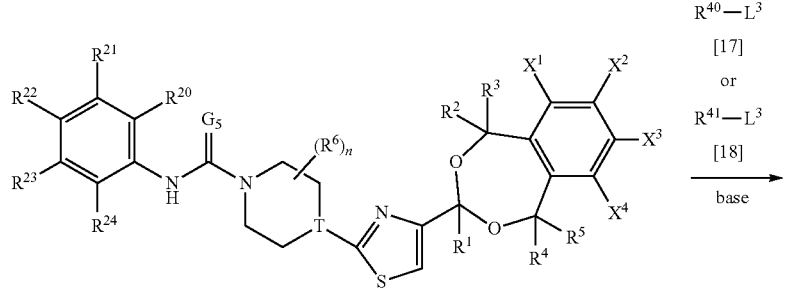

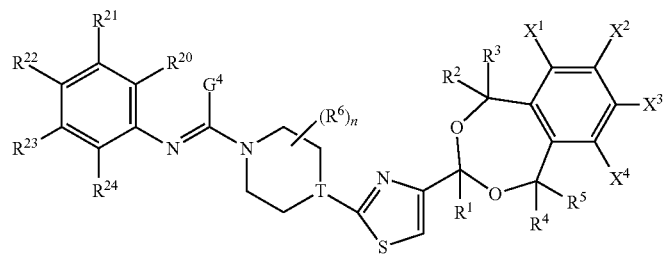

wherein $R^1$, $R^2$, $R^3$, $R^4$, $R^5$, $R^6$, $R^{20}$, $R^{21}$, $R^{22}$, $R^{23}$, $R^{24}$, $R^{40}$, $R^{41}$, $G^4$, $X^1$, $X^2$, $X^3$, $X^4$, T and n are as defined in 1, and $G^5$ is an oxygen atom or a sulfur atom, and $L^3$ is a leaving group.

[23] A compound or a salt thereof according to formula [3]:

[Formula 12]

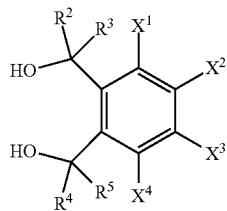

[3]

wherein, each of $R^2$, $R^3$, $R^4$ and $R^5$ is independently a hydrogen atom, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen, cyano or hydroxyl, or $R^2$ together with $R^3$ and $R^4$ together with $R^5$ are independently taken together with a carbon atom to which they are attached to form a carbonyl group (C=O);

each of $X^1$, $X^2$, $X^3$ and $X^4$ is independently a hydrogen atom, halogen, cyano, hydroxy, nitro, formyl, mercapto, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, carboxy, carbamoyl, $C_3$-$C_6$ cycloalkyl, $C_3$-$C_8$ halocycloalkyl, $C_3$-$C_6$ cycloalkoxy, $C_3$-$C_8$ halocycloalkoxy, $C_3$-$C_6$ alkynylalkoxy, $C_3$-$C_6$ haloalkynylalkoxy, $C_2$-$C_6$ alkoxyalkyl, $C_4$-$C_{10}$ cycloalkoxyalkyl, $C_2$-$C_6$ haloalkoxyalkyl, $C_4$-$C_{10}$ halocycloalkoxyalkyl, $C_3$-$C_8$ alkoxyalkoxyalkyl, $C_2$-$C_6$ alkoxyalkoxy, $C_4$-$C_{10}$ cycloalkylalkoxy, $C_1$-$C_6$ hydroxyalkyl, $C_4$-$C_{10}$ cycloalkylalkyl, $C_4$-$C_{10}$ alkylcycloalkyl, $C_6$-$C_{14}$ cycloalkylcycloalkyl, $C_4$-$C_{10}$ halocycloalkylalkyl, $C_6$-$C_{14}$ halocycloalkylcycloalkyl, $C_4$-$C_{10}$ haloalkylcycloalkyl, $C_5$-$C_{10}$ alkylcycloalkylalkyl, $C_3$-$C_8$ cycloalkenyl, $C_3$-$C_8$ halocycloalkenyl, $-SR^{25}$, $-S(O)R^{25}$, $-S(O)_2R^{25}$, $-OS(O)_2R^{25}$, $-(C_1$-$C_6$ alkyl)$S(O)_2R^{25}$, $C_2$-$C_6$ alkylthioalkyl, $C_2$-$C_6$ alkylsulfinylalkyl, $C_2$-$C_6$ alkylsulfonylalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ haloalkoxycarbonyl, $C_4$-$C_8$ cycloalkoxycarbonyl, $C_5$-$C_{10}$ cycloalkylalkoxycarbonyl, $C_2$-$C_6$ alkylcarbonyloxy, $C_2$-$C_6$ haloalkylcarbonyloxy, $C_4$-$C_8$ cycloalkylcarbonyloxy, $C_2$-$C_6$ alkoxycarbonyloxy, $C_2$-$C_6$ haloalkoxycarbonyloxy, $C_4$-$C_8$ cycloalkoxycarbonyloxy, $C_3$-$C_6$ alkylcarbonylalkoxy, $-NR^{26}R^{27}$, $C_2$-$C_6$ alkylaminoalkyl, $C_3$-$C_8$(dialkylamino)alkyl, $C_2$-$C_6$ haloalkylaminoalkyl, $C_4$-$C_{10}$ cycloalkylaminoalkyl, $C_1$-$C_6$ alkylsulfonylamino, $C_1$-$C_6$ haloalkylsulfonylamino, $C_2$-$C_6$ alkylaminocarbonyl, $C_3$-$C_{10}$(dialkylamino)carbonyl, $C_4$-$C_8$ cycloalkylaminocarbonyl, $C_2$-$C_8$ dialkylhydroxyamino, $C_2$-$C_8$(dialkylamino)hydroxy, $C_3$-$C_{10}$ trialkylhydrazinyl, $C_3$-$C_{10}$ trialkylsilyl, $C_4$-$C_{10}$ trialkylsilylalkyl, $C_5$-$C_{10}$ trialkylsilylalkynyl, $C_3$-$C_{10}$ trialkylsilyloxy, $C_4$-$C_{12}$ trialkylsilylalkyloxy, $C_5$-$C_{12}$ trialkylsilylalkoxyalkyl, $C_5$-$C_{12}$ trialkylsilylalkynyloxy, $C_2$-$C_6$ alkylsulfonyloxyalkyl, $C_2$-$C_6$ haloalkylsulfonyloxyalkyl, $-C(=NOR^{28})R^{29}$, $-C(=NR^{30})R^{29}$, $C_2$-$C_6$ cyanoalkyl, phenyl, phenoxy or benzyl, or $X^1$ together with $X^2$, $X^2$ together with $X^3$ and $X^3$ together with $X^4$ form a $C_2$-$C_6$ alkylene chain that may include an oxygen atom, a sulfur atom, a nitrogen atom, or they are taken together with a carbon atom to which they are attached to form a thiophene ring, a pyridine ring, a pyrrole ring, an imidazole ring, a benzene ring, a naphthalene ring, a pyrimidine ring, a furan ring, a pyrazine ring, a pyrazole ring or an oxazole ring;

$R^{25}$ is $C_1$-$C_8$ alkyl, $C_3$-$C_8$ cycloalkyl, $C_1$-$C_6$ haloalkyl, $C_3$-$C_8$ halocycloalkyl, $C_1$-$C_6$ alkylamino, phenyl or benzyl, and phenyl or benzyl may be substituted with at least one $R^{31}$;

$R^{31}$ is $C_1$-$C_6$ alkyl, $C_3$-$C_8$ cycloalkyl, $C_1$-$C_6$ haloalkyl, $C_1$-$C_6$ alkoxy, $C_1$-$C_6$ haloalkoxy, $C_3$-$C_8$ cycloalkoxy, $C_3$-$C_8$ halocycloalkyl, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, halogen, cyano or hydroxy;

each of $R^{26}$ and $R^{27}$ is independently a hydrogen atom, $C_1$-$C_6$ alkyl, $C_3$-$C_8$ cycloalkyl, $C_1$-$C_6$ haloalkyl, $C_3$-$C_8$ halocycloalkyl, $C_1$-$C_6$ alkoxy, $C_2$-$C_8$ dialkylamino, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ haloalkoxycarbonyl or $C_3$-$C_{10}$ (dialkylamino)carbonyl;

$R^{28}$ is a hydrogen atom, $C_1$-$C_6$ alkyl, $C_1$-$C_6$ haloalkyl or benzyl;

$R^{29}$ is a hydrogen atom, $C_1$-$C_6$ alkyl, $C_3$-$C_8$ cycloalkyl, $C_1$-$C_6$ haloalkyl, $C_3$-$C_8$ halocycloalkyl, $C_4$-$C_{10}$ cycloalkylalkyl, phenyl or benzyl;

$R^{30}$ is $C_1$-$C_6$ alkyl, $C_3$-$C_8$ cycloalkyl, $C_1$-$C_6$ haloalkyl, $C_3$-$C_8$ halocycloalkyl, $C_2$-$C_8$ dialkylamino, phenyl or benzyl;

[24] The compound or a salt thereof according to [23], wherein $R^2$ and $R^4$ are hydrogen atoms;

each of $R^3$ and $R^5$ is independently a hydrogen atom or methyl;

each of $X^1$, $X^2$, $X^3$ and $X^4$ is independently a hydrogen atom, halogen, cyano, hydroxy, nitro, formyl, mercapto, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_1$-$C_6$ hydroxyalkyl, $C_1$-$C_6$ alkoxy, $C_1$-$C_6$ haloalkoxy, carboxy, $C_3$-$C_6$ alkynylalkoxy, $C_2$-$C_6$ alkoxyalkyl, $-SR^{25}$, $-S(O)R^{25}$, $-S(O)_2R^{25}$, $-OS(O)_2R^{25}$, $C_2$-$C_6$ alkylthioalkyl, $C_2$-$C_6$ alkylcarbonyl, $C_2$-$C_6$ alkoxycarbonyl, $C_2$-$C_6$ alkylcarbonyloxy, $C_2$-$C_6$ alkoxycarbonyloxy, $-NR^{26}R^{27}$, $C_1$-$C_6$ alkylsulfonylamino, $C_2$-$C_6$ alkylaminoalkyl, $-C(=NOR^{28})R^{29}$, $C_2$-$C_6$ cyanoalkyl, phenyl, phenoxy or benzyl, or $X^1$ together with $X^2$, $X^2$ together with $X^3$ and $X^3$ together with $X^4$ form a $C_2$-$C_6$ alkylene chain that may contain an oxygen atom, or they are taken together with a carbon atom to which they are attached to form a benzene ring;

$R^{25}$ is $C_1$-$C_8$ alkyl, $C_3$-$C_6$ cycloalkyl, $C_1$-$C_6$ haloalkyl, or $C_1$-$C_6$ alkylamino;

each of $R^{26}$ and $R^{27}$ is independently a hydrogen atom, $C_1$-$C_6$ alkyl, $C_2$-$C_6$ alkylcarbonyl or $C_2$-$C_6$ alkoxycarbonyl;

each of $R^{28}$ and $R^{29}$ is independently a hydrogen atom or $C_1$-$C_6$ alkyl.

[25] The compound or a salt thereof according to [23] or [24], wherein $R^3$ and $R^5$ are hydrogen atoms;

each of $X^1$, $X^2$, $X^3$ and $X^4$ is independently a hydrogen atom, halogen, cyano, hydroxy, nitro, formyl, $C_1$-$C_4$ alkyl, $C_1$-$C_4$ haloalkyl, $C_1$-$C_4$ hydroxyalkyl, $C_1$-$C_4$ alkoxy, $C_1$-$C_4$ haloalkoxy, $-SR^{25}$, $-S(O)_2R^{25}$, $-OS(O)_2R^{25}$, $C_2$-$C_4$ alkylcarbonyloxy, $C_2$-$C_4$ alkoxycarbonyloxy, phenyl or $-C(=NOR^{28})R^{29}$;

$R^{25}$ is $C_1$-$C_4$ alkyl, cyclopropyl or $C_1$-$C_4$ haloalkyl;

each of $R^{28}$ and $R^{29}$ is independently a hydrogen atom or methyl.

[26] The compound or a salt thereof according to any of [23] to [25], wherein
each of $X^1$, $X^2$, $X^3$ and $X^4$ is independently a hydrogen atom, nitro, halogen, methyl, trifluoromethyl, methoxy, difluoromethoxy, trifluoromethoxy, methylsulfonyl, phenyl or $-OS(O)_2R^{25}$;

[27] The compound or a salt thereof according to any one of [23] to [26], wherein at least one of $X^1$, $X^2$, $X^3$, $X^4$ is $-OS(O)_2R^{25}$.

[28] The compound or a salt thereof according to any one of [23] to [27], wherein $X^1$ is methoxy, difluoromethoxy, or $-OS(O)_2R^{25}$;
$X^2$ is a hydrogen atom or $-OS(O)_2R^{25}$;
$X^3$ is a hydrogen atom or methyl; and
$X^4$ is a hydrogen atom, nitro, halogen, methyl, methoxy, difluoromethoxy, trifluoromethoxy, methylsulfonyloxy.

[29] A compound or a salt thereof according to any of [23] to [28] selected from
3-methylsulfonyloxy-1,2-benzenedimethanol,
3-ethylsulfonyloxy-1,2-benzenedimethanol,
3-fluoro-6-methylsulfonyloxy-1,2-benzenedimethanol,
4-methylsulfonyloxy-1,2-benzenedimethanol,
3-cyclopropylsulfonyloxy-1,2-benzenedimethanol,
3-methyl-6-methylsulfonyloxy-1,2-benzenedimethanol,
3-butylsulfonyloxy-1,2-benzenedimethanol,
3-propylsulfonyloxy-1,2-benzenedimethanol,
3-methoxy-6-methylsulfonyloxy-1,2-benzenedimethanol,
3-isopropylsulfonyloxy-1,2-benzenedimethanol,
4-ethylsulfonyloxy-1,2-benzenedimethanol,
3-(1,1,1-trifluoropropane-3-yl)sulfonyloxy-1,2-benzenedimethanol,
3-methylsulfonyloxy-6-nitro-1,2-benzenedimethanol,
4-fluoro-3-methylsulfonyloxy-1,2-benzenedimethanol,
3-methylsulfonyl-1,2-benzenedimethanol,
3-phenyl-1,2-benzenedimethanol,
3,4-dimethyl-6-methylsulfonyloxy-1,2-benzenedimethanol,
3-chloro-6-methylsulfonyloxy-1,2-benzenedimethanol,
3-bromo-6-methylsulfonyloxy-1,2-benzenedimethanol,
3-trifluoromethoxy-6-methoxy-1,2-benzenedimethanol,
3-difluoromethoxy-1,2-benzenedimethanol,
4-bromo-1,2-benzenedimethanol,
3-iodo-6-methylsulfonyloxy-1,2-benzenedimethanol,
3,6-bis(methylsulfonyloxy)-1,2-benzenedimethanol,
3-fluoro-6-methoxy-1,2-benzenedimethanol,
3-methoxy-6-methyl-1,2-benzenedimethanol, and
3-difluoromethoxy-6-methylsulfonyloxy-1,2-benzenedimethanol.

DESCRIPTION OF EMBODIMENTS

The present invention is described in detail below.

The above fused 11-membered compound of the present invention encompasses not just a fused 11-membered compound of formula [1], but also the salt, hydrate, solvate, substance of polymorphic crystalline forms, and an N-oxide of the fused 11-membered compound of formula [1]. The salt is not particularly limited, and examples of the salt include salts that are acceptable in agricultural chemical production, specifically, sodium salt, potassium salt, magnesium salt, calcium salt, aluminum salt, etc. In addition, all possible stereoisomers or enantiomers, and mixtures containing the two types of isomers at a given ratio are included in the scope of the present compound (fused 11-membered compound of formula [1]).

Formula [1] provides a general definition of the fused 11-membered compound that can be used in the present invention. Preferable definitions of the groups relating to the formula shown hereabove and hereunder are provided below. These definitions are applied to the final product shown by formula [1] and likewise to all intermediates.

A preferable embodiment is described below.

T is preferably CH.

$R^1$ is preferably a hydrogen atom.

$R^2$, $R^3$, $R^4$ and $R^5$ are preferably a hydrogen atom or methyl, and more preferably a hydrogen atom.

n is preferably 0 (that is, $R^6$ preferably does not exist).

Each of independent $X^1$, $X^2$, $X^3$ and $X^4$ is preferably a hydrogen atom, halogen, cyano, hydroxy, nitro, formyl, $C_1$-$C_4$ alkyl, $C_1$-$C_4$ haloalkyl, $C_1$-$C_4$ hydroxyalkyl, $C_1$-$C_4$ alkoxy, $C_1$-$C_4$ haloalkoxy, $-SR^{25}$, $-S(O)_2R^{25}$, $-OS(O)_2R^{25}$, $C_2$-$C_4$ alkylcarbonyloxy, $C_2$-$C_4$ alkoxycarbonyloxy, or $-C(=NOR^{28})R^{29}$, and more preferably at least one of $X^1$, $X^2$, $X^3$ and $X^4$ is $-OS(=O)_2R^{25}$, particularly preferably $X^1$ is $-OS(=O)_2R^{25}$, particularly preferably $X^2$ and $X^3$ are hydrogen atoms, particularly preferably $X^4$ is a hydrogen atom, nitro, halogen, methyl, methoxy, trifluoromethyl, difluoromethoxy, trifluoromethoxy or $-OS(O)_2R^{25}$, and most preferably $X^4$ is a hydrogen atom, nitro, methyl, a fluorine atom or methoxy.

$R^{25}$ is preferably $C_1$-$C_4$ alkyl, cyclopropyl or $C_1$-$C_4$ haloalkyl, and more preferably methyl.

$R^{28}$ is preferably a hydrogen atom or $C_1$-$C_4$ alkyl, and more preferably a hydrogen atom or methyl.

$R^{29}$ is preferably a hydrogen atom or $C_1$-$C_4$ alkyl, and more preferably a hydrogen atom or methyl.

A is preferably A-1 or A-2, and more preferably A-1.

Each of independent $R^7$ and $R^8$ is preferably $C_1$-$C_4$ alkyl or $C_1$-$C_4$ haloalkyl, and more preferably methyl, difluoromethyl or trifluoromethyl.

E is preferably $-CR^{32}R^{33}-$.

$R^9$, $R^{10}$, $R^{11}$, $R^{12}$, $R^{32}$ and $R^{33}$ are preferably hydrogen atoms.

$G^1$, $G^2$ and $G^3$ are preferably oxygen atoms.

Each of independent $R^{13}$, $R^{16}$, $R^{20}$ and $R^{23}$ is preferably a hydrogen atom, halogen, $C_1$-$C_4$ alkyl or $C_1$-$C_4$ haloalkyl, and more preferably a hydrogen atom, methyl, trifluoromethyl or a chlorine atom.

$R^{14}$, $R^{15}$, $R^{17}$, $R^{21}$, $R^{22}$ and $R^{24}$ are preferably hydrogen atoms.

Each of independent $R^{18}$ and $R^{19}$ is preferably a hydrogen atom, $C_1$-$C_4$ alkyl or $C_1$-$C_4$ haloalkyl, and more preferably a hydrogen atom, methyl or trifluoromethyl.

Z is preferably an oxygen atom.

$G^4$ is preferably $-OR^{40}$.

$R^{40}$ is preferably $C_1$-$C_4$ alkyl, and more preferably methyl.

The definitions and explanations of groups shown above may be combined as necessary in a general range or preferable range. In other words, each of the ranges can be combined with preferable ranges. Those ranges are applied to both the final product and the corresponding precursors and intermediates.

A preferable compound is a compound shown by formula [1] {wherein A is 2-[5-methyl-3-(trifluoromethyl)-1H-pyrazole-1-yl]acetyl}.

An additional preferable compound is a compound shown by formula [1] {wherein A is 2-[3,5-bis(trifluoromethyl)-1H-pyrazole-1-yl]acetyl}.

An additional preferable compound is a compound shown by formula [1] {wherein A is 2-[3,5-bis(difluoromethyl)-1H-pyrazole-1-yl]acetyl}.

An additional preferable compound is a compound shown by formula [1] {wherein A is 2-(3,5-dimethyl-1H-pyrazole-1-yl)acetyl}.

An additional preferable compound is a compound shown by formula [1] {wherein A is 2-(2,5-dimethylphenyl)acetyl}.

An additional preferable compound is a compound shown by formula [1] {wherein A is 2-(2,5-difluorophenyl)acetyl}.

An additional preferable compound is a compound shown by formula [1] {wherein A is 2-(2,5-dichlorophenyl)acetyl}.

An additional preferable compound is a compound shown by formula [1] {wherein A is 2-(2,5-dibromopheny)acetyl}.

An additional preferable compound is a compound shown by formula [1] {wherein A is 2-[2,5-bis(trifluoromethyl)phenyl]acetyl}.

An additional preferable compound is a compound shown by formula [1] {wherein A is 2-(5-bromo-2-methylphenyl)acetyl}.

An additional preferable compound is a compound shown by formula [1] {wherein A is 2-[2-methyl-5-(trifluoromethyl)phenyl]acetyl}.

An additional preferable compound is a compound shown by formula [1] {wherein A is 2-[2-fluoro-5-(trifluoromethyl)phenyl]acetyl}.

An additional preferable compound is a compound shown by formula [1] {wherein A is 2-[2-chloro-5-(trifluoromethyl)phenyl]acetyl}.

An additional preferable compound is a compound shown by formula [1] {wherein A is 2-[2-bromo-5-(trifluoromethyl)phenyl]acetyl}.

An additional preferable compound is a compound shown by formula [1] {wherein A is 2-[(propane-2-ylideneamino)oxy]acetyl}.

An additional preferable compound is a compound shown by formula [1] {wherein A is 2-[(1,1,1-trifluoropropane-2-ylideneamino)oxy]acetyl}.

An additional preferable compound is a compound shown by formula [1] {wherein A is 2-[(ethylideneamino)oxy]acetyl}.

An additional preferable compound is a compound shown by formula [1] {wherein A is 2-[(1,1,1-trifluoroethane-2-ylideneamino)oxy]acetyl}.

An additional preferable compound is a compound shown by formula [1] {wherein A is (Z)-[(2,5-dimethylphenyl)imino](methoxy)methyl}.

An additional preferable compound is a compound shown by formula [1] {wherein A is (Z)-[[2,5-bis(trifluoromethyl)phenyl]imino](methoxy)methyl}.

An additional preferable compound is a compound shown by formula [1] {wherein A is (Z)-[(2,5-chlorophenyl)imino](methoxy)methyl}.

An additional preferable compound is a compound shown by formula [1] {wherein A is (Z)-[[2-chloro-5-(trifluoromethyl)phenyl]imino](methoxy)methyl}.

An additional preferable compound is a compound shown by formula [1] {wherein at least one of $X^1$, $X^2$, $X^3$ and $X^4$ is methylsulfonyloxy}.

An additional preferable compound is a compound shown by formula [1] {wherein $X^1$ is methylsulfonyloxy, and $X^2$, $X^3$ and $X^4$ are hydrogen atoms}.

An additional preferable compound is a compound shown by formula [1] {wherein $X^1$ is methylsulfonyloxy, and $X^2$ and $X^3$ are hydrogen atoms, $X^4$ is a fluorine atom}.

An additional preferable compound is a compound shown by formula [1] {wherein $X^1$ is methylsulfonyloxy, and $X^2$ and $X^3$ are hydrogen atoms, and $X^4$ is methoxy}.

An additional preferable compound is a compound shown by formula [1] {wherein $X^1$ is methylsulfonyloxy, and $X^2$ and $X^3$ are hydrogen atoms, and $X^4$ is cyano}.

The terms used in the present specification are explained below.

Halogen encompasses fluorine, chlorine, bromine or iodine.

The notation of a symbol of an element and a subscript number like $C_1$-$C_6$ indicates that the number of elements in the group following the notation is within a range shown by the subscript number. For example, in this case, it can be seen that the number of carbon is 1-6, and a notation of $C_2$-$C_6$ shows that the number of carbon is 2-6.

A notation of a composite substituent following the notation of a symbol of an element and a subscript number like $C_1$-$C_6$ indicates that the number of elements in the the entire composite substituent is within a range shown by the subscript number. For example, concerning $C_4$-$C_8$ cycloalkylcarbonyloxy, it can be seen that the number of carbon in the entire cycloalkylcarbonyloxy is 4-8, and such compound includes a cyclopropylcarbonyl group, etc. Further, concerning $C_2$-$C_8$ cyanoalkyl, it can be seen that the number of carbon in the entire cyanoalkyl is 2-8. $C_2$-$C_8$ cyanoalkyl may include 1 or multiple cyano groups, and such compound includes a cyanomethyl.

An alkyl is a straight chain or branched chain alkyl having 1-8 carbons, preferably 1-6 carbons, unless limited otherwise, and examples include methyl, ethyl, n-propyl, isobutyl, n-butyl, sec-butyl, isobutyl, tert-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl, 1-ethyl-2-methylpropyl. The definition is applied to alkyls that form a part of a composite substituent, such as haloalkyl, alkylthio, alkylcarbonyl, alkylsulfonyloxy, unless otherwise defined. For example, in a composite substituent that includes an alkyl at the terminal, such as alkylcycloalkyl, that specific portion of cycloalkyl may be independently mono-substituted or poly-substituted by a same or different alkyl. The same is true of a composite substituent having other groups, such as alkenyl, alkoxy, hydroxy, halogen, at its terminal.

Cycloalkyl is a cycloalkyl having a branched chain with 3-8 carbons, preferably 3-6 carbons, unless limited otherwise. Examples include groups such as cyclopropyl, 1-methylcyclopropyl, 2-methylcyclopropyl, cyclobutyl, cyclopentyl, cyclohexyl, 4,4-dimethylcyclohexyl. The definition is applied to cycloalkyls that form a part of a composite substituent, such as halocycloalkyl, for example, unless otherwise defined.

Cycloalkenyl is a cycloalkenyl having a branched chain with 3-8 carbons, preferably 3-6 carbons, unless limited otherwise. Examples include groups of cyclopropenyl, 1-methylcyclopropenyl, cyclobutenyl, cyclopentenyl, cyclohexenyl. The definition is applied to cycloalkenyls that form a part of a composite substituent, such as halocycloalkenyl, for example, unless otherwise defined.

Cycloalkoxy is a cycloalkyl having a branched chain with 3-8 carbons, preferably 3-6 carbons, unless limited otherwise. Examples include groups of cyclopropyloxy, 1-methylcyclopropyloxy, cyclobutyloxy, cyclopentyloxy, cyclohexyloxy. The definition is applied to cycloalkoxys that form a part of a composite substituent, such as halocycloalkoxy, for example, unless otherwise defined.

The word "halo" in "halo-" (e.g., "haloalkyl") encompasses fluorine, chlorine, bromine and iodine. The halo-substitution shown by the prefix "halo" encompasses mono-substitution or poly-substitution, and preferably mono-substitution, di-substitution and tri-substitution.

Haloalkyl is straight chain or branched chain alkyl with 1-6 carbons, wherein hydrogen atoms in the group are partially or entirely substituted with at least one halogen atom, unless limited otherwise. Examples include groups of fluoromethyl, chloromethyl, bromomethyl, iodomethyl, difluoromethyl, dichloromethyl, dibromomethyl, diiodomethyl, trifluoromethyl, trichloromethyl, tribromomethyl, triiodomethyl, 1-chloroethyl, 1-bromoethyl, 2-trifluoroethyl, 3-chloropropyl, 3-bromopropyl, 4-chlorobutyl, 4-bromobutyl, 4-trifluorobutyl, 5-chloropentyl, 6-chlorohexyl. The definition is applied to haloalkyls that form a part of a composite substituent, such as haloalkylcarbonyl, for example, unless otherwise defined.

Alkenyl is a straight chain or branched chain alkenyl with 2-6 carbons, unless limited otherwise. Examples include groups such as vinyl, 1-propenyl, 2-propenyl, isopropenyl, 3-butenyl, 1,3-butadienyl, 4-pentenyl, 5-hexenyl. The definition is applied to alkenyls that form a part of a composite substituent, such as haloalkenyl, for example, unless otherwise defined.

Alkynyl is a straight chain or branched chain alkynyl with 2-6 carbons, unless limited otherwise. Examples include groups of ethynyl, 1-propynyl, 2-propynyl, 3-butynyl, 1-methyl-3-propynyl, 4-pentynyl, 5-hexynyl. The definition is applied to alkynyls that form a part of a composite substituent, such as haloalkynyl, for example, unless otherwise defined.

Alkoxy is a straight chain or branched chain alkoxy with 1-6 carbons, unless limited otherwise. Examples include groups of methoxy, ethoxy, propoxy, isopropoxy, butoxy, isobutoxy, sec-butoxy, tert-butoxy, pentyloxy, hexyloxy. The definition is applied to alkoxy that form a part of a composite substituent, such as haloalkoxy, alkoxycarbonyl, for example, unless otherwise defined.

Haloalkoxy is a straight chain or branched chain alkoxy with 1-6 carbons, which is substituted with 1 or more, preferably 1-10 halogen atoms, unless limited otherwise. Examples include groups such as fluoromethoxy, chloromethoxy, bromomethoxy, iodomethoxy, difluoromethoxy, dichloromethoxy, dibromomethoxy, diiodomethoxy, trifluoromethoxy, trichloromethoxy, tribromomethoxy, triiodomethoxy, 1-chloroethoxy, 1-bromoethoxy, 2-trifluoroethoxy, 3-chloropropoxy, 3-bromopropoxy, 4-chlorobutoxy, 4-bromobutoxy, 4-trifluorobutoxy, 5-chloropentoxy, 6-chlorohexyloxy. The definition is applied to haloalkoxy that form a part of a composite substituent, such as haloalkoxycarbonyl, for example, unless otherwise defined.

Alkylthio is an (alkyl)-S— group with 1-6 carbons, in which the alkyl section is as defined above, unless limited otherwise. Examples include groups such as methylthio, ethylthio, n-propylthio, isopropylthio. The definition is applied to alkylthio that form a part of a composite substituent, such as haloalkylthio, for example, unless otherwise defined.

Alkylsulfinyl is an (alkyl)-SO— group with 1-6 carbons, in which the alkyl section is as defined above, unless limited otherwise. Examples include groups such as methylsulfinyl, ethylsulfinyl, n-propylsulfinyl, isopropylsulfinyl. The definition is applied to alkylsulfinyl that form a part of a composite substituent, such as haloalkylsulfinyl, for example, unless otherwise defined.

Alkylsulfonyl is an (alkyl)-$SO_2$— group with 1-6 carbons, in which the alkyl section is as defined above, unless limited otherwise. Examples include groups of methylsulfonyl, ethylsulfonyl, n-propylsulfonyl, isopropylsulfonyl. The definition is applied to alkylsulfonyl that form a part of a composite substituent, such as haloalkylsulfonyl, for example, unless otherwise defined.

Hydroxyalkyl is a straight chain or branched chain alkyl group with 1-6 carbons, which is substituted with 1-5 hydroxy groups, unless limited otherwise. Examples include hydroxymethyl, hydroxyethyl, hydroxypropyl or hydroxyisopropyl.

Alkylsulfonyloxy is an (alkyl)-$S(O)_2O$— group with 1-6 carbons, in which the alkyl section is as defined above, unless limited otherwise. Examples include groups such as methylsulfonyloxy, ethylsulfonyloxy, n-propylsulfonyloxy, isopropylsulfonyloxy. The definition is applied to alkylsulfonyloxy that form a part of a composite substituent, such as haloalkylsulfonyloxy, for example, unless otherwise defined.

Alkylcarbonyl is an (alkyl)-C(=O)— group, in which the alkyl section is as defined above, unless limited otherwise. Examples include groups of formyl, acetyl, propionyl, butyryl, pivaloyl. The definition is applied to haloalkylcarbonyl that form a part of a composite substituent, such as haloalkylcarbonyl, for example, unless otherwise defined.

Alkylcarbonyloxy is an (alkyl)-C(=O)O— group, in which the alkyl section is as defined above, unless limited otherwise. Examples include groups of methylcarbonyloxy, ethylcarbonyloxy, propylcarbonyloxy. The definition is applied to haloalkylcarbonyloxy that form a part of a composite substituent, such as haloalkylcarbonyloxy, for example, unless otherwise defined.

The acid used in the reaction of the present invention includes, unless otherwise mentioned, a Bronsted acid that releases protons in the reaction system, and examples include inorganic acids such as hydrochloric acid, hydrobromic acid, and sulfuric acid, and organic acids such as acetic acid, trifluoroacetic acid, para-toluenesulfonic acid, trifluoromethanesulfonic acid. The Lewis acid used in the reaction of the present invention is a compound functioning as an electron pair receptor in the reaction system other than a hydrogen ion, and examples include zinc chloride, aluminum chloride, tin chloride, boron trichloride, boron trifluoride, trimethylsilyl trifluoromethanesulfonate.

The following notations in the tables of the present specification indicate the corresponding groups shown below.

For example,
Me shows a methyl group,
Et shows an ethyl group,
n-Pr shows an n-propyl group,
i-Pr shows an isopropyl group,
c-Pr shows a cyclopropyl group,
n-Bu shows an n-butyl group,
i-Bu shows an isobutyl group,
t-Bu shows a tert-butyl group,
n-Hex shows an n-hexyl group,
Ph shows a phenyl group,
Bn shows a benzyl group.

Typical production methods of the compound of the present invention represented by formula [1] is shown below as an example, but the present invention is not limited to these methods.

<Production Method 1>

The compound of the present invention represented by formula [1a] (which is formula [1] with A limited to A-1) may be produced by a method consisting of the reaction formulas exemplified below.

[Formula 13]

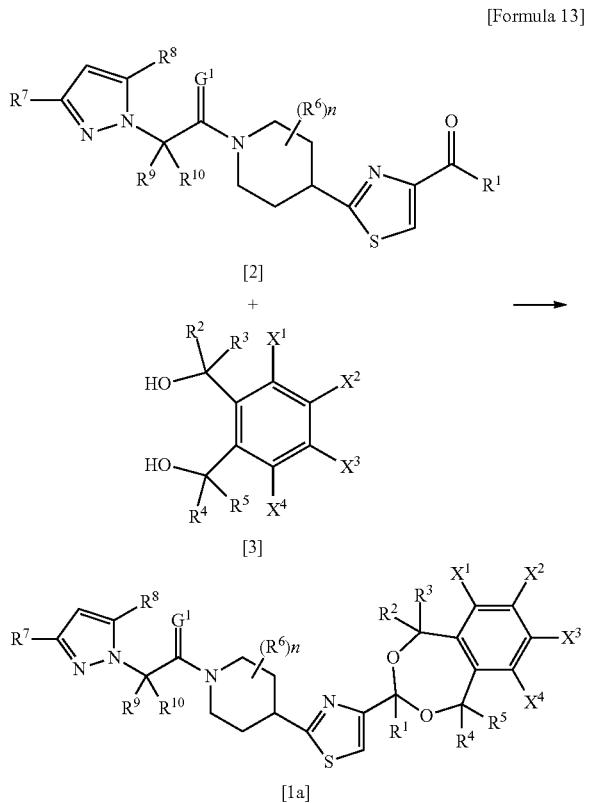

(wherein each of $R^1$, $R^2$, $R^3$, $R^4$, $R^5$, $R^6$, $R^7$, $R^8$, $R^9$, $R^{10}$, $G^1$, $X^1$, $X^2$, $X^3$, $X^4$, T and n is as shown in [1]).

A compound of formula [2] and a compound of formula [3] may be reacted under a presence of an acid or Lewis acid, preferably under a presence of acid, in a solvent to produce a compound of formula [1a] of the present invention.

The amount of compound of formula [3] to be used may be selected as necessary from a range of 1.0-10 mol against 1 mol of a compound of formula [2], and it is preferably 1.0-3.0 mol.

The following acids can be used in this step: inorganic acids such as hydrochloric acid, hydrobromic acid, sulfuric acid, etc. and organic acids such as acetic acid, trifluoroacetic acid, p-toluenesulfonic acid, trifluoromethanesulfonic acid, etc.

The following Lewis acids can be used in this step: zinc chloride, aluminum chloride, tin chloride, boron trichloride, boron trifluoride, trimethylsilyl-trifluoromethanesulfonate, etc.

The amount of acid or Lewis acid to be used may be selected as necessary from a range of 0.01-5 mol against 1 mol of a compound of formula [2], and it is preferably 0.1-1.0 mol.

Any solvent can be used in this step, as long as it does not inhibit the progress of this reaction, and examples include the following: nitriles such as acetonitrile; ethers such as diethyl ether, diisopropyl ether, tetrahydrofuran, dioxane, monoglyme, diglyme; halogenated hydrocarbons such as dichloromethane, dichloroethane, chloroform, carbon tetrachloride, tetrachloroethane; aromatic hydrocarbons such as benzene, chlorobenzene, nitrobenzene, toluene; amides such as N,N-dimethylformamide, N,N-dimethylacetamide; imidazolidinones such as 1,3-dimethyl-2-imidazolidinone; sulfur compounds such as dimethyl sulfoxide; a mixed solvent thereof.

The amount of solvent to be used may be selected as necessary from a range of 0.01-100 L against 1 mol of a compound of formula [2], and it is preferably 0.1-10 L.

The reaction temperature may be selected from −20° C. to the boiling point range of the inactive solvent to be used, and it is preferably 0° C. to 150° C.

The reaction time differs by the reaction temperature, reaction substrate, the reaction amount, etc., but it is normally 10 min. to 48 h.

The compound of formula [1a], which is the reaction target, is collected from the reaction system by a common method after the reaction has completed, and it can be purified by operations such as column chromatography, and recrystallization as necessary.

<Production Method 2>

The compound of the present invention represented by formula [1b] (which is formula [1] with A limited to A-2) may be produced by a method consisting of the reaction formulas exemplified below.

[Formula 14]

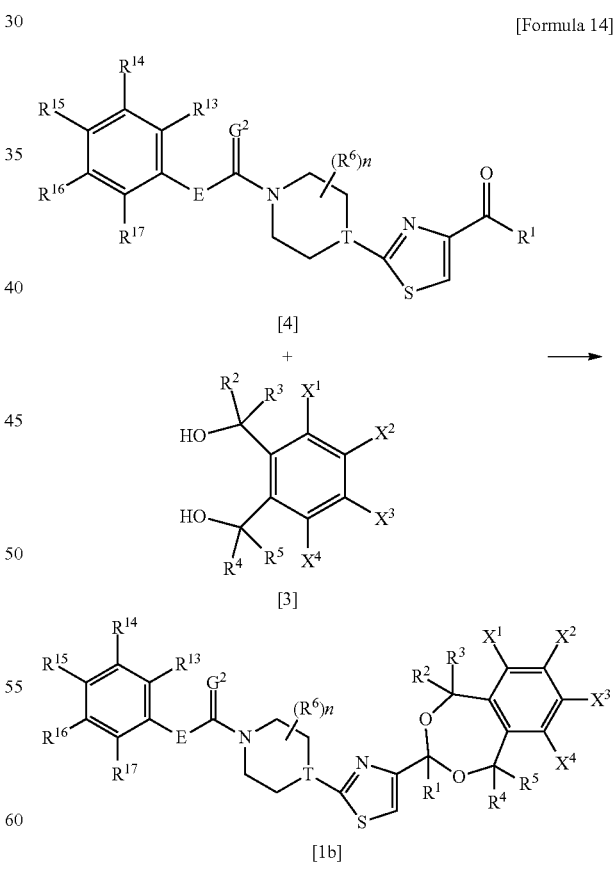

(wherein each of $R^1$, $R^2$, $R^3$, $R^4$, $R^5$, $R^6$, $R^{13}$, $R^{14}$, $R^{15}$, $R^{16}$, $R^{17}$, E, $G^2$, $X^1$, $X^2$, $X^3$, $X^4$, T and n is as defined in [1]).

A compound of formula [4] and a compound of formula [3] may be reacted under a presence of an acid or Lewis acid, preferably under a presence of acid, in a solvent to produce a compound of formula [1b] of the present invention.

The amount of compound of formula [3] to be used may be selected as necessary from a range of 1.0-10 mol against 1 mol of a compound of formula [4], and it is preferably 1.0-3.0 mol.

Acids, Lewis acids and solvents that can be used in this step are the same as those described in Production Method 1.

The amount of acid or Lewis acid to be used may be selected as necessary from a range of 0.01-5 mol against 1 mol of a compound of formula [4], and it is preferably 0.1-1.0 mol.

The amount of solvent to be used may be selected as necessary from a range of 0.01-100 L against 1 mol of a compound of formula [4], and it is preferably 0.1-10 L.

The reaction temperature may be selected from −20° C. to the boiling point range of the inactive solvent to be used, and it is preferably 0° C. to 150° C.

The reaction time differs by the reaction temperature, reaction substrate, the reaction amount, etc., but it is normally 10 min. to 48 h.

The compound of formula [1b], which is the reaction target, is collected from the reaction system by a common method after the reaction has completed, and it can be purified by operations such as column chromatography, and recrystallization as necessary.

<Production Method 3>

The compound of the present invention represented by formula [1c] (which is formula [1] with A limited to A-3) may be produced by a method consisting of the reaction formulas exemplified below.

A compound of formula [5] and a compound of formula [3] may be reacted under a presence of an acid or Lewis acid, preferably under a presence of acid, in a solvent to produce a compound of formula [1c] of the present invention.

The amount of compound of formula [3] to be used may be selected as necessary from a range of 1.0-10 mol against 1 mol of a compound of formula [5], and it is preferably 1.0-3.0 mol.

Acids, Lewis acids and solvents that can be used in this step are the same as those described in Production Method 1.

The amount of acid or Lewis acid to be used may be selected as necessary from a range of 0.01-5 mol against 1 mol of a compound of formula [5], and it is preferably 0.1-1.0 mol.

The amount of solvent to be used may be selected as necessary from a range of 0.01-100 L against 1 mol of a compound of formula [5], and it is preferably 0.1-10 L.

The reaction temperature may be selected from −20° C. to the boiling point range of the inactive solvent to be used, and it is preferably 0° C. to 150° C.

The reaction time differs by the reaction temperature, reaction substrate, the reaction amount, etc., but it is normally 10 min. to 48 h.

The compound of formula [1c], which is the reaction target, is collected from the reaction system by a common method after the reaction has completed, and it can be purified by operations such as column chromatography, and recrystallization as necessary.

<Production Method 4>

The compound of the present invention represented by formula [1d] (which is formula [1] with A limited to A-4) may be produced by a method consisting of the reaction formulas exemplified below.

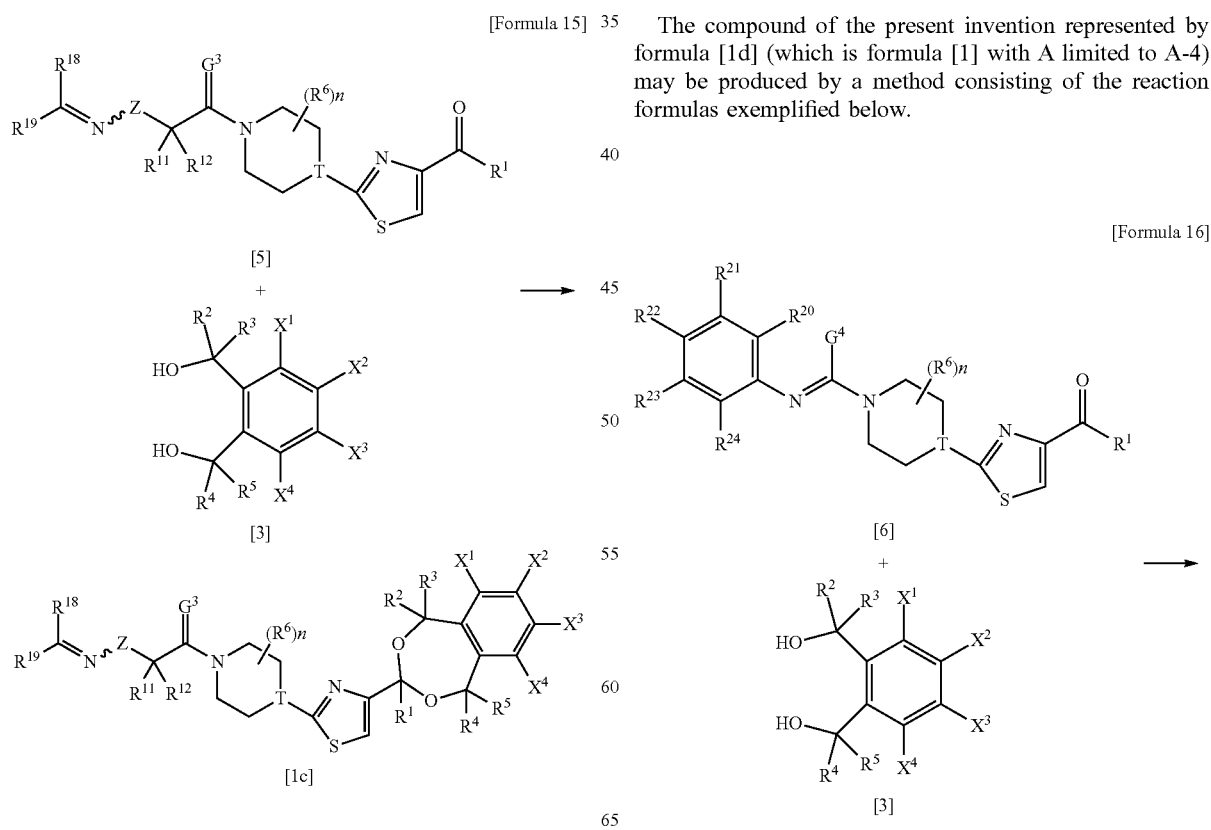

[Formula 15]

[Formula 16]

(wherein each of $R^1$, $R^2$, $R^3$, $R^4$, $R^5$, $R^6$, $R^{11}$, $R^{12}$, $R^{18}$, $R^{19}$, $G^3$, $X^1$, $X^2$, $X^3$, $X^4$, Z, T and n is as defined in [1]).

-continued

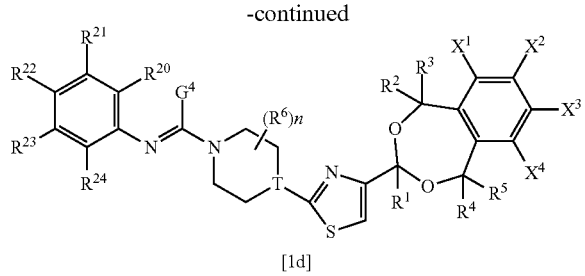

[1d]

(wherein each of $R^1$, $R^2$, $R^3$, $R^4$, $R^5$, $R^6$, $R^{20}$, $R^{21}$, $R^{22}$, $R^{23}$, $R^{24}$, $G^4$, $X^1$, $X^2$, $X^3$, $X^4$, T and n is as defined in [1]).

A compound of formula [6] and a compound of formula [3] may be reacted under a presence of an acid or Lewis acid, preferably under a presence of acid, in a solvent to produce a compound of formula [1d] of the present invention.

The amount of compound of formula [3] to be used may be selected as necessary from a range of 1.0-10 mol against 1 mol of a compound of formula [6], and it is preferably 1.0-3.0 mol.

Acids, Lewis acids and solvents that can be used in this step are the same as those described in Production Method 1.

The amount of acid or Lewis acid to be used may be selected as necessary from a range of 0.01-5 mol against 1 mol of a compound of formula [6], and it is preferably 0.1-1.0 mol.

The amount of solvent to be used may be selected as necessary from a range of 0.01-100 L against 1 mol of a compound of formula [6], and it is preferably 0.1-10 L.

The reaction temperature may be selected from −20° C. to the boiling point range of the inactive solvent to be used, and it is preferably 0° C. to 150° C.

The reaction time differs by the reaction temperature, reaction substrate, the reaction amount, etc., but it is normally 10 min. to 48 h.

The compound of formula [1d], which is the reaction target, is collected from the reaction system by a common method after the reaction has completed, and it can be purified by operations such as column chromatography, and recrystallization as necessary.

<Production Method 5>

The compound of the present invention represented by formula [1a] may be produced by a method consisting of the reaction formulas exemplified below.

(wherein each of $R^1$, $R^2$, $R^3$, $R^4$, $R^5$, $R^6$, $R^7$, $R^8$, $R^9$, $R^{10}$, $G^1$, $X^1$, $X^2$, $X^3$, $X^4$, T and n is as defined in [1], and $L^1$ is halogen such as a chlorine atom or a bromine atom).

(Step 1)

The compound of formula [1a] can also be produced by reacting a compound of formula [7] and a compound of formula [8] under a presence/absence of base, and under a presence of dehydration/condensation agent in a solvent.

The amount of compound of formula [8] to be used in this step may be selected as necessary from a range of 0.50-10 mol against 1 mol of a compound of formula [7], and it is preferably 1.0-1.2 mol.

The following dehydration/condensation agents can be used in this step: dicyclohexylcarbodiimide (DCC), N-(3-dimethylaminopropyl)-N'-ethylcarbodiimide (EDC or WSC), N,N-carbonyldiimidazole, 2-chloro-1,3-dimethyl-imidazolium chloride, 2-chloro-1-pyridinium iodide.

The amount of dehydration/condensation agent to be used in this reaction may be selected as necessary from a range of 1.0-10 mol against 1 mol of a compound of formula [7], and it is preferably 1.0-3.0 mol.

Examples of base that can be used in this sep are as follows: organic amines such as triethylamine, pyridine, 4-dimethylaminopyridine, N,N-dimethylaniline, 1,8-diazabicyclo[5,4,0]-7-undecene; metal carbonate salts such as sodium carbonate, potassium carbonate, magnesium carbonate, calcium carbonate; metal hydrogen carbonates such as sodium hydrogen carbonate, potassium hydrogen carbonate; metal carboxylic acid salts represented by metal acetate salts such as sodium acetate, potassium acetate, calcium acetate, magnesium acetate; metal alkoxides such as sodium methoxide, sodium ethoxide, sodium tert-butoxide, potassium methoxide, potassium tert-butoxide; metal hydroxides such as sodium hydroxide, potassium hydroxide, calcium hydroxide, magnesium hydroxide; metal hydrides such as lithium hydride, sodium hydride, calcium hydride.

The amount of base to be used in this reaction may be selected as necessary from a range of 0-100 mol against 1 mol of a compound of formula [7], and it is preferably 0-10 mol.

Solvents that can be used in this step are the same as those described in Production Method 1.

The amount of solvent to be used may be selected as necessary from a range of 0.01-100 L against 1 mol of a compound of formula [7], and it is preferably 0.1-10 L.

[Formula 17]

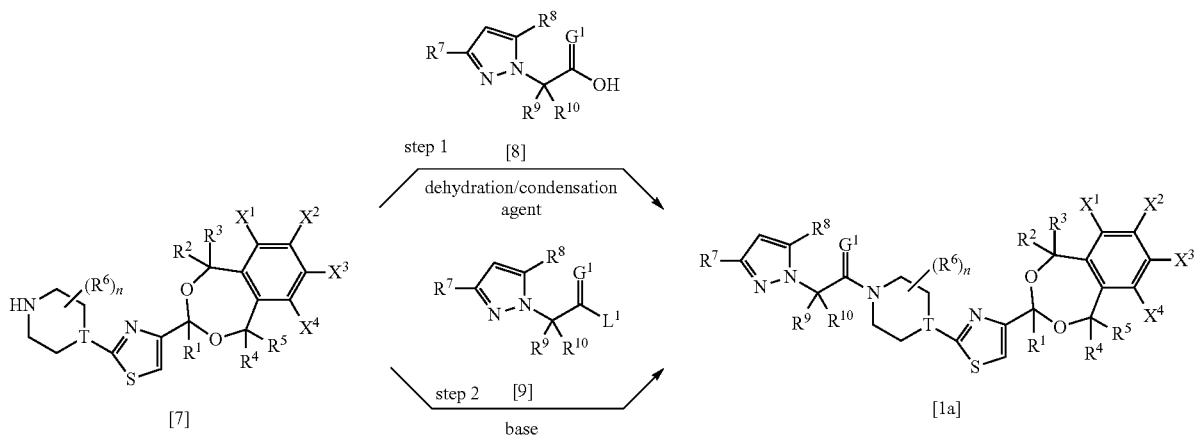

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

(Step 2)

The compound of formula [1a] can also be produced by reacting a compound of formula [7] and a compound of formula [9] under a presence of base in a solvent.

The amount of compound of formula [9] to be used may be selected as necessary from a range of 0.5-10 mol against 1 mol of a compound of formula [7], and it is preferably 1.0-1.2 mol.

Bases that can be used in this step are the same as those described in step 1.

The amount of base to be used in this reaction may be selected as necessary from a range of 0-100 mol against 1 mol of a compound of formula [7], and it is preferably 0-10 mol.

Solvents that can be used in this step are the same as those described in Production Method 1.

The amount of solvent to be used may be selected as necessary from a range of 0.01-100 L against 1 mol of a compound of formula [7], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [1a], which is the reaction target, is collected from the reaction system by a common method after the reaction has completed, and it can be purified by operations such as column chromatography, and recrystallization as necessary.

<Production Method 6>

The compound of the present invention represented by formula [1b] may be produced by a method consisting of the reaction formulas exemplified below.

(wherein each of $R^1$, $R^2$, $R^3$, $R^4$, $R^5$, $R^6$, $R^{13}$, $R^{14}$, $R^{15}$, $R^{16}$, $R^{17}$, E, $G^2$, $X^1$, $X^2$, $X^3$, $X^4$, T and n is as defined in [1], and $L^2$ is halogen such as a chlorine atom or a bromine atom).

(Step 1)

The compound of formula [1b] can also be produced by reacting a compound of formula [7] and a compound of formula [10] under a presence/absence of base, and under a presence of dehydration/condensation agent in a solvent.

The amount of compound of formula [10] to be used may be selected as necessary from a range of 0.50-10 mol against 1 mol of a compound of formula [7], and it is preferably 1.0-1.2 mol.

Dehydration/condensation agents and bases that can be used in this step are the same as those described in Production Method 5, step 1.

The amount of dehydration/condensation agent to be used in this reaction may be selected as necessary from a range of 1.0-10 mol against 1 mol of a compound of formula [7], and it is preferably 1.0-3.0 mol.

The amount of base to be used in this reaction may be selected as necessary from a range of 0-100 mol against 1 mol of a compound of formula [7], and it is preferably 0-10 mol.

Solvents that can be used in this step are the same as those described in Production Method 1.

The amount of solvent to be used in this reaction may be selected as necessary from a range of 0.01-100 L against 1 mol of a compound of formula [7], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

(Step 2)

The compound of formula [1b] can also be produced by reacting a compound of formula [7] and a compound of formula [11] under a presence of base in a solvent.

[Formula 18]

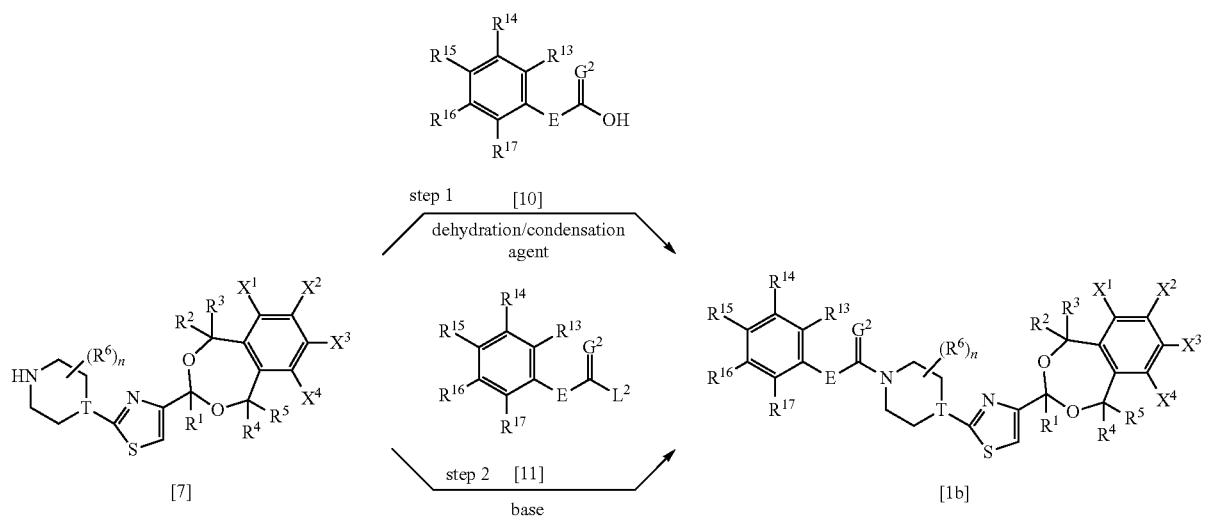

The amount of compound of formula [11] to be used in this step may be selected as necessary from a range of 0.5-10 mol against 1 mol of a compound of formula [7], and it is preferably 1.0-1.2 mol.

Bases that can be used in this step are the same as those described in Production Method 5, step 1.

The amount of base to be used in this reaction may be selected as necessary from a range of 0-100 mol against 1 mol of a compound of formula [7], and it is preferably 0-10 mol.

Solvents that can be used in this step are the same as those described in Production Method 1.

The amount of solvent to be used in this step may be selected as necessary from a range of 0.01-100 L against 1 mol of a compound of formula [7], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [1b], which is the reaction target, is collected from the reaction system by a common method after the reaction has completed, and it can be purified by operations such as column chromatography, and recrystallization as necessary.

<Production Method 7>

The compound of the present invention represented by formula [1c] may be produced by a method consisting of the reaction formulas exemplified below.

The amount of dehydration/condensation agent to be used in this reaction may be selected as necessary from a range of 1.0-10 mol against 1 mol of a compound of formula [7], and it is preferably 1.0-3.0 mol.

The amount of base to be used in this reaction may be selected as necessary from a range of 0-100 mol against 1 mol of a compound of formula [7], and it is preferably 0-10 mol.

Solvents that can be used in this step are the same as those described in Production Method 1.

The amount of solvent to be used in this reaction may be selected as necessary from a range of 0.01-100 L against 1 mol of a compound of formula [7], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

(Step 2)

The compound of formula [1c] can also be produced by reacting a compound of formula [7] and a compound of formula [13] under a presence of base in a solvent.

The amount of compound of formula [13] to be used in this step may be selected as necessary from a range of 0.5-10 mol against 1 mol of a compound of formula [7], and it is preferably 1.0-1.2 mol.

Bases that can be used in this step are the same as those described in Production Method 5, step 1.

[Formula 19]

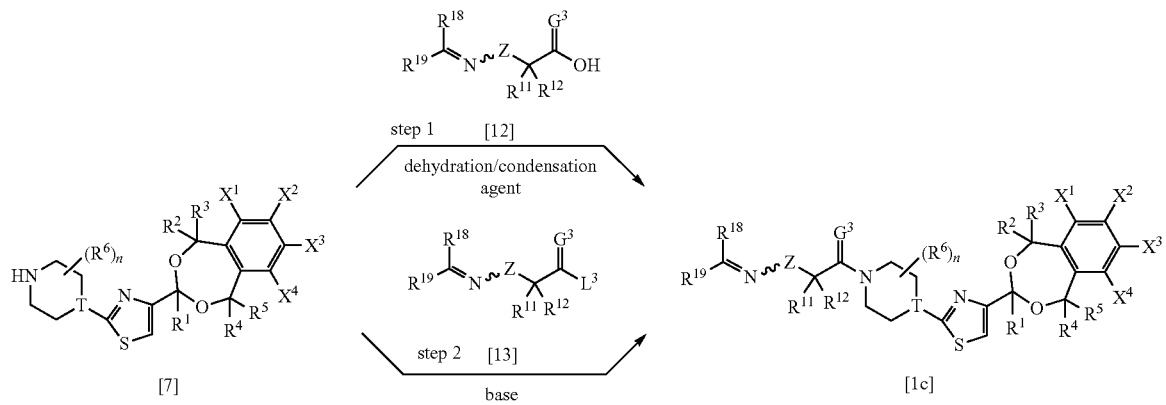

(wherein each of $R^1$, $R^2$, $R^3$, $R^4$, $R^5$, $R^6$, $R^{11}$, $R^{12}$, $R^{18}$, $R^{19}$, $G^3$, $X^1$, $X^2$, $X^3$, $X^4$, Z, T and n is as defined in [1], and $L^3$ is halogen such as a chlorine atom or a bromine atom).

(Step 1)

The compound of formula [1c] can also be produced by reacting a compound of formula [7] and a compound of formula [12] under a presence/absence of base, and under a presence of dehydration/condensation agent in a solvent.

The amount of compound of formula [12] to be used in this step may be selected as necessary from a range of 0.50-10 mol against 1 mol of a compound of formula [7], and it is preferably 1.0-1.2 mol.

Dehydration/condensation agents and bases that can be used in this step are the same as those described in Production Method 5.

The amount of base to be used in this reaction may be selected as necessary from a range of 0-100 mol against 1 mol of a compound of formula [7], and it is preferably 0-10 mol.

Solvents that can be used in this step are the same as those described in Production Method 1.

The amount of solvent to be used in this step may be selected as necessary from a range of 0.01-100 L against 1 mol of a compound of formula [7], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [1c], which is the reaction target, is collected from the reaction system by a common method after the reaction has completed, and it can be purified by operations such as column chromatography, and recrystallization as necessary.

<Production Method 8>

The compound of the present invention represented by formula [1d] may be produced by a method consisting of the reaction formulas exemplified below.

Solvents that can be used in this step are the same as those described in Production Method 1.

The amount of solvent to be used in this reaction may be selected as necessary from a range of 0.01-100 L against 1 mol of a compound of formula [14], and it is preferably 0.1-10 L.

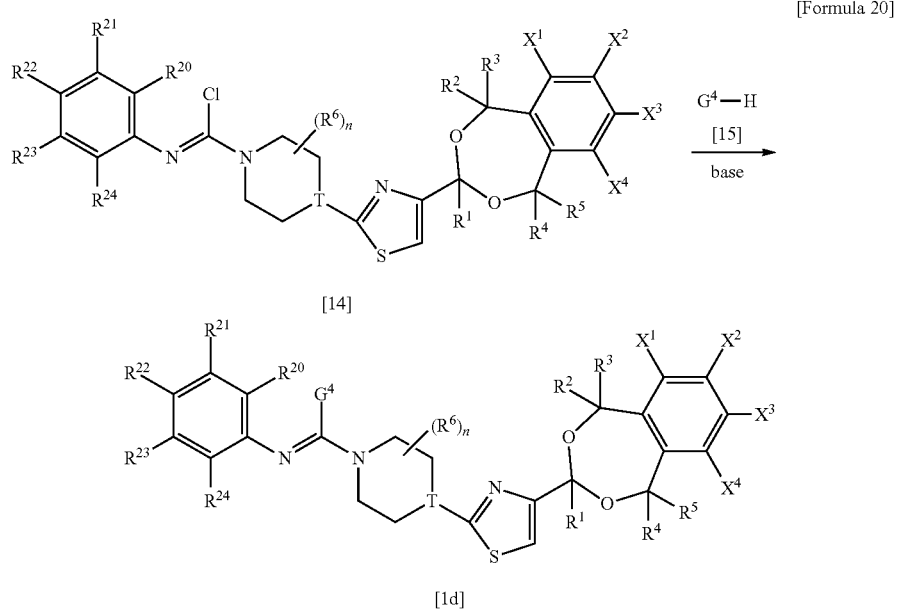

[Formula 20]

(wherein each of $R^1$, $R^2$, $R^3$, $R^4$, $R^5$, $R^6$, $R^{20}$, $R^{21}$, $R^{22}$, $R^{23}$, $R^{24}$, $G^4$, $X^1$, $X^2$, $X^3$, $X^4$, T and n is as defined in [1]).

The compound of formula [1d] can also be produced by reacting a compound of formula [14] and a compound of formula [15] under a presence of base in a solvent.

The amount of compound of formula [15] to be used in this step may be selected as necessary from a range of 0.50-10 mol against 1 mol of a compound of formula [14], and it is preferably 1.0-2.0 mol.

Bases that can be used in this step are the same as those described in Production Method 5, step 1.

The amount of base to be used in this reaction may be selected as necessary from a range of 1.0-100 mol against 1 mol of a compound of formula [14], and it is preferably 1.0-10 mol.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [1d], which is the reaction target, is collected from the reaction system by a common method after the reaction has completed, and it can be purified by operations such as column chromatography, and recrystallization as necessary.

<Production Method 9>

The compound of the present invention represented by formula [1d] may be produced by a method consisting of the reaction formulas exemplified below.

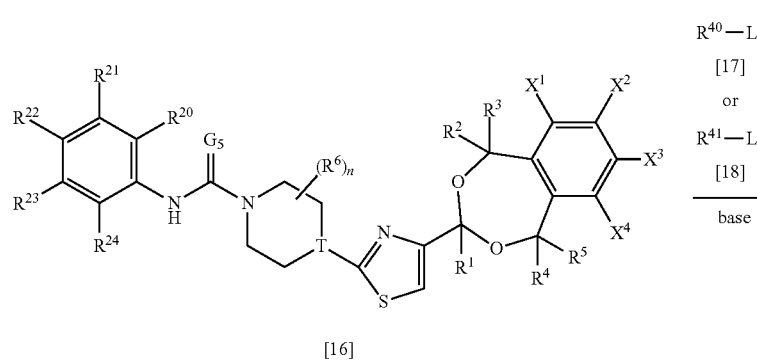

[Formula 21]

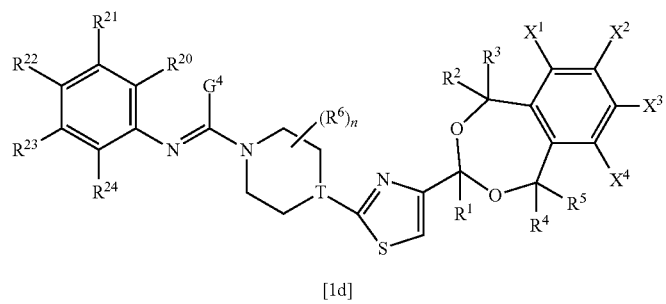

[1d]

(wherein each of R[1], R[2], R[3], R[4], R[5], R[6], R[20], R[21], R[23], R[24], R[40], R[41], G[4], X[1], X[2], X[3], X[4], T and n is as defined in [1], and G[5] is an oxygen atom or a sulfur atom, and L[3] is a leaving group).

L[3] is preferably halogen, methanesulfonyloxy or trifluoromethanesulfonyloxy.

The compound of formula [1d] can also be produced by reacting a compound of formula [16] and a compound of formula [17] or a compound of formula [18] under a presence/absence of base in a solvent.

The amount of compound of formula [17] or a compound of formula [18] to be used in this step may be selected as necessary from a range of 0.50-10 mol against 1 mol of a compound of formula [16], and it is preferably 1.0-5.0 mol.

Bases that can be used in this step are the same as those described in Production Method 5, step 1.

<Intermediate Production Method 1>

The amount of compound of formula [8] to be used in this step may be selected as necessary from a range of 0.50-10 mol against 1 mol of a compound of formula [19], and it is preferably 1.0-1.2 mol.

Dehydration/condensation agents and bases that can be used in this step are the same as those described in Production Method 5.

The amount of dehydration/condensation agent to be used in this reaction may be selected as necessary from a range of 1.0-10 mol against 1 mol of a compound of formula [19], and it is preferably 1.0-3.0 mol.

The amount of base to be used in this reaction may be selected as necessary from a range of 0-100 mol against 1 mol of a compound of formula [19], and it is preferably 0-10 mol.

Solvents that can be used in this step are the same as those described in Production Method 1.

[Formula 22]

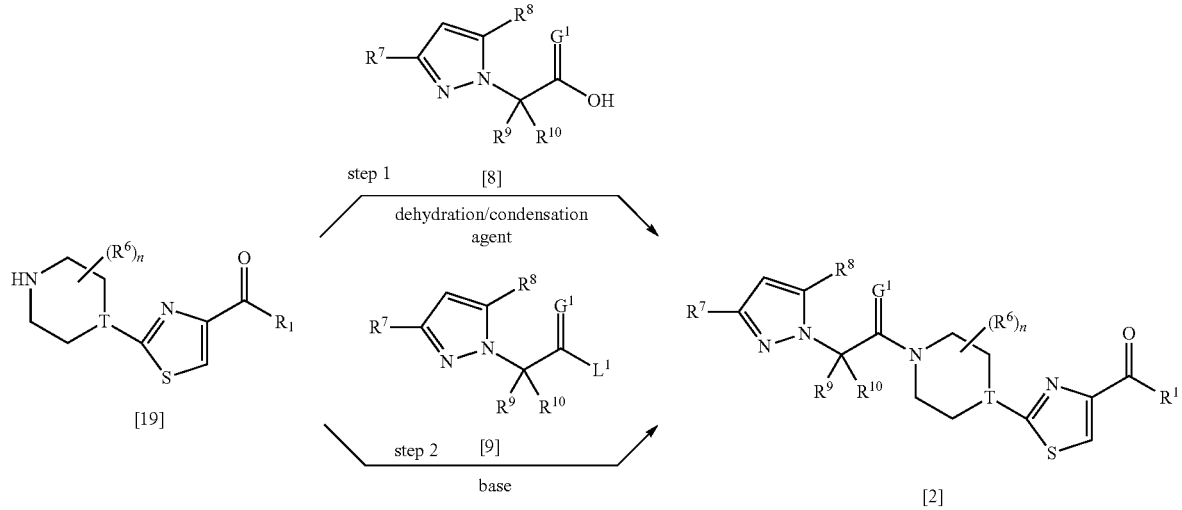

(wherein each of R[1], R[6], R[7], R[8], R[9], R[10], G[1], T and n is as defined in [1], and L[1] is halogen such as a chlorine atom or a bromine atom).

(Step 1)

The compound of formula [2] can be produced by reacting a compound of formula [19] and a compound of formula [8] under a presence/absence of base, and under a presence of a dehydration/condensation agent in a solvent.

The amount of solvent to be used in this reaction may be selected as necessary from a range of 0.01-100 L against 1 mol of a compound of formula [19], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

(Step 2)

The compound of formula [2] can also be produced by reacting a compound of formula [19] and a compound of formula [9] under a presence of base in a solvent.

The amount of compound of formula [9] to be used in this step may be selected as necessary from a range of 0.5-10 mol against 1 mol of a compound of formula [19], and it is preferably 1.0-1.2 mol.

Bases that can be used in this step are the same as those described in Production Method 5, step 1.

The amount of base to be used in this reaction may be selected as necessary from a range of 0-100 mol against 1 mol of a compound of formula [19], and it is preferably 0-10 mol.

Solvents that can be used in this step are the same as those described in Production Method 1.

The amount of solvent to be used in this step may be selected as necessary from a range of 0.01-100 L against 1 mol of a compound of formula [19], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [2], which is the reaction target, is collected from the reaction system by a common method after the reaction has completed, and it can be purified by operations such as column chromatography, and recrystallization as necessary.

<Intermediate Production Method 2>

[10] under a presence/absence of base, and under a presence of a dehydration/condensation agent in a solvent.

The amount of compound of formula [10] to be used in this step may be selected as necessary from a range of 0.5-10 mol against 1 mol of a compound of formula [19], and it is preferably 1.0-1.2 mol.

Dehydration/condensation agents and bases that can be used in this step are the same as those described in Production Method 5.

The amount of dehydration/condensation agent to be used in this reaction may be selected as necessary from a range of 1.0-10 mol against 1 mol of a compound of formula [19], and it is preferably 1.0-3.0 mol.

The amount of base to be used in this reaction may be selected as necessary from a range of 0-100 mol against 1 mol of a compound of formula [19], and it is preferably 0-10 mol.

Solvents that can be used in this step are the same as those described in Production Method 1.

The amount of solvent to be used in this reaction may be selected as necessary from a range of 0.01-100 L against 1 mol of a compound of formula [19], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

(Step 2)

The compound of formula [4] can also be produced by reacting a compound of formula [19] and a compound of formula [11] under a presence of base in a solvent.

[Formula 23]

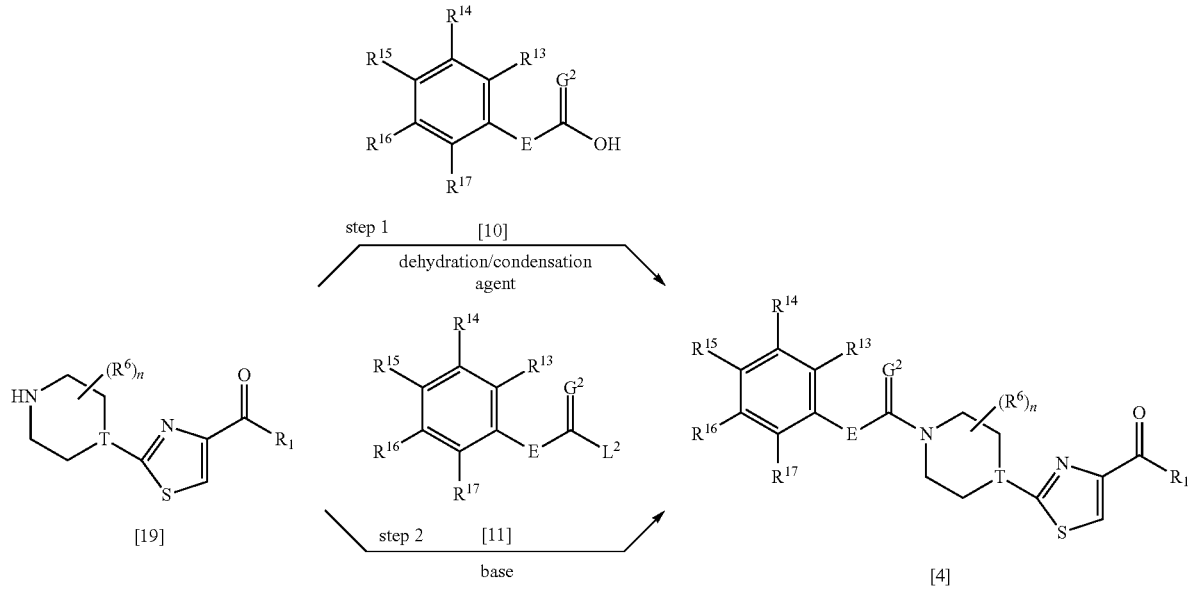

(wherein each of $R^1$, $R^6$, $R^{13}$, $R^{14}$, $R^{15}$, $R^{16}$, $R^{17}$, E, $G^2$, T and n is as defined in [1], and $L^2$ is halogen such as a chlorine atom or a bromine atom).

(Step 1)

The compound of formula [4] can be produced by reacting a compound of formula [19] and a compound of formula The amount of compound of formula [11] to be used in this step may be selected as necessary from a range of 0.5-10 mol against 1 mol of a compound of formula [19], and it is preferably 1.0-1.2 mol.

Bases that can be used in this step are the same as those described in Production Method 5, step 1.

The amount of base to be used in this reaction may be selected as necessary from a range of 0-100 mol against 1 mol of a compound of formula [19], and it is preferably 0-10 mol.

Solvents that can be used in this step are the same as those described in Production Method 1.

The amount of solvent to be used in this step may be selected as necessary from a range of 0.01-100 L against 1 mol of a compound of formula [19], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [4], which is the reaction target, is collected from the reaction system by a common method after the reaction has completed, and it can be purified by operations such as column chromatography, and recrystallization as necessary.

<Intermediate Production Method 3>

Solvents that can be used in this step are the same as those described in Production Method 1.

The amount of solvent to be used in this reaction may be selected as necessary from a range of 0.01-100 L against 1 mol of a compound of formula [19], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

(Step 2)

The compound of formula [5] can also be produced by reacting a compound of formula [19] and a compound of formula [13] under a presence of base in a solvent.

The amount of compound of formula [13] to be used in this step may be selected as necessary from a range of 0.5-10 mol against 1 mol of a compound of formula [19], and it is preferably 1.0-1.2 mol.

Bases that can be used in this step are the same as those described in Production Method 5, step 1.

[Formula 24]

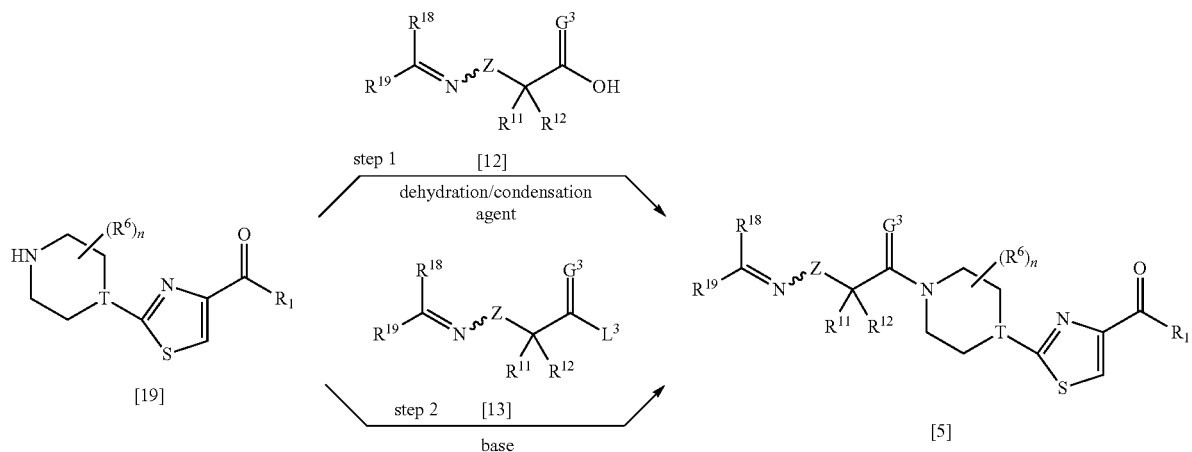

(wherein each of $R^1$, $R^6$, $R^{11}$, $R^{12}$, $R^{18}$, $R^{19}$, Z, $G^3$, T and n is as defined in [1], and $L^2$ is halogen such as a chlorine atom or a bromine atom).

(Step 1)

The compound of formula [5] can be produced by reacting a compound of formula [19] and a compound of formula [12] under a presence/absence of base, and under a presence of a dehydration/condensation agent in a solvent.

The amount of compound of formula [12] to be used in this step may be selected as necessary from a range of 0.5-10 mol against 1 mol of a compound of formula [19], and it is preferably 1.0-1.2 mol.

Dehydration/condensation agents and bases that can be used in this step are the same as those described in Production Method 5.

The amount of dehydration/condensation agent to be used in this reaction may be selected as necessary from a range of 1.0-10 mol against 1 mol of a compound of formula [19], and it is preferably 1.0-3.0 mol.

The amount of base to be used in this reaction may be selected as necessary from a range of 0-100 mol against 1 mol of a compound of formula [19], and it is preferably 0-10 mol.

The amount of base to be used in this reaction may be selected as necessary from a range of 0-100 mol against 1 mol of a compound of formula [19], and it is preferably 0-10 mol.

Solvents that can be used in this step are the same as those described in Production Method 1.

The amount of solvent to be used in this step may be selected as necessary from a range of 0.01-100 L against 1 mol of a compound of formula [19], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [5], which is the reaction target, is collected from the reaction system by a common method after the reaction has completed, and it can be purified by operations such as column chromatography, and recrystallization as necessary.

<Intermediate Production Method 4>

[Formula 25]

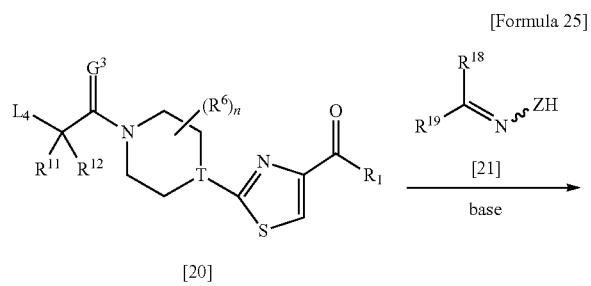

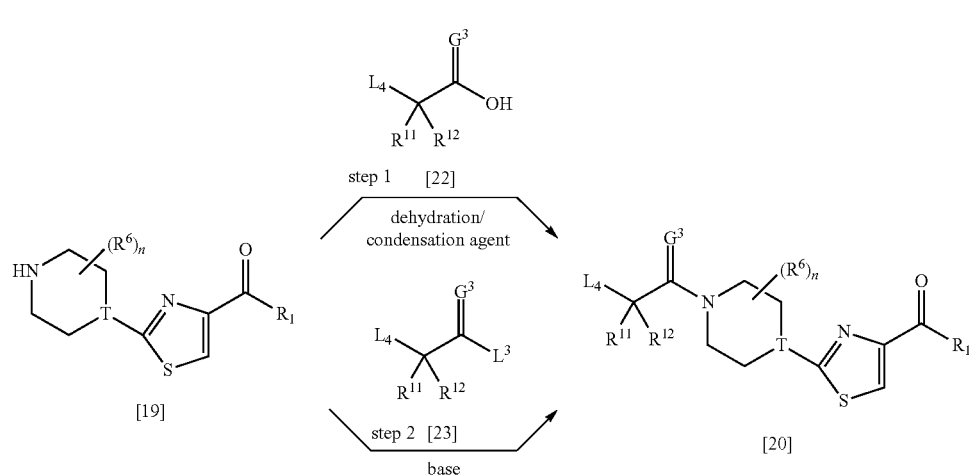

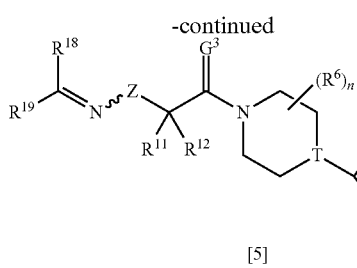

(wherein each of $R^1$, $R^6$, $R^{11}$, $R^{12}$, $R^{18}$, $R^{19}$, Z, $G^3$, T and n is as defined in [1], and $L^4$ is a leaving group such as halogen).

The compound of formula [5] can also be produced by reacting a compound of formula [20] and a compound of formula [21] under a presence of base in a solvent.

The amount of compound of formula [21] to be used in this step may be selected as necessary from a range of 0.5-10 mol against 1 mol of a compound of formula [20], and it is preferably 1.0-1.2 mol.

Bases that can be used in this step are the same as those described in Production Method 5, step 1.

The amount of base to be used in this reaction may be selected as necessary from a range of 0-100 mol against 1 mol of a compound of formula [20], and it is preferably 0-10 mol.

Solvents that can be used in this step are the same as those described in Production Method 1.

The amount of solvent to be used in this step may be selected as necessary from a range of 0.01-100 L against 1 mol of a compound of formula [20], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [5], which is the reaction target, is collected from the reaction system by a common method after the reaction has completed, and it can be purified by operations such as column chromatography, and recrystallization as necessary.

<Intermediate Production Method 5>

[Formula 26]

(wherein each of $R^1$, $R^6$, $R^{11}$, $R^{12}$, $R^{18}$, $R^{19}$, Z, $G^3$, T and n is as defined in [1], and $L^4$ is the same as described above).

(Step 1)

The compound of formula [20] can be produced by reacting a compound of formula [19] and a compound of formula [22] under a presence/absence of base, and under a presence of a dehydration/condensation agent in a solvent.

The amount of compound of formula [22] to be used in this step may be selected as necessary from a range of 0.5-10 mol against 1 mol of a compound of formula [19], and it is preferably 1.0-1.2 mol.

Dehydration/condensation agents and bases that can be used in this step are the same as those described in Production Method 5.

The amount of dehydration/condensation agent to be used in this reaction may be selected as necessary from a range of 1.0-10 mol against 1 mol of a compound of formula [19], and it is preferably 1.0-3.0 mol.

The amount of base to be used in this reaction may be selected as necessary from a range of 0-100 mol against 1 mol of a compound of formula [19], and it is preferably 0-10 mol.

Solvents that can be used in this step are the same as those described in Production Method 1.

The amount of solvent to be used in this step may be selected as necessary from a range of 0.01-100 L against 1 mol of a compound of formula [19], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

(Step 2)

The compound of formula [20] can also be produced by reacting a compound of formula [19] and a compound of formula [23] under a presence of base in a solvent.

The amount of compound of formula [23] to be used in this step may be selected as necessary from a range of 0.5-10 mol against 1 mol of a compound of formula [19], and it is preferably 1.0-1.2 mol.

Bases that can be used in this step are the same as those described in Production Method 5, step 1.

The amount of base to be used in this reaction may be selected as necessary from a range of 0-100 mol against 1 mol of a compound of formula [19], and it is preferably 0-10 mol.

Solvents that can be used in this step are the same as those described in Production Method 1.

The amount of solvent to be used in this step may be selected as necessary from a range of 0.01-100 L against 1 mol of a compound of formula [19], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [20], which is the reaction target, is collected from the reaction system by a common method after the reaction has completed, and it can be purified by operations such as column chromatography, and recrystallization as necessary.

<Intermediate Production Method 6>

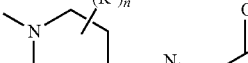

[Formula 27]

[24]

[25]

[26]

(wherein each of $R^1$, $R^6$, $R^{20}$, $R^{21}$, $R^{22}$, $R^{23}$, $R^{24}$, T and n is as defined in [1], and $G^5$ is the same as described above, and $L^5$ is a chlorine atom or imidazole-4-yl).

The compound of formula [6] used in Production Method 4 can be prepared by a method similar to Production Method 8, in which the compound of formula [26] obtained by Intermediate Production Method 6 is chlorinated using thionyl chloride, or by subjecting the compound of formula [26] to a method similar to Production Method 9.

The compound of formula [26] can be produced by reacting a compound of formula [24] and a compound of formula [25] under a presence of base in a solvent.

The compound of formula [24] is prepared from amine represented by a compound of formula [19], phosgene, thiophosgene or their equivalents, or carbodiimidazole.

The amount of compound of formula [25] to be used in this step may be selected as necessary from a range of 0.5-10 mol against 1 mol of a compound of formula [24], and it is preferably 1.0-1.2 mol.

Bases that can be used in this step are the same as those described in Production Method 5, step 1.

The amount of base to be used in this reaction may be selected as necessary from a range of 0-100 mol against 1 mol of a compound of formula [24], and it is preferably 0-10 mol.

Solvents that can be used in this step are the same as those described in Production Method 1.

The amount of solvent to be used in this step may be selected as necessary from a range of 0.01-100 L against 1 mol of a compound of formula [24], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [26], which is the reaction target, is collected from the reaction system by a common method after the reaction has completed, and it can be purified by operations such as column chromatography, and recrystallization as necessary.

<Intermediate Production Method 7>

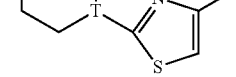

[Formula 28]

[27]

[3]

-continued

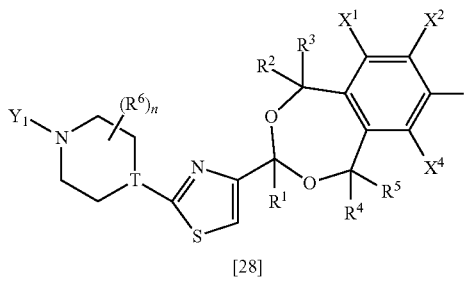

[28]

(wherein each of $R^1$, $R^2$, $R^3$, $R^4$, $R^5$, $R^6$, $X^1$, $X^2$, $X^3$, $X^4$, T and n is as defined in [1], and Y is an amine protective group such as 1,1-dimethylethyloxycarbonyl or benzyl).

A compound of formula [28] may be deprotected using a suitable method (refer to T. W. Greene and P. G. Wuts, Protective Groups in Organic Synthesis, ed. 4; Wiley: New York, 2007 concerning the method of an amine protective group) to prepare the compound of formula [7]. Various protective groups are suitable for amine protective groups, and the option of suitable protective groups should be obvious to a person skilled in the art of chemical synthesis. After deprotection, the amine of formula [7] may be isolated as acid salt or free amine by a well known basic method.

A compound of formula [27] and a compound of formula [3] may be reacted under a presence of an acid or Lewis acid in a solvent to produce a compound of formula [28] of the present invention.

The amount of compound of formula [3] to be used in this step may be selected as necessary from a range of 1.0-10 mol against 1 mol of a compound of formula [27], and it is preferably 1.0-3.0 mol.

Acids, Lewis acids and solvents that can be used in this step are the same as those described in Production Method 1.

The amount of acid or Lewis acid to be used may be selected as necessary from a range of 0.01-5 mol against 1 mol of a compound of formula [27], and it is preferably 0.1-1.0 mol.

The amount of solvent to be used may be selected as necessary from a range of 0.01-100 L against 1 mol of a compound of formula [27], and it is preferably 0.1-10 L.

The reaction temperature may be selected from −20° C. to the boiling point range of the inactive solvent to be used, and it is preferably 0° C. to 150° C.

The reaction time differs by the reaction temperature, reaction substrate, the reaction amount, etc., but it is normally 10 min. to 48 h.

The compound of formula [28], which is the reaction target, is collected from the reaction system by a common method after the reaction has completed, and it can be purified by operations such as column chromatography, and recrystallization as necessary.

<Intermediate Production Method 8>

[Formula 29]

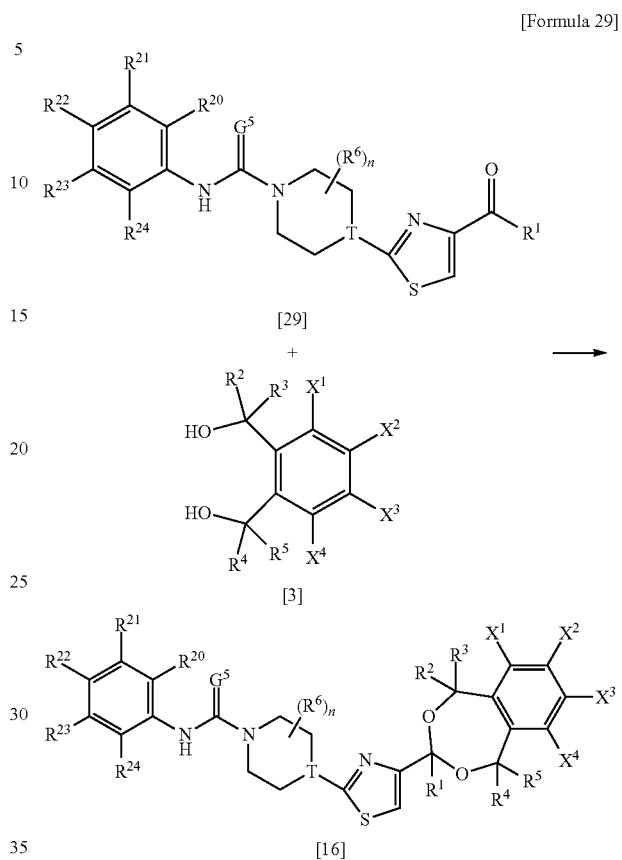

(wherein each of $R^1$, $R^2$, $R^3$, $R^4$, $R^5$, $R^6$, $R^{20}$, $R^{21}$, $R^{22}$, $R^{23}$, $R^{24}$, $X^1$, $X^2$, $X^3$, $X^4$, T and n is as defined in [1], and $G^5$ is the same as described above).

The compound of formula [16] obtained by Intermediate Production Method 8 may be chlorinated using thionyl chloride, etc. to prepare the compound of formula [14] used in Production Method 8.

A compound of formula [29] and a compound of formula [3] may be reacted under a presence of an acid or Lewis acid in a solvent to produce a compound of formula [16] of the present invention.

The amount of compound of formula [3] to be used in this step may be selected as necessary from a range of 1.0-10 mol against 1 mol of a compound of formula [29], and it is preferably 1.0-3.0 mol.

Acids, Lewis acids and solvents that can be used in this step are the same as those described in Production Method 1.

The amount of acid or Lewis acid to be used may be selected as necessary from a range of 0.01-5 mol against 1 mol of a compound of formula [29], and it is preferably 0.1-1.0 mol.

The amount of solvent to be used may be selected as necessary from a range of 0.01-100 L against 1 mol of a compound of formula [29], and it is preferably 0.1-10 L.

The reaction temperature may be selected from −20° C. to the boiling point range of the inactive solvent to be used, and it is preferably 0° C. to 150° C.

The reaction time differs by the reaction temperature, reaction substrate, the reaction amount, etc., but it is normally 10 min. to 48 h.

The compound of formula [16], which is the reaction target, is collected from the reaction system by a common method after the reaction has completed, and it can be purified by operations such as column chromatography, and recrystallization as necessary.

<Intermediate Production Method 9>

[Formula 30]

[30] → [3a]

(wherein each of $X^1$, $X^2$, $X^3$, $X^4$ is as defined in [1]).

The compound of formula [30] may be reduced using a reducing agent in a solvent to produce a compound of formula [3a].

The following reducing agent can be used in the present invention: lithium aluminum hydride, di-isobutyl aluminum hydride, borane, etc.

The amount of reducing agent to be used may be selected as necessary from a range of 1.0-10 mol against 1 mol of a compound of formula [30], and it is preferably 2.0-5.0 mol.

Solvents that can be used in this step are the same as those described in Production Method 1.

The amount of solvent to be used may be selected as necessary from a range of 0.01-100 L against 1 mol of a compound of formula [30], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [3a], which is the reaction target, is collected from the reaction system by a common method after the reaction has completed, and it can be purified by operations such as column chromatography, and recrystallization as necessary.

<Intermediate Production Method 10>

[Formula 31]

[31] → [3a]

(wherein each of $X^1$, $X^2$, $X^3$, $X^4$ is as defined in [1], and $R^{45}$ is a hydrogen atom or $C_1$-$C_4$ alkyl).

The compound of formula [3a] can also be produced by reducing a compound of formula [31] using a reducing agent in a solvent.

The reducing agent to be used in this step are the same as those described in Intermediate Production Method 9.

The amount of reducing agent to be used may be selected as necessary from a range of 1.0-10 mol against 1 mol of a compound of formula [31], and it is preferably 2.0-5.0 mol.

Solvents that can be used in this step are the same as those described in Production Method 1.

The amount of solvent to be used may be selected as necessary from a range of 0.01-100 L against 1 mol of a compound of formula [31], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [3a], which is the reaction target, is collected from the reaction system by a common method after the reaction has completed, and it can be purified by operations such as column chromatography, and recrystallization as necessary.

<Intermediate Production Method 11>

[Formula 32]

[32] → [3b]

(wherein each of $R^2$, $R^3$, $X^1$, $X^2$, $X^3$, $X^4$ is as defined in [1]).

The compound of formula [3b] can be produced by reducing a compound of formula [32] using a reducing agent in a solvent.

The reducing agent to be used in this step are the same as those described in Intermediate Production Method 9.

The amount of reducing agent to be used may be selected as necessary from a range of 1.0-10 mol against 1 mol of a compound of formula [32], and it is preferably 1.0-3.0 mol.

Solvents that can be used in this step are the same as those described in Production Method 1.

The amount of solvent to be used may be selected as necessary from a range of 0.01-100 L against 1 mol of a compound of formula [32], and it is preferably 0.1-10 L.

The reaction temperature may be selected from −20° C. to the boiling point range of the inactive solvent to be used, and it is preferably 0° C. to 100° C.

The reaction time differs by the reaction temperature, reaction substrate, the reaction amount, etc., but it is normally 10 min. to 48 h.

The compound of formula [3b], which is the reaction target, is collected from the reaction system by a common method after the reaction has completed, and it can be purified by operations such as column chromatography, and recrystallization as necessary.

<Intermediate Production Method 12>

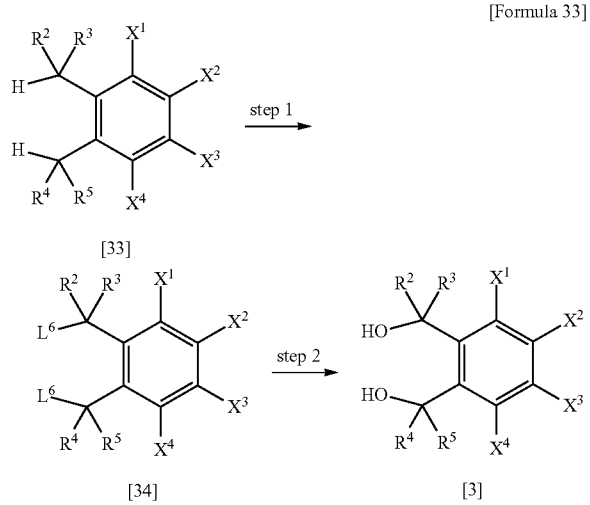

[Formula 33]

(wherein each of $R^2$, $R^3$, $R^4$, $R^5$, $X^1$, $X^2$, $X^3$, $X^4$ is as defined in [1], and $L^6$ is halogen such as a chlorine atom or bromine atom).

(Step 1)

The compound of formula [33] can be reacted using a halogenating agent in a solvent to produce the compound of formula [34].

The halogenating agent to be used in this step is as follows: N-bromosuccinimide, N-chlorosuccinimide, etc.

Radical reaction may be initiated in this reaction by irradiation or addition of radical initiators, such as azoisobutyl nitrile, benzoyl peroxide.

The amount of halogenating agent to be used may be selected as necessary from a range of 2.0-10 mol against 1 mol of a compound of formula [33], and it is preferably 2.0-4.0 mol.

Solvents that can be used in this step are the same as those described in Production Method 1.

The amount of solvent to be used may be selected as necessary from a range of 0.01-100 L against 1 mol of a compound of formula [33], and it is preferably 0.1-10 L.

The reaction temperature may be selected from −20° C. to the boiling point range of the inactive solvent to be used, and it is preferably 0° C. to 150° C.

The reaction time differs by the reaction temperature, reaction substrate, the reaction amount, etc., but it is normally 10 min. to 48 h.

The compound of formula [34], which is the reaction target, is collected from the reaction system by a common method after the reaction has completed, and it can be purified by operations such as column chromatography, and recrystallization as necessary.

(Step 2)

The compound of formula [3] can be produced by reacting a compound of formula [34] in a solvent using a basic solution, etc.

The basic solution to be used in this step includes the following: sodium hydroxide solution, calcium hydroxide solution, sodium hydrogen carbonate solution, potassium carbonate solution, etc.

The amount of basic solution to be used may be selected as necessary from a range of 2.0-10 mol against 1 mol of a compound of formula [34], and it is preferably 2.0-5.0 mol.

Solvents that can be used in this step are the same as those described in Production Method 1.

The amount of solvent to be used may be selected as necessary from a range of 0.01-100 L against 1 mol of a compound of formula [34], and it is preferably 0.1-10 L.

The reaction temperature may be selected from −0° C. to the boiling point range of the inactive solvent to be used, and it is preferably 0° C. to 150° C.

The reaction time differs by the reaction temperature, reaction substrate, the reaction amount, etc., but it is normally 10 min. to 48 h.

The compound of formula [3], which is the reaction target, is collected from the reaction system by a common method after the reaction has completed, and it can be purified by operations such as column chromatography, and recrystallization as necessary.

Cases can be assumed in which the reagents and reaction conditions for preparing the compound of formula [1] mentioned above are not compatible with specific functional groups in the intermediate. In those examples, it is possible to adopt protection/deprotection methods or mutual conversion of functional groups in synthesis to obtain the desired product. The use and options of protective groups are common for a person skilled in the art in the field of chemical synthesis. (Refer to T. W. Greene and P. G. Wuts, Protective Groups in Organic Synthesis, Ver. 4; Wiley: New York, 2007) A person skilled in the art would recognize that in some cases, additional synthesis steps of common methods not described herein are necessary to complete the synthesis of the compound of formula [1] after introducing specific reagents as explained in the individual schemes. A person skilled in the art would recognize that the combination of steps exemplified in the above schemes may need to be performed in orders that deviate from the proposed specific orders for preparing the compound of formula [1].

The methods described in this specification may be combined with well known methods in the conventional art to prepare the compounds shown in [Table 1] to [Table 160] shown below.

TABLE 1

| $X^1$ | $X^2$ | $X^3$ | $X^4$ |
|---|---|---|---|
| Br | H | H | Br |
| C(=NOMe)H | H | H | H |
| C≡CH | H | H | H |
| $CF_3$ | H | H | $CF_3$ |
| CH=$CH_2$ | H | H | H |
| $CH_2NMe_2$ | H | H | H |
| $CH_2SMe$ | H | H | H |
| Cl | Cl | Cl | Cl |
| Cl | Cl | H | H |
| Cl | H | H | Cl |
| CN | H | H | CN |
| $CO_2H$ | H | H | H |
| c-Pr | H | H | H |
| F | Br | H | F |
| F | C(=NOMe)H | H | H |
| F | $CF_3$ | H | F |
| F | Cl | H | F |

TABLE 1-continued

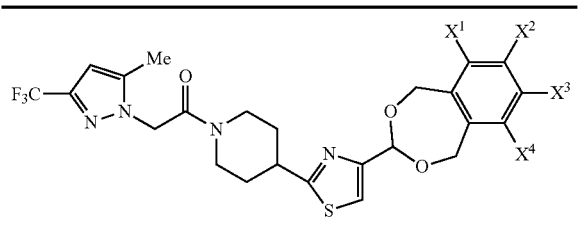

| X¹ | X² | X³ | X⁴ |
|---|---|---|---|
| F | CN | H | F |
| F | F | F | F |
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |

TABLE 1-continued

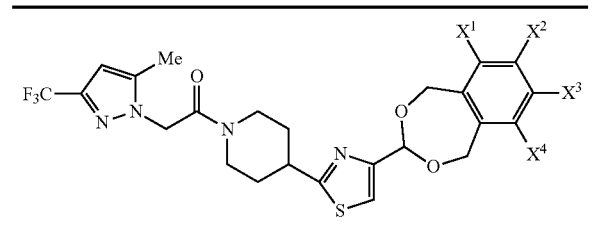

| X¹ | X² | X³ | X⁴ |
|---|---|---|---|
| Cl | H | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | H | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 2

| X¹ | X² | X³ | X⁴ | X¹ | X² | X³ | X⁴ |
|---|---|---|---|---|---|---|---|
| F | H | H | CHO | F | H | H | CH₂SMe |
| F | H | H | CN | F | H | H | Cl |
| F | H | H | CO₂Me | F | H | H | CO₂H |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | NH₂ | F | H | H | n-Bu |
| F | H | H | NHCOMe | F | H | H | NHCO₂Me |
| F | H | H | NHSO₂Me | F | H | H | NHMe |
| F | H | H | NO₂ | F | H | H | NMe₂ |
| F | H | H | OCF₃ | F | H | H | n-Pr |
| F | H | H | OCO₂Me | F | H | H | OCH₂C≡CH |
| F | H | H | OCOMe | F | H | H | OCO₂NMe₂ |
| F | H | H | OH | F | H | H | OEt |
| F | H | H | OPh | F | H | H | OMe |
| F | H | H | OSiMe₃ | F | H | H | OSiMe₂t-Bu |
| F | H | H | SH | F | H | H | Ph |
| F | H | H | SMe | F | H | H | SiMe₃ |
| F | H | H | SO₂Me | F | H | H | SO₂CF₃ |
| F | H | H | t-Bu | F | H | H | SOMe |
| F | H | Me | H | F | H | I | H |
| F | H | OCF₃ | H | F | H | NO₂ | H |
| F | H | OMe | H | F | H | OH | H |
| F | H | SO₂Me | H | F | H | OSO₂Me | H |
| F | I | H | H | F | I | H | F |
| F | Me | H | H | F | Me | H | F |
| F | NO₂ | H | H | F | NO₂ | H | F |
| F | OCF₃ | H | H | F | OCF₃ | H | F |
| F | OH | H | H | F | OH | H | F |
| F | OMe | H | H | F | OMe | H | F |
| F | SO₂Me | H | F | F | OSO₂Me | H | F |
| H | Br | Br | H | F | SO₂Me | H | H |
| H | C(=NOMe)H | H | H | H | Br | H | H |

TABLE 3

| $X^1$ | $X^2$ | $X^3$ | $X^4$ | $X^1$ | $X^2$ | $X^3$ | $X^4$ |
|---|---|---|---|---|---|---|---|
| H | CF$_3$ | CF$_3$ | H | H | C(=NOMe)Me | H | H |
| H | —CH=CH—CH=CH— | | H | H | CF$_3$ | H | H |
| H | —CH$_2$CH$_2$CH$_2$— | | H | H | —CH=N—CH=CH— | | H |
| H | Cl | Cl | H | H | —CH$_2$CH$_2$CH$_2$CH$_2$— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |
| H | —NH—CH=CH— | | H | H | —N=CH—N=CH— | | H |
| H | NO$_2$ | NO$_2$ | H | H | NO$_2$ | H | H |
| H | OCF$_3$ | OCF$_3$ | H | H | OCF$_3$ | H | H |
| H | —O—CH=N— | | H | H | —O—CH=CH— | | H |
| H | OH | OH | H | H | OH | H | H |
| H | OMe | OMe | H | H | OMe | H | H |
| H | OSO$_2$Et | H | H | H | OSO$_2$Bn | H | H |
| H | OSO$_2$Me | H | H | H | OSO$_2$i-Pr | H | H |
| H | OSO$_2$n-Bu | H | H | H | OSO$_2$Me | OSO$_2$Me | H |
| H | OSO$_2$Ph | H | H | H | OSO$_2$n-Pr | H | H |
| H | SO$_2$Me | H | H | H | —S—CH=CH— | | H |
| I | H | H | H | H | SO$_2$Me | SO$_2$Me | H |
| i-Pr | H | H | H | i-Bu | H | H | H |
| Me | H | H | Me | Me | H | H | H |
| NH$_2$ | H | H | H | n-Bu | H | H | H |
| NHCOMe | H | H | H | NHCO$_2$Me | H | H | H |
| NHSO$_2$Me | H | H | H | NHMe | H | H | H |
| NO$_2$ | H | H | H | NMe$_2$ | H | H | H |
| OCF$_3$ | H | H | H | n-Pr | H | H | H |
| OCH$_2$C≡CH | H | H | H | OCF$_3$ | H | H | OCF$_3$ |
| OCO$_2$NMe$_2$ | H | H | H | OCO$_2$Me | H | H | H |
| OEt | H | H | H | OCOMe | H | H | H |
| OMe | H | H | H | OH | H | H | H |
| OPh | H | H | H | OMe | H | H | OMe |
| OSiMe$_3$ | H | H | H | OSiMe$_2$t-Bu | H | H | H |

TABLE 4

| $X^1$ | $X^2$ | $X^3$ | $X^4$ | $X^1$ | $X^2$ | $X^3$ | $X^4$ |
|---|---|---|---|---|---|---|---|
| OSO$_2$CF$_3$ | H | H | Br | OSO$_2$Bn | H | H | H |
| OSO$_2$CF$_3$ | H | H | CN | OSO$_2$CF$_3$ | H | H | Cl |
| OSO$_2$CF$_3$ | H | H | Et | OSO$_2$CF$_3$ | H | H | c-Pr |
| OSO$_2$CF$_3$ | H | H | H | OSO$_2$CF$_3$ | H | H | F |
| OSO$_2$CF$_3$ | H | H | Me | OSO$_2$CF$_3$ | H | H | I |
| OSO$_2$CF$_3$ | H | H | NO$_2$ | OSO$_2$CF$_3$ | H | H | n-Bu |
| OSO$_2$CF$_3$ | H | H | OCF$_3$ | OSO$_2$CF$_3$ | H | H | n-Pr |
| OSO$_2$CF$_3$ | H | H | Oc-Pr | OSO$_2$CF$_3$ | H | H | OCHF$_2$ |
| OSO$_2$CF$_3$ | H | H | OH | OSO$_2$CF$_3$ | H | H | OEt |
| OSO$_2$CF$_3$ | H | H | On-Bu | OSO$_2$CF$_3$ | H | H | OMe |
| OSO$_2$CF$_3$ | H | H | Ot-Bu | OSO$_2$CF$_3$ | H | H | On-Pr |
| OSO$_2$CHF$_2$ | H | H | Br | OSO$_2$CF$_3$ | H | H | t-Bu |
| OSO$_2$CHF$_2$ | H | H | CN | OSO$_2$CHF$_2$ | H | H | Cl |
| OSO$_2$CHF$_2$ | H | H | Et | OSO$_2$CHF$_2$ | H | H | c-Pr |
| OSO$_2$CHF$_2$ | H | H | H | OSO$_2$CHF$_2$ | H | H | F |
| OSO$_2$CHF$_2$ | H | H | Me | OSO$_2$CHF$_2$ | H | H | I |
| OSO$_2$CHF$_2$ | H | H | NO$_2$ | OSO$_2$CHF$_2$ | H | H | n-Bu |
| OSO$_2$CHF$_2$ | H | H | OCF$_3$ | OSO$_2$CHF$_2$ | H | H | n-Pr |
| OSO$_2$CHF$_2$ | H | H | Oc-Pr | OSO$_2$CHF$_2$ | H | H | OCHF$_2$ |
| OSO$_2$CHF$_2$ | H | H | OH | OSO$_2$CHF$_2$ | H | H | OEt |
| OSO$_2$CHF$_2$ | H | H | On-Bu | OSO$_2$CHF$_2$ | H | H | OMe |
| OSO$_2$CHF$_2$ | H | H | Ot-Bu | OSO$_2$CHF$_2$ | H | H | On-Pr |
| OSO$_2$Et | H | H | Br | OSO$_2$CHF$_2$ | H | H | t-Bu |
| OSO$_2$Et | H | H | Cl | OSO$_2$Et | H | H | CF$_3$ |
| OSO$_2$Et | H | H | c-Pr | OSO$_2$Et | H | H | CN |
| OSO$_2$Et | H | H | F | OSO$_2$Et | H | H | Et |
| OSO$_2$Et | H | H | I | OSO$_2$Et | H | H | H |
| OSO$_2$Et | H | H | n-Bu | OSO$_2$Et | H | H | Me |
| OSO$_2$Et | H | H | n-Pr | OSO$_2$Et | H | H | NO$_2$ |
| OSO$_2$Et | H | H | OCHF$_2$ | OSO$_2$Et | H | H | OCF$_3$ |
| OSO$_2$Et | H | H | OEt | OSO$_2$Et | H | H | Oc-Pr |
| OSO$_2$Et | H | H | OMe | OSO$_2$Et | H | H | OH |
| OSO$_2$Et | H | H | On-Pr | OSO$_2$Et | H | H | On-Bu |
| OSO$_2$Et | H | H | t-Bu | OSO$_2$Et | H | H | Ot-Bu |

TABLE 5

| $X^1$ | $X^2$ | $X^3$ | $X^4$ | $X^1$ | $X^2$ | $X^3$ | $X^4$ |
|---|---|---|---|---|---|---|---|
| OSO$_2$i-Pr | H | H | CF$_3$ | OSO$_2$i-Pr | H | H | Br |
| OSO$_2$i-Pr | H | H | CN | OSO$_2$i-Pr | H | H | Cl |
| OSO$_2$i-Pr | H | H | Et | OSO$_2$i-Pr | H | H | c-Pr |
| OSO$_2$i-Pr | H | H | H | OSO$_2$i-Pr | H | H | F |
| OSO$_2$i-Pr | H | H | Me | OSO$_2$i-Pr | H | H | I |
| OSO$_2$i-Pr | H | H | NO$_2$ | OSO$_2$i-Pr | H | H | n-Bu |
| OSO$_2$i-Pr | H | H | OCF$_3$ | OSO$_2$i-Pr | H | H | n-Pr |
| OSO$_2$i-Pr | H | H | Oc-Pr | OSO$_2$i-Pr | H | H | OCHF$_2$ |
| OSO$_2$i-Pr | H | H | OH | OSO$_2$i-Pr | H | H | OEt |
| OSO$_2$i-Pr | H | H | On-Bu | OSO$_2$i-Pr | H | H | OMe |
| OSO$_2$i-Pr | H | H | Ot-Bu | OSO$_2$i-Pr | H | H | On-Pr |
| OSO$_2$Me | Br | H | H | OSO$_2$i-Pr | H | H | t-Bu |

TABLE 5-continued

| X¹ | X² | X³ | X⁴ | X¹ | X² | X³ | X⁴ |
|---|---|---|---|---|---|---|---|
| OSO₂Me | C(=NOMe)Me | H | H | OSO₂Me | C(=NOMe)H | H | H |
| OSO₂Me | —CH=CH—CH=CH— | | F | OSO₂Me | CF₃ | H | H |
| OSO₂Me | —CH=CH—CH=CH— | | OSO₂Me | OSO₂Me | —CH=CH—CH=CH— | | H |
| OSO₂Me | —CH=N—CH=CH— | | H | OSO₂Me | —CH=N—CH=CH— | | F |
| OSO₂Me | —CH₂CH₂CH₂— | | F | OSO₂Me | —CH=N—CH=CH— | | OSO₂Me |
| OSO₂Me | —CH₂CH₂CH₂— | | OSO₂Me | OSO₂Me | —CH₂CH₂CH₂— | | H |
| OSO₂Me | —CH₂CH₂CH₂CH₂— | | H | OSO₂Me | —CH₂CH₂CH₂CH₂— | | F |
| OSO₂Me | Cl | H | H | OSO₂Me | —CH₂CH₂CH₂CH₂— | | OSO₂Me |
| OSO₂Me | F | F | F | OSO₂Me | CN | H | H |
| OSO₂Me | F | H | F | OSO₂Me | F | F | OSO₂Me |
| OSO₂Me | H | Br | H | OSO₂Me | F | H | H |
| OSO₂Me | H | C(=NOMe)Me | H | OSO₂Me | H | C(=NOMe)H | H |
| OSO₂Me | H | Cl | H | OSO₂Me | H | CF₃ | H |
| OSO₂Me | H | F | F | OSO₂Me | H | CN | H |
| OSO₂Me | H | H | Bn | OSO₂Me | H | F | H |
| OSO₂Me | H | H | C(=NOMe)H | OSO₂Me | H | H | Br |
| OSO₂Me | H | H | C≡CH | OSO₂Me | H | H | C(=NOMe)Me |
| OSO₂Me | H | H | CF₃ | OSO₂Me | H | H | C₂F₅ |
| OSO₂Me | H | H | CH₂CN | OSO₂Me | H | H | CH=CH₂ |
| OSO₂Me | H | H | CH₂OMe | OSO₂Me | H | H | CH₂NMe₂ |
| OSO₂Me | H | H | CHO | OSO₂Me | H | H | CH₂SMe |
| OSO₂Me | H | H | CN | OSO₂Me | H | H | Cl |

TABLE 6

| X¹ | X² | X³ | X⁴ | X¹ | X² | X³ | X⁴ |
|---|---|---|---|---|---|---|---|
| OSO₂Me | H | H | CO₂Me | OSO₂Me | H | H | CO₂H |
| OSO₂Me | H | H | Et | OSO₂Me | H | H | c-Pr |
| OSO₂Me | H | H | H | OSO₂Me | H | H | F |
| OSO₂Me | H | H | I | OSO₂Me | H | H | H |
| OSO₂Me | H | H | i-Pr | OSO₂Me | H | H | i-Bu |
| OSO₂Me | H | H | n-Bu | OSO₂Me | H | H | Me |
| OSO₂Me | H | H | NHCO₂Me | OSO₂Me | H | H | NH₂ |
| OSO₂Me | H | H | NHMe | OSO₂Me | H | H | NHCOMe |
| OSO₂Me | H | H | NMe₂ | OSO₂Me | H | H | NHSO₂Me |
| OSO₂Me | H | H | n-Pr | OSO₂Me | H | H | NO₂ |
| OSO₂Me | H | H | OCHF₂ | OSO₂Me | H | H | OCF₃ |
| OSO₂Me | H | H | OCO₂Me | OSO₂Me | H | H | OCH₂C≡CH |
| OSO₂Me | H | H | OCOMe | OSO₂Me | H | H | OCO₂NMe₂ |
| OSO₂Me | H | H | OH | OSO₂Me | H | H | OEt |
| OSO₂Me | H | H | OPh | OSO₂Me | H | H | OMe |
| OSO₂Me | H | H | OSiMe₃ | OSO₂Me | H | H | OSiMe₂t-Bu |
| OSO₂Me | H | H | OSO₂Et | OSO₂Me | H | H | OSO₂Bn |
| OSO₂Me | H | H | OSO₂Me | OSO₂Me | H | H | OSO₂i-Pr |
| OSO₂Me | H | H | OSO₂n-Pr | OSO₂Me | H | H | OSO₂n-Bu |
| OSO₂Me | H | H | Ph | OSO₂Me | H | H | OSO₂Ph |
| OSO₂Me | H | H | SiMe₃ | OSO₂Me | H | H | SH |
| OSO₂Me | H | H | SO₂CF₃ | OSO₂Me | H | H | SMe |
| OSO₂Me | H | H | SOMe | OSO₂Me | H | H | SO₂Me |
| OSO₂Me | H | I | H | OSO₂Me | H | H | t-Bu |
| OSO₂Me | H | NO₂ | H | OSO₂Me | H | Me | H |
| OSO₂Me | H | OH | H | OSO₂Me | H | OCF₃ | H |
| OSO₂Me | H | OSO₂Bn | H | OSO₂Me | H | OMe | H |
| OSO₂Me | H | OSO₂i-Pr | H | OSO₂Me | H | OSO₂Et | H |
| OSO₂Me | H | OSO₂n-Bu | H | OSO₂Me | H | OSO₂Me | H |
| OSO₂Me | H | OSO₂Ph | H | OSO₂Me | H | OSO₂n-Pr | H |
| OSO₂Me | I | H | H | OSO₂Me | H | SO₂Me | H |
| OSO₂Me | —N=CH—CH=CH— | | F | OSO₂Me | Me | H | H |
| OSO₂Me | —N=CH—CH=CH— | | OSO₂Me | OSO₂Me | —N=CH—CH=CH— | | H |
| OSO₂Me | —N=CH—N=CH— | | H | OSO₂Me | —N=CH—N=CH— | | F |

TABLE 7

| X¹ | X² | X³ | X⁴ | X¹ | X² | X³ | X⁴ |
|---|---|---|---|---|---|---|---|
| OSO₂Me | —NH—CH=CH— | | F | OSO₂Me | —N=CH—N=CH— | | OSO₂Me |
| OSO₂Me | —NH—CH=CH— | | OSO₂Me | OSO₂Me | —NH—CH=CH— | | H |
| OSO₂Me | OCF₃ | H | H | OSO₂Me | NO₂ | H | H |
| OSO₂Me | —O—CH=CH— | | H | OSO₂Me | —O—CH=CH— | | F |
| OSO₂Me | —O—CH=N— | | F | OSO₂Me | —O—CH=CH— | | OSO₂Me |
| OSO₂Me | —O—CH=N— | | OSO₂Me | OSO₂Me | —O—CH=N— | | H |
| OSO₂Me | OMe | H | H | OSO₂Me | OH | H | H |

TABLE 7-continued

| X¹ | X² | X³ | X⁴ | X¹ | X² | X³ | X⁴ |
|---|---|---|---|---|---|---|---|
| OSO₂Me | OSO₂Et | H | H | OSO₂Me | OSO₂Bn | H | H |
| OSO₂Me | OSO₂i-Pr | H | H | OSO₂Me | OSO₂i-Pr | H | H |
| OSO₂Me | OSO₂Me | OSO₂Me | H | OSO₂Me | OSO₂Me | H | OSO₂Me |
| OSO₂Me | OSO₂n-Bu | H | H | OSO₂Me | OSO₂Me | OSO₂Me | OSO₂Me |
| OSO₂Me | OSO₂Ph | H | H | OSO₂Me | OSO₂n-Pr | H | H |
| OSO₂Me | —S—CH═CH— | | H | OSO₂Me | —S—CH═CH— | | F |
| OSO₂Me | SO₂Me | H | H | OSO₂Me | —S—CH═CH— | | OSO₂Me |
| OSO₂n-Bu | H | H | Cl | OSO₂n-Bu | H | H | Br |
| OSO₂n-Bu | H | H | c-Pr | OSO₂n-Bu | H | H | CN |
| OSO₂n-Bu | H | H | F | OSO₂n-Bu | H | H | Et |
| OSO₂n-Bu | H | H | I | OSO₂n-Bu | H | H | H |
| OSO₂n-Bu | H | H | n-Bu | OSO₂n-Bu | H | H | Me |
| OSO₂n-Bu | H | H | n-Pr | OSO₂n-Bu | H | H | NO₂ |
| OSO₂n-Bu | H | H | OCHF₂ | OSO₂n-Bu | H | H | OCF₃ |
| OSO₂n-Bu | H | H | OEt | OSO₂n-Bu | H | H | Oc-Pr |
| OSO₂n-Bu | H | H | OMe | OSO₂n-Bu | H | H | OH |
| OSO₂n-Bu | H | H | On-Pr | OSO₂n-Bu | H | H | On-Bu |
| OSO₂n-Bu | H | H | t-Bu | OSO₂n-Bu | H | H | Ot-Bu |
| OSO₂n-Pr | H | H | Cl | OSO₂n-Pr | H | H | Br |
| OSO₂n-Pr | H | H | c-Pr | OSO₂n-Pr | H | H | CN |
| OSO₂n-Pr | H | H | F | OSO₂n-Pr | H | H | Et |
| OSO₂n-Pr | H | H | I | OSO₂n-Pr | H | H | H |
| OSO₂n-Pr | H | H | n-Bu | OSO₂n-Pr | H | H | Me |
| OSO₂n-Pr | H | H | n-Pr | OSO₂n-Pr | H | H | NO₂ |
| OSO₂n-Pr | H | H | OCHF₂ | OSO₂n-Pr | H | H | OCF₃ |
| OSO₂n-Pr | H | H | OEt | OSO₂n-Pr | H | H | Oc-Pr |
| OSO₂n-Pr | H | H | OMe | OSO₂n-Pr | H | H | OH |

TABLE 8

| X¹ | X² | X³ | X⁴ | X¹ | X² | X³ | X⁴ |
|---|---|---|---|---|---|---|---|
| OSO₂n-Pr | H | H | On-Pr | OSO₂n-Pr | H | H | On-Bu |
| OSO₂n-Pr | H | H | t-Bu | OSO₂n-Pr | H | H | Ot-Bu |
| Ph | H | H | H | OSO₂Ph | H | H | H |
| SiMe₃ | H | H | H | SH | H | H | H |
| SO₂CF₃ | H | H | H | SMe | H | H | H |
| SO₂Me | H | H | SO₂Me | SO₂Me | H | H | H |
| t-Bu | H | H | H | SOMe | H | H | H |

TABLE 9

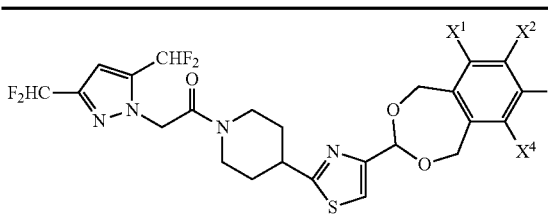

| X¹ | X² | X³ | X⁴ |
|---|---|---|---|
| Br | H | H | Br |
| C(═NOMe)H | H | H | H |
| C≡CH | H | H | H |
| CF₃ | H | H | CF₃ |
| CH═CH₂ | H | H | H |
| CH₂NMe₂ | H | H | H |
| CH₂SMe | H | H | H |
| Cl | Cl | Cl | Cl |
| Cl | Cl | H | H |
| Cl | H | H | Cl |
| CN | H | H | CN |
| CO₂H | H | H | H |
| c-Pr | H | H | H |
| F | Br | H | F |
| F | C(═NOMe)H | H | F |
| F | CF₃ | H | F |
| F | Cl | H | F |
| F | CN | H | F |
| F | F | F | F |

TABLE 9-continued

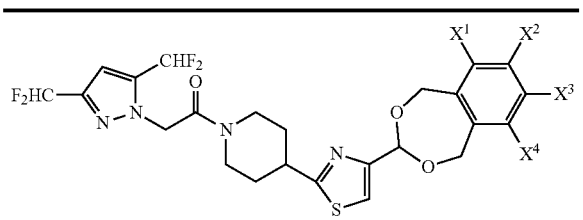

| X¹ | X² | X³ | X⁴ |
|---|---|---|---|
| F | F | C(═NOMe)H | H |
| F | H | CF₃ | H |
| F | H | CN | H |
| F | H | H | Bn |
| F | H | H | C(═NOMe)H |
| F | H | H | C≡CH |
| F | H | H | CF₃ |
| F | H | H | CH₂CN |
| F | H | H | CH₂OMe |
| F | H | H | H |
| Bn | H | H | H |
| Br | H | H | H |
| C(═NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |
| Cl | H | Cl | H |
| Cl | H | H | H |
| CN | H | H | H |
| CO₂Me | H | H | H |
| Et | H | H | H |
| F | Br | H | H |
| F | C(═NOMe)Me | H | H |
| F | CF₃ | H | H |
| F | Cl | H | H |
| F | CN | H | H |
| F | F | H | H |
| F | H | Br | H |
| F | H | C(═NOMe)Me | H |
| F | H | Cl | H |

TABLE 9-continued

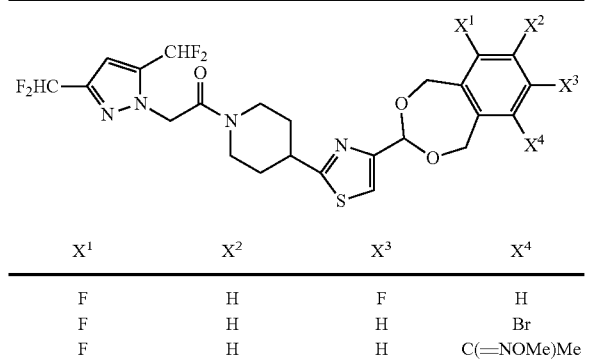

| X¹ | X² | X³ | X⁴ |
|---|---|---|---|
| F | H | F | H |
| F | H | H | Br |
| F | H | H | C(=NOMe)Me |

TABLE 9-continued

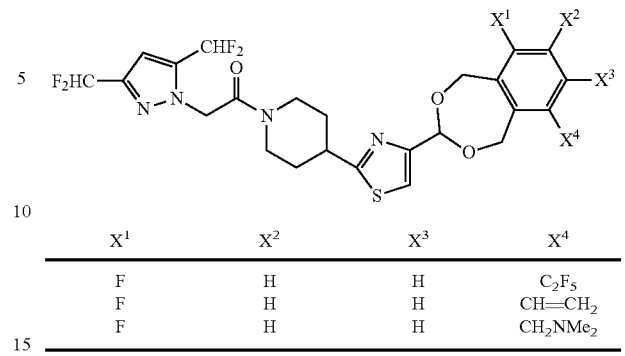

| X¹ | X² | X³ | X⁴ |
|---|---|---|---|
| F | H | H | $C_2F_5$ |
| F | H | H | CH=$CH_2$ |
| F | H | H | $CH_2NMe_2$ |

TABLE 10

| X¹ | X² | X³ | X⁴ | X¹ | X² | X³ | X⁴ |
|---|---|---|---|---|---|---|---|
| F | H | H | CHO | F | H | H | $CH_2SMe$ |
| F | H | H | CN | F | H | H | Cl |
| F | H | H | $CO_2Me$ | F | H | H | $CO_2H$ |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | $NH_2$ | F | H | H | n-Bu |
| F | H | H | NHCOMe | F | H | H | $NHCO_2Me$ |
| F | H | H | $NHSO_2Me$ | F | H | H | NHMe |
| F | H | H | $NO_2$ | F | H | H | $NMe_2$ |
| F | H | H | $OCF_3$ | F | H | H | n-Pr |
| F | H | H | $OCO_2Me$ | F | H | H | $OCH_2C\equiv CH$ |
| F | H | H | OCOMe | F | H | H | $OCO_2NMe_2$ |
| F | H | H | OH | F | H | H | OEt |
| F | H | H | OPh | F | H | H | OMe |
| F | H | H | $OSiMe_3$ | F | H | H | $OSiMe_2t$-Bu |
| F | H | H | SH | F | H | H | Ph |
| F | H | H | SMe | F | H | H | $SiMe_3$ |
| F | H | H | $SO_2Me$ | F | H | H | $SO_2CF_3$ |
| F | H | H | t-Bu | F | H | H | SOMe |
| F | H | Me | H | F | H | I | H |
| F | H | $OCF_3$ | H | F | H | $NO_2$ | H |
| F | H | OMe | H | F | H | OH | H |
| F | H | $SO_2Me$ | H | F | H | $OSO_2Me$ | H |
| F | I | H | H | F | I | H | F |
| F | Me | H | H | F | Me | H | F |
| F | $NO_2$ | H | H | F | $NO_2$ | H | F |
| F | $OCF_3$ | H | H | F | $OCF_3$ | H | F |
| F | OH | H | H | F | OH | H | F |
| F | OMe | H | H | F | OMe | H | F |
| F | $SO_2Me$ | H | F | F | $OSO_2Me$ | H | F |
| H | Br | Br | H | F | $SO_2Me$ | H | H |
| H | C(=NOMe)H | H | H | H | Br | H | H |

TABLE 11

| X¹ | X² | X³ | X⁴ | X¹ | X² | X³ | X⁴ |
|---|---|---|---|---|---|---|---|
| H | $CF_3$ | $CF_3$ | H | H | C(=NOMe)Me | H | H |
| H | —CH=CH—CH=CH— | | H | H | $CF_3$ | H | H |
| H | —$CH_2CH_2CH_2$— | | H | H | —CH=N—CH=CH— | | H |
| H | Cl | Cl | H | H | —$CH_2CH_2CH_2CH_2$— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |
| H | —NH—CH=CH— | | H | H | —N=CH—N=CH— | | H |
| H | $NO_2$ | $NO_2$ | H | H | $NO_2$ | H | H |
| H | $OCF_3$ | $OCF_3$ | H | H | $OCF_3$ | H | H |
| H | —O—CH=N— | | H | H | —O—CH=CH— | | H |
| H | OH | OH | H | H | OH | H | H |
| H | OMe | OMe | H | H | OMe | H | H |
| H | $OSO_2Et$ | H | H | H | $OSO_2Bn$ | H | H |

TABLE 11-continued

| X¹ | X² | X³ | X⁴ | X¹ | X² | X³ | X⁴ |
|---|---|---|---|---|---|---|---|
| H | OSO₂Me | H | H | H | OSO₂i-Pr | H | H |
| H | OSO₂n-Bu | H | H | H | OSO₂Me | OSO₂Me | H |
| H | OSO₂Ph | H | H | H | OSO₂n-Pr | H | H |
| H | SO₂Me | H | H | H | —S—CH=CH— | | H |
| I | H | H | H | H | SO₂Me | SO₂Me | H |
| i-Pr | H | H | H | i-Bu | H | H | H |
| Me | H | H | Me | Me | H | H | H |
| NH₂ | H | H | H | n-Bu | H | H | H |
| NHCOMe | H | H | H | NHCO₂Me | H | H | H |
| NHSO₂Me | H | H | H | NHMe | H | H | H |
| NO₂ | H | H | H | NMe₂ | H | H | H |
| OCF₃ | H | H | H | n-Pr | H | H | H |
| OCH₂C≡CH | H | H | H | OCF₃ | H | H | OCF₃ |
| OCO₂NMe₂ | H | H | H | OCO₂Me | H | H | H |
| OEt | H | H | H | OCOMe | H | H | H |
| OMe | H | H | H | OH | H | H | H |
| OPh | H | H | H | OMe | H | H | OMe |
| OSiMe₃ | H | H | H | OSiMe₂t-Bu | H | H | H |

TABLE 12

| X¹ | X² | X³ | X⁴ |
|---|---|---|---|
| OSO₂CF₃ | H | H | Br |
| OSO₂CF₃ | H | H | CN |
| OSO₂CF₃ | H | H | Et |
| OSO₂CF₃ | H | H | H |
| OSO₂CF₃ | H | H | Me |
| OSO₂CF₃ | H | H | NO₂ |
| OSO₂CF₃ | H | H | OCF₃ |
| OSO₂CF₃ | H | H | Oc-Pr |
| OSO₂CF₃ | H | H | OH |
| OSO₂CF₃ | H | H | On-Bu |
| OSO₂CF₃ | H | H | Ot-Bu |
| OSO₂CHF₂ | H | H | Br |
| OSO₂CHF₂ | H | H | CN |
| OSO₂CHF₂ | H | H | Et |
| OSO₂CHF₂ | H | H | H |
| OSO₂CHF₂ | H | H | Me |
| OSO₂CHF₂ | H | H | NO₂ |
| OSO₂CHF₂ | H | H | OCF₃ |
| OSO₂CHF₂ | H | H | Oc-Pr |
| OSO₂CHF₂ | H | H | OH |
| OSO₂CHF₂ | H | H | On-Bu |
| OSO₂CHF₂ | H | H | Ot-Bu |
| OSO₂Et | H | H | Br |
| OSO₂Et | H | H | Cl |
| OSO₂Et | H | H | c-Pr |
| OSO₂Et | H | H | F |
| OSO₂Et | H | H | I |
| OSO₂Et | H | H | n-Bu |
| OSO₂Et | H | H | n-Pr |
| OSO₂Et | H | H | OCHF₂ |
| OSO₂Et | H | H | OEt |
| OSO₂Et | H | H | OMe |
| OSO₂Et | H | H | On-Pr |
| OSO₂Et | H | H | t-Bu |
| OSO₂Bn | H | H | H |
| OSO₂CF₃ | H | H | Cl |
| OSO₂CF₃ | H | H | c-Pr |
| OSO₂CF₃ | H | H | F |
| OSO₂CF₃ | H | H | I |
| OSO₂CF₃ | H | H | n-Bu |
| OSO₂CF₃ | H | H | n-Pr |
| OSO₂CF₃ | H | H | OCHF₂ |
| OSO₂CF₃ | H | H | OEt |
| OSO₂CF₃ | H | H | OMe |
| OSO₂CF₃ | H | H | On-Pr |
| OSO₂CF₃ | H | H | t-Bu |
| OSO₂CHF₂ | H | H | Cl |
| OSO₂CHF₂ | H | H | c-Pr |
| OSO₂CHF₂ | H | H | F |
| OSO₂CHF₂ | H | H | I |
| OSO₂CHF₂ | H | H | n-Bu |
| OSO₂CHF₂ | H | H | n-Pr |
| OSO₂CHF₂ | H | H | OCHF₂ |
| OSO₂CHF₂ | H | H | OEt |
| OSO₂CHF₂ | H | H | OMe |
| OSO₂CHF₂ | H | H | On-Pr |
| OSO₂CHF₂ | H | H | t-Bu |
| OSO₂Et | H | H | CF₃ |
| OSO₂Et | H | H | CN |
| OSO₂Et | H | H | Et |
| OSO₂Et | H | H | H |
| OSO₂Et | H | H | Me |
| OSO₂Et | H | H | NO₂ |
| OSO₂Et | H | H | OCF₃ |
| OSO₂Et | H | H | Oc-Pr |
| OSO₂Et | H | H | OH |
| OSO₂Et | H | H | On-Bu |
| OSO₂Et | H | H | Ot-Bu |

TABLE 13

| X¹ | X² | X³ | X⁴ |
|---|---|---|---|
| OSO₂i-Pr | H | H | CF₃ |
| OSO₂i-Pr | H | H | CN |
| OSO₂i-Pr | H | H | Et |
| OSO₂i-Pr | H | H | H |
| OSO₂i-Pr | H | H | Me |
| OSO₂i-Pr | H | H | NO₂ |
| OSO₂i-Pr | H | H | OCF₃ |
| OSO₂i-Pr | H | H | Oc-Pr |
| OSO₂i-Pr | H | H | OH |
| OSO₂i-Pr | H | H | On-Bu |
| OSO₂i-Pr | H | H | Ot-Bu |
| OSO₂Me | Br | H | H |
| OSO₂Me | C(=NOMe)Me | H | H |
| OSO₂Me | —CH=CH—CH=CH— | | F |
| OSO₂Me | —CH=CH—CH=CH— | | OSO₂Me |
| OSO₂Me | —CH=N—CH=CH— | | H |
| OSO₂Me | —CH₂CH₂CH₂— | | F |
| OSO₂Me | —CH₂CH₂CH₂— | | OSO₂Me |
| OSO₂Me | —CH₂CH₂CH₂CH₂— | | H |
| OSO₂Me | Cl | H | H |
| OSO₂Me | F | F | F |
| OSO₂Me | F | H | F |
| OSO₂Me | H | Br | H |
| OSO₂Me | H | C(=NOMe)Me | H |
| OSO₂Me | H | Cl | H |
| OSO₂Me | H | F | F |
| OSO₂Me | H | H | Bn |
| OSO₂Me | H | H | C(=NOMe)H |
| OSO₂Me | H | H | C≡CH |

TABLE 13-continued

| $X^1$ | $X^2$ | $X^3$ | $X^4$ |
|---|---|---|---|
| OSO$_2$Me | H | H | CF$_3$ |
| OSO$_2$Me | H | H | CH$_2$CN |
| OSO$_2$Me | H | H | CH$_2$OMe |
| OSO$_2$Me | H | H | CHO |
| OSO$_2$Me | H | H | CN |
| OSO$_2$i-Pr | H | H | Br |
| OSO$_2$i-Pr | H | H | Cl |
| OSO$_2$i-Pr | H | H | c-Pr |
| OSO$_2$i-Pr | H | H | F |
| OSO$_2$i-Pr | H | H | I |
| OSO$_2$i-Pr | H | H | n-Bu |
| OSO$_2$i-Pr | H | H | n-Pr |
| OSO$_2$i-Pr | H | H | OCHF$_2$ |
| OSO$_2$i-Pr | H | H | OEt |
| OSO$_2$i-Pr | H | H | OMe |
| OSO$_2$i-Pr | H | H | On-Pr |
| OSO$_2$i-Pr | H | H | t-Bu |
| OSO$_2$Me | C(=NOMe)H | H | H |
| OSO$_2$Me | CF$_3$ | H | H |
| OSO$_2$Me | —CH=CH—CH=CH— | | H |
| OSO$_2$Me | —CH=N—CH=CH— | | F |
| OSO$_2$Me | —CH=N—CH=CH— | | OSO$_2$Me |
| OSO$_2$Me | —CH$_2$CH$_2$CH$_2$— | | H |
| OSO$_2$Me | —CH$_2$CH$_2$CH$_2$CH$_2$— | | F |
| OSO$_2$Me | —CH$_2$CH$_2$CH$_2$CH$_2$— | | OSO$_2$Me |
| OSO$_2$Me | CN | H | H |
| OSO$_2$Me | F | F | OSO$_2$Me |
| OSO$_2$Me | F | H | H |
| OSO$_2$Me | H | C(=NOMe)H | H |
| OSO$_2$Me | H | CF$_3$ | H |
| OSO$_2$Me | H | CN | H |
| OSO$_2$Me | H | F | H |
| OSO$_2$Me | H | H | Br |
| OSO$_2$Me | H | H | C(=NOMe)Me |
| OSO$_2$Me | H | H | C$_2$F$_5$ |
| OSO$_2$Me | H | H | CH=CH$_2$ |
| OSO$_2$Me | H | H | CH$_2$NMe$_2$ |
| OSO$_2$Me | H | H | CH$_2$SMe |
| OSO$_2$Me | H | H | Cl |

TABLE 14

| $X^1$ | $X^2$ | $X^3$ | $X^4$ |
|---|---|---|---|
| OSO$_2$Me | H | H | CO$_2$Me |
| OSO$_2$Me | H | H | Et |
| OSO$_2$Me | H | H | H |
| OSO$_2$Me | H | H | I |
| OSO$_2$Me | H | H | i-Pr |
| OSO$_2$Me | H | H | n-Bu |
| OSO$_2$Me | H | H | NHCO$_2$Me |
| OSO$_2$Me | H | H | NHMe |
| OSO$_2$Me | H | H | NMe$_2$ |
| OSO$_2$Me | H | H | n-Pr |
| OSO$_2$Me | H | H | OCHF$_2$ |
| OSO$_2$Me | H | H | OCO$_2$Me |
| OSO$_2$Me | H | H | OCOMe |
| OSO$_2$Me | H | H | OH |
| OSO$_2$Me | H | H | OPh |
| OSO$_2$Me | H | H | OSiMe$_3$ |
| OSO$_2$Me | H | H | OSO$_2$Et |
| OSO$_2$Me | H | H | OSO$_2$Me |
| OSO$_2$Me | H | H | OSO$_2$n-Pr |
| OSO$_2$Me | H | H | Ph |
| OSO$_2$Me | H | H | SiMe$_3$ |
| OSO$_2$Me | H | H | SO$_2$CF$_3$ |
| OSO$_2$Me | H | H | SOMe |
| OSO$_2$Me | H | I | H |
| OSO$_2$Me | H | NO$_2$ | H |
| OSO$_2$Me | H | OH | H |
| OSO$_2$Me | H | OSO$_2$Bn | H |
| OSO$_2$Me | H | OSO$_2$i-Pr | H |
| OSO$_2$Me | H | OSO$_2$n-Bu | H |
| OSO$_2$Me | H | OSO$_2$Ph | H |
| OSO$_2$Me | I | H | H |

TABLE 14-continued

| $X^1$ | $X^2$ | $X^3$ | $X^4$ |
|---|---|---|---|
| OSO$_2$Me | —N=CH—CH=CH— | | F |
| OSO$_2$Me | —N=CH—CH=CH— | | OSO$_2$Me |
| OSO$_2$Me | —N=CH—N=CH— | | H |
| OSO$_2$Me | H | H | CO$_2$H |
| OSO$_2$Me | H | H | c-Pr |
| OSO$_2$Me | H | H | F |
| OSO$_2$Me | H | H | H |
| OSO$_2$Me | H | H | i-Bu |
| OSO$_2$Me | H | H | Me |
| OSO$_2$Me | H | H | NH$_2$ |
| OSO$_2$Me | H | H | NHCOMe |
| OSO$_2$Me | H | H | NHSO$_2$Me |
| OSO$_2$Me | H | H | NO$_2$ |
| OSO$_2$Me | H | H | OCF$_3$ |
| OSO$_2$Me | H | H | OCH$_2$C≡CH |
| OSO$_2$Me | H | H | OCO$_2$NMe$_2$ |
| OSO$_2$Me | H | H | OEt |
| OSO$_2$Me | H | H | OMe |
| OSO$_2$Me | H | H | OSiMe$_2$t-Bu |
| OSO$_2$Me | H | H | OSO$_2$Bn |
| OSO$_2$Me | H | H | OSO$_2$i-Pr |
| OSO$_2$Me | H | H | OSO$_2$n-Bu |
| OSO$_2$Me | H | H | OSO$_2$Ph |
| OSO$_2$Me | H | H | SH |
| OSO$_2$Me | H | H | SMe |
| OSO$_2$Me | H | H | SO$_2$Me |
| OSO$_2$Me | H | H | t-Bu |
| OSO$_2$Me | H | Me | H |
| OSO$_2$Me | H | OCF$_3$ | H |
| OSO$_2$Me | H | OMe | H |
| OSO$_2$Me | H | OSO$_2$Et | H |
| OSO$_2$Me | H | OSO$_2$Me | H |
| OSO$_2$Me | H | OSO$_2$n-Pr | H |
| OSO$_2$Me | H | SO$_2$Me | H |
| OSO$_2$Me | Me | H | H |
| OSO$_2$Me | —N=CH—CH=CH— | | H |
| OSO$_2$Me | —N=CH—N=CH— | | F |

TABLE 15

| $X^1$ | $X^2$ | $X^3$ | $X^4$ |
|---|---|---|---|
| OSO$_2$Me | —NH—CH=CH— | | F |
| OSO$_2$Me | —NH—CH=CH— | | OSO$_2$Me |
| OSO$_2$Me | OCF$_3$ | H | H |
| OSO$_2$Me | —O—CH=CH— | | H |
| OSO$_2$Me | —O—CH=N— | | F |
| OSO$_2$Me | —O—CH=N— | | OSO$_2$Me |
| OSO$_2$Me | OMe | H | H |
| OSO$_2$Me | OSO$_2$Et | H | H |
| OSO$_2$Me | OSO$_2$Me | H | H |
| OSO$_2$Me | OSO$_2$Me | OSO$_2$Me | H |
| OSO$_2$Me | OSO$_2$n-Bu | H | H |
| OSO$_2$Me | OSO$_2$Ph | H | H |
| OSO$_2$Me | —S—CH=CH— | | H |
| OSO$_2$Me | SO$_2$Me | H | H |
| OSO$_2$n-Bu | H | H | Cl |
| OSO$_2$n-Bu | H | H | c-Pr |
| OSO$_2$n-Bu | H | H | F |
| OSO$_2$n-Bu | H | H | I |
| OSO$_2$n-Bu | H | H | n-Bu |
| OSO$_2$n-Bu | H | H | n-Pr |
| OSO$_2$n-Bu | H | H | OCHF$_2$ |
| OSO$_2$n-Bu | H | H | OEt |
| OSO$_2$n-Bu | H | H | OMe |
| OSO$_2$n-Bu | H | H | On-Pr |
| OSO$_2$n-Bu | H | H | t-Bu |
| OSO$_2$n-Pr | H | H | Cl |
| OSO$_2$n-Pr | H | H | c-Pr |
| OSO$_2$n-Pr | H | H | F |
| OSO$_2$n-Pr | H | H | I |
| OSO$_2$n-Pr | H | H | n-Bu |
| OSO$_2$n-Pr | H | H | n-Pr |
| OSO$_2$n-Pr | H | H | OCHF$_2$ |
| OSO$_2$n-Pr | H | H | OEt |

TABLE 15-continued

| $X^1$ | $X^2$ | $X^3$ | $X^4$ |
|---|---|---|---|
| OSO$_2$n-Pr | H | H | OMe |
| OSO$_2$Me | —N=CH—N=CH— | | OSO$_2$Me |
| OSO$_2$Me | —NH—CH=CH— | | H |
| OSO$_2$Me | NO$_2$ | H | H |
| OSO$_2$Me | —O—CH=CH— | | F |
| OSO$_2$Me | —O—CH=CH— | | OSO$_2$Me |
| OSO$_2$Me | —O—CH=N— | | H |
| OSO$_2$Me | OH | H | H |
| OSO$_2$Me | OSO$_2$Bn | H | H |
| OSO$_2$Me | OSO$_2$i-Pr | H | H |
| OSO$_2$Me | OSO$_2$Me | H | OSO$_2$Me |
| OSO$_2$Me | OSO$_2$Me | OSO$_2$Me | OSO$_2$Me |
| OSO$_2$Me | OSO$_2$n-Pr | H | H |
| OSO$_2$Me | —S—CH=CH— | | F |
| OSO$_2$Me | —S—CH=CH— | | OSO$_2$Me |
| OSO$_2$n-Bu | H | H | Br |
| OSO$_2$n-Bu | H | H | CN |
| OSO$_2$n-Bu | H | H | Et |
| OSO$_2$n-Bu | H | H | H |
| OSO$_2$n-Bu | H | H | Me |
| OSO$_2$n-Bu | H | H | NO$_2$ |
| OSO$_2$n-Bu | H | H | OCF$_3$ |
| OSO$_2$n-Bu | H | H | Oc-Pr |
| OSO$_2$n-Bu | H | H | OH |
| OSO$_2$n-Bu | H | H | On-Bu |
| OSO$_2$n-Bu | H | H | Ot-Bu |
| OSO$_2$n-Pr | H | H | Br |
| OSO$_2$n-Pr | H | H | CN |
| OSO$_2$n-Pr | H | H | Et |
| OSO$_2$n-Pr | H | H | H |
| OSO$_2$n-Pr | H | H | Me |
| OSO$_2$n-Pr | H | H | NO$_2$ |
| OSO$_2$n-Pr | H | H | OCF$_3$ |
| OSO$_2$n-Pr | H | H | Oc-Pr |
| OSO$_2$n-Pr | H | H | OH |

TABLE 16

| $X^1$ | $X^2$ | $X^3$ | $X^4$ |
|---|---|---|---|
| OSO$_2$n-Pr | H | H | On-Pr |
| OSO$_2$n-Pr | H | H | t-Bu |
| Ph | H | H | H |
| SiMe$_3$ | H | H | H |
| SO$_2$CF$_3$ | H | H | H |
| SO$_2$Me | H | H | SO$_2$Me |
| t-Bu | H | H | H |
| OSO$_2$n-Pr | H | H | On-Bu |
| OSO$_2$n-Pr | H | H | Ot-Bu |
| OSO$_2$Ph | H | H | H |
| SH | H | H | H |
| SMe | H | H | H |
| SO$_2$Me | H | H | H |
| SOMe | H | H | H |

TABLE 17

| $X^1$ | $X^2$ | $X^3$ | $X^4$ |
|---|---|---|---|
| Br | H | H | Br |
| C(=NOMe)H | H | H | H |
| C≡CH | H | H | H |
| CF$_3$ | H | H | CF$_3$ |

TABLE 17-continued

| $X^1$ | $X^2$ | $X^3$ | $X^4$ |
|---|---|---|---|
| CH=CH$_2$ | H | H | H |
| CH$_2$NMe$_2$ | H | H | H |
| CH$_2$SMe | H | H | H |
| Cl | Cl | Cl | Cl |
| Cl | Cl | H | H |
| Cl | H | H | Cl |
| CN | H | H | CN |
| CO$_2$H | H | H | H |
| c-Pr | H | H | H |
| F | Br | H | F |
| F | C(=NOMe)H | H | H |
| F | CF$_3$ | H | F |
| F | Cl | H | F |
| F | CN | H | F |
| F | F | F | F |
| F | F | H | H |
| F | H | C(=NOMe)H | H |
| F | H | CF$_3$ | H |
| F | H | CN | H |
| F | H | H | Bn |
| F | H | H | C(=NOMe)H |
| F | H | H | C≡CH |
| F | H | H | CF$_3$ |
| F | H | H | CH$_2$CN |
| F | H | H | CH$_2$OMe |
| Bn | H | H | H |
| Br | H | H | H |
| C(=NOMe)Me | H | H | H |
| C$_2$F$_5$ | H | H | H |
| CF$_3$ | H | H | H |
| CH$_2$CN | H | H | H |
| CH$_2$OMe | H | H | H |
| CHO | H | H | H |
| Cl | Cl | Cl | H |
| Cl | H | Cl | H |
| Cl | H | H | H |
| CN | H | H | H |
| CO$_2$Me | H | H | H |
| Et | H | H | H |
| F | Br | H | H |
| F | C(=NOMe)Me | H | H |
| F | CF$_3$ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C$_2$F$_5$ |
| F | H | H | CH=CH$_2$ |
| F | H | H | CH$_2$NMe$_2$ |

TABLE 18

| $X^1$ | $X^2$ | $X^3$ | $X^4$ |
|---|---|---|---|
| F | H | H | CHO |
| F | H | H | CN |
| F | H | H | CO$_2$Me |
| F | H | H | Et |
| F | H | H | H |
| F | H | H | i-Bu |

TABLE 18-continued

| X¹ | X² | X³ | X⁴ |
|---|---|---|---|
| F | H | H | Me |
| F | H | H | $NH_2$ |
| F | H | H | NHCOMe |
| F | H | H | $NHSO_2Me$ |
| F | H | H | $NO_2$ |
| F | H | H | $OCF_3$ |
| F | H | H | $OCO_2Me$ |
| F | H | H | OCOMe |
| F | H | H | OH |
| F | H | H | OPh |
| F | H | H | $OSiMe_3$ |
| F | H | H | SH |
| F | H | H | SMe |
| F | H | H | $SO_2Me$ |
| F | H | H | t-Bu |
| F | H | Me | H |
| F | H | $OCF_3$ | H |
| F | H | OMe | H |
| F | H | $SO_2Me$ | H |
| F | I | H | H |
| F | Me | H | H |
| F | $NO_2$ | H | H |
| F | $OCF_3$ | H | H |
| F | OH | H | H |
| F | OMe | H | H |
| F | $SO_2Me$ | H | F |
| H | Br | Br | H |
| H | C(=NOMe)H | H | H |
| F | H | H | $CH_2SMe$ |
| F | H | H | Cl |
| F | H | H | $CO_2H$ |
| F | H | H | c-Pr |
| F | H | H | F |
| F | H | H | I |
| F | H | H | i-Pr |
| F | H | H | n-Bu |
| F | H | H | $NHCO_2Me$ |
| F | H | H | NHMe |
| F | H | H | $NMe_2$ |
| F | H | H | n-Pr |
| F | H | H | $OCH_2C≡CH$ |
| F | H | H | $OCO_2NMe_2$ |
| F | H | H | OEt |
| F | H | H | OMe |
| F | H | H | $OSiMe_2t$-Bu |
| F | H | H | Ph |
| F | H | H | $SiMe_3$ |
| F | H | H | $SO_2CF_3$ |
| F | H | H | SOMe |
| F | H | I | H |
| F | H | $NO_2$ | H |
| F | H | OH | H |
| F | H | $OSO_2Me$ | H |
| F | I | H | F |
| F | Me | H | F |
| F | $NO_2$ | H | F |
| F | $OCF_3$ | H | F |
| F | OH | H | F |
| F | OMe | H | F |
| F | $OSO_2Me$ | H | F |
| F | $SO_2Me$ | H | H |
| H | Br | H | H |

TABLE 19

| X¹ | X² | X³ | X⁴ |
|---|---|---|---|
| H | $CF_3$ | $CF_3$ | H |
| H | —CH=CH—CH=CH— | | H |
| H | —$CH_2CH_2CH_2$— | | H |
| H | Cl | Cl | H |
| H | CN | H | H |
| H | F | H | H |
| H | I | H | H |
| H | Me | H | H |

TABLE 19-continued

| X¹ | X² | X³ | X⁴ |
|---|---|---|---|
| H | —N=CH—CH=CH— | | H |
| H | —NH—CH=CH— | | H |
| H | $NO_2$ | $NO_2$ | H |
| H | $OCF_3$ | $OCF_3$ | H |
| H | —O—CH=N— | | H |
| H | OH | OH | H |
| H | OMe | OMe | H |
| H | $OSO_2Et$ | H | H |
| H | $OSO_2Me$ | H | H |
| H | $OSO_2n$-Bu | H | H |
| H | $OSO_2Ph$ | H | H |
| H | $SO_2Me$ | H | H |
| I | H | H | H |
| i-Pr | H | H | H |
| Me | H | H | Me |
| $NH_2$ | H | H | H |
| NHCOMe | H | H | H |
| $NHSO_2Me$ | H | H | H |
| $NO_2$ | H | H | H |
| $OCF_3$ | H | H | H |
| $OCH_2C≡CH$ | H | H | H |
| $OCO_2NMe_2$ | H | H | H |
| OEt | H | H | H |
| OMe | H | H | H |
| OPh | H | H | H |
| $OSiMe_3$ | H | H | H |
| H | C(=NOMe)Me | H | H |
| H | $CF_3$ | H | H |
| H | —CH=N—CH=CH— | | H |
| H | —$CH_2CH_2CH_2CH_2$— | | H |
| H | CN | CN | H |
| H | F | F | H |
| H | I | I | H |
| H | Me | Me | H |
| H | —N=CH—N=CH— | | H |
| H | $NO_2$ | H | H |
| H | $OCF_3$ | H | H |
| H | —O—CH=CH— | | H |
| H | OH | H | H |
| H | OMe | H | H |
| H | $OSO_2Bn$ | H | H |
| H | $OSO_2i$-Pr | H | H |
| H | $OSO_2Me$ | $OSO_2Me$ | H |
| H | $OSO_2n$-Pr | H | H |
| H | —S—CH=CH— | | H |
| H | $SO_2Me$ | $SO_2Me$ | H |
| i-Bu | H | H | H |
| Me | H | H | H |
| n-Bu | H | H | H |
| $NHCO_2Me$ | H | H | H |
| NHMe | H | H | H |
| $NMe_2$ | H | H | H |
| n-Pr | H | H | H |
| $OCF_3$ | H | H | $OCF_3$ |
| $OCO_2Me$ | H | H | H |
| OCOMe | H | H | H |
| OH | H | H | H |
| OMe | H | H | OMe |
| $OSiMe_2t$-Bu | H | H | H |

TABLE 20

| X¹ | X² | X³ | X⁴ |
|---|---|---|---|
| $OSO_2CF_3$ | H | H | Br |
| $OSO_2CF_3$ | H | H | CN |
| $OSO_2CF_3$ | H | H | Et |
| $OSO_2CF_3$ | H | H | H |
| $OSO_2CF_3$ | H | H | Me |
| $OSO_2CF_3$ | H | H | $NO_2$ |
| $OSO_2CF_3$ | H | H | $OCF_3$ |
| $OSO_2CF_3$ | H | H | Oc-Pr |
| $OSO_2CF_3$ | H | H | OH |
| $OSO_2CF_3$ | H | H | On-Bu |

TABLE 20-continued

| X¹ | X² | X³ | X⁴ |
|---|---|---|---|
| OSO₂CF₃ | H | H | Ot-Bu |
| OSO₂CHF₂ | H | H | Br |
| OSO₂CHF₂ | H | H | CN |
| OSO₂CHF₂ | H | H | Et |
| OSO₂CHF₂ | H | H | H |
| OSO₂CHF₂ | H | H | Me |
| OSO₂CHF₂ | H | H | NO₂ |
| OSO₂CHF₂ | H | H | OCF₃ |
| OSO₂CHF₂ | H | H | Oc-Pr |
| OSO₂CHF₂ | H | H | OH |
| OSO₂CHF₂ | H | H | On-Bu |
| OSO₂CHF₂ | H | H | Ot-Bu |
| OSO₂Et | H | H | Br |
| OSO₂Et | H | H | Cl |
| OSO₂Et | H | H | c-Pr |
| OSO₂Et | H | H | F |
| OSO₂Et | H | H | I |
| OSO₂Et | H | H | n-Bu |
| OSO₂Et | H | H | n-Pr |
| OSO₂Et | H | H | OCHF₂ |
| OSO₂Et | H | H | OEt |
| OSO₂Et | H | H | OMe |
| OSO₂Et | H | H | On-Pr |
| OSO₂Et | H | H | t-Bu |
| OSO₂Bn | H | H | H |
| OSO₂CF₃ | H | H | Cl |
| OSO₂CF₃ | H | H | c-Pr |
| OSO₂CF₃ | H | H | F |
| OSO₂CF₃ | H | H | I |
| OSO₂CF₃ | H | H | n-Bu |
| OSO₂CF₃ | H | H | n-Pr |
| OSO₂CF₃ | H | H | OCHF₂ |
| OSO₂CF₃ | H | H | OEt |
| OSO₂CF₃ | H | H | OMe |
| OSO₂CF₃ | H | H | On-Pr |
| OSO₂CF₃ | H | H | t-Bu |
| OSO₂CHF₂ | H | H | Cl |
| OSO₂CHF₂ | H | H | c-Pr |
| OSO₂CHF₂ | H | H | F |
| OSO₂CHF₂ | H | H | I |
| OSO₂CHF₂ | H | H | n-Bu |
| OSO₂CHF₂ | H | H | n-Pr |
| OSO₂CHF₂ | H | H | OCHF₂ |
| OSO₂CHF₂ | H | H | OEt |
| OSO₂CHF₂ | H | H | OMe |
| OSO₂CHF₂ | H | H | On-Pr |
| OSO₂CHF₂ | H | H | t-Bu |
| OSO₂Et | H | H | CF₃ |
| OSO₂Et | H | H | CN |
| OSO₂Et | H | H | Et |
| OSO₂Et | H | H | H |
| OSO₂Et | H | H | Me |
| OSO₂Et | H | H | NO₂ |
| OSO₂Et | H | H | OCF₃ |
| OSO₂Et | H | H | Oc-Pr |
| OSO₂Et | H | H | OH |
| OSO₂Et | H | H | On-Bu |
| OSO₂Et | H | H | Ot-Bu |

TABLE 21

| X¹ | X² | X³ | X⁴ |
|---|---|---|---|
| OSO₂i-Pr | H | H | CF₃ |
| OSO₂i-Pr | H | H | CN |
| OSO₂i-Pr | H | H | Et |
| OSO₂i-Pr | H | H | H |
| OSO₂i-Pr | H | H | Me |
| OSO₂i-Pr | H | H | NO₂ |
| OSO₂i-Pr | H | H | OCF₃ |
| OSO₂i-Pr | H | H | Oc-Pr |
| OSO₂i-Pr | H | H | OH |
| OSO₂i-Pr | H | H | On-Bu |
| OSO₂i-Pr | H | H | Ot-Bu |
| OSO₂Me | Br | H | H |

TABLE 21-continued

| X¹ | X² | X³ | X⁴ |
|---|---|---|---|
| OSO₂Me | C(=NOMe)Me | H | H |
| OSO₂Me | —CH=CH—CH=CH— | | F |
| OSO₂Me | —CH=CH—CH=CH— | | OSO₂Me |
| OSO₂Me | —CH=N—CH=CH— | | H |
| OSO₂Me | —CH₂CH₂CH₂— | | F |
| OSO₂Me | —CH₂CH₂CH₂— | | OSO₂Me |
| OSO₂Me | —CH₂CH₂CH₂CH₂— | | H |
| OSO₂Me | Cl | H | H |
| OSO₂Me | F | F | F |
| OSO₂Me | F | H | F |
| OSO₂Me | H | Br | H |
| OSO₂Me | H | C(=NOMe)Me | H |
| OSO₂Me | H | Cl | H |
| OSO₂Me | H | F | F |
| OSO₂Me | H | H | Bn |
| OSO₂Me | H | H | C(=NOMe)H |
| OSO₂Me | H | H | C≡CH |
| OSO₂Me | H | H | CF₃ |
| OSO₂Me | H | H | CH₂CN |
| OSO₂Me | H | H | CH₂OMe |
| OSO₂Me | H | H | CHO |
| OSO₂Me | H | H | CN |
| OSO₂i-Pr | H | H | Br |
| OSO₂i-Pr | H | H | Cl |
| OSO₂i-Pr | H | H | c-Pr |
| OSO₂i-Pr | H | H | F |
| OSO₂i-Pr | H | H | I |
| OSO₂i-Pr | H | H | n-Bu |
| OSO₂i-Pr | H | H | n-Pr |
| OSO₂i-Pr | H | H | OCHF₂ |
| OSO₂i-Pr | H | H | OEt |
| OSO₂i-Pr | H | H | OMe |
| OSO₂i-Pr | H | H | On-Pr |
| OSO₂i-Pr | H | H | t-Bu |
| OSO₂Me | C(=NOMe)H | H | H |
| OSO₂Me | CF₃ | H | H |
| OSO₂Me | —CH=CH—CH=CH— | | H |
| OSO₂Me | —CH=N—CH=CH— | | F |
| OSO₂Me | —CH=N—CH=CH— | | OSO₂Me |
| OSO₂Me | —CH₂CH₂CH₂— | | H |
| OSO₂Me | —CH₂CH₂CH₂CH₂— | | F |
| OSO₂Me | —CH₂CH₂CH₂CH₂— | | OSO₂Me |
| OSO₂Me | CN | H | H |
| OSO₂Me | F | F | OSO₂Me |
| OSO₂Me | F | H | H |
| OSO₂Me | H | C(=NOMe)H | H |
| OSO₂Me | H | CF₃ | H |
| OSO₂Me | H | CN | H |
| OSO₂Me | H | F | H |
| OSO₂Me | H | H | Br |
| OSO₂Me | H | H | C(=NOMe)Me |
| OSO₂Me | H | H | C₂F₅ |
| OSO₂Me | H | H | CH=CH₂ |
| OSO₂Me | H | H | CH₂NMe₂ |
| OSO₂Me | H | H | CH₂SMe |
| OSO₂Me | H | H | Cl |

TABLE 22

| X¹ | X² | X³ | X⁴ |
|---|---|---|---|
| OSO₂Me | H | H | CO₂Me |
| OSO₂Me | H | H | Et |
| OSO₂Me | H | H | H |
| OSO₂Me | H | H | I |
| OSO₂Me | H | H | i-Pr |
| OSO₂Me | H | H | n-Bu |
| OSO₂Me | H | H | NHCO₂Me |
| OSO₂Me | H | H | NHMe |
| OSO₂Me | H | H | NMe₂ |
| OSO₂Me | H | H | n-Pr |
| OSO₂Me | H | H | OCHF₂ |
| OSO₂Me | H | H | OCO₂Me |
| OSO₂Me | H | H | OCOMe |
| OSO₂Me | H | H | OH |

TABLE 22-continued

| X¹ | X² | X³ | X⁴ |
|---|---|---|---|
| OSO₂Me | H | H | OPh |
| OSO₂Me | H | H | OSiMe₃ |
| OSO₂Me | H | H | OSO₂Et |
| OSO₂Me | H | H | OSO₂Me |
| OSO₂Me | H | H | OSO₂n-Pr |
| OSO₂Me | H | H | Ph |
| OSO₂Me | H | H | SiMe₃ |
| OSO₂Me | H | H | SO₂CF₃ |
| OSO₂Me | H | H | SOMe |
| OSO₂Me | H | I | H |
| OSO₂Me | H | NO₂ | H |
| OSO₂Me | H | OH | H |
| OSO₂Me | H | OSO₂Bn | H |
| OSO₂Me | H | OSO₂i-Pr | H |
| OSO₂Me | H | OSO₂n-Bu | H |
| OSO₂Me | H | OSO₂Ph | H |
| OSO₂Me | I | H | H |
| OSO₂Me | —N=CH—CH=CH— | | F |
| OSO₂Me | —N=CH—CH=CH— | | OSO₂Me |
| OSO₂Me | —N=CH—N=CH— | | H |
| OSO₂Me | H | H | CO₂H |
| OSO₂Me | H | H | c-Pr |
| OSO₂Me | H | H | F |
| OSO₂Me | H | H | H |
| OSO₂Me | H | H | i-Bu |
| OSO₂Me | H | H | Me |
| OSO₂Me | H | H | NH₂ |
| OSO₂Me | H | H | NHCOMe |
| OSO₂Me | H | H | NHSO₂Me |
| OSO₂Me | H | H | NO₂ |
| OSO₂Me | H | H | OCF₃ |
| OSO₂Me | H | H | OCH₂C≡CH |
| OSO₂Me | H | H | OCO₂NMe₂ |
| OSO₂Me | H | H | OEt |
| OSO₂Me | H | H | OMe |
| OSO₂Me | H | H | OSiMe₂t-Bu |
| OSO₂Me | H | H | OSO₂Bn |
| OSO₂Me | H | H | OSO₂i-Pr |
| OSO₂Me | H | H | OSO₂n-Bu |
| OSO₂Me | H | H | OSO₂Ph |
| OSO₂Me | H | H | SH |
| OSO₂Me | H | H | SMe |
| OSO₂Me | H | H | SO₂Me |
| OSO₂Me | H | H | t-Bu |
| OSO₂Me | H | Me | H |
| OSO₂Me | H | OCF₃ | H |
| OSO₂Me | H | OMe | H |
| OSO₂Me | H | OSO₂Et | H |
| OSO₂Me | H | OSO₂Me | H |
| OSO₂Me | H | OSO₂n-Pr | H |
| OSO₂Me | H | SO₂Me | H |
| OSO₂Me | Me | H | H |
| OSO₂Me | —N=CH—CH=CH— | | H |
| OSO₂Me | —N=CH—N=CH— | | F |

TABLE 23

| X¹ | X² | X³ | X⁴ |
|---|---|---|---|
| OSO₂Me | —NH—CH=CH— | | F |
| OSO₂Me | —NH—CH=CH— | | OSO₂Me |
| OSO₂Me | OCF₃ | H | H |
| OSO₂Me | —O—CH=CH— | | H |
| OSO₂Me | —O—CH=N— | | F |
| OSO₂Me | —O—CH=N— | | OSO₂Me |
| OSO₂Me | OMe | H | H |
| OSO₂Me | OSO₂Et | H | H |
| OSO₂Me | OSO₂Me | H | H |
| OSO₂Me | OSO₂Me | OSO₂Me | H |
| OSO₂Me | OSO₂n-Bu | H | H |
| OSO₂Me | OSO₂Ph | H | H |
| OSO₂Me | —S—CH=CH— | | H |
| OSO₂Me | SO₂Me | H | H |
| OSO₂n-Bu | H | H | Cl |
| OSO₂n-Bu | H | H | c-Pr |

TABLE 23-continued

| X¹ | X² | X³ | X⁴ |
|---|---|---|---|
| OSO₂n-Bu | H | H | F |
| OSO₂n-Bu | H | H | I |
| OSO₂n-Bu | H | H | n-Bu |
| OSO₂n-Bu | H | H | n-Pr |
| OSO₂n-Bu | H | H | OCHF₂ |
| OSO₂n-Bu | H | H | OEt |
| OSO₂n-Bu | H | H | OMe |
| OSO₂n-Bu | H | H | On-Pr |
| OSO₂n-Bu | H | H | t-Bu |
| OSO₂n-Pr | H | H | Cl |
| OSO₂n-Pr | H | H | c-Pr |
| OSO₂n-Pr | H | H | F |
| OSO₂n-Pr | H | H | I |
| OSO₂n-Pr | H | H | n-Bu |
| OSO₂n-Pr | H | H | n-Pr |
| OSO₂n-Pr | H | H | OCHF₂ |
| OSO₂n-Pr | H | H | OEt |
| OSO₂n-Pr | H | H | OMe |
| OSO₂Me | —N=CH—N=CH— | | OSO₂Me |
| OSO₂Me | —NH—CH=CH— | | H |
| OSO₂Me | NO₂ | H | H |
| OSO₂Me | —O—CH=CH— | | F |
| OSO₂Me | —O—CH=CH— | | OSO₂Me |
| OSO₂Me | —O—CH=N— | | H |
| OSO₂Me | OH | H | H |
| OSO₂Me | OSO₂Bn | H | H |
| OSO₂Me | OSO₂i-Pr | H | H |
| OSO₂Me | OSO₂Me | H | OSO₂Me |
| OSO₂Me | OSO₂Me | OSO₂Me | OSO₂Me |
| OSO₂Me | OSO₂n-Pr | H | H |
| OSO₂Me | —S—CH=CH— | | F |
| OSO₂Me | —S—CH=CH— | | OSO₂Me |
| OSO₂n-Bu | H | H | Br |
| OSO₂n-Bu | H | H | CN |
| OSO₂n-Bu | H | H | Et |
| OSO₂n-Bu | H | H | H |
| OSO₂n-Bu | H | H | Me |
| OSO₂n-Bu | H | H | NO₂ |
| OSO₂n-Bu | H | H | OCF₃ |
| OSO₂n-Bu | H | H | Oc-Pr |
| OSO₂n-Bu | H | H | OH |
| OSO₂n-Bu | H | H | On-Bu |
| OSO₂n-Bu | H | H | Ot-Bu |
| OSO₂n-Pr | H | H | Br |
| OSO₂n-Pr | H | H | CN |
| OSO₂n-Pr | H | H | Et |
| OSO₂n-Pr | H | H | H |
| OSO₂n-Pr | H | H | Me |
| OSO₂n-Pr | H | H | NO₂ |
| OSO₂n-Pr | H | H | OCF₃ |
| OSO₂n-Pr | H | H | Oc-Pr |
| OSO₂n-Pr | H | H | OH |

TABLE 24

| X¹ | X² | X³ | X⁴ |
|---|---|---|---|
| OSO₂n-Pr | H | H | On-Pr |
| OSO₂n-Pr | H | H | t-Bu |
| Ph | H | H | H |
| SiMe₃ | H | H | H |
| SO₂CF₃ | H | H | H |
| SO₂Me | H | H | SO₂Me |
| t-Bu | H | H | H |
| OSO₂n-Pr | H | H | On-Bu |
| OSO₂n-Pr | H | H | Ot-Bu |
| OSO₂Ph | H | H | H |
| SH | H | H | H |
| SMe | H | H | H |
| SO₂Me | H | H | H |
| SOMe | H | H | H |

TABLE 25

| X¹ | X² | X³ | X⁴ |
|---|---|---|---|
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | Cl | H |
| Cl | H | H | Cl |
| CN | H | H | CN |
| CO₂H | H | H | H |
| c-Pr | H | H | H |
| F | Br | H | F |
| F | C(=NOMe)H | H | H |
| F | CF₃ | H | F |
| F | Cl | H | F |
| F | CN | H | F |
| F | F | F | F |
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |
| Cl | H | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 26

| X¹ | X² | X³ | X⁴ |
|---|---|---|---|
| F | H | H | CHO |
| F | H | H | CN |
| F | H | H | CO₂Me |
| F | H | H | Et |
| F | H | H | H |
| F | H | H | i-Bu |
| F | H | H | Me |
| F | H | H | NH₂ |
| F | H | H | NHCOMe |
| F | H | H | NHSO₂Me |
| F | H | H | NO₂ |
| F | H | H | OCF₃ |
| F | H | H | OCO₂Me |
| F | H | H | OCOMe |
| F | H | H | OH |
| F | H | H | OPh |
| F | H | H | OSiMe₃ |
| F | H | H | SH |
| F | H | H | SMe |
| F | H | H | SO₂Me |
| F | H | H | t-Bu |
| F | H | Me | H |
| F | H | OCF₃ | H |
| F | H | OMe | H |
| F | H | SO₂Me | H |
| F | H | I | H |
| F | Me | H | H |
| F | NO₂ | H | H |
| F | OCF₃ | H | H |
| F | OH | H | H |
| F | OMe | H | H |
| F | SO₂Me | H | F |
| H | Br | Br | H |
| H | C(=NOMe)H | H | H |
| F | H | H | CH₂SMe |
| F | H | H | Cl |
| F | H | H | CO₂H |
| F | H | H | c-Pr |
| F | H | H | F |
| F | H | H | I |
| F | H | H | i-Pr |
| F | H | H | n-Bu |
| F | H | H | NHCO₂Me |
| F | H | H | NHMe |
| F | H | H | NMe₂ |
| F | H | H | n-Pr |
| F | H | H | OCH₂C≡CH |
| F | H | H | OCO₂NMe₂ |
| F | H | H | OEt |
| F | H | H | OMe |
| F | H | H | OSiMe₂t-Bu |
| F | H | H | Ph |
| F | H | H | SiMe₃ |
| F | H | H | SO₂CF₃ |
| F | H | H | SOMe |
| F | H | I | H |
| F | H | NO₂ | H |
| F | H | OH | H |
| F | H | OSO₂Me | H |
| F | I | H | F |
| F | Me | H | F |
| F | NO₂ | H | F |
| F | OCF₃ | H | F |
| F | OH | H | F |
| F | OMe | H | F |
| F | OSO₂Me | H | F |
| F | SO₂Me | H | H |
| H | Br | H | H |

TABLE 27

| X¹ | X² | X³ | X⁴ |
|---|---|---|---|
| H | CF₃ | CF₃ | H |
| H | —CH=CH—CH=CH— | | H |
| H | —CH₂CH₂CH₂— | | H |
| H | Cl | Cl | H |

TABLE 27-continued

| X$^1$ | X$^2$ | X$^3$ | X$^4$ |
|---|---|---|---|
| H | CN | H | H |
| H | F | H | H |
| H | I | H | H |
| H | Me | H | H |
| H | —N=CH—CH=CH— | | H |
| H | —NH—CH=CH— | | H |
| H | NO$_2$ | NO$_2$ | H |
| H | OCF$_3$ | OCF$_3$ | H |
| H | —O—CH=N— | | H |
| H | OH | OH | H |
| H | OMe | OMe | H |
| H | OSO$_2$Et | H | H |
| H | OSO$_2$Me | H | H |
| H | OSO$_2$n-Bu | H | H |
| H | OSO$_2$Ph | H | H |
| H | SO$_2$Me | H | H |
| I | H | H | H |
| i-Pr | H | H | H |
| Me | H | H | Me |
| NH$_2$ | H | H | H |
| NHCOMe | H | H | H |
| NHSO$_2$Me | H | H | H |
| NO$_2$ | H | H | H |
| OCF$_3$ | H | H | H |
| OCH$_2$C≡CH | H | H | H |
| OCO$_2$NMe$_2$ | H | H | H |
| OEt | H | H | H |
| OMe | H | H | H |
| OPh | H | H | H |
| OSiMe$_3$ | H | H | H |
| H | C(=NOMe)Me | H | H |
| H | CF$_3$ | H | H |
| H | —CH=N—CH=CH— | | H |
| H | —CH$_2$CH$_2$CH$_2$CH$_2$— | | H |
| H | CN | CN | H |
| H | F | F | H |
| H | H | H | H |
| H | I | I | H |
| H | Me | Me | H |
| H | —N=CH—N=CH— | | H |
| H | NO$_2$ | H | H |
| H | OCF$_3$ | H | H |
| H | —O—CH=CH— | | H |
| H | OH | H | H |
| H | OMe | H | H |
| H | OSO$_2$Bn | H | H |
| H | OSO$_2$i-Pr | H | H |
| H | OSO$_2$Me | SO$_2$Me | H |
| H | OSO$_2$n-Pr | H | H |
| H | —S—CH=CH— | | H |
| H | SO$_2$Me | SO$_2$Me | H |
| i-Bu | H | H | H |
| Me | H | H | H |
| n-Bu | H | H | H |
| NHCO$_2$Me | H | H | H |
| NHMe | H | H | H |
| NMe$_2$ | H | H | H |
| n-Pr | H | H | H |
| OCF$_3$ | H | H | OCF$_3$ |
| OCO$_2$Me | H | H | H |
| OCOMe | H | H | H |
| OH | H | H | H |
| OMe | H | H | OMe |
| OSiMe$_2$t-Bu | H | H | H |

TABLE 28

| X$^1$ | X$^2$ | X$^3$ | X$^4$ |
|---|---|---|---|
| OSO$_2$CF$_3$ | H | H | Br |
| OSO$_2$CF$_3$ | H | H | CN |
| OSO$_2$CF$_3$ | H | H | Et |
| OSO$_2$CF$_3$ | H | H | H |
| OSO$_2$CF$_3$ | H | H | Me |
| OSO$_2$CF$_3$ | H | H | NO$_2$ |

TABLE 28-continued

| X$^1$ | X$^2$ | X$^3$ | X$^4$ |
|---|---|---|---|
| OSO$_2$CF$_3$ | H | H | OCF$_3$ |
| OSO$_2$CF$_3$ | H | H | Oc-Pr |
| OSO$_2$CF$_3$ | H | H | OH |
| OSO$_2$CF$_3$ | H | H | On-Bu |
| OSO$_2$CF$_3$ | H | H | Ot-Bu |
| OSO$_2$CHF$_2$ | H | H | Br |
| OSO$_2$CHF$_2$ | H | H | CN |
| OSO$_2$CHF$_2$ | H | H | Et |
| OSO$_2$CHF$_2$ | H | H | H |
| OSO$_2$CHF$_2$ | H | H | Me |
| OSO$_2$CHF$_2$ | H | H | NO$_2$ |
| OSO$_2$CHF$_2$ | H | H | OCF$_3$ |
| OSO$_2$CHF$_2$ | H | H | Oc-Pr |
| OSO$_2$CHF$_2$ | H | H | OH |
| OSO$_2$CHF$_2$ | H | H | On-Bu |
| OSO$_2$CHF$_2$ | H | H | Ot-Bu |
| OSO$_2$Et | H | H | Br |
| OSO$_2$Et | H | H | Cl |
| OSO$_2$Et | H | H | c-Pr |
| OSO$_2$Et | H | H | F |
| OSO$_2$Et | H | H | I |
| OSO$_2$Et | H | H | n-Bu |
| OSO$_2$Et | H | H | n-Pr |
| OSO$_2$Et | H | H | OCHF$_2$ |
| OSO$_2$Et | H | H | OEt |
| OSO$_2$Et | H | H | OMe |
| OSO$_2$Et | H | H | On-Pr |
| OSO$_2$Et | H | H | t-Bu |
| OSO$_2$Bn | H | H | H |
| OSO$_2$CF$_3$ | H | H | Cl |
| OSO$_2$CF$_3$ | H | H | c-Pr |
| OSO$_2$CF$_3$ | H | H | F |
| OSO$_2$CF$_3$ | H | H | I |
| OSO$_2$CF$_3$ | H | H | n-Bu |
| OSO$_2$CF$_3$ | H | H | n-Pr |
| OSO$_2$CF$_3$ | H | H | OCHF$_2$ |
| OSO$_2$CF$_3$ | H | H | OEt |
| OSO$_2$CF$_3$ | H | H | OMe |
| OSO$_2$CF$_3$ | H | H | On-Pr |
| OSO$_2$CF$_3$ | H | H | t-Bu |
| OSO$_2$CHF$_2$ | H | H | Cl |
| OSO$_2$CHF$_2$ | H | H | c-Pr |
| OSO$_2$CHF$_2$ | H | H | F |
| OSO$_2$CHF$_2$ | H | H | I |
| OSO$_2$CHF$_2$ | H | H | n-Bu |
| OSO$_2$CHF$_2$ | H | H | n-Pr |
| OSO$_2$CHF$_2$ | H | H | OCHF$_2$ |
| OSO$_2$CHF$_2$ | H | H | OEt |
| OSO$_2$CHF$_2$ | H | H | OMe |
| OSO$_2$CHF$_2$ | H | H | On-Pr |
| OSO$_2$CHF$_2$ | H | H | t-Bu |
| OSO$_2$Et | H | H | CF$_3$ |
| OSO$_2$Et | H | H | CN |
| OSO$_2$Et | H | H | Et |
| OSO$_2$Et | H | H | H |
| OSO$_2$Et | H | H | Me |
| OSO$_2$Et | H | H | NO$_2$ |
| OSO$_2$Et | H | H | OCF$_3$ |
| OSO$_2$Et | H | H | Oc-Pr |
| OSO$_2$Et | H | H | OH |
| OSO$_2$Et | H | H | On-Bu |
| OSO$_2$Et | H | H | Ot-Bu |

TABLE 29

| X$^1$ | X$^2$ | X$^3$ | X$^4$ |
|---|---|---|---|
| OSO$_2$i-Pr | H | H | CF$_3$ |
| OSO$_2$i-Pr | H | H | CN |
| OSO$_2$i-Pr | H | H | Et |
| OSO$_2$i-Pr | H | H | H |
| OSO$_2$i-Pr | H | H | Me |
| OSO$_2$i-Pr | H | H | NO$_2$ |
| OSO$_2$i-Pr | H | H | OCF$_3$ |
| OSO$_2$i-Pr | H | H | Oc-Pr |

TABLE 29-continued

| $X^1$ | $X^2$ | $X^3$ | $X^4$ |
|---|---|---|---|
| $OSO_2$i-Pr | H | H | OH |
| $OSO_2$i-Pr | H | H | On-Bu |
| $OSO_2$i-Pr | H | H | Ot-Bu |
| $OSO_2$Me | Br | H | H |
| $OSO_2$Me | C(=NOMe)Me | H | H |
| $OSO_2$Me | —CH=CH—CH=CH— | | F |
| $OSO_2$Me | —CH=CH—CH=CH— | | $OSO_2$Me |
| $OSO_2$Me | —CH=N—CH=CH— | | H |
| $OSO_2$Me | —$CH_2CH_2CH_2$— | | F |
| $OSO_2$Me | —$CH_2CH_2CH_2$— | | $OSO_2$Me |
| $OSO_2$Me | —$CH_2CH_2CH_2CH_2$— | | H |
| $OSO_2$Me | Cl | H | H |
| $OSO_2$Me | F | F | F |
| $OSO_2$Me | F | H | F |
| $OSO_2$Me | H | Br | H |
| $OSO_2$Me | H | C(=NOMe)Me | H |
| $OSO_2$Me | H | Cl | H |
| $OSO_2$Me | H | F | F |
| $OSO_2$Me | H | H | Bn |
| $OSO_2$Me | H | H | C(=NOMe)H |
| $OSO_2$Me | H | H | C≡CH |
| $OSO_2$Me | H | H | $CF_3$ |
| $OSO_2$Me | H | H | $CH_2CN$ |
| $OSO_2$Me | H | H | $CH_2OMe$ |
| $OSO_2$Me | H | H | CHO |
| $OSO_2$Me | H | H | CN |
| $OSO_2$i-Pr | H | H | Br |
| $OSO_2$i-Pr | H | H | Cl |
| $OSO_2$i-Pr | H | H | c-Pr |
| $OSO_2$i-Pr | H | H | F |
| $OSO_2$i-Pr | H | H | I |
| $OSO_2$i-Pr | H | H | n-Bu |
| $OSO_2$i-Pr | H | H | n-Pr |
| $OSO_2$i-Pr | H | H | $OCHF_2$ |
| $OSO_2$i-Pr | H | H | OEt |
| $OSO_2$i-Pr | H | H | OMe |
| $OSO_2$i-Pr | H | H | On-Pr |
| $OSO_2$i-Pr | H | H | t-Bu |
| $OSO_2$Me | C(=NOMe)H | H | H |
| $OSO_2$Me | $CF_3$ | H | H |
| $OSO_2$Me | —CH=CH—CH=CH— | | H |
| $OSO_2$Me | —CH=N—CH=CH— | | F |
| $OSO_2$Me | —CH=N—CH=CH— | | $OSO_2$Me |
| $OSO_2$Me | —$CH_2CH_2CH_2$— | | H |
| $OSO_2$Me | —$CH_2CH_2CH_2CH_2$— | | F |
| $OSO_2$Me | —$CH_2CH_2CH_2CH_2$— | | $OSO_2$Me |
| $OSO_2$Me | CN | H | H |
| $OSO_2$Me | F | F | $OSO_2$Me |
| $OSO_2$Me | F | H | H |
| $OSO_2$Me | H | C(=NOMe)H | H |
| $OSO_2$Me | H | $CF_3$ | H |
| $OSO_2$Me | H | CN | H |
| $OSO_2$Me | H | F | H |
| $OSO_2$Me | H | H | Br |
| $OSO_2$Me | H | H | C(=NOMe)Me |
| $OSO_2$Me | H | H | $C_2F_5$ |
| $OSO_2$Me | H | H | CH=$CH_2$ |
| $OSO_2$Me | H | H | $CH_2NMe_2$ |
| $OSO_2$Me | H | H | $CH_2SMe$ |
| $OSO_2$Me | H | H | Cl |

TABLE 30

| $X^1$ | $X^2$ | $X^3$ | $X^4$ |
|---|---|---|---|
| $OSO_2$Me | H | H | $CO_2Me$ |
| $OSO_2$Me | H | H | Et |
| $OSO_2$Me | H | H | I |
| $OSO_2$Me | H | H | i-Pr |
| $OSO_2$Me | H | H | n-Bu |
| $OSO_2$Me | H | H | $NHCO_2Me$ |
| $OSO_2$Me | H | H | NHMe |
| $OSO_2$Me | H | H | $NMe_2$ |
| $OSO_2$Me | H | H | n-Pr |

TABLE 30-continued

| $X^1$ | $X^2$ | $X^3$ | $X^4$ |
|---|---|---|---|
| $OSO_2$Me | H | H | $OCHF_2$ |
| $OSO_2$Me | H | H | $OCO_2Me$ |
| $OSO_2$Me | H | H | OCOMe |
| $OSO_2$Me | H | H | OH |
| $OSO_2$Me | H | H | OPh |
| $OSO_2$Me | H | H | $OSiMe_3$ |
| $OSO_2$Me | H | H | $OSO_2$Et |
| $OSO_2$Me | H | H | $OSO_2$Me |
| $OSO_2$Me | H | H | $OSO_2$n-Pr |
| $OSO_2$Me | H | H | Ph |
| $OSO_2$Me | H | H | $SiMe_3$ |
| $OSO_2$Me | H | H | $SO_2CF_3$ |
| $OSO_2$Me | H | H | SOMe |
| $OSO_2$Me | H | I | H |
| $OSO_2$Me | H | $NO_2$ | H |
| $OSO_2$Me | H | OH | H |
| $OSO_2$Me | H | $OSO_2$Bn | H |
| $OSO_2$Me | H | $OSO_2$i-Pr | H |
| $OSO_2$Me | H | $OSO_2$n-Bu | H |
| $OSO_2$Me | H | $OSO_2$Ph | H |
| $OSO_2$Me | I | H | H |
| $OSO_2$Me | —N=CH—CH=CH— | | F |
| $OSO_2$Me | —N=CH—CH=CH— | | $OSO_2$Me |
| $OSO_2$Me | —N=CH—N=CH— | | H |
| $OSO_2$Me | H | H | $CO_2H$ |
| $OSO_2$Me | H | H | c-Pr |
| $OSO_2$Me | H | H | F |
| $OSO_2$Me | H | H | H |
| $OSO_2$Me | H | H | i-Bu |
| $OSO_2$Me | H | H | Me |
| $OSO_2$Me | H | H | $NH_2$ |
| $OSO_2$Me | H | H | NHCOMe |
| $OSO_2$Me | H | H | $NHSO_2$Me |
| $OSO_2$Me | H | H | $NO_2$ |
| $OSO_2$Me | H | H | $OCF_3$ |
| $OSO_2$Me | H | H | $OCH_2C$≡CH |
| $OSO_2$Me | H | H | $OCO_2NMe_2$ |
| $OSO_2$Me | H | H | OEt |
| $OSO_2$Me | H | H | OMe |
| $OSO_2$Me | H | H | $OSiMe_2$t-Bu |
| $OSO_2$Me | H | H | $OSO_2$Bn |
| $OSO_2$Me | H | H | $OSO_2$i-Pr |
| $OSO_2$Me | H | H | $OSO_2$n-Bu |
| $OSO_2$Me | H | H | $OSO_2$Ph |
| $OSO_2$Me | H | H | SH |
| $OSO_2$Me | H | H | SMe |
| $OSO_2$Me | H | H | $SO_2$Me |
| $OSO_2$Me | H | H | t-Bu |
| $OSO_2$Me | H | Me | H |
| $OSO_2$Me | H | $OCF_3$ | H |
| $OSO_2$Me | H | OMe | H |
| $OSO_2$Me | H | $OSO_2$Et | H |
| $OSO_2$Me | H | $OSO_2$Me | H |
| $OSO_2$Me | H | $OSO_2$n-Pr | H |
| $OSO_2$Me | H | $SO_2$Me | H |
| $OSO_2$Me | Me | H | H |
| $OSO_2$Me | —N=CH—CH=CH— | | H |
| $OSO_2$Me | —N=CH—N=CH— | | F |

TABLE 31

| $X^1$ | $X^2$ | $X^3$ | $X^4$ |
|---|---|---|---|
| $OSO_2$Me | —NH—CH=CH— | | F |
| $OSO_2$Me | —NH—CH=CH— | | $OSO_2$Me |
| $OSO_2$Me | $OCF_3$ | H | H |
| $OSO_2$Me | —O—CH=CH— | | H |
| $OSO_2$Me | —O—CH=N— | | F |
| $OSO_2$Me | —O—CH=N— | | $OSO_2$Me |
| $OSO_2$Me | OMe | H | H |
| $OSO_2$Me | $OSO_2$Et | H | H |
| $OSO_2$Me | $OSO_2$Me | H | H |
| $OSO_2$Me | $OSO_2$Me | $OSO_2$Me | H |
| $OSO_2$Me | $OSO_2$n-Bu | H | H |
| $OSO_2$Me | $OSO_2$Ph | H | H |

TABLE 31-continued

| X$^1$ | X$^2$ | X$^3$ | X$^4$ |
|---|---|---|---|
| OSO$_2$Me | —S—CH=CH— | | H |
| OSO$_2$Me | SO$_2$Me | H | H |
| OSO$_2$n-Bu | H | H | Cl |
| OSO$_2$n-Bu | H | H | c-Pr |
| OSO$_2$n-Bu | H | H | F |
| OSO$_2$n-Bu | H | H | I |
| OSO$_2$n-Bu | H | H | n-Bu |
| OSO$_2$n-Bu | H | H | n-Pr |
| OSO$_2$n-Bu | H | H | OCHF$_2$ |
| OSO$_2$n-Bu | H | H | OEt |
| OSO$_2$n-Bu | H | H | OMe |
| OSO$_2$n-Bu | H | H | On-Pr |
| OSO$_2$n-Bu | H | H | t-Bu |
| OSO$_2$n-Pr | H | H | Cl |
| OSO$_2$n-Pr | H | H | c-Pr |
| OSO$_2$n-Pr | H | H | F |
| OSO$_2$n-Pr | H | H | I |
| OSO$_2$n-Pr | H | H | n-Bu |
| OSO$_2$n-Pr | H | H | n-Pr |
| OSO$_2$n-Pr | H | H | OCHF$_2$ |
| OSO$_2$n-Pr | H | H | OEt |
| OSO$_2$n-Pr | H | H | OMe |
| OSO$_2$Me | —N=CH—N=CH— | | OSO$_2$Me |
| OSO$_2$Me | —NH—CH=CH— | | H |
| OSO$_2$Me | NO$_2$ | H | H |
| OSO$_2$Me | —O—CH=CH— | | F |
| OSO$_2$Me | —O—CH=CH— | | OSO$_2$Me |
| OSO$_2$Me | —O—CH=N— | | H |
| OSO$_2$Me | OH | H | H |
| OSO$_2$Me | OSO$_2$Bn | H | H |
| OSO$_2$Me | OSO$_2$i-Pr | H | H |
| OSO$_2$Me | OSO$_2$Me | H | OSO$_2$Me |
| OSO$_2$Me | OSO$_2$Me | OSO$_2$Me | OSO$_2$Me |
| OSO$_2$Me | OSO$_2$n-Pr | H | H |
| OSO$_2$Me | —S—CH=CH— | | F |
| OSO$_2$Me | —S—CH=CH— | | OSO$_2$Me |
| OSO$_2$n-Bu | H | H | Br |
| OSO$_2$n-Bu | H | H | CN |
| OSO$_2$n-Bu | H | H | Et |
| OSO$_2$n-Bu | H | H | H |
| OSO$_2$n-Bu | H | H | Me |
| OSO$_2$n-Bu | H | H | NO$_2$ |
| OSO$_2$n-Bu | H | H | OCF$_3$ |
| OSO$_2$n-Bu | H | H | Oc-Pr |
| OSO$_2$n-Bu | H | H | OH |
| OSO$_2$n-Bu | H | H | On-Bu |
| OSO$_2$n-Bu | H | H | Ot-Bu |
| OSO$_2$n-Pr | H | H | Br |
| OSO$_2$n-Pr | H | H | CN |
| OSO$_2$n-Pr | H | H | Et |
| OSO$_2$n-Pr | H | H | H |
| OSO$_2$n-Pr | H | H | Me |
| OSO$_2$n-Pr | H | H | NO$_2$ |
| OSO$_2$n-Pr | H | H | OCF$_3$ |
| OSO$_2$n-Pr | H | H | Oc-Pr |
| OSO$_2$n-Pr | H | H | OH |

TABLE 32

| X$^1$ | X$^2$ | X$^3$ | X$^4$ |
|---|---|---|---|
| OSO$_2$n-Pr | H | H | On-Pr |
| OSO$_2$n-Pr | H | H | t-Bu |
| Ph | H | H | H |
| SiMe$_3$ | H | H | H |
| SO$_2$CF$_3$ | H | H | H |
| SO$_2$Me | H | H | SO$_2$Me |
| t-Bu | H | H | H |
| OSO$_2$n-Pr | H | H | On-Bu |
| OSO$_2$n-Pr | H | H | Ot-Bu |
| OSO$_2$Ph | H | H | H |
| SH | H | H | H |
| SMe | H | H | H |
| SO$_2$Me | H | H | H |
| SOMe | H | H | H |

TABLE 33

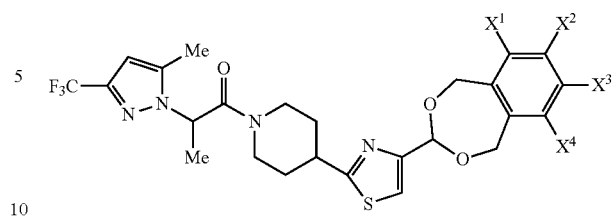

| X$^1$ | X$^2$ | X$^3$ | X$^4$ |
|---|---|---|---|
| Br | H | H | Br |
| C(=NOMe)H | H | H | H |
| C≡CH | H | H | H |
| CF$_3$ | H | H | CF$_3$ |
| CH=CH$_2$ | H | H | H |
| CH$_2$NMe$_2$ | H | H | H |
| CH$_2$SMe | H | H | H |
| Cl | Cl | Cl | Cl |
| Cl | Cl | H | H |
| Cl | H | H | Cl |
| CN | H | H | CN |
| CO$_2$H | H | H | H |
| c-Pr | H | H | H |
| F | Br | H | F |
| F | C(=NOMe)H | H | H |
| F | CF$_3$ | H | F |
| F | Cl | H | F |
| F | CN | H | F |
| F | F | F | F |
| F | F | H | H |
| F | H | C(=NOMe)H | H |
| F | H | CF$_3$ | H |
| F | H | CN | H |
| F | H | H | Bn |
| F | H | H | C(=NOMe)H |
| F | H | H | C≡CH |
| F | H | H | CF$_3$ |
| F | H | H | CH$_2$CN |
| F | H | H | CH$_2$OMe |
| Bn | H | H | H |
| Br | H | H | H |
| C(=NOMe)Me | H | H | H |
| C$_2$F$_5$ | H | H | H |
| CF$_3$ | H | H | H |
| CH$_2$CN | H | H | H |
| CH$_2$OMe | H | H | H |
| CHO | H | H | H |
| Cl | Cl | Cl | H |
| Cl | H | Cl | H |
| Cl | H | H | H |
| CN | H | H | H |
| CO$_2$Me | H | H | H |
| Et | H | H | H |
| F | Br | H | H |
| F | C(=NOMe)Me | H | H |
| F | CF$_3$ | H | H |
| F | Cl | H | H |
| F | CN | H | H |
| F | F | H | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C$_2$F$_5$ |
| F | H | H | CH=CH$_2$ |
| F | H | H | CH$_2$NMe$_2$ |

TABLE 34

| X¹ | X² | X³ | X⁴ |
|---|---|---|---|
| F | H | H | CHO |
| F | H | H | CN |
| F | H | H | CO₂Me |
| F | H | H | Et |
| F | H | H | H |
| F | H | H | i-Bu |
| F | H | H | Me |
| F | H | H | NH₂ |
| F | H | H | NHCOMe |
| F | H | H | NHSO₂Me |
| F | H | H | NO₂ |
| F | H | H | OCF₃ |
| F | H | H | OCO₂Me |
| F | H | H | OCOMe |
| F | H | H | OH |
| F | H | H | OPh |
| F | H | H | OSiMe₃ |
| F | H | H | SH |
| F | H | H | SMe |
| F | H | H | SO₂Me |
| F | H | H | t-Bu |
| F | H | Me | H |
| F | H | OCF₃ | H |
| F | H | OMe | H |
| F | H | SO₂Me | H |
| F | I | H | H |
| F | Me | H | H |
| F | NO₂ | H | H |
| F | OCF₃ | H | H |
| F | OH | H | H |
| F | OMe | H | H |
| F | SO₂Me | H | F |
| H | Br | Br | H |
| H | C(=NOMe)H | H | H |
| F | H | H | CH₂SMe |
| F | H | H | Cl |
| F | H | H | CO₂H |
| F | H | H | c-Pr |
| F | H | H | F |
| F | H | H | I |
| F | H | H | i-Pr |
| F | H | H | n-Bu |
| F | H | H | NHCO₂Me |
| F | H | H | NHMe |
| F | H | H | NMe₂ |
| F | H | H | n-Pr |
| F | H | H | OCH₂C≡CH |
| F | H | H | OCO₂NMe₂ |
| F | H | H | OEt |
| F | H | H | OMe |
| F | H | H | OSiMe₂t-Bu |
| F | H | H | Ph |
| F | H | H | SiMe₃ |
| F | H | H | SO₂CF₃ |
| F | H | H | SOMe |
| F | H | I | H |
| F | H | NO₂ | H |
| F | H | OH | H |
| F | H | OSO₂Me | H |
| F | I | H | F |
| F | Me | H | F |
| F | NO₂ | H | F |
| F | OCF₃ | H | F |
| F | OH | H | F |
| F | OMe | H | F |
| F | OSO₂Me | H | F |
| F | SO₂Me | H | H |
| H | Br | H | H |

TABLE 35

| X¹ | X² | X³ | X⁴ |
|---|---|---|---|
| H | CF₃ | CF₃ | H |
| H | —CH=CH—CH=CH— | | H |
| H | —CH₂CH₂CH₂— | | H |
| H | Cl | Cl | H |
| H | CN | H | H |
| H | F | H | H |
| H | I | H | H |
| H | Me | H | H |
| H | —N=CH—CH=CH— | | H |
| H | —NH—CH=CH— | | H |
| H | NO₂ | NO₂ | H |
| H | OCF₃ | OCF₃ | H |
| H | —O—CH=N— | | H |
| H | OH | OH | H |
| H | OMe | OMe | H |
| H | OSO₂Et | H | H |
| H | OSO₂Me | H | H |
| H | OSO₂n-Bu | H | H |
| H | OSO₂Ph | H | H |
| H | SO₂Me | H | H |
| I | H | H | H |
| i-Pr | H | H | H |
| Me | H | H | Me |
| NH₂ | H | H | H |
| NHCOMe | H | H | H |
| NHSO₂Me | H | H | H |
| NO₂ | H | H | H |
| OCF₃ | H | H | H |
| OCH₂C≡CH | H | H | H |
| OCO₂NMe₂ | H | H | H |
| OEt | H | H | H |
| OMe | H | H | H |
| OPh | H | H | H |
| OSiMe₃ | H | H | H |
| H | C(=NOMe)Me | H | H |
| H | CF₃ | H | H |
| H | —CH=N—CH=CH— | | H |
| H | —CH₂CH₂CH₂CH₂— | | H |
| H | CN | CN | H |
| H | F | F | H |
| H | H | H | H |
| H | I | I | H |
| H | Me | Me | H |
| H | —N=CH—N=CH— | | H |
| H | NO₂ | H | H |
| H | OCF₃ | H | H |
| H | —O—CH=CH— | | H |
| H | OH | H | H |
| H | OMe | H | H |
| H | OSO₂Bn | H | H |
| H | OSO₂i-Pr | H | H |
| H | OSO₂Me | OSO₂Me | H |
| H | OSO₂n-Pr | H | H |
| H | —S—CH=CH— | | H |
| H | SO₂Me | SO₂Me | H |
| i-Bu | H | H | H |
| Me | H | H | H |
| n-Bu | H | H | H |
| NHCO₂Me | H | H | H |
| NHMe | H | H | H |
| NMe₂ | H | H | H |
| n-Pr | H | H | H |
| OCF₃ | H | H | OCF₃ |
| OCO₂Me | H | H | H |
| OCOMe | H | H | H |
| OH | H | H | H |
| OMe | H | H | OMe |
| OSiMe₂t-Bu | H | H | H |

TABLE 36

| X¹ | X² | X³ | X⁴ |
|---|---|---|---|
| OSO₂CF₃ | H | H | Br |
| OSO₂CF₃ | H | H | CN |
| OSO₂CF₃ | H | H | Et |
| OSO₂CF₃ | H | H | H |

TABLE 36-continued

| X¹ | X² | X³ | X⁴ |
|---|---|---|---|
| OSO₂CF₃ | H | H | Me |
| OSO₂CF₃ | H | H | NO₂ |
| OSO₂CF₃ | H | H | OCF₃ |
| OSO₂CF₃ | H | H | Oc-Pr |
| OSO₂CF₃ | H | H | OH |
| OSO₂CF₃ | H | H | On-Bu |
| OSO₂CF₃ | H | H | Ot-Bu |
| OSO₂CHF₂ | H | H | Br |
| OSO₂CHF₂ | H | H | CN |
| OSO₂CHF₂ | H | H | Et |
| OSO₂CHF₂ | H | H | H |
| OSO₂CHF₂ | H | H | Me |
| OSO₂CHF₂ | H | H | NO₂ |
| OSO₂CHF₂ | H | H | OCF₃ |
| OSO₂CHF₂ | H | H | Oc-Pr |
| OSO₂CHF₂ | H | H | OH |
| OSO₂CHF₂ | H | H | On-Bu |
| OSO₂CHF₂ | H | H | Ot-Bu |
| OSO₂Et | H | H | Br |
| OSO₂Et | H | H | Cl |
| OSO₂Et | H | H | c-Pr |
| OSO₂Et | H | H | F |
| OSO₂Et | H | H | I |
| OSO₂Et | H | H | n-Bu |
| OSO₂Et | H | H | n-Pr |
| OSO₂Et | H | H | OCHF₂ |
| OSO₂Et | H | H | OEt |
| OSO₂Et | H | H | OMe |
| OSO₂Et | H | H | On-Pr |
| OSO₂Et | H | H | t-Bu |
| OSO₂Bn | H | H | H |
| OSO₂CF₃ | H | H | Cl |
| OSO₂CF₃ | H | H | c-Pr |
| OSO₂CF₃ | H | H | F |
| OSO₂CF₃ | H | H | I |
| OSO₂CF₃ | H | H | n-Bu |
| OSO₂CF₃ | H | H | n-Pr |
| OSO₂CF₃ | H | H | OCHF₂ |
| OSO₂CF₃ | H | H | OEt |
| OSO₂CF₃ | H | H | OMe |
| OSO₂CF₃ | H | H | On-Pr |
| OSO₂CF₃ | H | H | t-Bu |
| OSO₂CHF₂ | H | H | Cl |
| OSO₂CHF₂ | H | H | c-Pr |
| OSO₂CHF₂ | H | H | F |
| OSO₂CHF₂ | H | H | I |
| OSO₂CHF₂ | H | H | n-Bu |
| OSO₂CHF₂ | H | H | n-Pr |
| OSO₂CHF₂ | H | H | OCHF₂ |
| OSO₂CHF₂ | H | H | OEt |
| OSO₂CHF₂ | H | H | OMe |
| OSO₂CHF₂ | H | H | On-Pr |
| OSO₂CHF₂ | H | H | t-Bu |
| OSO₂Et | H | H | CF₃ |
| OSO₂Et | H | H | CN |
| OSO₂Et | H | H | Et |
| OSO₂Et | H | H | H |
| OSO₂Et | H | H | Me |
| OSO₂Et | H | H | NO₂ |
| OSO₂Et | H | H | OCF₃ |
| OSO₂Et | H | H | Oc-Pr |
| OSO₂Et | H | H | OH |
| OSO₂Et | H | H | On-Bu |
| OSO₂Et | H | H | Ot-Bu |

TABLE 37

| X¹ | X² | X³ | X⁴ |
|---|---|---|---|
| OSO₂i-Pr | H | H | CF₃ |
| OSO₂i-Pr | H | H | CN |
| OSO₂i-Pr | H | H | Et |
| OSO₂i-Pr | H | H | H |
| OSO₂i-Pr | H | H | Me |
| OSO₂i-Pr | H | H | NO₂ |

TABLE 37-continued

| X¹ | X² | X³ | X⁴ |
|---|---|---|---|
| OSO₂i-Pr | H | H | OCF₃ |
| OSO₂i-Pr | H | H | Oc-Pr |
| OSO₂i-Pr | H | H | OH |
| OSO₂i-Pr | H | H | On-Bu |
| OSO₂i-Pr | H | H | Ot-Bu |
| OSO₂Me | Br | H | H |
| OSO₂Me | C(=NOMe)Me | H | H |
| OSO₂Me | —CH=CH—CH=CH— | | F |
| OSO₂Me | —CH=CH—CH=CH— | | OSO₂Me |
| OSO₂Me | —CH=N—CH=CH— | | H |
| OSO₂Me | —CH₂CH₂CH₂— | | F |
| OSO₂Me | —CH₂CH₂CH₂— | | OSO₂Me |
| OSO₂Me | —CH₂CH₂CH₂CH₂— | | H |
| OSO₂Me | Cl | H | H |
| OSO₂Me | F | F | F |
| OSO₂Me | F | H | F |
| OSO₂Me | H | Br | H |
| OSO₂Me | H | C(=NOMe)Me | H |
| OSO₂Me | H | Cl | H |
| OSO₂Me | H | F | F |
| OSO₂Me | H | H | Bn |
| OSO₂Me | H | H | C(=NOMe)H |
| OSO₂Me | H | H | C≡CH |
| OSO₂Me | H | H | CF₃ |
| OSO₂Me | H | H | CH₂CN |
| OSO₂Me | H | H | CH₂OMe |
| OSO₂Me | H | H | CHO |
| OSO₂Me | H | H | CN |
| OSO₂i-Pr | H | H | Br |
| OSO₂i-Pr | H | H | Cl |
| OSO₂i-Pr | H | H | c-Pr |
| OSO₂i-Pr | H | H | F |
| OSO₂i-Pr | H | H | I |
| OSO₂i-Pr | H | H | n-Bu |
| OSO₂i-Pr | H | H | n-Pr |
| OSO₂i-Pr | H | H | OCHF₂ |
| OSO₂i-Pr | H | H | OEt |
| OSO₂i-Pr | H | H | OMe |
| OSO₂i-Pr | H | H | On-Pr |
| OSO₂i-Pr | H | H | t-Bu |
| OSO₂Me | C(=NOMe)H | H | H |
| OSO₂Me | CF₃ | H | H |
| OSO₂Me | —CH=CH—CH=CH— | | H |
| OSO₂Me | —CH=N—CH=CH— | | F |
| OSO₂Me | —CH=N—CH=CH— | | OSO₂Me |
| OSO₂Me | —CH₂CH₂CH₂— | | H |
| OSO₂Me | —CH₂CH₂CH₂CH₂— | | F |
| OSO₂Me | —CH₂CH₂CH₂CH₂— | | OSO₂Me |
| OSO₂Me | CN | H | H |
| OSO₂Me | F | F | OSO₂Me |
| OSO₂Me | F | H | H |
| OSO₂Me | H | C(=NOMe)H | H |
| OSO₂Me | H | CF₃ | H |
| OSO₂Me | H | CN | H |
| OSO₂Me | H | F | H |
| OSO₂Me | H | H | Br |
| OSO₂Me | H | H | C(=NOMe)Me |
| OSO₂Me | H | H | C₂F₅ |
| OSO₂Me | H | H | CH=CH₂ |
| OSO₂Me | H | H | CH₂NMe₂ |
| OSO₂Me | H | H | CH₂SMe |
| OSO₂Me | H | H | Cl |

TABLE 38

| X¹ | X² | X³ | X⁴ |
|---|---|---|---|
| OSO₂Me | H | H | CO₂Me |
| OSO₂Me | H | H | Et |
| OSO₂Me | H | H | H |
| OSO₂Me | H | H | I |
| OSO₂Me | H | H | i-Pr |
| OSO₂Me | H | H | n-Bu |
| OSO₂Me | H | H | NHCO₂Me |
| OSO₂Me | H | H | NHMe |

TABLE 38-continued

| X¹ | X² | X³ | X⁴ |
|---|---|---|---|
| OSO₂Me | H | H | NMe₂ |
| OSO₂Me | H | H | n-Pr |
| OSO₂Me | H | H | OCHF₂ |
| OSO₂Me | H | H | OCO₂Me |
| OSO₂Me | H | H | OCOMe |
| OSO₂Me | H | H | OH |
| OSO₂Me | H | H | OPh |
| OSO₂Me | H | H | OSiMe₃ |
| OSO₂Me | H | H | OSO₂Et |
| OSO₂Me | H | H | OSO₂Me |
| OSO₂Me | H | H | OSO₂n-Pr |
| OSO₂Me | H | H | Ph |
| OSO₂Me | H | H | SiMe₃ |
| OSO₂Me | H | H | SO₂CF₃ |
| OSO₂Me | H | H | SOMe |
| OSO₂Me | H | I | H |
| OSO₂Me | H | NO₂ | H |
| OSO₂Me | H | OH | H |
| OSO₂Me | H | OSO₂Bn | H |
| OSO₂Me | H | OSO₂i-Pr | H |
| OSO₂Me | H | OSO₂n-Bu | H |
| OSO₂Me | H | OSO₂Ph | H |
| OSO₂Me | I | H | H |
| OSO₂Me | —N=CH—CH=CH— | | F |
| OSO₂Me | —N=CH—CH=CH— | | OSO₂Me |
| OSO₂Me | —N=CH—N=CH— | | H |
| OSO₂Me | H | H | CO₂H |
| OSO₂Me | H | H | c-Pr |
| OSO₂Me | H | H | F |
| OSO₂Me | H | H | H |
| OSO₂Me | H | H | i-Bu |
| OSO₂Me | H | H | Me |
| OSO₂Me | H | H | NH₂ |
| OSO₂Me | H | H | NHCOMe |
| OSO₂Me | H | H | NHSO₂Me |
| OSO₂Me | H | H | NO₂ |
| OSO₂Me | H | H | OCF₃ |
| OSO₂Me | H | H | OCH₂C≡CH |
| OSO₂Me | H | H | OCO₂NMe₂ |
| OSO₂Me | H | H | OEt |
| OSO₂Me | H | H | OMe |
| OSO₂Me | H | H | OSiMe₂t-Bu |
| OSO₂Me | H | H | OSO₂Bn |
| OSO₂Me | H | H | OSO₂i-Pr |
| OSO₂Me | H | H | OSO₂n-Bu |
| OSO₂Me | H | H | OSO₂Ph |
| OSO₂Me | H | H | SH |
| OSO₂Me | H | H | SMe |
| OSO₂Me | H | H | SO₂Me |
| OSO₂Me | H | H | t-Bu |
| OSO₂Me | H | Me | H |
| OSO₂Me | H | OCF₃ | H |
| OSO₂Me | H | OMe | H |
| OSO₂Me | H | OSO₂Et | H |
| OSO₂Me | H | OSO₂Me | H |
| OSO₂Me | H | OSO₂n-Pr | H |
| OSO₂Me | H | SO₂Me | H |
| OSO₂Me | Me | H | H |
| OSO₂Me | —N=CH—CH=CH— | | H |
| OSO₂Me | —N=CH—N=CH— | | F |

TABLE 39

| X¹ | X² | X³ | X⁴ |
|---|---|---|---|
| OSO₂Me | —NH—CH=CH— | | F |
| OSO₂Me | —NH—CH=CH— | | OSO₂Me |
| OSO₂Me | OCF₃ | H | H |
| OSO₂Me | —O—CH=CH— | | H |
| OSO₂Me | —O—CH=N— | | F |
| OSO₂Me | —O—CH=N— | | OSO₂Me |
| OSO₂Me | OMe | H | H |
| OSO₂Me | OSO₂Et | H | H |
| OSO₂Me | OSO₂Me | H | H |
| OSO₂Me | OSO₂Me | OSO₂Me | H |

TABLE 39-continued

| X¹ | X² | X³ | X⁴ |
|---|---|---|---|
| OSO₂Me | OSO₂n-Bu | H | H |
| OSO₂Me | OSO₂Ph | H | H |
| OSO₂Me | —S—CH=CH— | | H |
| OSO₂Me | SO₂Me | H | H |
| OSO₂n-Bu | H | H | Cl |
| OSO₂n-Bu | H | H | c-Pr |
| OSO₂n-Bu | H | H | F |
| OSO₂n-Bu | H | H | I |
| OSO₂n-Bu | H | H | n-Bu |
| OSO₂n-Bu | H | H | n-Pr |
| OSO₂n-Bu | H | H | OCHF₂ |
| OSO₂n-Bu | H | H | OEt |
| OSO₂n-Bu | H | H | OMe |
| OSO₂n-Bu | H | H | On-Pr |
| OSO₂n-Bu | H | H | t-Bu |
| OSO₂n-Pr | H | H | Cl |
| OSO₂n-Pr | H | H | c-Pr |
| OSO₂n-Pr | H | H | F |
| OSO₂n-Pr | H | H | I |
| OSO₂n-Pr | H | H | n-Bu |
| OSO₂n-Pr | H | H | n-Pr |
| OSO₂n-Pr | H | H | OCHF₂ |
| OSO₂n-Pr | H | H | OEt |
| OSO₂n-Pr | H | H | OMe |
| OSO₂Me | —N=CH—N=CH— | | OSO₂Me |
| OSO₂Me | —NH—CH=CH— | | H |
| OSO₂Me | NO₂ | H | H |
| OSO₂Me | —O—CH=CH— | | F |
| OSO₂Me | —O—CH=CH— | | OSO₂Me |
| OSO₂Me | —O—CH=N— | | H |
| OSO₂Me | OH | H | H |
| OSO₂Me | OSO₂Bn | H | H |
| OSO₂Me | OSO₂i-Pr | H | H |
| OSO₂Me | OSO₂Me | H | OSO₂Me |
| OSO₂Me | OSO₂Me | OSO₂Me | OSO₂Me |
| OSO₂Me | OSO₂n-Pr | H | H |
| OSO₂Me | —S—CH=CH— | | F |
| OSO₂Me | —S—CH=CH— | | OSO₂Me |
| OSO₂n-Bu | H | H | Br |
| OSO₂n-Bu | H | H | CN |
| OSO₂n-Bu | H | H | Et |
| OSO₂n-Bu | H | H | H |
| OSO₂n-Bu | H | H | Me |
| OSO₂n-Bu | H | H | NO₂ |
| OSO₂n-Bu | H | H | OCF₃ |
| OSO₂n-Bu | H | H | Oc-Pr |
| OSO₂n-Bu | H | H | OH |
| OSO₂n-Bu | H | H | On-Bu |
| OSO₂n-Bu | H | H | Ot-Bu |
| OSO₂n-Pr | H | H | Br |
| OSO₂n-Pr | H | H | CN |
| OSO₂n-Pr | H | H | Et |
| OSO₂n-Pr | H | H | H |
| OSO₂n-Pr | H | H | Me |
| OSO₂n-Pr | H | H | NO₂ |
| OSO₂n-Pr | H | H | OCF₃ |
| OSO₂n-Pr | H | H | Oc-Pr |
| OSO₂n-Pr | H | H | OH |

TABLE 40

| X¹ | X² | X³ | X⁴ |
|---|---|---|---|
| OSO₂n-Pr | H | H | On-Pr |
| OSO₂n-Pr | H | H | t-Bu |
| Ph | H | H | H |
| SiMe₃ | H | H | H |
| SO₂CF₃ | H | H | H |
| SO₂Me | H | H | SO₂Me |
| t-Bu | H | H | H |
| OSO₂n-Pr | H | H | On-Bu |
| OSO₂n-Pr | H | H | Ot-Bu |
| OSO₂Ph | H | H | H |
| SH | H | H | H |
| SMe | H | H | H |

TABLE 40-continued

| $X^1$ | $X^2$ | $X^3$ | $X^4$ |
|---|---|---|---|
| SO2Me | H | H | H |
| SOMe | H | H | H |

TABLE 41

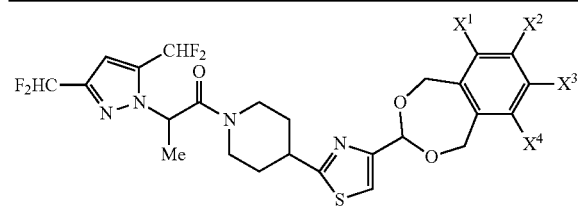

| $X^1$ | $X^2$ | $X^3$ | $X^4$ |
|---|---|---|---|
| Br | H | H | Br |
| C(=NOMe)H | H | H | H |
| C≡CH | H | H | H |
| CF3 | H | H | CF3 |
| CH=CH2 | H | H | H |
| CH2NMe2 | H | H | H |
| CH2SMe | H | H | H |
| Cl | Cl | Cl | Cl |
| Cl | Cl | H | H |
| Cl | H | H | Cl |
| CN | H | H | CN |
| CO2H | H | H | H |
| c-Pr | H | H | H |
| F | Br | H | F |
| F | C(=NOMe)H | H | H |
| F | CF3 | H | F |
| F | Cl | H | F |
| F | CN | H | F |
| F | F | F | F |
| F | F | H | H |
| F | H | C(=NOMe)H | H |
| F | H | CF3 | H |
| F | H | CN | H |
| F | H | H | Bn |
| F | H | H | C(=NOMe)H |
| F | H | H | C≡CH |
| F | H | H | CF3 |
| F | H | H | CH2CN |
| F | H | H | CH2OMe |
| Bn | H | H | H |
| Br | H | H | H |
| C(=NOMe)Me | H | H | H |
| C2F5 | H | H | H |
| CF3 | H | H | H |
| CH2CN | H | H | H |
| CH2OMe | H | H | H |
| CHO | H | H | H |
| Cl | Cl | Cl | H |
| Cl | Cl | H | H |
| Cl | H | H | H |
| CN | H | H | H |
| CO2Me | H | H | H |
| Et | H | H | H |
| F | Br | H | H |
| F | C(=NOMe)Me | H | H |
| F | CF3 | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C2F5 |
| F | H | H | CH=CH2 |
| F | H | H | CH2NMe2 |

TABLE 42

| $X^1$ | $X^2$ | $X^3$ | $X^4$ |
|---|---|---|---|
| F | H | H | CHO |
| F | H | H | CN |
| F | H | H | CO2Me |
| F | H | H | Et |
| F | H | H | H |
| F | H | H | i-Bu |
| F | H | H | Me |
| F | H | H | NH2 |
| F | H | H | NHCOMe |
| F | H | H | NHSO2Me |
| F | H | H | NO2 |
| F | H | H | OCF3 |
| F | H | H | OCO2Me |
| F | H | H | OCOMe |
| F | H | H | OH |
| F | H | H | OPh |
| F | H | H | OSiMe3 |
| F | H | H | SH |
| F | H | H | SMe |
| F | H | H | SO2Me |
| F | H | H | t-Bu |
| F | H | Me | H |
| F | H | OCF3 | H |
| F | H | OMe | H |
| F | H | SO2Me | H |
| F | I | H | H |
| F | Me | H | H |
| F | NO2 | H | H |
| F | OCF3 | H | H |
| F | OH | H | H |
| F | OMe | H | H |
| F | SO2Me | H | F |
| H | Br | Br | H |
| H | C(=NOMe)H | H | H |
| F | H | H | CH2SMe |
| F | H | H | Cl |
| F | H | H | CO2H |
| F | H | H | c-Pr |
| F | H | H | F |
| F | H | H | I |
| F | H | H | i-Pr |
| F | H | H | n-Bu |
| F | H | H | NHCO2Me |
| F | H | H | NHMe |
| F | H | H | NMe2 |
| F | H | H | n-Pr |
| F | H | H | OCH2C≡CH |
| F | H | H | OCO2NMe2 |
| F | H | H | OEt |
| F | H | H | OMe |
| F | H | H | OSiMe2t-Bu |
| F | H | H | Ph |
| F | H | H | SiMe3 |
| F | H | H | SO2CF3 |
| F | H | H | SOMe |
| F | H | I | H |
| F | H | NO2 | H |
| F | H | OH | H |
| F | H | OSO2Me | H |
| F | I | H | F |
| F | Me | H | F |
| F | NO2 | H | F |
| F | OCF3 | H | F |
| F | OH | H | F |
| F | OMe | H | F |
| F | OSO2Me | H | F |
| F | SO2Me | H | H |
| H | Br | H | H |

TABLE 43

| $X^1$ | $X^2$ | $X^3$ | $X^4$ |
|---|---|---|---|
| H | CF3 | CF3 | H |
| H | —CH=CH—CH=CH— | | H |

TABLE 43-continued

| $X^1$ | $X^2$ | $X^3$ | $X^4$ |
|---|---|---|---|
| H | —CH$_2$CH$_2$CH$_2$— | | H |
| H | Cl | Cl | H |
| H | CN | H | H |
| H | F | H | H |
| H | I | H | H |
| H | Me | H | H |
| H | —N=CH—CH=CH— | | H |
| H | —NH—CH=CH— | | H |
| H | NO$_2$ | NO$_2$ | H |
| H | OCF$_3$ | OCF$_3$ | H |
| H | —O—CH=N— | | H |
| H | OH | OH | H |
| H | OMe | OMe | H |
| H | OSO$_2$Et | H | H |
| H | OSO$_2$Me | H | H |
| H | OSO$_2$n-Bu | H | H |
| H | OSO$_2$Ph | H | H |
| H | SO$_2$Me | H | H |
| I | H | H | H |
| i-Pr | H | H | H |
| Me | H | H | Me |
| NH$_2$ | H | H | H |
| NHCOMe | H | H | H |
| NHSO$_2$Me | H | H | H |
| NO$_2$ | H | H | H |
| OCF$_3$ | H | H | H |
| OCH$_2$C≡CH | H | H | H |
| OCO$_2$NMe$_2$ | H | H | H |
| OEt | H | H | H |
| OMe | H | H | H |
| OPh | H | H | H |
| OSiMe$_3$ | H | H | H |
| H | C(=NOMe)Me | H | H |
| H | CF$_3$ | H | H |
| H | —CH=N—CH=CH— | | H |
| H | —CH$_2$CH$_2$CH$_2$— | | H |
| H | CN | CN | H |
| H | F | F | H |
| H | H | H | H |
| H | I | I | H |
| H | Me | Me | H |
| H | —N=CH—N=CH— | | H |
| H | NO$_2$ | H | H |
| H | OCF$_3$ | H | H |
| H | —O—CH=CH— | | H |
| H | OH | H | H |
| H | OMe | H | H |
| H | OSO$_2$Bn | H | H |
| H | OSO$_2$i-Pr | H | H |
| H | OSO$_2$Me | OSO$_2$Me | H |
| H | OSO$_2$n-Pr | H | H |
| H | —S—CH=CH— | | H |
| H | SO$_2$Me | SO$_2$Me | H |
| i-Bu | H | H | H |
| Me | H | H | H |
| n-Bu | H | H | H |
| NHCO$_2$Me | H | H | H |
| NHMe | H | H | H |
| NMe$_2$ | H | H | H |
| n-Pr | H | H | H |
| OCF$_3$ | H | H | OCF$_3$ |
| OCO$_2$Me | H | H | H |
| OCOMe | H | H | H |
| OH | H | H | H |
| OMe | H | H | OMe |
| OSiMe$_2$t-Bu | H | H | H |

TABLE 44

| $X^1$ | $X^2$ | $X^3$ | $X^4$ |
|---|---|---|---|
| OSO$_2$CF$_3$ | H | H | Br |
| OSO$_2$CF$_3$ | H | H | CN |
| OSO$_2$CF$_3$ | H | H | Et |
| OSO$_2$CF$_3$ | H | H | H |

TABLE 44-continued

| $X^1$ | $X^2$ | $X^3$ | $X^4$ |
|---|---|---|---|
| OSO$_2$CF$_3$ | H | H | Me |
| OSO$_2$CF$_3$ | H | H | NO$_2$ |
| OSO$_2$CF$_3$ | H | H | OCF$_3$ |
| OSO$_2$CF$_3$ | H | H | Oc-Pr |
| OSO$_2$CF$_3$ | H | H | OH |
| OSO$_2$CF$_3$ | H | H | On-Bu |
| OSO$_2$CF$_3$ | H | H | Ot-Bu |
| OSO$_2$CHF$_2$ | H | H | Br |
| OSO$_2$CHF$_2$ | H | H | CN |
| OSO$_2$CHF$_2$ | H | H | Et |
| OSO$_2$CHF$_2$ | H | H | H |
| OSO$_2$CHF$_2$ | H | H | Me |
| OSO$_2$CHF$_2$ | H | H | NO$_2$ |
| OSO$_2$CHF$_2$ | H | H | OCF$_3$ |
| OSO$_2$CHF$_2$ | H | H | Oc-Pr |
| OSO$_2$CHF$_2$ | H | H | OH |
| OSO$_2$CHF$_2$ | H | H | On-Bu |
| OSO$_2$CHF$_2$ | H | H | Ot-Bu |
| OSO$_2$Et | H | H | Br |
| OSO$_2$Et | H | H | Cl |
| OSO$_2$Et | H | H | c-Pr |
| OSO$_2$Et | H | H | F |
| OSO$_2$Et | H | H | I |
| OSO$_2$Et | H | H | n-Bu |
| OSO$_2$Et | H | H | n-Pr |
| OSO$_2$Et | H | H | OCHF$_2$ |
| OSO$_2$Et | H | H | OEt |
| OSO$_2$Et | H | H | OMe |
| OSO$_2$Et | H | H | On-Pr |
| OSO$_2$Et | H | H | t-Bu |
| OSO$_2$Bn | H | H | H |
| OSO$_2$CF$_3$ | H | H | Cl |
| OSO$_2$CF$_3$ | H | H | c-Pr |
| OSO$_2$CF$_3$ | H | H | F |
| OSO$_2$CF$_3$ | H | H | I |
| OSO$_2$CF$_3$ | H | H | n-Bu |
| OSO$_2$CF$_3$ | H | H | n-Pr |
| OSO$_2$CF$_3$ | H | H | OCHF$_2$ |
| OSO$_2$CF$_3$ | H | H | OEt |
| OSO$_2$CF$_3$ | H | H | OMe |
| OSO$_2$CF$_3$ | H | H | On-Pr |
| OSO$_2$CF$_3$ | H | H | t-Bu |
| OSO$_2$CHF$_2$ | H | H | Cl |
| OSO$_2$CHF$_2$ | H | H | c-Pr |
| OSO$_2$CHF$_2$ | H | H | F |
| OSO$_2$CHF$_2$ | H | H | I |
| OSO$_2$CHF$_2$ | H | H | n-Bu |
| OSO$_2$CHF$_2$ | H | H | n-Pr |
| OSO$_2$CHF$_2$ | H | H | OCHF$_2$ |
| OSO$_2$CHF$_2$ | H | H | OEt |
| OSO$_2$CHF$_2$ | H | H | OMe |
| OSO$_2$CHF$_2$ | H | H | On-Pr |
| OSO$_2$CHF$_2$ | H | H | t-Bu |
| OSO$_2$Et | H | H | CF$_3$ |
| OSO$_2$Et | H | H | CN |
| OSO$_2$Et | H | H | Et |
| OSO$_2$Et | H | H | H |
| OSO$_2$Et | H | H | Me |
| OSO$_2$Et | H | H | NO$_2$ |
| OSO$_2$Et | H | H | OCF$_3$ |
| OSO$_2$Et | H | H | Oc-Pr |
| OSO$_2$Et | H | H | OH |
| OSO$_2$Et | H | H | On-Bu |
| OSO$_2$Et | H | H | Ot-Bu |

TABLE 45

| $X^1$ | $X^2$ | $X^3$ | $X^4$ |
|---|---|---|---|
| OSO$_2$i-Pr | H | H | CF$_3$ |
| OSO$_2$i-Pr | H | H | CN |
| OSO$_2$i-Pr | H | H | Et |
| OSO$_2$i-Pr | H | H | H |
| OSO$_2$i-Pr | H | H | Me |
| OSO$_2$i-Pr | H | H | NO$_2$ |

TABLE 45-continued

| X¹ | X² | X³ | X⁴ |
|---|---|---|---|
| OSO₂i-Pr | H | H | OCF₃ |
| OSO₂i-Pr | H | H | Oc-Pr |
| OSO₂i-Pr | H | H | OH |
| OSO₂i-Pr | H | H | On-Bu |
| OSO₂i-Pr | H | H | Ot-Bu |
| OSO₂Me | Br | H | H |
| OSO₂Me | C(=NOMe)Me | H | H |
| OSO₂Me | —CH=CH—CH=CH— | | F |
| OSO₂Me | —CH=CH—CH=CH— | | OSO₂Me |
| OSO₂Me | —CH=N—CH=CH— | | H |
| OSO₂Me | —CH₂CH₂CH₂— | | F |
| OSO₂Me | —CH₂CH₂CH₂— | | OSO₂Me |
| OSO₂Me | —CH₂CH₂CH₂CH₂— | | H |
| OSO₂Me | Cl | H | H |
| OSO₂Me | F | F | F |
| OSO₂Me | F | H | F |
| OSO₂Me | H | Br | H |
| OSO₂Me | H | C(=NOMe)Me | H |
| OSO₂Me | H | Cl | H |
| OSO₂Me | H | F | F |
| OSO₂Me | H | H | Bn |
| OSO₂Me | H | H | C(=NOMe)H |
| OSO₂Me | H | H | C≡CH |
| OSO₂Me | H | H | CF₃ |
| OSO₂Me | H | H | CH₂CN |
| OSO₂Me | H | H | CH₂OMe |
| OSO₂Me | H | H | CHO |
| OSO₂Me | H | H | CN |
| OSO₂i-Pr | H | H | Br |
| OSO₂i-Pr | H | H | Cl |
| OSO₂i-Pr | H | H | c-Pr |
| OSO₂i-Pr | H | H | F |
| OSO₂i-Pr | H | H | I |
| OSO₂i-Pr | H | H | n-Bu |
| OSO₂i-Pr | H | H | n-Pr |
| OSO₂i-Pr | H | H | OCHF₂ |
| OSO₂i-Pr | H | H | OEt |
| OSO₂i-Pr | H | H | OMe |
| OSO₂i-Pr | H | H | On-Pr |
| OSO₂i-Pr | H | H | t-Bu |
| OSO₂Me | C(=NOMe)H | H | H |
| OSO₂Me | CF₃ | H | H |
| OSO₂Me | —CH=CH—CH=CH— | | H |
| OSO₂Me | —CH=N—CH=CH— | | F |
| OSO₂Me | —CH=N—CH=CH— | | OSO₂Me |
| OSO₂Me | —CH₂CH₂CH₂— | | H |
| OSO₂Me | —CH₂CH₂CH₂CH₂— | | F |
| OSO₂Me | —CH₂CH₂CH₂CH₂— | | OSO₂Me |
| OSO₂Me | CN | H | H |
| OSO₂Me | F | F | OSO₂Me |
| OSO₂Me | F | H | H |
| OSO₂Me | H | C(=NOMe)H | H |
| OSO₂Me | H | CF₃ | H |
| OSO₂Me | H | CN | H |
| OSO₂Me | H | F | H |
| OSO₂Me | H | H | Br |
| OSO₂Me | H | H | C(=NOMe)Me |
| OSO₂Me | H | H | C₂F₅ |
| OSO₂Me | H | H | CH=CH₂ |
| OSO₂Me | H | H | CH₂NMe₂ |
| OSO₂Me | H | H | CH₂SMe |
| OSO₂Me | H | H | Cl |

TABLE 46

| X¹ | X² | X³ | X⁴ |
|---|---|---|---|
| OSO₂Me | H | H | CO₂Me |
| OSO₂Me | H | H | Et |
| OSO₂Me | H | H | H |
| OSO₂Me | H | H | I |
| OSO₂Me | H | H | i-Pr |
| OSO₂Me | H | H | n-Bu |
| OSO₂Me | H | H | NHCO₂Me |
| OSO₂Me | H | H | NHMe |

TABLE 46-continued

| X¹ | X² | X³ | X⁴ |
|---|---|---|---|
| OSO₂Me | H | H | NMe₂ |
| OSO₂Me | H | H | n-Pr |
| OSO₂Me | H | H | OCHF₂ |
| OSO₂Me | H | H | OCO₂Me |
| OSO₂Me | H | H | OCOMe |
| OSO₂Me | H | H | OH |
| OSO₂Me | H | H | OPh |
| OSO₂Me | H | H | OSiMe₃ |
| OSO₂Me | H | H | OSO₂Et |
| OSO₂Me | H | H | OSO₂Me |
| OSO₂Me | H | H | OSO₂n-Pr |
| OSO₂Me | H | H | Ph |
| OSO₂Me | H | H | SiMe₃ |
| OSO₂Me | H | H | SO₂CF₃ |
| OSO₂Me | H | H | SOMe |
| OSO₂Me | H | I | H |
| OSO₂Me | H | NO₂ | H |
| OSO₂Me | H | OH | H |
| OSO₂Me | H | OSO₂Bn | H |
| OSO₂Me | H | OSO₂i-Pr | H |
| OSO₂Me | H | OSO₂n-Bu | H |
| OSO₂Me | H | OSO₂Ph | H |
| OSO₂Me | I | H | H |
| OSO₂Me | —N=CH—CH=CH— | | F |
| OSO₂Me | —N=CH—CH=CH— | | OSO₂Me |
| OSO₂Me | —N=CH—N=CH— | | H |
| OSO₂Me | H | H | CO₂H |
| OSO₂Me | H | H | c-Pr |
| OSO₂Me | H | H | F |
| OSO₂Me | H | H | H |
| OSO₂Me | H | H | i-Bu |
| OSO₂Me | H | H | Me |
| OSO₂Me | H | H | NH₂ |
| OSO₂Me | H | H | NHCOMe |
| OSO₂Me | H | H | NHSO₂Me |
| OSO₂Me | H | H | NO₂ |
| OSO₂Me | H | H | OCF₃ |
| OSO₂Me | H | H | OCH₂C≡CH |
| OSO₂Me | H | H | OCO₂NMe₂ |
| OSO₂Me | H | H | OEt |
| OSO₂Me | H | H | OMe |
| OSO₂Me | H | H | OSiMe₂t-Bu |
| OSO₂Me | H | H | OSO₂Bn |
| OSO₂Me | H | H | OSO₂i-Pr |
| OSO₂Me | H | H | OSO₂n-Bu |
| OSO₂Me | H | H | OSO₂Ph |
| OSO₂Me | H | H | SH |
| OSO₂Me | H | H | SMe |
| OSO₂Me | H | H | SO₂Me |
| OSO₂Me | H | H | t-Bu |
| OSO₂Me | H | Me | H |
| OSO₂Me | H | OCF₃ | H |
| OSO₂Me | H | OMe | H |
| OSO₂Me | H | OSO₂Et | H |
| OSO₂Me | H | OSO₂Me | H |
| OSO₂Me | H | OSO₂n-Pr | H |
| OSO₂Me | H | SO₂Me | H |
| OSO₂Me | Me | H | H |
| OSO₂Me | —N=CH—CH=CH— | | H |
| OSO₂Me | —N=CH—N=CH— | | F |

TABLE 47

| X¹ | X² | X³ | X⁴ |
|---|---|---|---|
| OSO₂Me | —NH—CH=CH— | | F |
| OSO₂Me | —NH—CH=CH— | | OSO₂Me |
| OSO₂Me | OCF₃ | H | H |
| OSO₂Me | —O—CH=CH— | | H |
| OSO₂Me | —O—CH=N— | | F |
| OSO₂Me | —O—CH=N— | | OSO₂Me |
| OSO₂Me | OMe | H | H |
| OSO₂Me | OSO₂Et | H | H |
| OSO₂Me | OSO₂Me | H | H |
| OSO₂Me | OSO₂Me | OSO₂Me | H |

TABLE 47-continued

| X¹ | X² | X³ | X⁴ |
|---|---|---|---|
| OSO₂Me | OSO₂n-Bu | H | H |
| OSO₂Me | OSO₂Ph | H | H |
| OSO₂Me | —S—CH=CH— | | H |
| OSO₂Me | SO₂Me | H | H |
| OSO₂n-Bu | H | H | Cl |
| OSO₂n-Bu | H | H | c-Pr |
| OSO₂n-Bu | H | H | F |
| OSO₂n-Bu | H | H | I |
| OSO₂n-Bu | H | H | n-Bu |
| OSO₂n-Bu | H | H | n-Pr |
| OSO₂n-Bu | H | H | OCHF₂ |
| OSO₂n-Bu | H | H | OEt |
| OSO₂n-Bu | H | H | OMe |
| OSO₂n-Bu | H | H | On-Pr |
| OSO₂n-Bu | H | H | t-Bu |
| OSO₂n-Pr | H | H | Cl |
| OSO₂n-Pr | H | H | c-Pr |
| OSO₂n-Pr | H | H | F |
| OSO₂n-Pr | H | H | I |
| OSO₂n-Pr | H | H | n-Bu |
| OSO₂n-Pr | H | H | n-Pr |
| OSO₂n-Pr | H | H | OCHF₂ |
| OSO₂n-Pr | H | H | OEt |
| OSO₂n-Pr | H | H | OMe |
| OSO₂Me | —N=CH—N=CH— | | OSO₂Me |
| OSO₂Me | —NH—CH=CH— | | H |
| OSO₂Me | NO₂ | H | H |
| OSO₂Me | —O—CH=CH— | | F |
| OSO₂Me | —O—CH=CH— | | OSO₂Me |
| OSO₂Me | —O—CH=N— | | H |
| OSO₂Me | OH | H | H |
| OSO₂Me | OSO₂Bn | H | H |
| OSO₂Me | OSO₂i-Pr | H | H |
| OSO₂Me | OSO₂Me | H | OSO₂Me |
| OSO₂Me | OSO₂Me | OSO₂Me | OSO₂Me |
| OSO₂Me | OSO₂n-Pr | H | H |
| OSO₂Me | —S—CH=CH— | | F |
| OSO₂Me | —S—CH=CH— | | OSO₂Me |
| OSO₂n-Bu | H | H | Br |
| OSO₂n-Bu | H | H | CN |
| OSO₂n-Bu | H | H | Et |
| OSO₂n-Bu | H | H | H |
| OSO₂n-Bu | H | H | Me |
| OSO₂n-Bu | H | H | NO₂ |
| OSO₂n-Bu | H | H | OCF₃ |
| OSO₂n-Bu | H | H | Oc-Pr |
| OSO₂n-Bu | H | H | OH |
| OSO₂n-Bu | H | H | On-Bu |
| OSO₂n-Bu | H | H | Ot-Bu |
| OSO₂n-Pr | H | H | Br |
| OSO₂n-Pr | H | H | CN |
| OSO₂n-Pr | H | H | Et |
| OSO₂n-Pr | H | H | H |
| OSO₂n-Pr | H | H | Me |
| OSO₂n-Pr | H | H | NO₂ |
| OSO₂n-Pr | H | H | OCF₃ |
| OSO₂n-Pr | H | H | Oc-Pr |
| OSO₂n-Pr | H | H | OH |

TABLE 48

| X¹ | X² | X³ | X⁴ |
|---|---|---|---|
| OSO₂n-Pr | H | H | On-Pr |
| OSO₂n-Pr | H | H | t-Bu |
| Ph | H | H | H |
| SiMe₃ | H | H | H |
| SO₂CF₃ | H | H | H |
| SO₂Me | H | H | SO₂Me |
| t-Bu | H | H | H |
| OSO₂n-Pr | H | H | On-Bu |
| OSO₂n-Pr | H | H | Ot-Bu |
| OSO₂Ph | H | H | H |
| SH | H | H | H |
| SMe | H | H | H |
| SO₂Me | H | H | H |
| SOMe | H | H | H |

TABLE 49

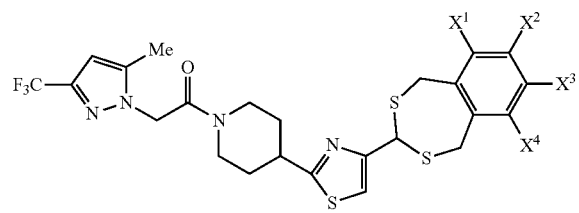

| X¹ | X² | X³ | X⁴ |
|---|---|---|---|
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | H | Cl |
| Cl | H | H | Cl |
| CN | H | H | CN |
| CO₂H | H | H | H |
| c-Pr | H | H | H |
| F | Br | H | F |
| F | C(=NOMe)H | H | H |
| F | CF₃ | H | F |
| F | Cl | H | F |
| F | CN | H | F |
| F | F | F | F |
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 50

| $X^1$ | $X^2$ | $X^3$ | $X^4$ |
|---|---|---|---|
| F | H | H | CHO |
| F | H | H | CN |
| F | H | H | CO$_2$Me |
| F | H | H | Et |
| F | H | H | H |
| F | H | H | i-Bu |
| F | H | H | Me |
| F | H | H | NH$_2$ |
| F | H | H | NHCOMe |
| F | H | H | NHSO$_2$Me |
| F | H | H | NO$_2$ |
| F | H | H | OCF$_3$ |
| F | H | H | OCO$_2$Me |
| F | H | H | OCOMe |
| F | H | H | OH |
| F | H | H | OPh |
| F | H | H | OSiMe$_3$ |
| F | H | H | SH |
| F | H | H | SMe |
| F | H | H | SO$_2$Me |
| F | H | H | t-Bu |
| F | H | Me | H |
| F | H | OCF$_3$ | H |
| F | H | OMe | H |
| F | H | SO$_2$Me | H |
| F | I | H | H |
| F | Me | H | H |
| F | NO$_2$ | H | H |
| F | OCF$_3$ | H | H |
| F | OH | H | H |
| F | OMe | H | H |
| F | SO$_2$Me | H | F |
| H | Br | Br | H |
| H | C(=NOMe)H | H | H |
| F | H | H | CH$_2$SMe |
| F | H | H | Cl |
| F | H | H | CO$_2$H |
| F | H | H | c-Pr |
| F | H | H | F |
| F | H | H | I |
| F | H | H | i-Pr |
| F | H | H | n-Bu |
| F | H | H | NHCO$_2$Me |
| F | H | H | NHMe |
| F | H | H | NMe$_2$ |
| F | H | H | n-Pr |
| F | H | H | OCH$_2$C≡CH |
| F | H | H | OCO$_2$NMe$_2$ |
| F | H | H | OEt |
| F | H | H | OMe |
| F | H | H | OSiMe$_2$t-Bu |
| F | H | H | Ph |
| F | H | H | SiMe$_3$ |
| F | H | H | SO$_2$CF$_3$ |
| F | H | H | SOMe |
| F | H | I | H |
| F | H | NO$_2$ | H |
| F | H | OH | H |
| F | H | OSO$_2$Me | H |
| F | I | H | F |
| F | Me | H | F |
| F | NO$_2$ | H | F |
| F | OCF$_3$ | H | F |
| F | OH | H | F |
| F | OMe | H | F |
| F | OSO$_2$Me | H | F |
| F | SO$_2$Me | H | H |
| H | Br | H | H |

TABLE 51

| $X^1$ | $X^2$ | $X^3$ | $X^4$ |
|---|---|---|---|
| H | CF$_3$ | CF$_3$ | H |
| H | —CH=CH—CH=CH— | | H |
| H | —CH$_2$CH$_2$CH$_2$— | | H |
| H | Cl | Cl | H |
| H | CN | H | H |
| H | F | H | H |
| H | I | H | H |
| H | Me | H | H |
| H | —N=CH—CH=CH— | | H |
| H | —NH—CH=CH— | | H |
| H | NO$_2$ | NO$_2$ | H |
| H | OCF$_3$ | OCF$_3$ | H |
| H | —O—CH=N— | | H |
| H | OH | OH | H |
| H | OMe | OMe | H |
| H | OSO$_2$Et | H | H |
| H | OSO$_2$Me | H | H |
| H | OSO$_2$n-Bu | H | H |
| H | OSO$_2$Ph | H | H |
| H | SO$_2$Me | H | H |
| I | H | H | H |
| i-Pr | H | H | H |
| Me | H | H | Me |
| NH$_2$ | H | H | H |
| NHCOMe | H | H | H |
| NHSO$_2$Me | H | H | H |
| NO$_2$ | H | H | H |
| OCF$_3$ | H | H | H |
| OCH$_2$C≡CH | H | H | H |
| OCO$_2$NMe$_2$ | H | H | H |
| OEt | H | H | H |
| OMe | H | H | H |
| OPh | H | H | H |
| OSiMe$_3$ | H | H | H |
| H | C(=NOMe)Me | H | H |
| H | CF$_3$ | H | H |
| H | —CH=N—CH=CH— | | H |
| H | —CH$_2$CH$_2$CH$_2$CH$_2$— | | H |
| H | CN | CN | H |
| H | F | F | H |
| H | H | H | H |
| H | I | I | H |
| H | Me | Me | H |
| H | —N=CH—N=CH— | | H |
| H | NO$_2$ | H | H |
| H | OCF$_3$ | H | H |
| H | —O—CH=CH— | | H |
| H | OH | H | H |
| H | OMe | H | H |
| H | OSO$_2$Bn | H | H |
| H | OSO$_2$i-Pr | H | H |
| H | OSO$_2$Me | OSO$_2$Me | H |
| H | OSO$_2$n-Pr | H | H |
| H | —S—CH=CH— | | H |
| H | SO$_2$Me | SO$_2$Me | H |
| i-Bu | H | H | H |
| Me | H | H | H |
| n-Bu | H | H | H |
| NHCO$_2$Me | H | H | H |
| NHMe | H | H | H |
| NMe$_2$ | H | H | H |
| n-Pr | H | H | H |
| OCF$_3$ | H | H | OCF$_3$ |
| OCO$_2$Me | H | H | H |
| OCOMe | H | H | H |
| OH | H | H | H |
| OMe | H | H | OMe |
| OSiMe$_2$t-Bu | H | H | H |

TABLE 52

| $X^1$ | $X^2$ | $X^3$ | $X^4$ |
|---|---|---|---|
| OSO$_2$CF$_3$ | H | H | Br |
| OSO$_2$CF$_3$ | H | H | CN |
| OSO$_2$CF$_3$ | H | H | Et |
| OSO$_2$CF$_3$ | H | H | H |

TABLE 52-continued

| X¹ | X² | X³ | X⁴ |
|---|---|---|---|
| OSO$_2$CF$_3$ | H | H | Me |
| OSO$_2$CF$_3$ | H | H | NO$_2$ |
| OSO$_2$CF$_3$ | H | H | OCF$_3$ |
| OSO$_2$CF$_3$ | H | H | Oc-Pr |
| OSO$_2$CF$_3$ | H | H | OH |
| OSO$_2$CF$_3$ | H | H | On-Bu |
| OSO$_2$CF$_3$ | H | H | Ot-Bu |
| OSO$_2$CHF$_2$ | H | H | Br |
| OSO$_2$CHF$_2$ | H | H | CN |
| OSO$_2$CHF$_2$ | H | H | Et |
| OSO$_2$CHF$_2$ | H | H | H |
| OSO$_2$CHF$_2$ | H | H | Me |
| OSO$_2$CHF$_2$ | H | H | NO$_2$ |
| OSO$_2$CHF$_2$ | H | H | OCF$_3$ |
| OSO$_2$CHF$_2$ | H | H | Oc-Pr |
| OSO$_2$CHF$_2$ | H | H | OH |
| OSO$_2$CHF$_2$ | H | H | On-Bu |
| OSO$_2$CHF$_2$ | H | H | Ot-Bu |
| OSO$_2$Et | H | H | Br |
| OSO$_2$Et | H | H | Cl |
| OSO$_2$Et | H | H | c-Pr |
| OSO$_2$Et | H | H | F |
| OSO$_2$Et | H | H | I |
| OSO$_2$Et | H | H | n-Bu |
| OSO$_2$Et | H | H | n-Pr |
| OSO$_2$Et | H | H | OCHF$_2$ |
| OSO$_2$Et | H | H | OEt |
| OSO$_2$Et | H | H | OMe |
| OSO$_2$Et | H | H | On-Pr |
| OSO$_2$Et | H | H | t-Bu |
| OSO$_2$Bn | H | H | H |
| OSO$_2$CF$_3$ | H | H | Cl |
| OSO$_2$CF$_3$ | H | H | c-Pr |
| OSO$_2$CF$_3$ | H | H | F |
| OSO$_2$CF$_3$ | H | H | I |
| OSO$_2$CF$_3$ | H | H | n-Bu |
| OSO$_2$CF$_3$ | H | H | n-Pr |
| OSO$_2$CF$_3$ | H | H | OCHF$_2$ |
| OSO$_2$CF$_3$ | H | H | OEt |
| OSO$_2$CF$_3$ | H | H | OMe |
| OSO$_2$CF$_3$ | H | H | On-Pr |
| OSO$_2$CF$_3$ | H | H | t-Bu |
| OSO$_2$CHF$_2$ | H | H | Cl |
| OSO$_2$CHF$_2$ | H | H | c-Pr |
| OSO$_2$CHF$_2$ | H | H | F |
| OSO$_2$CHF$_2$ | H | H | I |
| OSO$_2$CHF$_2$ | H | H | n-Bu |
| OSO$_2$CHF$_2$ | H | H | n-Pr |
| OSO$_2$CHF$_2$ | H | H | OCHF$_2$ |
| OSO$_2$CHF$_2$ | H | H | OEt |
| OSO$_2$CHF$_2$ | H | H | OMe |
| OSO$_2$CHF$_2$ | H | H | On-Pr |
| OSO$_2$CHF$_2$ | H | H | t-Bu |
| OSO$_2$Et | H | H | CF$_3$ |
| OSO$_2$Et | H | H | CN |
| OSO$_2$Et | H | H | Et |
| OSO$_2$Et | H | H | H |
| OSO$_2$Et | H | H | Me |
| OSO$_2$Et | H | H | NO$_2$ |
| OSO$_2$Et | H | H | OCF$_3$ |
| OSO$_2$Et | H | H | Oc-Pr |
| OSO$_2$Et | H | H | OH |
| OSO$_2$Et | H | H | On-Bu |
| OSO$_2$Et | H | H | Ot-Bu |

TABLE 53

| X¹ | X² | X³ | X⁴ |
|---|---|---|---|
| OSO$_2$i-Pr | H | H | CF$_3$ |
| OSO$_2$i-Pr | H | H | CN |
| OSO$_2$i-Pr | H | H | Et |
| OSO$_2$i-Pr | H | H | H |
| OSO$_2$i-Pr | H | H | Me |
| OSO$_2$i-Pr | H | H | NO$_2$ |
| OSO$_2$i-Pr | H | H | OCF$_3$ |
| OSO$_2$i-Pr | H | H | Oc-Pr |
| OSO$_2$i-Pr | H | H | OH |
| OSO$_2$i-Pr | H | H | On-Bu |
| OSO$_2$i-Pr | H | H | Ot-Bu |
| OSO$_2$Me | Br | H | H |
| OSO$_2$Me | C(=NOMe)Me | H | H |
| OSO$_2$Me | —CH=CH—CH=CH— | | F |
| OSO$_2$Me | —CH=CH—CH=CH— | | OSO$_2$Me |
| OSO$_2$Me | —CH=N—CH=CH— | | H |
| OSO$_2$Me | —CH$_2$CH$_2$CH$_2$— | | F |
| OSO$_2$Me | —CH$_2$CH$_2$CH$_2$— | | OSO$_2$Me |
| OSO$_2$Me | —CH$_2$CH$_2$CH$_2$CH$_2$— | | H |
| OSO$_2$Me | Cl | H | H |
| OSO$_2$Me | F | F | F |
| OSO$_2$Me | F | H | F |
| OSO$_2$Me | H | Br | H |
| OSO$_2$Me | H | C(=NOMe)Me | H |
| OSO$_2$Me | H | Cl | H |
| OSO$_2$Me | H | F | F |
| OSO$_2$Me | H | H | Bn |
| OSO$_2$Me | H | H | C(=NOMe)H |
| OSO$_2$Me | H | H | C≡CH |
| OSO$_2$Me | H | H | CF$_3$ |
| OSO$_2$Me | H | H | CH$_2$CN |
| OSO$_2$Me | H | H | CH$_2$OMe |
| OSO$_2$Me | H | H | CHO |
| OSO$_2$Me | H | H | CN |
| OSO$_2$i-Pr | H | H | Br |
| OSO$_2$i-Pr | H | H | Cl |
| OSO$_2$i-Pr | H | H | c-Pr |
| OSO$_2$i-Pr | H | H | F |
| OSO$_2$i-Pr | H | H | I |
| OSO$_2$i-Pr | H | H | n-Bu |
| OSO$_2$i-Pr | H | H | n-Pr |
| OSO$_2$i-Pr | H | H | OCHF$_2$ |
| OSO$_2$i-Pr | H | H | OEt |
| OSO$_2$i-Pr | H | H | OMe |
| OSO$_2$i-Pr | H | H | On-Pr |
| OSO$_2$i-Pr | H | H | t-Bu |
| OSO$_2$Me | C(=NOMe)H | H | H |
| OSO$_2$Me | CF$_3$ | H | H |
| OSO$_2$Me | —CH=CH—CH=CH— | | H |
| OSO$_2$Me | —CH=N—CH=CH— | | F |
| OSO$_2$Me | —CH=N—CH=CH— | | OSO$_2$Me |
| OSO$_2$Me | —CH$_2$CH$_2$CH$_2$— | | H |
| OSO$_2$Me | —CH$_2$CH$_2$CH$_2$CH$_2$— | | F |
| OSO$_2$Me | —CH$_2$CH$_2$CH$_2$CH$_2$— | | OSO$_2$Me |
| OSO$_2$Me | CN | H | H |
| OSO$_2$Me | F | F | OSO$_2$Me |
| OSO$_2$Me | F | H | H |
| OSO$_2$Me | H | C(=NOMe)H | H |
| OSO$_2$Me | H | CF$_3$ | H |
| OSO$_2$Me | H | CN | H |
| OSO$_2$Me | H | F | H |
| OSO$_2$Me | H | H | Br |
| OSO$_2$Me | H | H | C(=NOMe)Me |
| OSO$_2$Me | H | H | C$_2$F$_5$ |
| OSO$_2$Me | H | H | CH=CH$_2$ |
| OSO$_2$Me | H | H | CH$_2$NMe$_2$ |
| OSO$_2$Me | H | H | CH$_2$SMe |
| OSO$_2$Me | H | H | Cl |

TABLE 54

| X¹ | X² | X³ | X⁴ |
|---|---|---|---|
| OSO$_2$Me | H | H | CO$_2$Me |
| OSO$_2$Me | H | H | Et |
| OSO$_2$Me | H | H | H |
| OSO$_2$Me | H | H | I |
| OSO$_2$Me | H | H | i-Pr |
| OSO$_2$Me | H | H | n-Bu |
| OSO$_2$Me | H | H | NHCO$_2$Me |
| OSO$_2$Me | H | H | NHMe |

TABLE 54-continued

| X$^1$ | X$^2$ | X$^3$ | X$^4$ |
|---|---|---|---|
| OSO$_2$Me | H | H | NMe$_2$ |
| OSO$_2$Me | H | H | n-Pr |
| OSO$_2$Me | H | H | OCHF$_2$ |
| OSO$_2$Me | H | H | OCO$_2$Me |
| OSO$_2$Me | H | H | OCOMe |
| OSO$_2$Me | H | H | OH |
| OSO$_2$Me | H | H | OPh |
| OSO$_2$Me | H | H | OSiMe$_3$ |
| OSO$_2$Me | H | H | OSO$_2$Et |
| OSO$_2$Me | H | H | OSO$_2$Me |
| OSO$_2$Me | H | H | OSO$_2$n-Pr |
| OSO$_2$Me | H | H | Ph |
| OSO$_2$Me | H | H | SiMe$_3$ |
| OSO$_2$Me | H | H | SO$_2$CF$_3$ |
| OSO$_2$Me | H | H | SOMe |
| OSO$_2$Me | H | I | H |
| OSO$_2$Me | H | NO$_2$ | H |
| OSO$_2$Me | H | OH | H |
| OSO$_2$Me | H | OSO$_2$Bn | H |
| OSO$_2$Me | H | OSO$_2$i-Pr | H |
| OSO$_2$Me | H | OSO$_2$n-Bu | H |
| OSO$_2$Me | H | OSO$_2$Ph | H |
| OSO$_2$Me | I | H | H |
| OSO$_2$Me | —N=CH—CH=CH— | | F |
| OSO$_2$Me | —N=CH—CH=CH— | | OSO$_2$Me |
| OSO$_2$Me | —N=CH—N=CH— | | H |
| OSO$_2$Me | H | H | CO$_2$H |
| OSO$_2$Me | H | H | c-Pr |
| OSO$_2$Me | H | H | F |
| OSO$_2$Me | H | H | H |
| OSO$_2$Me | H | H | i-Bu |
| OSO$_2$Me | H | H | Me |
| OSO$_2$Me | H | H | NH$_2$ |
| OSO$_2$Me | H | H | NHCOMe |
| OSO$_2$Me | H | H | NHSO$_2$Me |
| OSO$_2$Me | H | H | NO$_2$ |
| OSO$_2$Me | H | H | OCF$_3$ |
| OSO$_2$Me | H | H | OCH$_2$C≡CH |
| OSO$_2$Me | H | H | OCO$_2$NMe$_2$ |
| OSO$_2$Me | H | H | OEt |
| OSO$_2$Me | H | H | OMe |
| OSO$_2$Me | H | H | OSiMe$_2$t-Bu |
| OSO$_2$Me | H | H | OSO$_2$Bn |
| OSO$_2$Me | H | H | OSO$_2$i-Pr |
| OSO$_2$Me | H | H | OSO$_2$n-Bu |
| OSO$_2$Me | H | H | OSO$_2$Ph |
| OSO$_2$Me | H | H | SH |
| OSO$_2$Me | H | H | SMe |
| OSO$_2$Me | H | H | SO$_2$Me |
| OSO$_2$Me | H | H | t-Bu |
| OSO$_2$Me | H | Me | H |
| OSO$_2$Me | H | OCF$_3$ | H |
| OSO$_2$Me | H | OMe | H |
| OSO$_2$Me | H | OSO$_2$Et | H |
| OSO$_2$Me | H | OSO$_2$Me | H |
| OSO$_2$Me | H | OSO$_2$n-Pr | H |
| OSO$_2$Me | H | SO$_2$Me | H |
| OSO$_2$Me | Me | H | H |
| OSO$_2$Me | —N=CH—CH=CH— | | H |
| OSO$_2$Me | —N=CH—N=CH— | | F |

TABLE 55

| X$^1$ | X$^2$ | X$^3$ | X$^4$ |
|---|---|---|---|
| OSO$_2$Me | —NH—CH=CH— | | F |
| OSO$_2$Me | —NH—CH=CH— | | OSO$_2$Me |
| OSO$_2$Me | OCF$_3$ | H | H |
| OSO$_2$Me | —O—CH=CH— | | H |
| OSO$_2$Me | —O—CH=N— | | F |
| OSO$_2$Me | —O—CH=N— | | OSO$_2$Me |
| OSO$_2$Me | OMe | H | H |
| OSO$_2$Me | OSO$_2$Et | H | H |
| OSO$_2$Me | OSO$_2$Me | H | H |
| OSO$_2$Me | OSO$_2$Me | OSO$_2$Me | H |

TABLE 55-continued

| X$^1$ | X$^2$ | X$^3$ | X$^4$ |
|---|---|---|---|
| OSO$_2$Me | OSO$_2$n-Bu | H | H |
| OSO$_2$Me | OSO$_2$Ph | H | H |
| OSO$_2$Me | —S—CH=CH— | | H |
| OSO$_2$Me | SO$_2$Me | H | H |
| OSO$_2$n-Bu | H | H | Cl |
| OSO$_2$n-Bu | H | H | c-Pr |
| OSO$_2$n-Bu | H | H | F |
| OSO$_2$n-Bu | H | H | I |
| OSO$_2$n-Bu | H | H | n-Bu |
| OSO$_2$n-Bu | H | H | n-Pr |
| OSO$_2$n-Bu | H | H | OCHF$_2$ |
| OSO$_2$n-Bu | H | H | OEt |
| OSO$_2$n-Bu | H | H | OMe |
| OSO$_2$n-Bu | H | H | On-Pr |
| OSO$_2$n-Bu | H | H | t-Bu |
| OSO$_2$n-Pr | H | H | Cl |
| OSO$_2$n-Pr | H | H | c-Pr |
| OSO$_2$n-Pr | H | H | F |
| OSO$_2$n-Pr | H | H | I |
| OSO$_2$n-Pr | H | H | n-Bu |
| OSO$_2$n-Pr | H | H | n-Pr |
| OSO$_2$n-Pr | H | H | OCHF$_2$ |
| OSO$_2$n-Pr | H | H | OEt |
| OSO$_2$n-Pr | H | H | OMe |
| OSO$_2$Me | —N=CH—N=CH— | | OSO$_2$Me |
| OSO$_2$Me | —NH—CH=CH— | | H |
| OSO$_2$Me | NO$_2$ | H | H |
| OSO$_2$Me | —O—CH=CH— | | F |
| OSO$_2$Me | —O—CH=CH— | | OSO$_2$Me |
| OSO$_2$Me | —O—CH=N— | | H |
| OSO$_2$Me | OH | H | H |
| OSO$_2$Me | OSO$_2$Bn | H | H |
| OSO$_2$Me | OSO$_2$i-Pr | H | H |
| OSO$_2$Me | OSO$_2$Me | H | OSO$_2$Me |
| OSO$_2$Me | OSO$_2$Me | OSO$_2$Me | OSO$_2$Me |
| OSO$_2$Me | OSO$_2$n-Pr | H | H |
| OSO$_2$Me | —S—CH=CH— | | F |
| OSO$_2$Me | —S—CH=CH— | | OSO$_2$Me |
| OSO$_2$n-Bu | H | H | Br |
| OSO$_2$n-Bu | H | H | CN |
| OSO$_2$n-Bu | H | H | Et |
| OSO$_2$n-Bu | H | H | H |
| OSO$_2$n-Bu | H | H | Me |
| OSO$_2$n-Bu | H | H | NO$_2$ |
| OSO$_2$n-Bu | H | H | OCF$_3$ |
| OSO$_2$n-Bu | H | H | Oc-Pr |
| OSO$_2$n-Bu | H | H | OH |
| OSO$_2$n-Bu | H | H | On-Bu |
| OSO$_2$n-Bu | H | H | Ot-Bu |
| OSO$_2$n-Pr | H | H | Br |
| OSO$_2$n-Pr | H | H | CN |
| OSO$_2$n-Pr | H | H | Et |
| OSO$_2$n-Pr | H | H | H |
| OSO$_2$n-Pr | H | H | Me |
| OSO$_2$n-Pr | H | H | NO$_2$ |
| OSO$_2$n-Pr | H | H | OCF$_3$ |
| OSO$_2$n-Pr | H | H | Oc-Pr |
| OSO$_2$n-Pr | H | H | OH |

TABLE 56

| X$^1$ | X$^2$ | X$^3$ | X$^4$ |
|---|---|---|---|
| OSO$_2$n-Pr | H | H | On-Pr |
| OSO$_2$n-Pr | H | H | t-Bu |
| Ph | H | H | H |
| SiMe$_3$ | H | H | H |
| SO$_2$CF$_3$ | H | H | H |
| SO$_2$Me | H | H | SO$_2$Me |
| t-Bu | H | H | H |
| OSO$_2$n-Pr | H | H | On-Bu |
| OSO$_2$n-Pr | H | H | Ot-Bu |
| OSO$_2$Ph | H | H | H |
| SH | H | H | H |
| SMe | H | H | H |

TABLE 56-continued

| X¹ | X² | X³ | X⁴ |
|---|---|---|---|
| SO₂Me | H | H | H |
| SOMe | H | H | H |

TABLE 57

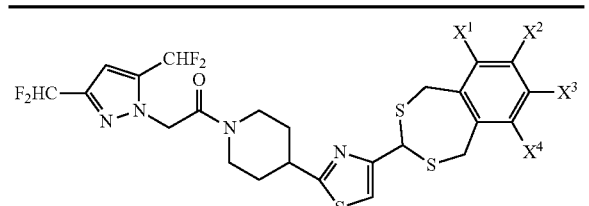

| X¹ | X² | X³ | X⁴ |
|---|---|---|---|
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | H | H |
| Cl | H | H | Cl |
| CN | H | H | CN |
| CO₂H | H | H | H |
| c-Pr | H | H | H |
| F | Br | H | F |
| F | C(=NOMe)H | H | H |
| F | CF₃ | H | F |
| F | Cl | H | F |
| F | CN | H | F |
| F | F | F | F |
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |
| Cl | Cl | H | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 58

| X¹ | X² | X³ | X⁴ |
|---|---|---|---|
| F | H | H | CHO |
| F | H | H | CN |
| F | H | H | CO₂Me |
| F | H | H | Et |
| F | H | H | H |
| F | H | H | i-Bu |
| F | H | H | Me |
| F | H | H | NH₂ |
| F | H | H | NHCOMe |
| F | H | H | NHSO₂Me |
| F | H | H | NO₂ |
| F | H | H | OCF₃ |
| F | H | H | OCO₂Me |
| F | H | H | OCOMe |
| F | H | H | OH |
| F | H | H | OPh |
| F | H | H | OSiMe₃ |
| F | H | H | SH |
| F | H | H | SMe |
| F | H | H | SO₂Me |
| F | H | H | t-Bu |
| F | H | Me | H |
| F | H | OCF₃ | H |
| F | H | OMe | H |
| F | H | SO₂Me | H |
| F | I | H | H |
| F | Me | H | H |
| F | NO₂ | H | H |
| F | OCF₃ | H | H |
| F | OH | H | H |
| F | OMe | H | H |
| F | SO₂Me | H | F |
| H | Br | Br | H |
| H | C(=NOMe)H | H | H |
| F | H | H | CH₂SMe |
| F | H | H | Cl |
| F | H | H | CO₂H |
| F | H | H | c-Pr |
| F | H | H | F |
| F | H | H | I |
| F | H | H | i-Pr |
| F | H | H | n-Bu |
| F | H | H | NHCO₂Me |
| F | H | H | NHMe |
| F | H | H | NMe₂ |
| F | H | H | n-Pr |
| F | H | H | OCH₂C≡CH |
| F | H | H | OCO₂NMe₂ |
| F | H | H | OEt |
| F | H | H | OMe |
| F | H | H | OSiMe₂t-Bu |
| F | H | H | Ph |
| F | H | H | SiMe₃ |
| F | H | H | SO₂CF₃ |
| F | H | H | SOMe |
| F | H | I | H |
| F | H | NO₂ | H |
| F | H | OH | H |
| F | H | OSO₂Me | H |
| F | I | H | F |
| F | Me | H | F |
| F | NO₂ | H | F |
| F | OCF₃ | H | F |
| F | OH | H | F |
| F | OMe | H | F |
| F | OSO₂Me | H | F |
| F | SO₂Me | H | H |
| H | Br | H | H |

TABLE 59

| X¹ | X² | X³ | X⁴ |
|---|---|---|---|
| H | CF₃ | CF₃ | H |
| H | —CH=CH—CH=CH— | | H |

TABLE 59-continued

| $X^1$ | $X^2$ | $X^3$ | $X^4$ |
|---|---|---|---|
| H | —CH$_2$CH$_2$CH$_2$— | | H |
| H | Cl | Cl | H |
| H | CN | H | H |
| H | F | H | H |
| H | I | H | H |
| H | Me | H | H |
| H | —N=CH—CH=CH— | | H |
| H | —NH—CH=CH— | | H |
| H | NO$_2$ | NO$_2$ | H |
| H | OCF$_3$ | OCF$_3$ | H |
| H | —O—CH=N— | | H |
| H | OH | OH | H |
| H | OMe | OMe | H |
| H | OSO$_2$Et | H | H |
| H | OSO$_2$Me | H | H |
| H | OSO$_2$n-Bu | H | H |
| H | OSO$_2$Ph | H | H |
| H | SO$_2$Me | H | H |
| I | H | H | H |
| i-Pr | H | H | H |
| Me | H | H | Me |
| NH$_2$ | H | H | H |
| NHCOMe | H | H | H |
| NHSO$_2$Me | H | H | H |
| NO$_2$ | H | H | H |
| OCF$_3$ | H | H | H |
| OCH$_2$C≡CH | H | H | H |
| OCO$_2$NMe$_2$ | H | H | H |
| OEt | H | H | H |
| OMe | H | H | H |
| OPh | H | H | H |
| OSiMe$_3$ | H | H | H |
| H | C(=NOMe)Me | H | H |
| H | CF$_3$ | H | H |
| H | —CH=N—CH=CH— | | H |
| H | —CH$_2$CH$_2$CH$_2$— | | H |
| H | CN | CN | H |
| H | F | F | H |
| H | H | H | H |
| H | I | I | H |
| H | Me | Me | H |
| H | —N=CH—N=CH— | | H |
| H | NO$_2$ | H | H |
| H | OCF$_3$ | H | H |
| H | —O—CH=CH— | | H |
| H | OH | H | H |
| H | OMe | H | H |
| H | OSO$_2$Bn | H | H |
| H | OSO$_2$i-Pr | H | H |
| H | OSO$_2$Me | OSO$_2$Me | H |
| H | OSO$_2$n-Pr | H | H |
| H | —S—CH=CH— | | H |
| H | SO$_2$Me | SO$_2$Me | H |
| i-Bu | H | H | H |
| Me | H | H | H |
| n-Bu | H | H | H |
| NHCO$_2$Me | H | H | H |
| NHMe | H | H | H |
| NMe$_2$ | H | H | H |
| n-Pr | H | H | H |
| OCF$_3$ | H | H | OCF$_3$ |
| OCO$_2$Me | H | H | H |
| OCOMe | H | H | H |
| OH | H | H | H |
| OMe | H | H | OMe |
| OSiMe$_2$t-Bu | H | H | H |

TABLE 60

| $X^1$ | $X^2$ | $X^3$ | $X^4$ |
|---|---|---|---|
| OSO$_2$CF$_3$ | H | H | Br |
| OSO$_2$CF$_3$ | H | H | CN |
| OSO$_2$CF$_3$ | H | H | Et |
| OSO$_2$CF$_3$ | H | H | H |

TABLE 60-continued

| $X^1$ | $X^2$ | $X^3$ | $X^4$ |
|---|---|---|---|
| OSO$_2$CF$_3$ | H | H | Me |
| OSO$_2$CF$_3$ | H | H | NO$_2$ |
| OSO$_2$CF$_3$ | H | H | OCF$_3$ |
| OSO$_2$CF$_3$ | H | H | Oc-Pr |
| OSO$_2$CF$_3$ | H | H | OH |
| OSO$_2$CF$_3$ | H | H | On-Bu |
| OSO$_2$CF$_3$ | H | H | Ot-Bu |
| OSO$_2$CHF$_2$ | H | H | Br |
| OSO$_2$CHF$_2$ | H | H | CN |
| OSO$_2$CHF$_2$ | H | H | Et |
| OSO$_2$CHF$_2$ | H | H | H |
| OSO$_2$CHF$_2$ | H | H | Me |
| OSO$_2$CHF$_2$ | H | H | NO$_2$ |
| OSO$_2$CHF$_2$ | H | H | OCF$_3$ |
| OSO$_2$CHF$_2$ | H | H | Oc-Pr |
| OSO$_2$CHF$_2$ | H | H | OH |
| OSO$_2$CHF$_2$ | H | H | On-Bu |
| OSO$_2$CHF$_2$ | H | H | Ot-Bu |
| OSO$_2$Et | H | H | Br |
| OSO$_2$Et | H | H | Cl |
| OSO$_2$Et | H | H | c-Pr |
| OSO$_2$Et | H | H | F |
| OSO$_2$Et | H | H | I |
| OSO$_2$Et | H | H | n-Bu |
| OSO$_2$Et | H | H | n-Pr |
| OSO$_2$Et | H | H | OCHF$_2$ |
| OSO$_2$Et | H | H | OEt |
| OSO$_2$Et | H | H | OMe |
| OSO$_2$Et | H | H | On-Pr |
| OSO$_2$Et | H | H | t-Bu |
| OSO$_2$Bn | H | H | H |
| OSO$_2$CF$_3$ | H | H | Cl |
| OSO$_2$CF$_3$ | H | H | c-Pr |
| OSO$_2$CF$_3$ | H | H | F |
| OSO$_2$CF$_3$ | H | H | I |
| OSO$_2$CF$_3$ | H | H | n-Bu |
| OSO$_2$CF$_3$ | H | H | n-Pr |
| OSO$_2$CF$_3$ | H | H | OCHF$_2$ |
| OSO$_2$CF$_3$ | H | H | OEt |
| OSO$_2$CF$_3$ | H | H | OMe |
| OSO$_2$CF$_3$ | H | H | On-Pr |
| OSO$_2$CF$_3$ | H | H | t-Bu |
| OSO$_2$CHF$_2$ | H | H | Cl |
| OSO$_2$CHF$_2$ | H | H | c-Pr |
| OSO$_2$CHF$_2$ | H | H | F |
| OSO$_2$CHF$_2$ | H | H | I |
| OSO$_2$CHF$_2$ | H | H | n-Bu |
| OSO$_2$CHF$_2$ | H | H | n-Pr |
| OSO$_2$CHF$_2$ | H | H | OCHF$_2$ |
| OSO$_2$CHF$_2$ | H | H | OEt |
| OSO$_2$CHF$_2$ | H | H | OMe |
| OSO$_2$CHF$_2$ | H | H | On-Pr |
| OSO$_2$CHF$_2$ | H | H | t-Bu |
| OSO$_2$Et | H | H | CF$_3$ |
| OSO$_2$Et | H | H | CN |
| OSO$_2$Et | H | H | Et |
| OSO$_2$Et | H | H | H |
| OSO$_2$Et | H | H | Me |
| OSO$_2$Et | H | H | NO$_2$ |
| OSO$_2$Et | H | H | OCF$_3$ |
| OSO$_2$Et | H | H | Oc-Pr |
| OSO$_2$Et | H | H | OH |
| OSO$_2$Et | H | H | On-Bu |
| OSO$_2$Et | H | H | Ot-Bu |

TABLE 61

| $X^1$ | $X^2$ | $X^3$ | $X^4$ |
|---|---|---|---|
| OSO$_2$i-Pr | H | H | CF$_3$ |
| OSO$_2$i-Pr | H | H | CN |
| OSO$_2$i-Pr | H | H | Et |
| OSO$_2$i-Pr | H | H | H |
| OSO$_2$i-Pr | H | H | Me |
| OSO$_2$i-Pr | H | H | NO$_2$ |

TABLE 61-continued

| X¹ | X² | X³ | X⁴ |
|---|---|---|---|
| OSO₂i-Pr | H | H | OCF₃ |
| OSO₂i-Pr | H | H | Oc-Pr |
| OSO₂i-Pr | H | H | OH |
| OSO₂i-Pr | H | H | On-Bu |
| OSO₂i-Pr | H | H | Ot-Bu |
| OSO₂Me | Br | H | H |
| OSO₂Me | C(=NOMe)Me | H | H |
| OSO₂Me | —CH=CH—CH=CH— | | F |
| OSO₂Me | —CH=CH—CH=CH— | | OSO₂Me |
| OSO₂Me | —CH=N—CH=CH— | | H |
| OSO₂Me | —CH₂CH₂CH₂— | | F |
| OSO₂Me | —CH₂CH₂CH₂— | | OSO₂Me |
| OSO₂Me | —CH₂CH₂CH₂CH₂— | | H |
| OSO₂Me | Cl | H | H |
| OSO₂Me | F | F | F |
| OSO₂Me | F | H | F |
| OSO₂Me | H | Br | H |
| OSO₂Me | H | C(=NOMe)Me | H |
| OSO₂Me | H | Cl | H |
| OSO₂Me | H | F | F |
| OSO₂Me | H | H | Bn |
| OSO₂Me | H | H | C(=NOMe)H |
| OSO₂Me | H | H | C≡CH |
| OSO₂Me | H | H | CF₃ |
| OSO₂Me | H | H | CH₂CN |
| OSO₂Me | H | H | CH₂OMe |
| OSO₂Me | H | H | CHO |
| OSO₂Me | H | H | CN |
| OSO₂i-Pr | H | H | Br |
| OSO₂i-Pr | H | H | Cl |
| OSO₂i-Pr | H | H | c-Pr |
| OSO₂i-Pr | H | H | F |
| OSO₂i-Pr | H | H | I |
| OSO₂i-Pr | H | H | n-Bu |
| OSO₂i-Pr | H | H | n-Pr |
| OSO₂i-Pr | H | H | OCHF₂ |
| OSO₂i-Pr | H | H | OEt |
| OSO₂i-Pr | H | H | OMe |
| OSO₂i-Pr | H | H | On-Pr |
| OSO₂i-Pr | H | H | t-Bu |
| OSO₂Me | C(=NOMe)H | H | H |
| OSO₂Me | CF₃ | H | H |
| OSO₂Me | —CH=CH—CH=CH— | | H |
| OSO₂Me | —CH=N—CH=CH— | | F |
| OSO₂Me | —CH=N—CH=CH— | | OSO₂Me |
| OSO₂Me | —CH₂CH₂CH₂— | | H |
| OSO₂Me | —CH₂CH₂CH₂CH₂— | | F |
| OSO₂Me | —CH₂CH₂CH₂CH₂— | | OSO₂Me |
| OSO₂Me | CN | H | H |
| OSO₂Me | F | F | OSO₂Me |
| OSO₂Me | F | H | H |
| OSO₂Me | H | C(=NOMe)H | H |
| OSO₂Me | H | CF₃ | H |
| OSO₂Me | H | CN | H |
| OSO₂Me | H | F | H |
| OSO₂Me | H | H | Br |
| OSO₂Me | H | H | C(=NOMe)Me |
| OSO₂Me | H | H | C₂F₅ |
| OSO₂Me | H | H | CH=CH₂ |
| OSO₂Me | H | H | CH₂NMe₂ |
| OSO₂Me | H | H | CH₂SMe |
| OSO₂Me | H | H | Cl |

TABLE 62

| X¹ | X² | X³ | X⁴ |
|---|---|---|---|
| OSO₂Me | H | H | CO₂Me |
| OSO₂Me | H | H | Et |
| OSO₂Me | H | H | H |
| OSO₂Me | H | H | I |
| OSO₂Me | H | H | i-Pr |
| OSO₂Me | H | H | n-Bu |
| OSO₂Me | H | H | NHCO₂Me |
| OSO₂Me | H | H | NHMe |
| OSO₂Me | H | H | NMe₂ |
| OSO₂Me | H | H | n-Pr |
| OSO₂Me | H | H | OCHF₂ |
| OSO₂Me | H | H | OCO₂Me |
| OSO₂Me | H | H | OCOMe |
| OSO₂Me | H | H | OH |
| OSO₂Me | H | H | OPh |
| OSO₂Me | H | H | OSiMe₃ |
| OSO₂Me | H | H | OSO₂Et |
| OSO₂Me | H | H | OSO₂Me |
| OSO₂Me | H | H | OSO₂n-Pr |
| OSO₂Me | H | H | Ph |
| OSO₂Me | H | H | SiMe₃ |
| OSO₂Me | H | H | SO₂CF₃ |
| OSO₂Me | H | H | SOMe |
| OSO₂Me | H | I | H |
| OSO₂Me | H | NO₂ | H |
| OSO₂Me | H | OH | H |
| OSO₂Me | H | OSO₂Bn | H |
| OSO₂Me | H | OSO₂i-Pr | H |
| OSO₂Me | H | OSO₂n-Bu | H |
| OSO₂Me | H | OSO₂Ph | H |
| OSO₂Me | I | H | H |
| OSO₂Me | —N=CH—CH=CH— | | F |
| OSO₂Me | —N=CH—CH=CH— | | OSO₂Me |
| OSO₂Me | —N=CH—N=CH— | | H |
| OSO₂Me | H | H | CO₂H |
| OSO₂Me | H | H | c-Pr |
| OSO₂Me | H | H | F |
| OSO₂Me | H | H | H |
| OSO₂Me | H | H | i-Bu |
| OSO₂Me | H | H | Me |
| OSO₂Me | H | H | NH₂ |
| OSO₂Me | H | H | NHCOMe |
| OSO₂Me | H | H | NHSO₂Me |
| OSO₂Me | H | H | NO₂ |
| OSO₂Me | H | H | OCF₃ |
| OSO₂Me | H | H | OCH₂C≡CH |
| OSO₂Me | H | H | OCO₂NMe₂ |
| OSO₂Me | H | H | OEt |
| OSO₂Me | H | H | OMe |
| OSO₂Me | H | H | OSiMe₂t-Bu |
| OSO₂Me | H | H | OSO₂Bn |
| OSO₂Me | H | H | OSO₂i-Pr |
| OSO₂Me | H | H | OSO₂n-Bu |
| OSO₂Me | H | H | OSO₂Ph |
| OSO₂Me | H | H | SH |
| OSO₂Me | H | H | SMe |
| OSO₂Me | H | H | SO₂Me |
| OSO₂Me | H | H | t-Bu |
| OSO₂Me | H | Me | H |
| OSO₂Me | H | OCF₃ | H |
| OSO₂Me | H | OMe | H |
| OSO₂Me | H | OSO₂Et | H |
| OSO₂Me | H | OSO₂Me | H |
| OSO₂Me | H | OSO₂n-Pr | H |
| OSO₂Me | H | SO₂Me | H |
| OSO₂Me | Me | H | H |
| OSO₂Me | —N=CH—CH=CH— | | H |
| OSO₂Me | —N=CH—N=CH— | | F |

TABLE 63

| X¹ | X² | X³ | X⁴ | X¹ | X² | X³ | X⁴ |
|---|---|---|---|---|---|---|---|
| OSO₂Me | —NH—CH=CH— | | F | OSO₂Me | —N=CH—N=CH— | | OSO₂Me |
| OSO₂Me | —NH—CH=CH— | | OSO₂Me | OSO₂Me | —NH—CH=CH— | | H |
| OSO₂Me | OCF₃ | H | H | OSO₂Me | NO₂ | H | H |
| OSO₂Me | —O—CH=CH— | | H | OSO₂Me | —O—CH=CH— | | F |
| OSO₂Me | —O—CH=N— | | F | OSO₂Me | —O—CH=CH— | | OSO₂Me |
| OSO₂Me | —O—CH=N— | | OSO₂Me | OSO₂Me | —O—CH=N— | | H |
| OSO₂Me | OMe | H | H | OSO₂Me | OH | H | H |
| OSO₂Me | OSO₂Et | H | H | OSO₂Me | OSO₂Bn | H | H |
| OSO₂Me | OSO₂Me | H | H | OSO₂Me | OSO₂i-Pr | H | H |
| OSO₂Me | OSO₂Me | OSO₂Me | H | OSO₂Me | OSO₂Me | H | OSO₂Me |
| OSO₂Me | OSO₂n-Bu | H | H | OSO₂Me | OSO₂Me | OSO₂Me | OSO₂Me |
| OSO₂Me | OSO₂Ph | H | H | OSO₂Me | OSO₂n-Pr | H | H |
| OSO₂Me | —S—CH=CH— | | H | OSO₂Me | —S—CH=CH— | | F |
| OSO₂Me | SO₂Me | H | H | OSO₂Me | —S—CH=CH— | | OSO₂Me |
| OSO₂n-Bu | H | H | Cl | OSO₂n-Bu | H | H | Br |
| OSO₂n-Bu | H | H | c-Pr | OSO₂n-Bu | H | H | CN |
| OSO₂n-Bu | H | H | F | OSO₂n-Bu | H | H | Et |
| OSO₂n-Bu | H | H | I | OSO₂n-Bu | H | H | H |
| OSO₂n-Bu | H | H | n-Bu | OSO₂n-Bu | H | H | Me |
| OSO₂n-Bu | H | H | n-Pr | OSO₂n-Bu | H | H | NO₂ |
| OSO₂n-Bu | H | H | OCHF₂ | OSO₂n-Bu | H | H | OCF₃ |
| OSO₂n-Bu | H | H | OEt | OSO₂n-Bu | H | H | Oc-Pr |
| OSO₂n-Bu | H | H | OMe | OSO₂n-Bu | H | H | OH |
| OSO₂n-Bu | H | H | On-Pr | OSO₂n-Bu | H | H | On-Bu |
| OSO₂n-Bu | H | H | t-Bu | OSO₂n-Bu | H | H | Ot-Bu |
| OSO₂n-Pr | H | H | Cl | OSO₂n-Pr | H | H | Br |
| OSO₂n-Pr | H | H | c-Pr | OSO₂n-Pr | H | H | CN |
| OSO₂n-Pr | H | H | F | OSO₂n-Pr | H | H | Et |
| OSO₂n-Pr | H | H | I | OSO₂n-Pr | H | H | H |
| OSO₂n-Pr | H | H | n-Bu | OSO₂n-Pr | H | H | Me |
| OSO₂n-Pr | H | H | n-Pr | OSO₂n-Pr | H | H | NO₂ |
| OSO₂n-Pr | H | H | OCHF₂ | OSO₂n-Pr | H | H | OCF₃ |
| OSO₂n-Pr | H | H | OEt | OSO₂n-Pr | H | H | Oc-Pr |
| OSO₂n-Pr | H | H | OMe | OSO₂n-Pr | H | H | OH |

TABLE 64

| X¹ | X² | X³ | X⁴ | X¹ | X² | X³ | X⁴ |
|---|---|---|---|---|---|---|---|
| OSO₂n-Pr | H | H | On-Pr | OSO₂n-Pr | H | H | On-Bu |
| OSO₂n-Pr | H | H | t-Bu | OSO₂n-Pr | H | H | Ot-Bu |
| Ph | H | H | H | OSO₂Ph | H | H | H |
| SiMe₃ | H | H | H | SH | H | H | H |
| SO₂CF₃ | H | H | H | SMe | H | H | H |
| SO₂Me | H | H | SO₂Me | SO₂Me | H | H | H |
| t-Bu | H | H | H | SOMe | H | H | H |

TABLE 65

[Structure: F₃C-pyrazole-Me connected via CH₂C(O) to piperidine-thiazole-dioxepine-aryl(X¹,X²,X³,X⁴)-Me]

| X¹ | X² | X³ | X⁴ |
|---|---|---|---|
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | H | H |
| Cl | H | H | Cl |
| CN | H | H | CN |
| CO₂H | H | H | H |

TABLE 65-continued

[Structure: F₃C-pyrazole-Me connected via CH₂C(O) to piperidine-thiazole-dioxepine-aryl(X¹,X²,X³,X⁴)-Me]

| X¹ | X² | X³ | X⁴ |
|---|---|---|---|
| c-Pr | H | H | H |
| F | Br | H | F |
| F | C(=NOMe)H | H | H |
| F | CF₃ | H | F |
| F | Cl | H | F |
| F | CN | H | F |
| F | F | H | F |
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |

TABLE 65-continued

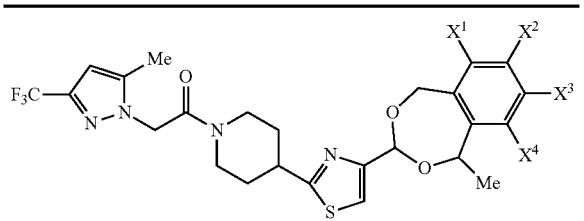

| X¹ | X² | X³ | X⁴ |
|---|---|---|---|
| Cl | H | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |

TABLE 65-continued

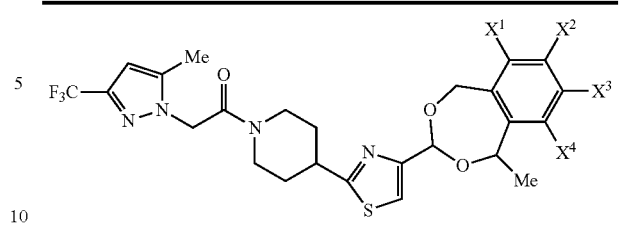

| X¹ | X² | X³ | X⁴ |
|---|---|---|---|
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 66

| X¹ | X² | X³ | X⁴ | X¹ | X² | X³ | X⁴ |
|---|---|---|---|---|---|---|---|
| F | H | H | CHO | F | H | H | CH₂SMe |
| F | H | H | CN | F | H | H | Cl |
| F | H | H | CO₂Me | F | H | H | CO₂H |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | NH₂ | F | H | H | n-Bu |
| F | H | H | NHCOMe | F | H | H | NHCO₂Me |
| F | H | H | NHSO₂Me | F | H | H | NHMe |
| F | H | H | NO₂ | F | H | H | NMe₂ |
| F | H | H | OCF₃ | F | H | H | n-Pr |
| F | H | H | OCO₂Me | F | H | H | OCH₂C≡CH |
| F | H | H | OCOMe | F | H | H | OCO₂NMe₂ |
| F | H | H | OH | F | H | H | OEt |
| F | H | H | OPh | F | H | H | OMe |
| F | H | H | OSiMe₃ | F | H | H | OSiMe₂t-Bu |
| F | H | H | SH | F | H | H | Ph |
| F | H | H | SMe | F | H | H | SiMe₃ |
| F | H | H | SO₂Me | F | H | H | SO₂CF₃ |
| F | H | H | t-Bu | F | H | H | SOMe |
| F | H | Me | H | F | H | I | H |
| F | H | OCF₃ | H | F | H | NO₂ | H |
| F | H | OMe | H | F | H | OH | H |
| F | H | SO₂Me | H | F | H | OSO₂Me | H |
| F | I | H | H | F | I | H | F |
| F | Me | H | H | F | Me | H | F |
| F | NO₂ | H | H | F | NO₂ | H | F |
| F | OCF₃ | H | H | F | OCF₃ | H | F |
| F | OH | H | H | F | OH | H | F |
| F | OMe | H | H | F | OMe | H | F |
| F | SO₂Me | H | F | F | OSO₂Me | H | F |
| H | Br | Br | H | F | SO₂Me | H | H |
| H | C(=NOMe)H | H | H | H | Br | H | H |

TABLE 67

| X¹ | X² | X³ | X⁴ | X¹ | X² | X³ | X⁴ |
|---|---|---|---|---|---|---|---|
| H | CF₃ | CF₃ | H | H | C(=NOMe)Me | H | H |
| H | —CH=CH—CH=CH— | | H | H | CF₃ | H | H |
| H | —CH₂CH₂CH₂— | | H | H | —CH=N—CH=CH— | | H |
| H | Cl | Cl | H | H | —CH₂CH₂CH₂CH₂— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |

TABLE 67-continued

| $X^1$ | $X^2$ | $X^3$ | $X^4$ | $X^1$ | $X^2$ | $X^3$ | $X^4$ |
|---|---|---|---|---|---|---|---|
| H | —NH—CH=CH— | | H | H | —N=CH—N=CH— | | H |
| H | $NO_2$ | $NO_2$ | H | H | $NO_2$ | H | H |
| H | $OCF_3$ | $OCF_3$ | H | H | $OCF_3$ | H | H |
| H | —O—CH=N— | | H | H | —O—CH=CH— | | H |
| H | OH | OH | H | H | OH | H | H |
| H | OMe | OMe | H | H | OMe | H | H |
| H | $OSO_2Et$ | H | H | H | $OSO_2Bn$ | H | H |
| H | $OSO_2Me$ | H | H | H | $OSO_2$i-Pr | H | H |
| H | $OSO_2$n-Bu | H | H | H | $OSO_2Me$ | $OSO_2Me$ | H |
| H | $OSO_2Ph$ | H | H | H | $OSO_2$n-Pr | H | H |
| H | $SO_2Me$ | H | H | H | —S—CH=CH— | | H |
| I | H | H | H | $SO_2Me$ | H | $SO_2Me$ | H |
| i-Pr | H | H | H | i-Bu | H | H | H |
| Me | H | H | Me | Me | H | H | H |
| $NH_2$ | H | H | H | n-Bu | H | H | H |
| NHCOMe | H | H | H | $NHCO_2Me$ | H | H | H |
| $NHSO_2Me$ | H | H | H | NHMe | H | H | H |
| $NO_2$ | H | H | H | $NMe_2$ | H | H | H |
| $OCF_3$ | H | H | H | n-Pr | H | H | H |
| $OCH_2C≡CH$ | H | H | H | $OCF_3$ | H | H | $OCF_3$ |
| $OCO_2NMe_2$ | H | H | H | $OCO_2Me$ | H | H | H |
| OEt | H | H | H | OCOMe | H | H | H |
| OMe | H | H | H | OH | H | H | H |
| OPh | H | H | H | OMe | H | H | OMe |
| $OSiMe_3$ | H | H | H | $OSiMe_2$t-Bu | H | H | H |

TABLE 68

| $X^1$ | $X^2$ | $X^3$ | $X^4$ | $X^1$ | $X^2$ | $X^3$ | $X^4$ |
|---|---|---|---|---|---|---|---|
| $OSO_2CF_3$ | H | H | Br | $OSO_2Bn$ | H | H | H |
| $OSO_2CF_3$ | H | H | CN | $OSO_2CF_3$ | H | H | Cl |
| $OSO_2CF_3$ | H | H | Et | $OSO_2CF_3$ | H | H | c-Pr |
| $OSO_2CF_3$ | H | H | H | $OSO_2CF_3$ | H | H | F |
| $OSO_2CF_3$ | H | H | Me | $OSO_2CF_3$ | H | H | I |
| $OSO_2CF_3$ | H | H | $NO_2$ | $OSO_2CF_3$ | H | H | n-Bu |
| $OSO_2CF_3$ | H | H | $OCF_3$ | $OSO_2CF_3$ | H | H | n-Pr |
| $OSO_2CF_3$ | H | H | Oc-Pr | $OSO_2CF_3$ | H | H | $OCHF_2$ |
| $OSO_2CF_3$ | H | H | OH | $OSO_2CF_3$ | H | H | OEt |
| $OSO_2CF_3$ | H | H | On-Bu | $OSO_2CF_3$ | H | H | OMe |
| $OSO_2CF_3$ | H | H | Ot-Bu | $OSO_2CF_3$ | H | H | On-Pr |
| $OSO_2CHF_2$ | H | H | Br | $OSO_2CF_3$ | H | H | t-Bu |
| $OSO_2CHF_2$ | H | H | CN | $OSO_2CHF_2$ | H | H | Cl |
| $OSO_2CHF_2$ | H | H | Et | $OSO_2CHF_2$ | H | H | c-Pr |
| $OSO_2CHF_2$ | H | H | H | $OSO_2CHF_2$ | H | H | F |
| $OSO_2CHF_2$ | H | H | Me | $OSO_2CHF_2$ | H | H | I |
| $OSO_2CHF_2$ | H | H | $NO_2$ | $OSO_2CHF_2$ | H | H | n-Bu |
| $OSO_2CHF_2$ | H | H | $OCF_3$ | $OSO_2CHF_2$ | H | H | n-Pr |
| $OSO_2CHF_2$ | H | H | Oc-Pr | $OSO_2CHF_2$ | H | H | $OCHF_2$ |
| $OSO_2CHF_2$ | H | H | OH | $OSO_2CHF_2$ | H | H | OEt |
| $OSO_2CHF_2$ | H | H | On-Bu | $OSO_2CHF_2$ | H | H | OMe |
| $OSO_2CHF_2$ | H | H | Ot-Bu | $OSO_2CHF_2$ | H | H | On-Pr |
| $OSO_2Et$ | H | H | Br | $OSO_2CHF_2$ | H | H | t-Bu |
| $OSO_2Et$ | H | H | Cl | $OSO_2Et$ | H | H | $CF_3$ |
| $OSO_2Et$ | H | H | c-Pr | $OSO_2Et$ | H | H | CN |
| $OSO_2Et$ | H | H | F | $OSO_2Et$ | H | H | Et |
| $OSO_2Et$ | H | H | I | $OSO_2Et$ | H | H | H |
| $OSO_2Et$ | H | H | n-Bu | $OSO_2Et$ | H | H | Me |
| $OSO_2Et$ | H | H | n-Pr | $OSO_2Et$ | H | H | $NO_2$ |
| $OSO_2Et$ | H | H | $OCHF_2$ | $OSO_2Et$ | H | H | $OCF_3$ |
| $OSO_2Et$ | H | H | OEt | $OSO_2Et$ | H | H | Oc-Pr |
| $OSO_2Et$ | H | H | OMe | $OSO_2Et$ | H | H | OH |
| $OSO_2Et$ | H | H | On-Pr | $OSO_2Et$ | H | H | On-Bu |
| $OSO_2Et$ | H | H | t-Bu | $OSO_2Et$ | H | H | Ot-Bu |

TABLE 69

| $X^1$ | $X^2$ | $X^3$ | $X^4$ | $X^1$ | $X^2$ | $X^3$ | $X^4$ |
|---|---|---|---|---|---|---|---|
| $OSO_2$i-Pr | H | H | $CF_3$ | $OSO_2$i-Pr | H | H | Br |
| $OSO_2$i-Pr | H | H | CN | $OSO_2$i-Pr | H | H | Cl |
| $OSO_2$i-Pr | H | H | Et | $OSO_2$i-Pr | H | H | c-Pr |
| $OSO_2$i-Pr | H | H | H | $OSO_2$i-Pr | H | H | F |
| $OSO_2$i-Pr | H | H | Me | $OSO_2$i-Pr | H | H | I |
| $OSO_2$i-Pr | H | H | $NO_2$ | $OSO_2$i-Pr | H | H | n-Bu |
| $OSO_2$i-Pr | H | H | $OCF_3$ | $OSO_2$i-Pr | H | H | n-Pr |
| $OSO_2$i-Pr | H | H | Oc-Pr | $OSO_2$i-Pr | H | H | $OCHF_2$ |
| $OSO_2$i-Pr | H | H | OH | $OSO_2$i-Pr | H | H | OEt |
| $OSO_2$i-Pr | H | H | On-Bu | $OSO_2$i-Pr | H | H | OMe |
| $OSO_2$i-Pr | H | H | Ot-Bu | $OSO_2$i-Pr | H | H | On-Pr |
| $OSO_2Me$ | Br | H | H | $OSO_2$i-Pr | H | H | t-Bu |
| $OSO_2Me$ | C(=NOMe)Me | H | H | $OSO_2Me$ | C(=NOMe)H | H | H |
| $OSO_2Me$ | —CH=CH—CH=CH— | | F | $OSO_2Me$ | $CF_3$ | H | H |
| $OSO_2Me$ | —CH=CH—CH=CH— | | $OSO_2Me$ | $OSO_2Me$ | —CH=CH—CH=CH— | | H |
| $OSO_2Me$ | —CH=N—CH=CH— | | H | $OSO_2Me$ | —CH=N—CH=CH— | | F |
| $OSO_2Me$ | —$CH_2CH_2CH_2$— | | F | $OSO_2Me$ | —CH=N—CH=CH— | | $OSO_2Me$ |
| $OSO_2Me$ | —$CH_2CH_2CH_2$— | | $OSO_2Me$ | $OSO_2Me$ | —$CH_2CH_2CH_2$— | | H |
| $OSO_2Me$ | —$CH_2CH_2CH_2CH_2$— | | H | $OSO_2Me$ | —$CH_2CH_2CH_2CH_2$— | | F |
| $OSO_2Me$ | Cl | H | H | $OSO_2Me$ | —$CH_2CH_2CH_2CH_2$— | | $OSO_2Me$ |
| $OSO_2Me$ | F | F | F | $OSO_2Me$ | CN | H | H |

TABLE 69-continued

| X¹ | X² | X³ | X⁴ | X¹ | X² | X³ | X⁴ |
|---|---|---|---|---|---|---|---|
| OSO₂Me | F | H | F | OSO₂Me | F | F | OSO₂Me |
| OSO₂Me | H | Br | H | OSO₂Me | F | H | H |
| OSO₂Me | H | C(=NOMe)Me | H | OSO₂Me | H | C(=NOMe)H | H |
| OSO₂Me | H | Cl | H | OSO₂Me | H | CF₃ | H |
| OSO₂Me | H | F | F | OSO₂Me | H | CN | H |
| OSO₂Me | H | H | Bn | OSO₂Me | H | F | H |
| OSO₂Me | H | H | C(=NOMe)H | OSO₂Me | H | H | Br |
| OSO₂Me | H | H | C≡CH | OSO₂Me | H | H | C(=NOMe)Me |
| OSO₂Me | H | H | CF₃ | OSO₂Me | H | H | C₂F₅ |
| OSO₂Me | H | H | CH₂CN | OSO₂Me | H | H | CH=CH₂ |
| OSO₂Me | H | H | CH₂OMe | OSO₂Me | H | H | CH₂NMe₂ |
| OSO₂Me | H | H | CHO | OSO₂Me | H | H | CH₂SMe |
| OSO₂Me | H | H | CN | OSO₂Me | H | H | Cl |

TABLE 70

| X¹ | X² | X³ | X⁴ | X¹ | X² | X³ | X⁴ |
|---|---|---|---|---|---|---|---|
| OSO₂Me | H | H | CO₂Me | OSO₂Me | H | H | CO₂H |
| OSO₂Me | H | H | Et | OSO₂Me | H | H | c-Pr |
| OSO₂Me | H | H | H | OSO₂Me | H | H | F |
| OSO₂Me | H | H | I | OSO₂Me | H | H | H |
| OSO₂Me | H | H | i-Pr | OSO₂Me | H | H | i-Bu |
| OSO₂Me | H | H | n-Bu | OSO₂Me | H | H | Me |
| OSO₂Me | H | H | NHCO₂Me | OSO₂Me | H | H | NH₂ |
| OSO₂Me | H | H | NHMe | OSO₂Me | H | H | NHCOMe |
| OSO₂Me | H | H | NMe₂ | OSO₂Me | H | H | NHSO₂Me |
| OSO₂Me | H | H | n-Pr | OSO₂Me | H | H | NO₂ |
| OSO₂Me | H | H | OCHF₂ | OSO₂Me | H | H | OCF₃ |
| OSO₂Me | H | H | OCO₂Me | OSO₂Me | H | H | OCH₂C≡CH |
| OSO₂Me | H | H | OCOMe | OSO₂Me | H | H | OCO₂NMe₂ |
| OSO₂Me | H | H | OH | OSO₂Me | H | H | OEt |
| OSO₂Me | H | H | OPh | OSO₂Me | H | H | OMe |
| OSO₂Me | H | H | OSiMe₃ | OSO₂Me | H | H | OSiMe₂t-Bu |
| OSO₂Me | H | H | OSO₂Et | OSO₂Me | H | H | OSO₂Bn |
| OSO₂Me | H | H | OSO₂Me | OSO₂Me | H | H | OSO₂i-Pr |
| OSO₂Me | H | H | OSO₂n-Pr | OSO₂Me | H | H | OSO₂n-Bu |
| OSO₂Me | H | H | Ph | OSO₂Me | H | H | OSO₂Ph |
| OSO₂Me | H | H | SiMe₃ | OSO₂Me | H | H | SH |
| OSO₂Me | H | H | SO₂CF₃ | OSO₂Me | H | H | SMe |
| OSO₂Me | H | H | SOMe | OSO₂Me | H | H | SO₂Me |
| OSO₂Me | H | I | H | OSO₂Me | H | H | t-Bu |
| OSO₂Me | H | NO₂ | H | OSO₂Me | H | Me | H |
| OSO₂Me | H | OH | H | OSO₂Me | H | OCF₃ | H |
| OSO₂Me | H | OSO₂Bn | H | OSO₂Me | H | OMe | H |
| OSO₂Me | H | OSO₂i-Pr | H | OSO₂Me | H | OSO₂Et | H |
| OSO₂Me | H | OSO₂n-Bu | H | OSO₂Me | H | OSO₂Me | H |
| OSO₂Me | H | OSO₂Ph | H | OSO₂Me | H | OSO₂n-Pr | H |
| OSO₂Me | I | H | H | OSO₂Me | H | SO₂Me | H |
| OSO₂Me | —N=CH—CH=CH— | | F | OSO₂Me | Me | H | H |
| OSO₂Me | —N=CH—CH=CH— | | OSO₂Me | OSO₂Me | —N=CH—CH=CH— | | H |
| OSO₂Me | —N=CH—N=CH— | | H | OSO₂Me | —N=CH—N=CH— | | F |

TABLE 71

| X¹ | X² | X³ | X⁴ | X¹ | X² | X³ | X⁴ |
|---|---|---|---|---|---|---|---|
| OSO₂Me | —NH—CH=CH— | | F | OSO₂Me | —N=CH—N=CH— | | OSO₂Me |
| OSO₂Me | —NH—CH=CH— | | OSO₂Me | OSO₂Me | —NH—CH=CH— | | H |
| OSO₂Me | OCF₃ | H | H | OSO₂Me | NO₂ | H | H |
| OSO₂Me | —O—CH=CH— | | H | OSO₂Me | —O—CH=CH— | | F |
| OSO₂Me | —O—CH=N— | | F | OSO₂Me | —O—CH=CH— | | OSO₂Me |
| OSO₂Me | —O—CH=N— | | OSO₂Me | OSO₂Me | —O—CH=N— | | H |
| OSO₂Me | OMe | H | H | OSO₂Me | OH | H | H |
| OSO₂Me | OSO₂Et | H | H | OSO₂Me | OSO₂Bn | H | H |
| OSO₂Me | OSO₂Me | H | H | OSO₂Me | OSO₂i-Pr | H | H |
| OSO₂Me | OSO₂Me | OSO₂Me | H | OSO₂Me | OSO₂Me | H | OSO₂Me |
| OSO₂Me | OSO₂n-Bu | H | H | OSO₂Me | OSO₂Me | OSO₂Me | OSO₂Me |
| OSO₂Me | OSO₂Ph | H | H | OSO₂Me | OSO₂n-Pr | H | H |
| OSO₂Me | —S—CH=CH— | | H | OSO₂Me | —S—CH=CH— | | F |
| OSO₂Me | SO₂Me | H | H | OSO₂Me | —S—CH=CH— | | OSO₂Me |
| OSO₂n-Bu | H | H | Cl | OSO₂n-Bu | H | H | Br |
| OSO₂n-Bu | H | H | c-Pr | OSO₂n-Bu | H | H | CN |

TABLE 71-continued

| X¹ | X² | X³ | X⁴ | X¹ | X² | X³ | X⁴ |
|---|---|---|---|---|---|---|---|
| OSO₂n-Bu | H | H | F | OSO₂n-Bu | H | H | Et |
| OSO₂n-Bu | H | H | I | OSO₂n-Bu | H | H | H |
| OSO₂n-Bu | H | H | n-Bu | OSO₂n-Bu | H | H | Me |
| OSO₂n-Bu | H | H | n-Pr | OSO₂n-Bu | H | H | NO₂ |
| OSO₂n-Bu | H | H | OCHF₂ | OSO₂n-Bu | H | H | OCF₃ |
| OSO₂n-Bu | H | H | OEt | OSO₂n-Bu | H | H | Oc-Pr |
| OSO₂n-Bu | H | H | OMe | OSO₂n-Bu | H | H | OH |
| OSO₂n-Bu | H | H | On-Pr | OSO₂n-Bu | H | H | On-Bu |
| OSO₂n-Bu | H | H | t-Bu | OSO₂n-Bu | H | H | Ot-Bu |
| OSO₂n-Pr | H | H | Cl | OSO₂n-Pr | H | H | Br |
| OSO₂n-Pr | H | H | c-Pr | OSO₂n-Pr | H | H | CN |
| OSO₂n-Pr | H | H | F | OSO₂n-Pr | H | H | Et |
| OSO₂n-Pr | H | H | I | OSO₂n-Pr | H | H | H |
| OSO₂n-Pr | H | H | n-Bu | OSO₂n-Pr | H | H | Me |
| OSO₂n-Pr | H | H | n-Pr | OSO₂n-Pr | H | H | NO₂ |
| OSO₂n-Pr | H | H | OCHF₂ | OSO₂n-Pr | H | H | OCF₃ |
| OSO₂n-Pr | H | H | OEt | OSO₂n-Pr | H | H | Oc-Pr |
| OSO₂n-Pr | H | H | OMe | OSO₂n-Pr | H | H | OH |

TABLE 72

| X¹ | X² | X³ | X⁴ | X¹ | X² | X³ | X⁴ |
|---|---|---|---|---|---|---|---|
| OSO₂n-Pr | H | H | On-Pr | OSO₂n-Pr | H | H | On-Bu |
| OSO₂n-Pr | H | H | t-Bu | OSO₂n-Pr | H | H | Ot-Bu |
| Ph | H | H | H | OSO₂Ph | H | H | H |
| SiMe₃ | H | H | H | SH | H | H | H |
| SO₂CF₃ | H | H | H | SMe | H | H | H |
| SO₂Me | H | H | SO₂Me | SO₂Me | H | H | H |
| t-Bu | H | H | H | SOMe | H | H | H |

TABLE 73

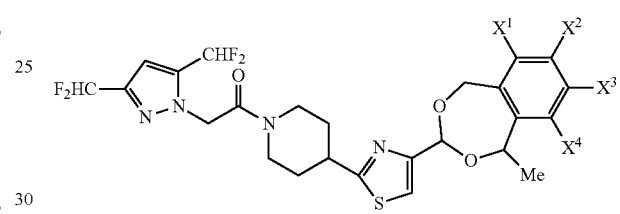

| X¹ | X² | X³ | X⁴ |
|---|---|---|---|
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | H | H |
| Cl | H | H | Cl |
| CN | H | H | CN |
| CO₂H | H | H | H |
| c-Pr | H | H | H |
| F | Br | H | F |
| F | C(=NOMe)H | H | H |
| F | CF₃ | H | F |
| F | Cl | H | F |
| F | CN | H | F |
| F | F | F | F |
| F | F | F | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |

TABLE 73-continued

| X¹ | X² | X³ | X⁴ |
|---|---|---|---|
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |
| Cl | H | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 74

| $X^1$ | $X^2$ | $X^3$ | $X^4$ | $X^1$ | $X^2$ | $X^3$ | $X^4$ |
|---|---|---|---|---|---|---|---|
| F | H | H | CHO | F | H | H | CH$_2$SMe |
| F | H | H | CN | F | H | H | Cl |
| F | H | H | CO$_2$Me | F | H | H | CO$_2$H |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | NH$_2$ | F | H | H | n-Bu |
| F | H | H | NHCOMe | F | H | H | NHCO$_2$Me |
| F | H | H | NHSO$_2$Me | F | H | H | NHMe |
| F | H | H | NO$_2$ | F | H | H | NMe$_2$ |
| F | H | H | OCF$_3$ | F | H | H | n-Pr |
| F | H | H | OCO$_2$Me | F | H | H | OCH$_2$C≡CH |
| F | H | H | OCOMe | F | H | H | OCO$_2$NMe$_2$ |
| F | H | H | OH | F | H | H | OEt |
| F | H | H | OPh | F | H | H | OMe |
| F | H | H | OSiMe$_3$ | F | H | H | OSiMe$_2$t-Bu |
| F | H | H | SH | F | H | H | Ph |
| F | H | H | SMe | F | H | H | SiMe$_3$ |
| F | H | H | SO$_2$Me | F | H | H | SO$_2$CF$_3$ |
| F | H | H | t-Bu | F | H | H | SOMe |
| F | H | Me | H | F | H | I | H |
| F | H | OCF$_3$ | H | F | H | NO$_2$ | H |
| F | H | OMe | H | F | H | OH | H |
| F | H | SO$_2$Me | H | F | H | OSO$_2$Me | H |
| F | I | H | H | F | I | H | F |
| F | Me | H | H | F | Me | H | F |
| F | NO$_2$ | H | H | F | NO$_2$ | H | F |
| F | OCF$_3$ | H | H | F | OCF$_3$ | H | F |
| F | OH | H | H | F | OH | H | F |
| F | OMe | H | H | F | OMe | H | F |
| F | SO$_2$Me | H | F | F | OSO$_2$Me | H | F |
| H | Br | Br | H | F | SO$_2$Me | H | H |
| H | C(=NOMe)H | H | H | F | Br | H | H |

TABLE 75

| $X^1$ | $X^2$ | $X^3$ | $X^4$ | $X^1$ | $X^2$ | $X^3$ | $X^4$ |
|---|---|---|---|---|---|---|---|
| H | CF$_3$ | CF$_3$ | H | H | C(=NOMe)Me | H | H |
| H | —CH=CH—CH=CH— | | H | H | CF$_3$ | H | H |
| H | —CH$_2$CH$_2$CH$_2$— | | H | H | —CH=N—CH=CH— | | H |
| H | Cl | Cl | H | H | —CH$_2$CH$_2$CH$_2$CH$_2$— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |
| H | —NH—CH=CH— | | H | H | —N=CH—N=CH— | | H |
| H | NO$_2$ | NO$_2$ | H | H | NO$_2$ | H | H |
| H | OCF$_3$ | OCF$_3$ | H | H | OCF$_3$ | H | H |
| H | —O—CH=N— | | H | H | —O—CH=CH— | | H |
| H | OH | OH | H | H | OH | H | H |
| H | OMe | OMe | H | H | OMe | H | H |
| H | OSO$_2$Et | H | H | H | OSO$_2$Bn | H | H |
| H | OSO$_2$Me | H | H | H | OSO$_2$i-Pr | H | H |
| H | OSO$_2$n-Bu | H | H | H | OSO$_2$Me | OSO$_2$Me | H |
| H | OSO$_2$Ph | H | H | H | OSO$_2$n-Pr | H | H |
| H | SO$_2$Me | H | H | H | —S—CH=CH— | | H |
| I | H | H | H | H | SO$_2$Me | SO$_2$Me | H |
| i-Pr | H | H | H | H | i-Bu | H | H |
| Me | H | H | Me | Me | H | H | H |
| NH$_2$ | H | H | H | n-Bu | H | H | H |
| NHCOMe | H | H | H | NHCO$_2$Me | H | H | H |
| NHSO$_2$Me | H | H | H | NHMe | H | H | H |
| NO$_2$ | H | H | H | NMe$_2$ | H | H | H |
| OCF$_3$ | H | H | H | n-Pr | H | H | H |
| OCH$_2$C≡CH | H | H | H | OCF$_3$ | H | H | OCF$_3$ |
| OCO$_2$NMe$_2$ | H | H | H | OCO$_2$Me | H | H | H |
| OEt | H | H | H | OCOMe | H | H | H |
| OMe | H | H | H | OH | H | H | H |
| OPh | H | H | H | OMe | H | H | OMe |
| OSiMe$_3$ | H | H | H | OSiMe$_2$t-Bu | H | H | H |

TABLE 76

| X¹ | X² | X³ | X⁴ | X¹ | X² | X³ | X⁴ |
|---|---|---|---|---|---|---|---|
| OSO₂CF₃ | H | H | Br | OSO₂Bn | H | H | H |
| OSO₂CF₃ | H | H | CN | OSO₂CF₃ | H | H | Cl |
| OSO₂CF₃ | H | H | Et | OSO₂CF₃ | H | H | c-Pr |
| OSO₂CF₃ | H | H | H | OSO₂CF₃ | H | H | F |
| OSO₂CF₃ | H | H | Me | OSO₂CF₃ | H | H | I |
| OSO₂CF₃ | H | H | NO₂ | OSO₂CF₃ | H | H | n-Bu |
| OSO₂CF₃ | H | H | OCF₃ | OSO₂CF₃ | H | H | n-Pr |
| OSO₂CF₃ | H | H | Oc-Pr | OSO₂CF₃ | H | H | OCHF₂ |
| OSO₂CF₃ | H | H | OH | OSO₂CF₃ | H | H | OEt |
| OSO₂CF₃ | H | H | On-Bu | OSO₂CF₃ | H | H | OMe |
| OSO₂CF₃ | H | H | Ot-Bu | OSO₂CF₃ | H | H | On-Pr |
| OSO₂CHF₂ | H | H | Br | OSO₂CF₃ | H | H | t-Bu |
| OSO₂CHF₂ | H | H | CN | OSO₂CHF₂ | H | H | Cl |
| OSO₂CHF₂ | H | H | Et | OSO₂CHF₂ | H | H | c-Pr |
| OSO₂CHF₂ | H | H | H | OSO₂CHF₂ | H | H | F |
| OSO₂CHF₂ | H | H | Me | OSO₂CHF₂ | H | H | I |
| OSO₂CHF₂ | H | H | NO₂ | OSO₂CHF₂ | H | H | n-Bu |
| OSO₂CHF₂ | H | H | OCF₃ | OSO₂CHF₂ | H | H | n-Pr |
| OSO₂CHF₂ | H | H | Oc-Pr | OSO₂CHF₂ | H | H | OCHF₂ |
| OSO₂CHF₂ | H | H | OH | OSO₂CHF₂ | H | H | OEt |
| OSO₂CHF₂ | H | H | On-Bu | OSO₂CHF₂ | H | H | OMe |
| OSO₂CHF₂ | H | H | Ot-Bu | OSO₂CHF₂ | H | H | On-Pr |
| OSO₂Et | H | H | Br | OSO₂CHF₂ | H | H | t-Bu |
| OSO₂Et | H | H | Cl | OSO₂Et | H | H | CF₃ |
| OSO₂Et | H | H | c-Pr | OSO₂Et | H | H | CN |
| OSO₂Et | H | H | F | OSO₂Et | H | H | Et |
| OSO₂Et | H | H | I | OSO₂Et | H | H | H |
| OSO₂Et | H | H | n-Bu | OSO₂Et | H | H | Me |
| OSO₂Et | H | H | n-Pr | OSO₂Et | H | H | NO₂ |
| OSO₂Et | H | H | OCHF₂ | OSO₂Et | H | H | OCF₃ |
| OSO₂Et | H | H | OEt | OSO₂Et | H | H | Oc-Pr |
| OSO₂Et | H | H | OMe | OSO₂Et | H | H | OH |
| OSO₂Et | H | H | On-Pr | OSO₂Et | H | H | On-Bu |
| OSO₂Et | H | H | t-Bu | OSO₂Et | H | H | Ot-Bu |

TABLE 77

| X¹ | X² | X³ | X⁴ | X¹ | X² | X³ | X⁴ |
|---|---|---|---|---|---|---|---|
| OSO₂i-Pr | H | H | CF₃ | OSO₂i-Pr | H | H | Br |
| OSO₂i-Pr | H | H | CN | OSO₂i-Pr | H | H | Cl |
| OSO₂i-Pr | H | H | Et | OSO₂i-Pr | H | H | c-Pr |
| OSO₂i-Pr | H | H | H | OSO₂i-Pr | H | H | F |
| OSO₂i-Pr | H | H | Me | OSO₂i-Pr | H | H | I |
| OSO₂i-Pr | H | H | NO₂ | OSO₂i-Pr | H | H | n-Bu |
| OSO₂i-Pr | H | H | OCF₃ | OSO₂i-Pr | H | H | n-Pr |
| OSO₂i-Pr | H | H | Oc-Pr | OSO₂i-Pr | H | H | OCHF₂ |
| OSO₂i-Pr | H | H | OH | OSO₂i-Pr | H | H | OEt |
| OSO₂i-Pr | H | H | On-Bu | OSO₂i-Pr | H | H | OMe |
| OSO₂i-Pr | H | H | Ot-Bu | OSO₂i-Pr | H | H | On-Pr |
| OSO₂Me | Br | H | H | OSO₂i-Pr | H | H | t-Bu |
| OSO₂Me | C(=NOMe)Me | H | H | OSO₂Me | C(=NOMe)H | H | H |
| OSO₂Me | —CH=CH—CH=CH— | | F | OSO₂Me | CF₃ | H | H |
| OSO₂Me | —CH=CH—CH=CH— | | OSO₂Me | OSO₂Me | —CH=CH—CH=CH— | | H |
| OSO₂Me | —CH=N—CH=CH— | | H | OSO₂Me | —CH=N—CH=CH— | | F |
| OSO₂Me | —CH₂CH₂CH₂— | | F | OSO₂Me | —CH₂CH₂CH₂— | | OSO₂Me |
| OSO₂Me | —CH₂CH₂CH₂— | | OSO₂Me | OSO₂Me | —CH₂CH₂CH₂— | | H |
| OSO₂Me | —CH₂CH₂CH₂CH₂— | | H | OSO₂Me | —CH₂CH₂CH₂CH₂— | | F |
| OSO₂Me | Cl | H | H | OSO₂Me | —CH₂CH₂CH₂CH₂— | | OSO₂Me |
| OSO₂Me | F | F | F | OSO₂Me | CN | H | H |
| OSO₂Me | F | F | H | OSO₂Me | F | F | OSO₂Me |
| OSO₂Me | H | Br | H | OSO₂Me | F | H | H |
| OSO₂Me | H | C(=NOMe)Me | H | OSO₂Me | H | C(=NOMe)H | H |
| OSO₂Me | H | Cl | H | OSO₂Me | H | CF₃ | H |
| OSO₂Me | H | F | F | OSO₂Me | H | CN | H |
| OSO₂Me | H | H | Bn | OSO₂Me | H | F | H |
| OSO₂Me | H | H | C(=NOMe)H | OSO₂Me | H | H | Br |
| OSO₂Me | H | H | C≡CH | OSO₂Me | H | H | C(=NOMe)Me |
| OSO₂Me | H | H | CF₃ | OSO₂Me | H | H | C₂F₅ |
| OSO₂Me | H | H | CH₂CN | OSO₂Me | H | H | CH=CH₂ |
| OSO₂Me | H | H | CH₂OMe | OSO₂Me | H | H | CH₂NMe₂ |
| OSO₂Me | H | H | CHO | OSO₂Me | H | H | CH₂SMe |
| OSO₂Me | H | H | CN | OSO₂Me | H | H | Cl |

TABLE 78

| X¹ | X² | X³ | X⁴ | X¹ | X² | X³ | X⁴ |
|---|---|---|---|---|---|---|---|
| OSO₂Me | H | H | CO₂Me | OSO₂Me | H | H | CO₂H |
| OSO₂Me | H | H | Et | OSO₂Me | H | H | c-Pr |
| OSO₂Me | H | H | H | OSO₂Me | H | H | F |
| OSO₂Me | H | H | I | OSO₂Me | H | H | H |
| OSO₂Me | H | H | i-Pr | OSO₂Me | H | H | i-Bu |
| OSO₂Me | H | H | n-Bu | OSO₂Me | H | H | Me |
| OSO₂Me | H | H | NHCO₂Me | OSO₂Me | H | H | NH₂ |
| OSO₂Me | H | H | NHMe | OSO₂Me | H | H | NHCOMe |
| OSO₂Me | H | H | NMe₂ | OSO₂Me | H | H | NHSO₂Me |
| OSO₂Me | H | H | n-Pr | OSO₂Me | H | H | NO₂ |
| OSO₂Me | H | H | OCHF₂ | OSO₂Me | H | H | OCF₃ |
| OSO₂Me | H | H | OCO₂Me | OSO₂Me | H | H | OCH₂C≡CH |

TABLE 78-continued

| X¹ | X² | X³ | X⁴ | X¹ | X² | X³ | X⁴ |
|---|---|---|---|---|---|---|---|
| OSO₂Me | H | H | OCOMe | OSO₂Me | H | H | OCO₂NMe₂ |
| OSO₂Me | H | H | OH | OSO₂Me | H | H | OEt |
| OSO₂Me | H | H | OPh | OSO₂Me | H | H | OMe |
| OSO₂Me | H | H | OSiMe₃ | OSO₂Me | H | H | OSiMe₂t-Bu |
| OSO₂Me | H | H | OSO₂Et | OSO₂Me | H | H | OSO₂Bn |
| OSO₂Me | H | H | OSO₂Me | OSO₂Me | H | H | OSO₂i-Pr |
| OSO₂Me | H | H | OSO₂n-Pr | OSO₂Me | H | H | OSO₂n-Bu |
| OSO₂Me | H | H | Ph | OSO₂Me | H | H | OSO₂Ph |
| OSO₂Me | H | H | SiMe₃ | OSO₂Me | H | H | SH |
| OSO₂Me | H | H | SO₂CF₃ | OSO₂Me | H | H | SMe |
| OSO₂Me | H | H | SOMe | OSO₂Me | H | H | SO₂Me |
| OSO₂Me | H | I | H | OSO₂Me | H | H | t-Bu |
| OSO₂Me | H | NO₂ | H | OSO₂Me | H | Me | H |
| OSO₂Me | H | OH | H | OSO₂Me | H | OCF₃ | H |
| OSO₂Me | H | OSO₂Bn | H | OSO₂Me | H | OMe | H |
| OSO₂Me | H | OSO₂i-Pr | H | OSO₂Me | H | OSO₂Et | H |
| OSO₂Me | H | OSO₂n-Bu | H | OSO₂Me | H | OSO₂Me | H |
| OSO₂Me | H | OSO₂Ph | H | OSO₂Me | H | OSO₂n-Pr | H |
| OSO₂Me | I | H | H | OSO₂Me | H | SO₂Me | H |
| OSO₂Me | —N=CH—CH=CH— | | F | OSO₂Me | Me | H | H |
| OSO₂Me | —N=CH—CH=CH— | | OSO₂Me | OSO₂Me | —N=CH—CH=CH— | | H |
| OSO₂Me | —N=CH—N=CH— | | H | OSO₂Me | —N=CH—N=CH— | | F |

TABLE 79

| X¹ | X² | X³ | X⁴ | X¹ | X² | X³ | X⁴ |
|---|---|---|---|---|---|---|---|
| OSO₂Me | —NH—CH=CH— | | F | OSO₂Me | —N=CH—N=CH— | | OSO₂Me |
| OSO₂Me | —NH—CH=CH— | | OSO₂Me | OSO₂Me | —NH—CH=CH— | | H |
| OSO₂Me | OCF₃ | H | H | OSO₂Me | NO₂ | H | H |
| OSO₂Me | —O—CH=CH— | | H | OSO₂Me | —O—CH=CH— | | F |
| OSO₂Me | —O—CH=N— | | F | OSO₂Me | —O—CH=CH— | | OSO₂Me |
| OSO₂Me | —O—CH=N— | | OSO₂Me | OSO₂Me | —O—CH=N— | | H |
| OSO₂Me | OMe | H | H | OSO₂Me | OH | H | H |
| OSO₂Me | OSO₂Et | H | H | OSO₂Me | OSO₂Bn | H | H |
| OSO₂Me | OSO₂Me | H | H | OSO₂Me | OSO₂i-Pr | H | H |
| OSO₂Me | OSO₂Me | OSO₂Me | H | OSO₂Me | OSO₂Me | H | OSO₂Me |
| OSO₂Me | OSO₂n-Bu | H | H | OSO₂Me | OSO₂Me | OSO₂Me | OSO₂Me |
| OSO₂Me | OSO₂Ph | H | H | OSO₂Me | OSO₂n-Pr | H | H |
| OSO₂Me | —S—CH=CH— | | H | OSO₂Me | —S—CH=CH— | | F |
| OSO₂Me | SO₂Me | H | H | OSO₂Me | —S—CH=CH— | | OSO₂Me |
| OSO₂n-Bu | H | H | Cl | OSO₂n-Bu | H | H | Br |
| OSO₂n-Bu | H | H | c-Pr | OSO₂n-Bu | H | H | CN |
| OSO₂n-Bu | H | H | F | OSO₂n-Bu | H | H | Et |
| OSO₂n-Bu | H | H | I | OSO₂n-Bu | H | H | H |
| OSO₂n-Bu | H | H | n-Bu | OSO₂n-Bu | H | H | Me |
| OSO₂n-Bu | H | H | n-Pr | OSO₂n-Bu | H | H | NO₂ |
| OSO₂n-Bu | H | H | OCHF₂ | OSO₂n-Bu | H | H | OCF₃ |
| OSO₂n-Bu | H | H | OEt | OSO₂n-Bu | H | H | Oc-Pr |
| OSO₂n-Bu | H | H | OMe | OSO₂n-Bu | H | H | OH |
| OSO₂n-Bu | H | H | On-Pr | OSO₂n-Bu | H | H | On-Bu |
| OSO₂n-Bu | H | H | t-Bu | OSO₂n-Bu | H | H | Ot-Bu |
| OSO₂n-Pr | H | H | Cl | OSO₂n-Pr | H | H | Br |
| OSO₂n-Pr | H | H | c-Pr | OSO₂n-Pr | H | H | CN |
| OSO₂n-Pr | H | H | F | OSO₂n-Pr | H | H | Et |
| OSO₂n-Pr | H | H | I | OSO₂n-Pr | H | H | H |
| OSO₂n-Pr | H | H | n-Bu | OSO₂n-Pr | H | H | Me |
| OSO₂n-Pr | H | H | n-Pr | OSO₂n-Pr | H | H | NO₂ |
| OSO₂n-Pr | H | H | OCHF₂ | OSO₂n-Pr | H | H | OCF₃ |
| OSO₂n-Pr | H | H | OEt | OSO₂n-Pr | H | H | Oc-Pr |
| OSO₂n-Pr | H | H | OMe | OSO₂n-Pr | H | H | OH |

TABLE 80

| X¹ | X² | X³ | X⁴ | X¹ | X² | X³ | X⁴ |
|---|---|---|---|---|---|---|---|
| OSO₂n-Pr | H | H | On-Pr | OSO₂n-Pr | H | H | On-Bu |
| OSO₂n-Pr | H | H | t-Bu | OSO₂n-Pr | H | H | Ot-Bu |
| Ph | H | H | H | OSO₂Ph | H | H | H |
| SiMe₃ | H | H | H | SH | H | H | H |
| SO₂CF₃ | H | H | H | SMe | H | H | H |
| SO₂Me | H | H | SO₂Me | SO₂Me | H | H | H |
| t-Bu | H | H | SOMe | H | H | H | |

TABLE 81

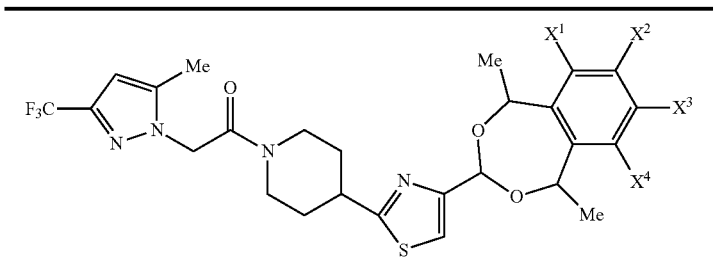

| X¹ | X² | X³ | X⁴ |
|---|---|---|---|
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | H | H |
| Cl | H | H | Cl |
| CN | H | H | CN |
| CO₂H | H | H | H |
| c-Pr | H | H | H |
| F | Br | H | F |
| F | C(=NOMe)H | H | H |
| F | CF₃ | H | F |
| F | Cl | H | F |
| F | CN | H | F |
| F | F | F | F |
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |
| Cl | H | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 82

| $X^1$ | $X^2$ | $X^3$ | $X^4$ | $X^1$ | $X^2$ | $X^3$ | $X^4$ |
|---|---|---|---|---|---|---|---|
| F | H | H | CHO | F | H | H | $CH_2SMe$ |
| F | H | H | CN | F | H | H | Cl |
| F | H | H | $CO_2Me$ | F | H | H | $CO_2H$ |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | $NH_2$ | F | H | H | n-Bu |
| F | H | H | NHCOMe | F | H | H | $NHCO_2Me$ |
| F | H | H | $NHSO_2Me$ | F | H | H | NHMe |
| F | H | H | $NO_2$ | F | H | H | $NMe_2$ |
| F | H | H | $OCF_3$ | F | H | H | n-Pr |
| F | H | H | $OCO_2Me$ | F | H | H | $OCH_2C{\equiv}CH$ |
| F | H | H | OCOMe | F | H | H | $OCO_2NMe_2$ |
| F | H | H | OH | F | H | H | OEt |
| F | H | H | OPh | F | H | H | OMe |
| F | H | H | $OSiMe_3$ | F | H | H | $OSiMe_2$t-Bu |
| F | H | H | SH | F | H | H | Ph |
| F | H | H | SMe | F | H | H | $SiMe_3$ |
| F | H | H | $SO_2Me$ | F | H | H | $SO_2CF_3$ |
| F | H | H | t-Bu | F | H | H | SOMe |
| F | H | Me | H | F | H | I | H |
| F | H | $OCF_3$ | H | F | H | $NO_2$ | H |
| F | H | OMe | H | F | H | OH | H |
| F | H | $SO_2Me$ | H | F | H | $OSO_2Me$ | H |
| F | I | H | H | F | I | H | F |
| F | Me | H | H | F | Me | H | F |
| F | $NO_2$ | H | H | F | $NO_2$ | H | F |
| F | $OCF_3$ | H | H | F | $OCF_3$ | H | F |
| F | OH | H | H | F | OH | H | F |
| F | OMe | H | H | F | OMe | H | F |
| F | $SO_2Me$ | H | F | F | $OSO_2Me$ | H | F |
| H | Br | Br | H | F | $SO_2Me$ | H | H |
| H | C(=NOMe)H | H | H | H | Br | H | H |

TABLE 83

| $X^1$ | $X^2$ | $X^3$ | $X^4$ | $X^1$ | $X^2$ | $X^3$ | $X^4$ |
|---|---|---|---|---|---|---|---|
| H | $CF_3$ | $CF_3$ | H | H | C(=NOMe)Me | H | H |
| H | —CH=CH—CH=CH— | | H | H | $CF_3$ | H | H |
| H | —$CH_2CH_2CH_2$— | | H | H | —CH=N—CH=CH— | | H |
| H | Cl | Cl | H | H | —$CH_2CH_2CH_2CH_2$— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |
| H | —NH—CH=CH— | | H | H | —N=CH—N=CH— | | H |
| H | $NO_2$ | $NO_2$ | H | H | $NO_2$ | H | H |
| H | $OCF_3$ | $OCF_3$ | H | H | $OCF_3$ | H | H |
| H | —O—CH=N— | | H | H | —O—CH=CH— | | H |
| H | OH | OH | H | H | OH | H | H |
| H | OMe | OMe | H | H | OMe | H | H |
| H | $OSO_2Et$ | H | H | H | $OSO_2Bn$ | H | H |
| H | $OSO_2Me$ | H | H | H | $OSO_2$i-Pr | H | H |
| H | $OSO_2$n-Bu | H | H | H | $OSO_2Me$ | $OSO_2Me$ | H |
| H | $OSO_2Ph$ | H | H | H | $OSO_2$n-Pr | H | H |
| H | $SO_2Me$ | H | H | H | —S—CH=CH— | | H |
| I | H | H | H | H | $SO_2Me$ | $SO_2Me$ | H |
| i-Pr | H | H | H | H | i-Bu | H | H |
| Me | H | H | Me | Me | H | H | H |
| $NH_2$ | H | H | H | n-Bu | H | H | H |
| NHCOMe | H | H | H | $NHCO_2Me$ | H | H | H |
| $NHSO_2Me$ | H | H | H | NHMe | H | H | H |
| $NO_2$ | H | H | H | $NMe_2$ | H | H | H |
| $OCF_3$ | H | H | H | n-Pr | H | H | H |
| $OCH_2C{\equiv}CH$ | H | H | H | $OCF_3$ | H | H | $OCF_3$ |
| $OCO_2NMe_2$ | H | H | H | $OCO_2Me$ | H | H | H |
| OEt | H | H | H | OCOMe | H | H | H |
| OMe | H | H | H | OH | H | H | H |
| OPh | H | H | H | OMe | H | H | OMe |
| $OSiMe_3$ | H | H | H | $OSiMe_2$t-Bu | H | H | H |

TABLE 84

| X¹ | X² | X³ | X⁴ | X¹ | X² | X³ | X⁴ |
|---|---|---|---|---|---|---|---|
| OSO$_2$CF$_3$ | H | H | Br | OSO$_2$Bn | H | H | H |
| OSO$_2$CF$_3$ | H | H | CN | OSO$_2$CF$_3$ | H | H | Cl |
| OSO$_2$CF$_3$ | H | H | Et | OSO$_2$CF$_3$ | H | H | c-Pr |
| OSO$_2$CF$_3$ | H | H | H | OSO$_2$CF$_3$ | H | H | F |
| OSO$_2$CF$_3$ | H | H | Me | OSO$_2$CF$_3$ | H | H | I |
| OSO$_2$CF$_3$ | H | H | NO$_2$ | OSO$_2$CF$_3$ | H | H | n-Bu |
| OSO$_2$CF$_3$ | H | H | OCF$_3$ | OSO$_2$CF$_3$ | H | H | n-Pr |
| OSO$_2$CF$_3$ | H | H | Oc-Pr | OSO$_2$CF$_3$ | H | H | OCHF$_2$ |
| OSO$_2$CF$_3$ | H | H | OH | OSO$_2$CF$_3$ | H | H | OEt |
| OSO$_2$CF$_3$ | H | H | On-Bu | OSO$_2$CF$_3$ | H | H | OMe |
| OSO$_2$CF$_3$ | H | H | Ot-Bu | OSO$_2$CF$_3$ | H | H | On-Pr |
| OSO$_2$CHF$_2$ | H | H | Br | OSO$_2$CF$_3$ | H | H | t-Bu |
| OSO$_2$CHF$_2$ | H | H | CN | OSO$_2$CHF$_2$ | H | H | Cl |
| OSO$_2$CHF$_2$ | H | H | Et | OSO$_2$CHF$_2$ | H | H | c-Pr |
| OSO$_2$CHF$_2$ | H | H | H | OSO$_2$CHF$_2$ | H | H | F |
| OSO$_2$CHF$_2$ | H | H | Me | OSO$_2$CHF$_2$ | H | H | I |
| OSO$_2$CHF$_2$ | H | H | NO$_2$ | OSO$_2$CHF$_2$ | H | H | n-Bu |
| OSO$_2$CHF$_2$ | H | H | OCF$_3$ | OSO$_2$CHF$_2$ | H | H | n-Pr |
| OSO$_2$CHF$_2$ | H | H | Oc-Pr | OSO$_2$CHF$_2$ | H | H | OCHF$_2$ |
| OSO$_2$CHF$_2$ | H | H | OH | OSO$_2$CHF$_2$ | H | H | OEt |
| OSO$_2$CHF$_2$ | H | H | On-Bu | OSO$_2$CHF$_2$ | H | H | OMe |
| OSO$_2$CHF$_2$ | H | H | Ot-Bu | OSO$_2$CHF$_2$ | H | H | On-Pr |
| OSO$_2$Et | H | H | Br | OSO$_2$CHF$_2$ | H | H | t-Bu |
| OSO$_2$Et | H | H | Cl | OSO$_2$Et | H | H | CF$_3$ |
| OSO$_2$Et | H | H | c-Pr | OSO$_2$Et | H | H | CN |
| OSO$_2$Et | H | H | F | OSO$_2$Et | H | H | Et |
| OSO$_2$Et | H | H | I | OSO$_2$Et | H | H | H |
| OSO$_2$Et | H | H | n-Bu | OSO$_2$Et | H | H | Me |
| OSO$_2$Et | H | H | n-Pr | OSO$_2$Et | H | H | NO$_2$ |
| OSO$_2$Et | H | H | OCHF$_2$ | OSO$_2$Et | H | H | OCF$_3$ |
| OSO$_2$Et | H | H | OEt | OSO$_2$Et | H | H | Oc-Pr |
| OSO$_2$Et | H | H | OMe | OSO$_2$Et | H | H | OH |
| OSO$_2$Et | H | H | On-Pr | OSO$_2$Et | H | H | On-Bu |
| OSO$_2$Et | H | H | t-Bu | OSO$_2$Et | H | H | Ot-Bu |

TABLE 85

| X¹ | X² | X³ | X⁴ | X¹ | X² | X³ | X⁴ |
|---|---|---|---|---|---|---|---|
| OSO$_2$i-Pr | H | H | CF$_3$ | OSO$_2$i-Pr | H | H | Br |
| OSO$_2$i-Pr | H | H | CN | OSO$_2$i-Pr | H | H | Cl |
| OSO$_2$i-Pr | H | H | Et | OSO$_2$i-Pr | H | H | c-Pr |
| OSO$_2$i-Pr | H | H | H | OSO$_2$i-Pr | H | H | F |
| OSO$_2$i-Pr | H | H | Me | OSO$_2$i-Pr | H | H | I |
| OSO$_2$i-Pr | H | H | NO$_2$ | OSO$_2$i-Pr | H | H | n-Bu |
| OSO$_2$i-Pr | H | H | OCF$_3$ | OSO$_2$i-Pr | H | H | n-Pr |
| OSO$_2$i-Pr | H | H | Oc-Pr | OSO$_2$i-Pr | H | H | OCHF$_2$ |
| OSO$_2$i-Pr | H | H | OH | OSO$_2$i-Pr | H | H | OEt |
| OSO$_2$i-Pr | H | H | On-Bu | OSO$_2$i-Pr | H | H | OMe |
| OSO$_2$i-Pr | H | H | Ot-Bu | OSO$_2$i-Pr | H | H | On-Pr |
| OSO$_2$Me | Br | H | H | OSO$_2$i-Pr | H | H | t-Bu |
| OSO$_2$Me | C(=NOMe)Me | H | H | OSO$_2$Me | C(=NOMe)H | H | H |
| OSO$_2$Me | —CH=CH—CH=CH— | | F | OSO$_2$Me | CF$_3$ | H | H |
| OSO$_2$Me | —CH=CH—CH=CH— | | OSO$_2$Me | OSO$_2$Me | —CH=CH—CH=CH— | | H |
| OSO$_2$Me | —CH=N—CH=CH— | | H | OSO$_2$Me | —CH=N—CH=CH— | | F |
| OSO$_2$Me | —CH$_2$CH$_2$CH$_2$— | | F | OSO$_2$Me | —CH=N—CH=CH— | | OSO$_2$Me |
| OSO$_2$Me | —CH$_2$CH$_2$CH$_2$— | | OSO$_2$Me | OSO$_2$Me | —CH$_2$CH$_2$CH$_2$— | | H |
| OSO$_2$Me | —CH$_2$CH$_2$CH$_2$CH$_2$— | | H | OSO$_2$Me | —CH$_2$CH$_2$CH$_2$CH$_2$— | | F |
| OSO$_2$Me | Cl | H | H | OSO$_2$Me | —CH$_2$CH$_2$CH$_2$CH$_2$— | | OSO$_2$Me |
| OSO$_2$Me | F | F | F | OSO$_2$Me | CN | H | H |
| OSO$_2$Me | F | H | F | OSO$_2$Me | F | F | OSO$_2$Me |
| OSO$_2$Me | H | Br | H | OSO$_2$Me | F | H | H |
| OSO$_2$Me | H | C(=NOMe)Me | H | OSO$_2$Me | H | C(=NOMe)H | H |
| OSO$_2$Me | H | Cl | H | OSO$_2$Me | H | CF$_3$ | H |
| OSO$_2$Me | H | F | F | OSO$_2$Me | H | CN | H |
| OSO$_2$Me | H | H | Bn | OSO$_2$Me | H | F | H |
| OSO$_2$Me | H | H | C(=NOMe)H | OSO$_2$Me | H | H | Br |
| OSO$_2$Me | H | H | C≡CH | OSO$_2$Me | H | H | C(=NOMe)Me |
| OSO$_2$Me | H | H | CF$_3$ | OSO$_2$Me | H | H | C$_2$F$_5$ |
| OSO$_2$Me | H | H | CH$_2$CN | OSO$_2$Me | H | H | CH=CH$_2$ |
| OSO$_2$Me | H | H | CH$_2$OMe | OSO$_2$Me | H | H | CH$_2$NMe$_2$ |
| OSO$_2$Me | H | H | CHO | OSO$_2$Me | H | H | CH$_2$SMe |
| OSO$_2$Me | H | H | CN | OSO$_2$Me | H | H | Cl |

TABLE 86

| X¹ | X² | X³ | X⁴ | X¹ | X² | X³ | X⁴ |
|---|---|---|---|---|---|---|---|
| OSO$_2$Me | H | H | CO$_2$Me | OSO$_2$Me | H | H | CO$_2$H |
| OSO$_2$Me | H | H | Et | OSO$_2$Me | H | H | c-Pr |
| OSO$_2$Me | H | H | H | OSO$_2$Me | H | H | F |
| OSO$_2$Me | H | H | I | OSO$_2$Me | H | H | H |
| OSO$_2$Me | H | H | i-Pr | OSO$_2$Me | H | H | i-Bu |
| OSO$_2$Me | H | H | n-Bu | OSO$_2$Me | H | H | Me |
| OSO$_2$Me | H | H | NHCO$_2$Me | OSO$_2$Me | H | H | NH$_2$ |
| OSO$_2$Me | H | H | NHMe | OSO$_2$Me | H | H | NHCOMe |
| OSO$_2$Me | H | H | NMe$_2$ | OSO$_2$Me | H | H | NHSO$_2$Me |
| OSO$_2$Me | H | H | n-Pr | OSO$_2$Me | H | H | NO$_2$ |
| OSO$_2$Me | H | H | OCHF$_2$ | OSO$_2$Me | H | H | OCF$_3$ |
| OSO$_2$Me | H | H | OCO$_2$Me | OSO$_2$Me | H | H | OCH$_2$C≡CH |

TABLE 86-continued

| X¹ | X² | X³ | X⁴ | X¹ | X² | X³ | X⁴ |
|---|---|---|---|---|---|---|---|
| OSO₂Me | H | H | OCOMe | OSO₂Me | H | H | OCO₂NMe₂ |
| OSO₂Me | H | H | OH | OSO₂Me | H | H | OEt |
| OSO₂Me | H | H | OPh | OSO₂Me | H | H | OMe |
| OSO₂Me | H | H | OSiMe₃ | OSO₂Me | H | H | OSiMe₂t-Bu |
| OSO₂Me | H | H | OSO₂Et | OSO₂Me | H | H | OSO₂Bn |
| OSO₂Me | H | H | OSO₂Me | OSO₂Me | H | H | OSO₂i-Pr |
| OSO₂Me | H | H | OSO₂n-Pr | OSO₂Me | H | H | OSO₂n-Bu |
| OSO₂Me | H | H | Ph | OSO₂Me | H | H | OSO₂Ph |
| OSO₂Me | H | H | SiMe₃ | OSO₂Me | H | H | SH |
| OSO₂Me | H | H | SO₂CF₃ | OSO₂Me | H | H | SMe |
| OSO₂Me | H | H | SOMe | OSO₂Me | H | H | SO₂Me |
| OSO₂Me | H | I | H | OSO₂Me | H | H | t-Bu |
| OSO₂Me | H | NO₂ | H | OSO₂Me | H | Me | H |
| OSO₂Me | H | OH | H | OSO₂Me | H | OCF₃ | H |
| OSO₂Me | H | OSO₂Bn | H | OSO₂Me | H | OMe | H |
| OSO₂Me | H | OSO₂i-Pr | H | OSO₂Me | H | OSO₂Et | H |
| OSO₂Me | H | OSO₂n-Bu | H | OSO₂Me | H | OSO₂Me | H |
| OSO₂Me | H | OSO₂Ph | H | OSO₂Me | H | OSO₂n-Pr | H |
| OSO₂Me | I | H | H | OSO₂Me | H | SO₂Me | H |
| OSO₂Me | —N=CH—CH=CH— | | F | OSO₂Me | Me | H | H |
| OSO₂Me | —N=CH—CH=CH— | | OSO₂Me | OSO₂Me | —N=CH—CH=CH— | | H |
| OSO₂Me | —N=CH—N=CH— | | H | OSO₂Me | —N=CH—N=CH— | | F |

TABLE 87

| X¹ | X² | X³ | X⁴ | X¹ | X² | X³ | X⁴ |
|---|---|---|---|---|---|---|---|
| OSO₂Me | —NH—CH=CH— | | F | OSO₂Me | —N=CH—N=CH— | | OSO₂Me |
| OSO₂Me | —NH—CH=CH— | | OSO₂Me | OSO₂Me | —NH—CH=CH— | | H |
| OSO₂Me | OCF₃ | H | H | OSO₂Me | NO₂ | H | H |
| OSO₂Me | —O—CH=CH— | | H | OSO₂Me | —O—CH=CH— | | F |
| OSO₂Me | —O—CH=N— | | F | OSO₂Me | —O—CH=CH— | | OSO₂Me |
| OSO₂Me | —O—CH=N— | | OSO₂Me | OSO₂Me | —O—CH=N— | | H |
| OSO₂Me | OMe | H | H | OSO₂Me | OH | H | H |
| OSO₂Me | OSO₂Et | H | H | OSO₂Me | OSO₂Bn | H | H |
| OSO₂Me | OSO₂Me | H | H | OSO₂Me | OSO₂i-Pr | H | H |
| OSO₂Me | OSO₂Me | OSO₂Me | H | OSO₂Me | OSO₂Me | H | OSO₂Me |
| OSO₂Me | OSO₂n-Bu | H | H | OSO₂Me | OSO₂Me | OSO₂Me | OSO₂Me |
| OSO₂Me | OSO₂Ph | H | H | OSO₂Me | OSO₂n-Pr | H | H |
| OSO₂Me | —S—CH=CH— | | H | OSO₂Me | —S—CH=CH— | | F |
| OSO₂Me | SO₂Me | H | H | OSO₂Me | —S—CH=CH— | | OSO₂Me |
| OSO₂n-Bu | H | H | Cl | OSO₂n-Bu | H | H | Br |
| OSO₂n-Bu | H | H | c-Pr | OSO₂n-Bu | H | H | CN |
| OSO₂n-Bu | H | H | F | OSO₂n-Bu | H | H | Et |
| OSO₂n-Bu | H | H | I | OSO₂n-Bu | H | H | H |
| OSO₂n-Bu | H | H | n-Bu | OSO₂n-Bu | H | H | Me |
| OSO₂n-Bu | H | H | n-Pr | OSO₂n-Bu | H | H | NO₂ |
| OSO₂n-Bu | H | H | OCHF₂ | OSO₂n-Bu | H | H | OCF₃ |
| OSO₂n-Bu | H | H | OEt | OSO₂n-Bu | H | H | Oc-Pr |
| OSO₂n-Bu | H | H | OMe | OSO₂n-Bu | H | H | OH |
| OSO₂n-Bu | H | H | On-Pr | OSO₂n-Bu | H | H | On-Bu |
| OSO₂n-Bu | H | H | t-Bu | OSO₂n-Bu | H | H | Ot-Bu |
| OSO₂n-Pr | H | H | Cl | OSO₂n-Pr | H | H | Br |
| OSO₂n-Pr | H | H | c-Pr | OSO₂n-Pr | H | H | CN |
| OSO₂n-Pr | H | H | F | OSO₂n-Pr | H | H | Et |
| OSO₂n-Pr | H | H | I | OSO₂n-Pr | H | H | H |
| OSO₂n-Pr | H | H | n-Bu | OSO₂n-Pr | H | H | Me |
| OSO₂n-Pr | H | H | n-Pr | OSO₂n-Pr | H | H | NO₂ |
| OSO₂n-Pr | H | H | OCHF₂ | OSO₂n-Pr | H | H | OCF₃ |
| OSO₂n-Pr | H | H | OEt | OSO₂n-Pr | H | H | Oc-Pr |
| OSO₂n-Pr | H | H | OMe | OSO₂n-Pr | H | H | OH |

TABLE 88

| X¹ | X² | X³ | X⁴ | X¹ | X² | X³ | X⁴ |
|---|---|---|---|---|---|---|---|
| OSO₂n-Pr | H | H | On-Pr | OSO₂n-Pr | H | H | XOn-Bu |
| OSO₂n-Pr | H | H | t-Bu | OSO₂n-Pr | H | H | Ot-Bu |
| Ph | H | H | H | OSO₂Ph | H | H | H |
| SiMe₃ | H | H | H | SH | H | H | H |
| SO₂CF₃ | H | H | H | SMe | H | H | H |
| SO₂Me | H | H | SO₂Me | SO₂Me | H | H | H |
| t-Bu | H | H | H | SOMe | H | H | H |

TABLE 89

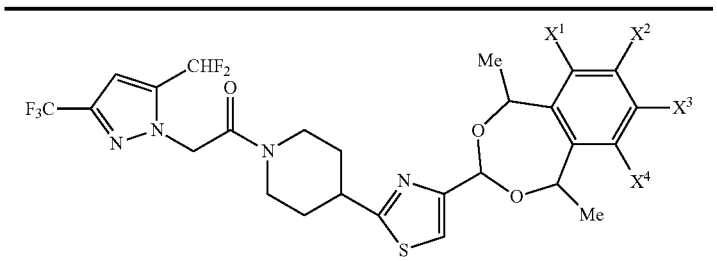

| X¹ | X² | X³ | X⁴ |
| --- | --- | --- | --- |
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | H | H |
| Cl | H | H | Cl |
| CN | H | H | CN |
| CO₂H | H | H | H |
| c-Pr | H | H | H |
| F | Br | H | F |
| F | C(=NOMe)H | H | H |
| F | CF₃ | H | F |
| F | Cl | H | F |
| F | CN | H | F |
| F | F | F | F |
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |
| Cl | H | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 90

| $X^1$ | $X^2$ | $X^3$ | $X^4$ | $X^1$ | $X^2$ | $X^3$ | $X^4$ |
|---|---|---|---|---|---|---|---|
| F | H | H | CHO | F | H | H | $CH_2SMe$ |
| F | H | H | CN | F | H | H | Cl |
| F | H | H | $CO_2Me$ | F | H | H | $CO_2H$ |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | $NH_2$ | F | H | H | n-Bu |
| F | H | H | NHCOMe | F | H | H | $NHCO_2Me$ |
| F | H | H | $NHSO_2Me$ | F | H | H | NHMe |
| F | H | H | $NO_2$ | F | H | H | $NMe_2$ |
| F | H | H | $OCF_3$ | F | H | H | n-Pr |
| F | H | H | $OCO_2Me$ | F | H | H | $OCH_2C\equiv CH$ |
| F | H | H | OCOMe | F | H | H | $OCO_2NMe_2$ |
| F | H | H | OH | F | H | H | OEt |
| F | H | H | OPh | F | H | H | OMe |
| F | H | H | $OSiMe_3$ | F | H | H | $OSiMe_2$t-Bu |
| F | H | H | SH | F | H | H | Ph |
| F | H | H | SMe | F | H | H | $SiMe_3$ |
| F | H | H | $SO_2Me$ | F | H | H | $SO_2CF_3$ |
| F | H | H | t-Bu | F | H | H | SOMe |
| F | H | Me | H | F | H | I | H |
| F | H | $OCF_3$ | H | F | H | $NO_2$ | H |
| F | H | OMe | H | F | H | OH | H |
| F | H | $SO_2Me$ | H | F | H | $OSO_2Me$ | H |
| F | I | H | H | F | I | H | F |
| F | Me | H | H | F | Me | H | F |
| F | $NO_2$ | H | H | F | $NO_2$ | H | F |
| F | $OCF_3$ | H | H | F | $OCF_3$ | H | F |
| F | OH | H | H | F | OH | H | F |
| F | OMe | H | H | F | OMe | H | F |
| F | $SO_2Me$ | H | F | F | $OSO_2Me$ | H | F |
| H | Br | Br | H | F | $SO_2Me$ | H | H |
| H | C(=NOMe)H | H | H | H | Br | H | H |

TABLE 91

| $X^1$ | $X^2$ | $X^3$ | $X^4$ | $X^1$ | $X^2$ | $X^3$ | $X^4$ |
|---|---|---|---|---|---|---|---|
| H | $CF_3$ | $CF_3$ | H | H | C(=NOMe)Me | H | H |
| H | —CH=CH—CH=CH— | | H | H | $CF_3$ | H | H |
| H | —$CH_2CH_2CH_2$— | | H | H | —CH=N—CH=CH— | | H |
| H | Cl | Cl | H | H | —$CH_2CH_2CH_2CH_2$— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |
| H | —NH—CH=CH— | | H | H | —N=CH—N=CH— | | H |
| H | $NO_2$ | $NO_2$ | H | H | $NO_2$ | H | H |
| H | $OCF_3$ | $OCF_3$ | H | H | $OCF_3$ | H | H |
| H | —O—CH=N— | | H | H | —O—CH=CH— | | H |
| H | OH | OH | H | H | OH | H | H |
| H | OMe | OMe | H | H | OMe | H | H |
| H | $OSO_2Et$ | H | H | H | $OSO_2Bn$ | H | H |
| H | $OSO_2Me$ | H | H | H | $OSO_2$i-Pr | H | H |
| H | $OSO_2$n-Bu | H | H | H | $OSO_2Me$ | $OSO_2Me$ | H |
| H | $OSO_2Ph$ | H | H | H | $OSO_2$n-Pr | H | H |
| H | $SO_2Me$ | H | H | H | —S—CH=CH— | | H |
| I | H | H | H | H | $SO_2Me$ | $SO_2Me$ | H |
| i-Pr | H | H | H | H | i-Bu | H | H |
| Me | H | H | H | Me | Me | H | H |
| $NH_2$ | H | H | H | n-Bu | H | H | H |
| NHCOMe | H | H | H | $NHCO_2Me$ | H | H | H |
| $NHSO_2Me$ | H | H | H | NHMe | H | H | H |
| $NO_2$ | H | H | H | $NMe_2$ | H | H | H |
| $OCF_3$ | H | H | H | n-Pr | H | H | H |
| $OCH_2C\equiv CH$ | H | H | H | $OCF_3$ | H | H | $OCF_3$ |
| $OCO_2NMe_2$ | H | H | H | $OCO_2Me$ | H | H | H |
| OEt | H | H | H | OCOMe | H | H | H |
| OMe | H | H | H | OH | H | H | H |
| OPh | H | H | H | OMe | H | H | OMe |
| $OSiMe_3$ | H | H | H | $OSiMe_2$t-Bu | H | H | H |

TABLE 92

| X¹ | X² | X³ | X⁴ | X¹ | X² | X³ | X⁴ |
|---|---|---|---|---|---|---|---|
| OSO₂CF₃ | H | H | Br | OSO₂Bn | H | H | H |
| OSO₂CF₃ | H | H | CN | OSO₂CF₃ | H | H | Cl |
| OSO₂CF₃ | H | H | Et | OSO₂CF₃ | H | H | c-Pr |
| OSO₂CF₃ | H | H | H | OSO₂CF₃ | H | H | F |
| OSO₂CF₃ | H | H | Me | OSO₂CF₃ | H | H | I |
| OSO₂CF₃ | H | H | NO₂ | OSO₂CF₃ | H | H | n-Bu |
| OSO₂CF₃ | H | H | OCF₃ | OSO₂CF₃ | H | H | n-Pr |
| OSO₂CF₃ | H | H | Oc-Pr | OSO₂CF₃ | H | H | OCHF₂ |
| OSO₂CF₃ | H | H | OH | OSO₂CF₃ | H | H | OEt |
| OSO₂CF₃ | H | H | On-Bu | OSO₂CF₃ | H | H | OMe |
| OSO₂CF₃ | H | H | Ot-Bu | OSO₂CF₃ | H | H | On-Pr |
| OSO₂CHF₂ | H | H | Br | OSO₂CF₃ | H | H | t-Bu |
| OSO₂CHF₂ | H | H | CN | OSO₂CHF₂ | H | H | Cl |
| OSO₂CHF₂ | H | H | Et | OSO₂CHF₂ | H | H | c-Pr |
| OSO₂CHF₂ | H | H | H | OSO₂CHF₂ | H | H | F |
| OSO₂CHF₂ | H | H | Me | OSO₂CHF₂ | H | H | I |
| OSO₂CHF₂ | H | H | NO₂ | OSO₂CHF₂ | H | H | n-Bu |
| OSO₂CHF₂ | H | H | OCF₃ | OSO₂CHF₂ | H | H | n-Pr |
| OSO₂CHF₂ | H | H | Oc-Pr | OSO₂CHF₂ | H | H | OCHF₂ |
| OSO₂CHF₂ | H | H | OH | OSO₂CHF₂ | H | H | OEt |
| OSO₂CHF₂ | H | H | On-Bu | OSO₂CHF₂ | H | H | OMe |
| OSO₂CHF₂ | H | H | Ot-Bu | OSO₂CHF₂ | H | H | On-Pr |
| OSO₂Et | H | H | Br | OSO₂CHF₂ | H | H | t-Bu |
| OSO₂Et | H | H | Cl | OSO₂Et | H | H | CF₃ |
| OSO₂Et | H | H | c-Pr | OSO₂Et | H | H | CN |
| OSO₂Et | H | H | F | OSO₂Et | H | H | Et |
| OSO₂Et | H | H | I | OSO₂Et | H | H | H |
| OSO₂Et | H | H | n-Bu | OSO₂Et | H | H | Me |
| OSO₂Et | H | H | n-Pr | OSO₂Et | H | H | NO₂ |
| OSO₂Et | H | H | OCHF₂ | OSO₂Et | H | H | OCF₃ |
| OSO₂Et | H | H | OEt | OSO₂Et | H | H | Oc-Pr |
| OSO₂Et | H | H | OMe | OSO₂Et | H | H | OH |
| OSO₂Et | H | H | On-Pr | OSO₂Et | H | H | On-Bu |
| OSO₂Et | H | H | t-Bu | OSO₂Et | H | H | Ot-Bu |

TABLE 93

| X¹ | X² | X³ | X⁴ | X¹ | X² | X³ | X⁴ |
|---|---|---|---|---|---|---|---|
| OSO₂i-Pr | H | H | CF₃ | OSO₂i-Pr | H | H | Br |
| OSO₂i-Pr | H | H | CN | OSO₂i-Pr | H | H | Cl |
| OSO₂i-Pr | H | H | Et | OSO₂i-Pr | H | H | c-Pr |
| OSO₂i-Pr | H | H | H | OSO₂i-Pr | H | H | F |
| OSO₂i-Pr | H | H | Me | OSO₂i-Pr | H | H | I |
| OSO₂i-Pr | H | H | NO₂ | OSO₂i-Pr | H | H | n-Bu |
| OSO₂i-Pr | H | H | OCF₃ | OSO₂i-Pr | H | H | n-Pr |
| OSO₂i-Pr | H | H | Oc-Pr | OSO₂i-Pr | H | H | OCHF₂ |
| OSO₂i-Pr | H | H | OH | OSO₂i-Pr | H | H | OEt |
| OSO₂i-Pr | H | H | On-Bu | OSO₂i-Pr | H | H | OMe |
| OSO₂i-Pr | H | H | Ot-Bu | OSO₂i-Pr | H | H | On-Pr |
| OSO₂Me | Br | H | H | OSO₂i-Pr | H | H | t-Bu |
| OSO₂Me | C(=NOMe)Me | H | H | OSO₂Me | C(=NOMe)H | H | H |
| OSO₂Me | —CH=CH—CH=CH— | | F | OSO₂Me | CF₃ | H | H |
| OSO₂Me | —CH=CH—CH=CH— | | OSO₂Me | OSO₂Me | —CH=CH—CH=CH— | | H |
| OSO₂Me | —CH=N—CH=CH— | | H | OSO₂Me | —CH=N—CH=CH— | | F |
| OSO₂Me | —CH₂CH₂CH₂— | | F | OSO₂Me | —CH₂CH₂CH₂— | | OSO₂Me |
| OSO₂Me | —CH₂CH₂CH₂— | | OSO₂Me | OSO₂Me | —CH₂CH₂CH₂— | | H |
| OSO₂Me | —CH₂CH₂CH₂CH₂— | | H | OSO₂Me | —CH₂CH₂CH₂CH₂— | | F |
| OSO₂Me | Cl | H | H | OSO₂Me | —CH₂CH₂CH₂CH₂— | | OSO₂Me |
| OSO₂Me | F | F | F | OSO₂Me | CN | H | H |
| OSO₂Me | F | H | F | OSO₂Me | F | F | OSO₂Me |
| OSO₂Me | H | Br | H | OSO₂Me | F | H | H |
| OSO₂Me | H | C(=NOMe)Me | H | OSO₂Me | H | C(=NOMe)H | H |
| OSO₂Me | H | Cl | H | OSO₂Me | H | CF₃ | H |
| OSO₂Me | H | F | F | OSO₂Me | H | CN | H |
| OSO₂Me | H | H | Bn | OSO₂Me | H | F | H |
| OSO₂Me | H | H | C(=NOMe)H | OSO₂Me | H | H | Br |
| OSO₂Me | H | H | C≡CH | OSO₂Me | H | H | C(=NOMe)Me |
| OSO₂Me | H | H | CF₃ | OSO₂Me | H | H | C₂F₅ |
| OSO₂Me | H | H | CH₂CN | OSO₂Me | H | H | CH=CH₂ |
| OSO₂Me | H | H | CH₂OMe | OSO₂Me | H | H | CH₂NMe₂ |
| OSO₂Me | H | H | CHO | OSO₂Me | H | H | CH₂SMe |
| OSO₂Me | H | H | CN | OSO₂Me | H | H | Cl |

TABLE 94

| X¹ | X² | X³ | X⁴ | X¹ | X² | X³ | X⁴ |
|---|---|---|---|---|---|---|---|
| OSO₂Me | H | H | CO₂Me | OSO₂Me | H | H | CO₂H |
| OSO₂Me | H | H | Et | OSO₂Me | H | H | c-Pr |
| OSO₂Me | H | H | H | OSO₂Me | H | H | F |
| OSO₂Me | H | H | I | OSO₂Me | H | H | H |
| OSO₂Me | H | H | i-Pr | OSO₂Me | H | H | i-Bu |
| OSO₂Me | H | H | n-Bu | OSO₂Me | H | H | Me |
| OSO₂Me | H | H | NHCO₂Me | OSO₂Me | H | H | NH₂ |
| OSO₂Me | H | H | NHMe | OSO₂Me | H | H | NHCOMe |
| OSO₂Me | H | H | NMe₂ | OSO₂Me | H | H | NHSO₂Me |
| OSO₂Me | H | H | n-Pr | OSO₂Me | H | H | NO₂ |
| OSO₂Me | H | H | OCHF₂ | OSO₂Me | H | H | OCF₃ |
| OSO₂Me | H | H | OCO₂Me | OSO₂Me | H | H | OCH₂C≡CH |

TABLE 94-continued

| X¹ | X² | X³ | X⁴ | X¹ | X² | X³ | X⁴ |
|---|---|---|---|---|---|---|---|
| OSO₂Me | H | H | OCOMe | OSO₂Me | H | H | OCO₂NMe₂ |
| OSO₂Me | H | H | OH | OSO₂Me | H | H | OEt |
| OSO₂Me | H | H | OPh | OSO₂Me | H | H | OMe |
| OSO₂Me | H | H | OSiMe₃ | OSO₂Me | H | H | OSiMe₂t-Bu |
| OSO₂Me | H | H | OSO₂Et | OSO₂Me | H | H | OSO₂Bn |
| OSO₂Me | H | H | OSO₂Me | OSO₂Me | H | H | OSO₂i-Pr |
| OSO₂Me | H | H | OSO₂n-Pr | OSO₂Me | H | H | OSO₂n-Bu |
| OSO₂Me | H | H | Ph | OSO₂Me | H | H | OSO₂Ph |
| OSO₂Me | H | H | SiMe₃ | OSO₂Me | H | H | SH |
| OSO₂Me | H | H | SO₂CF₃ | OSO₂Me | H | H | SMe |
| OSO₂Me | H | H | SOMe | OSO₂Me | H | H | SO₂Me |
| OSO₂Me | H | I | H | OSO₂Me | H | H | t-Bu |
| OSO₂Me | H | NO₂ | H | OSO₂Me | H | Me | H |
| OSO₂Me | H | OH | H | OSO₂Me | H | OCF₃ | H |
| OSO₂Me | H | OSO₂Bn | H | OSO₂Me | H | OMe | H |
| OSO₂Me | H | OSO₂i-Pr | H | OSO₂Me | H | OSO₂Et | H |
| OSO₂Me | H | OSO₂n-Bu | H | OSO₂Me | H | OSO₂Me | H |
| OSO₂Me | H | OSO₂Ph | H | OSO₂Me | H | OSO₂n-Pr | H |
| OSO₂Me | I | H | H | OSO₂Me | H | SO₂Me | H |
| OSO₂Me | —N=CH—CH=CH— | | F | OSO₂Me | Me | H | H |
| OSO₂Me | —N=CH—CH=CH— | | OSO₂Me | OSO₂Me | —N=CH—CH=CH— | | H |
| OSO₂Me | —N=CH—N=CH— | | H | OSO₂Me | —N=CH—N=CH— | | F |

TABLE 95

| X¹ | X² | X³ | X⁴ | X¹ | X² | X³ | X⁴ |
|---|---|---|---|---|---|---|---|
| OSO₂Me | —NH—CH=CH— | | F | OSO₂Me | —N=CH—N=CH— | | OSO₂Me |
| OSO₂Me | —NH—CH=CH— | | OSO₂Me | OSO₂Me | —NH—CH=CH— | | H |
| OSO₂Me | OCF₃ | H | H | OSO₂Me | NO₂ | H | H |
| OSO₂Me | —O—CH=CH— | | H | OSO₂Me | —O—CH=CH— | | F |
| OSO₂Me | —O—CH=N— | | F | OSO₂Me | —O—CH=CH— | | OSO₂Me |
| OSO₂Me | —O—CH=N— | | OSO₂Me | OSO₂Me | —O—CH=N— | | H |
| OSO₂Me | OMe | H | H | OSO₂Me | OH | H | H |
| OSO₂Me | OSO₂Et | H | H | OSO₂Me | OSO₂Bn | H | H |
| OSO₂Me | OSO₂Me | H | H | OSO₂Me | OSO₂i-Pr | H | H |
| OSO₂Me | OSO₂Me | OSO₂Me | H | OSO₂Me | OSO₂Me | H | OSO₂Me |
| OSO₂Me | OSO₂n-Bu | H | H | OSO₂Me | OSO₂Me | OSO₂Me | OSO₂Me |
| OSO₂Me | OSO₂Ph | H | H | OSO₂Me | OSO₂n-Pr | H | H |
| OSO₂Me | —S—CH=CH— | | H | OSO₂Me | —S—CH=CH— | | F |
| OSO₂Me | SO₂Me | H | H | OSO₂Me | —S—CH=CH— | | OSO₂Me |
| OSO₂n-Bu | H | H | Cl | OSO₂n-Bu | H | H | Br |
| OSO₂n-Bu | H | H | c-Pr | OSO₂n-Bu | H | H | CN |
| OSO₂n-Bu | H | H | F | OSO₂n-Bu | H | H | Et |
| OSO₂n-Bu | H | H | I | OSO₂n-Bu | H | H | H |
| OSO₂n-Bu | H | H | n-Bu | OSO₂n-Bu | H | H | Me |
| OSO₂n-Bu | H | H | n-Pr | OSO₂n-Bu | H | H | NO₂ |
| OSO₂n-Bu | H | H | OCHF₂ | OSO₂n-Bu | H | H | OCF₃ |
| OSO₂n-Bu | H | H | OEt | OSO₂n-Bu | H | H | Oc-Pr |
| OSO₂n-Bu | H | H | OMe | OSO₂n-Bu | H | H | OH |
| OSO₂n-Bu | H | H | On-Pr | OSO₂n-Bu | H | H | On-Bu |
| OSO₂n-Bu | H | H | t-Bu | OSO₂n-Bu | H | H | Ot-Bu |
| OSO₂n-Pr | H | H | Cl | OSO₂n-Pr | H | H | Br |
| OSO₂n-Pr | H | H | c-Pr | OSO₂n-Pr | H | H | CN |
| OSO₂n-Pr | H | H | F | OSO₂n-Pr | H | H | Et |
| OSO₂n-Pr | H | H | I | OSO₂n-Pr | H | H | H |
| OSO₂n-Pr | H | H | n-Bu | OSO₂n-Pr | H | H | Me |
| OSO₂n-Pr | H | H | n-Pr | OSO₂n-Pr | H | H | NO₂ |
| OSO₂n-Pr | H | H | OCHF₂ | OSO₂n-Pr | H | H | OCF₃ |
| OSO₂n-Pr | H | H | OEt | OSO₂n-Pr | H | H | Oc-Pr |
| OSO₂n-Pr | H | H | OMe | OSO₂n-Pr | H | H | OH |

TABLE 96

| X¹ | X² | X³ | X⁴ | X¹ | X² | X³ | X⁴ |
|---|---|---|---|---|---|---|---|
| OSO₂n-Pr | H | H | On-Pr | OSO₂n-Pr | H | H | On-Bu |
| OSO₂n-Pr | H | H | t-Bu | OSO₂n-Pr | H | H | Ot-Bu |
| Ph | H | H | H | OSO₂Ph | H | H | H |
| SiMe₃ | H | H | H | SH | H | H | H |
| SO₂CF₃ | H | H | H | SMe | H | H | H |
| SO₂Me | H | H | SO₂Me | SO₂Me | H | H | H |
| t-Bu | H | H | H | SOMe | H | H | H |

TABLE 97

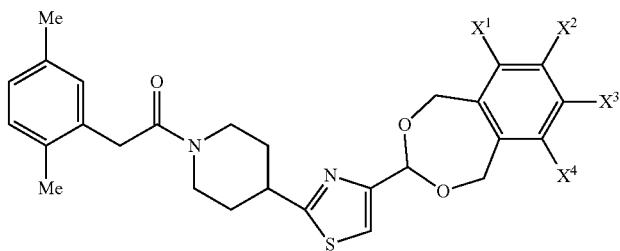

| X¹ | X² | X³ | X⁴ |
|---|---|---|---|
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | H | H |
| Cl | H | H | Cl |
| CN | H | H | CN |
| CO₂H | H | H | H |
| c-Pr | H | H | H |
| F | Br | H | F |
| F | C(=NOMe)H | H | H |
| F | CF₃ | H | F |
| F | Cl | H | F |
| F | CN | H | F |
| F | F | F | F |
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |
| Cl | H | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 98

| $X^1$ | $X^2$ | $X^3$ | $X^4$ | $X^1$ | $X^2$ | $X^3$ | $X^4$ |
|---|---|---|---|---|---|---|---|
| F | H | H | CHO | F | H | H | $CH_2SMe$ |
| F | H | H | CN | F | H | H | Cl |
| F | H | H | $CO_2Me$ | F | H | H | $CO_2H$ |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | $NH_2$ | F | H | H | n-Bu |
| F | H | H | NHCOMe | F | H | H | $NHCO_2Me$ |
| F | H | H | $NHSO_2Me$ | F | H | H | NHMe |
| F | H | H | $NO_2$ | F | H | H | $NMe_2$ |
| F | H | H | $OCF_3$ | F | H | H | n-Pr |
| F | H | H | $OCO_2Me$ | F | H | H | $OCH_2C{\equiv}CH$ |
| F | H | H | OCOMe | F | H | H | $OCO_2NMe_2$ |
| F | H | H | OH | F | H | H | OEt |
| F | H | H | OPh | F | H | H | OMe |
| F | H | H | $OSiMe_3$ | F | H | H | $OSiMe_2$t-Bu |
| F | H | H | SH | F | H | H | Ph |
| F | H | H | SMe | F | H | H | $SiMe_3$ |
| F | H | H | $SO_2Me$ | F | H | H | $SO_2CF_3$ |
| F | H | H | t-Bu | F | H | H | SOMe |
| F | H | Me | H | F | H | I | H |
| F | H | $OCF_3$ | H | F | H | $NO_2$ | H |
| F | H | OMe | H | F | H | OH | H |
| F | H | $SO_2Me$ | H | F | H | $OSO_2Me$ | H |
| F | I | H | H | F | I | H | F |
| F | Me | H | H | F | Me | H | F |
| F | $NO_2$ | H | H | F | $NO_2$ | H | F |
| F | $OCF_3$ | H | H | F | $OCF_3$ | H | F |
| F | OH | H | H | F | OH | H | F |
| F | OMe | H | H | F | OMe | H | F |
| F | $SO_2Me$ | H | F | F | $OSO_2Me$ | H | F |
| H | Br | Br | H | F | $SO_2Me$ | H | H |
| H | C(=NOMe)H | H | H | H | Br | H | H |

TABLE 99

| $X^1$ | $X^2$ | $X^3$ | $X^4$ | $X^1$ | $X^2$ | $X^3$ | $X^4$ |
|---|---|---|---|---|---|---|---|
| H | $CF_3$ | $CF_3$ | H | H | C(=NOMe)Me | H | H |
| H | —CH=CH—CH=CH— | | H | H | $CF_3$ | H | H |
| H | —$CH_2CH_2CH_2$— | | H | H | —CH=N—CH=CH— | | H |
| H | Cl | Cl | H | H | —$CH_2CH_2CH_2CH_2$— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |
| H | —NH—CH=CH— | | H | H | —N=CH—N=CH— | | H |
| H | $NO_2$ | $NO_2$ | H | H | $NO_2$ | H | H |
| H | $OCF_3$ | $OCF_3$ | H | H | $OCF_3$ | H | H |
| H | —O—CH=N— | | H | H | —O—CH=CH— | | H |
| H | OH | OH | H | H | OH | H | H |
| H | OMe | OMe | H | H | OMe | H | H |
| H | $OSO_2Et$ | H | H | H | $OSO_2Bn$ | H | H |
| H | $OSO_2Me$ | H | H | H | $OSO_2$i-Pr | H | H |
| H | $OSO_2$n-Bu | H | H | H | $OSO_2Me$ | $OSO_2Me$ | H |
| H | $OSO_2Ph$ | H | H | H | $OSO_2$n-Pr | H | H |
| H | $SO_2Me$ | H | H | H | —S—CH=CH— | | H |
| I | H | H | H | H | $SO_2Me$ | $SO_2Me$ | H |
| i-Pr | H | H | H | H | i-Bu | H | H |
| Me | H | H | Me | Me | H | H | H |
| $NH_2$ | H | H | H | n-Bu | H | H | H |
| NHCOMe | H | H | H | $NHCO_2Me$ | H | H | H |
| $NHSO_2Me$ | H | H | H | NHMe | H | H | H |
| $NO_2$ | H | H | H | $NMe_2$ | H | H | H |
| $OCF_3$ | H | H | H | n-Pr | H | H | H |
| $OCH_2C{\equiv}CH$ | H | H | H | $OCF_3$ | H | H | $OCF_3$ |
| $OCO_2NMe_2$ | H | H | H | $OCO_2Me$ | H | H | H |
| OEt | H | H | H | OCOMe | H | H | H |
| OMe | H | H | H | OH | H | H | H |
| OPh | H | H | H | OMe | H | H | OMe |
| $OSiMe_3$ | H | H | H | $OSiMe_2$t-Bu | H | H | H |

TABLE 100

| X¹ | X² | X³ | X⁴ | X¹ | X² | X³ | X⁴ |
|---|---|---|---|---|---|---|---|
| OSO$_2$CF$_3$ | H | H | Br | OSO$_2$Bn | H | H | H |
| OSO$_2$CF$_3$ | H | H | CN | OSO$_2$CF$_3$ | H | H | Cl |
| OSO$_2$CF$_3$ | H | H | Et | OSO$_2$CF$_3$ | H | H | c-Pr |
| OSO$_2$CF$_3$ | H | H | H | OSO$_2$CF$_3$ | H | H | F |
| OSO$_2$CF$_3$ | H | H | Me | OSO$_2$CF$_3$ | H | H | I |
| OSO$_2$CF$_3$ | H | H | NO$_2$ | OSO$_2$CF$_3$ | H | H | n-Bu |
| OSO$_2$CF$_3$ | H | H | OCF$_3$ | OSO$_2$CF$_3$ | H | H | n-Pr |
| OSO$_2$CF$_3$ | H | H | Oc-Pr | OSO$_2$CF$_3$ | H | H | OCHF$_2$ |
| OSO$_2$CF$_3$ | H | H | OH | OSO$_2$CF$_3$ | H | H | OEt |
| OSO$_2$CF$_3$ | H | H | On-Bu | OSO$_2$CF$_3$ | H | H | OMe |
| OSO$_2$CF$_3$ | H | H | Ot-Bu | OSO$_2$CF$_3$ | H | H | On-Pr |
| OSO$_2$CHF$_2$ | H | H | Br | OSO$_2$CF$_3$ | H | H | t-Bu |
| OSO$_2$CHF$_2$ | H | H | CN | OSO$_2$CHF$_2$ | H | H | Cl |
| OSO$_2$CHF$_2$ | H | H | Et | OSO$_2$CHF$_2$ | H | H | c-Pr |
| OSO$_2$CHF$_2$ | H | H | H | OSO$_2$CHF$_2$ | H | H | F |
| OSO$_2$CHF$_2$ | H | H | Me | OSO$_2$CHF$_2$ | H | H | I |
| OSO$_2$CHF$_2$ | H | H | NO$_2$ | OSO$_2$CHF$_2$ | H | H | n-Bu |
| OSO$_2$CHF$_2$ | H | H | OCF$_3$ | OSO$_2$CHF$_2$ | H | H | n-Pr |
| OSO$_2$CHF$_2$ | H | H | Oc-Pr | OSO$_2$CHF$_2$ | H | H | OCHF$_2$ |
| OSO$_2$CHF$_2$ | H | H | OH | OSO$_2$CHF$_2$ | H | H | OEt |
| OSO$_2$CHF$_2$ | H | H | On-Bu | OSO$_2$CHF$_2$ | H | H | OMe |
| OSO$_2$CHF$_2$ | H | H | Ot-Bu | OSO$_2$CHF$_2$ | H | H | On-Pr |
| OSO$_2$Et | H | H | Br | OSO$_2$CHF$_2$ | H | H | t-Bu |
| OSO$_2$Et | H | H | Cl | OSO$_2$Et | H | H | CF$_3$ |
| OSO$_2$Et | H | H | c-Pr | OSO$_2$Et | H | H | CN |
| OSO$_2$Et | H | H | F | OSO$_2$Et | H | H | Et |
| OSO$_2$Et | H | H | I | OSO$_2$Et | H | H | H |
| OSO$_2$Et | H | H | n-Bu | OSO$_2$Et | H | H | Me |
| OSO$_2$Et | H | H | n-Pr | OSO$_2$Et | H | H | NO$_2$ |
| OSO$_2$Et | H | H | OCHF$_2$ | OSO$_2$Et | H | H | OCF$_3$ |
| OSO$_2$Et | H | H | OEt | OSO$_2$Et | H | H | Oc-Pr |
| OSO$_2$Et | H | H | OMe | OSO$_2$Et | H | H | OH |
| OSO$_2$Et | H | H | On-Pr | OSO$_2$Et | H | H | On-Bu |
| OSO$_2$Et | H | H | t-Bu | OSO$_2$Et | H | H | Ot-Bu |

TABLE 101

| X¹ | X² | X³ | X⁴ | X¹ | X² | X³ | X⁴ |
|---|---|---|---|---|---|---|---|
| OSO$_2$i-Pr | H | H | CF$_3$ | OSO$_2$i-Pr | H | H | Br |
| OSO$_2$i-Pr | H | H | CN | OSO$_2$i-Pr | H | H | Cl |
| OSO$_2$i-Pr | H | H | Et | OSO$_2$i-Pr | H | H | c-Pr |
| OSO$_2$i-Pr | H | H | H | OSO$_2$i-Pr | H | H | F |
| OSO$_2$i-Pr | H | H | Me | OSO$_2$i-Pr | H | H | I |
| OSO$_2$i-Pr | H | H | NO$_2$ | OSO$_2$i-Pr | H | H | n-Bu |
| OSO$_2$i-Pr | H | H | OCF$_3$ | OSO$_2$i-Pr | H | H | n-Pr |
| OSO$_2$i-Pr | H | H | Oc-Pr | OSO$_2$i-Pr | H | H | OCHF$_2$ |
| OSO$_2$i-Pr | H | H | OH | OSO$_2$i-Pr | H | H | OEt |
| OSO$_2$i-Pr | H | H | On-Bu | OSO$_2$i-Pr | H | H | OMe |
| OSO$_2$i-Pr | H | H | Ot-Bu | OSO$_2$i-Pr | H | H | On-Pr |
| OSO$_2$Me | Br | H | H | OSO$_2$i-Pr | H | H | t-Bu |
| OSO$_2$Me | C(=NOMe)Me | H | H | OSO$_2$Me | C(=NOMe)H | H | H |
| OSO$_2$Me | —CH=CH—CH=CH— | | F | OSO$_2$Me | CF$_3$ | H | H |
| OSO$_2$Me | —CH=CH—CH=CH— | | OSO$_2$Me | OSO$_2$Me | —CH=CH—CH=CH— | | H |
| OSO$_2$Me | —CH=N—CH=CH— | | H | OSO$_2$Me | —CH=N—CH=CH— | | F |
| OSO$_2$Me | —CH$_2$CH$_2$CH$_2$— | | F | OSO$_2$Me | —CH$_2$CH$_2$CH$_2$— | | OSO$_2$Me |
| OSO$_2$Me | —CH$_2$CH$_2$CH$_2$— | | OSO$_2$Me | OSO$_2$Me | —CH$_2$CH$_2$CH$_2$— | | H |
| OSO$_2$Me | —CH$_2$CH$_2$CH$_2$CH$_2$— | | H | OSO$_2$Me | —CH$_2$CH$_2$CH$_2$CH$_2$— | | F |
| OSO$_2$Me | Cl | H | H | OSO$_2$Me | —CH$_2$CH$_2$CH$_2$CH$_2$— | | OSO$_2$Me |
| OSO$_2$Me | F | F | F | OSO$_2$Me | CN | H | H |
| OSO$_2$Me | F | H | F | OSO$_2$Me | F | F | OSO$_2$Me |
| OSO$_2$Me | H | Br | H | OSO$_2$Me | F | H | H |
| OSO$_2$Me | H | C(=NOMe)Me | H | OSO$_2$Me | H | C(=NOMe)H | H |
| OSO$_2$Me | H | Cl | H | OSO$_2$Me | H | CF$_3$ | H |
| OSO$_2$Me | H | F | F | OSO$_2$Me | H | CN | H |
| OSO$_2$Me | H | H | Bn | OSO$_2$Me | H | F | H |
| OSO$_2$Me | H | H | C(=NOMe)H | OSO$_2$Me | H | H | Br |
| OSO$_2$Me | H | H | C≡CH | OSO$_2$Me | H | H | C(=NOMe)Me |
| OSO$_2$Me | H | H | CF$_3$ | OSO$_2$Me | H | H | C$_2$F$_5$ |
| OSO$_2$Me | H | H | CH$_2$CN | OSO$_2$Me | H | H | CH=CH$_2$ |
| OSO$_2$Me | H | H | CH$_2$OMe | OSO$_2$Me | H | H | CH$_2$NMe$_2$ |
| OSO$_2$Me | H | H | CHO | OSO$_2$Me | H | H | CH$_2$SMe |
| OSO$_2$Me | H | H | CN | OSO$_2$Me | H | H | Cl |

TABLE 102

| X¹ | X² | X³ | X⁴ | X¹ | X² | X³ | X⁴ |
|---|---|---|---|---|---|---|---|
| OSO$_2$Me | H | H | CO$_2$Me | OSO$_2$Me | H | H | CO$_2$H |
| OSO$_2$Me | H | H | Et | OSO$_2$Me | H | H | c-Pr |
| OSO$_2$Me | H | H | H | OSO$_2$Me | H | H | F |
| OSO$_2$Me | H | H | I | OSO$_2$Me | H | H | H |
| OSO$_2$Me | H | H | i-Pr | OSO$_2$Me | H | H | i-Bu |
| OSO$_2$Me | H | H | n-Bu | OSO$_2$Me | H | H | Me |
| OSO$_2$Me | H | H | NHCO$_2$Me | OSO$_2$Me | H | H | NH$_2$ |
| OSO$_2$Me | H | H | NHMe | OSO$_2$Me | H | H | NHCOMe |
| OSO$_2$Me | H | H | NMe$_2$ | OSO$_2$Me | H | H | NHSO$_2$Me |
| OSO$_2$Me | H | H | n-Pr | OSO$_2$Me | H | H | NO$_2$ |
| OSO$_2$Me | H | H | OCHF$_2$ | OSO$_2$Me | H | H | OCF$_3$ |
| OSO$_2$Me | H | H | OCO$_2$Me | OSO$_2$Me | H | H | OCH$_2$C≡CH |

TABLE 102-continued

| X¹ | X² | X³ | X⁴ | X¹ | X² | X³ | X⁴ |
|---|---|---|---|---|---|---|---|
| OSO₂Me | H | H | OCOMe | OSO₂Me | H | H | OCO₂NMe₂ |
| OSO₂Me | H | H | OH | OSO₂Me | H | H | OEt |
| OSO₂Me | H | H | OPh | OSO₂Me | H | H | OMe |
| OSO₂Me | H | H | OSiMe₃ | OSO₂Me | H | H | OSiMe₂t-Bu |
| OSO₂Me | H | H | OSO₂Et | OSO₂Me | H | H | OSO₂Bn |
| OSO₂Me | H | H | OSO₂Me | OSO₂Me | H | H | OSO₂i-Pr |
| OSO₂Me | H | H | OSO₂n-Pr | OSO₂Me | H | H | OSO₂n-Bu |
| OSO₂Me | H | H | Ph | OSO₂Me | H | H | OSO₂Ph |
| OSO₂Me | H | H | SiMe₃ | OSO₂Me | H | H | SH |
| OSO₂Me | H | H | SO₂CF₃ | OSO₂Me | H | H | SMe |
| OSO₂Me | H | H | SOMe | OSO₂Me | H | H | SO₂Me |
| OSO₂Me | H | I | H | OSO₂Me | H | H | t-Bu |
| OSO₂Me | H | NO₂ | H | OSO₂Me | H | Me | H |
| OSO₂Me | H | OH | H | OSO₂Me | H | OCF₃ | H |
| OSO₂Me | H | OSO₂Bn | H | OSO₂Me | H | OMe | H |
| OSO₂Me | H | OSO₂i-Pr | H | OSO₂Me | H | OSO₂Et | H |
| OSO₂Me | H | OSO₂n-Bu | H | OSO₂Me | H | OSO₂Me | H |
| OSO₂Me | H | OSO₂Ph | H | OSO₂Me | H | OSO₂n-Pr | H |
| OSO₂Me | I | H | H | OSO₂Me | H | SO₂Me | H |
| OSO₂Me | —N=CH—CH=CH— | | F | OSO₂Me | Me | H | H |
| OSO₂Me | —N=CH—CH=CH— | | OSO₂Me | OSO₂Me | —N=CH—CH=CH— | | H |
| OSO₂Me | —N=CH—N=CH— | | H | OSO₂Me | —N=CH—N=CH— | | F |

TABLE 103

| X¹ | X² | X³ | X⁴ | X¹ | X² | X³ | X⁴ |
|---|---|---|---|---|---|---|---|
| OSO₂Me | —NH—CH=CH— | | F | OSO₂Me | —N=CH—N=CH— | | OSO₂Me |
| OSO₂Me | —NH—CH=CH— | | OSO₂Me | OSO₂Me | —NH—CH=CH— | | H |
| OSO₂Me | OCF₃ | H | H | OSO₂Me | NO₂ | H | H |
| OSO₂Me | —O—CH=CH— | | H | OSO₂Me | —O—CH=CH— | | F |
| OSO₂Me | —O—CH=N— | | F | OSO₂Me | —O—CH=CH— | | OSO₂Me |
| OSO₂Me | —O—CH=N— | | OSO₂Me | OSO₂Me | —O—CH=N— | | H |
| OSO₂Me | OMe | H | H | OSO₂Me | OH | H | H |
| OSO₂Me | OSO₂Et | H | H | OSO₂Me | OSO₂Bn | H | H |
| OSO₂Me | OSO₂Me | H | H | OSO₂Me | OSO₂i-Pr | H | H |
| OSO₂Me | OSO₂Me | OSO₂Me | H | OSO₂Me | OSO₂Me | H | OSO₂Me |
| OSO₂Me | OSO₂n-Bu | H | H | OSO₂Me | OSO₂Me | OSO₂Me | OSO₂Me |
| OSO₂Me | OSO₂Ph | H | H | OSO₂Me | OSO₂n-Pr | H | H |
| OSO₂Me | —S—CH=CH— | | H | OSO₂Me | —S—CH=CH— | | F |
| OSO₂Me | SO₂Me | H | H | OSO₂Me | —S—CH=CH— | | OSO₂Me |
| OSO₂n-Bu | H | H | Cl | OSO₂n-Bu | H | H | Br |
| OSO₂n-Bu | H | H | c-Pr | OSO₂n-Bu | H | H | CN |
| OSO₂n-Bu | H | H | F | OSO₂n-Bu | H | H | Et |
| OSO₂n-Bu | H | H | I | OSO₂n-Bu | H | H | H |
| OSO₂n-Bu | H | H | n-Bu | OSO₂n-Bu | H | H | Me |
| OSO₂n-Bu | H | H | n-Pr | OSO₂n-Bu | H | H | NO₂ |
| OSO₂n-Bu | H | H | OCHF₂ | OSO₂n-Bu | H | H | OCF₃ |
| OSO₂n-Bu | H | H | OEt | OSO₂n-Bu | H | H | Oc-Pr |
| OSO₂n-Bu | H | H | OMe | OSO₂n-Bu | H | H | OH |
| OSO₂n-Bu | H | H | On-Pr | OSO₂n-Bu | H | H | On-Bu |
| OSO₂n-Bu | H | H | t-Bu | OSO₂n-Bu | H | H | Ot-Bu |
| OSO₂n-Pr | H | H | Cl | OSO₂n-Pr | H | H | Br |
| OSO₂n-Pr | H | H | c-Pr | OSO₂n-Pr | H | H | CN |
| OSO₂n-Pr | H | H | F | OSO₂n-Pr | H | H | Et |
| OSO₂n-Pr | H | H | I | OSO₂n-Pr | H | H | H |
| OSO₂n-Pr | H | H | n-Bu | OSO₂n-Pr | H | H | Me |
| OSO₂n-Pr | H | H | n-Pr | OSO₂n-Pr | H | H | NO₂ |
| OSO₂n-Pr | H | H | OCHF₂ | OSO₂n-Pr | H | H | OCF₃ |
| OSO₂n-Pr | H | H | OEt | OSO₂n-Pr | H | H | Oc-Pr |
| OSO₂n-Pr | H | H | OMe | OSO₂n-Pr | H | H | OH |

TABLE 104

| X¹ | X² | X³ | X⁴ | X¹ | X² | X³ | X⁴ |
|---|---|---|---|---|---|---|---|
| OSO₂n-Pr | H | H | On-Pr | OSO₂n-Pr | H | H | On-Bu |
| OSO₂n-Pr | H | H | t-Bu | OSO₂n-Pr | H | H | Ot-Bu |
| Ph | H | H | H | OSO₂Ph | H | H | H |
| SiMe₃ | H | H | H | SH | H | H | H |
| SO₂CF₃ | H | H | H | SMe | H | H | H |
| SO₂Me | H | H | SO₂Me | SO₂Me | H | H | H |
| t-Bu | H | H | H | SOMe | H | H | H |

TABLE 105

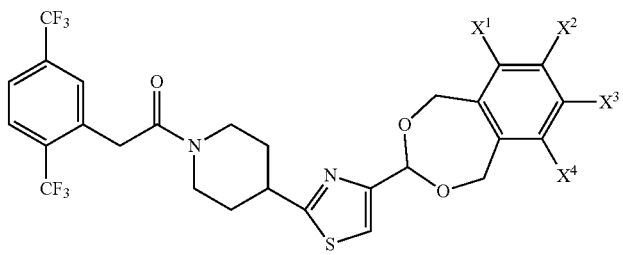

| $X^1$ | $X^2$ | $X^3$ | $X^4$ |
|---|---|---|---|
| Br | H | H | Br |
| C(=NOMe)H | H | H | H |
| C≡CH | H | H | H |
| $CF_3$ | H | H | $CF_3$ |
| CH=$CH_2$ | H | H | H |
| $CH_2NMe_2$ | H | H | H |
| $CH_2SMe$ | H | H | H |
| Cl | Cl | Cl | Cl |
| Cl | Cl | H | H |
| Cl | H | H | Cl |
| CN | H | H | CN |
| $CO_2H$ | H | H | H |
| c-Pr | H | H | H |
| F | Br | H | F |
| F | C(=NOMe)H | H | H |
| F | $CF_3$ | H | F |
| F | Cl | H | F |
| F | CN | H | F |
| F | F | F | F |
| F | F | H | H |
| F | H | C(=NOMe)H | H |
| F | H | $CF_3$ | H |
| F | H | CN | H |
| F | H | H | Bn |
| F | H | H | C(=NOMe)H |
| F | H | H | C≡CH |
| F | H | H | $CF_3$ |
| F | H | H | $CH_2CN$ |
| F | H | H | $CH_2OMe$ |
| Bn | H | H | H |
| Br | H | H | H |
| C(=NOMe)Me | H | H | H |
| $C_2F_5$ | H | H | H |
| $CF_3$ | H | H | H |
| $CH_2CN$ | H | H | H |
| $CH_2OMe$ | H | H | H |
| CHO | H | H | H |
| Cl | Cl | Cl | H |
| Cl | H | Cl | H |
| Cl | H | H | H |
| CN | H | H | H |
| $CO_2Me$ | H | H | H |
| Et | H | H | H |
| F | Br | H | H |
| F | C(=NOMe)Me | H | H |
| F | $CF_3$ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | $C_2F_5$ |
| F | H | H | CH=$CH_2$ |
| F | H | H | $CH_2NMe_2$ |

TABLE 106

| $X^1$ | $X^2$ | $X^3$ | $X^4$ | $X^1$ | $X^2$ | $X^3$ | $X^4$ |
|---|---|---|---|---|---|---|---|
| F | H | H | CHO | F | H | H | $CH_2SMe$ |
| F | H | H | CN | F | H | H | Cl |
| F | H | H | $CO_2Me$ | F | H | H | $CO_2H$ |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | $NH_2$ | F | H | H | n-Bu |
| F | H | H | NHCOMe | F | H | H | $NHCO_2Me$ |
| F | H | H | $NHSO_2Me$ | F | H | H | NHMe |
| F | H | H | $NO_2$ | F | H | H | $NMe_2$ |
| F | H | H | $OCF_3$ | F | H | H | n-Pr |
| F | H | H | $OCO_2Me$ | F | H | H | $OCH_2C\equiv CH$ |
| F | H | H | OCOMe | F | H | H | $OCO_2NMe_2$ |
| F | H | H | OH | F | H | H | OEt |
| F | H | H | OPh | F | H | H | OMe |
| F | H | H | $OSiMe_3$ | F | H | H | $OSiMe_2$t-Bu |
| F | H | H | SH | F | H | H | Ph |
| F | H | H | SMe | F | H | H | $SiMe_3$ |
| F | H | H | $SO_2Me$ | F | H | H | $SO_2CF_3$ |
| F | H | H | t-Bu | F | H | H | SOMe |
| F | H | Me | H | F | H | I | H |
| F | H | $OCF_3$ | H | F | H | $NO_2$ | H |
| F | H | OMe | H | F | H | OH | H |
| F | H | $SO_2Me$ | H | F | H | $OSO_2Me$ | H |
| F | I | H | H | F | I | H | F |
| F | Me | H | H | F | Me | H | F |
| F | $NO_2$ | H | H | F | $NO_2$ | H | F |
| F | $OCF_3$ | H | H | F | $OCF_3$ | H | F |
| F | OH | H | H | F | OH | H | F |
| F | OMe | H | H | F | OMe | H | F |
| F | $SO_2Me$ | H | F | F | $OSO_2Me$ | H | F |
| H | Br | Br | H | F | $SO_2Me$ | H | H |
| H | C(=NOMe)H | H | H | H | Br | H | H |

TABLE 107

| $X^1$ | $X^2$ | $X^3$ | $X^4$ | $X^1$ | $X^2$ | $X^3$ | $X^4$ |
|---|---|---|---|---|---|---|---|
| H | $CF_3$ | $CF_3$ | H | H | C(=NOMe)Me | H | H |
| H | —CH=CH—CH=CH— | | H | H | $CF_3$ | H | H |
| H | —$CH_2CH_2CH_2$— | | H | H | —CH=N—CH=CH— | | H |
| H | Cl | Cl | H | H | —$CH_2CH_2CH_2CH_2$— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |
| H | —NH—CH=CH— | | H | H | —N=CH—N=CH— | | H |
| H | $NO_2$ | $NO_2$ | H | H | $NO_2$ | H | H |
| H | $OCF_3$ | $OCF_3$ | H | H | $OCF_3$ | H | H |
| H | —O—CH=N— | | H | H | —O—CH=CH— | | H |
| H | OH | OH | H | H | OH | H | H |
| H | OMe | OMe | H | H | OMe | H | H |
| H | $OSO_2Et$ | H | H | H | $OSO_2Bn$ | H | H |
| H | $OSO_2Me$ | H | H | H | $OSO_2$i-Pr | H | H |
| H | $OSO_2$n-Bu | H | H | H | $OSO_2Me$ | $OSO_2Me$ | H |
| H | $OSO_2Ph$ | H | H | H | $OSO_2$n-Pr | H | H |
| H | $SO_2Me$ | H | H | H | —S—CH=CH— | | H |
| I | H | H | H | H | $SO_2Me$ | $SO_2Me$ | H |
| i-Pr | H | H | H | H | i-Bu | H | H |
| Me | H | H | Me | Me | H | H | H |
| $NH_2$ | H | H | H | n-Bu | H | H | H |
| NHCOMe | H | H | H | $NHCO_2Me$ | H | H | H |
| $NHSO_2Me$ | H | H | H | NHMe | H | H | H |
| $NO_2$ | H | H | H | $NMe_2$ | H | H | H |
| $OCF_3$ | H | H | H | n-Pr | H | H | H |
| $OCH_2C\equiv CH$ | H | H | H | $OCF_3$ | H | H | $OCF_3$ |
| $OCO_2NMe_2$ | H | H | H | $OCO_2Me$ | H | H | H |
| OEt | H | H | H | OCOMe | H | H | H |
| OMe | H | H | H | OH | H | H | H |
| OPh | H | H | H | OMe | H | H | OMe |
| $OSiMe_3$ | H | H | H | $OSiMe_2$t-Bu | H | H | H |

TABLE 108

| $X^1$ | $X^2$ | $X^3$ | $X^4$ | $X^1$ | $X^2$ | $X^3$ | $X^4$ |
|---|---|---|---|---|---|---|---|
| $OSO_2CF_3$ | H | H | Br | $OSO_2Bn$ | H | H | H |
| $OSO_2CF_3$ | H | H | CN | $OSO_2CF_3$ | H | H | Cl |
| $OSO_2CF_3$ | H | H | Et | $OSO_2CF_3$ | H | H | c-Pr |
| $OSO_2CF_3$ | H | H | H | $OSO_2CF_3$ | H | H | F |
| $OSO_2CF_3$ | H | H | Me | $OSO_2CF_3$ | H | H | I |
| $OSO_2CF_3$ | H | H | $NO_2$ | $OSO_2CF_3$ | H | H | n-Bu |
| $OSO_2CF_3$ | H | H | $OCF_3$ | $OSO_2CF_3$ | H | H | n-Pr |
| $OSO_2CF_3$ | H | H | Oc-Pr | $OSO_2CF_3$ | H | H | $OCHF_2$ |
| $OSO_2CF_3$ | H | H | OH | $OSO_2CF_3$ | H | H | OEt |
| $OSO_2CF_3$ | H | H | On-Bu | $OSO_2CF_3$ | H | H | OMe |
| $OSO_2CF_3$ | H | H | Ot-Bu | $OSO_2CF_3$ | H | H | On-Pr |
| $OSO_2CHF_2$ | H | H | Br | $OSO_2CF_3$ | H | H | t-Bu |
| $OSO_2CHF_2$ | H | H | CN | $OSO_2CHF_2$ | H | H | Cl |
| $OSO_2CHF_2$ | H | H | Et | $OSO_2CHF_2$ | H | H | c-Pr |
| $OSO_2CHF_2$ | H | H | H | $OSO_2CHF_2$ | H | H | F |
| $OSO_2CHF_2$ | H | H | Me | $OSO_2CHF_2$ | H | H | I |
| $OSO_2CHF_2$ | H | H | $NO_2$ | $OSO_2CHF_2$ | H | H | n-Bu |
| $OSO_2CHF_2$ | H | H | $OCF_3$ | $OSO_2CHF_2$ | H | H | n-Pr |
| $OSO_2CHF_2$ | H | H | Oc-Pr | $OSO_2CHF_2$ | H | H | $OCHF_2$ |
| $OSO_2CHF_2$ | H | H | OH | $OSO_2CHF_2$ | H | H | OEt |
| $OSO_2CHF_2$ | H | H | On-Bu | $OSO_2CHF_2$ | H | H | OMe |
| $OSO_2CHF_2$ | H | H | Ot-Bu | $OSO_2CHF_2$ | H | H | On-Pr |
| $OSO_2Et$ | H | H | Br | $OSO_2CHF_2$ | H | H | t-Bu |
| $OSO_2Et$ | H | H | Cl | $OSO_2Et$ | H | H | $CF_3$ |
| $OSO_2Et$ | H | H | c-Pr | $OSO_2Et$ | H | H | CN |
| $OSO_2Et$ | H | H | F | $OSO_2Et$ | H | H | Et |
| $OSO_2Et$ | H | H | I | $OSO_2Et$ | H | H | H |
| $OSO_2Et$ | H | H | n-Bu | $OSO_2Et$ | H | H | Me |
| $OSO_2Et$ | H | H | n-Pr | $OSO_2Et$ | H | H | $NO_2$ |
| $OSO_2Et$ | H | H | $OCHF_2$ | $OSO_2Et$ | H | H | $OCF_3$ |
| $OSO_2Et$ | H | H | OEt | $OSO_2Et$ | H | H | Oc-Pr |
| $OSO_2Et$ | H | H | OMe | $OSO_2Et$ | H | H | OH |
| $OSO_2Et$ | H | H | On-Pr | $OSO_2Et$ | H | H | On-Bu |
| $OSO_2Et$ | H | H | t-Bu | $OSO_2Et$ | H | H | Ot-Bu |

TABLE 109

| $X^1$ | $X^2$ | $X^3$ | $X^4$ | $X^1$ | $X^2$ | $X^3$ | $X^4$ |
|---|---|---|---|---|---|---|---|
| $OSO_2$i-Pr | H | H | $CF_3$ | $OSO_2$i-Pr | H | H | Br |
| $OSO_2$i-Pr | H | H | CN | $OSO_2$i-Pr | H | H | Cl |
| $OSO_2$i-Pr | H | H | Et | $OSO_2$i-Pr | H | H | c-Pr |
| $OSO_2$i-Pr | H | H | H | $OSO_2$i-Pr | H | H | F |
| $OSO_2$i-Pr | H | H | Me | $OSO_2$i-Pr | H | H | I |
| $OSO_2$i-Pr | H | H | $NO_2$ | $OSO_2$i-Pr | H | H | n-Bu |
| $OSO_2$i-Pr | H | H | $OCF_3$ | $OSO_2$i-Pr | H | H | n-Pr |
| $OSO_2$i-Pr | H | H | Oc-Pr | $OSO_2$i-Pr | H | H | $OCHF_2$ |
| $OSO_2$i-Pr | H | H | OH | $OSO_2$i-Pr | H | H | OEt |
| $OSO_2$i-Pr | H | H | On-Bu | $OSO_2$i-Pr | H | H | OMe |
| $OSO_2$i-Pr | H | H | Ot-Bu | $OSO_2$i-Pr | H | H | On-Pr |
| $OSO_2Me$ | Br | H | H | $OSO_2$i-Pr | H | H | t-Bu |
| $OSO_2Me$ | C(=NOMe)Me | H | H | $OSO_2Me$ | C(=NOMe)H | H | H |
| $OSO_2Me$ | —CH=CH—CH=CH— | | F | $OSO_2Me$ | $CF_3$ | H | H |
| $OSO_2Me$ | —CH=CH—CH=CH— | | $OSO_2Me$ | $OSO_2Me$ | —CH=CH—CH=CH— | | H |
| $OSO_2Me$ | —CH=N—CH=CH— | | H | $OSO_2Me$ | —CH=N—CH=CH— | | F |
| $OSO_2Me$ | —$CH_2CH_2CH_2$— | | F | $OSO_2Me$ | —CH=N—CH=CH— | | $OSO_2Me$ |
| $OSO_2Me$ | —$CH_2CH_2CH_2$— | | $OSO_2Me$ | $OSO_2Me$ | —$CH_2CH_2CH_2$— | | H |
| $OSO_2Me$ | —$CH_2CH_2CH_2CH_2$— | | H | $OSO_2Me$ | —$CH_2CH_2CH_2$— | | F |
| $OSO_2Me$ | Cl | H | H | $OSO_2Me$ | —$CH_2CH_2CH_2CH_2$— | | $OSO_2Me$ |
| $OSO_2Me$ | F | F | F | $OSO_2Me$ | CN | H | H |
| $OSO_2Me$ | F | H | F | $OSO_2Me$ | F | F | $OSO_2Me$ |
| $OSO_2Me$ | H | Br | H | $OSO_2Me$ | F | H | H |
| $OSO_2Me$ | H | C(=NOMe)Me | H | $OSO_2Me$ | H | C(=NOMe)H | H |
| $OSO_2Me$ | H | Cl | H | $OSO_2Me$ | H | $CF_3$ | H |
| $OSO_2Me$ | H | F | F | $OSO_2Me$ | H | CN | H |
| $OSO_2Me$ | H | H | Bn | $OSO_2Me$ | H | F | H |
| $OSO_2Me$ | H | H | C(=NOMe)H | $OSO_2Me$ | H | H | Br |
| $OSO_2Me$ | H | H | C≡CH | $OSO_2Me$ | H | H | C(=NOMe)Me |
| $OSO_2Me$ | H | H | $CF_3$ | $OSO_2Me$ | H | H | $C_2F_5$ |
| $OSO_2Me$ | H | H | $CH_2CN$ | $OSO_2Me$ | H | H | CH=$CH_2$ |
| $OSO_2Me$ | H | H | $CH_2OMe$ | $OSO_2Me$ | H | H | $CH_2NMe_2$ |
| $OSO_2Me$ | H | H | CHO | $OSO_2Me$ | H | H | $CH_2SMe$ |
| $OSO_2Me$ | H | H | CN | $OSO_2Me$ | H | H | Cl |

TABLE 110

| $X^1$ | $X^2$ | $X^3$ | $X^4$ | $X^1$ | $X^2$ | $X^3$ | $X^4$ |
|---|---|---|---|---|---|---|---|
| $OSO_2Me$ | H | H | $CO_2Me$ | $OSO_2Me$ | H | H | $CO_2H$ |
| $OSO_2Me$ | H | H | Et | $OSO_2Me$ | H | H | c-Pr |
| $OSO_2Me$ | H | H | H | $OSO_2Me$ | H | H | F |
| $OSO_2Me$ | H | H | I | $OSO_2Me$ | H | H | H |
| $OSO_2Me$ | H | H | i-Pr | $OSO_2Me$ | H | H | i-Bu |
| $OSO_2Me$ | H | H | n-Bu | $OSO_2Me$ | H | H | Me |
| $OSO_2Me$ | H | H | $NHCO_2Me$ | $OSO_2Me$ | H | H | $NH_2$ |
| $OSO_2Me$ | H | H | NHMe | $OSO_2Me$ | H | H | NHCOMe |
| $OSO_2Me$ | H | H | $NMe_2$ | $OSO_2Me$ | H | H | $NHSO_2Me$ |
| $OSO_2Me$ | H | H | n-Pr | $OSO_2Me$ | H | H | $NO_2$ |
| $OSO_2Me$ | H | H | $OCHF_2$ | $OSO_2Me$ | H | H | $OCF_3$ |
| $OSO_2Me$ | H | H | $OCO_2Me$ | $OSO_2Me$ | H | H | $OCH_2C$≡CH |

TABLE 110-continued

| X¹ | X² | X³ | X⁴ | X¹ | X² | X³ | X⁴ |
|---|---|---|---|---|---|---|---|
| OSO$_2$Me | H | H | OCOMe | OSO$_2$Me | H | H | OCO$_2$NMe$_2$ |
| OSO$_2$Me | H | H | OH | OSO$_2$Me | H | H | OEt |
| OSO$_2$Me | H | H | OPh | OSO$_2$Me | H | H | OMe |
| OSO$_2$Me | H | H | OSiMe$_3$ | OSO$_2$Me | H | H | OSiMe$_2$t-Bu |
| OSO$_2$Me | H | H | OSO$_2$Et | OSO$_2$Me | H | H | OSO$_2$Bn |
| OSO$_2$Me | H | H | OSO$_2$Me | OSO$_2$Me | H | H | OSO$_2$i-Pr |
| OSO$_2$Me | H | H | OSO$_2$n-Pr | OSO$_2$Me | H | H | OSO$_2$n-Bu |
| OSO$_2$Me | H | H | Ph | OSO$_2$Me | H | H | OSO$_2$Ph |
| OSO$_2$Me | H | H | SiMe$_3$ | OSO$_2$Me | H | H | SH |
| OSO$_2$Me | H | H | SO$_2$CF$_3$ | OSO$_2$Me | H | H | SMe |
| OSO$_2$Me | H | H | SOMe | OSO$_2$Me | H | H | SO$_2$Me |
| OSO$_2$Me | H | I | H | OSO$_2$Me | H | H | t-Bu |
| OSO$_2$Me | H | NO$_2$ | H | OSO$_2$Me | H | Me | H |
| OSO$_2$Me | H | OH | H | OSO$_2$Me | H | OCF$_3$ | H |
| OSO$_2$Me | H | OSO$_2$Bn | H | OSO$_2$Me | H | OMe | H |
| OSO$_2$Me | H | OSO$_2$i-Pr | H | OSO$_2$Me | H | OSO$_2$Et | H |
| OSO$_2$Me | H | OSO$_2$n-Bu | H | OSO$_2$Me | H | OSO$_2$Me | H |
| OSO$_2$Me | H | OSO$_2$Ph | H | OSO$_2$Me | H | OSO$_2$n-Pr | H |
| OSO$_2$Me | I | H | H | OSO$_2$Me | H | SO$_2$Me | H |
| OSO$_2$Me | —N=CH—CH=CH— | | F | OSO$_2$Me | Me | H | H |
| OSO$_2$Me | —N=CH—CH=CH— | | OSO$_2$Me | OSO$_2$Me | —N=CH—CH=CH— | | H |
| OSO$_2$Me | —N=CH—N=CH— | | H | OSO$_2$Me | —N=CH—N=CH— | | F |

TABLE 111

| X¹ | X² | X³ | X⁴ | X¹ | X² | X³ | X⁴ |
|---|---|---|---|---|---|---|---|
| OSO$_2$Me | —NH—CH=CH— | | F | OSO$_2$Me | —N=CH—N=CH— | | OSO$_2$Me |
| OSO$_2$Me | —NH—CH=CH— | | OSO$_2$Me | OSO$_2$Me | —NH—CH=CH— | | H |
| OSO$_2$Me | OCF$_3$ | H | H | OSO$_2$Me | NO$_2$ | H | H |
| OSO$_2$Me | —O—CH=CH— | | H | OSO$_2$Me | —O—CH=CH— | | F |
| OSO$_2$Me | —O—CH=N— | | F | OSO$_2$Me | —O—CH=CH— | | OSO$_2$Me |
| OSO$_2$Me | —O—CH=N— | | OSO$_2$Me | OSO$_2$Me | —O—CH=N— | | H |
| OSO$_2$Me | OMe | H | H | OSO$_2$Me | OH | H | H |
| OSO$_2$Me | OSO$_2$Et | H | H | OSO$_2$Me | OSO$_2$Bn | H | H |
| OSO$_2$Me | OSO$_2$Me | H | H | OSO$_2$Me | OSO$_2$i-Pr | H | H |
| OSO$_2$Me | OSO$_2$Me | OSO$_2$Me | H | OSO$_2$Me | OSO$_2$Me | H | OSO$_2$Me |
| OSO$_2$Me | OSO$_2$n-Bu | H | H | OSO$_2$Me | OSO$_2$Me | OSO$_2$Me | OSO$_2$Me |
| OSO$_2$Me | OSO$_2$Ph | H | H | OSO$_2$Me | OSO$_2$n-Pr | H | H |
| OSO$_2$Me | —S—CH=CH— | | H | OSO$_2$Me | —S—CH=CH— | | F |
| OSO$_2$Me | SO$_2$Me | H | H | OSO$_2$Me | —S—CH=CH— | | OSO$_2$Me |
| OSO$_2$n-Bu | H | H | Cl | OSO$_2$n-Bu | H | H | Br |
| OSO$_2$n-Bu | H | H | c-Pr | OSO$_2$n-Bu | H | H | CN |
| OSO$_2$n-Bu | H | H | F | OSO$_2$n-Bu | H | H | Et |
| OSO$_2$n-Bu | H | H | I | OSO$_2$n-Bu | H | H | H |
| OSO$_2$n-Bu | H | H | n-Bu | OSO$_2$n-Bu | H | H | Me |
| OSO$_2$n-Bu | H | H | n-Pr | OSO$_2$n-Bu | H | H | NO$_2$ |
| OSO$_2$n-Bu | H | H | OCHF$_2$ | OSO$_2$n-Bu | H | H | OCF$_3$ |
| OSO$_2$n-Bu | H | H | OEt | OSO$_2$n-Bu | H | H | Oc-Pr |
| OSO$_2$n-Bu | H | H | OMe | OSO$_2$n-Bu | H | H | OH |
| OSO$_2$n-Bu | H | H | On-Pr | OSO$_2$n-Bu | H | H | On-Bu |
| OSO$_2$n-Bu | H | H | t-Bu | OSO$_2$n-Bu | H | H | Ot-Bu |
| OSO$_2$n-Pr | H | H | Cl | OSO$_2$n-Pr | H | H | Br |
| OSO$_2$n-Pr | H | H | c-Pr | OSO$_2$n-Pr | H | H | CN |
| OSO$_2$n-Pr | H | H | F | OSO$_2$n-Pr | H | H | Et |
| OSO$_2$n-Pr | H | H | I | OSO$_2$n-Pr | H | H | H |
| OSO$_2$n-Pr | H | H | n-Bu | OSO$_2$n-Pr | H | H | Me |
| OSO$_2$n-Pr | H | H | n-Pr | OSO$_2$n-Pr | H | H | NO$_2$ |
| OSO$_2$n-Pr | H | H | OCHF$_2$ | OSO$_2$n-Pr | H | H | OCF$_3$ |
| OSO$_2$n-Pr | H | H | OEt | OSO$_2$n-Pr | H | H | Oc-Pr |
| OSO$_2$n-Pr | H | H | OMe | OSO$_2$n-Pr | H | H | OH |

TABLE 112

| X¹ | X² | X³ | X⁴ | X¹ | X² | X³ | X⁴ |
|---|---|---|---|---|---|---|---|
| OSO$_2$n-Pr | H | H | On-Pr | OSO$_2$n-Pr | H | H | On-Bu |
| OSO$_2$n-Pr | H | H | t-Bu | OSO$_2$n-Pr | H | H | Ot-Bu |
| Ph | H | H | H | OSO$_2$Ph | H | H | H |
| SiMe$_3$ | H | H | H | SH | H | H | H |
| SO$_2$CF$_3$ | H | H | H | SMe | H | H | H |
| SO$_2$Me | H | H | SO$_2$Me | SO$_2$Me | H | H | H |
| t-Bu | H | H | H | SOMe | H | H | H |

TABLE 113

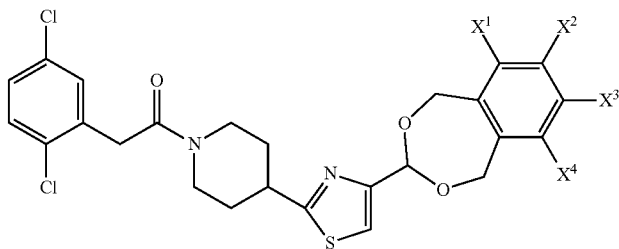

| $X^1$ | $X^2$ | $X^3$ | $X^4$ |
|---|---|---|---|
| Br | H | H | Br |
| C(=NOMe)H | H | H | H |
| C≡CH | H | H | H |
| $CF_3$ | H | H | $CF_3$ |
| CH=$CH_2$ | H | H | H |
| $CH_2NMe_2$ | H | H | H |
| $CH_2SMe$ | H | H | H |
| Cl | Cl | Cl | Cl |
| Cl | Cl | H | H |
| Cl | H | H | Cl |
| CN | H | H | CN |
| $CO_2H$ | H | H | H |
| c-Pr | H | H | H |
| F | Br | H | F |
| F | C(=NOMe)H | H | H |
| F | $CF_3$ | H | F |
| F | Cl | H | F |
| F | CN | H | F |
| F | F | F | F |
| F | F | H | H |
| F | H | C(=NOMe)H | H |
| F | H | $CF_3$ | H |
| F | H | CN | H |
| F | H | H | Bn |
| F | H | H | C(=NOMe)H |
| F | H | H | C≡CH |
| F | H | H | $CF_3$ |
| F | H | H | $CH_2CN$ |
| F | H | H | $CH_2OMe$ |
| Bn | H | H | H |
| Br | H | H | H |
| C(=NOMe)Me | H | H | H |
| $C_2F_5$ | H | H | H |
| $CF_3$ | H | H | H |
| $CH_2CN$ | H | H | H |
| $CH_2OMe$ | H | H | H |
| CHO | H | H | H |
| Cl | Cl | Cl | H |
| Cl | H | Cl | H |
| Cl | H | H | H |
| CN | H | H | H |
| $CO_2Me$ | H | H | H |
| Et | H | H | H |
| F | Br | H | H |
| F | C(=NOMe)Me | H | H |
| F | $CF_3$ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | $C_2F_5$ |
| F | H | H | CH=$CH_2$ |
| F | H | H | $CH_2NMe_2$ |

TABLE 114

| $X^1$ | $X^2$ | $X^3$ | $X^4$ |
|---|---|---|---|
| F | H | H | CHO |
| F | H | H | CN |
| F | H | H | CO$_2$Me |
| F | H | H | Et |
| F | H | H | H |
| F | H | H | i-Bu |
| F | H | H | Me |
| F | H | H | NH$_2$ |
| F | H | H | NHCOMe |
| F | H | H | NHSO$_2$Me |
| F | H | H | NO$_2$ |
| F | H | H | OCF$_3$ |
| F | H | H | OCO$_2$Me |
| F | H | H | OCOMe |
| F | H | H | OH |
| F | H | H | OPh |
| F | H | H | OSiMe$_3$ |
| F | H | H | SH |
| F | H | H | SMe |
| F | H | H | SO$_2$Me |
| F | H | H | t-Bu |
| F | H | Me | H |
| F | H | OCF$_3$ | H |
| F | H | OMe | H |
| F | H | SO$_2$Me | H |
| F | I | H | H |
| F | Me | H | H |
| F | NO$_2$ | H | H |
| F | OCF$_3$ | H | H |
| F | OH | H | H |
| F | OMe | H | H |
| F | SO$_2$Me | H | F |
| H | Br | Br | H |
| H | C(=NOMe)H | H | H |
| F | H | H | CH$_2$SMe |
| F | H | H | Cl |
| F | H | H | CO$_2$H |
| F | H | H | c-Pr |
| F | H | H | F |
| F | H | H | I |
| F | H | H | i-Pr |
| F | H | H | n-Bu |
| F | H | H | NHCO$_2$Me |
| F | H | H | NHMe |
| F | H | H | NMe$_2$ |
| F | H | H | n-Pr |
| F | H | H | OCH$_2$C≡CH |
| F | H | H | OCO$_2$NMe$_2$ |
| F | H | H | OEt |
| F | H | H | OMe |
| F | H | H | OSiMe$_2$t-Bu |
| F | H | H | Ph |
| F | H | H | SiMe$_3$ |
| F | H | H | SO$_2$CF$_3$ |
| F | H | H | SOMe |
| F | H | I | H |
| F | H | NO$_2$ | H |
| F | H | OH | H |
| F | H | OSO$_2$Me | H |
| F | I | H | F |
| F | Me | H | F |
| F | NO$_2$ | H | F |
| F | OCF$_3$ | H | F |
| F | OH | H | F |
| F | OMe | H | F |
| F | OSO$_2$Me | H | F |
| F | SO$_2$Me | H | H |
| H | Br | H | H |

TABLE 115

| $X^1$ | $X^2$ | $X^3$ | $X^4$ |
|---|---|---|---|
| H | CF$_3$ | CF$_3$ | H |
| H | —CH=CH—CH=CH— | | H |

TABLE 115-continued

| $X^1$ | $X^2$ | $X^3$ | $X^4$ |
|---|---|---|---|
| H | —CH$_2$CH$_2$CH$_2$— | | H |
| H | Cl | Cl | H |
| H | CN | H | H |
| H | F | H | H |
| H | I | H | H |
| H | Me | H | H |
| H | —N=CH—CH=CH— | | H |
| H | —NH—CH=CH— | | H |
| H | NO$_2$ | NO$_2$ | H |
| H | OCF$_3$ | OCF$_3$ | H |
| H | —O—CH=N— | | H |
| H | OH | OH | H |
| H | OMe | OMe | H |
| H | OSO$_2$Et | H | H |
| H | OSO$_2$Me | H | H |
| H | OSO$_2$n-Bu | H | H |
| H | OSO$_2$Ph | H | H |
| H | SO$_2$Me | H | H |
| I | H | H | H |
| i-Pr | H | H | H |
| Me | H | H | Me |
| NH$_2$ | H | H | H |
| NHCOMe | H | H | H |
| NHSO$_2$Me | H | H | H |
| NO$_2$ | H | H | H |
| OCF$_3$ | H | H | H |
| OCH$_2$C≡CH | H | H | H |
| OCO$_2$NMe$_2$ | H | H | H |
| OEt | H | H | H |
| OMe | H | H | H |
| OPh | H | H | H |
| OSiMe$_3$ | H | H | H |
| H | C(=NOMe)Me | H | H |
| H | CF$_3$ | H | H |
| H | —CH=N—CH=CH— | | H |
| H | —CH$_2$CH$_2$CH$_2$CH$_2$— | | H |
| H | CN | CN | H |
| H | F | F | H |
| H | H | H | H |
| H | I | I | H |
| H | Me | Me | H |
| H | —N=CH—N=CH— | | H |
| H | NO$_2$ | H | H |
| H | OCF$_3$ | H | H |
| H | —O—CH=CH— | | H |
| H | OH | H | H |
| H | OMe | H | H |
| H | OSO$_2$Bn | H | H |
| H | OSO$_2$i-Pr | H | H |
| H | OSO$_2$Me | OSO$_2$Me | H |
| H | OSO$_2$n-Pr | H | H |
| H | —S—CH=CH— | | H |
| H | SO$_2$Me | SO$_2$Me | H |
| i-Bu | H | H | H |
| Me | H | H | H |
| n-Bu | H | H | H |
| NHCO$_2$Me | H | H | H |
| NHMe | H | H | H |
| NMe$_2$ | H | H | H |
| n-Pr | H | H | H |
| OCF$_3$ | H | H | OCF$_3$ |
| OCO$_2$Me | H | H | H |
| OCOMe | H | H | H |
| OH | H | H | H |
| OMe | H | H | OMe |
| OSiMe$_2$t-Bu | H | H | H |

TABLE 116

| $X^1$ | $X^2$ | $X^3$ | $X^4$ |
|---|---|---|---|
| OSO$_2$CF$_3$ | H | H | Br |
| OSO$_2$CF$_3$ | H | H | CN |
| OSO$_2$CF$_3$ | H | H | Et |
| OSO$_2$CF$_3$ | H | H | H |

TABLE 116-continued

| X¹ | X² | X³ | X⁴ |
|---|---|---|---|
| OSO₂CF₃ | H | H | Me |
| OSO₂CF₃ | H | H | NO₂ |
| OSO₂CF₃ | H | H | OCF₃ |
| OSO₂CF₃ | H | H | Oc-Pr |
| OSO₂CF₃ | H | H | OH |
| OSO₂CF₃ | H | H | On-Bu |
| OSO₂CF₃ | H | H | Ot-Bu |
| OSO₂CHF₂ | H | H | Br |
| OSO₂CHF₂ | H | H | CN |
| OSO₂CHF₂ | H | H | Et |
| OSO₂CHF₂ | H | H | H |
| OSO₂CHF₂ | H | H | Me |
| OSO₂CHF₂ | H | H | NO₂ |
| OSO₂CHF₂ | H | H | OCF₃ |
| OSO₂CHF₂ | H | H | Oc-Pr |
| OSO₂CHF₂ | H | H | OH |
| OSO₂CHF₂ | H | H | On-Bu |
| OSO₂CHF₂ | H | H | Ot-Bu |
| OSO₂Et | H | H | Br |
| OSO₂Et | H | H | Cl |
| OSO₂Et | H | H | c-Pr |
| OSO₂Et | H | H | F |
| OSO₂Et | H | H | I |
| OSO₂Et | H | H | n-Bu |
| OSO₂Et | H | H | n-Pr |
| OSO₂Et | H | H | OCHF₂ |
| OSO₂Et | H | H | OEt |
| OSO₂Et | H | H | OMe |
| OSO₂Et | H | H | On-Pr |
| OSO₂Et | H | H | t-Bu |
| OSO₂Bn | H | H | H |
| OSO₂CF₃ | H | H | Cl |
| OSO₂CF₃ | H | H | c-Pr |
| OSO₂CF₃ | H | H | F |
| OSO₂CF₃ | H | H | I |
| OSO₂CF₃ | H | H | n-Bu |
| OSO₂CF₃ | H | H | n-Pr |
| OSO₂CF₃ | H | H | OCHF₂ |
| OSO₂CF₃ | H | H | OEt |
| OSO₂CF₃ | H | H | OMe |
| OSO₂CF₃ | H | H | On-Pr |
| OSO₂CF₃ | H | H | t-Bu |
| OSO₂CHF₂ | H | H | Cl |
| OSO₂CHF₂ | H | H | c-Pr |
| OSO₂CHF₂ | H | H | F |
| OSO₂CHF₂ | H | H | I |
| OSO₂CHF₂ | H | H | n-Bu |
| OSO₂CHF₂ | H | H | n-Pr |
| OSO₂CHF₂ | H | H | OCHF₂ |
| OSO₂CHF₂ | H | H | OEt |
| OSO₂CHF₂ | H | H | OMe |
| OSO₂CHF₂ | H | H | On-Pr |
| OSO₂CHF₂ | H | H | t-Bu |
| OSO₂Et | H | H | CF₃ |
| OSO₂Et | H | H | CN |
| OSO₂Et | H | H | Et |
| OSO₂Et | H | H | H |
| OSO₂Et | H | H | Me |
| OSO₂Et | H | H | NO₂ |
| OSO₂Et | H | H | OCF₃ |
| OSO₂Et | H | H | Oc-Pr |
| OSO₂Et | H | H | OH |
| OSO₂Et | H | H | On-Bu |
| OSO₂Et | H | H | Ot-Bu |

TABLE 117

| X¹ | X² | X³ | X⁴ |
|---|---|---|---|
| OSO₂i-Pr | H | H | CF₃ |
| OSO₂i-Pr | H | H | CN |
| OSO₂i-Pr | H | H | Et |
| OSO₂i-Pr | H | H | H |
| OSO₂i-Pr | H | H | Me |
| OSO₂i-Pr | H | H | NO₂ |
| OSO₂i-Pr | H | H | OCF₃ |
| OSO₂i-Pr | H | H | Oc-Pr |

TABLE 117-continued

| X¹ | X² | X³ | X⁴ |
|---|---|---|---|
| OSO₂i-Pr | H | H | OH |
| OSO₂i-Pr | H | H | On-Bu |
| OSO₂i-Pr | H | H | Ot-Bu |
| OSO₂Me | Br | H | H |
| OSO₂Me | C(=NOMe)Me | H | H |
| OSO₂Me | —CH=CH—CH=CH— | | F |
| OSO₂Me | —CH=CH—CH=CH— | | OSO₂Me |
| OSO₂Me | —CH=N—CH=CH— | | H |
| OSO₂Me | —CH₂CH₂CH₂— | | F |
| OSO₂Me | —CH₂CH₂CH₂— | | OSO₂Me |
| OSO₂Me | —CH₂CH₂CH₂CH₂— | | H |
| OSO₂Me | Cl | H | H |
| OSO₂Me | F | F | F |
| OSO₂Me | F | H | F |
| OSO₂Me | H | Br | H |
| OSO₂Me | H | C(=NOMe)Me | H |
| OSO₂Me | H | Cl | H |
| OSO₂Me | H | F | F |
| OSO₂Me | H | H | Bn |
| OSO₂Me | H | H | C(=NOMe)H |
| OSO₂Me | H | H | C≡CH |
| OSO₂Me | H | H | CF₃ |
| OSO₂Me | H | H | CH₂CN |
| OSO₂Me | H | H | CH₂OMe |
| OSO₂Me | H | H | CHO |
| OSO₂Me | H | H | CN |
| OSO₂i-Pr | H | H | Br |
| OSO₂i-Pr | H | H | Cl |
| OSO₂i-Pr | H | H | c-Pr |
| OSO₂i-Pr | H | H | F |
| OSO₂i-Pr | H | H | I |
| OSO₂i-Pr | H | H | n-Bu |
| OSO₂i-Pr | H | H | n-Pr |
| OSO₂i-Pr | H | H | OCHF₂ |
| OSO₂i-Pr | H | H | OEt |
| OSO₂i-Pr | H | H | OMe |
| OSO₂i-Pr | H | H | On-Pr |
| OSO₂i-Pr | H | H | t-Bu |
| OSO₂Me | C(=NOMe)H | H | H |
| OSO₂Me | CF₃ | H | H |
| OSO₂Me | —CH=CH—CH=CH— | | H |
| OSO₂Me | —CH=N—CH=CH— | | F |
| OSO₂Me | —CH=N—CH=CH— | | OSO₂Me |
| OSO₂Me | —CH₂CH₂CH₂— | | H |
| OSO₂Me | —CH₂CH₂CH₂CH₂— | | F |
| OSO₂Me | —CH₂CH₂CH₂CH₂— | | OSO₂Me |
| OSO₂Me | CN | H | H |
| OSO₂Me | F | F | OSO₂Me |
| OSO₂Me | F | H | H |
| OSO₂Me | H | C(=NOMe)H | H |
| OSO₂Me | H | CF₃ | H |
| OSO₂Me | H | CN | H |
| OSO₂Me | H | F | H |
| OSO₂Me | H | H | Br |
| OSO₂Me | H | H | C(=NOMe)Me |
| OSO₂Me | H | H | C₂F₅ |
| OSO₂Me | H | H | CH=CH₂ |
| OSO₂Me | H | H | CH₂NMe₂ |
| OSO₂Me | H | H | CH₂SMe |
| OSO₂Me | H | H | Cl |

TABLE 118

| X¹ | X² | X³ | X⁴ |
|---|---|---|---|
| OSO₂Me | H | H | CO₂Me |
| OSO₂Me | H | H | Et |
| OSO₂Me | H | H | H |
| OSO₂Me | H | H | I |
| OSO₂Me | H | H | i-Pr |
| OSO₂Me | H | H | n-Bu |
| OSO₂Me | H | H | NHCO₂Me |
| OSO₂Me | H | H | NHMe |
| OSO₂Me | H | H | NMe₂ |
| OSO₂Me | H | H | n-Pr |
| OSO₂Me | H | H | OCHF₂ |
| OSO₂Me | H | H | OCO₂Me |

TABLE 118-continued

| X¹ | X² | X³ | X⁴ |
|---|---|---|---|
| OSO₂Me | H | H | OCOMe |
| OSO₂Me | H | H | OH |
| OSO₂Me | H | H | OPh |
| OSO₂Me | H | H | OSiMe₃ |
| OSO₂Me | H | H | OSO₂Et |
| OSO₂Me | H | H | OSO₂Me |
| OSO₂Me | H | H | OSO₂n-Pr |
| OSO₂Me | H | H | Ph |
| OSO₂Me | H | H | SiMe₃ |
| OSO₂Me | H | H | SO₂CF₃ |
| OSO₂Me | H | H | SOMe |
| OSO₂Me | H | I | H |
| OSO₂Me | H | NO₂ | H |
| OSO₂Me | H | OH | H |
| OSO₂Me | H | OSO₂Bn | H |
| OSO₂Me | H | OSO₂i-Pr | H |
| OSO₂Me | H | OSO₂n-Bu | H |
| OSO₂Me | H | OSO₂Ph | H |
| OSO₂Me | I | H | H |
| OSO₂Me | —N=CH—CH=CH— | | F |
| OSO₂Me | —N=CH—CH=CH— | | OSO₂Me |
| OSO₂Me | —N=CH—N=CH— | | H |
| OSO₂Me | H | H | CO₂H |
| OSO₂Me | H | H | c-Pr |
| OSO₂Me | H | H | F |
| OSO₂Me | H | H | H |
| OSO₂Me | H | H | i-Bu |
| OSO₂Me | H | H | Me |
| OSO₂Me | H | H | NH₂ |
| OSO₂Me | H | H | NHCOMe |
| OSO₂Me | H | H | NHSO₂Me |
| OSO₂Me | H | H | NO₂ |
| OSO₂Me | H | H | OCF₃ |
| OSO₂Me | H | H | OCH₂C≡CH |
| OSO₂Me | H | H | OCO₂NMe₂ |
| OSO₂Me | H | H | OEt |
| OSO₂Me | H | H | OMe |
| OSO₂Me | H | H | OSiMe₂t-Bu |
| OSO₂Me | H | H | OSO₂Bn |
| OSO₂Me | H | H | OSO₂i-Pr |
| OSO₂Me | H | H | OSO₂n-Bu |
| OSO₂Me | H | H | OSO₂Ph |
| OSO₂Me | H | H | SH |
| OSO₂Me | H | H | SMe |
| OSO₂Me | H | H | SO₂Me |
| OSO₂Me | H | H | t-Bu |
| OSO₂Me | H | Me | H |
| OSO₂Me | H | OCF₃ | H |
| OSO₂Me | H | OMe | H |
| OSO₂Me | H | OSO₂Et | H |
| OSO₂Me | H | OSO₂Me | H |
| OSO₂Me | H | OSO₂n-Pr | H |
| OSO₂Me | H | SO₂Me | H |
| OSO₂Me | Me | H | H |
| OSO₂Me | —N=CH—CH=CH— | | H |
| OSO₂Me | —N=CH—N=CH— | | F |

TABLE 119

| X¹ | X² | X³ | X⁴ |
|---|---|---|---|
| OSO₂Me | —NH—CH=CH— | | F |
| OSO₂Me | —NH—CH=CH— | | OSO₂Me |
| OSO₂Me | OCF₃ | H | H |
| OSO₂Me | —O—CH=CH— | | H |
| OSO₂Me | —O—CH=N— | | F |
| OSO₂Me | —O—CH=N— | | OSO₂Me |
| OSO₂Me | OMe | H | H |
| OSO₂Me | OSO₂Et | H | H |
| OSO₂Me | OSO₂Me | H | H |
| OSO₂Me | OSO₂Me | OSO₂Me | H |
| OSO₂Me | OSO₂n-Bu | H | H |
| OSO₂Me | OSO₂Ph | H | H |
| OSO₂Me | —S—CH=CH— | | H |
| OSO₂Me | SO₂Me | H | H |

TABLE 119-continued

| X¹ | X² | X³ | X⁴ |
|---|---|---|---|
| OSO₂n-Bu | H | H | Cl |
| OSO₂n-Bu | H | H | c-Pr |
| OSO₂n-Bu | H | H | F |
| OSO₂n-Bu | H | H | I |
| OSO₂n-Bu | H | H | n-Bu |
| OSO₂n-Bu | H | H | n-Pr |
| OSO₂n-Bu | H | H | OCHF₂ |
| OSO₂n-Bu | H | H | OEt |
| OSO₂n-Bu | H | H | OMe |
| OSO₂n-Bu | H | H | On-Pr |
| OSO₂n-Bu | H | H | t-Bu |
| OSO₂n-Pr | H | H | Cl |
| OSO₂n-Pr | H | H | c-Pr |
| OSO₂n-Pr | H | H | F |
| OSO₂n-Pr | H | H | I |
| OSO₂n-Pr | H | H | n-Bu |
| OSO₂n-Pr | H | H | n-Pr |
| OSO₂n-Pr | H | H | OCHF₂ |
| OSO₂n-Pr | H | H | OEt |
| OSO₂n-Pr | H | H | OMe |
| OSO₂Me | —N=CH—N=CH— | | OSO₂Me |
| OSO₂Me | —NH—CH=CH— | | H |
| OSO₂Me | NO₂ | H | H |
| OSO₂Me | —O—CH=CH— | | F |
| OSO₂Me | —O—CH=CH— | | OSO₂Me |
| OSO₂Me | —O—CH=N— | | H |
| OSO₂Me | OH | H | H |
| OSO₂Me | OSO₂Bn | H | H |
| OSO₂Me | OSO₂i-Pr | H | H |
| OSO₂Me | OSO₂Me | H | OSO₂Me |
| OSO₂Me | OSO₂Me | OSO₂Me | OSO₂Me |
| OSO₂Me | OSO₂n-Pr | H | H |
| OSO₂Me | —S—CH=CH— | | F |
| OSO₂Me | —S—CH=CH— | | OSO₂Me |
| OSO₂n-Bu | H | H | Br |
| OSO₂n-Bu | H | H | CN |
| OSO₂n-Bu | H | H | Et |
| OSO₂n-Bu | H | H | H |
| OSO₂n-Bu | H | H | Me |
| OSO₂n-Bu | H | H | NO₂ |
| OSO₂n-Bu | H | H | OCF₃ |
| OSO₂n-Bu | H | H | Oc-Pr |
| OSO₂n-Bu | H | H | OH |
| OSO₂n-Bu | H | H | On-Bu |
| OSO₂n-Bu | H | H | Ot-Bu |
| OSO₂n-Pr | H | H | Br |
| OSO₂n-Pr | H | H | CN |
| OSO₂n-Pr | H | H | Et |
| OSO₂n-Pr | H | H | H |
| OSO₂n-Pr | H | H | Me |
| OSO₂n-Pr | H | H | NO₂ |
| OSO₂n-Pr | H | H | OCF₃ |
| OSO₂n-Pr | H | H | Oc-Pr |
| OSO₂n-Pr | H | H | OH |

TABLE 120

| X¹ | X² | X³ | X⁴ |
|---|---|---|---|
| OSO₂n-Pr | H | H | On-Pr |
| OSO₂n-Pr | H | H | t-Bu |
| Ph | H | H | H |
| SiMe₃ | H | H | H |
| SO₂CF₃ | H | H | H |
| SO₂Me | H | H | SO₂Me |
| t-Bu | H | H | H |
| OSO₂n-Pr | H | H | On-Bu |
| OSO₂n-Pr | H | H | Ot-Bu |
| OSO₂Ph | H | H | H |
| SH | H | H | H |
| SMe | H | H | H |
| SO₂Me | H | H | H |
| SOMe | H | H | H |

TABLE 121

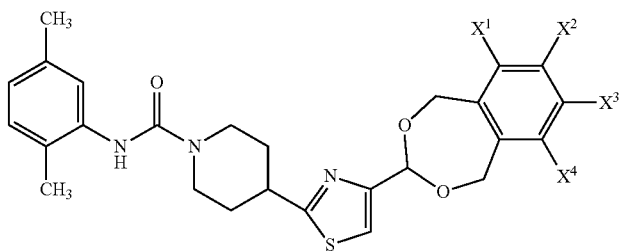

| $X^1$ | $X^2$ | $X^3$ | $X^4$ |
|---|---|---|---|
| Br | H | H | Br |
| C(=NOMe)H | H | H | H |
| C≡CH | H | H | H |
| $CF_3$ | H | H | $CF_3$ |
| CH=$CH_2$ | H | H | H |
| $CH_2NMe_2$ | H | H | H |
| $CH_2SMe$ | H | H | H |
| Cl | Cl | Cl | Cl |
| Cl | Cl | H | H |
| Cl | H | H | Cl |
| CN | H | H | CN |
| $CO_2H$ | H | H | H |
| c-Pr | H | H | H |
| F | Br | H | F |
| F | C(=NOMe)H | H | H |
| F | $CF_3$ | H | F |
| F | Cl | H | F |
| F | CN | H | F |
| F | F | F | F |
| F | F | H | H |
| F | H | C(=NOMe)H | H |
| F | H | $CF_3$ | H |
| F | H | CN | H |
| F | H | H | Bn |
| F | H | H | C(=NOMe)H |
| F | H | H | C≡CH |
| F | H | H | $CF_3$ |
| F | H | H | $CH_2CN$ |
| F | H | H | $CH_2OMe$ |
| Bn | H | H | H |
| Br | H | H | H |
| C(=NOMe)Me | H | H | H |
| $C_2F_5$ | H | H | H |
| $CF_3$ | H | H | H |
| $CH_2CN$ | H | H | H |
| $CH_2OMe$ | H | H | H |
| CHO | H | H | H |
| Cl | Cl | Cl | H |
| Cl | H | Cl | H |
| Cl | H | H | H |
| CN | H | H | H |
| $CO_2Me$ | H | H | H |
| Et | H | H | H |
| F | Br | H | H |
| F | C(=NOMe)Me | H | H |
| F | $CF_3$ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |

TABLE 121-continued

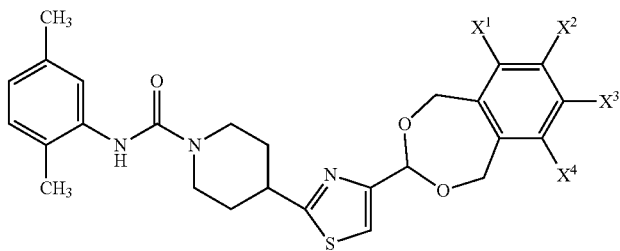

| X$^1$ | X$^2$ | X$^3$ | X$^4$ |
|---|---|---|---|
| F | H | H | C$_2$F$_5$ |
| F | H | H | CH=CH$_2$ |
| F | H | H | CH$_2$NMe$_2$ |

TABLE 122

| X$^1$ | X$^2$ | X$^3$ | X$^4$ |
|---|---|---|---|
| F | H | H | CHO |
| F | H | H | CN |
| F | H | H | CO$_2$Me |
| F | H | H | Et |
| F | H | H | H |
| F | H | H | i-Bu |
| F | H | H | Me |
| F | H | H | NH$_2$ |
| F | H | H | NHCOMe |
| F | H | H | NHSO$_2$Me |
| F | H | H | NO$_2$ |
| F | H | H | OCF$_3$ |
| F | H | H | OCO$_2$Me |
| F | H | H | OCOMe |
| F | H | H | OH |
| F | H | H | OPh |
| F | H | H | OSiMe$_3$ |
| F | H | H | SH |
| F | H | H | SMe |
| F | H | H | SO$_2$Me |
| F | H | H | t-Bu |
| F | H | Me | H |
| F | H | OCF$_3$ | H |
| F | H | OMe | H |
| F | H | SO$_2$Me | H |
| F | I | H | H |
| F | Me | H | H |
| F | NO$_2$ | H | H |
| F | OCF$_3$ | H | H |
| F | OH | H | H |
| F | OMe | H | H |
| F | SO$_2$Me | H | F |
| H | Br | Br | H |
| H | C(=NOMe)H | H | H |
| F | H | H | CH$_2$SMe |
| F | H | H | Cl |
| F | H | H | CO$_2$H |
| F | H | H | c-Pr |
| F | H | H | F |
| F | H | H | I |
| F | H | H | i-Pr |
| F | H | H | n-Bu |
| F | H | H | NHCO$_2$Me |
| F | H | H | NHMe |
| F | H | H | NMe$_2$ |
| F | H | H | n-Pr |
| F | H | H | OCH$_2$C≡CH |
| F | H | H | OCO$_2$NMe$_2$ |
| F | H | H | OEt |
| F | H | H | OMe |
| F | H | H | OSiMe$_2$t-Bu |
| F | H | H | Ph |
| F | H | H | SiMe$_3$ |
| F | H | H | SO$_2$CF$_3$ |
| F | H | H | SOMe |

TABLE 122-continued

| X$^1$ | X$^2$ | X$^3$ | X$^4$ |
|---|---|---|---|
| F | H | I | H |
| F | H | NO$_2$ | H |
| F | H | OH | H |
| F | H | OSO$_2$Me | H |
| F | I | H | F |
| F | Me | H | F |
| F | NO$_2$ | H | F |
| F | OCF$_3$ | H | F |
| F | OH | H | F |
| F | OMe | H | F |
| F | OSO$_2$Me | H | F |
| F | SO$_2$Me | H | H |
| H | Br | H | H |

TABLE 123

| X$^1$ | X$^2$ | X$^3$ | X$^4$ |
|---|---|---|---|
| H | CF$_3$ | CF$_3$ | H |
| H | —CH=CH—CH=CH— | | H |
| H | —CH$_2$CH$_2$CH$_2$— | | H |
| H | Cl | Cl | H |
| H | CN | H | H |
| H | F | H | H |
| H | I | H | H |
| H | Me | H | H |
| H | —N=CH—CH=CH— | | H |
| H | —NH—CH=CH— | | H |
| H | NO$_2$ | NO$_2$ | H |
| H | OCF$_3$ | OCF$_3$ | H |
| H | —O—CH=N— | | H |
| H | OH | OH | H |
| H | OMe | OMe | H |
| H | OSO$_2$Et | H | H |
| H | OSO$_2$Me | H | H |
| H | OSO$_2$n-Bu | H | H |
| H | OSO$_2$Ph | H | H |
| H | SO$_2$Me | H | H |
| I | H | H | H |
| i-Pr | H | H | H |
| Me | H | H | Me |
| NH$_2$ | H | H | H |
| NHCOMe | H | H | H |
| NHSO$_2$Me | H | H | H |
| NO$_2$ | H | H | H |
| OCF$_3$ | H | H | H |
| OCH$_2$C≡CH | H | H | H |
| OCO$_2$NMe$_2$ | H | H | H |
| OEt | H | H | H |
| OMe | H | H | H |
| OPh | H | H | H |
| OSiMe$_3$ | H | H | H |
| H | C(=NOMe)Me | H | H |

TABLE 123-continued

| $X^1$ | $X^2$ | $X^3$ | $X^4$ |
|---|---|---|---|
| H | $CF_3$ | H | H |
| H | —CH=N—CH=CH— | | H |
| H | —$CH_2CH_2CH_2CH_2$— | | H |
| H | CN | CN | H |
| H | F | F | H |
| H | H | H | H |
| H | I | I | H |
| H | Me | Me | H |
| H | —N=CH—N=CH— | | H |
| H | $NO_2$ | H | H |
| H | $OCF_3$ | H | H |
| H | —O—CH=CH— | | H |
| H | OH | H | H |
| H | OMe | H | H |
| H | $OSO_2Bn$ | H | H |
| H | $OSO_2$i-Pr | H | H |
| H | $OSO_2Me$ | $OSO_2Me$ | H |
| H | $OSO_2$n-Pr | H | H |
| H | —S—CH=CH— | | H |
| H | $SO_2Me$ | $SO_2Me$ | H |
| i-Bu | H | H | H |
| Me | H | H | H |
| n-Bu | H | H | H |
| $NHCO_2Me$ | H | H | H |
| NHMe | H | H | H |
| $NMe_2$ | H | H | H |
| n-Pr | H | H | H |
| $OCF_3$ | H | H | $OCF_3$ |
| $OCO_2Me$ | H | H | H |
| OCOMe | H | H | H |
| OH | H | H | H |
| OMe | H | H | OMe |
| $OSiMe_2$t-Bu | H | H | H |

TABLE 124

| $X^1$ | $X^2$ | $X^3$ | $X^4$ |
|---|---|---|---|
| $OSO_2CF_3$ | H | H | Br |
| $OSO_2CF_3$ | H | H | CN |
| $OSO_2CF_3$ | H | H | Et |
| $OSO_2CF_3$ | H | H | H |
| $OSO_2CF_3$ | H | H | Me |
| $OSO_2CF_3$ | H | H | $NO_2$ |
| $OSO_2CF_3$ | H | H | $OCF_3$ |
| $OSO_2CF_3$ | H | H | Oc-Pr |
| $OSO_2CF_3$ | H | H | OH |
| $OSO_2CF_3$ | H | H | On-Bu |
| $OSO_2CF_3$ | H | H | Ot-Bu |
| $OSO_2CHF_2$ | H | H | Br |
| $OSO_2CHF_2$ | H | H | CN |
| $OSO_2CHF_2$ | H | H | Et |
| $OSO_2CHF_2$ | H | H | H |
| $OSO_2CHF_2$ | H | H | Me |
| $OSO_2CHF_2$ | H | H | $NO_2$ |
| $OSO_2CHF_2$ | H | H | $OCF_3$ |
| $OSO_2CHF_2$ | H | H | Oc-Pr |
| $OSO_2CHF_2$ | H | H | OH |
| $OSO_2CHF_2$ | H | H | On-Bu |
| $OSO_2CHF_2$ | H | H | Ot-Bu |
| $OSO_2Et$ | H | H | Br |
| $OSO_2Et$ | H | H | Cl |
| $OSO_2Et$ | H | H | c-Pr |
| $OSO_2Et$ | H | H | F |
| $OSO_2Et$ | H | H | I |
| $OSO_2Et$ | H | H | n-Bu |
| $OSO_2Et$ | H | H | n-Pr |
| $OSO_2Et$ | H | H | $OCHF_2$ |
| $OSO_2Et$ | H | H | OEt |
| $OSO_2Et$ | H | H | OMe |
| $OSO_2Et$ | H | H | On-Pr |
| $OSO_2Et$ | H | H | t-Bu |
| $OSO_2Bn$ | H | H | H |
| $OSO_2CF_3$ | H | H | Cl |
| $OSO_2CF_3$ | H | H | c-Pr |

TABLE 124-continued

| $X^1$ | $X^2$ | $X^3$ | $X^4$ |
|---|---|---|---|
| $OSO_2CF_3$ | H | H | F |
| $OSO_2CF_3$ | H | H | I |
| $OSO_2CF_3$ | H | H | n-Bu |
| $OSO_2CF_3$ | H | H | n-Pr |
| $OSO_2CF_3$ | H | H | $OCHF_2$ |
| $OSO_2CF_3$ | H | H | OEt |
| $OSO_2CF_3$ | H | H | OMe |
| $OSO_2CF_3$ | H | H | On-Pr |
| $OSO_2CF_3$ | H | H | t-Bu |
| $OSO_2CHF_2$ | H | H | Cl |
| $OSO_2CHF_2$ | H | H | c-Pr |
| $OSO_2CHF_2$ | H | H | F |
| $OSO_2CHF_2$ | H | H | I |
| $OSO_2CHF_2$ | H | H | n-Bu |
| $OSO_2CHF_2$ | H | H | n-Pr |
| $OSO_2CHF_2$ | H | H | $OCHF_2$ |
| $OSO_2CHF_2$ | H | H | OEt |
| $OSO_2CHF_2$ | H | H | OMe |
| $OSO_2CHF_2$ | H | H | On-Pr |
| $OSO_2CHF_2$ | H | H | t-Bu |
| $OSO_2Et$ | H | H | $CF_3$ |
| $OSO_2Et$ | H | H | CN |
| $OSO_2Et$ | H | H | Et |
| $OSO_2Et$ | H | H | H |
| $OSO_2Et$ | H | H | Me |
| $OSO_2Et$ | H | H | $NO_2$ |
| $OSO_2Et$ | H | H | $OCF_3$ |
| $OSO_2Et$ | H | H | Oc-Pr |
| $OSO_2Et$ | H | H | OH |
| $OSO_2Et$ | H | H | On-Bu |
| $OSO_2Et$ | H | H | Ot-Bu |

TABLE 125

| $X^1$ | $X^2$ | $X^3$ | $X^4$ |
|---|---|---|---|
| $OSO_2$i-Pr | H | H | $CF_3$ |
| $OSO_2$i-Pr | H | H | CN |
| $OSO_2$i-Pr | H | H | Et |
| $OSO_2$i-Pr | H | H | H |
| $OSO_2$i-Pr | H | H | Me |
| $OSO_2$i-Pr | H | H | $NO_2$ |
| $OSO_2$i-Pr | H | H | $OCF_3$ |
| $OSO_2$i-Pr | H | H | Oc-Pr |
| $OSO_2$i-Pr | H | H | OH |
| $OSO_2$i-Pr | H | H | On-Bu |
| $OSO_2$i-Pr | H | H | Ot-Bu |
| $OSO_2Me$ | Br | H | H |
| $OSO_2Me$ | C(=NOMe)Me | H | H |
| $OSO_2Me$ | —CH=CH—CH=CH— | | F |
| $OSO_2Me$ | —CH=CH—CH=CH— | | $OSO_2Me$ |
| $OSO_2Me$ | —CH=N—CH=CH— | | H |
| $OSO_2Me$ | —$CH_2CH_2CH_2$— | | F |
| $OSO_2Me$ | —$CH_2CH_2CH_2$— | | $OSO_2Me$ |
| $OSO_2Me$ | —$CH_2CH_2CH_2CH_2$— | | H |
| $OSO_2Me$ | Cl | H | H |
| $OSO_2Me$ | F | F | F |
| $OSO_2Me$ | F | H | F |
| $OSO_2Me$ | H | Br | H |
| $OSO_2Me$ | H | C(=NOMe)Me | H |
| $OSO_2Me$ | H | Cl | H |
| $OSO_2Me$ | H | F | F |
| $OSO_2Me$ | H | H | Bn |
| $OSO_2Me$ | H | H | C(=NOMe)H |
| $OSO_2Me$ | H | H | C≡CH |
| $OSO_2Me$ | H | H | $CF_3$ |
| $OSO_2Me$ | H | H | $CH_2CN$ |
| $OSO_2Me$ | H | H | $CH_2OMe$ |
| $OSO_2Me$ | H | H | CHO |
| $OSO_2Me$ | H | H | CN |
| $OSO_2$i-Pr | H | H | Br |
| $OSO_2$i-Pr | H | H | Cl |
| $OSO_2$i-Pr | H | H | c-Pr |
| $OSO_2$i-Pr | H | H | F |
| $OSO_2$i-Pr | H | H | I |

TABLE 125-continued

| X¹ | X² | X³ | X⁴ |
|---|---|---|---|
| OSO$_2$i-Pr | H | H | n-Bu |
| OSO$_2$i-Pr | H | H | n-Pr |
| OSO$_2$i-Pr | H | H | OCHF$_2$ |
| OSO$_2$i-Pr | H | H | OEt |
| OSO$_2$i-Pr | H | H | OMe |
| OSO$_2$i-Pr | H | H | On-Pr |
| OSO$_2$i-Pr | H | H | t-Bu |
| OSO$_2$Me | C(=NOMe)H | H | H |
| OSO$_2$Me | CF$_3$ | H | H |
| OSO$_2$Me | —CH=CH—CH=CH— | | H |
| OSO$_2$Me | —CH=N—CH=CH— | | F |
| OSO$_2$Me | —CH=N—CH=CH— | | OSO$_2$Me |
| OSO$_2$Me | —CH$_2$CH$_2$CH$_2$— | | H |
| OSO$_2$Me | —CH$_2$CH$_2$CH$_2$CH$_2$— | | F |
| OSO$_2$Me | —CH$_2$CH$_2$CH$_2$CH$_2$— | | OSO$_2$Me |
| OSO$_2$Me | CN | H | H |
| OSO$_2$Me | F | F | OSO$_2$Me |
| OSO$_2$Me | F | H | H |
| OSO$_2$Me | H | C(=NOMe)H | H |
| OSO$_2$Me | H | CF$_3$ | H |
| OSO$_2$Me | H | CN | H |
| OSO$_2$Me | H | F | H |
| OSO$_2$Me | H | H | Br |
| OSO$_2$Me | H | H | C(=NOMe)Me |
| OSO$_2$Me | H | H | C$_2$F$_5$ |
| OSO$_2$Me | H | H | CH=CH$_2$ |
| OSO$_2$Me | H | H | CH$_2$NMe$_2$ |
| OSO$_2$Me | H | H | CH$_2$SMe |
| OSO$_2$Me | H | H | Cl |

TABLE 126

| X¹ | X² | X³ | X⁴ |
|---|---|---|---|
| OSO$_2$Me | H | H | CO$_2$Me |
| OSO$_2$Me | H | H | Et |
| OSO$_2$Me | H | H | H |
| OSO$_2$Me | H | H | I |
| OSO$_2$Me | H | H | i-Pr |
| OSO$_2$Me | H | H | n-Bu |
| OSO$_2$Me | H | H | NHCO$_2$Me |
| OSO$_2$Me | H | H | NHMe |
| OSO$_2$Me | H | H | NMe$_2$ |
| OSO$_2$Me | H | H | n-Pr |
| OSO$_2$Me | H | H | OCHF$_2$ |
| OSO$_2$Me | H | H | OCO$_2$Me |
| OSO$_2$Me | H | H | OCOMe |
| OSO$_2$Me | H | H | OH |
| OSO$_2$Me | H | H | OPh |
| OSO$_2$Me | H | H | OSiMe$_3$ |
| OSO$_2$Me | H | H | OSO$_2$Et |
| OSO$_2$Me | H | H | OSO$_2$Me |
| OSO$_2$Me | H | H | OSO$_2$n-Pr |
| OSO$_2$Me | H | H | Ph |
| OSO$_2$Me | H | H | SiMe$_3$ |
| OSO$_2$Me | H | H | SO$_2$CF$_3$ |
| OSO$_2$Me | H | H | SOMe |
| OSO$_2$Me | H | I | H |
| OSO$_2$Me | H | NO$_2$ | H |
| OSO$_2$Me | H | OH | H |
| OSO$_2$Me | H | OSO$_2$Bn | H |
| OSO$_2$Me | H | OSO$_2$i-Pr | H |
| OSO$_2$Me | H | OSO$_2$n-Bu | H |
| OSO$_2$Me | H | OSO$_2$Ph | H |
| OSO$_2$Me | I | H | H |
| OSO$_2$Me | —N=CH—CH=CH— | | F |
| OSO$_2$Me | —N=CH—CH=CH— | | OSO$_2$Me |
| OSO$_2$Me | —N=CH—N=CH— | | H |
| OSO$_2$Me | H | H | CO$_2$H |
| OSO$_2$Me | H | H | c-Pr |
| OSO$_2$Me | H | H | F |
| OSO$_2$Me | H | H | H |
| OSO$_2$Me | H | H | i-Bu |
| OSO$_2$Me | H | H | Me |
| OSO$_2$Me | H | H | NH$_2$ |

TABLE 126-continued

| X¹ | X² | X³ | X⁴ |
|---|---|---|---|
| OSO$_2$Me | H | H | NHCOMe |
| OSO$_2$Me | H | H | NHSO$_2$Me |
| OSO$_2$Me | H | H | NO$_2$ |
| OSO$_2$Me | H | H | OCF$_3$ |
| OSO$_2$Me | H | H | OCH$_2$C≡CH |
| OSO$_2$Me | H | H | OCO$_2$NMe$_2$ |
| OSO$_2$Me | H | H | OEt |
| OSO$_2$Me | H | H | OMe |
| OSO$_2$Me | H | H | OSiMe$_2$t-Bu |
| OSO$_2$Me | H | H | OSO$_2$Bn |
| OSO$_2$Me | H | H | OSO$_2$i-Pr |
| OSO$_2$Me | H | H | OSO$_2$n-Bu |
| OSO$_2$Me | H | H | OSO$_2$Ph |
| OSO$_2$Me | H | H | SH |
| OSO$_2$Me | H | H | SMe |
| OSO$_2$Me | H | H | SO$_2$Me |
| OSO$_2$Me | H | H | t-Bu |
| OSO$_2$Me | H | Me | H |
| OSO$_2$Me | H | OCF$_3$ | H |
| OSO$_2$Me | H | OMe | H |
| OSO$_2$Me | H | OSO$_2$Et | H |
| OSO$_2$Me | H | OSO$_2$Me | H |
| OSO$_2$Me | H | OSO$_2$n-Pr | H |
| OSO$_2$Me | H | SO$_2$Me | H |
| OSO$_2$Me | Me | H | H |
| OSO$_2$Me | —N=CH—CH=CH— | | H |
| OSO$_2$Me | —N=CH—N=CH— | | F |

TABLE 127

| X¹ | X² | X³ | X⁴ |
|---|---|---|---|
| OSO$_2$Me | —NH—CH=CH— | | F |
| OSO$_2$Me | —NH—CH=CH— | | OSO$_2$Me |
| OSO$_2$Me | OCF$_3$ | H | H |
| OSO$_2$Me | —O—CH=CH— | | H |
| OSO$_2$Me | —O—CH=N— | | F |
| OSO$_2$Me | —O—CH=N— | | OSO$_2$Me |
| OSO$_2$Me | OMe | H | H |
| OSO$_2$Me | OSO$_2$Et | H | H |
| OSO$_2$Me | OSO$_2$Me | H | H |
| OSO$_2$Me | OSO$_2$Me | OSO$_2$Me | H |
| OSO$_2$Me | OSO$_2$n-Bu | H | H |
| OSO$_2$Me | OSO$_2$Ph | H | H |
| OSO$_2$Me | —S—CH=CH— | | H |
| OSO$_2$Me | SO$_2$Me | H | H |
| OSO$_2$n-Bu | H | H | Cl |
| OSO$_2$n-Bu | H | H | c-Pr |
| OSO$_2$n-Bu | H | H | F |
| OSO$_2$n-Bu | H | H | I |
| OSO$_2$n-Bu | H | H | n-Bu |
| OSO$_2$n-Bu | H | H | n-Pr |
| OSO$_2$n-Bu | H | H | OCHF$_2$ |
| OSO$_2$n-Bu | H | H | OEt |
| OSO$_2$n-Bu | H | H | OMe |
| OSO$_2$n-Bu | H | H | On-Pr |
| OSO$_2$n-Bu | H | H | t-Bu |
| OSO$_2$n-Pr | H | H | Cl |
| OSO$_2$n-Pr | H | H | c-Pr |
| OSO$_2$n-Pr | H | H | F |
| OSO$_2$n-Pr | H | H | I |
| OSO$_2$n-Pr | H | H | n-Bu |
| OSO$_2$n-Pr | H | H | n-Pr |
| OSO$_2$n-Pr | H | H | OCHF$_2$ |
| OSO$_2$n-Pr | H | H | OEt |
| OSO$_2$n-Pr | H | H | OMe |
| OSO$_2$Me | —N=CH—N=CH— | | OSO$_2$Me |
| OSO$_2$Me | —NH—CH=CH— | | H |
| OSO$_2$Me | NO$_2$ | H | H |
| OSO$_2$Me | —O—CH=CH— | | F |
| OSO$_2$Me | —O—CH=CH— | | OSO$_2$Me |
| OSO$_2$Me | —O—CH=N— | | H |
| OSO$_2$Me | OH | H | H |
| OSO$_2$Me | OSO$_2$Bn | H | H |
| OSO$_2$Me | OSO$_2$i-Pr | H | H |

TABLE 127-continued

| X¹ | X² | X³ | X⁴ |
|---|---|---|---|
| OSO₂Me | OSO₂Me | H | OSO₂Me |
| OSO₂Me | OSO₂Me | OSO₂Me | OSO₂Me |
| OSO₂Me | OSO₂n-Pr | H | H |
| OSO₂Me | —S—CH=CH— | | F |
| OSO₂Me | —S—CH=CH— | | OSO₂Me |
| OSO₂n-Bu | H | H | Br |
| OSO₂n-Bu | H | H | CN |
| OSO₂n-Bu | H | H | Et |
| OSO₂n-Bu | H | H | H |
| OSO₂n-Bu | H | H | Me |
| OSO₂n-Bu | H | H | NO₂ |
| OSO₂n-Bu | H | H | OCF₃ |
| OSO₂n-Bu | H | H | Oc-Pr |
| OSO₂n-Bu | H | H | OH |
| OSO₂n-Bu | H | H | On-Bu |
| OSO₂n-Bu | H | H | Ot-Bu |
| OSO₂n-Pr | H | H | Br |
| OSO₂n-Pr | H | H | CN |
| OSO₂n-Pr | H | H | Et |
| OSO₂n-Pr | H | H | H |
| OSO₂n-Pr | H | H | Me |
| OSO₂n-Pr | H | H | NO₂ |
| OSO₂n-Pr | H | H | OCF₃ |
| OSO₂n-Pr | H | H | Oc-Pr |
| OSO₂n-Pr | H | H | OH |

TABLE 128

| X¹ | X² | X³ | X⁴ |
|---|---|---|---|
| OSO₂n-Pr | H | H | On-Pr |
| OSO₂n-Pr | H | H | t-Bu |
| Ph | H | H | H |
| SiMe₃ | H | H | H |
| SO₂CF₃ | H | H | H |
| SO₂Me | H | H | SO₂Me |
| t-Bu | H | H | H |
| OSO₂n-Pr | H | H | On-Bu |
| OSO₂n-Pr | H | H | Ot-Bu |
| OSO₂Ph | H | H | H |
| SH | H | H | H |
| SMe | H | H | H |
| SO₂Me | H | H | H |
| SOMe | H | H | H |

TABLE 129

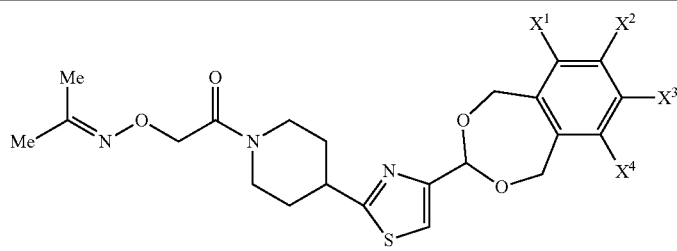

| X¹ | X² | X³ | X⁴ |
|---|---|---|---|
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | H | H |
| Cl | H | H | Cl |
| CN | H | H | CN |
| CO₂H | H | H | H |
| c-Pr | H | H | H |
| F | Br | H | F |
| F | C(=NOMe)H | H | H |
| F | CF₃ | H | F |
| F | Cl | H | F |
| F | CN | H | F |
| F | F | F | F |
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |

TABLE 129-continued

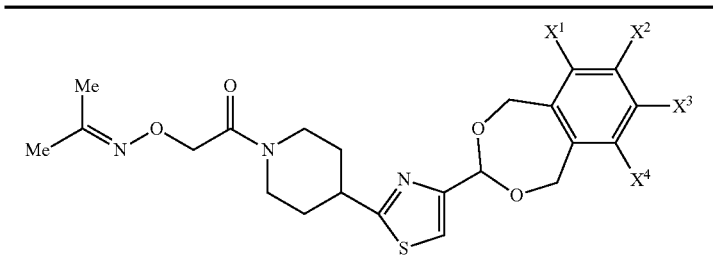

| X¹ | X² | X³ | X⁴ |
|---|---|---|---|
| CHO | H | H | H |
| Cl | Cl | Cl | H |
| Cl | H | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 130

| X¹ | X² | X³ | X⁴ | X¹ | X² | X³ | X⁴ |
|---|---|---|---|---|---|---|---|
| F | H | H | CHO | F | H | H | CH₂SMe |
| F | H | H | CN | F | H | H | Cl |
| F | H | H | CO₂Me | F | H | H | CO₂H |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | NH₂ | F | H | H | n-Bu |
| F | H | H | NHCOMe | F | H | H | NHCO₂Me |
| F | H | H | NHSO₂Me | F | H | H | NHMe |
| F | H | H | NO₂ | F | H | H | NMe₂ |
| F | H | H | OCF₃ | F | H | H | n-Pr |
| F | H | H | OCO₂Me | F | H | H | OCH₂C≡CH |
| F | H | H | OCOMe | F | H | H | OCO₂NMe₂ |
| F | H | H | OH | F | H | H | OEt |
| F | H | H | OPh | F | H | H | OMe |
| F | H | H | OSiMe₃ | F | H | H | OSiMe₂t-Bu |
| F | H | H | SH | F | H | H | Ph |
| F | H | H | SMe | F | H | H | SiMe₃ |
| F | H | H | SO₂Me | F | H | H | SO₂CF₃ |
| F | H | H | t-Bu | F | H | H | SOMe |
| F | H | Me | H | F | H | I | H |
| F | H | OCF₃ | H | F | H | NO₂ | H |
| F | H | OMe | H | F | H | OH | H |
| F | H | SO₂Me | H | F | H | OSO₂Me | H |
| F | I | H | H | F | I | H | F |
| F | Me | H | H | F | Me | H | F |
| F | NO₂ | H | H | F | NO₂ | H | F |
| F | OCF₃ | H | H | F | OCF₃ | H | F |
| F | OH | H | H | F | OH | H | F |
| F | OMe | H | H | F | OMe | H | F |
| F | SO₂Me | H | F | F | OSO₂Me | H | F |
| H | Br | Br | H | F | SO₂Me | H | H |
| H | C(=NOMe)H | H | H | H | Br | H | H |

TABLE 131

| $X^1$ | $X^2$ | $X^3$ | $X^4$ | $X^1$ | $X^2$ | $X^3$ | $X^4$ |
|---|---|---|---|---|---|---|---|
| H | CF$_3$ | CF$_3$ | H | H | C(=NOMe)Me | H | H |
| H | —CH=CH—CH=CH— | | H | H | CF$_3$ | H | H |
| H | —CH$_2$CH$_2$CH$_2$— | | H | H | —CH=N—CH=CH— | | H |
| H | Cl | Cl | H | H | —CH$_2$CH$_2$CH$_2$CH$_2$— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |
| H | —NH—CH=CH— | | H | H | —N=CH—N=CH— | | H |
| H | NO$_2$ | NO$_2$ | H | H | NO$_2$ | H | H |
| H | OCF$_3$ | OCF$_3$ | H | H | OCF$_3$ | H | H |
| H | —O—CH=N— | | H | H | —O—CH=CH— | | H |
| H | OH | OH | H | H | OH | H | H |
| H | OMe | OMe | H | H | OMe | H | H |
| H | OSO$_2$Et | H | H | H | OSO$_2$Bn | H | H |
| H | OSO$_2$Me | H | H | H | OSO$_2$i-Pr | H | H |
| H | OSO$_2$n-Bu | H | H | H | OSO$_2$Me | OSO$_2$Me | H |
| H | OSO$_2$Ph | H | H | H | OSO$_2$n-Pr | H | H |
| H | SO$_2$Me | H | H | H | —S—CH=CH— | | H |
| I | H | H | H | H | SO$_2$Me | SO$_2$Me | H |
| i-Pr | H | H | H | i-Bu | H | H | H |
| Me | H | H | Me | Me | H | H | H |
| NH$_2$ | H | H | H | n-Bu | H | H | H |
| NHCOMe | H | H | H | NHCO$_2$Me | H | H | H |
| NHSO$_2$Me | H | H | H | NHMe | H | H | H |
| NO$_2$ | H | H | H | NMe$_2$ | H | H | H |
| OCF$_3$ | H | H | H | n-Pr | H | H | H |
| OCH$_2$C≡CH | H | H | H | OCF$_3$ | H | H | OCF$_3$ |
| OCO$_2$NMe$_2$ | H | H | H | OCO$_2$Me | H | H | H |
| OEt | H | H | H | OCOMe | H | H | H |
| OMe | H | H | H | OH | H | H | H |
| OPh | H | H | H | OMe | H | H | OMe |
| OSiMe$_3$ | H | H | H | OSiMe$_2$t-Bu | H | H | H |

TABLE 132

| $X^1$ | $X^2$ | $X^3$ | $X^4$ | $X^1$ | $X^2$ | $X^3$ | $X^4$ |
|---|---|---|---|---|---|---|---|
| OSO$_2$CF$_3$ | H | H | Br | OSO$_2$Bn | H | H | H |
| OSO$_2$CF$_3$ | H | H | CN | OSO$_2$CF$_3$ | H | H | Cl |
| OSO$_2$CF$_3$ | H | H | Et | OSO$_2$CF$_3$ | H | H | c-Pr |
| OSO$_2$CF$_3$ | H | H | H | OSO$_2$CF$_3$ | H | H | F |
| OSO$_2$CF$_3$ | H | H | Me | OSO$_2$CF$_3$ | H | H | I |
| OSO$_2$CF$_3$ | H | H | NO$_2$ | OSO$_2$CF$_3$ | H | H | n-Bu |
| OSO$_2$CF$_3$ | H | H | OCF$_3$ | OSO$_2$CF$_3$ | H | H | n-Pr |
| OSO$_2$CF$_3$ | H | H | Oc-Pr | OSO$_2$CF$_3$ | H | H | OCHF$_2$ |
| OSO$_2$CF$_3$ | H | H | OH | OSO$_2$CF$_3$ | H | H | OEt |
| OSO$_2$CF$_3$ | H | H | On-Bu | OSO$_2$CF$_3$ | H | H | OMe |
| OSO$_2$CF$_3$ | H | H | Ot-Bu | OSO$_2$CF$_3$ | H | H | On-Pr |
| OSO$_2$CHF$_2$ | H | H | Br | OSO$_2$CF$_3$ | H | H | t-Bu |
| OSO$_2$CHF$_2$ | H | H | CN | OSO$_2$CHF$_2$ | H | H | Cl |
| OSO$_2$CHF$_2$ | H | H | Et | OSO$_2$CHF$_2$ | H | H | c-Pr |
| OSO$_2$CHF$_2$ | H | H | H | OSO$_2$CHF$_2$ | H | H | F |
| OSO$_2$CHF$_2$ | H | H | Me | OSO$_2$CHF$_2$ | H | H | I |
| OSO$_2$CHF$_2$ | H | H | NO$_2$ | OSO$_2$CHF$_2$ | H | H | n-Bu |
| OSO$_2$CHF$_2$ | H | H | OCF$_3$ | OSO$_2$CHF$_2$ | H | H | n-Pr |
| OSO$_2$CHF$_2$ | H | H | Oc-Pr | OSO$_2$CHF$_2$ | H | H | OCHF$_2$ |
| OSO$_2$CHF$_2$ | H | H | OH | OSO$_2$CHF$_2$ | H | H | OEt |
| OSO$_2$CHF$_2$ | H | H | On-Bu | OSO$_2$CHF$_2$ | H | H | OMe |
| OSO$_2$CHF$_2$ | H | H | Ot-Bu | OSO$_2$CHF$_2$ | H | H | On-Pr |
| OSO$_2$Et | H | H | Br | OSO$_2$CHF$_2$ | H | H | t-Bu |
| OSO$_2$Et | H | H | Cl | OSO$_2$Et | H | H | CF$_3$ |
| OSO$_2$Et | H | H | c-Pr | OSO$_2$Et | H | H | CN |
| OSO$_2$Et | H | H | F | OSO$_2$Et | H | H | Et |
| OSO$_2$Et | H | H | I | OSO$_2$Et | H | H | H |
| OSO$_2$Et | H | H | n-Bu | OSO$_2$Et | H | H | Me |
| OSO$_2$Et | H | H | n-Pr | OSO$_2$Et | H | H | NO$_2$ |
| OSO$_2$Et | H | H | OCHF$_2$ | OSO$_2$Et | H | H | OCF$_3$ |
| OSO$_2$Et | H | H | OEt | OSO$_2$Et | H | H | Oc-Pr |
| OSO$_2$Et | H | H | OMe | OSO$_2$Et | H | H | OH |
| OSO$_2$Et | H | H | On-Pr | OSO$_2$Et | H | H | On-Bu |
| OSO$_2$Et | H | H | t-Bu | OSO$_2$Et | H | H | Ot-Bu |

TABLE 133

| $X^1$ | $X^2$ | $X^3$ | $X^4$ | $X^1$ | $X^2$ | $X^3$ | $X^4$ |
|---|---|---|---|---|---|---|---|
| OSO$_2$i-Pr | H | H | CF$_3$ | OSO$_2$i-Pr | H | H | Br |
| OSO$_2$i-Pr | H | H | CN | OSO$_2$i-Pr | H | H | Cl |
| OSO$_2$i-Pr | H | H | Et | OSO$_2$i-Pr | H | H | c-Pr |
| OSO$_2$i-Pr | H | H | H | OSO$_2$i-Pr | H | H | F |
| OSO$_2$i-Pr | H | H | Me | OSO$_2$i-Pr | H | H | I |
| OSO$_2$i-Pr | H | H | NO$_2$ | OSO$_2$i-Pr | H | H | n-Bu |
| OSO$_2$i-Pr | H | H | OCF$_3$ | OSO$_2$i-Pr | H | H | n-Pr |
| OSO$_2$i-Pr | H | H | Oc-Pr | OSO$_2$i-Pr | H | H | OCHF$_2$ |
| OSO$_2$i-Pr | H | H | OH | OSO$_2$i-Pr | H | H | OEt |
| OSO$_2$i-Pr | H | H | On-Bu | OSO$_2$i-Pr | H | H | OMe |

TABLE 133-continued

| X¹ | X² | X³ | X⁴ | X¹ | X² | X³ | X⁴ |
|---|---|---|---|---|---|---|---|
| OSO$_2$i-Pr | H | H | Ot-Bu | OSO$_2$i-Pr | H | H | On-Pr |
| OSO$_2$Me | Br | H | H | OSO$_2$i-Pr | H | H | t-Bu |
| OSO$_2$Me | C(=NOMe)Me | H | H | OSO$_2$Me | C(=NOMe)H | H | H |
| OSO$_2$Me | —CH=CH—CH=CH— | | F | OSO$_2$Me | CF$_3$ | H | H |
| OSO$_2$Me | —CH=CH—CH=CH— | | OSO$_2$Me | OSO$_2$Me | —CH=CH—CH=CH— | | H |
| OSO$_2$Me | —CH=N—CH=CH— | | H | OSO$_2$Me | —CH=N—CH=CH— | | F |
| OSO$_2$Me | —CH$_2$CH$_2$CH$_2$— | | F | OSO$_2$Me | —CH=N—CH=CH— | | OSO$_2$Me |
| OSO$_2$Me | —CH$_2$CH$_2$CH$_2$— | | OSO$_2$Me | OSO$_2$Me | —CH$_2$CH$_2$CH$_2$— | | H |
| OSO$_2$Me | —CH$_2$CH$_2$CH$_2$CH$_2$— | | H | OSO$_2$Me | —CH$_2$CH$_2$CH$_2$CH$_2$— | | F |
| OSO$_2$Me | Cl | H | H | OSO$_2$Me | —CH$_2$CH$_2$CH$_2$CH$_2$— | | OSO$_2$Me |
| OSO$_2$Me | F | F | F | OSO$_2$Me | CN | H | H |
| OSO$_2$Me | F | H | F | OSO$_2$Me | F | F | OSO$_2$Me |
| OSO$_2$Me | H | Br | H | OSO$_2$Me | F | H | H |
| OSO$_2$Me | H | C(=NOMe)Me | H | OSO$_2$Me | H | C(=NOMe)H | H |
| OSO$_2$Me | H | Cl | H | OSO$_2$Me | H | CF$_3$ | H |
| OSO$_2$Me | H | F | F | OSO$_2$Me | H | CN | H |
| OSO$_2$Me | H | H | Bn | OSO$_2$Me | H | F | H |
| OSO$_2$Me | H | H | C(=NOMe)H | OSO$_2$Me | H | H | Br |
| OSO$_2$Me | H | H | C≡CH | OSO$_2$Me | H | H | C(=NOMe)Me |
| OSO$_2$Me | H | H | CF$_3$ | OSO$_2$Me | H | H | C$_2$F$_5$ |
| OSO$_2$Me | H | H | CH$_2$CN | OSO$_2$Me | H | H | CH=CH$_2$ |
| OSO$_2$Me | H | H | CH$_2$OMe | OSO$_2$Me | H | H | CH$_2$NMe$_2$ |
| OSO$_2$Me | H | H | CHO | OSO$_2$Me | H | H | CH$_2$SMe |
| OSO$_2$Me | H | H | CN | OSO$_2$Me | H | H | Cl |

TABLE 134

| X¹ | X² | X³ | X⁴ | X¹ | X² | X³ | X⁴ |
|---|---|---|---|---|---|---|---|
| OSO$_2$Me | H | H | CO$_2$Me | OSO$_2$Me | H | H | CO$_2$H |
| OSO$_2$Me | H | H | Et | OSO$_2$Me | H | H | c-Pr |
| OSO$_2$Me | H | H | H | OSO$_2$Me | H | H | F |
| OSO$_2$Me | H | H | I | OSO$_2$Me | H | H | H |
| OSO$_2$Me | H | H | i-Pr | OSO$_2$Me | H | H | i-Bu |
| OSO$_2$Me | H | H | n-Bu | OSO$_2$Me | H | H | Me |
| OSO$_2$Me | H | H | NHCO$_2$Me | OSO$_2$Me | H | H | NH$_2$ |
| OSO$_2$Me | H | H | NHMe | OSO$_2$Me | H | H | NHCOMe |
| OSO$_2$Me | H | H | NMe$_2$ | OSO$_2$Me | H | H | NHSO$_2$Me |
| OSO$_2$Me | H | H | n-Pr | OSO$_2$Me | H | H | NO$_2$ |
| OSO$_2$Me | H | H | OCHF$_2$ | OSO$_2$Me | H | H | OCF$_3$ |
| OSO$_2$Me | H | H | OCO$_2$Me | OSO$_2$Me | H | H | OCH$_2$C≡CH |
| OSO$_2$Me | H | H | OCOMe | OSO$_2$Me | H | H | OCO$_2$NMe$_2$ |
| OSO$_2$Me | H | H | OH | OSO$_2$Me | H | H | OEt |
| OSO$_2$Me | H | H | OPh | OSO$_2$Me | H | H | OMe |
| OSO$_2$Me | H | H | OSiMe$_3$ | OSO$_2$Me | H | H | OSiMe$_2$t-Bu |
| OSO$_2$Me | H | H | OSO$_2$Et | OSO$_2$Me | H | H | OSO$_2$Bn |
| OSO$_2$Me | H | H | OSO$_2$Me | OSO$_2$Me | H | H | OSO$_2$i-Pr |
| OSO$_2$Me | H | H | OSO$_2$n-Pr | OSO$_2$Me | H | H | OSO$_2$n-Bu |
| OSO$_2$Me | H | H | Ph | OSO$_2$Me | H | H | OSO$_2$Ph |
| OSO$_2$Me | H | H | SiMe$_3$ | OSO$_2$Me | H | H | SH |
| OSO$_2$Me | H | H | SO$_2$CF$_3$ | OSO$_2$Me | H | H | SMe |
| OSO$_2$Me | H | H | SOMe | OSO$_2$Me | H | H | SO$_2$Me |
| OSO$_2$Me | H | I | H | OSO$_2$Me | H | H | t-Bu |
| OSO$_2$Me | H | NO$_2$ | H | OSO$_2$Me | H | Me | H |
| OSO$_2$Me | H | OH | H | OSO$_2$Me | H | OCF$_3$ | H |
| OSO$_2$Me | H | OSO$_2$Bn | H | OSO$_2$Me | H | OMe | H |
| OSO$_2$Me | H | OSO$_2$i-Pr | H | OSO$_2$Me | H | OSO$_2$Et | H |
| OSO$_2$Me | H | OSO$_2$n-Bu | H | OSO$_2$Me | H | OSO$_2$Me | H |
| OSO$_2$Me | H | OSO$_2$Ph | H | OSO$_2$Me | H | OSO$_2$n-Pr | H |
| OSO$_2$Me | I | H | H | OSO$_2$Me | H | SO$_2$Me | H |
| OSO$_2$Me | —N=CH—CH=CH— | | F | OSO$_2$Me | Me | H | H |
| OSO$_2$Me | —N=CH—CH=CH— | | OSO$_2$Me | OSO$_2$Me | —N=CH—CH=CH— | | H |
| OSO$_2$Me | —N=CH—N=CH— | | H | OSO$_2$Me | —N=CH—N=CH— | | F |

TABLE 135

| X¹ | X² | X³ | X⁴ | X¹ | X² | X³ | X⁴ |
|---|---|---|---|---|---|---|---|
| OSO$_2$Me | —NH—CH=CH— | | F | OSO$_2$Me | —N=CH—N=CH— | | OSO$_2$Me |
| OSO$_2$Me | —NH—CH=CH— | | OSO$_2$Me | OSO$_2$Me | —NH—CH=CH— | | H |
| OSO$_2$Me | OCF$_3$ | H | H | OSO$_2$Me | NO$_2$ | H | H |
| OSO$_2$Me | —O—CH=CH— | | H | OSO$_2$Me | —O—CH=CH— | | F |
| OSO$_2$Me | —O—CH=N— | | F | OSO$_2$Me | —O—CH=CH— | | OSO$_2$Me |

TABLE 135-continued

| X¹ | X² | X³ | X⁴ | X¹ | X² | X³ | X⁴ |
|---|---|---|---|---|---|---|---|
| OSO₂Me | —O—CH=N— | | OSO₂Me | OSO₂Me | —O—CH=N— | | H |
| OSO₂Me | OMe | H | H | OSO₂Me | OH | H | H |
| OSO₂Me | OSO₂Et | H | H | OSO₂Me | OSO₂Bn | H | H |
| OSO₂Me | OSO₂Me | H | H | OSO₂Me | OSO₂i-Pr | H | H |
| OSO₂Me | OSO₂Me | OSO₂Me | H | OSO₂Me | OSO₂Me | H | OSO₂Me |
| OSO₂Me | OSO₂n-Bu | H | H | OSO₂Me | OSO₂Me | OSO₂Me | OSO₂Me |
| OSO₂Me | OSO₂Ph | H | H | OSO₂Me | OSO₂n-Pr | H | H |
| OSO₂Me | —S—CH=CH— | | H | OSO₂Me | —S—CH=CH— | | F |
| OSO₂Me | SO₂Me | H | H | OSO₂Me | —S—CH=CH— | | OSO₂Me |
| OSO₂n-Bu | H | H | Cl | OSO₂n-Bu | H | H | Br |
| OSO₂n-Bu | H | H | c-Pr | OSO₂n-Bu | H | H | CN |
| OSO₂n-Bu | H | H | F | OSO₂n-Bu | H | H | Et |
| OSO₂n-Bu | H | H | I | OSO₂n-Bu | H | H | H |
| OSO₂n-Bu | H | H | n-Bu | OSO₂n-Bu | H | H | Me |
| OSO₂n-Bu | H | H | n-Pr | OSO₂n-Bu | H | H | NO₂ |
| OSO₂n-Bu | H | H | OCHF₂ | OSO₂n-Bu | H | H | OCF₃ |
| OSO₂n-Bu | H | H | OEt | OSO₂n-Bu | H | H | Oc-Pr |
| OSO₂n-Bu | H | H | OMe | OSO₂n-Bu | H | H | OH |
| OSO₂n-Bu | H | H | On-Pr | OSO₂n-Bu | H | H | On-Bu |
| OSO₂n-Bu | H | H | t-Bu | OSO₂n-Bu | H | H | Ot-Bu |
| OSO₂n-Pr | H | H | Cl | OSO₂n-Pr | H | H | Br |
| OSO₂n-Pr | H | H | c-Pr | OSO₂n-Pr | H | H | CN |
| OSO₂n-Pr | H | H | F | OSO₂n-Pr | H | H | Et |
| OSO₂n-Pr | H | H | I | OSO₂n-Pr | H | H | H |
| OSO₂n-Pr | H | H | n-Bu | OSO₂n-Pr | H | H | Me |
| OSO₂n-Pr | H | H | n-Pr | OSO₂n-Pr | H | H | NO₂ |
| OSO₂n-Pr | H | H | OCHF₂ | OSO₂n-Pr | H | H | OCF₃ |
| OSO₂n-Pr | H | H | OEt | OSO₂n-Pr | H | H | Oc-Pr |
| OSO₂n-Pr | H | H | OMe | OSO₂n-Pr | H | H | OH |

TABLE 136

| X¹ | X² | X³ | X⁴ | X¹ | X² | X³ | X⁴ | X¹ | X² | X³ | X⁴ | X¹ | X² | X³ | X⁴ |
|---|---|---|---|---|---|---|---|---|---|---|---|---|---|---|---|
| OSO₂n-Pr | H | H | On-Pr | OSO₂n-Pr | H | H | On-Bu | SO₂CF₃ | H | H | H | SMe | H | H | H |
| OSO₂n-Pr | H | H | t-Bu | OSO₂n-Pr | H | H | Ot-Bu | SO₂Me | H | H | SO₂Me | SO₂Me | H | H | H |
| Ph | H | H | H | OSO₂Ph | H | H | H | t-Bu | H | H | H | SOMe | H | H | H |
| SiMe₃ | H | H | H | SH | H | H | H | | | | | | | | |

TABLE 137

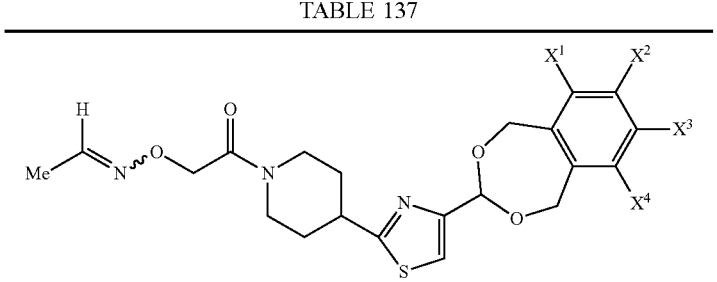

| X¹ | X² | X³ | X⁴ |
|---|---|---|---|
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | H | H |
| Cl | H | H | Cl |
| CN | H | H | CN |
| CO₂H | H | H | H |
| c-Pr | H | H | H |
| F | Br | H | F |
| F | C(=NOMe)H | H | H |
| F | CF₃ | H | F |
| F | Cl | H | F |
| F | CN | H | F |
| F | F | F | F |

TABLE 137-continued

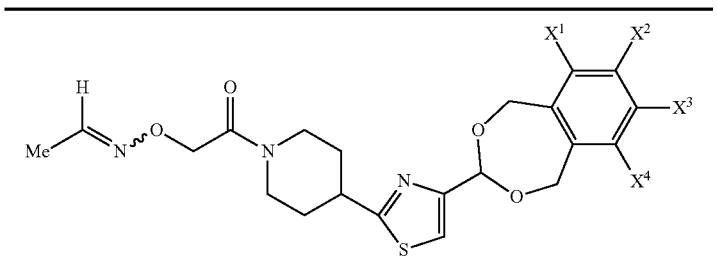

| X¹ | X² | X³ | X⁴ |
|---|---|---|---|
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |
| Cl | H | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 138

| X¹ | X² | X³ | X⁴ | X¹ | X² | X³ | X⁴ |
|---|---|---|---|---|---|---|---|
| F | H | H | CHO | F | H | H | CH₂SMe |
| F | H | H | CN | F | H | H | Cl |
| F | H | H | CO₂Me | F | H | H | CO₂H |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | NH₂ | F | H | H | n-Bu |
| F | H | H | NHCOMe | F | H | H | NHCO₂Me |
| F | H | H | NHSO₂Me | F | H | H | NHMe |
| F | H | H | NO₂ | F | H | H | NMe₂ |
| F | H | H | OCF₃ | F | H | H | n-Pr |
| F | H | H | OCO₂Me | F | H | H | OCH₂C≡CH |
| F | H | H | OCOMe | F | H | H | OCO₂NMe₂ |
| F | H | H | OH | F | H | H | OEt |
| F | H | H | OPh | F | H | H | OMe |
| F | H | H | OSiMe₃ | F | H | H | OSiMe₂t-Bu |
| F | H | H | SH | F | H | H | Ph |
| F | H | H | SMe | F | H | H | SiMe₃ |

TABLE 138-continued

| X¹ | X² | X³ | X⁴ | X¹ | X² | X³ | X⁴ |
|---|---|---|---|---|---|---|---|
| F | H | H | SO₂Me | F | H | H | SO₂CF₃ |
| F | H | H | t-Bu | F | H | H | SOMe |
| F | H | Me | H | F | H | I | H |
| F | H | OCF₃ | H | F | H | NO₂ | H |
| F | H | OMe | H | F | H | OH | H |
| F | H | SO₂Me | H | F | H | OSO₂Me | H |
| F | I | H | H | F | I | H | F |
| F | Me | H | H | F | Me | H | F |
| F | NO₂ | H | H | F | NO₂ | H | F |
| F | OCF₃ | H | H | F | OCF₃ | H | F |
| F | OH | H | H | F | OH | H | F |
| F | OMe | H | H | F | OMe | H | F |
| F | SO₂Me | H | F | F | OSO₂Me | H | F |
| H | Br | Br | H | F | SO₂Me | H | H |
| H | C(=NOMe)H | H | H | H | Br | H | H |

TABLE 139

| X¹ | X² | X³ | X⁴ | X¹ | X² | X³ | X⁴ |
|---|---|---|---|---|---|---|---|
| H | CF₃ | CF₃ | H | H | C(=NOMe)Me | H | H |
| H | —CH=CH—CH=CH— | | H | H | CF₃ | H | H |
| H | —CH₂CH₂CH₂— | | H | H | —CH=N—CH=CH— | | H |
| H | Cl | Cl | H | H | —CH₂CH₂CH₂— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |
| H | —NH—CH=CH— | | H | H | —N=CH—N=CH— | | H |
| H | NO₂ | NO₂ | H | H | NO₂ | H | H |
| H | OCF₃ | OCF₃ | H | H | OCF₃ | H | H |
| H | —O—CH=N— | | H | H | —O—CH=CH— | | H |
| H | OH | OH | H | H | OH | H | H |
| H | OMe | OMe | H | H | OMe | H | H |
| H | OSO₂Et | H | H | H | OSO₂Bn | H | H |
| H | OSO₂Me | H | H | H | OSO₂i-Pr | H | H |
| H | OSO₂n-Bu | H | H | H | OSO₂Me | OSO₂Me | H |
| H | OSO₂Ph | H | H | H | OSO₂n-Pr | H | H |
| H | SO₂Me | H | H | H | —S—CH=CH— | | H |
| I | H | H | H | H | SO₂Me | SO₂Me | H |
| i-Pr | H | H | H | i-Bu | H | H | H |
| Me | H | H | Me | Me | H | H | H |
| NH₂ | H | H | H | n-Bu | H | H | H |
| NHCOMe | H | H | H | NHCO₂Me | H | H | H |
| NHSO₂Me | H | H | H | NHMe | H | H | H |
| NO₂ | H | H | H | NMe₂ | H | H | H |
| OCF₃ | H | H | H | n-Pr | H | H | H |
| OCH₂C≡CH | H | H | H | OCF₃ | H | H | OCF₃ |
| OCO₂NMe₂ | H | H | H | OCO₂Me | H | H | H |
| OEt | H | H | H | OCOMe | H | H | H |
| OMe | H | H | H | OH | H | H | H |
| OPh | H | H | H | OMe | H | H | OMe |
| OSiMe₃ | H | H | H | OSiMe₂t-Bu | H | H | H |

TABLE 140

| X¹ | X² | X³ | X⁴ | X¹ | X² | X³ | X⁴ | X¹ | X² | X³ | X⁴ | X¹ | X² | X³ | X⁴ |
|---|---|---|---|---|---|---|---|---|---|---|---|---|---|---|---|
| OSO₂CF₃ | H | H | Br | OSO₂Bn | H | H | H | OSO₂CHF₂ | H | H | CN | OSO₂CHF₂ | H | H | Cl |
| OSO₂CF₃ | H | H | CN | OSO₂CF₃ | H | H | Cl | OSO₂CHF₂ | H | H | Et | OSO₂CHF₂ | H | H | c-Pr |
| OSO₂CF₃ | H | H | Et | OSO₂CF₃ | H | H | c-Pr | OSO₂CHF₂ | H | H | H | OSO₂CHF₂ | H | H | F |
| OSO₂CF₃ | H | H | H | OSO₂CF₃ | H | H | F | OSO₂CHF₂ | H | H | Me | OSO₂CHF₂ | H | H | I |
| OSO₂CF₃ | H | H | Me | OSO₂CF₃ | H | H | I | OSO₂CHF₂ | H | H | NO₂ | OSO₂CHF₂ | H | H | n-Bu |
| OSO₂CF₃ | H | H | NO₂ | OSO₂CF₃ | H | H | n-Bu | OSO₂CHF₂ | H | H | OCF₃ | OSO₂CHF₂ | H | H | n-Pr |
| OSO₂CF₃ | H | H | OCF₃ | OSO₂CF₃ | H | H | n-Pr | OSO₂CHF₂ | H | H | Oc-Pr | OSO₂CHF₂ | H | H | OCHF₂ |
| OSO₂CF₃ | H | H | Oc-Pr | OSO₂CF₃ | H | H | OCHF₂ | OSO₂CHF₂ | H | H | OH | OSO₂CHF₂ | H | H | OEt |
| OSO₂CF₃ | H | H | OH | OSO₂CF₃ | H | H | OEt | OSO₂CHF₂ | H | H | On-Bu | OSO₂CHF₂ | H | H | OMe |
| OSO₂CF₃ | H | H | On-Bu | OSO₂CF₃ | H | H | OMe | OSO₂CHF₂ | H | H | Ot-Bu | OSO₂CHF₂ | H | H | On-Pr |
| OSO₂CF₃ | H | H | Ot-Bu | OSO₂CF₃ | H | H | On-Pr | OSO₂Et | H | H | Br | OSO₂CHF₂ | H | H | t-Bu |
| OSO₂CHF₂ | H | H | Br | OSO₂CF₃ | H | H | t-Bu | OSO₂Et | H | H | Cl | OSO₂Et | H | H | CF₃ |

TABLE 140-continued

| X¹ | X² | X³ | X⁴ | X¹ | X² | X³ | X⁴ |
|---|---|---|---|---|---|---|---|
| OSO₂Et | H | H | c-Pr | OSO₂Et | H | H | CN |
| OSO₂Et | H | H | F | OSO₂Et | H | H | Et |
| OSO₂Et | H | H | I | OSO₂Et | H | H | H |
| OSO₂Et | H | H | n-Bu | OSO₂Et | H | H | Me |
| OSO₂Et | H | H | n-Pr | OSO₂Et | H | H | NO₂ |
| OSO₂Et | H | H | OCHF₂ | OSO₂Et | H | H | OCF₃ |

TABLE 140-continued

| X¹ | X² | X³ | X⁴ | X¹ | X² | X³ | X⁴ |
|---|---|---|---|---|---|---|---|
| OSO₂Et | H | H | OEt | OSO₂Et | H | H | Oc-Pr |
| OSO₂Et | H | H | OMe | OSO₂Et | H | H | OH |
| OSO₂Et | H | H | On-Pr | OSO₂Et | H | H | On-Bu |
| OSO₂Et | H | H | t-Bu | OSO₂Et | H | H | Ot-Bu |

TABLE 141

| X¹ | X² | X³ | X⁴ | X¹ | X² | X³ | X⁴ |
|---|---|---|---|---|---|---|---|
| OSO₂i-Pr | H | H | CF₃ | OSO₂i-Pr | H | H | Br |
| OSO₂i-Pr | H | H | CN | OSO₂i-Pr | H | H | Cl |
| OSO₂i-Pr | H | H | Et | OSO₂i-Pr | H | H | c-Pr |
| OSO₂i-Pr | H | H | H | OSO₂i-Pr | H | H | F |
| OSO₂i-Pr | H | H | Me | OSO₂i-Pr | H | H | I |
| OSO₂i-Pr | H | H | NO₂ | OSO₂i-Pr | H | H | n-Bu |
| OSO₂i-Pr | H | H | OCF₃ | OSO₂i-Pr | H | H | n-Pr |
| OSO₂i-Pr | H | H | Oc-Pr | OSO₂i-Pr | H | H | OCHF₂ |
| OSO₂i-Pr | H | H | OH | OSO₂i-Pr | H | H | OEt |
| OSO₂i-Pr | H | H | On-Bu | OSO₂i-Pr | H | H | OMe |
| OSO₂i-Pr | H | H | Ot-Bu | OSO₂i-Pr | H | H | On-Pr |
| OSO₂Me | Br | H | H | OSO₂i-Pr | H | H | t-Bu |
| OSO₂Me | C(=NOMe)Me | H | H | OSO₂Me | C(=NOMe)H | H | H |
| OSO₂Me | —CH=CH—CH=CH— | | F | OSO₂Me | CF₃ | H | H |
| OSO₂Me | —CH=CH—CH=CH— | | OSO₂Me | OSO₂Me | —CH=CH—CH=CH— | | H |
| OSO₂Me | —CH=N—CH=CH— | | H | OSO₂Me | —CH=N—CH=CH— | | F |
| OSO₂Me | —CH₂CH₂CH₂— | | F | OSO₂Me | —CH=N—CH=CH— | | OSO₂Me |
| OSO₂Me | —CH₂CH₂CH₂— | | OSO₂Me | OSO₂Me | —CH₂CH₂CH₂— | | H |
| OSO₂Me | —CH₂CH₂CH₂CH₂— | | H | OSO₂Me | —CH₂CH₂CH₂CH₂— | | F |
| OSO₂Me | Cl | H | H | OSO₂Me | —CH₂CH₂CH₂CH₂— | | OSO₂Me |
| OSO₂Me | F | F | F | OSO₂Me | CN | H | H |
| OSO₂Me | F | H | F | OSO₂Me | F | F | OSO₂Me |
| OSO₂Me | H | Br | H | OSO₂Me | F | H | H |
| OSO₂Me | H | C(=NOMe)Me | H | OSO₂Me | H | C(=NOMe)H | H |
| OSO₂Me | H | Cl | H | OSO₂Me | H | CF₃ | H |
| OSO₂Me | H | F | F | OSO₂Me | H | CN | H |
| OSO₂Me | H | H | Bn | OSO₂Me | H | F | H |
| OSO₂Me | H | H | C(=NOMe)H | OSO₂Me | H | H | Br |
| OSO₂Me | H | H | C≡CH | OSO₂Me | H | H | C(=NOMe)Me |
| OSO₂Me | H | H | CF₃ | OSO₂Me | H | H | C₂F₅ |
| OSO₂Me | H | H | CH₂CN | OSO₂Me | H | H | CH=CH₂ |
| OSO₂Me | H | H | CH₂OMe | OSO₂Me | H | H | CH₂NMe₂ |
| OSO₂Me | H | H | CHO | OSO₂Me | H | H | CH₂SMe |
| OSO₂Me | H | H | CN | OSO₂Me | H | H | Cl |

TABLE 142

| X¹ | X² | X³ | X⁴ | X¹ | X² | X³ | X⁴ |
|---|---|---|---|---|---|---|---|
| OSO₂Me | H | H | CO₂Me | OSO₂Me | H | H | CO₂H |
| OSO₂Me | H | H | Et | OSO₂Me | H | H | c-Pr |
| OSO₂Me | H | H | H | OSO₂Me | H | H | F |
| OSO₂Me | H | H | I | OSO₂Me | H | H | H |
| OSO₂Me | H | H | i-Pr | OSO₂Me | H | H | i-Bu |
| OSO₂Me | H | H | n-Bu | OSO₂Me | H | H | Me |
| OSO₂Me | H | H | NHCO₂Me | OSO₂Me | H | H | NH₂ |
| OSO₂Me | H | H | NHMe | OSO₂Me | H | H | NHCOMe |
| OSO₂Me | H | H | NMe₂ | OSO₂Me | H | H | NHSO₂Me |
| OSO₂Me | H | H | n-Pr | OSO₂Me | H | H | NO₂ |
| OSO₂Me | H | H | OCHF₂ | OSO₂Me | H | H | OCF₃ |
| OSO₂Me | H | H | OCO₂Me | OSO₂Me | H | H | OCH₂C≡CH |
| OSO₂Me | H | H | OCOMe | OSO₂Me | H | H | OCO₂NMe₂ |
| OSO₂Me | H | H | OH | OSO₂Me | H | H | OEt |
| OSO₂Me | H | H | OPh | OSO₂Me | H | H | OMe |
| OSO₂Me | H | H | OSiMe₃ | OSO₂Me | H | H | OSiMe₂t-Bu |
| OSO₂Me | H | H | OSO₂Et | OSO₂Me | H | H | OSO₂Bn |
| OSO₂Me | H | H | OSO₂Me | OSO₂Me | H | H | OSO₂i-Pr |
| OSO₂Me | H | H | OSO₂n-Pr | OSO₂Me | H | H | OSO₂n-Bu |
| OSO₂Me | H | H | Ph | OSO₂Me | H | H | OSO₂Ph |

TABLE 142-continued

| X¹ | X² | X³ | X⁴ | X¹ | X² | X³ | X⁴ |
|---|---|---|---|---|---|---|---|
| OSO₂Me | H | H | SiMe₃ | OSO₂Me | H | H | SH |
| OSO₂Me | H | H | SO₂CF₃ | OSO₂Me | H | H | SMe |
| OSO₂Me | H | H | SOMe | OSO₂Me | H | H | SO₂Me |
| OSO₂Me | H | I | H | OSO₂Me | H | H | t-Bu |
| OSO₂Me | H | NO₂ | H | OSO₂Me | H | Me | H |
| OSO₂Me | H | OH | H | OSO₂Me | H | OCF₃ | H |
| OSO₂Me | H | OSO₂Bn | H | OSO₂Me | H | OMe | H |
| OSO₂Me | H | OSO₂i-Pr | H | OSO₂Me | H | OSO₂Et | H |
| OSO₂Me | H | OSO₂n-Bu | H | OSO₂Me | H | OSO₂Me | H |
| OSO₂Me | H | OSO₂Ph | H | OSO₂Me | H | OSO₂n-Pr | H |
| OSO₂Me | I | H | H | OSO₂Me | H | SO₂Me | H |
| OSO₂Me | —N=CH—CH=CH— | | F | OSO₂Me | Me | H | H |
| OSO₂Me | —N=CH—CH=CH— | | OSO₂Me | OSO₂Me | —N=CH—CH=CH— | | H |
| OSO₂Me | —N=CH—N=CH— | | H | OSO₂Me | —N=CH—N=CH— | | F |

TABLE 143

| X¹ | X² | X³ | X⁴ | X¹ | X² | X³ | X⁴ |
|---|---|---|---|---|---|---|---|
| OSO₂Me | —NH—CH=CH— | | F | OSO₂Me | —N=CH—N=CH— | | OSO₂Me |
| OSO₂Me | —NH—CH=CH— | | OSO₂Me | OSO₂Me | —NH—CH=CH— | | H |
| OSO₂Me | OCF₃ | H | H | OSO₂Me | NO₂ | H | H |
| OSO₂Me | —O—CH=CH— | | H | OSO₂Me | —O—CH=CH— | | F |
| OSO₂Me | —O—CH=N— | | F | OSO₂Me | —O—CH=CH— | | OSO₂Me |
| OSO₂Me | —O—CH=N— | | OSO₂Me | OSO₂Me | —O—CH=N— | | H |
| OSO₂Me | OMe | H | H | OSO₂Me | OH | H | H |
| OSO₂Me | OSO₂Et | H | H | OSO₂Me | OSO₂Bn | H | H |
| OSO₂Me | OSO₂Me | H | H | OSO₂Me | OSO₂i-Pr | H | H |
| OSO₂Me | OSO₂Me | OSO₂Me | H | OSO₂Me | OSO₂Me | H | OSO₂Me |
| OSO₂Me | OSO₂n-Bu | H | H | OSO₂Me | OSO₂Me | OSO₂Me | OSO₂Me |
| OSO₂Me | OSO₂Ph | H | H | OSO₂Me | OSO₂n-Pr | H | H |
| OSO₂Me | —S—CH=CH— | | H | OSO₂Me | —S—CH=CH— | | F |
| OSO₂Me | SO₂Me | H | H | OSO₂Me | —S—CH=CH— | | OSO₂Me |
| OSO₂n-Bu | H | H | Cl | OSO₂n-Bu | H | H | Br |
| OSO₂n-Bu | H | H | c-Pr | OSO₂n-Bu | H | H | CN |
| OSO₂n-Bu | H | H | F | OSO₂n-Bu | H | H | Et |
| OSO₂n-Bu | H | H | I | OSO₂n-Bu | H | H | H |
| OSO₂n-Bu | H | H | n-Bu | OSO₂n-Bu | H | H | Me |
| OSO₂n-Bu | H | H | n-Pr | OSO₂n-Bu | H | H | NO₂ |
| OSO₂n-Bu | H | H | OCHF₂ | OSO₂n-Bu | H | H | OCF₃ |
| OSO₂n-Bu | H | H | OEt | OSO₂n-Bu | H | H | Oc-Pr |
| OSO₂n-Bu | H | H | OMe | OSO₂n-Bu | H | H | OH |
| OSO₂n-Bu | H | H | On-Pr | OSO₂n-Bu | H | H | On-Bu |
| OSO₂n-Bu | H | H | t-Bu | OSO₂n-Bu | H | H | Ot-Bu |
| OSO₂n-Pr | H | H | Cl | OSO₂n-Pr | H | H | Br |
| OSO₂n-Pr | H | H | c-Pr | OSO₂n-Pr | H | H | CN |
| OSO₂n-Pr | H | H | F | OSO₂n-Pr | H | H | Et |
| OSO₂n-Pr | H | H | I | OSO₂n-Pr | H | H | H |
| OSO₂n-Pr | H | H | n-Bu | OSO₂n-Pr | H | H | Me |
| OSO₂n-Pr | H | H | n-Pr | OSO₂n-Pr | H | H | NO₂ |
| OSO₂n-Pr | H | H | OCHF₂ | OSO₂n-Pr | H | H | OCF₃ |
| OSO₂n-Pr | H | H | OEt | OSO₂n-Pr | H | H | Oc-Pr |
| OSO₂n-Pr | H | H | OMe | OSO₂n-Pr | H | H | OH |

TABLE 144

| X¹ | X² | X³ | X⁴ | X¹ | X² | X³ | X⁴ |
|---|---|---|---|---|---|---|---|
| OSO₂n-Pr | H | H | On-Pr | OSO₂n-Pr | H | H | On-Bu |
| OSO₂n-Pr | H | H | t-Bu | OSO₂n-Pr | H | H | Ot-Bu |
| Ph | H | H | H | OSO₂Ph | H | H | H |
| SiMe₃ | H | H | H | SH | H | H | H |
| SO₂CF₃ | H | H | H | SMe | H | H | H |
| SO₂Me | H | H | SO₂Me | SO₂Me | H | H | H |
| t-Bu | H | H | H | SOMe | H | H | H |

TABLE 145

| X¹ | X² | X³ | X⁴ |
|---|---|---|---|
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | H | H |
| Cl | H | H | Cl |
| CN | H | H | CN |
| CO₂H | H | H | H |
| c-Pr | H | H | H |
| F | Br | H | F |
| F | C(=NOMe)H | H | H |
| F | CF₃ | H | F |
| F | Cl | H | F |
| F | CN | H | F |
| F | F | F | F |
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |
| Cl | H | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 146

| $X^1$ | $X^2$ | $X^3$ | $X^4$ | $X^1$ | $X^2$ | $X^3$ | $X^4$ |
|---|---|---|---|---|---|---|---|
| F | H | H | CHO | F | H | H | $CH_2SMe$ |
| F | H | H | CN | F | H | H | Cl |
| F | H | H | $CO_2Me$ | F | H | H | $CO_2H$ |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | $NH_2$ | F | H | H | n-Bu |
| F | H | H | NHCOMe | F | H | H | $NHCO_2Me$ |
| F | H | H | $NHSO_2Me$ | F | H | H | NHMe |
| F | H | H | $NO_2$ | F | H | H | $NMe_2$ |
| F | H | H | $OCF_3$ | F | H | H | n-Pr |
| F | H | H | $OCO_2Me$ | F | H | H | $OCH_2C{\equiv}CH$ |
| F | H | H | OCOMe | F | H | H | $OCO_2NMe_2$ |
| F | H | H | OH | F | H | H | OEt |
| F | H | H | OPh | F | H | H | OMe |
| F | H | H | $OSiMe_3$ | F | H | H | $OSiMe_2$t-Bu |
| F | H | H | SH | F | H | H | Ph |
| F | H | H | SMe | F | H | H | $SiMe_3$ |
| F | H | H | $SO_2Me$ | F | H | H | $SO_2CF_3$ |
| F | H | H | t-Bu | F | H | H | SOMe |
| F | H | Me | H | F | H | I | H |
| F | H | $OCF_3$ | H | F | H | $NO_2$ | H |
| F | H | OMe | H | F | H | OH | H |
| F | H | $SO_2Me$ | H | F | H | $OSO_2Me$ | H |
| F | I | H | H | F | I | H | F |
| F | Me | H | H | F | Me | H | F |
| F | $NO_2$ | H | H | F | $NO_2$ | H | F |
| F | $OCF_3$ | H | H | F | $OCF_3$ | H | F |
| F | OH | H | H | F | OH | H | F |
| F | OMe | H | H | F | OMe | H | F |
| F | $SO_2Me$ | H | F | F | $OSO_2Me$ | H | F |
| H | Br | Br | H | F | $SO_2Me$ | H | H |
| H | C(=NOMe)H | H | H | H | Br | H | H |

TABLE 147

| $X^1$ | $X^2$ | $X^3$ | $X^4$ | $X^1$ | $X^2$ | $X^3$ | $X^4$ |
|---|---|---|---|---|---|---|---|
| H | $CF_3$ | $CF_3$ | H | H | C(=NOMe)Me | H | H |
| H | —CH=CH—CH=CH— | | H | H | $CF_3$ | H | H |
| H | —$CH_2CH_2CH_2$— | | H | H | —CH=N—CH=CH— | | H |
| H | Cl | Cl | H | H | —$CH_2CH_2CH_2CH_2$— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |
| H | —NH—CH=CH— | | H | H | —N=CH—N=CH— | | H |
| H | $NO_2$ | $NO_2$ | H | H | $NO_2$ | H | H |
| H | $OCF_3$ | $OCF_3$ | H | H | $OCF_3$ | H | H |
| H | —O—CH=N— | | H | H | —O—CH=CH— | | H |
| H | OH | OH | H | H | OH | H | H |
| H | OMe | OMe | H | H | OMe | H | H |
| H | $OSO_2Et$ | H | H | H | $OSO_2Bn$ | H | H |
| H | $OSO_2Me$ | H | H | H | $OSO_2$i-Pr | H | H |
| H | $OSO_2$n-Bu | H | H | H | $OSO_2Me$ | $OSO_2Me$ | H |
| H | $OSO_2Ph$ | H | H | H | $OSO_2$n-Pr | H | H |
| H | $SO_2Me$ | H | H | H | —S—CH=CH— | | H |
| I | H | H | H | H | $SO_2Me$ | $SO_2Me$ | H |
| i-Pr | H | H | H | H | i-Bu | H | H |
| Me | H | H | H | Me | Me | H | H |
| $NH_2$ | H | H | H | n-Bu | H | H | H |
| NHCOMe | H | H | H | $NHCO_2Me$ | H | H | H |
| $NHSO_2Me$ | H | H | H | NHMe | H | H | H |
| $NO_2$ | H | H | H | $NMe_2$ | H | H | H |
| $OCF_3$ | H | H | H | n-Pr | H | H | H |
| $OCH_2C{\equiv}CH$ | H | H | H | $OCF_3$ | H | H | $OCF_3$ |
| $OCO_2NMe_2$ | H | H | H | $OCO_2Me$ | H | H | H |
| OEt | H | H | H | OCOMe | H | H | H |
| OMe | H | H | H | OH | H | H | H |
| OPh | H | H | H | OMe | H | H | OMe |
| $OSiMe_3$ | H | H | H | $OSiMe_2$t-Bu | H | H | H |

TABLE 148

| $X^1$ | $X^2$ | $X^3$ | $X^4$ | $X^1$ | $X^2$ | $X^3$ | $X^4$ |
|---|---|---|---|---|---|---|---|
| OSO$_2$CF$_3$ | H | H | Br | OSO$_2$Bn | H | H | H |
| OSO$_2$CF$_3$ | H | H | CN | OSO$_2$CF$_3$ | H | H | Cl |
| OSO$_2$CF$_3$ | H | H | Et | OSO$_2$CF$_3$ | H | H | c-Pr |
| OSO$_2$CF$_3$ | H | H | H | OSO$_2$CF$_3$ | H | H | F |
| OSO$_2$CF$_3$ | H | H | Me | OSO$_2$CF$_3$ | H | H | I |
| OSO$_2$CF$_3$ | H | H | NO$_2$ | OSO$_2$CF$_3$ | H | H | n-Bu |
| OSO$_2$CF$_3$ | H | H | OCF$_3$ | OSO$_2$CF$_3$ | H | H | n-Pr |
| OSO$_2$CF$_3$ | H | H | Oc-Pr | OSO$_2$CF$_3$ | H | H | OCHF$_2$ |
| OSO$_2$CF$_3$ | H | H | OH | OSO$_2$CF$_3$ | H | H | OEt |
| OSO$_2$CF$_3$ | H | H | On-Bu | OSO$_2$CF$_3$ | H | H | OMe |
| OSO$_2$CF$_3$ | H | H | Ot-Bu | OSO$_2$CF$_3$ | H | H | On-Pr |
| OSO$_2$CHF$_2$ | H | H | Br | OSO$_2$CF$_3$ | H | H | t-Bu |
| OSO$_2$CHF$_2$ | H | H | CN | OSO$_2$CHF$_2$ | H | H | Cl |
| OSO$_2$CHF$_2$ | H | H | Et | OSO$_2$CHF$_2$ | H | H | c-Pr |
| OSO$_2$CHF$_2$ | H | H | H | OSO$_2$CHF$_2$ | H | H | F |
| OSO$_2$CHF$_2$ | H | H | Me | OSO$_2$CHF$_2$ | H | H | I |
| OSO$_2$CHF$_2$ | H | H | NO$_2$ | OSO$_2$CHF$_2$ | H | H | n-Bu |
| OSO$_2$CHF$_2$ | H | H | OCF$_3$ | OSO$_2$CHF$_2$ | H | H | n-Pr |
| OSO$_2$CHF$_2$ | H | H | Oc-Pr | OSO$_2$CHF$_2$ | H | H | OCHF$_2$ |
| OSO$_2$CHF$_2$ | H | H | OH | OSO$_2$CHF$_2$ | H | H | OEt |
| OSO$_2$CHF$_2$ | H | H | On-Bu | OSO$_2$CHF$_2$ | H | H | OMe |
| OSO$_2$CHF$_2$ | H | H | Ot-Bu | OSO$_2$CHF$_2$ | H | H | On-Pr |
| OSO$_2$Et | H | H | Br | OSO$_2$CHF$_2$ | H | H | t-Bu |
| OSO$_2$Et | H | H | Cl | OSO$_2$Et | H | H | CF$_3$ |
| OSO$_2$Et | H | H | c-Pr | OSO$_2$Et | H | H | CN |
| OSO$_2$Et | H | H | F | OSO$_2$Et | H | H | Et |
| OSO$_2$Et | H | H | I | OSO$_2$Et | H | H | H |
| OSO$_2$Et | H | H | n-Bu | OSO$_2$Et | H | H | Me |
| OSO$_2$Et | H | H | n-Pr | OSO$_2$Et | H | H | NO$_2$ |
| OSO$_2$Et | H | H | OCHF$_2$ | OSO$_2$Et | H | H | OCF$_3$ |
| OSO$_2$Et | H | H | OEt | OSO$_2$Et | H | H | Oc-Pr |
| OSO$_2$Et | H | H | OMe | OSO$_2$Et | H | H | OH |
| OSO$_2$Et | H | H | On-Pr | OSO$_2$Et | H | H | On-Bu |
| OSO$_2$Et | H | H | t-Bu | OSO$_2$Et | H | H | Ot-Bu |

TABLE 149

| $X^1$ | $X^2$ | $X^3$ | $X^4$ | $X^1$ | $X^2$ | $X^3$ | $X^4$ |
|---|---|---|---|---|---|---|---|
| OSO$_2$i-Pr | H | H | CF$_3$ | OSO$_2$i-Pr | H | H | Br |
| OSO$_2$i-Pr | H | H | CN | OSO$_2$i-Pr | H | H | Cl |
| OSO$_2$i-Pr | H | H | Et | OSO$_2$i-Pr | H | H | c-Pr |
| OSO$_2$i-Pr | H | H | H | OSO$_2$i-Pr | H | H | F |
| OSO$_2$i-Pr | H | H | Me | OSO$_2$i-Pr | H | H | I |
| OSO$_2$i-Pr | H | H | NO$_2$ | OSO$_2$i-Pr | H | H | n-Bu |
| OSO$_2$i-Pr | H | H | OCF$_3$ | OSO$_2$i-Pr | H | H | n-Pr |
| OSO$_2$i-Pr | H | H | Oc-Pr | OSO$_2$i-Pr | H | H | OCHF$_2$ |
| OSO$_2$i-Pr | H | H | OH | OSO$_2$i-Pr | H | H | OEt |
| OSO$_2$i-Pr | H | H | On-Bu | OSO$_2$i-Pr | H | H | OMe |
| OSO$_2$i-Pr | H | H | Ot-Bu | OSO$_2$i-Pr | H | H | On-Pr |
| OSO$_2$Me | Br | H | H | OSO$_2$i-Pr | H | H | t-Bu |
| OSO$_2$Me | C(=NOMe)Me | H | H | OSO$_2$Me | C(=NOMe)H | H | H |
| OSO$_2$Me | —CH=CH—CH=CH— | | F | OSO$_2$Me | CF$_3$ | H | H |
| OSO$_2$Me | —CH=CH—CH=CH— | | OSO$_2$Me | OSO$_2$Me | —CH=CH—CH=CH— | | H |
| OSO$_2$Me | —CH=N—CH=CH— | | H | OSO$_2$Me | —CH=N—CH=CH— | | F |
| OSO$_2$Me | —CH$_2$CH$_2$CH$_2$— | | F | OSO$_2$Me | —CH=N—CH=CH— | | OSO$_2$Me |
| OSO$_2$Me | —CH$_2$CH$_2$CH$_2$— | | OSO$_2$Me | OSO$_2$Me | —CH$_2$CH$_2$CH$_2$— | | H |
| OSO$_2$Me | —CH$_2$CH$_2$CH$_2$CH$_2$— | | H | OSO$_2$Me | —CH$_2$CH$_2$CH$_2$CH$_2$— | | F |
| OSO$_2$Me | Cl | H | H | OSO$_2$Me | —CH$_2$CH$_2$CH$_2$CH$_2$— | | OSO$_2$Me |
| OSO$_2$Me | F | F | F | OSO$_2$Me | CN | H | H |
| OSO$_2$Me | F | H | F | OSO$_2$Me | F | F | OSO$_2$Me |
| OSO$_2$Me | H | Br | H | OSO$_2$Me | F | H | H |
| OSO$_2$Me | H | C(=NOMe)Me | H | OSO$_2$Me | H | C(=NOMe)H | H |
| OSO$_2$Me | H | Cl | H | OSO$_2$Me | H | CF$_3$ | H |
| OSO$_2$Me | H | F | F | OSO$_2$Me | H | CN | H |
| OSO$_2$Me | H | H | Bn | OSO$_2$Me | H | F | H |
| OSO$_2$Me | H | H | C(=NOMe)H | OSO$_2$Me | H | H | Br |
| OSO$_2$Me | H | H | C≡CH | OSO$_2$Me | H | H | C(=NOMe)Me |
| OSO$_2$Me | H | H | CF$_3$ | OSO$_2$Me | H | H | C$_2$F$_5$ |
| OSO$_2$Me | H | H | CH$_2$CN | OSO$_2$Me | H | H | CH=CH$_2$ |
| OSO$_2$Me | H | H | CH$_2$OMe | OSO$_2$Me | H | H | CH$_2$NMe$_2$ |
| OSO$_2$Me | H | H | CHO | OSO$_2$Me | H | H | CH$_2$SMe |
| OSO$_2$Me | H | H | CN | OSO$_2$Me | H | H | Cl |

TABLE 150

| $X^1$ | $X^2$ | $X^3$ | $X^4$ | $X^1$ | $X^2$ | $X^3$ | $X^4$ |
|---|---|---|---|---|---|---|---|
| OSO$_2$Me | H | H | CO$_2$Me | OSO$_2$Me | H | H | CO$_2$H |
| OSO$_2$Me | H | H | Et | OSO$_2$Me | H | H | c-Pr |
| OSO$_2$Me | H | H | H | OSO$_2$Me | H | H | F |
| OSO$_2$Me | H | H | I | OSO$_2$Me | H | H | H |
| OSO$_2$Me | H | H | i-Pr | OSO$_2$Me | H | H | i-Bu |
| OSO$_2$Me | H | H | n-Bu | OSO$_2$Me | H | H | Me |
| OSO$_2$Me | H | H | NHCO$_2$Me | OSO$_2$Me | H | H | NH$_2$ |
| OSO$_2$Me | H | H | NHMe | OSO$_2$Me | H | H | NHCOMe |
| OSO$_2$Me | H | H | NMe$_2$ | OSO$_2$Me | H | H | NHSO$_2$Me |
| OSO$_2$Me | H | H | n-Pr | OSO$_2$Me | H | H | NO$_2$ |
| OSO$_2$Me | H | H | OCHF$_2$ | OSO$_2$Me | H | H | OCF$_3$ |
| OSO$_2$Me | H | H | OCO$_2$Me | OSO$_2$Me | H | H | OCH$_2$C≡CH |

TABLE 150-continued

| X¹ | X² | X³ | X⁴ | X¹ | X² | X³ | X⁴ |
|---|---|---|---|---|---|---|---|
| OSO₂Me | H | H | OCOMe | OSO₂Me | H | H | OCO₂NMe₂ |
| OSO₂Me | H | H | OH | OSO₂Me | H | H | OEt |
| OSO₂Me | H | H | OPh | OSO₂Me | H | H | OMe |
| OSO₂Me | H | H | OSiMe₃ | OSO₂Me | H | H | OSiMe₂t-Bu |
| OSO₂Me | H | H | OSO₂Et | OSO₂Me | H | H | OSO₂Bn |
| OSO₂Me | H | H | OSO₂Me | OSO₂Me | H | H | OSO₂i-Pr |
| OSO₂Me | H | H | OSO₂n-Pr | OSO₂Me | H | H | OSO₂n-Bu |
| OSO₂Me | H | H | Ph | OSO₂Me | H | H | OSO₂Ph |
| OSO₂Me | H | H | SiMe₃ | OSO₂Me | H | H | SH |
| OSO₂Me | H | H | SO₂CF₃ | OSO₂Me | H | H | SMe |
| OSO₂Me | H | H | SOMe | OSO₂Me | H | H | SO₂Me |
| OSO₂Me | H | I | H | OSO₂Me | H | H | t-Bu |
| OSO₂Me | H | NO₂ | H | OSO₂Me | H | Me | H |
| OSO₂Me | H | OH | H | OSO₂Me | H | OCF₃ | H |
| OSO₂Me | H | OSO₂Bn | H | OSO₂Me | H | OMe | H |
| OSO₂Me | H | OSO₂i-Pr | H | OSO₂Me | H | OSO₂Et | H |
| OSO₂Me | H | OSO₂n-Bu | H | OSO₂Me | H | OSO₂Me | H |
| OSO₂Me | H | OSO₂Ph | H | OSO₂Me | H | OSO₂n-Pr | H |
| OSO₂Me | I | H | H | OSO₂Me | H | SO₂Me | H |
| OSO₂Me | —N=CH—CH=CH— | | F | OSO₂Me | Me | H | H |
| OSO₂Me | —N=CH—CH=CH— | | OSO₂Me | OSO₂Me | —N=CH—CH=CH— | | H |
| OSO₂Me | —N=CH—N=CH— | | H | OSO₂Me | —N=CH—N=CH— | | F |

TABLE 151

| X¹ | X² | X³ | X⁴ | X¹ | X² | X³ | X⁴ |
|---|---|---|---|---|---|---|---|
| OSO₂Me | —NH—CH=CH— | | F | OSO₂Me | —N=CH—N=CH— | | OSO₂Me |
| OSO₂Me | —NH—CH=CH— | | OSO₂Me | OSO₂Me | —NH—CH=CH— | | H |
| OSO₂Me | OCF₃ | H | H | OSO₂Me | NO₂ | H | H |
| OSO₂Me | —O—CH=CH— | | H | OSO₂Me | —O—CH=CH— | | F |
| OSO₂Me | —O—CH=N— | | F | OSO₂Me | —O—CH=CH— | | OSO₂Me |
| OSO₂Me | —O—CH=N— | | OSO₂Me | OSO₂Me | —O—CH=N— | | H |
| OSO₂Me | OMe | H | H | OSO₂Me | OH | H | H |
| OSO₂Me | OSO₂Et | H | H | OSO₂Me | OSO₂Bn | H | H |
| OSO₂Me | OSO₂Me | H | H | OSO₂Me | OSO₂i-Pr | H | H |
| OSO₂Me | OSO₂Me | OSO₂Me | H | OSO₂Me | OSO₂Me | H | OSO₂Me |
| OSO₂Me | OSO₂n-Bu | H | H | OSO₂Me | OSO₂Me | OSO₂Me | OSO₂Me |
| OSO₂Me | OSO₂Ph | H | H | OSO₂Me | OSO₂n-Pr | H | H |
| OSO₂Me | —S—CH=CH— | | H | OSO₂Me | —S—CH=CH— | | F |
| OSO₂Me | SO₂Me | H | H | OSO₂Me | —S—CH=CH— | | OSO₂Me |
| OSO₂n-Bu | H | H | Cl | OSO₂n-Bu | H | H | Br |
| OSO₂n-Bu | H | H | c-Pr | OSO₂n-Bu | H | H | CN |
| OSO₂n-Bu | H | H | F | OSO₂n-Bu | H | H | Et |
| OSO₂n-Bu | H | H | I | OSO₂n-Bu | H | H | H |
| OSO₂n-Bu | H | H | n-Bu | OSO₂n-Bu | H | H | Me |
| OSO₂n-Bu | H | H | n-Pr | OSO₂n-Bu | H | H | NO₂ |
| OSO₂n-Bu | H | H | OCHF₂ | OSO₂n-Bu | H | H | OCF₃ |
| OSO₂n-Bu | H | H | OEt | OSO₂n-Bu | H | H | Oc-Pr |
| OSO₂n-Bu | H | H | OMe | OSO₂n-Bu | H | H | OH |
| OSO₂n-Bu | H | H | On-Pr | OSO₂n-Bu | H | H | On-Bu |
| OSO₂n-Bu | H | H | t-Bu | OSO₂n-Bu | H | H | Ot-Bu |
| OSO₂n-Pr | H | H | Cl | OSO₂n-Pr | H | H | Br |
| OSO₂n-Pr | H | H | c-Pr | OSO₂n-Pr | H | H | CN |
| OSO₂n-Pr | H | H | F | OSO₂n-Pr | H | H | Et |
| OSO₂n-Pr | H | H | I | OSO₂n-Pr | H | H | H |
| OSO₂n-Pr | H | H | n-Bu | OSO₂n-Pr | H | H | Me |
| OSO₂n-Pr | H | H | n-Pr | OSO₂n-Pr | H | H | NO₂ |
| OSO₂n-Pr | H | H | OCHF₂ | OSO₂n-Pr | H | H | OCF₃ |
| OSO₂n-Pr | H | H | OEt | OSO₂n-Pr | H | H | Oc-Pr |
| OSO₂n-Pr | H | H | OMe | OSO₂n-Pr | H | H | OH |

TABLE 152

| X¹ | X² | X³ | X⁴ | X¹ | X² | X³ | X⁴ |
|---|---|---|---|---|---|---|---|
| OSO₂n-Pr | H | H | On-Pr | OSO₂n-Pr | H | H | On-Bu |
| OSO₂n-Pr | H | H | t-Bu | OSO₂n-Pr | H | H | Ot-Bu |
| Ph | H | H | H | OSO₂Ph | H | H | H |
| SiMe₃ | H | H | H | SH | H | H | H |
| SO₂CF₃ | H | H | H | SMe | H | H | H |
| SO₂Me | H | H | H | SO₂Me | SO₂Me | H | H |
| t-Bu | H | H | H | SOMe | H | H | H |

TABLE 153

| X¹ | X² | X³ | X⁴ |
|---|---|---|---|
| Br | H | H | Br |
| C(=NOMe)H | H | H | H |
| C≡CH | H | H | H |
| CF₃ | H | H | CF₃ |
| CH=CH₂ | H | H | H |
| CH₂NMe₂ | H | H | H |
| CH₂SMe | H | H | H |
| Cl | Cl | Cl | Cl |
| Cl | Cl | H | H |
| Cl | H | H | Cl |
| CN | H | H | CN |
| CO₂H | H | H | H |
| c-Pr | H | H | H |
| F | Br | H | F |
| F | C(=NOMe)H | H | H |
| F | CF₃ | H | F |
| F | Cl | H | F |
| F | CN | H | F |
| F | F | F | F |
| F | F | H | H |
| F | H | C(=NOMe)H | H |
| F | H | CF₃ | H |
| F | H | CN | H |
| F | H | H | Bn |
| F | H | H | C(=NOMe)H |
| F | H | H | C≡CH |
| F | H | H | CF₃ |
| F | H | H | CH₂CN |
| F | H | H | CH₂OMe |
| Bn | H | H | H |
| Br | H | H | H |
| C(=NOMe)Me | H | H | H |
| C₂F₅ | H | H | H |
| CF₃ | H | H | H |
| CH₂CN | H | H | H |
| CH₂OMe | H | H | H |
| CHO | H | H | H |
| Cl | Cl | Cl | H |
| Cl | H | Cl | H |
| Cl | H | H | H |
| CN | H | H | H |
| CO₂Me | H | H | H |
| Et | H | H | H |
| F | Br | H | H |
| F | C(=NOMe)Me | H | H |
| F | CF₃ | H | H |
| F | Cl | H | H |
| F | CN | H | H |
| F | F | F | H |
| F | H | Br | H |
| F | H | C(=NOMe)Me | H |
| F | H | Cl | H |
| F | H | F | H |
| F | H | H | Br |
| F | H | H | C(=NOMe)Me |
| F | H | H | C₂F₅ |
| F | H | H | CH=CH₂ |
| F | H | H | CH₂NMe₂ |

TABLE 154

| $X^1$ | $X^2$ | $X^3$ | $X^4$ | $X^1$ | $X^2$ | $X^3$ | $X^4$ |
|---|---|---|---|---|---|---|---|
| F | H | H | CHO | F | H | H | $CH_2SMe$ |
| F | H | H | CN | F | H | H | Cl |
| F | H | H | $CO_2Me$ | F | H | H | $CO_2H$ |
| F | H | H | Et | F | H | H | c-Pr |
| F | H | H | H | F | H | H | F |
| F | H | H | i-Bu | F | H | H | I |
| F | H | H | Me | F | H | H | i-Pr |
| F | H | H | $NH_2$ | F | H | H | n-Bu |
| F | H | H | NHCOMe | F | H | H | $NHCO_2Me$ |
| F | H | H | $NHSO_2Me$ | F | H | H | NHMe |
| F | H | H | $NO_2$ | F | H | H | $NMe_2$ |
| F | H | H | $OCF_3$ | F | H | H | n-Pr |
| F | H | H | $OCO_2Me$ | F | H | H | $OCH_2C\equiv CH$ |
| F | H | H | OCOMe | F | H | H | $OCO_2NMe_2$ |
| F | H | H | OH | F | H | H | OEt |
| F | H | H | OPh | F | H | H | OMe |
| F | H | H | $OSiMe_3$ | F | H | H | $OSiMe_2$t-Bu |
| F | H | H | SH | F | H | H | Ph |
| F | H | H | SMe | F | H | H | $SiMe_3$ |
| F | H | H | $SO_2Me$ | F | H | H | $SO_2CF_3$ |
| F | H | H | t-Bu | F | H | H | SOMe |
| F | H | Me | H | F | H | I | H |
| F | H | $OCF_3$ | H | F | H | $NO_2$ | H |
| F | H | OMe | H | F | H | OH | H |
| F | H | $SO_2Me$ | H | F | H | $OSO_2Me$ | H |
| F | I | H | H | F | I | H | F |
| F | Me | H | H | F | Me | H | F |
| F | $NO_2$ | H | H | F | $NO_2$ | H | F |
| F | $OCF_3$ | H | H | F | $OCF_3$ | H | F |
| F | OH | H | H | F | OH | H | F |
| F | OMe | H | H | F | OMe | H | F |
| F | $SO_2Me$ | H | F | F | $OSO_2Me$ | H | F |
| H | Br | Br | H | F | $SO_2Me$ | H | H |
| H | C(=NOMe)H | H | H | H | Br | H | H |

TABLE 155

| $X^1$ | $X^2$ | $X^3$ | $X^4$ | $X^1$ | $X^2$ | $X^3$ | $X^4$ |
|---|---|---|---|---|---|---|---|
| H | $CF_3$ | $CF_3$ | H | H | C(=NOMe)Me | H | H |
| H | —CH=CH—CH=CH— | | H | H | $CF_3$ | H | H |
| H | —$CH_2CH_2CH_2$— | | H | H | —CH=N—CH=CH— | | H |
| H | Cl | Cl | H | H | —$CH_2CH_2CH_2CH_2$— | | H |
| H | CN | H | H | H | CN | CN | H |
| H | F | H | H | H | F | F | H |
| H | I | H | H | H | H | H | H |
| H | Me | H | H | H | I | I | H |
| H | —N=CH—CH=CH— | | H | H | Me | Me | H |
| H | —NH—CH=CH— | | H | H | —N=CH—N=CH— | | H |
| H | $NO_2$ | $NO_2$ | H | H | $NO_2$ | H | H |
| H | $OCF_3$ | $OCF_3$ | H | H | $OCF_3$ | H | H |
| H | —O—CH=N— | | H | H | —O—CH=CH— | | H |
| H | OH | OH | H | H | OH | H | H |
| H | OMe | OMe | H | H | OMe | H | H |
| H | $OSO_2Et$ | H | H | H | $OSO_2Bn$ | H | H |
| H | $OSO_2Me$ | H | H | H | $OSO_2$i-Pr | H | H |
| H | $OSO_2$n-Bu | H | H | H | $OSO_2Me$ | $OSO_2Me$ | H |
| H | $OSO_2Ph$ | H | H | H | $OSO_2$n-Pr | H | H |
| H | $SO_2Me$ | H | H | H | —S—CH=CH— | | H |
| I | H | H | H | H | $SO_2Me$ | $SO_2Me$ | H |
| i-Pr | H | H | H | H | i-Bu | H | H |
| Me | H | H | Me | Me | H | H | H |
| $NH_2$ | H | H | H | n-Bu | H | H | H |
| NHCOMe | H | H | H | $NHCO_2Me$ | H | H | H |
| $NHSO_2Me$ | H | H | H | NHMe | H | H | H |
| $NO_2$ | H | H | H | $NMe_2$ | H | H | H |
| $OCF_3$ | H | H | H | n-Pr | H | H | H |
| $OCH_2C\equiv CH$ | H | H | H | $OCF_3$ | H | H | $OCF_3$ |
| $OCO_2NMe_2$ | H | H | H | $OCO_2Me$ | H | H | H |
| OEt | H | H | H | OCOMe | H | H | H |
| OMe | H | H | H | OH | H | H | H |
| OPh | H | H | H | OMe | H | H | OMe |
| $OSiMe_3$ | H | H | H | $OSiMe_2$t-Bu | H | H | H |

TABLE 156

| X¹ | X² | X³ | X⁴ | X¹ | X² | X³ | X⁴ |
|---|---|---|---|---|---|---|---|
| OSO₂CF₃ | H | H | Br | OSO₂Bn | H | H | H |
| OSO₂CF₃ | H | H | CN | OSO₂CF₃ | H | H | Cl |
| OSO₂CF₃ | H | H | Et | OSO₂CF₃ | H | H | c-Pr |
| OSO₂CF₃ | H | H | H | OSO₂CF₃ | H | H | F |
| OSO₂CF₃ | H | H | Me | OSO₂CF₃ | H | H | I |
| OSO₂CF₃ | H | H | NO₂ | OSO₂CF₃ | H | H | n-Bu |
| OSO₂CF₃ | H | H | OCF₃ | OSO₂CF₃ | H | H | n-Pr |
| OSO₂CF₃ | H | H | Oc-Pr | OSO₂CF₃ | H | H | OCHF₂ |
| OSO₂CF₃ | H | H | OH | OSO₂CF₃ | H | H | OEt |
| OSO₂CF₃ | H | H | On-Bu | OSO₂CF₃ | H | H | OMe |
| OSO₂CF₃ | H | H | Ot-Bu | OSO₂CF₃ | H | H | On-Pr |
| OSO₂CHF₂ | H | H | Br | OSO₂CF₃ | H | H | t-Bu |
| OSO₂CHF₂ | H | H | CN | OSO₂CHF₂ | H | H | Cl |
| OSO₂CHF₂ | H | H | Et | OSO₂CHF₂ | H | H | c-Pr |
| OSO₂CHF₂ | H | H | H | OSO₂CHF₂ | H | H | F |
| OSO₂CHF₂ | H | H | Me | OSO₂CHF₂ | H | H | I |
| OSO₂CHF₂ | H | H | NO₂ | OSO₂CHF₂ | H | H | n-Bu |
| OSO₂CHF₂ | H | H | OCF₃ | OSO₂CHF₂ | H | H | n-Pr |
| OSO₂CHF₂ | H | H | Oc-Pr | OSO₂CHF₂ | H | H | OCHF₂ |
| OSO₂CHF₂ | H | H | OH | OSO₂CHF₂ | H | H | OEt |
| OSO₂CHF₂ | H | H | On-Bu | OSO₂CHF₂ | H | H | OMe |
| OSO₂CHF₂ | H | H | Ot-Bu | OSO₂CHF₂ | H | H | On-Pr |
| OSO₂Et | H | H | Br | OSO₂CHF₂ | H | H | t-Bu |
| OSO₂Et | H | H | Cl | OSO₂Et | H | H | CF₃ |
| OSO₂Et | H | H | c-Pr | OSO₂Et | H | H | CN |
| OSO₂Et | H | H | F | OSO₂Et | H | H | Et |
| OSO₂Et | H | H | I | OSO₂Et | H | H | H |
| OSO₂Et | H | H | n-Bu | OSO₂Et | H | H | Me |
| OSO₂Et | H | H | n-Pr | OSO₂Et | H | H | NO₂ |
| OSO₂Et | H | H | OCHF₂ | OSO₂Et | H | H | OCF₃ |
| OSO₂Et | H | H | OEt | OSO₂Et | H | H | Oc-Pr |
| OSO₂Et | H | H | OMe | OSO₂Et | H | H | OH |
| OSO₂Et | H | H | On-Pr | OSO₂Et | H | H | On-Bu |
| OSO₂Et | H | H | t-Bu | OSO₂Et | H | H | Ot-Bu |

TABLE 158

| X¹ | X² | X³ | X⁴ |
|---|---|---|---|
| OSO₂Me | H | H | CO₂Me |
| OSO₂Me | H | H | Et |
| OSO₂Me | H | H | H |
| OSO₂Me | H | H | I |
| OSO₂Me | H | H | i-Pr |
| OSO₂Me | H | H | n-Bu |
| OSO₂Me | H | H | NHCO₂Me |
| OSO₂Me | H | H | NHMe |
| OSO₂Me | H | H | NMe₂ |
| OSO₂Me | H | H | n-Pr |
| OSO₂Me | H | H | OCHF₂ |
| OSO₂Me | H | H | OCO₂Me |
| OSO₂Me | H | H | OCOMe |
| OSO₂Me | H | H | OH |
| OSO₂Me | H | H | OPh |
| OSO₂Me | H | H | OSiMe₃ |
| OSO₂Me | H | H | OSO₂Et |
| OSO₂Me | H | H | OSO₂Me |
| OSO₂Me | H | H | OSO₂n-Pr |
| OSO₂Me | H | H | Ph |
| OSO₂Me | H | H | SiMe₃ |
| OSO₂Me | H | H | SO₂CF₃ |
| OSO₂Me | H | H | SOMe |
| OSO₂Me | H | I | H |
| OSO₂Me | H | NO₂ | H |
| OSO₂Me | H | OH | H |
| OSO₂Me | H | OSO₂Bn | H |
| OSO₂Me | H | OSO₂i-Pr | H |
| OSO₂Me | H | OSO₂n-Bu | H |
| OSO₂Me | H | OSO₂Ph | H |
| OSO₂Me | I | H | H |
| OSO₂Me | —N=CH—CH=CH— | | F |
| OSO₂Me | —N=CH—CH=CH— | | OSO₂Me |
| OSO₂Me | —N=CH—N=CH— | | H |
| OSO₂Me | H | H | CO₂H |

TABLE 157

| X¹ | X² | X³ | X⁴ | X¹ | X² | X³ | X⁴ |
|---|---|---|---|---|---|---|---|
| OSO₂i-Pr | H | H | CF₃ | OSO₂i-Pr | H | H | Br |
| OSO₂i-Pr | H | H | CN | OSO₂i-Pr | H | H | Cl |
| OSO₂i-Pr | H | H | Et | OSO₂i-Pr | H | H | c-Pr |
| OSO₂i-Pr | H | H | H | OSO₂i-Pr | H | H | F |
| OSO₂i-Pr | H | H | Me | OSO₂i-Pr | H | H | I |
| OSO₂i-Pr | H | H | NO₂ | OSO₂i-Pr | H | H | n-Bu |
| OSO₂i-Pr | H | H | OCF₃ | OSO₂i-Pr | H | H | n-Pr |
| OSO₂i-Pr | H | H | Oc-Pr | OSO₂i-Pr | H | H | OCHF₂ |
| OSO₂i-Pr | H | H | OH | OSO₂i-Pr | H | H | OEt |
| OSO₂i-Pr | H | H | On-Bu | OSO₂i-Pr | H | H | OMe |
| OSO₂i-Pr | H | H | Ot-Bu | OSO₂i-Pr | H | H | On-Pr |
| OSO₂Me | Br | H | H | OSO₂i-Pr | H | H | t-Bu |
| OSO₂Me | C(=NOMe)Me | H | H | OSO₂Me | C(=NOMe)H | H | H |
| OSO₂Me | —CH=CH—CH=CH— | | F | OSO₂Me | CF₃ | H | H |
| OSO₂Me | —CH=CH—CH=CH— | | OSO₂Me | OSO₂Me | —CH=CH—CH=CH— | | H |
| OSO₂Me | —CH=N—CH=CH— | | H | OSO₂Me | —CH=N—CH=CH— | | F |
| OSO₂Me | —CH₂CH₂CH₂— | | F | OSO₂Me | —CH=N—CH=CH— | | OSO₂Me |
| OSO₂Me | —CH₂CH₂CH₂— | | OSO₂Me | OSO₂Me | —CH₂CH₂CH₂— | | H |
| OSO₂Me | —CH₂CH₂CH₂CH₂— | | H | OSO₂Me | —CH₂CH₂CH₂CH₂— | | F |
| OSO₂Me | Cl | H | H | OSO₂Me | —CH₂CH₂CH₂CH₂— | | OSO₂Me |
| OSO₂Me | F | F | F | OSO₂Me | CN | H | H |
| OSO₂Me | F | H | F | OSO₂Me | F | F | OSO₂Me |
| OSO₂Me | H | Br | H | OSO₂Me | F | H | H |
| OSO₂Me | H | C(=NOMe)Me | H | OSO₂Me | H | C(=NOMe)H | H |
| OSO₂Me | H | Cl | H | OSO₂Me | H | CF₃ | H |
| OSO₂Me | H | F | F | OSO₂Me | H | CN | H |
| OSO₂Me | H | H | Bn | OSO₂Me | H | F | H |
| OSO₂Me | H | H | C(=NOMe)H | OSO₂Me | H | H | Br |
| OSO₂Me | H | H | C≡CH | OSO₂Me | H | H | C(=NOMe)Me |
| OSO₂Me | H | H | CF₃ | OSO₂Me | H | H | C₂F₅ |
| OSO₂Me | H | H | CH₂CN | OSO₂Me | H | H | CH=CH₂ |
| OSO₂Me | H | H | CH₂OMe | OSO₂Me | H | H | CH₂NMe₂ |
| OSO₂Me | H | H | CHO | OSO₂Me | H | H | CH₂SMe |
| OSO₂Me | H | H | CN | OSO₂Me | H | H | Cl |

TABLE 158-continued

| $X^1$ | $X^2$ | $X^3$ | $X^4$ |
|---|---|---|---|
| OSO$_2$Me | H | H | c-Pr |
| OSO$_2$Me | H | H | F |
| OSO$_2$Me | H | H | H |
| OSO$_2$Me | H | H | i-Bu |
| OSO$_2$Me | H | H | Me |
| OSO$_2$Me | H | H | NH$_2$ |
| OSO$_2$Me | H | H | NHCOMe |
| OSO$_2$Me | H | H | NHSO$_2$Me |
| OSO$_2$Me | H | H | NO$_2$ |
| OSO$_2$Me | H | H | OCF$_3$ |
| OSO$_2$Me | H | H | OCH$_2$C≡CH |
| OSO$_2$Me | H | H | OCO$_2$NMe$_2$ |
| OSO$_2$Me | H | H | OEt |
| OSO$_2$Me | H | H | OMe |
| OSO$_2$Me | H | H | OSiMe$_2$t-Bu |
| OSO$_2$Me | H | H | OSO$_2$Bn |
| OSO$_2$Me | H | H | OSO$_2$i-Pr |
| OSO$_2$Me | H | H | OSO$_2$n-Bu |
| OSO$_2$Me | H | H | OSO$_2$Ph |
| OSO$_2$Me | H | H | SH |
| OSO$_2$Me | H | H | SMe |
| OSO$_2$Me | H | H | SO$_2$Me |
| OSO$_2$Me | H | H | t-Bu |
| OSO$_2$Me | H | Me | H |
| OSO$_2$Me | H | OCF$_3$ | H |
| OSO$_2$Me | H | OMe | H |
| OSO$_2$Me | H | OSO$_2$Et | H |
| OSO$_2$Me | H | OSO$_2$Me | H |
| OSO$_2$Me | H | OSO$_2$n-Pr | H |
| OSO$_2$Me | H | SO$_2$Me | H |
| OSO$_2$Me | Me | H | H |
| OSO$_2$Me | —N=CH—CH=CH— | | H |
| OSO$_2$Me | —N=CH—N=CH— | | F |

TABLE 159

| $X^1$ | $X^2$ | $X^3$ | $X^4$ | $X^1$ | $X^2$ | $X^3$ | $X^4$ |
|---|---|---|---|---|---|---|---|
| OSO$_2$Me | —NH—CH=CH— | | F | OSO$_2$Me | —N=CH—N=CH— | | OSO$_2$Me |
| OSO$_2$Me | —NH—CH=CH— | | OSO$_2$Me | OSO$_2$Me | —NH—CH=CH— | | H |
| OSO$_2$Me | OCF$_3$ | H | H | OSO$_2$Me | NO$_2$ | H | H |
| OSO$_2$Me | —O—CH=CH— | | H | OSO$_2$Me | —O—CH=CH— | | F |
| OSO$_2$Me | —O—CH=N— | | F | OSO$_2$Me | —O—CH=CH— | | OSO$_2$Me |
| OSO$_2$Me | —O—CH=N— | | OSO$_2$Me | OSO$_2$Me | —O—CH=N— | | H |
| OSO$_2$Me | OMe | H | H | OSO$_2$Me | OH | H | H |
| OSO$_2$Me | OSO$_2$Et | H | H | OSO$_2$Me | OSO$_2$Bn | H | H |
| OSO$_2$Me | OSO$_2$Me | H | H | OSO$_2$Me | OSO$_2$i-Pr | H | H |
| OSO$_2$Me | OSO$_2$Me | OSO$_2$Me | H | OSO$_2$Me | OSO$_2$Me | H | OSO$_2$Me |
| OSO$_2$Me | OSO$_2$n-Bu | H | H | OSO$_2$Me | OSO$_2$Me | OSO$_2$Me | OSO$_2$Me |
| OSO$_2$Me | OSO$_2$Ph | H | H | OSO$_2$Me | OSO$_2$n-Pr | H | H |
| OSO$_2$Me | —S—CH=CH— | | H | OSO$_2$Me | —S—CH=CH— | | F |
| OSO$_2$Me | SO$_2$Me | H | H | OSO$_2$Me | —S—CH=CH— | | OSO$_2$Me |
| OSO$_2$n-Bu | H | H | Cl | OSO$_2$n-Bu | H | H | Br |
| OSO$_2$n-Bu | H | H | c-Pr | OSO$_2$n-Bu | H | H | CN |
| OSO$_2$n-Bu | H | H | F | OSO$_2$n-Bu | H | H | Et |
| OSO$_2$n-Bu | H | H | I | OSO$_2$n-Bu | H | H | H |
| OSO$_2$n-Bu | H | H | n-Bu | OSO$_2$n-Bu | H | H | Me |
| OSO$_2$n-Bu | H | H | n-Pr | OSO$_2$n-Bu | H | H | NO$_2$ |
| OSO$_2$n-Bu | H | H | OCHF$_2$ | OSO$_2$n-Bu | H | H | OCF$_3$ |
| OSO$_2$n-Bu | H | H | OEt | OSO$_2$n-Bu | H | H | Oc-Pr |
| OSO$_2$n-Bu | H | H | OMe | OSO$_2$n-Bu | H | H | OH |
| OSO$_2$n-Bu | H | H | On-Pr | OSO$_2$n-Bu | H | H | On-Bu |
| OSO$_2$n-Bu | H | H | t-Bu | OSO$_2$n-Bu | H | H | Ot-Bu |
| OSO$_2$n-Pr | H | H | Cl | OSO$_2$n-Pr | H | H | Br |
| OSO$_2$n-Pr | H | H | c-Pr | OSO$_2$n-Pr | H | H | CN |
| OSO$_2$n-Pr | H | H | F | OSO$_2$n-Pr | H | H | Et |
| OSO$_2$n-Pr | H | H | I | OSO$_2$n-Pr | H | H | H |
| OSO$_2$n-Pr | H | H | n-Bu | OSO$_2$n-Pr | H | H | Me |
| OSO$_2$n-Pr | H | H | n-Pr | OSO$_2$n-Pr | H | H | NO$_2$ |
| OSO$_2$n-Pr | H | H | OCHF$_2$ | OSO$_2$n-Pr | H | H | OCF$_3$ |
| OSO$_2$n-Pr | H | H | OEt | OSO$_2$n-Pr | H | H | Oc-Pr |
| OSO$_2$n-Pr | H | H | OMe | OSO$_2$n-Pr | H | H | OH |

TABLE 160

| $X^1$ | $X^2$ | $X^3$ | $X^4$ | $X^1$ | $X^2$ | $X^3$ | $X^4$ |
|---|---|---|---|---|---|---|---|
| OSO$_2$n-Pr | H | H | On-Pr | OSO$_2$n-Pr | H | H | On-Bu |
| OSO$_2$n-Pr | H | H | t-Bu | OSO$_2$n-Pr | H | H | Ot-Bu |
| Ph | H | H | H | OSO$_2$Ph | H | H | H |
| SiMe$_3$ | H | H | H | SH | H | H | H |
| SO$_2$CF$_3$ | H | H | H | SMe | H | H | H |
| SO$_2$Me | H | H | SO$_2$Me | SO$_2$Me | H | H | H |
| t-Bu | H | H | H | SOMe | H | H | H |

The fungicides or agricultural chemical composition of the present invention contains the compound of formula [1] of the present invention or a salt thereof that is acceptable as an agricultural chemical as the active component. Further, the present invention relates to an agricultural chemical composition containing 1 type or 2 or more types of the compound of formula [1] of the present invention or a salt thereof that is acceptable as an agricultural chemical, and a carrier that is acceptable as an agricultural chemical formulation, more specifically to a fungicidal composition.

The compound of formula [1] of the present invention or a fungicidal composition of the present invention can be used to preventatively or therapeutically control phytopathogenic microorganisms or plant diseases caused thereby. In other words, the present invention also relates to a method for using the compound of formula [1] of the present invention or a fungicidal composition of the present invention to control the plant disease that occurs in plants or part of plants.

The compound of formula [1] of the present invention and the fungicidal composition of the present invention possess extremely powerful fungicidal property, and they may be used to control phytopathogenic microorganisms including protists such as Plasmodiophoromycota, or Oomycota; Fungus such as Zygomycota, Ascomycota, Basidiomycota and Deuteromycota; bacteria such as Pseudomonadaceae, Rhizobiaceae, Enterobacteriaceae, Corynebacteriaceae, and Streptomycetaceae; and plant diseases caused thereby. In particular, the compound of formula [1] of the present invention and the fungicidal composition according to the present invention show high fungicidal activity to protists belonging to Oomycota, so they have good control effect for plant diseases caused by those protists.

Examples of phytopathogenic microorganisms that can be controlled by the present invention are listed below without being limited thereby.

Examples of pathogenic microorganism belonging to Oomycota include protists of the *Albugo* genus which is the pathogen of white rust (e.g. *Albugo candida*); protists of the *Aphanomyces* genus which is the pathogen of root rot, damping-off (e.g. *Aphanomyces euteiches*); protists of the *Bremia* genus which is the pathogen of downy mildew (e.g. *Bremia lactucae*); protists of the *Peronospora* genus which is the pathogen of downy mildew (e.g. *Peronospora pisi, Peronospora brassicae, Peronospora parasitica, Peronospora tabacina*); protists of the *Plasmopara* genus which is the pathogen of downy mildew (e.g. *Plasmopara viticola*); protists of the *Pseudoperonospora* genus which is the pathogen of downy mildew (e.g. *Pseudoperonospora cubensis, Pseudoperonospora humuli*); protists of the *Phytophthora* genus which is the pathogen of late blight, white powdery rot, brown rot, red stele, heart rot, *phytophthora* rot (e.g. *Phytophthora cactorum, Phytophthora capsici, Phytophthora cinnamoni, Phytophthora infestans, Phytophthora megasperma, Phytophthora parasitica*); protists of the *Pythium* genus which is the pathogen of root rot, damping-off, browning root rot, bed rot (e.g. *Pythium aphanidermatum, Pythium ultimum*).

Examples of pathogenic microorganism belonging to Cercozoa include protists of the *Plasmodiophora* genus which is the pathogen of clubroot (e.g. *Plasmodiophora brassicae*).

Examples of pathogenic microorganism belonging to Zygomycota include fungus of the *Rhizopus* genus which is the pathogen of seedling blight, bulb rot, *Rhizopus* rot, soft rot (e.g. *Rhizopus stolonifer*).

Examples of pathogenic microorganism belonging to Ascomycota include the following: Fungus of the *Ascochyta* genus which is the pathogen of ray blight, brown spot, *Ascochyta* leaf spot, leaf spot (e.g. *Ascochyta lentis*); Fungus of the *Blumeria* genus which is the pathogen of powdery mildew (e.g. *Blumeria graminis*); Fungus of the *Claviceps* genus which is the pathogen of ergot, false smut (e.g. *Claviceps purpurea*); Fungus of the *Cochliobolus* genus which is the pathogen of southern leaf blight, spot blotch, brown stripe (e.g. *Cochliobolus sativus, Cochliobolus miyabeanus, Cochliobolus sativus*); Fungus of the *Diaporthe* genus which is the pathogen of *diaporthe* canker (e.g. *Diaporthe citri*); Fungus of the *Elsinoe* genus which is the pathogen of anthracnose, scab, sphaceloma scab, white scab, leaf spot (e.g. *Elsinoe fawcettii, Erysiphe graminis, Erysiphe polygoni*); Fungus of the *Gaeumannomyces* genus which is the pathogen of take-all (e.g. *Gaeumannomyces graminis*); Fungus of the *Gibberella* genus which is the pathogen of twig blight, bakanae disease, bud rot, stub dieback (e.g. *Gibberella zeae*); Fungus of the *Glomerella* genus which is the pathogen of anthracnose, ripe rot, red rot, leaf spot (e.g. *Glomerella cingulata*); Fungus of the *Guignardia* genus (e.g. *Guignardia bidwellii*); Fungus of the *Helminthosporium* genus which is the pathogen of stem rot, silver scurf, zonate leaf spot (e.g. *Helminthosporium sigmoideum, Helminthosporium solani, Helminthosporium triticirepentis, Helminthosporium zonatum*); Fungus of the *Leptosphaeria* genus which is the pathogen of blight, ring spot (e.g. *Leptosphaeria juncina, Leptosphaeria maculans, Leptosphaeria sacchari*); Fungus of the *Magnaporthe* genus which is the pathogen of stem rot (e.g. *Magnaporthe grisea, Magnaporthe salvinii*); Fungus of the *Monilinia* genus which is the pathogen of brown rot, blossom blight (e.g. *Monilinia fructicola, Monilinia laxa, Monilinia mali*); Fungus of the *Monographella* genus which is the pathogen of leaf scald, snow mold (e.g. *Monographella albescensa, Monographella nivalis*); Fungus of the *Mycosphaerella* genus which is the pathogen of black leaf blight, leaf spot (e.g. *Mycosphaerella arachidicola, Mycosphaerella fijiensis, Mycosphaerella graminicola*); Fungus of the *Phaeomoniella* genus which is the pathogen of the *Phaeomoniella* disease (e.g. *Phaeomoniella chlamydospora*); Fungus of the *Phaeosphaeria* genus which is the pathogen of glume blotch (e.g. *Phaeosphaeria nodorum*); Fungus of the *Podosphaera* genus which is the pathogen of powdery mildew (e.g. *Podosphaera leucotricha, Podosphaera tridactyla*); Fungus of the *Pyrenophora* genus which is the pathogen of stripe, net blotch (e.g. *Pyrenophora graminea, Pyrenophora teres*); Fungus of the *Sclerotinia* genus which is the pathogen of downy mildew, *sclerotinia* rot (e.g. *Sclerotinia sclerotiorum*); Fungus of the *Sclerotium* genus which is the pathogen of southern blight, white rot (e.g. *Sclerotium rolfsii*); Fungus of the *Sphaerotheca* genus which is the pathogen of powdery mildew (e.g. *Sphaerotheca fuliginea, Sphacelotheca reiliana*); Fungus of the *Sphaerulina* genus which is the pathogen of *cercospora* leaf spot (e.g. *Sphaerulina oryzina*); Fungus of the *Tapesia* genus which is the pathogen of the *Tapesia* disease (e.g. *Tapesia acuformis*); Fungus of the *Taphrina* genus which is the pathogen of leaf curl, plum pockets (e.g. *Taphrina deformans, Taphrina pruni*); Fungus of the *Uncinula* genus which is the pathogen of powdery mildew (e.g. *Uncinula necator, Uncinuliella simulans*); Fungus of the *Venturia* genus which is the pathogen of scab (e.g. *Venturia inaequalis, Venturia nashicola*);

Examples of pathogenic microorganism belonging to Basidiomycota include the following: Fungus of the *Ceratobasidium* genus which is the pathogen of foot-rot, winter stem rot (e.g. *Ceratobasidium graminerum*); Fungus of the *Corticium* genus which is the pathogen of foot-rot, winter stem rot (e.g. *Corticium graminerum*); Fungus of the *Exobasidium* genus which is the pathogen of leaf gall, witches broom, net blister blight (e.g. *Exobasidium pentasporium, Exobasidium reticulatum, Exobasidium vexans*); Fungus of the *Fomitiporia* genus which is the pathogen of the Dwarf disease (e.g. *Fomitiporia mediterranea*); Fungus of the *Ganoderma* genus which is the pathogen of Stem rot (e.g. *Ganoderma boninense*); Fungus of the *Gymnosporangium* genus which is the pathogenic bacteria of rust (e.g. *Gymnosporangium sabinae, Gymnosporangium sabinae*); Fungus of the *Hemileia* genus which is the pathogenic bacteria of rust (e.g. *Hemileia vastatrix*); Fungus of the *Nectria* genus which is the pathogen of coral spot disease, *nectria* blight (e.g. *Nectria galligena*); Fungus of the *Phakopsora* genus which is the pathogen of red rust, rust (e.g. *Phakopsora meibomiae, Phakopsora pachyrhizi*); Fungus of the *Puccinia* genus which is the pathogen of rust, stem rust, leaf rust (e.g. *Puccinia arachidis, Puccinia graminis, Puccinia hordei, Puccinia recondita, Puccinia striiformis*); Fungus of the *Tilletia* genus which is the pathogenic bacteria of Stinking smut (e.g. *Tilletia caries*); Fungus of the *Typhula* genus which is the pathogen of *typhula* snow blight, *typhula* rot (e.g. *Typhula incarnata, Typhula ishikariensis*); Fungus of the *Urocystis* genus which is the pathogen of smut (e.g. *Urocystis cepulae, Urocystis occulta*); Fungus of the *Uromyces* genus which is the pathogen of rust (e.g. *Uromyces appendiculatus, Uromyces phaseoli*); Fungus of the *Ustilago* genus which is the pathogen of smut, loose smut (e.g. *Ustilago maydis, Ustilago nuda*).

Examples of pathogenic microorganism belonging to Deuteromycota include the following: Fungus of the *Alternaria* genus which is the pathogen of *Alternaria* blotch, *Alternaria* leaf spot, *Alternaria* black rot, leaf blight, early blight, early blight (ring spot) (e.g. *Alternaria brassicicola, Alternaria solani*); Fungus of the *Aspergillus* genus which is the pathogen of crown rot (e.g. *Aspergillus flavus*); Fungus of the *Botrytis* genus which is the pathogen of gray mold, neck rot, red spot (e.g. *Botrytis cinerea*); Fungus of the *Cercosporidium* genus which is the pathogen of leaf spot (e.g. *Cercosporidium personatum*); Fungus of the *Cercospora* genus which is the pathogen of leaf spot, leaf spot (brown spot), brown round spot, leaf blight, purple stain (e.g. *Cercospora arachidicola, Cercospora beticola, Cercospora chaae, Cercospora kikuchii*); Fungus of the *Cladosporium* genus which is the pathogen of scab, false blast, leaf blotch (e.g. *Cladosporium cucumerinum, Cladosporium cladosporioides, Cladosporium herbarum*); Fungus of the *Colletotrichum* genus which is the pathogen of anthracnose, ripe rot (e.g. *Colletotrichum coccodes, Colletotrichum graminicola, Colletotrichum lindemuthanium, Colletotrichum orbiculare*); Fungus of the *Fusarium* genus which is the pathogen of stem rot, *Fusarium* wilt, dry rot, root rot, *Fusarium* wilt (e.g. *Fusarium culmorum, Fusarium graminearum, Fusarium oxysporum, Fusarium roseum*); Fungus of the *Gloeosporium* genus which is the pathogen of anthracnose (e.g. *Gloeosporium laeticolor*); Fungus of the *Macrophomina* genus which is the pathogen of leaf spot, *Macrophoma* leaf spot, branch canker (e.g. *Macrophoma theicola, Macrophomina phaseolina*); Fungus of the *Microdochium* genus which is the pathogen of anthracnose (e.g. *Microdochium nivale*); Fungus of the *Penicillium* genus which is the pathogen of blue mold, common green mold (e.g. *Penicillium expansum, Penicillium purpurogenum*); Fungus of the *Phoma* genus which is the pathogen of leaf spot, fruit rot, root rot (e.g. *Phoma lingam, Phoma dauci*); Fungus of the *Phomopsis* genus which is the pathogen of *Phomopsis* canker, stem blight (e.g. *Phomopsis sojae, Phomopsis viticola*); Fungus of the *Pseudocercosporella* genus which is the pathogen of eye spot (e.g. *Pseudocercosporella herpotrichoides*); Fungus of the *Pyricularia* genus which is the pathogen of blast (e.g. *Pyricularia oryzae*); Fungus of the *Ramularia* genus which is the pathogen of *Ramularia* leaf spot (e.g. *Ramularia areola, Ramularia collo-cygni*); Fungus of the *Rhizoctonia* genus which is the pathogen of damping-off, *Rhizoctonia* root rot, stem rot, sheath blight (e.g. *Rhizopus oryzae, Rhizoctonia solani*); Fungus of the *Rhynchosporium* genus which is the pathogen of leaf blotch (e.g. *Rhynchosporium secalis*); Fungus of the *Sarocladium* genus which is the pathogen of sheath rot (e.g. *Sarocladium oryzae*); Fungus of the *Septoria* genus which is the pathogen of black spotted leaf blight, leaf blight, *Septoria* leaf spot (e.g. *Septoria apii, Septoria lycopersici, Septoria nodorum, Septoria tritici*); Fungus of the *Stagonospora* genus which is the pathogen of red leaf spot, leaf scorch (e.g. *Stagonospora nodorum*); Fungus of the *Thielaviopsis* genus which is the pathogen of black root rot, root rot (e.g. *Thielaviopsis basicola*); Fungus of the *Verticilium* genus which is the pathogen of *verticillium* wilt (e.g. *Verticilium alboatrum, Verticillium dahliae*);

Examples of pathogenic microorganism belonging to Xanthomonadaceae include bacteria of the *Xanthomonas* genus which is the pathogen of bacterial leaf blight, bacterial spot, bacterial brown spot (e.g. *Xanthomonas campestris* pv. *oryzae, Xanthomonas campestris* pv. *vesicatoria*).

Examples of pathogenic microorganism belonging to Pseudomonadaceae include bacteria of the *Pseudomonas* genus which is the pathogen of sheath blown rot, bacterial wilt (e.g. *Pseudomonas syringae* pv. *lachrymans, Pseudomonas syringae* pv. *mori*).

Examples of pathogenic microorganism belonging to Enterobacteriaceae include bacteria of the *Erwinia* genus which is the pathogen of bacterial soft rot (e.g. *Erwinia amylovora, Erwinia carotovora* subsp. *carotovora*). Examples of pathogenic microorganism belonging to Corynebacteriaceae include bacteria of the *Corynebacterium* genus which is the pathogen of fasciation (e.g. *Corynebacterium facians*).

Examples of pathogenic microorganism belonging to Streptomycetaceae include bacteria of the *Streptmyces* genus which is the pathogen of Soil smelling yellow rice (e.g. *Streptmyces flavovirens*).

The compound of formula [1] of the present invention or a fungicidal composition of the present invention can be applied to all plants or a part of plants, and the soil surrounding the plant, or the soil to seed seeds, rice patties, water for slop culture and equipments for cultivation by misting, spreading, spreading as powder, spraying, dispersing, immersing, lavaging, inserting, sprinkling (exposing to water), bubbling, depositing, dressing, soaking, drenching, fumigating, smoking, hazing and painting to control plant-pathogenic microorganisma or plant diseases caused thereby. By all plants, this document refers to plants or group of plants such as wild plants, bred plants, naturally occurring plants, cultivated plants, and they include plants created by breeding methods such as introduction breeding, breeding by separation, crossbreeding, heterosis breeding, mutation breeding, polyploid breeding, gene recombination (gene introduction) or marker aided selection.

A treatment with the compound of formula [1] of the present invention or a fungicidal composition of the present invention to control plant pathogenic bacteria or plant diseases caused thereby can be performed through out the breeding period and storage period of the plant whether it is before or after infection by phytopathogenic microorganism. A part of a plant is all parts constituting the plant including the leaf, stem, trunk, branch, flower, fruiting body, fruit, seed, root, tuber and rhizome, or combinations thereof.

The fungicidal composition of the present invention can be used by adjusting the treatment amount of the compound of formula [1] of the present invention so that it is effective but it does not show toxicity against plants to control phytopathogenic microorganisms or plant diseases caused thereby. An amount that is effective but does not show toxicity against plants is an amount that can sufficiently control phytopathogenic microorganisms or plant disease caused thereby, and this amount may vary in a comparatively wide range according to the microorganism to be controlled, the plant to which it is applied, the natural environment of use and the components of the composition of the present invention.

Examples of plants that can be treated with the compound of formula [1] of the present invention or a fungicidal composition of the present invention are given below without being limited thereby.

Malvaceae plants, such as okra, cotton. Sterculiaceae plants, such as cacao tree. Chenopodiaceae plants, such as spinach. Sapotaceae plants, such as miracle fruit. Rubiaceae plants, such as coffee, *Coffea canephora*. Cannabaceae plants, such as *Humulus lupulus*. Brassicaceae plants, such as *Brassica campestris*, turnip, cauliflower, cabbage, *Brassica chinensis* komatsuna, Japanese radish, pak choi, Chinese cabbage, broccoli. Poaceae plants such as rice, barley, wheat, sugarcane, *Zoysia*, corn, rye. Cucurbitaceae plants such as pumpkin, cucumber, watermelon, zucchini, winter melon, *Momordica charantia*, Chayote, *Cucumis melo*, melon, *Lagenaria siceraria*. Anacardiaceae plants such as mango. Nyctaginaceae plants such as *Pisonia umbellifera*. Clusiaceae plants such as *Garcinia mangostana*. Ebenaceae plants such as Japanese persimmon. Asteraceae plants such as *Sanchu* lettuce, leaf lettuce, lettuce, *Chrysanthemum morifolium, Chrysanthemum coronarium*, chicory, burdock, sunflower, fuki. Betulaceae plants. Malpighiaceae plants such as acerola. Lauraceae plants. Elaeagnaceae plants such as *Juglans mandshurica* var. *sachalinensis*, black walnuts. Moraceae plants such as fig, rubber tree. Dennstaedtiaceae plants such as bracken. Pedaliaceae plants such as sesame. Punicaceae plants such as pomegranate. Araceae plants such as Amorphophalus, Araceae. Blechnaceae plants such as leontiasis. Lamiaceae plants such as f. *viridis*, f. *purpurea*. Tiliaceae plants such as *Corchorus olitorius*. Zingiberaceae plants such as turmeric, ginger, *Zingiber officinale, Zingiber mioga*. Apiaceae plants such as parsley, celery, carrots. Polygonaceae plants such as buckwheat. Ericaceae plants such as *Rhododendron*. Theaceae plants such as *Camellia sinensis*. Solanaceae plants such as tobacco, red pepper, pepper, tomato, potato, egg plant. Caryophyllaceae plants such as carnation. Bromeliaceae plants such as pineapples. Cabombaceae plants such as *Brasenia schreberi*. Musaceae plants such as banana. Caricaceae plants such as *papaya*. Rosaceae plants such as apricot, strawberry, *Prunus mume, Pseudocydonia sinensis, Prunus salicina, Pyrus communis, Pyrus pyrifolia* var. *culta*, nectarine, rose, Eriobotrya, black raspberry, quince, Miniature rose, peach, apple. Convolvulaceae plants such as sweet potato. Amaranthaceae plants such as sugar beet. Vitaceae plants such as grape. Fagaceae plants such as chestnut. Crassulaceae plants such as *Yatsugashira* (a type of *Colocasia antiquorum* Schott. var. *esculenta* Engl). Fabaceae plants such as azuki, kidney bean, pea, black azuki, *Vigna unguiculata*, Viciafaba, soy beans, black beans, peanuts. Rutaceae plants such as *Poncirus, Citrus Kawano natsudaidai*, orange, *Fortunella*, grapefruit, *Zanthoxylum piperitum, Citrus sudachi, Citrus aurantium, Citrus tachibana*, Tahichi Lime, *Citrus natsudaidai, Citrus hassaku, Citrus unshiu, Citrus maxima, Citrus poonensis, Citrus junos*, lime, lemon. Oleaceae plants such as olive. Arecaceae plants such as coconut. Trochodendraceae plants such as *Phytolacca esculenta*. Dioscoreaceae plants such as *Dioscorea batatas*, yam. Liliaceae plants such as asparagus, tulip, onion, garlic, *Allium fistulosum, Allium bakeri*, shallot, lilly. Moringaceae plants such as *Moringa oleifera* Lam. And also, gene recombinant plants thereof.

A further embodiment of the present invention relates to seeds treated with the compound of formula [1] of the present invention or a fungicidal composition of the present invention. The seed of the present invention is used to prevent plant diseases caused by phytopathogenic microorganisms from occurring. When seeds that are infected with phytopathogenic microorganisms or that have phytopathogenic microorganisms attached to them (hereinafter referred to as "contaminated seeds") contaminate healthy seeds, the contaminated seed becomes the infection source of phytopathogenic microorganism, and diseases spread to healthy plants that are cultivated nearby. Hence, the seeds of the present invention treated with the compound of formula [1] of the present invention or a fungicidal composition of the present invention, which have high fungicidal activity against plant disease microorganisms, are effective methods to prevent occurrence of plant diseases and spread of pathogenic microorganisms to healthy plants.

The fungicidal composition of the present invention can be used for seeds of all plants. The use of seeds according to the present invention will be effective as a means for preventing plant diseases by phytopathogenic microorganism especially in rice, wheat, barley, rye, corn, soy beans, cotton, potato, and sugarbeet, which are cultivated in a large scale, and have a tendency to experience enhanced damage from the propagation of diseases caused by contaminated seeds. In addition, treating seeds of gene recombined crops with the compound of formula [1] of the present invention or a fungicidal composition of the present invention is effective as a means for preventing plant diseases caused by phytopathogenic microorganism.

Examples of gene recombination plants that can be treated with the compound of formula [1] of the present invention or a fungicide composition of the present invention are provided below without being limited thereby.

Plants that have been transformed so that they are resistant to herbicide, for example, glyphosate resistant plants, bialaphos resistant plants, bromoxynil resistant plants, sulfonyl urea type herbicide resistant crops, imidazolidinone type herbicide resistant crops, 2,4-D resistant crops, dicamba resistant plants, isoxaflutole resistant plants, mesotrione resistant plants, etc.

Plants that have been transformed so that they are resistant to insect pests, for example, plants that have been transformed to produce Bt toxin (pesticidal toxin of *Bacillus thuringiensis*), plants that have been transformed to produce natural enemy attractants.

Plants that have been transformed so that they are resistant to plant diseases, for example, virus resistant plants, plantas that have been transformed to produce defensin. Plants that have been transformed to improve storability by expanding the harvesting period of fruits, for example, plants that have been transformed to inhibit the production of polygalacturonase, plants that have been transformed to inhibit the production of ethylene biosynthetic enzyme.

Plants that have been transformed to improve safety of crops, for example, plants that produce mycotoxin degradation enzyme.

Plants that have been transformed to be useful in breeding, for example, plants that have been transformed to exhibit male sterility transduction.

Transformed plants given useful features as a raw material of bioethanol, for example, plants that produce heat-resistant α-amylase.

Plants that have been transformed to be resistant to environmental stress, for example, plants showing dry resistance using RNA chaperon, plants that stock glycinebetaine that is a compatible solute contained abundantly in low temperature resistant plants, plants that stock compatible solute, proline, plants that stock trehalose having strong waterholding capacity, and showing dry resistance, plants that produce excessive enzymes that delete reactive oxygen species, plants that show resistance to iron deficiency in alkaline soil by producing mugineic acids, plants that show resistance to iron deficiency by producing mugineic acids, etc.

Plants that are transformed to produce specific functional nutrients, for example, plants that produce excessive oleic acid, plants that produce excessive stearidonic acid, plants that produce excessive lycine, pro-vitamin A enhancing crop, vitamin E enhancing crop, plants that produce excessive anthocyanin, plants that produce allergin of cedar and minimize cedar pollinosis, etc.

The compound of formula [1] of the present invention or a fungicidal composition of the present invention has a high fungicidal effect against microorganisms, so it can be used for protecting industrial materials from propagation of microorganisms. Non-limiting examples of industrial materials include wood, plastic material, paper material, leather material, tile, ceramic, cement, paint, cooling lubricant and adhesive. The treatment of industrial materials can be conducted by misting, spreading, spreading as powder, spraying, dispersing, soaking, drenching, sprinkling (exposing to water), bubbling, depositing, dressing, coating, blowing, fumigating, smoking, hazing and painting and mixing.

The fungicidal composition of the present invention may include additives normally used in agricultural chemical formulations as necessary. Additives include carriers such as solid carriers or liquid carriers, surfactants, binders, adhesives, thickeners, coloring agents, spreaders, antifreezing agents, anticonsolidation agents, disintegrators, stabilizer, etc., and additionally preservatives and plant fragments may be used as additive components as necessary.

The additive components may be used alone or in a combination of two or more types thereof.

The above additive components are explained below.

Examples of solid carriers include natural minerals such as quartz, clay, kaolinite, pyrophyllite, sericite, talc, chalk, bentonite, attapulgite, montmorillonite, acid clay, attapulgite, zeolite, natural rock, diatomaceous earth, calcite, marble, pumice, sepiolite, dolomite; inorganic salts such as calcium carbonate, ammonium sulfate or other ammonium salts, sodium sulfate, calcium chloride, potassium chloride; organic solid carriers such as synthetic silicate, synthetic silicate salt, alumina, particulate silica, silicate, starch, cellulose, plant powders; plastic carriers such as polyethylene, polypropylene, polyvinylidene chloride. They can be used alone or in a combination of two or more types thereof.

Examples of liquid carriers include alcohols that are categorized into monohydric alcohols such as methanol, ethanol, propanol, isopropanol, butanol, and multihydric alcohols such as ethyleneglycol, diethyleneglycol, propyleneglycol, hexylene glycol, polyethyleneglycol, polypropyleneglycol glycerin; multihydric alcohol derivatives such as propylene type glycol ethers; ketones such as acetone, methylethylketone, methylisobutylketone, diisbutylketone, cyclohexanone, isophorone; ethers such as ethyl ether, dioxane, cellosolve, dipropyl ether, tetrahydrofuran; aliphatic hydrocarbons such as normal paraffin, naphthene, isoparaffin, kerosine, mineral oil; aromatic hydrocarbons such as benzene, toluene, xylene, solvent naphtha, alkylnaphthalene; halogenated hydrocarbons such as dichloroethane, chloroform, carbon tetrachloride; esters such as ethyl acetate, diisopropylphthalate, dibutylphthalate, dioctyl phthalate, adipic acid dimethyl; lactones such as γ-butyrolactone; amides such as dimethylformamide, diethylformamide, dimethylacetamide, N-alkylpyrrolidine; nitriles such as acetonitrile; sulfur compounds such as dimethylsulfoxide; vegetable oils such as soy bean oil, rape-seed oil, cottonseed oil, castor oil; water. They can be used alone or in a combination of two or more types thereof.

Surfactants are not particularly limited, but surfactants that gelatinize or show bloating tendency in water are preferable. Examples include nonionic surfactants such as sorbitan fatty acid ester, polyoxyethylenesorbitan fatty acid ester, sucrose fatty acid ester, polyoxyethylene fatty acid ester, polyoxyethylene resinate ester, polyoxyethylene fatty acid diester, polyoxyethylene alkyl ether, polyoxyethylene alkylphenol ether, polyoxyethylene dialkylphenyl ether, polyoxyethylene alkylphenol formalin condensate, polyoxyethylene polyoxypropylene block polymer, alkylpolyoxyethylene polypropylene block polymer ether, polyoxyethylene alkyl amine, polyoxyethylene fatty acid amide, polyoxyethylene fatty acid bisphenyl ether, polyalkylenebenzyl phenyl ether, polyoxyalkylene styrene phenyl ether, acetylenediol, polyoxyalkylene-added acetylenediol, polyoxyethylene ether-type silicone, ester-type silicone, fluorine-type surfactant, polyoxyethylene castor oil, polyoxyethylene hydrogenated castor oil; anionic surfactants such as alkylsulfuric acid salt, polyoxyethylene alkyl ether sulfuric acid salt, polyoxyethylene alkylphenyl ether sulfuric acid salt, alkylbenzene sulfonic acid salt, lignin sulfonic acid salt, alkylsulfosuccinate salt, naphthalene sulfonic acid salt, alkylnaphthalene sulfonic acid salt, salt of naphthalene sulfonic acid formalin condensate, salt of alkylnaphthalene sulfonic acid formalin condensate, fatty acid salt, polycarboxylic acid salt, N-methyl fatty acid sarcosinate, resinate salt, polyoxyethylene alkyl ether phosphoric acid salt, polyoxyethylene alkylphenyl ether phosphoric acid salt; cationic surfactants such as lauryl amine hydrochloric acid salt, stearyl amine hydrochloric acid salt, oleyl amine hydrochloric acid salt, stearyl amine acetic acid salt, stearylaminopropyl amine hydrochloric acid salt, alkyl amine salts such as alkyl trimethyl ammonium chloride, alkyldimethyl benzalkonium chloride; amphoteric surfactants such as amino acid type or betaine type. These surfactants can be used alone or in a combination of two or more types thereof.

Further, examples of binders and adhesion additives include carboxymethyl cellulose or a salt thereof, dextrin, aqueous starch, xanthan gum, guar gum, sucrose, polyvinyl pyrrolidone, gum arabic, polyvinyl alcohol, polyvinyl acetate, sodium polyacrylate, polyethyleneglycol having an average molecular weight of 6,000-20,000, polyethylene oxide having an average molecular weight of 100,000-5 million, natural phospholipids (e.g. cephalin acid, lecithin acid). These binders and adhesion additives can be used alone or as a combination of two or more types thereof. Examples of thickeners include aqueous polymer such as xanthan gum, guar gum, carboxymethyl cellulose, polyvinyl pyrrolidone, carboxyvinylpolymer, acrylic polymer, starch derivatives, polysaccharides, and inorganic particulates such as high purity bentonite, white carbon. These thickeners can be used alone or in a combination of two or more types thereof. Examples of coloring agents include inorganic pigments such as iron oxide, titanium oxide, prussian blue, organic dyes such as alizarin dye, azo dye, metal phthalocyanine dye. These coloring agents may be used alone or in a combination or two or more types thereof.

Examples of spreaders include aqueous salts of silicone-type surfactants, cellulose powders, dextrin, processed starch, aminopolycarboxylic acid chelate compound, cross-linked polyvinyl pyrrolidone, maleic acid and styrene acid, methacrylic acid copolymer, half ester of a polymer of multihydric alcohol and dicarbonic acid anhydride, polystyrene sulfonic acid. These spreaders can be used alone or in a combination of two or more types thereof. Examples of stickers include various surfactants such as sodium dialkyl sulfosuccinate, polyoxyethylene alkyl ether, polyoxyethylene alkylphenyl ether, polyoxyethylene fatty acid ester; and paraffin, terpene, poly amide resin, polyacrylic acid salt, polyoxyethylene, wax, polyvinylalkyl ether, alkylphenol formalin condensate, synthetic resin emulsion. These stickers may be used alone or in a combination of two or more types thereof.

Examples of antifreezing agents include multihydric alcohol such as ethyleneglycol, diethyleneglycol, propyleneglycol, glycerin. These antifreezing agents may be used alone or in a combination of two or more types thereof.

Examples of anticonsolidation agents include saccharides such as starch, alginic acid, mannose, galactose, etc.; and polyvinyl pyrrolidone, white carbon, ester gum, petroleum resin, etc. These anticonsolidation agents may be used alone or in a combination of two or more types thereof. Examples of disintegrators include sodium tripolyphosphate, sodium hexametaphosphate, stearic acid metal salt, cellulose powders, dextrin, copolymer of methacrylic acid ester, polyvinyl pyrrolidone, aminopolycarboxylic acid chelate compound, styrene sulfonate-isobutylene, maleic anhydride copolymer, starch-polyacrylonitrile graft copolymer, etc. These disintegrators may be used alone or in a combination of two or more types thereof.

Examples of stabilizers include drying agents such as zeolite, calx, magnesium oxide; antioxidants of phenol type, amine type, sulfur type, phosphoric acid type, etc.; UV absorbers of salicylic acid type, benzophenone type, etc. These stabilizers may be used alone or in a combination of two or more types thereof.

Examples of preservatives include potassium sorbate, 1,2-benzthiazolin-3-one. These preservatives may be used alone or in a combination of two or more types thereof.

Examples of plant fragments include sawdust, coconut shell, corncob, tobacco stem, etc.

When the above additive components are incorporated in the fungicides and agricultural chemical composition of the present invention, the range of percentage content based on mass of carriers is normally 5-95%, preferably 20-90%, the percentage content of surfactants is normally 0.1-30%, preferably 0.5-10%, and that of other additives is 0.1-30%, preferably 0.5-10%.

The fungicides and agricultural chemical compositon of the present invention may be used as drugs suitable for agricultural/horticultural fungicides such as granule, powder granule, microgranule, liquid formulation, water soluble powder, oil solution, emulsifiable concentration, spreading oil, emulsion, microemulsion, suspoemulsion, EW (emulsion oil in water), microcapsule, wettable powder, suspension concentrate, floable, tablet, granule wettable powder, dry floable, water dispersible granule, aerozol, paste, cyclodextrin inclusion compound, jumbo agent, pack agent, water soluble bag, dust formation, smoking pesticide, fumigant, etc.

These embodiments may be obtained by a common method of mixing at least one type of the compound of the present invention and an appropriate solid or liquid carrier, and optionally, appropriate auxiliary substances (e.g. surfactants, solvents, stabilizers) for improving the dispersibility of the active component or other properties.

To use the obtained product, it should be spread after diluting to a suitable concentration or directly applied.

The compound of formula [1] of the present invention may be used alone or as a pharmaceutical formulation thereof, and pharmaceutical formulation of its mixture with germicides/fungicides, bactericides, miticides, nematicides, pesticides, microbial pesticides, herbicides, plant hormone agents, plant growth regulator substances, synergists, attractants, repellants, coloring matter, fertilizer or a mixture of 1 type of the active component or a combination of 2 or more types thereof may be used as a pest control agent. Such use leads to expectation of expansion of the effect, the object of control (disease, insect damage, weeds), expansion of period of use, or a reduction of the amount of drug, obtaining synergistic effects, or prevention of the development of resistance in the object of control. In many cases, the activity of a mixture is greater than the activity of individual use, and leads to achieving a cooperative drug effect with the combined component.

The following combined components in a mixture are developed in large numbers: germicides/fungicides, bactericides, pesticides, miticides, nematicides, pesticides of snails, ingestion inhibitors, herbicides, algicides, miticides, nematicides, microbial pesticides, pheromone agents, natural fungicides, natural pestides. They are known by the Pesticide Manual (2013) published by British Crop Production Council, the Complete Guide of the Association's Agrichemical (2014) published by the National Federation of Agricultural Cooperative Associations, and the SHIBUYA INDEX (ver. 17) published by the National Agricultural Community Education Association. Examples are provided below without being limited thereby.

Examples of fungicides and bactericides include 2-phenylphenol, 8-hydroxyquinoline sulfate, acibenzolar-S-methyl, acypetacs, acypetacs-copper, acypetacs-zinc, albendazole, aldimorph, allicin, allyl alcohol, ametoctradin, amicarthiazol, amisulbrom, amobam, ampropylfos, anilazine, asomate, aureofungin, azaconazole, azithiram, azoxystrobin, barium polysulfide, benalaxyl, benalaxyl-M, benodanil, benomyl, benquinox, bentaluron, benthiavalicarb-isopropyl, benthiazole, benzalkonium chloride, benzamacril, benzamorf, benzohydroxamic acid, benzovindiflupyr, berberine, bethoxazin, bifujunzhi, biphenyl, bismerthiazol, bitertanol, bithionol, bixafen, blasticidin-S, boscalid, bromothalonil, bromuconazole, bronopol, bupirimate, Burgundy mixture, buthiobate, butylamine, calcium polysulfide, captan, carbamorph, carbendazim, carbon disulfide, carboxin, carpropamid, carvacrol, carvone, cellocidin, Cheshunt mixture, chinomethionat, chitosan, chlobenthiazone, chloramphenicol, chloraniformethan, chloranil, chlorfenazole, chlorodinitronaphthalenes, chloroneb, chloropicrin, chlorothalonil, chlorquinox, chlozolinate, climbazole, clotrimazole, copper acetate, basic copper carbonate, copper hydroxide, copper naphthenate, copper oleate, copper oxychloride, copper silicate, copper sulfate, basic copper sulfate, copper zinc chromate, coumoxystrobin, cufraneb, cuprobam, cuprous oxide, cyanogen, cyazofamid, cyclafuramid, cycloheximide, cyflufenamid, cymoxanil, cypendazole, cyproconazole, cyprodinil, dazomet, DBCP, debacarb, decafentin, dehydroacetic acid, dichlofluanid, dichlone, dichlorophen, dichlozoline, diclobutrazol, diclocymet, diclomezine, dicloran, diethofencarb, diethyl pyrocarbonate, difenoconazole, diflumetorim, dimetachlone, dimethirimol, dimethomorph, dimoxystrobin, diniconazole, diniconazole, diniconazole-M, dinobuton, dinocap, dinocap-4, dinocap-6, dinocton, dinopenton, dinosulfon, dinoterbon, diphenylamine, dipyrithione, disulfiram, ditalimfos, dithianon, dithioether, DNOC, dodemorph, dodicin, dodine, drazoxolon, EBP, edifenphos, enoxastrobin, epoxiconazole, etaconazole, etem, ethaboxam, ethirimol, ethoxyquin, ethylicin, etridiazole, famoxadone, fenamidone, fenaminosulf, fenaminstrobin, fenapanil, fenarimol, fenbuconazole, fenfuram, fenhexamid, fenitropan, fenjuntong, fenoxanil, fenpiclonil, fenpropidin, fenpropimorph, fenpyrazamine, ferbam, ferimzone, fluazinam, fludioxonil, flufenoxystrobin, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, fosetyl-A1, fuberidazole, furalaxyl, furametpyr, furcarbanil, furconazole, furconazole-cis, furfural, furmecyclox, furophanate, glyodin, griseofulvin, guazatine, halacrinate, hexachlorobutadiene, hexachlorophene, hexaconazole, hexylthiofos, huanjunzuo, hydrargaphen, hymexazol, imazalil, imibenconazole, iminoctadine, iminoctadine-triacetate, iminoctadine-albesilate, inezin, iodocarb, ipconazole, iprobenfos, iprodione, iprovalicarb, isofetamid, isoprothiolane, isopyrazam, isotianil, isovaledione, izopamfos, jiaxiangjunzhi, kasugamycin, kejunlin, kresoxim-methyl, mancopper, mancozeb, mandestrobin, mandipropamid, maneb, mebenil, mecarbinzid, mepanipyrim, mepronil, meptyldinocap, metalaxyl, metalaxyl-M, metam, metazoxolon, metconazole, methasulfocarb, methfuroxam, methyl iodide, methyl isothiocyanate, metiram, metominostrobin, metrafenone, metsulfovax, milneb, moroxydine, myclobutanil, myclozolin, nabam, natamycin, nitrostyrene, nitrothal-isopropyl, nuarimol, octhilinone, ofurace, orysastrobin, osthol, oxadixyl, oxathiapiprolin, oxine-copper, oxolinic acid, oxpoconazole, oxycarboxin, oxytetracycline, parinol, pefurazoate, penconazole, pencycuron, penflufen, pentachlorophenol, pentachlorophenyl laurate, penthiopyrad, phenamacril, phenazine oxide, phosdiphen, fthalide, picarbutrazox, picoxystrobin, piperalin, polycarbamate, polyoxins, polyoxorim, polyoxorim-zinc, potassium azide, potassium polysulfide, potassium thiocyanate, probenazole, prochloraz, procymidone, propamidine, propamocarb, propiconazole, propineb, proquinazid, prothiocarb, prothioconazole, pydiflumetofen, pyracarbolid, pyraclostrobin, pyrametostrobin, pyraoxystrobin, pyraziflumid, pyrazophos, pyribencarb, pyridinitril, pyrifenox, pyrimethanil, pyriofenone, pyrisoxazole, pyroquilon, pyroxychlor, pyroxyfur, quinacetol, quinazamid, quinconazole, quinoxyfen, quintozene, rabenzazole, saijunmao, saisentong, salicylanilide, sanguinarine, santonin, sedaxane, silthiofam, simeconazole, sodium orthophenylphenoxide, sodium pentachlorophenoxide, sodium polysulfide, sodium tetrathiocarbonate, spiroxamine, streptomycin, sulfur, sultropen, tebuconazole, tebufloquin, tecloftalam, tecnazene, tecoram, tetraconazole, thiabendazole, thiadifluor, thicyofen, thifluzamide, thiochlorfenphim, thiadiazole-copper, thiomersal, thiophanate, thiophanate-methyl, thioquinox, thiram, tiadinil, tioxymid, tolclofos-methyl, tolprocarb, tolylfluanid, tolylmercury acetate, triadimefon, triadimenol, triamiphos, triarimol, triazbutil, triazoxide, trichlamide, trichlorotrinitrobenzenes, triclopyricarb, tricyclazole, tridemorph, trifloxystrobin, triflumizole, triforine, triticonazole, uniconazole, uniconazole-P, urbacide, validamycin, validamycin A, valifenalate, vangard, vinclozolin, xinjunan, zarilamid, zinc naphthenate, zinc thiazole, zinc trichlorophenoxide, zineb, ziram, zoxamide, BAF-1107, BAF-045, BAF-1120, BAG-010, KUF-1411, MIF-1002, MIF-1002, MIF-1102, NC-233, NF-180, S-2399, SYJ-247, SYJ-252, SYJ-264, SYJ-269.

Examples of pesticides, acaricides, nematicides, snail pesticides and ingestion inhibitors include 1,2-dichloropropane, 1,3-dichloropropene, abamectin, acephate, acequinocyl, acetamiprid, acethion, acetophos, acetoprole, acrinathrin, acrylonitrile, afidopyropen, alanycarb, aldoxycarb, allethrin, allicin, allosamidin, allyxycarb, alpha-cypermethrin, alpha-endosulfan, amidithion, amidoflumet, aminocarb, amiton, amitraz, anabasine, aramite, athidathion, azadirachtin, azamethiphos, azinphos-ethyl, azinphos-methyl, azobenzene, azocyclotin, azothoate, *Bacillus thuringiensis* kurstaki, *Bacillus thuringiensis* Buibui, *Bacillus thuringiensis* aisawai, barium hexafluorosilicate, barthrin, benclothiaz, bendiocarb, benfuracarb, benoxafos, bensultap, benzoximate, benzyl benzoate, beta-cyfluthrin, beta-cypermethrin, bifenazate, bifenthrin, bifujunzhi, binapacryl, bioallethrin, bioethanomethrin, biopermethrin, bistrifluron, borax, boric acid, brofenvalerate, broflanilid, brofluthrinate, bromethrin, bromfenvinfos, bromoacetamide, bromocyclen, bromo-DDT, bromophos, bromophos-ethyl, bromopropylate, bufencarb, buprofezin, butacarb, butathiofos, butethrin, butocarboxim, butonate, butoxycarboxim, cadusafos, calcium polysulfide, calvinphos, camphechlor, carbanolate, carbaryl, carbofuran, carbon disulfide, carbon tetrachloride, carbonyl sulfide, carbophenothion, carbosulfan, cartap, carvacrol, chinomethionat, chloramine phosphorus, chlorantraniliprole, chlorbenside, chlorbenzuron, chlorbicyclen, chlordecone, chlorempenthrin, chlorethoxyfos, chlorfenapyr, chlorfenethol, chlorfenson, chlorfensulphide, chlorfenvinphos, chlorfluazuron, chlormephos, chloroform, chloromebuform, chloromethiuron, chloropicrin, chloroprallethrin, chloropropylate, chlorphoxim, chlorprazophos, chlorpyrifos, chlorpyrifos-methyl, chlorthiophos, chromafenozide, cinerin I, cinerin II, cinerins, cismethrin, clenpirin, cloethocarb, clofentezine, closantel, clothianidin, colophonate, copper naphthenate, copper oleate, copper sulfate, coumaphos, coumithoate, CPMC, crotamiton, crotoxyphos, crufomate, cryolite, cyanofenphos, cyanogen, cyanophos, cyanthoate, cyantraniliprole, cyclaniliprole, cyclethrin, cycloprate, cycloprothrin, cyenopyrafen, cyflumetofen, cyfluthrin, cyhalodiamide, cyhalothrin, cyhexatin, cymiazole, cypermethrin, cyromazine, cythioate, dayoutong, dazomet, DBCP, DCIP, decarbofuran, deltamethrin, demephion, demephion-O, demephion-S, demeton, demeton-methyl, demeton-O, demeton-O-methyl, demeton-S, demeton-S-methyl, demeton-S-methylsulphon, d-fanshiluquebingjuzhi, diafenthiuron, dialifos, diamidafos, diatomaceous earth, diazinon, dicapthon, dichlofenthion, dichlofluanid, dichlorbenzuron, dichlorvos, dicloromezotiaz, dicofol, dicresyl, dicrotophos, dicyclanil, dienochlor, diflovidazin, diflubenzuron, dilor, dimefluthrin, dimefox, dimetan, dimethacarb, dimethoate, dimethrin, dimethylvinphos, dimetilan, dinex, dinobuton, dinocap, dinocap-4, dinocap-6, dinocton, dinopenton, dinoprop, dinosam, dinosulfon, dinotefuran, dinoterbon, diofenolan, dioxabenzofos, dioxacarb, dioxathion, diphenyl sulfone, dipymetitrone, disulfiram, disulfoton, dithicrofos, dithioether, d-limonene, DNOC, dofenapyn, doramectin, ecdysterone, emamectin, EMPC, empenthrin, endothion, endrin, EPN, epofenonane, eprinomectin, epsilon-metofluthrin, epsilon-momfluorothrin, esdepallethrine, esfenvalerate, etaphos, ethiofencarb, ethion, ethiprole, ethoate-methyl, ethoprophos, ethyl formate, ethyl-DDD, ethylene dibromide, ethylene dichloride, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion-ethyl, fentrifanil, fenvalerate, ferric phosphate, fipronil, flometoquin, flonicamid, fluacrypyrim, fluazaindolizine, fluazuron, flubendiamide, flubenzimine, flucofuron, flucycloxuron, flucycloxuron, flucythrinate, fluenetil, fluensulfone, flufenerim, flufenoxuron, flufenoxystrobin, flufenprox, flufiprole, fluhexafon, flumethrin, fluorbenside, flupyradifurone, fluralaner, flursulamid, fluvalinate, fluxametamide, fonofos, formetanate, formetanate hydrochloride, formothion, formparanate, fosmethilan, fospirate, fosthiazate, fosthietan, furamethrin, furan tebufenozide, furathiocarb, furethrin, furfural, gamma-cyhalothrin, gamma-HCH, genit, guazatine, halfenprox, halofenozide, HCH, HEOD, heptafluthrin, heptenophos, heterophos, hexachlorophene, hexaflumuron, hexythiazox, HHDN, hydramethylnon, hydroprene, hyquincarb, imicyafos, imidacloprid, imidaclothiz, imiprothrin, indoxacarb, IPSP, isamidofos, isazofos, isobenzan, isocarbophos, isodrin, isofenphos, isofenphos-methyl, isolan, isoprocarb, isoprothiolane, isothioate, isoxathion, ivermectin, japothrins, jasmolin I, jasmolin II, jiahuangchongzong, jodfenphos, juvenile hormone I, juvenile hormone II, juvenile hormone III, kadethrin, kappa-bifenthrin, kappa-tefluthrin, kelevan, kinoprene, lambda-cyhalothrin, lepimectin, leptophos, lirimfos, lufenuron, lythidathion, malathion, malonoben, maltodextrin, matrine, mazidox, mecarbam, mecarphon, medimeform, menazon, meperfluthrin, mephosfolan, mesulfen, mesulfenfos, metaflumizone, metaldehyde, metam, methacrifos, methidathion, methiocarb, methocrotophos, methomyl, methoprene, methothrin, methoxychlor, methoxyfenozide, methyl iodide, methyl isothiocyanate, methylacetophos, methylchloroform, methylene chloride, metofluthrin, metolcarb, metoxadiazone, mevinphos, mexacarbate, milbemectin, milbemycin oxime, mipafox, mirex, MNAF, momfluorothrin, morphothion, moxidectin, naftalofos, naled, naphthalene, niclosamide, nicotine, nifluridide, nikkomycins, nitenpyram, nithiazine, nitrilacarb, nornicotine, novaluron, noviflumuron, omethoate, oxamyl, oxydemeton-methyl, oxydeprofos, oxydisulfoton, oxymatrine, paichongding, para-dichlorobenzene, penfluron, pentachlorophenol, pentmethrin, permethrin, phenkapton, phenothrin, phenproxide, phenthoate, phorate, phosalone, phosfolan, phosfolan-methyl, phosglycin, phosmet, phosnichlor, phosphine, phosphocarb, phostin, phoxim, phoxim-methyl, pirimetaphos, pirimicarb, pirimioxyphos, pirimiphos-ethyl, pirimiphos-methyl, plifenate, polythialan, potassium thiocyanate, prallethrin, precocene I, precocene II, precocene III, primidophos, proclonol, profenofos, profluthrin, promacyl, promecarb, propaphos, propargite, proparthrin, propetamphos, propoxur, prothidathion, prothiofos, prothoate, protrifenbute, pyflubumide, pymetrozine, pyraclofos, pyrafluprole, pyramat, pyrazophos, pyrazothion, pyresmethrin, pyrethrin I, pyrethrin II, pyrethrins, pyridaben, pyridalyl, pyridaphenthion, pyrifluquinazon, pyrimidifen, pyriminostrobin, pyrimitate, pyriprole, pyriproxyfen, pyrolan, quassia, quinalphos, quinalphos-methyl, quinothion, quintiofos, rafoxanide, resmethrin, rhodojaponin-III, rotenone, ryania, sabadilla, sanguinarine, schradan, selamectin, semiamitraz, semiamitraz chloride, silafluofen, silica gel, sodium fluoride, sodium hexafluorosilicate, sodium pentachlorophenoxide, sodium tetrathiocarbonate, sodium thiocyanate, sophamide, spinetoram, spinosad, spirodiclofen, spiromesifen, spirotetramat, sulcofuron, sulcofuron-sodium, sulfiram, sulfluramid, sulfotep, sulfoxaflor, sulfoxime, sulfur, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetramethylfluthrin, tetranactin, tetraniliprole, tetrasul, theta-cypermethrin, thiacloprid, thiamethoxam, thiapronil, thicrofos, thiocarboxime, thiocyclam, thiodicarb, thiofanox, thiofluoximate, thiometon, thionazin, thioquinox, thiosultap, thiosultap-sodium, tioxazafen, tirpate, tolfenpyrad, tralocythrin, tralomethrin, tralopyril, transpermethrin, triarathene, triazamate, triazophos, trichlorfon, trichlormetaphos-3, trichloronat, trifenmorph, trifenofos, triflumezopyrim, triflumuron, trimethacarb, triprene, triptolide, valerate, vamidothion, vaniliprole, xiaochongliulin, XMC, xylenols, xylylcarb, yishijing, zeta-cypermethrin, zolaprofos, α-ecdysone, AKD-1193, DKN-2601, IKI-3106, KUI-1103, KUI-1301, KYIF-1402, ME5382, MIE-1209, MIE-1405, MSI-1301, MSI-1302, NA-89, NC-515, ZDI-2501, ZDI-2502.

Examples of herbicides and algaecides include 2,3,6-TBA, 2,4,5-TB, 2,4-D, 2,4-DB, 2,4-DEB, 2,4-DEP, 3,4-DA, 3,4-DB, 3,4-DP, 4-CPA, 4-CPB, 4-CPP, acetochlor, acifluorfen, aclonifen, acrolein, allidochlor, alloxydim, allyl alcohol, alorac, ametridione, ametryn, amibuzin, amicarbazone, amidosulfuron, aminocyclopyrachlor, aminopyralid, amiprofos-methyl, amiprophos, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, bentranil, benzadox, benzalkonium chloride, benzfendizone, benzipram, benzobicyclon, benzofenap, benzofluor, benzoylprop, benzthiazuron, bethoxazin, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornidine, chlornitrofen, chloropon, chlorotoluron, chloroxuron, chloroxynil, chlorprocarb, chlorpropham, chlorsulfuron, chlorthal, chlorthiamid, cinidon-ethyl, cinmethylin, cinosulfuron, cisanilide, clacyfos, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanamide, cyanatryn, cyanazine, cyanogen, cybutryne, cycloate, cyclopyrimorate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichlone, dichloralurea, dichlormate, dichlorophen, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoterb, diphenamid, dipropalin, dipropetryn, diquat, disul, dithioether, dithiopyr, diuron, DMPA, DNOC, DSMA, EBEP, eglinazine, endothal, epronaz, EPTC, erbon, erlujixiancaoan, esprocarb, ethachlor, ethalfluralin, ethametsulfuron, ethaprochlor, ethidimuron, ethiolate, ethiozin, ethofumesate, ethoxyfen, ethoxysulfuron, etinofen, etnipromid, etobenzanid, EXD, fenasulam, fenoprop, fenoxaprop, fenoxaprop-P, fenoxasulfone, fenquinotrione, fenteracol, fenthiaprop, fentin, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, fucaojing, fucaomi, funaihecaoling, furyloxyfen, glufosinate, glufosinate-P, glyphosate, halauxifen, halosafen, halosulfuron, haloxydine, haloxyfop, haloxyfop-P, herbimycin, hexachloroacetone, hexaflurate, hexazinone, huancaiwo, huangcaoling, hydrated lime, imazamethabenz, imazamox, imazapic, imazapyr, imazaquin, imazethapyr, imazosulfuron, indanofan, indaziflam, iodobonil, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, kuicaoxi, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiopyrisulfuron, methiozolin, methiuron, methometon, methoprotryne, methoxyphenone, methyl bromide, methyl iodide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monosulfuron, monuron, morfamquat, MSMA, nabam, naproanilide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenyl laurate, pentanochlor, pentoxazone, perfluidone, pethoxamid, phenisopham, phenmedipham, phenmedipham-ethyl, phenobenzuron, picloram, picolinafen, pinoxaden, piperophos, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribambenzisopropyl, pyribambenz-propyl, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, sebuthylazine, secbumeton, sethoxydim, shuangjiaancaolin, siduron, simazine, simeton, simetryn, SMA, S-metolachlor, sodium chlorate, sulcotrione, sulfallate, sulfentrazone, sulfometuron, sulfosulfuron, sulglycapin, swep, tavron, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone, thifensulfuron, thiobencarb, tiafenacil, tiocarbazil, tioclorim, tolpyralate, topramezone, tralkoxydim, triafamone, triallate, triasulfuron, triaziflam, tribenuron, tricamba, triclopyr, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, xylachlor, zuomihuanglong, DAH-500, SL-261.

Examples of microbial pesticides include Nuclear polyhedrosis virus (NPV), Granulosis virus (GV), Cytoplasmic polyhedrosis virus (CPV), *Steinernema carpocapsae, Steinernema glaseri, Monacrosporium phymatophagum, Steinernema kushidai, Pasteuria penetrans, Agrobacterium radiobacter, Bacillus subtilis, Bucillus amyloliquefaciens, Erwinia carotovora, Pseudomonas fluorescens, Talaromyces flavus, Trichoderma atroviride, Bacillus thuringiensis, Beauveria brongniartii, Beauveria bassiana, Paecilomyces fumosoroseus, Verticillium lecanii, Xanthomonas campestris, Encarsia formosa, Eretmocerus eremicus, Eretmocerus mundus, Aphidoletes aphidimyza, Aphidoletes aphidimyza, Diglyphus isaea, Dacnusa sibirica, Phytoseiulus persimilis, Amblyseius cucumeris, Amblyseius californicus, Orius strigicollis.*

Examples of pheromone agents (insect pest attractants) include brevicomin, ceralure, codlelure, cue-lure, disparlure, dominicalure-1, eugenol, frontalin, gossyplure, grandlure, hexalure, ipsdienol, ipsenol, japonilure, latilure, lineatin, litlure, looplure, medlure, megatomoic acid, methyl eugenol, moguchun, muscalure, orfralure, oryctalure, ostramone, rescalure, siglure, sulcatol, trimedlure, trunc-call, α-multistriatin.

Examples of pheromone agents (insect pest repellants) include acrep, butopyronoxyl, camphor, d-camphor, carboxide, dibutyl phthalate, diethyltoluamide, dimethyl carbate, dimethyl phthalate, dibutyl succinate, ethohexadiol, hexamide, icaridin, methoquin-butyl, methylneodecanamide, 2-(octylthio)ethanol, oxamate, quwenzhi, quyingding, rebemide, zengxiaoan.

Examples of natural fungicides and natural pesticides include machine oils, methylphenyl acetate, α-pinene, protein hydrolysate, (Z)-1-Tetradecen-1-ol, Turpentine.

The fungicidal composition of the present invention may include one type or two or more types of compounds shown by formula [1] of the present invention or a salt thereof.

The percentages of respective compounds of formula [1] of the present invention in the fungicidal composition of the present invention are appropriately selected as necessary, and if the composition is in the form of powders or granules, it should be selected from the range of 0.001-10 wt %, preferably 0.005-5 wt %. If the composition is in the form of emulsions or wettable powders, it should be selected from the range of selected from the range of 1-50 wt %, preferably 5-30 wt %. Also, if the composition is in the form of floable agents, it should be selected from the range of selected from the range of 1-50 wt %, preferably 5-30 wt %.

The application amount of the fungicidal composition of the present invention differs by the types of compounds used, the subject crop, the subject disease, the tendency of occurrence, environmental conditions, and the formulation shape to be used, but if the composition is used in the original shape as in powders and granules, it may be selected as necessary as active components from the range of 1 g-50 kg, preferably 10 g-10 kg per 1 hectare. Further, if the composition is to be used in a liquid state as in emulsions, wettable powder or floable agents, it may be selected as necessary from the range of 0.1-50,000 ppm, preferably 10-10,000 ppm.

EXAMPLES

A person skilled in the art would recognize that the compound and intermediate of formula [1] in the present specification may be subjected to various electrophilic reaction, nucleophilic reaction, radical reaction, organic metal reaction, oxidation reaction, reduction reaction, to add substituents or to modify existing substituents.

A person skilled in the art making use of the above description should be able to use the present invention to the full extent without further explanation. Hence, the following Examples just exemplify the invention, and they do not limit this disclosure in any sense. The steps in the examples explains the procedures of the steps in the entire synthetic evolvement, and the starting material in each step does not necessarily have to be prepared by the performance of specific preparation methods shown in other examples or steps.

Note that "%" shows a weight percentage and "part" shows a weight part in the following description.

(1) Preparation of 4-[4-(6,9-difluoro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine (Compound 1-3)

The compound 4-(4-formyl-2-thiazolyl)-1-[2-[5-methyl-3-(trifluoromethyl)-1H-pyrazole-1-yl]acetyl]piperidine (210 mg) (compound in WO 2008/013622) and 3,6-difluoro-1,2-benzene dimethanol (210 mg) and para-toluene sulfonic acid monohydrate (11 mg) were dissolved in toluene (15 mL), and the mixture was subjected to heating/reflux using a Dean-Stark device for 1 hr. After the reaction mixture was cooled to room temperature, it was diluted with ethyl acetate and washed with water and brine. The organic layer was dried with anhydrous sodium sulfate, then the inorganic substance was filtered out, and the solvent was distilled under reduced pressure. The residue was purified using silica gel flash chromatography (eluted with ethyl acetate-hexane: 40%-100%) by automatic flash purification system (produced by Biotage AB/Isolera™) to obtain the subject compound as a white amorphous solid (245 mg, yield 83%).

(2) Preparation of 4-[4-(6-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine (Compound 1-6)

The compound 4-(4-formyl-2-thiazolyl)-1-[2-[5-methyl-3-(trifluoromethyl)-1H-pyrazole-1-yl]acetyl]piperidine (200 mg) and 3-methylsulfonyloxy-1,2-benzenedimethanol (121 mg) and para-toluenesulfonic acid monohydrate (20 mg) were dissolved in toluene (20 mL), then reacted and purified similarly to the preparation of Compound 1-3 to obtain the subject compound as a white amorphous solid (298 mg, yield 96%).

(3) Preparation of 4-[4-(6-fluoro-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine (Compound 1-8)

The compound 4-(4-formyl-2-thiazolyl)-1-[2-[5-methyl-3-(trifluoromethyl)-1H-pyrazole-1-yl]acetyl]piperidine (220 mg) and 3-fluoro-6-methylsulfonyloxy-1,2-benzenedimethanol (150 mg) and para-toluenesulfonic acid monohydrate (20 mg) were dissolved in toluene (15 mL), then reacted and purified similarly to the preparation of Compound 1-3 to obtain the subject compound as a white amorphous solid (297 mg, yield 84%). Methanol was added to the resulting amorphous solid, and the substance was dissolved under heating/reflux and then the solution was left at room temperature to obtain a white crystal (melting point 151° C.)

(4) Preparation of 4-[4-(6-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine (Compound 1-38)

The compound 4-(4-formyl-2-thiazolyl)-1-[2-[3,5-bis(difluoromethyl)-1H-pyrazole-1-yl]acetyl]piperidine (202 mg) (compound in WO 2010/066353) and 3-methylsulfonyloxy-1,2-benzenedimethanol (232 mg) and para-toluenesulfonic acid monohydrate (5 mg) were dissolved in toluene (15 mL), then reacted and purified similarly to the preparation of Compound 1-3 to obtain the subject compound as a white amorphous solid (164 mg, yield 53%).

(5) Preparation of 4-[4-(6-methoxy-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine (Compound 1-39)

The compound 4-(4-formyl-2-thiazolyl)-1-[2-[3,5-bis(difluoromethyl)-1H-pyrazole-1-yl]acetyl]piperidine (202 mg) and 3-methoxy-6-methylsulfonyloxy-1,2-benzenedimethanol (232 mg) and para-toluenesulfonic acid monohydrate (5 mg) were dissolved in toluene (15 mL), then reacted and purified similarly to the preparation of Compound 1-3 to obtain the subject compound as a white amorphous solid (268 mg, yield 75%).

(6) Preparation of 4-[4-(6-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine (Compound 1-42)

The compound 4-(4-formyl-2-thiazolyl)-1-[2-[3,5-bis(trifluoromethyl)-1H-pyrazole-1-yl]acetyl]piperidine (200 mg) (synthesized in the same way as 4-(4-formyl-2-thiazolyl)-1-[2-[5-methyl-3-(trifluoromethyl)-1H-pyrazole-1-yl]acetyl]piperidine) and 3-methylsulfonyloxy-1,2-benzenedimethanol (109 mg) and para-toluenesulfonic acid monohydrate (5 mg) were dissolved in toluene (100 mL), then reacted and purified similarly to the preparation of Compound 1-3 to obtain the subject compound as a white amorphous solid (96 mg, yield 31%).

(7) Preparation of 4-[4-(6,9-difluoro-1,5-dihydro-3H-2,4-benzodioxepin-3-yl)-2-thiazolyl]-1-[2-[3,5-bis(trifluoromethyl)-1H-pyrazole-1-yl]acetyl]piperidine (Compound 1-50)

The compound 4-(4-formyl-2-thiazolyl)-1-[2-[3,5-bis(trifluoromethyl)-1H-pyrazole-1-yl]acetyl]piperidine (200 mg) and 3,6-difluoro-1,2-benzenedimethanol (82 mg) and para-toluenesulfonic acid monohydrate (5 mg) were dissolved in toluene (100 mL), then reacted and purified similarly to the preparation of Compound 1-3 to obtain the subject compound as a white amorphous solid (183 mg, yield 53%).

(8) Preparation of 4-[4-(6-fluoro-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine (Compound 1-62)

The compound 4-(4-formyl-2-thiazolyl)-1-[2-[3,5-bis(difluoromethyl)-1H-pyrazole-1-yl]acetyl]piperidine (202 mg) and 3-fluoro-6-methylsulfonyloxy-1,2-benzenedimethanol (250 mg) and para-toluenesulfonic acid monohydrate (5 mg) were dissolved in toluene (15 mL), then reacted and purified similarly to the preparation of Compound 1-3 to obtain the subject compound as a white amorphous solid (105 mg, yield 33%).

(9) Preparation of 4-[4-(6-methylsulfonyloxy-1,5-dihydro-3H-2,4-benzodioxepin-3-yl)-2-thiazolyl]-1-[2-(2,5-dimethylphenyl)acetyl]piperidine (Compound 2-1)

The compound 4-(4-formyl-2-thiazolyl)-1-[2-(2,5-dimethylphenyl)acetyl]piperidine (200 mg) and 3-methylsulfonyloxy-1,2-benzenedimethanol (142 mg) and para-toluenesulfonic acid monohydrate (20 mg) were dissolved in toluene (15 mL), then reacted and purified similarly to the preparation of Compound 1-3 to obtain the subject compound as a white amorphous solid (206 mg, yield 64%).

(10) Preparation of 4-[4-(6-methylsulfonyloxy-1,5-dihydro-3H-2,4-benzodioxepin-3-yl)-2-thiazolyl]-1-[2-(2,5-dichlorophenyl)acetyl]piperidine (Compound 2-2)

The compound 4-(4-formyl-2-thiazolyl)-1-[2-(2,5-dichlorophenyl)acetyl]piperidine (191 mg) and 3-methylsulfonyloxy-1,2-benzenedimethanol (232 mg) and para-toluenesulfonic acid monohydrate (5 mg) were dissolved in toluene (15 mL), then reacted and purified similarly to the preparation of Compound 1-3 to obtain the subject compound as a white amorphous solid (267 mg, yield 72%).

(11) Preparation of 4-[4-(6,9-difluoro-1,5-dihydro-3H-2,4-benzodioxepin-3-yl)-2-thiazolyl]-1-[2-(2,5-dichlorophenyl)acetyl]piperidine (Compound 2-4)

The compound 4-(4-formyl-2-thiazolyl)-1-[2-(2,5-dichlorophenyl)acetyl]piperidine (191 mg) and 3,6-difluoro-1,2-benzenedimethanol (174 mg) and para-toluenesulfonic acid monohydrate (5 mg) were dissolved in toluene (15 mL), then reacted and purified similarly to the preparation of Compound 1-3 to obtain the subject compound as a white amorphous solid (231 mg, yield 86%).

(12) Preparation of 4-[4-(6-methylsulfonyloxy-1,5-dihydro-3H-2,4-benzodioxepin-3-yl)-2-thiazolyl]-1-[N-(2,5-dimethylphenyl)carbamoyl]piperidine (Compound 2-5)

Step 1: Preparation of 4-(4-formyl-2-thiazolyl)piperidine trifluoroacetic acid salt The compound 4-(4-formyl-2-thiazolyl)piperidine carboxylic acid 1,1-dimethylethyl ester (3.9 g) (compound of WO 2008/013622) was dissolved in dichloromethane (65 mL), then trifluoroacetic acid (15.2 mL) was added, and the mixture was stirred at room temperature overnight. Trifluoroacetic acid was distilled under reduced pressure, which led to the generation of 4-(4-formyl-2-thiazolyl)piperidine trifluoroacetic acid salt.

Step 2: Preparation of 4-(4-formyl-2-thiazolyl)-1-[N-(2,5-dimethylphenyl)carbamoyl]piperidine Triphosgene (1.88 g) was dissolved in dichloromethane (50 mL), then pyridine (1.37 g) was added under ice cold condition, and after the mixture was stirred for 10 min., 2,5-dimethylaniline (1.92 g) was dropped. The residue was dissolved with dichloromethane (45 mL), to which 4-(4-formyl-2-thiazolyl)piperidine trifluoroacetic acid salt (4.0 g) of step 1 and triethyl amine (4.0 g) were added under ice cold condition, and the mixture was stirred under room temperature. Water was added to the reaction mixture, and extraction was performed using dichloromethane, after which the obtained product was washed with water and brine. The organic layer was dried with anhydrous sodium sulfate, then the inorganic substance was filtered out, and the solvent was distilled under reduced pressure. The residue was purified using silica gel flash chromatography (eluted with ethyl acetate-hexane: 50%-100%) by automatic flash purification system (produced by Biotage AB/Isolera™) to obtain 4-(4-formyl-2-thiazolyl)-1-[N-(2,5-dimethylphenyl)carbamoyl]piperidine as a yellow amorphous solid (3.8 g, yield 84%).

Step 3: Preparation of 4-[4-(6-methylsulfonyloxy-1,5-dihydro-3H-2,4-benzodioxepin-3-yl)-2-thiazolyl]-1-[N-(2,5-dimethylphenyl)carbamoyl]piperidine The compound 4-(4-formyl-2-thiazolyl)-1-[N-(2,5-dimethylphenyl)carbamoyl]piperidine (300 mg) and 3-methylsulfonyloxy-1,2-benzenedimethanol (300 mg) and para-toluenesulfonic acid monohydrate (5 mg) were dissolved in toluene (15 mL), then reacted and purified similarly to the preparation of Compound 1-3 to obtain the subject compound as a white amorphous solid (250 mg, yield 52%).

(13) Preparation of 4-[4-(6-methylsulfonyloxy-1,5-dihydro-3H-2,4-benzodioxepin-3-yl)-2-thiazolyl]-1-[2-[(propane-2-ylideneamino)oxy]acetyl]piperidine (Compound 3-1)

Step 1: Preparation of 4-(4-formyl-2-thiazolyl)piperidine

The compound 4-(4-formyl-2-thiazolyl)piperidine carboxylic acid 1,1-dimethylethyl ester (2.0 g) was dissolved in dichloromethane (68 mL), then trifluoroacetic acid (10 mL) was added, and the mixture was stirred at room temperature overnight. Trifluoroacetic acid was distilled under reduced pressure, saturated potassium carbonate solution was added and extraction was performed using chloroform. The organic layer was dried with anhydrous sodium sulfate, then the inorganic substance was filtered out, and the solvent was distilled under reduced pressure to obtain 4-(4-formyl-2-thiazolyl)piperidine (1.37 g, yield 84%).

Step 2: Preparation of 4-(4-formyl-2-thiazolyl)-1-(2-bromoacetyl)piperidine

The compound 4-(4-formyl-2-thiazolyl)piperidine (1.37 g) was dissolved in dichloromethane (57 mL), then bromoacetic acid (0.87 g) and N-(3-dimethylaminopropyl)-N'-ethylcarbodiimide (1.2 g) were added, and the mixture was stirred at room temperature for 2 hours. Water was added to the reaction mixture, and extraction was performed using dichloromethane, after which the obtained product was washed with water and brine. The organic layer was dried with anhydrous sodium sulfate, then the inorganic substance was filtered out, and the solvent was distilled under reduced pressure. The residue was purified using flash chromatography (eluted with ethyl acetate-hexane: 25%-100%) by automatic flash purification system (produced by Biotage AB/Isolera™) to obtain 4-(4-formyl-2-thiazolyl)-1-(2-bromoacetyl)piperidine as a yellow amorphous solid (0.8 mg, yield 36%).

Step 3: Preparation of 4-(4-formyl-2-thiazolyl)-1-[2-[(propane-2-ylideneamino)oxy]acetyl]piperidine The compound 4-(4-formyl-2-thiazolyl)-1-(2-bromoacetyl)piperidine (0.7 g) was dissolved in N,N-dimethylformamide (50 mL), then acetoxime (0.24 g) and potassium carbonate (0.61 g) were added, and the mixture was stirred at 90° C. for 4 hours. Water was added to the reaction mixture, and extraction was performed using chloroform, after which the obtained product was washed with water and brine. The organic layer was dried with anhydrous sodium sulfate, then the inorganic substance was filtered out, and the solvent was distilled under reduced pressure. The residue was purified using flash chromatography (eluted with ethyl acetate-hexane: 33%-100%) by automatic flash purification system (produced by Biotage AB/Isolera™) to obtain 4-(4-formyl-2-thiazolyl)-1-[2-[(propane-2-ylideneamino)oxy]acetyl]piperidine as a yellow amorphous solid (100 mg, yield 13%).

Step 4: Preparation of 4-[4-(6-methylsulfonyloxy-1,5-dihydro-3H-2,4-benzodioxepin-3-yl)-2-thiazolyl]-1-[2-[(propane-2-ylideneamino)oxy]acetyl]piperidine The compound 4-(4-formyl-2-thiazolyl)-1-[2-[(propane-2-ylideneamino)oxy]acetyl]piperidine (100 mg) and 3-methylsulfonyloxy-1,2-benzenedimethanol (113 mg) and para-toluenesulfonic acid monohydrate (5 mg) were dissolved in toluene (15 mL), then reacted and purified similarly to the preparation of Compound 1-3 to obtain the subject compound as a white amorphous solid ((30 mg, yield 19%).

(14) Preparation of 4-[4-(6-methylsulfonyloxy-1,5-dihydro-3H-2,4-benzodioxepin-3-yl)-2-thiazolyl]-1-[(Z)-[(2,5-dimethylphenyl)imino](methoxy)methyl]piperidine (Compound 4-1)

The compound 4-[4-(6-methylsulfonyloxy-1,5-dihydro-3H-2,4-benzodioxepin-3-yl)-2-thiazolyl]-1-[N-(2,5-dimethylphenyl)carbamoyl]piperidine (compound produced in Example (12)) (230 mg) was dissolved in tetrahydrofuran (10 mL), then sodium hydride (44 mg, oiliness 50%) was added under ice cold condition, and the the mixture was stirred for 10 min. To the solution, methyl iodide (140 mg) was added under ice cold condition, and the mixture was stirred under room temperature overnight. Water (10 mL) was added to the reaction mixture, and extraction was performed using ethyl acetate. The organic layer was dried with anhydrous sodium sulfate, then the inorganic substance was filtered out, and the solvent was distilled under reduced pressure. The residue was purified using silica gel flash chromatography (eluted with ethyl acetate-hexane: 10%-50%) by automatic flash purification system (produced by Biotage AB/Isolera™) to obtain the subject compound as a yellow amorphous solid (37 mg, yield 16%).

In (15)-(18) below, the production examples of production starting material used in the above (1)-(14) are shown.

(15) Preparation of 3,6-difluoro-1,2-benzenedimethanol

To 27 mL of tetrahydrofuran, lithium aluminum hydride (870 mg) and 3,6-difluoro phthalic anhydride were dissolved in that order under ice cold condition, and the reaction mixture was subjected to heating/reflux for 2 hr. The reaction mixture was cooled to room temperature, then water was added under ice cold condition and the liquid was stirred at room temperature for 1 hr. The solution was filtered using a celite, and the solvent was distilled under reduced pressure to obtain the subject compound as a white crystal (640 mg, yield 68%).

$^1$H-NMR (CDCl$_3$/TMS δ (ppm) value): 2.89 (brs, 2H), 4.84 (s, 4H), 7.03 (dd, 2H)

(16) Preparation of 3-methylsulfonyloxy-1,2-benzenedimethanol

The compound 3-methylsulfonyloxy phthalic anhydride (2.2 g) (compound of WO 2004/000796) was dissolved in tetrahydrofuran (60 mL), then borane tetrahydrofuran complex (0.9M tetrahydrofuran solution, 50 mL) was added, and the the mixture was stirred at 60° C. for 6 hr. After the reaction completed, methanol was added under ice cold condition, and the solvent was distilled under reduced pressure. The residue was diluted using ethyl acetate, and washed with 1N hydrochloric acid, brine. The organic layer was dried with anhydrous sodium sulfate, then the inorganic substance was filtered out, and the solvent was distilled under reduced pressure. The residue was purified using silica gel flash chromatography (eluted with ethyl acetate-hexane: 30%-100%) by automatic flash purification system (produced by Biotage AB/Isolera™) to obtain 3-methylsulfonyloxy-1,2-benzenedimethanol as a white crystal (1.36 mg, yield 64%, melting point 56-58° C.).

$^1$H-NMR (DMSO-d6/TMS δ (ppm) value): 3.42 (s, 3H), 4.57 (d, 2H), 4.70 (d, 2H), 4.98 (t, 1H), 5.27 (t, 1H), 7.25 (d, 1H), 7.36 (t, 1H), 7.46 (d, 1H)

(17) Preparation of 3-fluoro-6-methylsulfonyloxy-1,2-benzenedimethanol

Step 1: Preparation of 5-fluoro-2-methylsulfonyloxyphthalide

The compound 5-fluoro-2-hydroxyphthalide (200 mg) (compound of WO 2003/076424) was dissolved in N,N-dimethylformamide (10 mL), then methylsulfonyl chloride (150 mg) and triethyl amine (133 mg) were added, and the the mixture was stirred at room temperature over night. The reaction mixture was diluted with ethyl acetate and washed with brine. The organic layer was dried with anhydrous sodium sulfate, then the inorganic substance was filtered out, and the solvent was distilled under reduced pressure to obtain 5-fluoro-2-methylsulfonyloxyphthalide as a white crystal (290 mg, yield 100%).

Step 2: Preparation of 3-fluoro-6-methylsulfonyloxy-1,2-benzenedimethanol

The compound 5-fluoro-2-methylsulfonyloxyphthalide (290 mg) was dissolved in tetrahydrofuran (10 mL), then lithium aluminum hydride (45 mg) was added, and the the mixture was stirred at room temperature for 30 min. To the reaction mixture, 1N hydrochloric acid was added under ice cold condition, and the mixture was stirred at room temperature for 1 hr. The reaction mixture was subjected to extraction using dichloromethane, and washed with brine. The organic layer was dried with anhydrous sodium sulfate, and the inorganic substance was filtered out, then the solvent was distilled under reduced pressure to obtain 3-fluoro-6-methylsulfonyloxy-1,2-benzenedimethanol as a white crystal (290 mg, yield 100%, melting point 85-87° C.).

$^1$H-NMR (CDCl$_3$/TMS δ (ppm) value): 3.28 (s, 3H), 3.45 (brs, 2H), 4.84 (s, 4H), 7.11 (dd, 1H), 7.25-7.28 (m, 1H)

(18) Preparation of 3-methoxy-6-methylsulfonyloxy-1,2-benzenedimethanol

Step 1: Preparation of 2,3-bis(methoxycarbonyl)-1-methoxy-4-methylsulfonyloxybenzene The compound 2,3-bis(methoxycarbonyl)-4-methoxyphenol (2.0 g) (compound of Synthetic Communication, 43(2), 260-267; 2013) was dissolved in tetrahydrofuran (30 mL), then methylsulfonyl chloride (1.05 g) and triethyl amine (1.01 g) were added, and the the mixture was stirred at room temperature for 1 hr. Water was added to the reaction mixture, and extraction was performed using ethyl acetate, after which the obtained product was washed with water and brine. The organic layer was dried with anhydrous sodium sulfate, then the inorganic substance was filtered out, and the solvent was distilled under reduced pressure to obtain 2,3-bis(methoxycarbonyl)-1-methoxy-4-methylsulfonyloxybenzene as a white crystal (2.5 g, yield 100%).

Step 2: Preparation of 3-methoxy-6-methylsulfonyloxy-1,2-benzenedimethanol

The compound 2,3-bis(methoxycarbonyl)-1-methoxy-4-methylsulfonyloxybenzene (2.5 g) was dissolved in tetrahydrofuran (30 mL), then lithium aluminum hydride (620 mg) was added under ice cold condition, and the mixture was stirred under ice cold condition for 1 hr. To the reaction mixture, 1N hydrochloric acid was added under ice cold condition, and the mixture was stirred at room temperature for 1 hr. The reaction mixture was subjected to extraction using ethyl acetate, and washed with brine. The organic layer was dried with anhydrous sodium sulfate, then the inorganic substance was filtered out, and the result was distilled under reduced pressure. The residue was purified using silica gel flash chromatography (eluted with ethyl acetate-hexane: 30%-100%) by automatic flash purification system (produced by Biotage AB/Isolera™) to obtain 3-methoxy-6-methylsulfonyloxy-1,2-benzenedimethanol as a white crystal (906 mg, yield 42%).

$^1$H-NMR (DMSO-d6/TMS δ (ppm) value): 3.39 (s, 3H), 3.81 (s, 3H), 4.62-4.64 (m, 4H), 4.84 (t, 1H), 5.06 (t, 1H), 7.03 (d, 1H), 7.28 (d, 1H)

The compounds shown in [Table 161] to [Table 170] were synthesized by the same production method.

TABLE 161

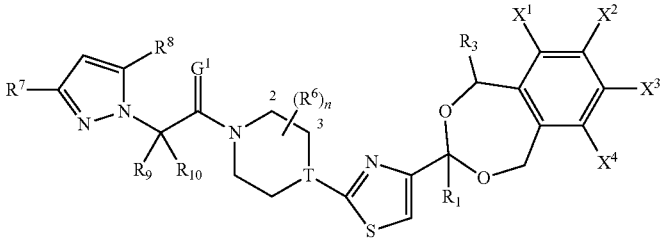

[1a]

| No. | $R^7$ | $R^8$ | $R^9$ | $R^{10}$ | $G^1$ | $R^6$ | n | T | $R^1$ | $R^3$ | $X^1$ | $X^2$ | $X^3$ | $X^4$ |
|---|---|---|---|---|---|---|---|---|---|---|---|---|---|---|
| 1-1 | $CF_3$ | Me | H | H | O | — | 0 | CH | H | H | H | H | H | H |
| 1-2 | $CF_3$ | Me | H | H | O | — | 0 | CH | H | H | F | H | H | H |
| 1-3 | $CF_3$ | Me | H | H | O | — | 0 | CH | H | H | F | H | H | F |
| 1-4 | $CF_3$ | Me | H | H | O | — | 0 | CH | H | H | H | Me | Me | H |
| 1-5 | $CF_3$ | Me | H | H | O | — | 0 | CH | H | H | H | Cl | Cl | H |
| 1-6 | $CF_3$ | Me | H | H | O | — | 0 | CH | H | H | $OSO_2Me$ | H | H | H |
| 1-7 | $CF_3$ | Me | H | H | O | — | 0 | CH | H | H | $OSO_2Et$ | H | H | H |
| 1-8 | $CF_3$ | Me | H | H | O | — | 0 | CH | H | H | $OSO_2Me$ | H | H | F |
| 1-9 | $CF_3$ | Me | H | H | O | — | 0 | CH | H | H | H | $OSO_2Me$ | H | H |
| 1-10 | $CF_3$ | Me | H | H | O | — | 0 | CH | H | H | H | —CH=CH—CH=CH— | | H |
| 1-11 | $CF_3$ | Me | H | H | O | — | 0 | CH | H | H | H | F | H | H |
| 1-12 | $CF_3$ | Me | H | H | O | — | 0 | CH | H | H | $NO_2$ | H | H | H |
| 1-13 | $CF_3$ | Me | H | H | O | — | 0 | CH | H | H | $OSO_2$c-Pr | H | H | H |
| 1-14 | $CF_3$ | Me | H | H | O | — | 0 | CH | H | H | Me | H | H | H |
| 1-15 | $CF_3$ | Me | H | H | O | — | 0 | CH | H | H | Br | H | H | H |
| 1-16 | $CF_3$ | Me | H | H | O | — | 0 | CH | H | H | H | $CF_3$ | H | H |
| 1-17 | $CF_3$ | Me | H | H | O | — | 0 | CH | H | H | F | F | F | F |
| 1-18 | $CF_3$ | Me | H | H | O | — | 0 | CH | H | Me | H | H | H | H |
| 1-19 | $CF_3$ | Me | H | H | O | — | 0 | CH | H | H | $OSO_2Me$ | H | H | Me |
| 1-20 | $CF_3$ | Me | H | H | O | — | 0 | CH | H | H | H | Me | H | H |
| 1-21 | $CF_3$ | Me | H | H | O | — | 0 | CH | H | H | $OSO_2$n-Bu | H | H | H |
| 1-22 | $CF_3$ | Me | H | H | O | — | 0 | CH | H | H | $OSO_2$n-Pr | H | H | H |
| 1-23 | $CF_3$ | Me | H | H | O | — | 0 | CH | H | H | Cl | H | H | H |
| 1-24 | $CF_3$ | Me | H | H | O | — | 0 | CH | H | H | OMe | H | H | Br |
| 1-25 | $CF_3$ | Me | H | H | O | — | 0 | CH | H | H | $OSO_2$n-$C_8H_{17}$ | H | H | H |
| 1-26 | $CF_3$ | Me | H | H | O | — | 0 | CH | H | H | $OSO_2Me$ | H | H | OMe |
| 1-27 | $CF_3$ | Me | H | H | O | — | 0 | CH | H | H | H | $NO_2$ | H | H |
| 1-28 | $CF_3$ | Me | H | H | O | — | 0 | CH | H | H | $OSO_2$i-Pr | H | H | H |
| 1-29 | $CF_3$ | Me | H | H | O | — | 0 | CH | H | H | H | $OSO_2Et$ | H | H |
| 1-30 | $CF_3$ | Me | H | H | O | — | 0 | CH | H | H | $OSO_2CH_2CH_2CF_3$ | H | H | H |
| 1-31 | $CF_3$ | Me | H | H | O | — | 0 | CH | H | H | H | —$CH_2CH_2CH_2$— | | H |
| 1-32 | $CF_3$ | Me | H | H | O | — | 0 | CH | H | H | $OSO_2Me$ | H | H | $NO_2$ |
| 1-33 | $CF_3$ | Me | H | H | O | — | 0 | CH | H | H | OH | H | H | H |
| 1-34 | $CF_3$ | Me | H | H | O | — | 0 | CH | H | H | OC(=O)c-Pr | H | H | H |
| 1-35 | $CHF_2$ | $CHF_2$ | H | H | O | — | 0 | CH | H | H | F | H | H | H |
| 1-36 | $CF_3$ | Me | H | H | O | — | 0 | CH | H | H | $OSO_2CF_3$ | H | H | H |
| 1-37 | $CF_3$ | Me | H | H | O | — | 0 | CH | H | H | OC(=O)OMe | H | H | H |
| 1-38 | $CHF_2$ | $CHF_2$ | H | H | O | — | 0 | CH | H | H | $OSO_2Me$ | H | H | H |
| 1-39 | $CHF_2$ | $CHF_2$ | H | H | O | — | 0 | CH | H | H | $OSO_2Me$ | H | H | OMe |
| 1-40 | $CF_3$ | Me | H | H | O | — | 0 | CH | H | H | H | Cl | H | H |

TABLE 161-continued

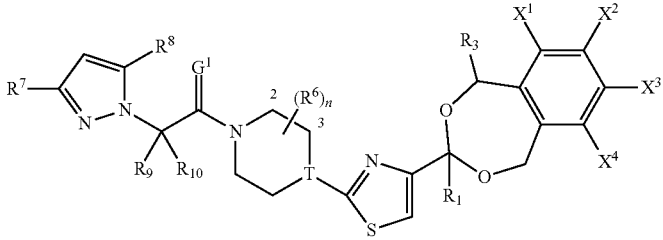

| No. | R⁷ | R⁸ | R⁹ | R¹⁰ | G¹ | R⁶ | n | T | R¹ | R³ | X¹ | X² | X³ | X⁴ |
|---|---|---|---|---|---|---|---|---|---|---|---|---|---|---|
| 1-41 | $CF_3$ | $CF_3$ | H | H | O | — | 0 | CH | H | H | F | H | H | H |
| 1-42 | $CF_3$ | $CF_3$ | H | H | O | — | 0 | CH | H | H | $OSO_2Me$ | H | H | H |
| 1-43 | $CF_3$ | Me | H | H | O | — | 0 | CH | H | H | $NHSO_2Me$ | H | H | H |

TABLE 162

| No. | R⁷ | R⁸ | R⁹ | R¹⁰ | G¹ | R⁶ | n | T | R¹ | R³ | X¹ | X² | X³ | X⁴ |
|---|---|---|---|---|---|---|---|---|---|---|---|---|---|---|
| 1-44 | $CHF_2$ | $CHF_2$ | H | H | O | — | 0 | CH | H | H | $OSO_2Me$ | H | H | Me |
| 1-45 | $CF_3$ | Me | H | H | O | — | 0 | CH | H | H | $OSO_2Me$ | F | H | H |
| 1-46 | $CF_3$ | Me | H | H | O | — | 0 | CH | H | H | OMe | H | H | $NO_2$ |
| 1-47 | $CF_3$ | Me | H | H | O | — | 0 | CH | H | H | $SO_2Me$ | H | H | H |
| 1-48 | $CF_3$ | Me | H | H | O | — | 0 | CH | H | H | $OSO_2Ph$ | H | H | H |
| 1-49 | $CHF_2$ | $CHF_2$ | H | H | O | — | 0 | CH | H | H | H | $NO_2$ | H | H |
| 1-50 | $CF_3$ | $CF_3$ | H | H | O | — | 0 | CH | H | H | F | H | H | F |
| 1-51 | $CHF_2$ | $CHF_2$ | H | H | O | — | 0 | CH | H | H | F | H | H | F |
| 1-52 | $CF_3$ | Me | H | H | O | — | 0 | CH | H | H | $CH_2OH$ | H | H | H |
| 1-53 | $CHF_2$ | $CHF_2$ | H | H | O | — | 0 | CH | H | H | $OSO_2$i-Pr | H | H | H |
| 1-54 | $CHF_2$ | $CHF_2$ | H | H | O | — | 0 | CH | H | H | $OSO_2$n-Bu | H | H | H |
| 1-55 | $CHF_2$ | $CHF_2$ | F | H | O | — | 0 | CH | H | H | F | F | F | F |
| 1-56 | $CF_3$ | Me | H | H | O | — | 0 | CH | H | H | Ph | H | H | H |
| 1-57 | $CHF_2$ | $CHF_2$ | H | H | O | — | 0 | CH | H | H | OMe | H | H | Br |
| 1-58 | $CHF_2$ | $CHF_2$ | H | H | O | — | 0 | CH | H | H | Cl | H | H | H |
| 1-59 | $CHF_2$ | $CHF_2$ | H | H | O | — | 0 | CH | H | H | $OSO_2$n-$C_8H_{17}$ | H | H | H |
| 1-60 | $CHF_2$ | $CHF_2$ | H | H | O | — | 0 | CH | H | H | H | $CF_3$ | H | H |
| 1-61 | $CHF_2$ | $CHF_2$ | H | H | O | — | 0 | CH | H | H | H | —$CH_2CH_2CH_2$— | | H |
| 1-62 | $CHF_2$ | $CHF_2$ | H | H | O | — | 0 | CH | H | H | $OSO_2Me$ | H | H | F |
| 1-63 | $CF_3$ | Me | H | H | O | — | 0 | CH | H | H | C(=NOMe)H | H | H | H |
| 1-64 | $CF_3$ | Me | H | H | O | — | 0 | CH | H | H | $OSO_2Me$ | H | Me | Me |
| 1-65 | $CF_3$ | Me | H | H | O | — | 0 | CH | H | H | $OSO_2Me$ | H | H | Cl |
| 1-66 | $CF_3$ | Me | H | H | O | — | 0 | CH | H | H | $OSO_2Me$ | H | H | Br |
| 1-67 | $CF_3$ | $CF_3$ | H | H | O | — | 0 | CH | H | H | $OSO_2$i-Pr | H | H | H |
| 1-68 | $CF_3$ | $CF_3$ | H | H | O | — | 0 | CH | H | H | $OSO_2$n-Bu | H | H | H |
| 1-69 | $CF_3$ | Me | H | H | O | — | 0 | CH | H | H | $CH_2Cl$ | H | H | H |
| 1-70 | $CF_3$ | Me | H | H | O | — | 0 | CH | H | H | CHO | H | H | H |
| 1-71 | $CF_3$ | Me | H | H | O | — | 0 | CH | H | H | C(=NNMe₂)H | H | H | H |
| 1-72 | $CF_3$ | Me | H | H | O | — | 0 | CH | H | H | $CH_2CN$ | H | H | H |
| 1-73 | $CHF_2$ | $CHF_2$ | H | H | O | — | 0 | CH | H | H | Ph | H | H | H |
| 1-74 | $CHF_2$ | $CHF_2$ | H | H | O | — | 0 | CH | H | H | OMe | H | H | $NO_2$ |
| 1-75 | $CHF_2$ | $CHF_2$ | H | H | O | — | 0 | CH | Me | H | H | H | H | H |
| 1-76 | $CHF_2$ | $CHF_2$ | H | H | O | — | 0 | CH | H | H | H | H | H | H |
| 1-77 | $CHF_2$ | $CHF_2$ | H | H | O | — | 0 | CH | H | H | H | —CH=CH—CH=CH— | | H |
| 1-78 | $CHF_2$ | $CHF_2$ | H | H | O | — | 0 | CH | H | H | H | t-Bu | H | H |
| 1-79 | $CF_3$ | Me | H | H | O | — | 0 | CH | H | H | H | t-Bu | H | H |
| 1-80 | $CHF_2$ | $CHF_2$ | F | H | O | — | 0 | CH | H | H | H | F | H | H |
| 1-81 | $CHF_2$ | $CHF_2$ | H | H | O | — | 0 | CH | H | H | H | $CF_3$ | H | H |
| 1-82 | $CF_3$ | $CF_3$ | H | H | O | — | 0 | CH | H | H | OMe | H | H | Br |
| 1-83 | $CF_3$ | $CF_3$ | H | H | O | — | 0 | CH | H | H | OMe | H | H | $NO_2$ |
| 1-84 | $CF_3$ | $CF_3$ | H | H | O | — | 0 | CH | H | H | F | F | F | F |
| 1-85 | $CF_3$ | $CF_3$ | H | H | O | — | 0 | CH | H | H | H | H | H | H |
| 1-86 | $CF_3$ | Me | H | H | O | — | 0 | CH | H | H | OMe | H | H | $OCF_3$ |
| 1-87 | $CF_3$ | $CF_3$ | H | H | O | — | 0 | CH | H | H | $OSO_2Me$ | H | H | F |
| 1-88 | $CF_3$ | $CF_3$ | H | H | O | — | 0 | CH | Me | H | H | H | H | H |
| 1-89 | $CF_3$ | $CF_3$ | H | H | O | — | 0 | CH | H | H | H | —CH=CH—CH=CH— | | H |
| 1-90 | $CF_3$ | Me | H | H | O | — | 0 | CH | H | H | $OSO_2NMe_2$ | H | H | H |
| 1-91 | $CF_3$ | $CF_3$ | H | H | O | — | 0 | CH | H | H | H | F | H | H |
| 1-92 | $CF_3$ | $CF_3$ | H | H | O | — | 0 | CH | H | H | H | t-Bu | H | H |
| 1-93 | $CF_3$ | $CF_3$ | H | H | O | — | 0 | CH | H | H | Cl | H | H | H |
| 1-94 | $CF_3$ | Me | H | H | O | — | 0 | CH | H | H | $OCHF_2$ | H | H | H |
| 1-95 | $CF_3$ | $CF_3$ | H | H | O | — | 0 | CH | H | H | H | $NO_2$ | H | H |
| 1-96 | $CF_3$ | Me | H | H | O | — | 0 | CH | H | H | C(=NOH)H | H | H | H |

TABLE 163

| No. | R⁷ | R⁸ | R⁹ | R¹⁰ | G¹ | R⁶ | n | T | R¹ | R³ | X¹ | X² | X³ | X⁴ |
|---|---|---|---|---|---|---|---|---|---|---|---|---|---|---|
| 1-97  | CF₃  | Me   | H | H | O | — | 0 | CH | H | H | CHF₂       | H      | H  | H      |
| 1-98  | CF₃  | Me   | H | H | O | — | 0 | CH | H | H | H          | Br     | H  | H      |
| 1-99  | CHF₂ | CHF₂ | H | H | O | — | 0 | CH | H | H | H          | Br     | H  | H      |
| 1-100 | CF₃  | Me   | H | H | O | — | 0 | CH | H | H | Br         | H      | H  | Br     |
| 1-101 | CF₃  | Me   | H | H | O | — | 0 | CH | H | H | OSO₂Me     | H      | H  | I      |
| 1-102 | CF₃  | Me   | H | H | O | — | 0 | CH | H | H | OSO₂Me     | H      | H  | Cl     |
| 1-103 | CF₃  | Me   | H | H | O | — | 0 | CH | H | H | OSO₂Me     | H      | H  | OSO₂Me |
| 1-104 | CF₃  | Me   | H | H | O | — | 0 | CH | H | H | CN         | H      | H  | H      |
| 1-105 | Me   | Me   | H | H | O | — | 0 | CH | H | H | OSO₂Me     | H      | H  | H      |
| 1-106 | CF₃  | Me   | H | H | S | — | 0 | CH | H | H | OSO₂Me     | H      | H  | H      |
| 1-107 | CF₃  | Me   | H | H | S | — | 0 | CH | H | H | OSO₂Me     | H      | H  | F      |
| 1-108 | CF₃  | Cl   | H | H | O | — | 0 | CH | H | H | OSO₂Me     | H      | H  | OMe    |
| 1-109 | Cl   | Cl   | H | H | O | — | 0 | CH | H | H | OSO₂Me     | H      | H  | OMe    |
| 1-110 | CF₃  | CF₃  | H | H | O | — | 0 | CH | H | H | OMe        | H      | H  | Cl     |
| 1-111 | CF₃  | CF₃  | H | H | O | — | 0 | CH | H | H | Br         | H      | H  | H      |
| 1-112 | CHF₂ | CHF₂ | H | H | O | — | 0 | CH | H | H | OMe        | H      | H  | Cl     |
| 1-113 | CHF₂ | CHF₂ | H | H | O | — | 0 | CH | H | H | Br         | H      | H  | H      |
| 1-114 | CF₃  | CF₃  | H | H | O | — | 0 | CH | H | H | NO₂        | H      | H  | H      |
| 1-115 | Me   | Me   | H | H | O | — | 0 | CH | H | H | OSO₂Me     | H      | H  | OMe    |
| 1-116 | CHF₂ | CHF₂ | H | H | O | — | 0 | CH | H | H | OSO₂Me     | H      | H  | Cl     |
| 1-117 | CF₃  | CF₃  | H | H | O | — | 0 | CH | H | H | OSO₂Me     | H      | H  | OMe    |
| 1-118 | CF₃  | CF₃  | H | H | O | — | 0 | CH | H | H | OSO₂Me     | H      | H  | Cl     |
| 1-119 | CHCl₂| CHCl₂| H | H | O | — | 0 | CH | H | H | OSO₂Me     | H      | H  | H      |
| 1-120 | Me   | Me   | H | H | O | — | 0 | CH | H | H | OSO₂Me     | H      | H  | F      |
| 1-121 | CHF₂ | CHF₂ | H | H | O | — | 0 | CH | H | H | OSO₂Me     | H      | Me | Me     |
| 1-122 | CF₃  | CF₃  | H | H | O | — | 0 | CH | H | H | OSO₂Me     | H      | Me | Me     |
| 1-123 | CF₃  | CF₃  | H | H | O | — | 0 | CH | H | H | OSO₂Me     | H      | H  | Br     |
| 1-124 | CHF₂ | CHF₂ | H | H | O | — | 0 | CH | H | H | OSO₂Me     | H      | H  | NO₂    |
| 1-125 | CHF₂ | CHF₂ | H | H | O | — | 0 | CH | H | H | OSO₂Me     | H      | H  | Br     |
| 1-126 | CHF₂ | CHF₂ | H | H | O | — | 0 | CH | H | H | NO₂        | H      | H  | H      |
| 1-127 | CF₃  | Me   | H | H | O | — | 0 | N  | H | H | OSO₂Me     | H      | H  | H      |
| 1-128 | CF₃  | CF₃  | H | H | O | — | 0 | CH | H | H | OSO₂Me     | H      | H  | NO₂    |
| 1-129 | CF₃  | CF₃  | H | H | O | — | 0 | CH | H | H | OSO₂Me     | H      | H  | I      |
| 1-130 | CHF₂ | CHF₂ | H | H | O | — | 0 | CH | H | H | OSO₂Me     | H      | H  | I      |
| 1-131 | CF₃  | CF₃  | H | H | O | — | 0 | CH | H | H | OSO₂Me     | F      | H  | H      |
| 1-132 | CHF₂ | CHF₂ | H | H | O | — | 0 | CH | H | H | OSO₂Me     | F      | H  | H      |
| 1-133 | CF₃  | Me   | H | H | O | — | 0 | CH | H | H | OMe        | H      | H  | F      |
| 1-134 | CF₃  | CF₃  | H | H | O | — | 0 | CH | H | H | OMe        | H      | H  | Me     |
| 1-135 | CF₃  | Me   | H | H | O | — | 0 | CH | H | H | OMe        | H      | H  | H      |
| 1-136 | CHF₂ | CHF₂ | H | H | O | — | 0 | CH | H | H | OCHF₂      | H      | H  | H      |
| 1-137 | CF₃  | CF₃  | H | H | O | — | 0 | CH | H | H | OCHF₂      | H      | H  | H      |
| 1-138 | CHF₂ | CHF₂ | H | H | O | — | 0 | CH | H | H | H          | OSO₂Me | H  | H      |
| 1-139 | CF₃  | CF₃  | H | H | O | — | 0 | CH | H | H | H          | OSO₂Me | H  | H      |
| 1-140 | CF₃  | CF₃  | H | H | O | — | 0 | CH | H | H | OMe        | H      | H  | H      |
| 1-141 | CHF₂ | CHF₂ | H | H | O | — | 0 | CH | H | H | OMe        | H      | H  | H      |
| 1-142 | CF₃  | CF₃  | H | H | O | — | 0 | CH | H | H | OMe        | H      | H  | F      |
| 1-143 | CF₃  | Me   | H | H | O | — | 0 | CH | H | H | OSO₂Me     | H      | H  | OCHF₂  |
| 1-144 | CF₃  | Me   | H | H | O | — | 0 | CH | H | H | OAc        | H      | H  | H      |
| 1-145 | CHF₂ | CHF₂ | H | H | O | — | 0 | CH | H | H | C(=NOH)H   | H      | H  | H      |
| 1-146 | CHF₂ | CHF₂ | H | H | O | — | 0 | CH | H | H | OSO₂Me     | H      | H  | OSO₂Me |

TABLE 164

| No. | R⁷ | R⁸ | R⁹ | R¹⁰ | G¹ | R⁶ | n | T | R¹ | R³ | X¹ | X² | X³ | X⁴ |
|---|---|---|---|---|---|---|---|---|---|---|---|---|---|---|
| 1-147 | CF₃  | CF₃  | H  | H | O | —    | 0 | CH | H  | H | OSO₂Me   | H | H | OSO₂Me |
| 1-148 | CHF₂ | CHF₂ | H  | H | O | —    | 0 | CH | H  | H | CN       | H | H | H      |
| 1-149 | CF₃  | CF₃  | H  | H | O | —    | 0 | CH | H  | H | C(=NOH)H | H | H | H      |
| 1-150 | CF₃  | CF₃  | H  | H | O | —    | 0 | CH | H  | H | CN       | H | H | H      |
| 1-151 | CHF₂ | CHF₂ | H  | H | O | —    | 0 | N  | H  | H | OSO₂Me   | H | H | H      |
| 1-152 | CF₃  | Me   | Me | H | O | —    | 0 | CH | H  | H | OSO₂Me   | H | H | H      |
| 1-153 | CHF₂ | Me   | H  | H | O | —    | 0 | CH | H  | H | OSO₂Me   | H | H | F      |
| 1-154 | CF₃  | Me   | H  | H | O | —    | 0 | CH | Me | H | OSO₂Me   | H | H | F      |
| 1-155 | CF₃  | Me   | F  | F | O | —    | 0 | CH | H  | H | OSO₂Me   | H | H | F      |
| 1-156 | CF₃  | Me   | Me | H | O | —    | 0 | CH | H  | H | OSO₂Me   | H | H | F      |
| 1-157 | CF₃  | Me   | H  | H | O | 3-Me | 1 | CH | H  | H | OSO₂Me   | H | H | F      |
| 1-158 | CHF₂ | CHF₂ | H  | H | S | —    | 0 | CH | H  | H | OSO₂Me   | H | H | H      |
| 1-159 | CF₃  | Me   | H  | H | O | 2-Me | 1 | CH | H  | H | OSO₂Me   | H | H | F      |
| 1-160 | CHF₂ | CHF₂ | Me | H | O | —    | 0 | CH | H  | H | OSO₂Me   | H | H | F      |
| 1-161 | CF₃  | Me   | H  | H | O | —    | 0 | CH | H  | H | OH       | H | H | F      |

TABLE 165

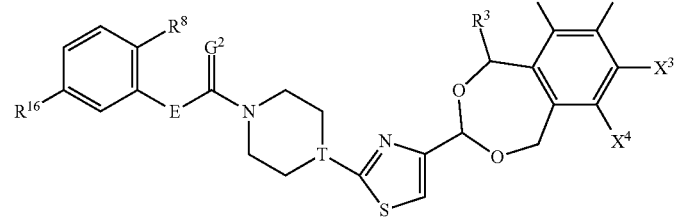

[1b]

| No. | $R^{13}$ | $R^{16}$ | E | $G^2$ | T | $R^3$ | $X^1$ | $X^2$ | $X^3$ | $X^4$ |
|---|---|---|---|---|---|---|---|---|---|---|
| 2-1 | Me | Me | CH$_2$ | O | CH | H | OSO$_2$Me | H | H | H |
| 2-2 | Cl | Cl | CH$_2$ | O | CH | H | OSO$_2$Me | H | H | H |
| 2-3 | Cl | Cl | CH$_2$ | O | CH | H | F | H | H | H |
| 2-4 | Cl | Cl | CH$_2$ | O | CH | H | F | H | H | F |
| 2-5 | Me | Me | NH | O | CH | H | OSO$_2$Me | H | H | H |
| 2-6 | Me | Me | CH$_2$ | O | CH | H | F | H | H | F |
| 2-7 | Me | Me | CH$_2$ | O | CH | H | F | H | H | H |
| 2-8 | Me | Me | CH$_2$ | O | CH | H | OSO$_2$Me | H | H | F |
| 2-9 | Me | Me | CH$_2$ | O | CH | H | OMe | H | H | NO$_2$ |
| 2-10 | Me | Me | CH$_2$ | O | CH | H | H | F | H | H |
| 2-11 | Me | Me | CH$_2$ | O | CH | H | H | H | H | H |
| 2-12 | Me | Me | CH$_2$ | O | CH | H | OSO$_2$n-Bu | H | H | H |
| 2-13 | Me | Me | CH$_2$ | O | CH | Me | H | H | H | H |
| 2-14 | Me | Me | NH | O | CH | H | OSO$_2$Me | H | H | F |
| 2-15 | Me | Me | NH | O | CH | H | F | H | H | F |
| 2-16 | Cl | Cl | CH$_2$ | O | CH | H | OSO$_2$Me | H | H | F |
| 2-17 | Me | Me | CH$_2$ | O | CH | H | Br | H | H | H |
| 2-18 | Me | Me | CH$_2$ | O | CH | H | H | NO$_2$ | H | H |
| 2-19 | Cl | Cl | CH$_2$ | O | CH | H | Br | H | H | H |
| 2-20 | Me | Me | CH$_2$ | O | CH | H | OMe | H | H | Cl |
| 2-21 | Cl | Cl | CH$_2$ | O | CH | H | H | NO$_2$ | H | H |
| 2-22 | Cl | Cl | CH$_2$ | O | CH | H | Cl | H | H | H |
| 2-23 | Cl | Cl | CH$_2$ | O | CH | H | OMe | H | H | Cl |
| 2-24 | Me | Me | CH$_2$ | O | CH | H | OMe | H | H | Br |
| 2-25 | Cl | Cl | CH$_2$ | O | CH | H | OMe | H | H | Br |
| 2-26 | Cl | Cl | CH$_2$ | O | CH | H | OSO$_2$Me | H | H | OMe |
| 2-27 | Me | Me | CH$_2$ | O | CH | H | F | F | F | F |
| 2-28 | Me | Me | CH$_2$ | O | CH | H | OSO$_2$Me | H | H | OMe |
| 2-29 | Cl | Cl | CH$_2$ | O | CH | H | F | F | F | F |
| 2-30 | CF$_3$ | CF$_3$ | CH$_2$ | O | CH | H | OSO$_2$Me | H | H | H |
| 2-31 | Me | Me | CH$_2$ | O | CH | H | OSO$_2$Me | H | Me | Me |
| 2-32 | Cl | Cl | CH$_2$ | O | CH | H | OSO$_2$Me | H | Me | Me |
| 2-33 | Me | Me | CH$_2$ | O | CH | H | OSO$_2$Me | H | H | Br |
| 2-34 | Cl | Cl | CH$_2$ | O | CH | H | OSO$_2$Me | H | H | NO$_2$ |
| 2-35 | Cl | Cl | CH$_2$ | O | CH | H | OSO$_2$Me | H | H | Br |
| 2-36 | Cl | Cl | CH$_2$ | O | CH | H | NO$_2$ | H | H | H |
| 2-37 | Me | Me | CH$_2$ | O | CH | H | OSO$_2$Me | H | H | NO$_2$ |

TABLE 166

| No. | $R^{13}$ | $R^{16}$ | E | $G^2$ | T | $R^3$ | $X^1$ | $X^2$ | $X^3$ | $X^4$ |
|---|---|---|---|---|---|---|---|---|---|---|
| 2-38 | Me | Me | CH$_2$ | O | CH | H | OSO$_2$Me | H | H | Cl |
| 2-39 | Me | Me | CH$_2$ | O | CH | H | NO$_2$ | H | H | H |
| 2-40 | Me | Me | CH$_2$ | O | CH | H | OSO$_2$Me | H | H | I |
| 2-41 | Cl | Cl | CH$_2$ | O | CH | H | OSO$_2$Me | H | H | Cl |
| 2-42 | Me | Me | CH$_2$ | O | CH | H | OSO$_2$Me | F | H | H |
| 2-43 | Cl | Cl | CH$_2$ | O | CH | H | OSO$_2$Me | F | H | H |
| 2-44 | Cl | Cl | CH$_2$ | O | CH | H | OSO$_2$Me | H | H | I |
| 2-45 | Me | Me | CH$_2$ | O | CH | H | OMe | H | H | Me |
| 2-46 | Cl | Cl | CH$_2$ | O | CH | H | OMe | H | H | Me |
| 2-47 | Me | Me | CH$_2$ | O | CH | H | OCHF$_2$ | H | H | H |
| 2-48 | Cl | Cl | CH$_2$ | O | CH | H | OCHF$_2$ | H | H | H |
| 2-49 | Cl | Cl | CH$_2$ | O | CH | H | H | OSO$_2$Me | H | H |
| 2-50 | Me | Me | CH$_2$ | O | CH | H | OMe | H | H | H |
| 2-51 | Cl | Cl | CH$_2$ | O | CH | H | OMe | H | H | H |
| 2-52 | Me | Me | CH$_2$ | O | CH | H | OMe | H | H | F |
| 2-53 | Me | Me | CH$_2$ | O | CH | H | OSO$_2$Me | H | H | OSO$_2$Me |
| 2-54 | Me | Me | CH$_2$ | O | N | H | OSO$_2$Me | H | H | H |
| 2-55 | Me | Me | NMe | O | CH | H | OSO$_2$Me | H | H | F |

TABLE 166-continued

| No. | R13 | R16 | E | G2 | T | R3 | X1 | X2 | X3 | X4 |
|---|---|---|---|---|---|---|---|---|---|---|
| 2-56 | Me | Me | NMe | O | CH | H | OSO2Me | H | H | H |
| 2-57 | Me | Me | CH2 | S | CH | H | OSO2Me | H | H | F |

TABLE 167

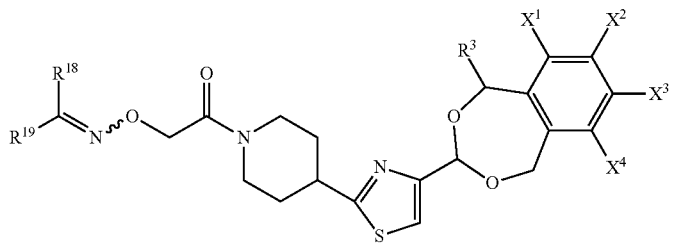

[1c]

| No. | R18 | R19 | R3 | X1 | X2 | X3 | X4 |
|---|---|---|---|---|---|---|---|
| 3-1 | Me | Me | H | OSO2Me | H | H | H |
| 3-2 | H | CF3 | H | F | H | H | H |
| 3-3 | H | CF3 | H | OSO2Me | H | H | F |
| 3-4 | H | CF3 | H | F | H | H | F |
| 3-5 | H | CF3 | H | OSO2Me | H | H | OMe |
| 3-6 | H | CF3 | H | OSO2Me | H | H | H |

TABLE 168

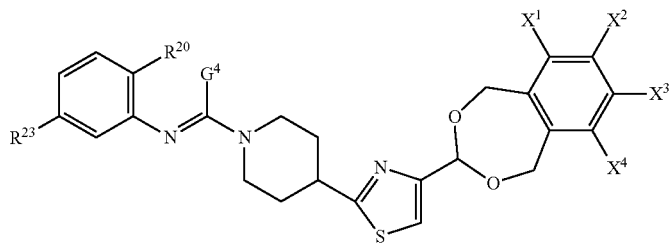

[1d]

| No. | R20 | R23 | G4 | X1 | X2 | X3 | X4 |
|---|---|---|---|---|---|---|---|
| 4-1 | Me | Me | OMe | OSO2Me | H | H | H |

TABLE 169

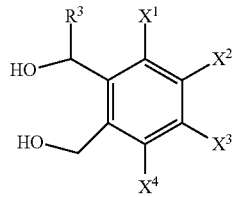 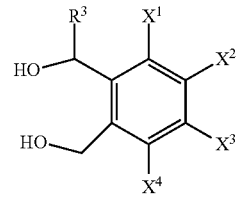

[3]

| No. | R3 | X1 | X2 | X3 | X4 | No. | R3 | X1 | X2 | X3 | X4 |
|---|---|---|---|---|---|---|---|---|---|---|---|
| 5-1 | H | H | H | H | H | 5-9 | H | H | OSO2Me | H | H |
| 5-2 | H | F | H | H | H | 5-10 | H | H | —CH=CH—CH=CH— | | H |
| 5-3 | H | F | H | H | F | 5-11 | H | H | F | H | H |
| 5-4 | H | H | Me | Me | H | 5-12 | H | NO2 | H | H | H |
| 5-5 | H | H | Cl | Cl | H | 5-13 | H | OSO2c-Pr | H | H | H |
| 5-6 | H | OSO2Me | H | H | H | 5-14 | H | Me | H | H | H |
| 5-7 | H | OSO2Et | H | H | H | 5-15 | H | Br | H | H | H |
| 5-8 | H | OSO2Me | H | H | F | 5-16 | H | H | CF3 | H | H |

TABLE 169-continued

[3]

Structure: benzene ring with $R^3$-CH(OH)- at position 1, $X^1$ at position 2, $X^2$ at position 3, $X^3$ at position 4, $X^4$ at position 5, and HO-CH2- at position 6.

| No. | $R^3$ | $X^1$ | $X^2$ | $X^3$ | $X^4$ |
|---|---|---|---|---|---|
| 5-17 | H | F | F | F | F |
| 5-18 | Me | H | H | H | H |
| 5-19 | H | $OSO_2Me$ | H | H | Me |
| 5-20 | H | H | Me | H | H |
| 5-21 | H | $OSO_2$n-Bu | H | H | H |
| 5-22 | H | $OSO_2$n-Pr | H | H | H |
| 5-23 | H | Cl | H | H | H |
| 5-24 | H | OMe | H | H | Br |
| 5-25 | H | $OSO_2$n-$C_8H_{17}$ | H | H | H |
| 5-26 | H | $OSO_2Me$ | H | H | OMe |
| 5-27 | H | H | $NO_2$ | H | H |
| 5-28 | H | $OSO_2$i-Pr | H | H | H |
| 5-29 | H | H | $OSO_2Et$ | H | H |
| 5-30 | H | $OSO_2CH_2CH_2CF_3$ | H | H | H |
| 5-31 | H | H | —$CH_2CH_2CH_2$— | | H |
| 5-32 | H | $OSO_2Me$ | H | H | $NO_2$ |
| 5-33 | H | OH | H | H | H |
| 5-34 | H | OC(=O)c-Pr | H | H | H |
| 5-35 | H | $OSO_2CF_3$ | H | H | H |
| 5-36 | H | OC(=O)OMe | H | H | H |
| 5-37 | H | H | H | Cl | H |
| 5-38 | H | $NHSO_2Me$ | H | H | H |
| 5-39 | H | $OSO_2Me$ | F | H | H |
| 5-40 | H | OMe | H | H | $NO_2$ |

TABLE 170

| No. | $R^3$ | $X^1$ | $X^2$ | $X^3$ | $X^4$ |
|---|---|---|---|---|---|
| 5-41 | H | $SO_2Me$ | H | H | H |
| 5-42 | H | $OSO_2Ph$ | H | H | H |
| 5-43 | H | $CH_2OH$ | H | H | H |
| 5-44 | H | Ph | H | H | H |
| 5-45 | H | C(=NOMe)H | H | H | H |
| 5-46 | H | $OSO_2Me$ | H | Me | Me |
| 5-47 | H | $OSO_2Me$ | H | H | Cl |
| 5-48 | H | $OSO_2Me$ | H | H | Br |
| 5-49 | H | $CH_2Cl$ | H | H | H |
| 5-50 | H | CHO | H | H | H |
| 5-51 | H | C(=$NNMe_2$)H | H | H | H |
| 5-52 | H | $CH_2CN$ | H | H | H |
| 5-53 | H | H | t-Bu | H | H |
| 5-54 | H | OMe | H | H | $OCF_3$ |
| 5-55 | H | $OSO_2NMe_2$ | H | H | H |
| 5-56 | H | $OCHF_2$ | H | H | H |
| 5-57 | H | C(=NOH)H | H | H | H |
| 5-58 | H | $CHF_2$ | H | H | H |
| 5-59 | H | H | H | Br | H |
| 5-60 | H | Br | H | H | Br |
| 5-61 | H | $OSO_2Me$ | H | H | I |
| 5-62 | H | $OSO_2Me$ | H | H | $OSO_2Me$ |
| 5-63 | H | CN | H | H | H |
| 5-64 | H | OMe | H | H | F |
| 5-65 | H | OMe | H | H | Me |
| 5-66 | H | OMe | H | H | H |
| 5-67 | H | $OSO_2Me$ | H | H | $OCHF_2$ |
| 5-68 | H | OAc | H | H | H |
| 5-69 | H | OH | H | H | F |

The $^1$H-NMR data ($CDCl_3$/TMS δ (ppm) value) of the compounds obtained by the above Examples and the compounds of the present invention, and compounds of formula [3] produced by similar methods are shown in [Table 171] to [Table 186].

TABLE 171

| No. | $CDCl_3$/TMS δ (ppm) |
|---|---|
| 1-1 | 1.75 (m, 2H), 2.22 (m, 2H), 2.32 (s, 3H), 2.84 (t, 1H), 3.27-3.36 (m, 2H), 4.04 (d, 1H), 4.60 (d, 1H), 5.02 (m, 6H), 6.03 (s, 1H), 6.33 (s, 1H), 7.19 (m, 2H), 7.23 (m, 2H), 7.39 (s, 1H) |
| 1-2 | 1.75 (m, 2H), 2.27 (m, 2H), 2.32 (s, 3H), 2.87 (t, 1H), 3.25-3.36 (m, 2H), 4.04 (d, 1H), 4.61 (d, 1H), 4.93-5.06 (m, 5H), 5.24 (d, 1H), 6.03 (s, 1H), 6.34 (s, 1H), 6.95 (m, 2H), 7.12 (m, 1H), 7.39 (s, 1H) |
| 1-3 | 1.75 (m, 2H), 2.22 (m, 2H), 2.32 (s, 3H), 2.85 (t, 1H), 3.25-3.36 (m, 2H), 4.05 (d, 1H), 4.60 (d, 1H), 4.91-5.06 (m, 5H), 5.17 (d, 1H), 6.04 (s, 1H), 6.34 (s, 1H), 6.91 (dd, 2H), 7.40 (s, 1H) |
| 1-4 | 1.75 (m, 2H), 2.23 (m, 8H), 2.32 (s, 3H), 2.84 (t, 1H), 3.29-3.35 (m, 2H), 4.03 (d, 1H), 4.59 (d, 1H), 4.96 (m, 6H), 6.01 (s, 1H), 6.33 (s, 1H), 6.95 (s, 2H), 7.37 (s, 1H) |
| 1-5 | 1.74 (m, 2H), 2.22 (m, 2H), 2.25 (s, 3H), 2.67 (t, 1H), 3.25-3.34 (m, 2H), 4.04 (d, 1H), 4.60 (d, 1H), 4.69 (d, 2H), 4.87-5.03 (m, 4H), 6.00 (s, 1H), 6.34 (s, 1H), 7.26 (s, 2H), 7.47 (s, 1H) |
| 1-6 | 1.75 (m, 2H), 2.20 (m, 2H), 2.31 (s, 3H), 2.85 (t, 1H), 3.20 (s, 3H), 3.25-3.36 (m, 2H), 4.03 (d, 1H), 4.59 (d, 1H), 4.92-5.08 (m, 5H), 5.26 (d, 1H), 6.03 (s, 1H), 6.33 (s, 1H), 7.12 (m, 1H), 7.21 (m, 2H) 7.39 (s, 1H) |
| 1-7 | 1.56 (t, 2H), 1.75 (m, 2H), 2.26 (m, 2H), 2.31 (s, 3H), 2.84 (t, 1H), 3.24-3.38 (m, 4H), 4.02 (d, 1H), 4.59 (d, 1H), 4.94-5.08 (m, 5H), 5.27 (d, 1H), 6.02 (s, 1H), 6.33 (s, 1H), 7.11 (d, 1H), 7.21 (m, 2H), 7.39 (s, 1H) |
| 1-8 | 1.75 (m, 2H), 2.21 (m, 2H), 2.31 (s, 3H), 2.85 (t, 1H), 3.20 (s, 3H), 3.23-3.48 (m, 2H), 4.03 (d, 1H), 4.59 (d, 1H), 4.96 (m, 4H), 5.20 (d, 2H), 6.03 (s, 1H), 6.33 (s, 1H), 6.99 (dd, 1H), 7.18 (dd, 1H), 7.40 (s, 1H) |
| 1-9 | 1.74 (m, 2H), 2.21 (m, 2H), 2.34 (s, 3H), 2.85 (t, 1H), 3.20 (s, 3H), 3.23-3.47 (m, 2H), 4.01 (d, 1H), 4.59 (d, 1H), 5.00 (m, 6H), 6.03 (s, 1H), 6.33 (s, 1H), 7.12 (m, 2H), 7.22 (m, 1H), 7.39 (s, 1H) |
| 1-10 | 1.77 (m, 2H), 2.22 (m, 2H), 2.32 (s, 3H), 2.84 (t, 1H), 3.27-3.37 (m, 2H), 4.04 (d, 1H), 4.60 (d, 1H), 4.98 (dd, 2H), 5.19 (m, 4H), 6.08 (s, 1H), 6.33 (s, 1H), 7.40 (s, 1H), 7.48 (m, 2H), 7.68 (s, 2H), 7.80 (m, 2H) |
| 1-11 | 1.76 (m, 2H), 2.20 (m, 2H), 2.31 (s, 3H), 2.83 (t, 1H), 3.23-3.35 (m, 2H), 4.02 (d, 1H), 4.60 (d, 1H), 4.99 (m, 6H), 6.02 (s, 1H), 6.33 (s, 1H), 6.91 (m, 2H), 7.14 (m, 1H), 7.38 (s, 1H) |
| 1-12 | 1.78 (m, 2H), 2.22 (m, 2H), 2.32 (s, 3H), 2.86 (t, 1H), 3.29-3.37 (m, 2H), 4.05 (d, 1H), 4.61 (d, 1H), 4.95 (m, 3H), 5.13 (m, 2H), 5.30 (d, 1H), 6.06 (s, 1H), 6.33 (s, 1H), 7.38 (m, 3H), 7.84 (m, 1H) |

TABLE 171-continued

| No. | CDCl$_3$/TMS δ (ppm) |
|---|---|
| 1-13 | 1.16 (dd, 1H), 1.32 (dd, 1H), 1.78 (m, 2H), 2.21 (m, 2H), 2.32 (s, 3H), 2.65 (m, 1H), 2.85 (t, 1H), 3.27-3.37 (m, 2H), 4.03 (d, 1H), 4.60 (d, 1H), 5.06 (m, 5H), 5.31 (d, 1H), 6.03 (s, 1H), 6.33 (s, 1H), 7.11 (m, 1H), 7.25 (m, 2H), 7.38 (s, 1H) |
| 1-14 | 1.75 (m, 2H), 2.14-2.36 (m, 8H), 2.84 (t, 1H), 3.24-3.36 (m, 2H), 4.03 (d, 1H), 4.60 (d, 1H), 4.98 (m, 5H), 5.15 (d, 1H), 6.04 (s, 1H), 6.33 (s, 1H), 7.00 (d, 1H), 7.11 (m, 2H), 7.39 (s, 1H) |
| 1-15 | 1.76 (m, 2H), 2.22 (m, 2H), 2.32 (s, 3H), 2.88 (t, 1H), 3.25-3.36 (m, 2H), 4.04 (d, 1H), 4.60 (d, 1H), 5.00 (m, 5H), 5.25 (d, 1H), 6.03 (s, 1H), 6.33 (s, 1H), 7.07 (m, 2H), 7.44 (s, 1H), 7.46 (d, 1H) |
| 1-16 | 1.75 (m, 2H), 2.22 (m, 2H), 2.32 (s, 3H), 2.88 (t, 1H), 3.25-3.36 (m, 2H), 4.04 (d, 1H), 4.60 (d, 1H), 5.00-5.10 (m, 6H), 6.05 (s, 1H), 6.33 (s, 1H), 7.27 (m, 1H), 7.40 (m, 2H), 7.49 (d, 1H) |
| 1-17 | 1.75 (m, 2H), 2.20 (m, 2H), 2.32 (s, 3H), 2.84 (t, 1H), 3.25-3.35 (m, 2H), 4.05 (d, 1H), 4.61 (d, 1H), 4.92 (d, 2H), 5.07 (d, 2H), 5.16 (d, 2H), 6.02 (s, 1H), 6.33 (s, 1H), 7.39 (s, 1H) |

TABLE 172

| No. | CDCl$_3$/TMS δ (ppm) |
|---|---|
| 1-18 | 1.75 (m, 5H), 2.20 (m, 2H), 2.32 (s, 3H), 2.89 (t, 1H), 3.27-3.35 (m, 2H), 4.02 (d, 1H), 4.59 (d, 1H), 4.93-5.06 (m, 4H), 5.27 (q, 1H), 6.13 (s, 1H), 6.33 (s, 1H), 7.19-7.31 (m, 4H), 7.37 (s, 1H) |
| 1-19 | 1.75 (m, 2H), 2.21 (m, 2H), 2.26 (s, 3H), 2.31 (s, 3H), 2.85 (t, 1H), 3.18 (s, 3H), 3.22-3.36 (m, 2H), 4.02 (d, 1H), 4.59 (d, 1H), 4.87-5.12 (m, 4H), 5.11 (d, 1H), 6.03 (s, 1H), 6.33 (s, 1H), 7.09 (s, 2H), 7.39 (s, 1H) |
| 1-20 | 1.76 (m, 2H), 2.24 (m, 2H), 2.31 (s, 3H), 2.32 (s, 3H), 2.80 (t, 1H), 3.22-3.34 (m, 2H), 4.02 (d, 1H), 4.59 (d, 1H), 4.98 (m, 6H), 6.02 (s, 1H), 6.33 (s, 1H), 7.04 (m, 3H), 7.37 (s, 1H) |
| 1-21 | 0.99 (t, 3H), 1.54 (m, 2H), 1.77 (m, 2H), 1.99 (m, 2H), 2.21 (m, 2H), 2.32 (s, 3H), 2.85 (t, 1H), 3.24-3.37 (m, 4H), 4.03 (d, 1H), 4.60 (d, 1H), 4.94-5.08 (m, 5H), 5.26 (d, 1H), 6.03 (s, 1H), 6.33 (s, 1H), 7.11 (d, 1H), 7.20 (d, 1H), 7.24 (m, 1H), 7.39 (s, 1H) |
| 1-22 | 1.14 (t, 3H), 1.70 (m, 2H), 2.04 (m, 2H), 2.22 (m, 2H), 2.31 (s, 3H), 2.84 (t, 1H), 3.24-3.37 (m, 4H), 4.02 (d, 1H), 4.60 (d, 1H), 4.99-5.08 (m, 5H), 5.29 (d, 1H), 6.02 (s, 1H), 6.32 (s, 1H), 7.11 (d, 1H), 7.22 (m, 2H), 7.39 (s, 1H) |
| 1-23 | 1.74 (m, 2H), 2.22 (m, 2H), 2.32 (s, 3H), 2.85 (t, 1H), 3.25-3.34 (m, 2H), 4.02 (d, 1H), 4.61 (d, 1H), 4.89-5.06 (m, 5H), 5.29 (d, 1H), 6.03 (s, 1H), 6.33 (s, 1H), 7.03 (d, 1H), 7.14 (t, 1H), 7.24 (d, 1H), 7.40 (s, 1H) |
| 1-24 | 1.78 (m, 2H), 2.22 (m, 2H), 2.32 (s, 3H), 2.85 (t, 1H), 3.25-3.36 (m, 2H), 3.79 (s, 3H), 4.03 (d, 1H), 4.60 (d, 1H), 4.90-5.04 (m, 4H), 5.15 (m, 2H), 6.03 (s, 1H), 6.33 (s, 1H), 6.65 (d, 1H), 7.39 (m, 2H), |
| 1-25 | 0.89 (t, 3H), 1.31 (m, 8H), 1.51 (m, 2H), 1.77 (m, 2H), 2.00 (m, 2H), 2.22 (m, 2H), 2.32 (s, 3H), 2.85 (t, 1H), 3.25-3.39 (m, 4H), 4.04 (d, 1H), 4.60 (d, 1H), 4.94-5.08 (m, 5H), 5.27 (d, 2H), 6.03 (s, 1H), 6.34 (s, 1H), 7.11 (d, 1H), 7.21 (m, 2H), 7.39 (s, 1H) |
| 1-26 | 1.75 (m, 2H), 2.20 (m, 2H), 2.31 (s, 3H), 2.86 (t, 1H), 3.16 (s, 3H), 3.25-3.35 (m, 2H), 3.82 (s, 3H), 4.03 (d, 1H), 4.59 (d, 1H), 4.89-5.03 (m, 4H), 5.18 (m, 2H), 6.02 (s, 1H), 6.33 (s, 1H), 6.78 (d, 1H), 7.16 (d, 1H), 7.39 (m, 2H) |
| 1-27 | 1.76 (m, 2H), 2.22 (m, 2H), 2.37 (s, 3H), 2.85 (t, 1H), 3.16 (s, 3H), 3.25-3.36 (m, 2H), 4.05 (d, 1H), 4.61 (d, 1H), 4.94-5.05 (m, 5H), 5.12 (m, 1H), 6.06 (s, 1H), 6.34 (s, 1H), 7.32 (d, 1H), 7.40 (s, 1H), 8.03 (s, 1H), 8.08 (m, 1H) |
| 1-28 | 1.56 (m, 6H), 1.77 (m, 2H), 2.26 (m, 2H), 2.31 (s, 3H), 2.85 (t, 1H), 3.27-3.38 (m, 2H), 3.54 (m, 1H), 4.02 (d, 1H), 4.60 (d, 1H), 4.93-5.08 (m, 5H), 5.28 (d, 1H), 6.02 (s, 1H), 6.33 (s, 1H), 7.09 (d, 1H), 7.21 (m, 2H), 7.39 (s, 1H) |
| 1-29 | 1.53 (t, 3H), 1.76 (m, 2H), 2.21 (m, 2H), 2.31 (s, 3H), 2.81 (t, 1H), 3.24-3.35 (m, 4H), 4.02 (d, 1H), 4.60 (d, 1H), 4.99 (m, 6H), 6.03 (s, 1H), 6.33 (s, 1H), 7.10 (m, 2H), 7.20 (d, 1H), 7.38 (s, 1H) |
| 1-30 | 1.76 (m, 2H), 2.26 (m, 2H), 2.32 (s, 3H), 2.85 (m, 3H), 3.24-3.36 (m, 2H), 3.55 (m, 1H), 4.04 (d, 1H), 4.60 (d, 1H), 4.93-5.05 (m, 5H), 5.23 (d, 1H), 6.03 (s, 1H), 6.33 (s, 1H), 7.16 (m, 2H), 7.29 (m, 1H), 7.39 (s, 1H) |
| 1-31 | 1.73 (m, 2H), 2.07 (m, 2H), 2.20 (m, 2H), 2.31 (s, 3H), 2.85 (m, 5H), 3.23-3.34 (m, 2H), 4.02 (d, 1H), 4.59 (d, 1H), 4.99 (m, 6H), 6.02 (s, 1H), 6.33 (s, 1H), 7.06 (s, 2H), 7.37 (s, 1H) |
| 1-32 | 1.77 (m, 2H), 2.28 (m, 2H), 2.33 (s, 3H), 2.87 (t, 1H), 3.31 (s, 3H), 3.32 (m, 2H), 4.06 (d, 1H), 4.60 (d, 1H), 4.98-5.33 (m, 6H), 6.05 (s, 1H), 6.34 (s, 1H), 7.40 (m, 2H), 7.94 (d, 1H) |
| 1-33 | 1.71 (m, 2H), 2.21 (m, 2H), 2.30 (s, 3H), 2.80 (t, 1H), 3.20-3.31 (m, 2H), 3.97 (d, 1H), 4.56 (d, 1H), 4.89-5.00 (m, 5H), 5.30 (d, 1H), 6.02 (s, 1H), 6.33 (s, 1H), 6.64 (d, 1H), 6.68 (d, 1H), 6.73 (brs, 1H), 6.99 (t, 1H), 7.38 (s, 1H) |

TABLE 173

| No. | CDCl₃/TMS δ (ppm) |
|---|---|
| 1-34 | 1.02 (m, 2H), 1.15 (m, 2H), 1.76 (m, 2H), 1.84 (m, 1H), 2.21 (m, 2H), 2.31 (s, 3H), 2.84 (t, 1H), 3.24-3.34 (m, 2H), 4.04 (d, 1H), 4.60 (d, 1H), 4.83 (d, 1H), 4.92-5.07 (m, 5H), 6.01 (s, 1H), 6.33 (s, 1H), 6.97 (d, 1H), 7.03 (d, 1H), 7.22 (t, 1H), 7.38 (s, 1H) |
| 1-35 | 1.78 (m, 2H), 1.84 (m, 1H), 2.25 (dd, 2H), 2.88 (t, 1H), 3.33 (m, 2H), 3.92 (d, 1H), 4.60 (d, 1H), 4.83 (d, 1H), 4.93-5.15 (m, 5H), 5.24 (d, 1H), 6.04 (s, 1H), 6.51-7.01 (m, 5H), 7.28 (m, 1H), 7.39 (s, 1H) |
| 1-36 | 1.78 (m, 2H), 1.84 (m, 1H), 2.23 (m, 2H), 2.37 (s, 3H), 2.85 (t, 1H), 3.25-3.36 (m, 2H), 4.05 (d, 1H), 4.60 (d, 1H), 4.94-5.11 (m, 5H), 5.23 (d, 1H), 6.04 (s, 1H), 6.34 (s, 1H), 7.19 (m, 2H), 7.30 (d, 1H), 7.40 (s, 1H) |
| 1-37 | 1.78 (m, 2H), 2.22 (m, 2H), 2.32 (s, 3H), 2.85 (t, 1H), 3.20-3.33 (m, 2H), 4.04 (d, 1H), 4.60 (d, 1H), 4.86-5.13 (m, 6H), 6.02 (s, 1H), 6.33 (s, 1H), 7.06 (m, 2H), 7.23 (d, 1H), 7.39 (s, 1H) |
| 1-38 | 1.78 (m, 2H), 2.25 (dd, 2H), 2.92 (t, 1H), 3.21 (s, 3H), 3.35 (m, 2H), 3.91 (d, 1H), 4.61 (d, 1H), 4.83 (d, 1H), 4.96-5.15 (m, 3H), 5.15 (d, 1H), 5.26 (d, 1H), 6.03 (s, 1H), 6.53-7.02 (m, 3H), 7.13 (d, 1H), 7.21 (m, 2H), 7.40 (s, 1H) |
| 1-39 | 1.83 (m, 2H), 2.24 (dd, 2H), 2.90 (t, 1H), 3.23 (s, 3H), 3.35 (m, 2H), 3.82 (s, 3H), 3.91 (d, 1H), 4.60 (d, 1H), 4.93 (t, 2H), 5.14-5.23 (m, 4H), 5.26 (d, 1H), 6.02 (s, 1H), 6.53-7.02 (m, 4H), 7.16 (d, 1H), 7.40 (s, 1H) |
| 1-40 | 1.76 (m, 2H), 2.20 (m, 2H), 2.31 (s, 3H), 2.83 (t, 1H), 3.26-3.32 (m, 2H), 4.03 (d, 1H), 4.59 (d, 1H), 4.91-5.01 (m, 6H), 6.01 (s, 1H), 6.33 (s, 1H), 7.10 (d, 1H), 7.16-7.19 (m, 2H), 7.38 (s, 1H) |
| 1-41 | 1.75-1.84 (m, 2H), 2.20 (d, 2H), 2.30 (d, 2H), 2.88 (t, 1H), 3.28-3.38 (m, 2H), 3.84 (d, 1H), 4.59 (d, 1H), 4.93-5.06 (m, 3H), 5.18-5.26 (m, 3H), 6.04 (s, 1H), 6.93-7.16 (m, 3H), 7.16-7.18 (m, 1H), 7.40 (s, 1H) |
| 1-42 | 1.79-1.88 (m, 2H), 2.21 (d, 2H), 2.30 (d, 2H), 2.90 (t, 1H), 3.21 (s, 3H), 3.29-3.38 (m, 2H), 3.85 (d, 1H), 4.59 (d, 1H), 4.99-5.09 (m, 3H), 5.19 (s, 2H), 5.26 (d, 1H), 6.03 (s, 1H), 6.95 (s, 1H), 7.13 (d, 1H), 7.20-7.27 (m, 1H), 7.40 (s, 1H) |
| 1-43 | 1.68-1.75 (m, 2H), 2.09-2.18 (m, 2H), 2.31 (s, 3H), 2.91 (m, 1H), 2.97 (s, 3H), 3.22-3.28 (m, 2H), 3.95 (dd, 1H), 4.41-4.54 (m, 3H), 4.73 (dd, 1H), 4.91-5.03 (m, 3H), 6.33 (s, 1H), 6.85 (s, 1H), 7.02 (d, 1H) 7.25-7.30 (m, 2H), 7.60 (d, 1H) |
| 1-44 | 1.76-1.88 (m, 2H), 2.20-2.31 (m, 5H), 2.90 (t, 1H), 3.18 (s, 3H), 3.29-3.39 (m, 2H), 3.92 (d, 1H), 4.60 (d, 1H), 4.90 (d, 1H), 4.98 (d, 1H), 5.09-5.23 (m, 4H), 6.04 (s, 1H), 6.53-7.00 (m, 3H), 7.11 (s, 2H), 7.40 (s, 1H) |
| 1-45 | 1.74-1.80 (m, 2H), 2.17-2.27 (m, 2H), 2.32 (s, 3H), 2.86 (t, 1H), 3.24-3.36 (m, 5H), 4.03 (d, 1H), 4.59 (d, 1H), 4.90-5.04 (m, 5H), 5.28 (d, 1H), 6.02 (s, 1H), 6.33 (s, 1H), 7.07 (s, 2H), 7.39 (s, 1H) |
| 1-46 | 1.79 (m, 2H), 2.18-2.31 (m, 2H), 2.37 (s, 3H), 2.86 (t, 1H), 3.29-3.37 (m, 2H), 3.90 (s, 3H), 4.08 (d, 1H), 4.60 (d, 1H), 4.92-5.00 (m, 3H), 5.14 (dd, 2H), 5.30 (d, 1H), 6.04 (s, 1H), 6.34 (s, 1H), 6.83 (d, 1H), 7.40 (s, 1H), 7.99 (d, 1H) |
| 1-47 | 1.72-1.83 (m, 2H), 2.17,-2.32 (m, 2H), 2.37 (s, 3H), 2.85 (t, 1H), 3.12 (s, 3H), 3.28-3.36 (m, 2H), 4.04 (d, 1H), 4.60 (d, 1H), 4.98-5.15 (m, 4H), 5.27 (d, 1H), 5.62 (d, 1H), 6.05 (s, 1H), 6.33 (s, 1H), 7.40-7.45 (m, 3H), 7.98 (m, 1H) |
| 1-48 | 1.73-1.82 (m, 2H), 2.17-2.28 (m, 2H), 2.32 (s, 3H), 2.85 (t, 1H), 3.28-3.35 (m, 2H), 4.04 (d, 1H), 4.60 (d, 1H), 4.72 (d, 1H), 4.88-5.02 (m, 5H), 5.93 (s, 1H), 6.33 (s, 1H), 6.84 (d, 1H), 7.05 (d, 1H), 7.14 (t, 1H), 7.32 (s, 1H), 7.55 (t, 2H), 7.69 (d, 1H), 7.86 (d, 2H) |
| 1-49 | 1.78-1.88 (m, 2H), 2.25 (dd, 2H), 2.88 (t, 1H), 3.14-3.38 (m, 2H), 3.92 (d, 1H), 4.61 (d, 1H), 5.00 (d, 2H), 5.11-5.19 (m, 4H), 6.06 (s, 1H), 6.53-7.02 (m, 3H), 7.32 (d, 1H), 7.40 (s, 1H), 8.04-8.11 (m, 2H) |

TABLE 174

| No. | CDCl₃/TMS δ (ppm) |
|---|---|
| 1-50 | 1.78-1.92 (m, 2H), 2.26 (dd, 2H), 2.89 (t, 1H), 3.30-3.40 (m, 2H), 3.85 (d, 1H), 4.60 (d, 1H), 4.93 (d, 2H), 5.15-5.22 (m, 4H), 6.04 (s, 1H), 6.89-6.95 (m, 3H), 7.41 (s, 1H) |
| 1-51 | 1.78-1.88 (m, 2H), 2.26 (dd, 2H), 2.88 (t, 1H), 3.29-3.38 (m, 2H), 3.92 (d, 1H), 4.61 (d, 1H), 4.93 (d, 2H), 5.10-5.19 (m, 4H), 6.04 (s, 1H), 6.53-7.02 (m, 5H), 7.41 (s, 1H) |
| 1-52 | 1.71-1.80 (m, 2H), 2.19 (dd, 2H), 2.30 (s, 3H), 2.81 (t, 1H), 3.24-3.37 (m, 2H), 4.01 (d, 1H), 4.56 (d, 1H), 4.66 (s, 2H), 4.90-5.05 (m, 5H), 5.25 (d, 1H), 6.01 (s, 1H), 6.33 (s, 1H), 7.10 (d, 1H), 7.12-7.28 (m, 3H), 7.38 (s, 1H) |
| 1-53 | 1.58 (d, 6H), 1.74-1.90 (m, 2H), 2.24 (dd, 2H), 2.88 (t, 1H), 3.21-3.29 (m, 2H), 3.49-3.60 (m, 1H), 3.90 (d, 1H), 4.57 (d, 1H), 4.93-5.08 (m, 3H), 5.14 (s, 2H), 5.28 (d, 1H), 6.03 (s, 1H), 6.53-7.11 (m, 3H), 7.19-7.25 (m, 2H), 7.40 (s, 1H) |
| 1-54 | 0.99 (t, 3H), 1.48-1.56 (m, 2H), 1.82-1.90 (m, 2H), 1.92-2.04 (m, 2H), 2.22 (dd, 2H), 2.88 (t, 1H), 3.24-3.39 (m, 4H), 3.90 (d, 1H), 4.58 (d, 1H), 4.94-5.17 (m, 5H), 5.27 (d, 2H), 6.03 (s, 1H), 6.53-7.10 (m, 3H), 7.11 (d, 1H), 7.19-7.28 (m, 3H), 7.40 (s, 1H) |
| 1-55 | 1.74-1.88 (m, 2H), 2.24 (dd, 2H), 2.87 (t, 1H), 3.27-3.37 (m, 2H), 3.91 (d, 1H), 4.60 (d, 1H), 4.91 (d, 2H), 5.10-5.18 (m, 4H), 6.02 (s, 1H), 6.53-7.10 (m, 3H), 7.40 (s, 1H) |
| 1-56 | 1.72-1.79 (m, 2H), 2.14-2.25 (m, 2H), 2.31 (s, 3H), 2.83 (t, 1H), 3.25-3.31 (m, 2H), 4.02 (d, 1H), 4.58 (d, 1H), 4.86-5.12 (m, 6H), 6.01 (s, 1H), 6.33 (s, 1H), 7.17 (d, 1H), 7.25-7.29 (m, 3H), 7.33-7.42 (m, 5H) |
| 1-57 | 1.76-1.91 (m, 2H), 2.26 (dd, 2H), 2.89 (t, 1H), 3.25-3.39 (m, 2H), 3.80 (s, 3H), 3.91 (d, 1H), 4.60 (d, 1H), 4.88-4.99 (m, 2H), 5.11-5.20 (m, 4H), 6.03 (s, 1H), 6.53-7.02 (m, 4H), 7.36-7.40 (m, 2H) |

TABLE 174-continued

| No. | CDCl$_3$/TMS δ (ppm) |
| --- | --- |
| 1-58 | 1.78-1.90 (m, 2H), 2.25 (dd, 2H), 2.88 (t, 1H), 3.32-3.38 (m, 2H), 3.92 (d, 1H), 4.61 (d, 1H), 4.91 (d, 1H), 5.05 (dd, 2H), 5.15 (s, 2H), 5.29 (d, 1H), 6.04 (s, 1H), 6.53-6.88 (m, 3H), 7.02-7.05 (m, 1H), 7.15 (t, 1H), 7.20-7.29 (m, 2H), 7.41 (s, 1H) |
| 1-59 | 0.89 (t, 3H), 1.22-1.39 (m, 8H), 1.43-1.52 (m, 2H), 1.74-1.90 (m, 2H), 1.95-2.04 (m, 2H), 2.24 (dd, 2H), 2.88 (t, 1H), 3.34-3.40 (m, 4H), 3.91 (d, 1H), 4.59 (d, 1H), 4.94-5.18 (m, 5H), 5.27 (d, 1H), 6.03 (s, 1H), 6.53-7.02 (m, 3H), 7.11 (d, 1H), 7.19-7.27 (m, 2H), 7.40 (s, 1H) |
| 1-60 | 1.77-1.87 (m, 2H), 2.25 (dd, 2H), 2.91 (t, 1H), 3.28-3.38 (m, 2H), 3.92 (d, 1H), 4.60 (d, 1H), 4.98-5.19 (m, 6H), 6.05 (s, 1H), 6.53-7.02 (m, 3H), 7.27 (m, 1H), 7.40-7.42 (m, 2H), 7.50 (d, 1H) |
| 1-61 | 1.74-1.88 (m, 2H), 2.04-2.09 (m, 2H), 2.24 (dd, 2H), 2.84-2.93 (m, 5H), 3.26-3.38 (m, 2H), 3.90 (d, 1H), 4.59 (d, 1H), 4.94-5.04 (m, 4H), 5.14 (s, 2H), 6.03 (s, 1H), 6.53-7.02 (m, 3H), 7.06 (s, 2H), 7.38 (s, 1H) |
| 1-62 | 1.78-1.88 (m, 2H), 2.25 (dd, 2H), 2.89 (t, 1H), 3.21 (s, 3H), 3.29-3.38 (m, 2H), 3.92 (d, 1H), 4.60 (d, 1H), 4.96 (dd, 2H), 5.14-5.22 (m, 4H), 6.03 (s, 1H), 6.53-6.98 (m, 3H), 7.01 (d, 1H), 7.18-7.21 (m, 1H), 7.41 (s, 1H) |
| 1-63 | 1.72-1.80 (m, 2H), 2.22 (dd, 2H), 2.31 (s, 3H), 2.84 (t, 1H), 3.24-3.36 (m, 2H), 3.97 (s, 3H), 4.04 (d, 1H), 4.60 (d, 1H), 4.89-5.09 (m, 5H), 5.41 (d, 1H), 6.05 (s, 1H), 6.33 (s, 1H), 7.16 (d, 1H), 7.22-7.26 (m, 1H), 7.40 (s, 1H), 7.44 (d, 1H), 8.26 (s, 1H) |
| 1-64 | 1.73-1.85 (m, 2H), 2.14 (s, 3H), 2.17-2.30 (m, 5H), 2.32 (s, 3H), 2.87 (t, 1H), 3.18 (s, 3H), 3.23-3.39 (m, 2H), 4.04 (d, 1H), 4.60 (d, 1H), 4.91-5.05 (m, 4H), 5.17 (dd, 2H), 6.02 (s, 1H), 6.34 (s, 1H), 7.02 (s, 1H), 7.38 (s, 1H) |
| 1-65 | 1.72-1.84 (m, 2H), 2.17-2.28 (m, 2H), 2.32 (s, 3H), 2.85 (t, 1H), 3.24-3.37 (m, 2H), 3.79 (s, 3H), 4.03 (d, 1H), 4.60 (d, 1H), 4.89-5.04 (m, 4H), 5.14 (dd, 2H), 6.03 (s, 1H), 6.33 (s, 1H), 6.71 (d, 1H), 7.19 (d, 1H), 7.39 (s, 1H) |
| 1-66 | 1.72-1.86 (m, 2H), 2.17-2.29 (m, 2H), 2.36 (s, 3H), 2.86 (t, 1H), 3.24 (s, 3H), 3.25-3.39 (m, 2H), 4.03 (d, 1H), 4.60 (d, 1H), 4.94-5.05 (m, 4H), 5.20 (dd, 2H), 6.03 (s, 1H), 6.33 (s, 1H), 7.09 (d, 1H), 7.40 (s, 1H), 7.48 (d, 1H) |

TABLE 175

| No. | CDCl$_3$/TMS δ (ppm) |
| --- | --- |
| 1-67 | 1.52-1.69 (m, 6H), 1.72-1.90 (m, 2H), 2.24 (dd, 2H), 2.89 (t, 1H), 3.24-3.40 (m, 2H), 3.53 (m, 1H), 3.84 (d, 1H), 4.59 (d, 1H), 4.93-5.33 (m, 6H), 6.03 (s, 1H), 6.95 (s, 1H), 7.10 (d, 1H), 7.17-7.30 (m, 2H), 7.40 (s, 1H) |
| 1-68 | 0.99 (t, 3H), 1.51-1.61 (m, 2H), 1.71-1.90 (m, 2H), 1.91-2.02 (m, 2H), 2.25 (dd, 2H), 2.89 (t, 1H), 3.27-3.40 (m, 4H), 3.53 (m, 1H), 3.84 (d, 1H), 4.60 (d, 1H), 4.96-5.31 (m, 6H), 6.03 (s, 1H), 6.95 (s, 1H), 7.11 (d, 1H), 7.20 (d, 1H), 7.22-7.28 (d, 1H), 7.40 (s, 1H) |
| 1-69 | 1.70-1.85 (m, 2H), 2.22 (m, 2H), 2.32 (s, 3H), 2.85 (t, 1H), 3.22-3.38 (m, 2H), 4.03 (d, 1H), 4.55-4.67 (m, 3H), 4.94-5.07 (m, 5H), 5.30 (d, 1H), 6.05 (s, 1H), 6.33 (s, 1H), 7.14-7.22 (m, 3H), 7.40 (s, 1H) |
| 1-70 | 1.71-1.84 (m, 2H), 2.23 (m, 2H), 2.33 (s, 3H), 2.86 (t, 1H), 3.24-3.39 (m, 2H), 4.04 (d, 1H), 4.61 (d, 1H), 4.90-5.14 (m, 4H), 5.35 (d, 1H), 5.63 (d, 1H), 6.07 (s, 1H), 6.34 (s, 1H), 7.37-7.45 (m, 3H), 7.73 (s, 1H), 10.11 (s, 1H) |
| 1-71 | 1.70-1.84 (m, 2H), 2.21 (m, 2H), 2.31 (s, 3H), 2.84 (t, 1H), 2.98 (s, 6H), 3.26-3.38 (m, 2H), 4.02 (d, 1H), 4.60 (d, 1H), 4.90-5.12 (m, 5H), 5.47 (d, 1H), 6.05 (s, 1H), 6.33 (s, 1H), 7.02 (d, 1H), 7.18 (t, 1H), 7.33 (s, 1H), 7.39 (s, 1H), 7.50 (d, 1H) |
| 1-72 | 1.71-1.82 (m, 2H), 2.22 (m, 2H), 2.32 (s, 3H), 2.85 (t, 1H), 3.25-3.36 (m, 2H), 3.69 (s, 2H), 4.04 (d, 1H), 4.60 (d, 1H), 4.92-5.15 (m, 6H), 6.05 (s, 1H), 6.33 (s, 1H), 7.16 (d, 1H), 7.21 (m, 2H), 7.39 (s, 1H) |
| 1-73 | 1.71-1.90 (m, 2H), 2.23 (dd, 2H), 2.88 (t, 1H), 3.24-3.39 (m, 2H), 3.89 (d, 1H), 4.59 (d, 1H), 4.88 (d, 1H), 5.02-5.20 (m, 5H), 6.01 (s, 1H), 6.53-7.01 (m, 3H), 7.15-7.22 (m, 2H), 7.25-7.48 (m, 7H) |
| 1-74 | 1.73-1.95 (m, 2H), 2.25 (dd, 2H), 2.89 (t, 1H), 3.28-3.43 (m, 2H), 3.90-4.01 (m, 4H), 4.60 (d, 1H), 4.94 (d, 1H), 5.10-5.21 (m, 4H), 5.30 (d, 1H), 6.05 (s, 1H), 6.53-7.02 (m, 4H), 7.43 (s, 1H), 8.00 (d, 1H) |
| 1-75 | 1.64 (d, 3H), 1.75-1.94 (m, 2H), 2.25 (dd, 2H), 2.90 (t, 1H), 3.26-3.40 (m, 2H), 3.91 (d, 1H), 4.58 (d, 1H), 5.14-5.24 (m, 5H), 6.10 (s, 1H), 6.53-7.02 (m, 3H), 7.11-7.26 (m, 4H), 7.41 (s, 1H) |
| 1-76 | 1.73-1.92 (m, 2H), 2.24 (dd, 2H), 2.87 (t, 1H), 3.25-3.40 (m, 2H), 3.90 (d, 1H), 4.60 (d, 1H), 5.02-5.20 (m, 6H), 6.04 (s, 1H), 6.53-7.02 (m, 3H), 7.17-7.25 (m, 4H), 7.39 (s, 1H) |
| 1-77 | 1.74-1.91 (m, 2H), 2.24 (dd, 2H), 2.87 (t, 1H), 3.24-3.40 (m, 2H), 3.91 (d, 1H), 4.60 (d, 1H), 5.10-5.27 (m, 6H), 6.09 (s, 1H), 6.53-7.02 (m, 3H), 7.40 (s, 1H), 7.47-7.50 (m, 2H), 7.68 (s, 2H), 7.79-7.82 (m, 2H) |
| 1-78 | 1.31 (s, 9H), 1.71-1.91 (m, 2H), 2.24 (dd, 2H), 2.87 (t, 1H), 3.25-3.40 (m, 2H), 3.90 (d, 1H), 4.59 (d, 1H), 4.99-5.20 (m, 6H), 6.03 (s, 1H), 6.53-7.02 (m, 3H), 7.12 (d, 1H), 7.20 (s, 1H), 7.24-7.28 (m, 1H), 7.40 (s, 1H) |
| 1-79 | 1.31 (s, 9H), 1.70-1.84 (m, 2H), 2.21 (m, 2H), 2.32 (s, 3H), 2.84 (t, 1H), 3.24-3.38 (m, 2H), 4.04 (d, 1H), 4.60 (d, 1H), 4.92-5.10 (m, 6H), 6.03 (s, 1H), 6.33 (s, 1H), 7.12 (d, 1H), 7.20-7.31 (m, 2H), 7.38 (s, 1H) |
| 1-80 | 1.73-1.92 (m, 2H), 2.24 (m, 2H), 2.87 (t, 1H), 3.30-3.37 (m, 2H), 3.90 (d, 1H), 4.60 (d, 1H), 4.91-5.21 (m, 6H), 6.02 (s, 1H), 6.53-7.02 (m, 5H), 7.12 (m, 1H), 7.39 (s, 1H) |

TABLE 175-continued

| No. | CDCl$_3$/TMS δ (ppm) |
|---|---|
| 1-81 | 1.73-1.94 (m, 2H), 2.25 (dd, 2H), 2.82 (t, 1H), 3.28-3.40 (m, 2H), 3.92 (d, 1H), 4.60 (d, 1H), 4.98-5.20 (m, 6H), 6.05 (s, 1H), 6.53-7.02 (m, 3H), 7.25-7.28 (m, 1H), 7.40 (s, 1H), 7.42 (s, 1H), 7.50 (d, 1H) |
| 1-82 | 1.72-1.91 (m, 2H), 2.25 (dd, 2H), 2.89 (t, 1H), 3.29-3.39 (m, 2H), 3.83-3.90 (m, 4H), 4.59 (d, 1H), 4.90-5.25 (m, 6H), 6.03 (s, 1H), 6.65 (d, 1H), 6.95 (s, 1H), 7.37-7.41 (m, 2H) |

TABLE 176

| No. | CDCl$_3$/TMS δ (ppm) |
|---|---|
| 1-83 | 1.75-1.92 (m, 2H), 2.26 (dd, 2H), 2.90 (t, 1H), 3.30-3.41 (m, 2H), 3.84-3.92 (m, 4H), 4.60 (d, 1H), 4.94 (d, 1H), 5.10-5.19 (m, 4H), 5.30 (d, 1H), 6.05 (s, 1H), 6.83 (d, 1H), 6.96 (s, 1H), 7.40 (s, 1H), 8.00 (d, 1H) |
| 1-84 | 1.70-1.89 (m, 2H), 2.25 (dd, 2H), 2.89 (t, 1H), 3.29-3.39 (m, 2H), 3.86 (d, 1H), 4.60 (d, 1H), 4.92 (d, 2H), 5.15-5.27 (m, 4H), 6.03 (s, 1H), 6.96 (s, 1H), 7.40 (s, 1H) |
| 1-85 | 1.74-1.91 (m, 2H), 2.24 (dd, 2H), 2.87 (t, 1H), 3.27-3.38 (m, 2H), 3.82 (d, 1H), 4.58 (d, 1H), 5.02 (s, 4H), 5.18 (s, 2H), 6.04 (s, 1H), 6.95 (s, 1H), 7.17-7.27 (m, 4H), 7.40 (s, 1H) |
| 1-86 | 1.72-1.84 (m, 2H), 2.22 (m, 2H), 2.37 (s, 3H), 2.85 (t, 1H), 3.25-3.40 (m, 2H), 3.81 (s, 3H), 4.04 (d, 1H), 4.60 (d, 1H), 4.89-5.19 (m, 6H), 6.02 (s, 1H), 6.34 (s, 1H), 6.76 (d, 1H), 7.10 (d, 1H), 7.39 (s, 1H) |
| 1-87 | 1.75-1.92 (m, 2H), 2.25 (m, 2H), 2.90 (t, 1H), 3.21 (s, 3H), 3.29-3.41 (m, 2H), 3.84 (d, 1H), 4.58 (d, 1H), 4.93-4.99 (m, 2H), 5.14-5.25 (m, 4H), 6.04 (s, 1H), 6.95 (s, 1H), 7.01 (d, 1H), 7.17-7.20 (m, 1H), 7.41 (s, 1H) |
| 1-88 | 1.64 (d, 1H), 1.73-1.93 (m, 2H), 2.26 (m, 2H), 2.91 (t, 1H), 3.27-3.40 (m, 2H), 3.84 (d, 1H), 4.59 (d, 1H), 5.03 (s, 2H), 5.14-5.27 (m, 3H), 6.10 (s, 1H), 6.95 (s, 1H), 7.11-7.31 (m, 4H), 7.40 (s, 1H) |
| 1-89 | 1.70-1.88 (m, 2H), 2.22 (dd, 2H), 2.87 (t, 1H), 3.22-3.36 (m, 2H), 3.79 (d, 1H), 4.57 (d, 1H), 5.10-5.27 (m, 6H), 6.08 (s, 1H), 6.95 (s, 1H), 7.40 (s, 1H), 7.44-7.50 (m, 2H), 7.67 (s, 2H), 7.77-7.83 (m, 2H) |
| 1-90 | 1.70-1.82 (m, 2H), 2.22 (m, 2H), 2.36 (s, 3H), 2.85 (t, 1H), 3.03 (s, 6H), 3.22-3.38 (m, 2H), 4.03 (d, 1H), 4.59 (d, 1H), 4.92-5.07 (m, 5H), 5.32 (d, 1H), 6.03 (s, 1H), 6.33 (s, 1H), 7.08 (dd, 1H), 7.24-7.28 (m, 2H), 7.39 (s, 1H) |
| 1-91 | 1.71-1.89 (m, 2H), 2.24 (dd, 2H), 2.84 (t, 1H), 3.25-3.39 (m, 2H), 3.84 (d, 1H), 4.58 (d, 1H), 4.91-5.07 (m, 4H), 5.14-5.25 (m, 2H), 6.03 (s, 1H), 6.86-6.97 (m, 3H), 7.11-7.16 (m, 1H), 7.40 (s, 1H) |
| 1-92 | 1.31 (s, 9H), 1.74-1.90 (m, 2H), 2.24 (dd, 2H), 2.88 (t, 1H), 3.28-3.40 (m, 2H), 3.84 (d, 1H), 4.58 (d, 1H), 5.00-5.07 (m, 4H), 5.18 (s, 2H), 6.04 (s, 1H), 6.95 (s, 1H), 7.12 (d, 1H), 7.20 (s, 1H), 7.25 (d, 1H), 7.39 (s, 1H) |
| 1-93 | 1.70-1.91 (m, 2H), 2.25 (dd, 2H), 2.89 (t, 1H), 3.29-3.38 (m, 2H), 3.84 (d, 1H), 4.59 (d, 1H), 4.91 (d, 1H), 5.01-5.24 (m, 4H), 5.30 (d, 2H), 6.04 (s, 1H), 6.95 (s, 1H), 7.04 (d, 1H), 7.15 (t, 1H), 7.26 (d, 1H), 7.41 (s, 1H) |
| 1-94 | 1.71-1.84 (m, 2H), 2.22 (m, 2H), 2.85 (t, 1H), 3.22-3.38 (m, 2H), 4.04 (d, 1H), 4.60 (d, 1H), 4.92-5.08 (m, 5H), 5.25 (d, 1H), 6.03 (s, 1H), 6.31-6.68 (m, 2H), 7.01 (s, 1H), 7.03 (s, 1H), 7.22 (t, 1H), 7.39 (s, 1H) |
| 1-95 | 1.75-1.92 (m, 2H), 2.25 (dd, 2H), 2.89 (t, 1H), 3.30-3.38 (m, 2H), 3.86 (d, 1H), 4.60 (d, 1H), 5.01 (d, 2H), 5.11-5.26 (m, 4H), 6.06 (s, 1H), 6.96 (s, 1H), 7.32 (d, 1H), 7.42 (s, 1H), 8.03 (s, 1H), 8.09 (d, 1H) |
| 1-96 | 1.67-1.79 (m, 2H), 2.17 (m, 2H), 2.29 (s, 3H), 2.81 (t, 1H), 3.22-3.30 (m, 2H), 3.98 (d, 1H), 4.57 (d, 1H), 4.90-5.08 (m, 5H), 5.31-5.37 (m, 1H), 6.06 (s, 1H), 6.33 (s, 1H), 7.14 (d, 1H), 7.22 (t, 1H), 7.38-7.91 (m, 2H), 8.30 (s, 1H), 9.40 (d, 1H) |
| 1-97 | 1.71-1.84 (m, 2H), 2.22 (m, 2H), 2.32 (s, 3H), 2.85 (t, 1H), 3.25-3.36 (m, 2H), 4.04 (d, 1H), 4.60 (d, 1H), 4.98-5.10 (m, 5H), 5.27 (d, 1H), 6.04 (s, 1H), 6.33 (s, 1H), 6.71 (t, 1H), 7.26-7.32 (m, 2H), 7.39-7.41 (m, 1H) |
| 1-98 | 1.70-1.82 (m, 2H), 2.22 (m, 2H), 2.32 (s, 3H), 2.84 (t, 1H), 3.24-3.35 (m, 2H), 4.03 (d, 1H), 4.60 (d, 1H), 4.90-5.05 (m, 6H), 6.03 (s, 1H), 6.33 (s, 1H), 7.17-7.25 (m, 3H), 7.39 (s, 1H) |
| 1-99 | 1.73-1.89 (m, 2H), 2.24 (dd, 2H), 2.87 (t, 1H), 3.30-3.39 (m, 2H), 3.90 (d, 1H), 4.60 (d, 1H), 4.91-5.20 (m, 6H), 6.04 (s, 1H), 6.53-7.02 (m, 3H), 7.17-7.25 (m, 3H), 7.39 (s, 1H) |

TABLE 177

| No. | CDCl$_3$/TMS δ (ppm) |
|---|---|
| 1-100 | 1.71-1.87 (m, 2H), 2.23 (m, 2H), 2.32 (s, 3H), 2.85 (t, 1H), 3.26-3.39 (m, 2H), 4.05 (d, 1H), 4.61 (d, 1H), 4.91-5.08 (m, 4H), 5.09 (d, 2H), 6.04 (s, 1H), 6.34 (s, 1H), 7.30 (s, 2H), 7.41 (s, 1H) |
| 1-101 | 1.70-1.87 (m, 2H), 2.23 (m, 2H), 2.36 (s, 3H), 2.85 (t, 1H), 3.21 (s, 3H), 3.24-3.38 (m, 2H), 4.02 (d, 1H), 4.60 (d, 1H), 4.88-5.22 (m, 6H), 6.03 (s, 1H), 6.33 (s, 1H), 6.93 (d, 1H), 7.40 (s, 1H), 7.77 (d, 1H) |
| 1-102 | 1.74-1.85 (m, 2H), 2.22 (m, 2H), 2.37 (s, 3H), 2.86 (t, 1H), 3.21 (s, 3H), 3.24-3.37 (m, 2H), 4.04 (d, 1H), 4.60 (d, 1H), 4.94-5.07 (m, 4H), 5.17-5.27 (m, 2H), 6.03 (s, 1H), 6.34 (s, 1H), 7.16 (d, 1H), 7.31 (d, 1H), 7.40 (s, 1H) |

TABLE 177-continued

| No. | CDCl$_3$/TMS δ (ppm) |
|---|---|
| 1-103 | 1.73-1.85 (m, 2H), 2.22 (m, 2H), 2.32 (s, 3H), 2.86 (t, 1H), 3.23 (s, 6H), 3.27-3.36 (m, 2H), 4.03 (d, 1H), 4.59 (d, 1H), 4.97-5.01 (m, 4H), 5.22 (d, 2H), 6.02 (s, 1H), 6.33 (s, 1H), 7.27 (s, 2H), 7.39 (s, 1H) |
| 1-104 | 1.71-1.84 (m, 2H), 2.23 (m, 2H), 2.32 (s, 3H), 2.86 (t, 1H), 3.25-3.36 (m, 2H), 4.05 (d, 1H), 4.61 (d, 1H), 4.94-5.14 (m, 5H), 5.34 (d, 1H), 6.05 (s, 1H), 6.34 (s, 1H), 7.31-7.39 (m, 2H), 7.40 (s, 1H), 7.56 (d, 1H) |
| 1-105 | 1.69-1.82 (m, 2H), 2.15-2.27 (m, 8H), 2.81 (t, 1H), 3.20 (s, 3H), 3.21-3.37 (m, 2H), 4.05 (d, 1H), 4.62 (d, 1H), 4.86-5.09 (m, 5H), 5.25 (d, 1H), 5.85 (s, 1H), 6.03 (s, 1H), 7.12 (d, 1H), 7.21-7.29 (m, 2H), 7.38 (s, 1H) |
| 1-106 | 1.80-1.95 (m, 2H), 2.25 (m, 2H), 2.47 (s, 3H), 2.81 (t, 1H), 3.20 (s, 3H), 3.30-3.57 (m, 2H), 4.75 (d, 1H), 4.77-5.08 (m, 3H), 5.24-5.30 (m, 3H), 5.43 (d, 1H), 6.02 (s, 1H), 6.32 (s, 1H), 7.12 (d, 1H), 7.21-7.28 (m, 2H), 7.39 (s, 1H) |
| 1-107 | 1.80-1.96 (m, 2H), 2.27 (m, 2H), 2.47 (s, 3H), 3.20 (s, 3H), 3.29-3.56 (m, 3H), 4.75 (d, 1H), 4.77-4.99 (m, 2H), 5.19 (d, 2H), 5.32 (s, 2H), 5.43 (d, 1H), 6.02 (s, 1H), 6.32 (s, 1H), 7.00 (dd, 1H), 7.17-7.20 (m, 1H), 7.40 (s, 1H) |
| 1-108 | 1.75-1.94 (m, 2H), 2.25 (dd, 2H), 2.87 (t, 1H), 3.17 (s, 3H), 3.28-3.40 (m, 3H), 3.83 (s, 3H), 3.89 (d, 1H), 4.60 (d, 1H), 4.89-5.23 (m, 6H), 6.03 (s, 1H), 6.55 (s, 1H), 6.78 (d, 1H), 7.16 (d, 1H), 7.40 (s, 1H) |
| 1-109 | 1.74-1.91 (m, 2H), 2.24 (dd, 2H), 2.87 (t, 1H), 3.17 (s, 3H), 3.21-3.38 (m, 2H), 3.80-3.34 (m, 4H), 4.61 (d, 1H), 4.89-4.97 (m, 4H), 5.15-5.23 (m, 2H), 6.02 (s, 1H), 6.28 (s, 1H), 6.78 (d, 1H), 7.16 (d, 1H), 7.39 (s, 1H) |
| 1-110 | 1.75-1.92 (m, 2H), 2.25 (dd, 2H), 2.89 (t, 1H), 3.32-3.38 (m, 2H), 3.79-3.89 (m, 4H), 4.59 (d, 1H), 4.90-5.00 (m, 2H), 5.14-5.21 (m, 4H), 6.03 (s, 1H), 6.71 (d, 1H), 6.95 (s, 1H), 7.19 (d, 1H), 7.41 (s, 1H) |
| 1-111 | 1.72-1.91 (m, 2H), 2.25 (dd, 2H), 2.89 (t, 1H), 3.35-3.40 (m, 2H), 3.84 (d, 1H), 4.59 (d, 1H), 4.91 (d, 1H), 5.03-5.30 (m, 5H), 6.04 (s, 1H), 6.95 (s, 1H), 7.04-7.12 (m, 2H), 7.41-7.48 (m, 2H) |
| 1-112 | 1.75-1.92 (m, 2H), 2.25 (dd, 2H), 2.89 (t, 1H), 3.38-3.40 (m, 2H), 3.80 (s, 3H), 3.91 (d, 1H), 4.60 (d, 1H), 4.90-5.00 (m, 2H), 5.11-5.23 (m, 4H), 6.03 (s, 1H), 6.53-7.02 (m, 4H), 7.20 (d, 1H), 7.40 (s, 1H) |
| 1-113 | 1.73-1.89 (m, 2H), 2.25 (dd, 2H), 2.88 (t, 1H), 3.35-3.41 (m, 2H), 3.90 (d, 1H), 4.60 (d, 1H), 4.90-5.28 (m, 6H), 6.04 (s, 1H), 6.53-7.02 (m, 3H), 7.05-7.11 (m, 2H), 7.40 (s, 1H), 7.45 (d, 1H) |
| 1-114 | 1.75-1.95 (m, 2H), 2.26 (dd, 2H), 2.90 (t, 1H), 3.29-3.40 (m, 2H), 3.86 (d, 1H), 4.60 (d, 1H), 4.98 (d, 1H), 5.11-5.35 (m, 5H), 6.06 (s, 1H), 6.96 (s, 1H), 7.34-7.44 (m, 3H), 7.87 (d, 1H) |
| 1-115 | 1.68-1.83 (m, 2H), 2.15-2.24 (m, 8H), 2.79 (t, 1H), 3.16 (s, 3H), 3.20-3.37 (m, 2H), 3.82 (s, 3H), 4.06 (d, 1H), 4.61 (d, 1H), 4.86-4.97 (m, 4H), 5.14-5.22 (m, 2H), 5.85 (s, 1H), 6.02 (s, 1H), 6.78 (d, 1H), 7.16 (d, 1H), 7.38 (s, 1H) |

TABLE 178

| No. | CDCl$_3$/TMS δ (ppm) |
|---|---|
| 1-116 | 1.75-1.91 (m, 2H), 2.25 (dd, 2H), 2.89 (t, 1H), 3.21 (s, 3H), 3.24-3.39 (m, 2H), 3.91 (d, 1H), 4.59 (d, 1H), 4.96-5.03 (m, 2H), 5.11-5.27 (m, 4H), 6.03 (s, 1H), 6.53-7.02 (m, 3H), 7.16 (d, 1H), 7.30 (d, 1H), 7.40 (s, 1H) |
| 1-117 | 1.75-1.92 (m, 2H), 2.26 (dd, 2H), 2.91 (t, 1H), 3.17 (s, 3H), 3.29-3.39 (m, 2H), 3.82-3.87 (m, 4H), 4.58 (d, 1H), 4.89-4.97 (m, 2H), 5.14-5.23 (m, 4H), 6.03 (s, 1H), 6.78 (d, 1H), 6.95 (s, 1H), 7.17 (d, 1H), 7.40 (s, 1H) |
| 1-118 | 1.77-1.92 (m, 2H), 2.26 (dd, 2H), 2.91 (t, 1H), 3.21 (s, 3H), 3.30-3.38 (m, 2H), 3.85 (d, 1H), 4.59 (d, 1H), 4.96-5.03 (m, 2H), 5.14-5.30 (m, 4H), 6.04 (s, 1H), 6.96 (s, 1H), 7.16 (d, 1H), 7.31 (d, 1H), 7.42 (s, 1H) |
| 1-119 | 1.70-1.87 (m, 2H), 2.22 (m, 2H), 2.87 (t, 1H), 3.20 (s, 3H), 3.22-3.38 (m, 2H), 3.99 (d, 1H), 4.59 (d, 1H), 4.98-5.28 (m, 6H), 6.02 (s, 1H), 6.72 (s, 1H), 6.89 (s, 1H), 6.95 (s, 1H), 7.12 (d, 1H), 7.21-7.26 (m, 2H), 7.32-7.40 (m, 2H) |
| 1-120 | 1.69-1.80 (m, 2H), 2.14-2.26 (m, 8H), 2.81 (t, 1H), 3.20 (s, 3H), 3.22-3.38 (m, 2H), 4.07 (d, 1H), 4.63 (d, 1H), 4.83-4.99 (m, 4H), 5.17-5.21 (m, 2H), 5.85 (s, 1H), 6.03 (s, 1H), 7.00 (dd, 1H), 7.17-7.21 (m, 1H), 7.39 (s, 1H) |
| 1-121 | 1.75-1.90 (m, 2H), 2.11-2.37 (m, 8H), 2.89 (t, 1H), 3.17 (s, 3H), 3.27-3.39 (m, 2H), 3.91 (d, 1H), 4.59 (d, 1H), 4.91-4.97 (m, 2H), 5.11-5.21 (m, 4H), 6.03 (s, 1H), 6.53-6.88 (m, 3H), 7.02 (s, 1H), 7.39 (s, 1H) |
| 1-122 | 1.76-1.91 (m, 2H), 2.16-2.35 (m, 8H), 2.90 (t, 1H), 3.18 (s, 3H), 3.32-3.39 (m, 2H), 3.85 (d, 1H), 4.59 (d, 1H), 4.92-4.97 (m, 2H), 5.15-5.24 (m, 4H), 6.03 (s, 1H), 6.95 (s, 1H), 7.02 (s, 1H), 7.40 (s, 1H) |
| 1-123 | 1.75-1.91 (m, 2H), 2.26 (dd, 2H), 2.88 (t, 1H), 3.22 (s, 3H), 3.28-3.40 (m, 2H), 3.86 (d, 1H), 4.59 (d, 1H), 4.99 (d, 2H), 5.19-5.24 (m, 4H), 6.04 (s, 1H), 6.96 (s, 1H), 7.10 (d, 1H), 7.42 (s, 1H), 7.50 (d, 1H) |
| 1-124 | 1.70-1.93 (m, 2H), 2.25 (dd, 2H), 2.89 (t, 1H), 3.27-3.40 (m, 5H), 3.91 (d, 1H), 4.59 (d, 1H), 5.00-5.32 (m, 6H), 6.04 (s, 1H), 6.52-6.87 (m, 3H), 7.37-7.43 (m, 2H), 7.92 (m, 1H) |
| 1-125 | 1.72-1.90 (m, 2H), 2.25 (dd, 2H), 2.89 (t, 1H), 3.21 (s, 3H), 3.25-3.38 (m, 2H), 3.91 (d, 1H), 4.59 (d, 1H), 4.98 (d, 2H), 5.11-5.23 (m, 4H), 6.03 (s, 1H), 6.53-7.02 (m, 3H), 7.09 (d, 1H), 7.41 (s, 1H), 7.48 (d, 1H) |

TABLE 178-continued

| No. | CDCl$_3$/TMS δ (ppm) |
|---|---|
| 1-126 | 1.78-1.92 (m, 2H), 2.26 (dd, 2H), 2.89 (t, 1H), 3.29-3.41 (m, 2H), 3.92 (d, 1H), 4.61 (d, 1H), 4.95 (d, 1H), 5.09-5.19 (m, 4H), 5.30 (d, 1H), 6.06 (s, 1H), 7.35-7.41 (m, 3H), 7.86 (d, 1H) |
| 1-127 | 2.33 (s, 3H), 3.16 (s, 3H), 3.47-3.58 (m, 4H), 3.68-3.79 (m, 4H), 4.90-5.08 (m, 5H), 5.26 (d, 1H), 5.84 (s, 1H), 6.34 (s, 1H), 6.79 (s, 1H), 7.10 (d, 1H), 7.20-7.28 (m, 2H) |
| 1-128 | 1.74-1.94 (m, 2H), 2.26 (dd, 2H), 2.92 (t, 1H), 3.30-3.41 (m, 5H), 3.86 (d, 1H), 4.59 (d, 1H), 5.01-5.32 (m, 6H), 6.05 (s, 1H), 6.96 (s, 1H), 7.40 (s, 1H), 7.43 (d, 1H), 7.93 (d, 1H) |
| 1-129 | 1.76-1.93 (m, 2H), 2.26 (dd, 2H), 2.91 (t, 1H), 3.21 (s, 3H), 3.30-3.40 (m, 2H), 3.86 (d, 1H), 4.59 (d, 1H), 4.90-5.27 (m, 6H), 6.04 (s, 1H), 6.93-6.96 (m, 2H), 7.42 (s, 1H), 7.78 (d, 1H) |
| 1-130 | 1.74-1.92 (m, 2H), 2.25 (dd, 2H), 2.89 (t, 1H), 3.21 (s, 3H), 3.22-3.39 (m, 2H), 3.91 (d, 1H), 4.59 (d, 1H), 4.89-5.00 (m, 2H), 5.09-5.22 (m, 2H), 6.03 (s, 1H), 6.53-7.02 (m, 4H), 7.41 (s, 1H), 7.78 (d, 1H) |
| 1-131 | 1.73-1.92 (m, 2H), 2.26 (dd, 2H), 2.90 (t, 1H), 3.25-3.40 (m, 5H), 3.85 (d, 1H), 4.58 (d, 1H), 4.91-5.31 (m, 6H), 6.02 (s, 1H), 6.95 (s, 1H), 7.07 (m, 2H), 7.40 (s, 1H) |
| 1-132 | 1.75-1.91 (m, 2H), 2.24 (dd, 2H), 2.89 (t, 1H), 3.25-3.38 (m, 5H), 3.91 (d, 1H), 4.58 (d, 1H), 4.91-5.30 (m, 6H), 6.02 (s, 1H), 6.53-7.01 (m, 3H), 7.07 (m, 2H), 7.39 (s, 1H) |

TABLE 179

| No. | CDCl$_3$/TMS δ (ppm) |
|---|---|
| 1-133 | 1.72-1.83 (m, 2H), 2.23 (m, 2H), 2.32 (s, 3H), 2.85 (t, 1H), 3.25-3.37 (m, 2H), 3.78 (s, 3H), 4.05 (d, 1H), 4.60 (d, 1H), 4.88-5.02 (m, 4H), 5.13-5.20 (m, 2H), 6.03 (s, 1H), 6.33 (s, 1H), 6.69-6.72 (m, 1H), 6.89 (dd, 1H), 7.39 (s, 1H) |
| 1-134 | 1.75-1.92 (m, 2H), 2.19-2.32 (m, 5H), 2.90 (t, 1H), 3.18 (s, 3H), 3.29-3.40 (m, 2H), 3.84 (d, 1H), 4.59 (d, 1H), 4.92-5.22 (m, 6H), 6.04 (s, 1H), 6.95 (s, 1H), 7.10 (s, 2H), 7.41 (s, 1H) |
| 1-135 | 1.71-1.84 (m, 2H), 2.22 (m, 2H), 2.32 (s, 3H), 2.84 (t, 1H), 3.22-3.37 (m, 2H), 3.81 (s, 3H), 4.02 (d, 1H), 4.60 (d, 1H), 4.90-5.03 (m, 5H), 5.27 (d, 1H), 6.03 (s, 1H), 6.33 (s, 1H), 6.74-6.80 (m, 2H), 7.17 (dd, 1H), 7.38 (s, 1H) |
| 1-136 | 1.72-1.90 (m, 2H), 2.26 (m, 2H), 2.88 (t, 1H), 3.27-3.39 (m, 2H), 3.91 (d, 1H), 4.59 (d, 1H), 4.79-5.27 (m, 6H), 6.03 (s, 1H), 6.33 (s, 1H), 6.49-6.88 (m, 3H), 7.01-7.03 (m, 2H), 7.20-7.24 (m, 1H), 7.40 (s, 1H) |
| 1-137 | 1.74-1.91 (m, 2H), 2.25 (dd, 2H), 2.89 (t, 1H), 3.29-3.37 (m, 2H), 3.84 (d, 1H), 4.59 (d, 1H), 4.92-5.28 (m, 6H), 6.03 (s, 1H), 6.49 (t, 1H), 6.95 (s, 1H), 7.01-7.03 (m, 2H), 7.20-7.24 (m, 1H), 7.40 (s, 1H) |
| 1-138 | 1.72-1.90 (m, 2H), 2.24 (dd, 2H), 2.87 (t, 1H), 3.14-3.36 (m, 2H), 3.91 (d, 1H), 4.60 (d, 1H), 4.94-5.14 (m, 6H), 6.03 (s, 1H), 6.67-7.02 (m, 3H), 7.11-7.23 (m, 3H), 7.39 (s, 1H) |
| 1-139 | 1.72-1.89 (m, 2H), 2.25 (dd, 2H), 2.88 (t, 1H), 3.32-3.40 (m, 2H), 3.85 (d, 1H), 4.59 (d, 1H), 4.95-5.06 (m, 4H), 5.18 (s, 2H), 6.04 (s, 1H), 6.95 (s, 1H), 7.12-7.23 (m, 3H), 7.40 (s, 1H) |
| 1-140 | 1.73-1.90 (m, 2H), 2.25 (dd, 2H), 2.89 (t, 1H), 3.28-3.39 (m, 2H), 3.81-3.86 (m, 4H), 4.58 (d, 1H), 4.61-5.29 (m, 6H), 6.03 (s, 1H), 6.75-6.78 (m, 2H), 6.95 (s, 1H), 7.16 (d, 1H), 7.40 (s, 1H) |
| 1-141 | 1.75-1.90 (m, 2H), 2.25 (dd, 2H), 2.89 (t, 1H), 3.26-3.39 (m, 2H), 3.78 (s, 3H), 3.91 (d, 1H), 4.60 (d, 1H), 4.88-4.94 (m, 2H), 5.10-5.21 (m, 4H), 6.04 (s, 1H), 6.53-7.02 (m, 6H), 7.40 (s, 1H) |
| 1-142 | 1.77-1.90 (m, 2H), 2.26 (dd, 2H), 2.89 (t, 1H), 3.29-3.39 (m, 2H), 3.78-3.84 (m, 4H), 4.59 (d, 1H), 4.88-4.94 (m, 2H), 5.13-5.22 (m, 4H), 6.04 (s, 1H), 6.69-6.72 (m, 1H), 6.89 (t, 1H), 6.95 (s, 1H), 7.40 (s, 1H) |
| 1-143 | 1.75-1.85 (m, 2H), 2.23 (m, 2H), 2.32 (s, 3H), 2.86 (t, 1H), 3.22 (s, 3H), 3.24-3.39 (m, 2H), 4.04 (d, 1H), 4.60 (d, 1H), 4.94-5.04 (m, 4H), 5.20 (d, 2H), 6.02 (s, 1H), 6.32-6.68 (m, 2H), 7.07 (d, 1H), 7.22 (d, 1H), 7.39 (s, 1H) |
| 1-144 | 1.70-1.85 (m, 2H), 2.20-2.46 (m, 8H), 2.85 (t, 1H), 3.25-3.38 (m, 2H), 4.04 (d, 1H), 4.60 (d, 1H), 4.82 (d, 1H), 4.94-5.07 (m, 5H), 6.01 (s, 1H), 6.34 (m, 2H), 6.97 (d, 1H), 7.04 (d, 1H), 7.22-7.30 (m, 1H), 7.38 (s, 1H) |
| 1-145 | 1.70-1.88 (m, 2H), 2.26 (dd, 2H), 2.87 (t, 1H), 3.25-3.38 (m, 2H), 3.89 (d, 1H), 4.58 (d, 1H), 4.94-5.20 (m, 5H), 5.35 (d, 1H), 6.07 (s, 1H), 6.53-7.02 (m, 3H), 7.16 (d, 1H), 7.24 (dd, 1H), 7.39-7.42 (m, 2H), 8.31 (s, 1H), 8.59 (brs, 1H) |
| 1-146 | 1.75-1.90 (m, 2H), 2.25 (dd, 2H), 2.90 (t, 1H), 3.24 (s, 6H), 3.27-3.38 (m, 2H), 3.92 (d, 1H), 4.59 (d, 1H), 5.00 (d, 2H), 5.14-5.21 (m, 4H), 6.02 (s, 1H), 6.53-6.72 (m, 4H), 7.27 (m, 1H), 7.40 (s, 1H) |
| 1-147 | 1.75-1.92 (m, 2H), 2.25 (dd, 2H), 2.91 (t, 1H), 3.24 (s, 6H), 3.29-3.38 (m, 2H), 3.84 (d, 1H), 4.56 (d, 1H), 5.00 (d, 2H), 5.19-5.25 (m, 4H), 6.02 (s, 1H), 7.27 (m, 2H), 7.41 (s, 1H) |
| 1-148 | 1.73-1.91 (m, 2H), 2.26 (dd, 2H), 2.89 (t, 1H), 3.28-3.40 (m, 2H), 3.91 (d, 1H), 4.61 (d, 1H), 4.95-5.20 (m, 5H), 5.33 (d, 1H), 6.06 (s, 1H), 6.53-7.02 (m, 3H), 7.31-7.39 (m, 2H), 7.41 (s, 1H), 7.56 (d, 1H) |

TABLE 180

| No. | CDCl$_3$/TMS δ (ppm) |
|---|---|
| 1-149 | 1.75-1.96 (m, 2H), 2.26 (dd, 2H), 2.91 (t, 1H), 3.29-3.40 (m, 2H), 3.84 (d, 1H), 4.58 (d, 1H), 4.95 (d, 1H), 5.06-5.19 (m, 4H), 5.35 (d, 1H), 6.06 (s, 1H), 6.95 (s, 1H), 7.21-7.30 (m, 2H), 7.41-7.44 (m, 2H), 8.31 (s, 1H) |
| 1-150 | 1.74-1.92 (m, 2H), 2.26 (dd, 2H), 2.89 (t, 1H), 3.28-3.42 (m, 2H), 3.85 (d, 1H), 4.60 (d, 1H), 4.95-5.36 (m, 6H), 6.06 (s, 1H), 6.95 (s, 1H), 7.31-7.37 (m, 2H), 7.42 (s, 1H), 7.55 (d, 1H) |
| 1-151 | 3.20 (s, 3H), 3.50-3.77 (m, 8H), 4.91-5.28 (m, 6H), 5.85 (s, 1H), 6.53-7.02 (m, 4H), 7.11 (d, 1H), 7.20-7.30 (m, 2H) |
| 1-152 | 1.65-1.74 (m, 3H), 1.91-1.99 (m, 2H), 2.10-2.23 (m, 1H), 2.30-2.33 (m, 3H), 2.74-3.12 (m, 2H), 3.19-3.29 (m, 5H), 3.90 (t, 1H), 4.65 (dd, 1H), 4.97-5.07 (m, 3H), 5.24 (d, 1H), 5.32-5.39 (m, 1H), 6.01 (s, 1H), 6.31 (s, 1H), 7.12 (d, 1H), 7.20-7.29 (m, 2H), 7.36 (s, 1H) |
| 1-153 | 1.74-1.83 (m, 2H), 2.22 (m, 2H), 2.30 (s, 3H), 2.86 (t, 1H), 3.20 (s, 3H), 3.22-3.37 (m, 2H), 4.03 (d, 1H), 4.61 (d, 1H), 4.90-5.07 (m, 4H), 5.19 (d, 2H), 6.03 (s, 1H), 6.29 (s, 1H), 6.62 (t, 1H), 6.99 (dd, 1H), 7.17-7.27 (m, 1H), 7.39 (s, 1H) |
| 1-154 | 1.75-1.83 (m, 5H), 2.23 (m, 2H), 2.32 (s, 3H), 2.87 (t, 1H), 3.19 (s, 3H), 3.24-3.37 (m, 2H), 4.04 (d, 1H), 4.60 (d, 1H), 4.80-5.06 (m, 6H), 6.33 (s, 1H), 6.95 (dd, 1H), 7.13-7.17 (m, 1H), 7.38 (s, 1H) |
| 1-155 | 1.89-1.97 (m, 2H), 2.08 (d, 1H), 2.28 (d, 1H), 2.56 (s, 3H), 3.04 (t, 1H), 3.14-3.21 (m, 4H), 3.31-3.38 (m, 1H), 3.80 (d, 1H), 4.80 (d, 1H), 4.96 (dd, 2H), 5.19 (d, 2H), 6.03 (s, 1H), 6.46 (s, 1H), 6.99 (dd, 1H), 7.17-7.20 (m, 1H), 7.40 (s, 1H) |
| 1-156 | 1.55-1.87 (m, 4H), 2.00 (dd, 1H), 2.70 (m, 1H), 2.30 and 3.34 (s, 3H), 2.74-3.13 (m, 2H), 3.18-3.29 (m, 4H), 3.90 (t, 1H), 4.57 and 4.72 (d, 1H), 4.91-4.98 (m, 2H), 5.18 (d, 2H), 5.37 (q, 1H), 6.01 (s, 1H), 6.32 (s, 1H), 6.99 (dd, 1H), 7.17-7.20 (m, 1H), 7.36 (s, 1H) |
| 1-157 | 0.75-0.91 (m, 3H), 1.59-1.95 (m, 1H), 1.98-2.17 (m, 1H), 2.30-2.51 (m, 5H), 2.68-3.40 (m, 5H), 3.46-3.50 (m, 1H), 3.78-4.69 (m, 2H), 4.91-5.10 (m, 4H), 5.15-5.27 (m, 2H), 6.04 (s, 1H), 6.33 (s, 1H), 6.97-7.02 (m, 1H), 7.17-7.20 (m, 1H), 7.39-7.41 (m, 1H) |
| 1-158 | 1.74-1.90 (m, 2H), 2.26 (dd, 2H), 2.89 (t, 1H), 3.21 (s, 3H), 3.28-3.39 (m, 2H), 3.92 (d, 1H), 4.59 (d, 1H), 4.98 (d, 2H), 5.18 (dd, 4H), 6.03 (s, 1H), 6.53-7.02 (m, 4H), 7.17-7.20 (m, 1H), 7.41 (s, 1H) |
| 1-159 | 1.09-1.36 (m, 3H), 1.61-1.76 (m, 1H), 1.84-2.02 (m, 1H), 2.17-2.34 (m, 5H), 2.87-3.90 (m, 6H), 4.38-4.63 (m, 1H), 4.90-5.08 (m, 4H), 5.17-5.22 (m, 2H), 6.03 (s, 1H), 6.34 (s, 1H), 6.97-7.02 (m, 1H), 7.17-7.20 (m, 1H), 7.39-7.41 (m, 1H) |
| 1-160 | 1.15-1.28 (m, 1H), 1.61-1.88 (m, 4H), 2.02-2.30 (m, 2H), 2.74-3.37 (m, 6H), 3.80-3.97 (m, 1H), 4.52-4.77 (m, 1H), 4.90-4.99 (m, 2H), 5.13-5.24 (m, 2H), 5.55 (q, 1H), 6.01 (s, 1H), 6.57-7.01 (m, 4H), 7.17-7.19 (m, 1H), 7.38-7.39 (m, 1H) |
| 1-161 | 1.70-1.81 (m, 2H), 2.20 (dd, 2H), 2.30 (s, 3H), 2.82 (t, 1H), 3.24-3.32 (m, 2H), 3.99 (d, 1H), 4.56 (d, 1H), 4.88 (d, 2H), 4.99 (d, 2H), 5.11-5.21 (m, 2H), 6.02 (s, 1H), 6.33 (s, 1H), 6.55-6.58 (m, 1H), 6.74 (dd, 1H), 7.39 (s, 1H) |
| 2-1 | 1.60 (m, 1H), 1.74 (m, 1H), 2.10 (m, 1H), 2.19 (m, 1H), 2.24 (s, 3H), 2.34 (s, 3H), 2.79 (t, 1H), 3.14 (m, 1H), 3.19 (s, 3H), 3.28 (m, 1H), 3.67 (s, 2H), 3.87 (d, 1H), 4.77 (d, 1H), 4.94-5.08 (m, 3H), 5.25 (d, 1H), 6.02 (s, 1H), 6.96 (m, 2H), 7.06 (d, 1H), 7.09 (d, 1H), 7.21 (m, 2H), 7.37 (s, 1H) |
| 2-2 | 1.66-1.81 (m, 2H), 2.20 (d, 2H), 2.83 (t, 1H), 3.20 (s, 3H), 3.16-3.24 (m, 2H), 3.81 (s, 2H), 3.96 (d, 1H), 4.72 (d, 1H), 4.95-5.28 (m, 3H), 5.26 (d, 1H), 6.03 (s, 1H), 7.12 (d, 1H), 7.14-7.32 (m, 2H), 7.38 (s, 1H) |
| 2-3 | 1.69-1.81 (m, 2H), 2.20 (d, 2H), 2.82 (t, 1H), 3.22 (t, 1H), 3.29-3.34 (m, 1H), 3.81 (s, 2H), 3.96 (d, 1H), 4.72 (d, 1H), 4.93-5.26 (m, 3H), 5.24 (d, 1H), 6.03 (s, 1H), 6.92-6.97 (m, 2H), 7.15-7.21 (m, 2H), 7.30-7.32 (m, 2H), 7.38 (s, 1H) |

TABLE 181

| No. | CDCl$_3$/TMS δ (ppm) |
|---|---|
| 2-4 | 1.69-1.79 (m, 2H), 2.24 (d, 2H), 2.83 (t, 1H), 3.22 (t, 1H), 3.29-3.35 (m, 1H), 3.81 (s, 2H), 3.96 (d, 1H), 4.72 (d, 1H), 4.92 (d, 2H), 5.17 (d, 2H), 6.04 (s, 1H), 6.90 (d, 1H), 6.91 (d, 1H), 7.15-7.30 (m, 2H), 7.31-7.33 (m, 2H), 7.39 (s, 1H) |
| 2-5 | 1.81-1.92 (m, 2H), 2.21-2.27 (m, 5H), 2.31 (s, 3H), 3.06 (t, 2H), 3.30 (s, 3H), 3.25-3.33 (m, 1H), 4.16 (d, 2H), 4.98-5.05 (m, 3H), 5.26 (d, 1H), 6.04 (s, 1H), 6.13 (s, 1H), 6.83 (d, 1H), 7.04 (d, 1H), 7.13 (d, 1H), 7.21-7.28 (m, 1H), 7.36-7.41 (m, 2H), 7.46 (s, 1H) |
| 2-6 | 1.52-1.81 (m, 2H), 2.14 (dd, 2H), 2.24 (s, 3H), 2.29 (s, 3H), 2.80 (t, 1H), 3.17 (t, 1H), 3.24-3.34 (m, 1H), 3.67 (s, 2H), 3.86 (d, 1H), 4.77 (d, 1H), 4.92 (d, 2H), 5.16 (d, 2H), 6.03 (s, 1H), 6.90 (dd, 2H), 6.97 (d, 1H), 7.06 (d, 1H), 7.38 (s, 1H) |
| 2-7 | 1.52-1.80 (m, 2H), 2.18 (dd, 2H), 2.22 (s, 3H), 2.29 (s, 3H), 2.79 (t, 1H), 3.13 (t, 1H), 3.25-3.31 (m, 1H), 3.67 (s, 2H), 3.87 (d, 1H), 4.77 (d, 1H), 4.93 (d, 2H), 5.13 (d, 1H), 5.23 (d, 1H), 6.02 (s, 1H), 6.92-6.98 (m, 4H), 7.06 (d, 1H), 7.15-7.19 (m, 1H), 7.37 (s, 1H) |
| 2-8 | 1.54-1.82 (m, 2H), 2.14 (dd, 2H), 2.24 (s, 3H), 2.29 (s, 3H), 2.80 (t, 1H), 3.15 (t, 1H), 3.20 (s, 3H), 3.24-3.32 (m, 1H), 3.67 (s, 2H), 3.87 (d, 1H), 4.77 (d, 1H), 4.93 (dd, 2H), 5.18 (dd, 2H), 6.02 (s, 1H), 6.96-6.99 (m, 3H), 7.06 (d, 1H), 7.15-7.19 (m, 1H), 7.38 (s, 1H) |
| 2-9 | 1.55-1.83 (m, 2H), 2.15 (dd, 2H), 2.23 (s, 3H), 2.29 (s, 3H), 2.80 (t, 1H), 3.17 (t, 1H), 3.25-3.34 (m, 1H), 3.67 (s, 2H), 3.86-3.98 (m, 4H), 4.77 (d, 1H), 4.93 (d, 1H), 5.17 (dd, |

TABLE 181-continued

| No. | CDCl$_3$/TMS δ (ppm) |
|---|---|
| | 2H), 5.29 (d, 1H), 6.03 (s, 1H), 6.82 (d, 1H), 6.96-6.98 (m, 2H), 7.06 (d, 1H), 7.38 (s, 1H), 7.99 (d, 1H) |
| 2-10 | 1.54-1.80 (m, 2H), 2.13 (dd, 2H), 2.24 (s, 3H), 2.29 (s, 3H), 2.78 (t, 1H), 3.16 (t, 1H), 3.25-3.32 (m, 1H), 3.67 (s, 2H), 3.86 (d, 1H), 4.77 (d, 1H), 4.90-5.04 (m, 4H), 6.01 (s, 1H), 6.87-6.97 (m, 4H), 7.06 (d, 1H), 7.12 (m, 1H), 7.36 (s, 1H) |
| 2-11 | 1.53-1.80 (m, 2H), 2.14 (dd, 2H), 2.23 (s, 3H), 2.29 (s, 3H), 2.79 (t, 1H), 3.13 (t, 1H), 3.25-3.32 (m, 1H), 3.67 (s, 2H), 3.86 (d, 1H), 4.76 (d, 1H), 5.01 (s, 4H), 6.02 (s, 1H), 6.96-6.98 (m, 2H), 7.06 (d, 1H), 7.15-7.26 (m, 4H), 7.37 (s, 1H) |
| 2-12 | 0.99 (t, 1H), 1.50-1.82 (m, 4H), 1.95-2.04 (m, 2H), 2.14 (dd, 2H), 2.24 (s, 3H), 2.29 (s, 3H), 2.79 (t, 1H), 3.14 (t, 1H), 3.23-3.34 (m, 3H), 3.67 (s, 2H), 3.87 (d, 1H), 4.78 (d, 1H), 4.93-5.07 (m, 3H), 5.06 (d, 1H), 6.02 (s, 1H), 6.96-6.98 (m, 2H), 7.05-7.11 (m, 2H), 7.19-7.26 (m, 2H), 7.37 (s, 1H) |
| 2-13 | 1.53-1.83 (m, 5H), 2.14 (dd, 2H), 2.24 (s, 3H), 2.29 (s, 3H), 2.82 (t, 1H), 3.14 (t, 1H), 3.24-3.32 (m, 1H), 3.67 (s, 2H), 3.86 (d, 1H), 4.76 (d, 1H), 5.12 (s, 2H), 5.18 (q, 1H), 6.09 (s, 1H), 6.96-6.98 (m, 2H), 7.05-7.25 (m, 5H), 7.37 (s, 1H) |
| 2-14 | 1.80-1.92 (m, 2H), 2.18-2.28 (m, 5H), 2.31 (s, 3H), 3.07 (t, 2H), 3.20 (s, 3H), 3.23-3.36 (m, 1H), 4.17 (d, 2H), 4.96 (dd, 2H), 5.20 (dd, 2H), 6.04 (s, 1H), 6.12 (s, 1H), 6.83 (d, 1H), 6.85-7.05 (m, 2H), 7.17-7.22 (m, 1H), 7.41 (s, 1H), 7.48 (s, 1H) |
| 2-15 | 1.80-1.92 (m, 2H), 2.20-2.27 (m, 5H), 2.31 (s, 3H), 3.07 (t, 2H), 3.27-3.35 (m, 1H), 4.17 (d, 2H), 4.93 (d, 2H), 5.17 (d, 2H), 6.05 (s, 1H), 6.12 (s, 1H), 6.84 (d, 1H), 6.83-6.92 (m, 2H), 7.04 (d, 1H), 7.40 (s, 1H), 7.47 (s, 1H) |
| 2-16 | 1.68-1.83 (m, 2H), 2.19 (d, 2H), 2.83 (t, 1H), 3.20-3.37 (m, 5H), 3.81 (s, 2H), 3.96 (d, 1H), 4.72 (d, 1H), 4.95 (dd, 1H), 5.19 (d, 1H), 6.03 (s, 1H), 7.00 (dd, 1H), 7.17-7.19 (m, 1H), 7.30-7.33 (m, 2H), 7.39 (s, 1H) |
| 2-17 | 1.54-1.83 (m, 2H), 2.13 (dd, 2H), 2.24 (s, 3H), 2.29 (s, 3H), 2.79 (t, 1H), 3.13 (t, 1H), 3.24-3.34 (m, 1H), 3.67 (s, 2H), 3.86 (d, 1H), 4.77 (d, 1H), 4.88-5.07 (m, 3H), 5.24 (d, 1H), 6.02 (s, 1H), 6.96-7.08 (m, 5H), 7.38 (s, 1H), 7.44 (m, 1H) |

TABLE 182

| No. | CDCl$_3$/TMS δ (ppm) |
|---|---|
| 2-18 | 1.55-1.80 (m, 2H), 2.14 (dd, 2H), 2.24 (s, 3H), 2.29 (s, 3H), 2.80 (t, 1H), 3.13 (t, 1H), 3.25-3.32 (m, 1H), 3.67 (s, 2H), 3.86 (d, 1H), 4.77 (d, 1H), 4.90 (d, 1H), 5.01 (dd, 2H), 5.28 (d, 1H), 6.02 (s, 1H), 6.96 (d, 2H), 7.05 (m, 2H), 7.14 (t, 1H), 7.25 (d, 1H), 7.38 (s, 1H) |
| 2-19 | 1.64-1.83 (m, 2H), 2.20 (d, 2H), 2.83 (t, 1H), 3.19-3.37 (m, 2H), 3.80 (s, 2H), 3.96 (d, 1H), 4.02 (d, 1H), 4.90 (d, 1H), 5.03 (m, 2H), 5.24 (d, 1H), 6.03 (s, 1H), 7.01-7.07 (m, 2H), 7.18 (d, 1H), 7.30-7.32 (m, 2H), 7.39 (s, 1H), 7.44 (d, 1H) |
| 2-20 | 1.54-1.81 (m, 2H), 2.14 (d, 2H), 2.24 (s, 3H), 2.29 (s, 3H), 2.80 (t, 1H), 3.14 (t, 1H), 3.25-3.31 (m, 1H), 3.67 (s, 2H), 3.79 (s, 3H), 3.86 (d, 1H), 4.77 (d, 1H), 4.92 (dd, 2H), 5.17 (dd, 2H), 6.02 (s, 1H), 6.70 (d, 1H), 6.97 (d, 2H), 7.06 (d, 1H), 7.19 (d, 1H), 7.37 (s, 1H) |
| 2-21 | 1.65-1.83 (m, 2H), 2.20 (d, 2H), 2.82 (t, 1H), 3.20-3.37 (m, 2H), 3.80 (s, 2H), 3.96 (d, 1H), 4.72 (d, 1H), 5.00 (d, 2H), 5.12 (d, 2H), 6.06 (s, 1H), 7.20 (d, 1H), 7.31-7.33 (d, 3H), 7.39 (s, 1H), 8.03 (s, 1H), 8.09 (d, 1H) |
| 2-22 | 1.67-1.83 (m, 2H), 2.20 (d, 2H), 2.83 (t, 1H), 3.18-3.37 (m, 2H), 3.80 (s, 2H), 3.96 (d, 1H), 4.72 (d, 1H), 4.90 (d, 1H), 5.01 (dd, 2H), 5.29 (d, 1H), 6.03 (s, 1H), 7.04 (d, 1H), 7.14 (dd, 1H), 7.19 (d, 1H), 7.25 (m, 1H), 7.30-732 (m, 2H), 7.88 (s, 1H) |
| 2-23 | 1.67-1.82 (m, 2H), 2.20 (d, 2H), 2.83 (t, 1H), 3.19-3.35 (m, 2H), 3.79-3.80 (m, 5H), 3.96 (d, 1H), 4.70 (d, 1H), 4.94 (dd, 2H), 5.17 (dd, 2H), 6.02 (s, 1H), 6.70 (d, 1H), 7.19 (d, 2H), 7.30-7.32 (m, 2H), 7.38 (s, 1H) |
| 2-24 | 1.57-1.81 (m, 2H), 2.15 (d, 2H), 2.24 (s, 3H), 2.29 (s, 3H), 2.80 (t, 1H), 3.14 (t, 1H), 3.26-3.32 (m, 1H), 3.67 (s, 2H), 3.75 (s, 3H), 3.85 (d, 1H), 4.76 (d, 1H), 4.93 (dd, 2H), 5.15 (d, 2H), 6.02 (s, 1H), 6.65 (d, 1H), 6.96-6.98 (m, 2H), 7.06 (d, 1H), 7.36-7.38 (m, 2H) |
| 2-25 | 1.65-1.82 (m, 2H), 2.20 (d, 2H), 2.82 (t, 1H), 3.18-3.36 (m, 2H), 3.79-3.80 (m, 5H), 3.95 (d, 1H), 4.71 (d, 1H), 4.93 (dd, 2H), 5.15 (d, 2H), 6.02 (s, 1H), 6.65 (d, 1H), 7.18 (d, 1H), 7.29-7.38 (m, 4H) |
| 2-26 | 1.65-1.81 (m, 2H), 2.20 (d, 2H), 2.83 (t, 1H), 3.19 (s, 3H), 3.20-3.35 (m, 2H), 3.82 (s, 2 + 3H), 3.96 (d, 1H), 4.72 (d, 1H), 4.93 (dd, 2H), 5.18 (dd, 2H), 6.02 (s, 1H), 6.68 (d, 1H), 7.15-7.21 (m, 2H), 7.30-7.32 (m, 2H), 7.38 (s, 1H) |
| 2-27 | 1.55-1.80 (m, 2H), 2.14 (dd, 2H), 2.24 (s, 3H), 2.29 (s, 3H), 2.79 (t, 1H), 3.14 (t, 1H), 3.23-3.32 (m, 1H), 3.67 (s, 2H), 3.87 (d, 1H), 4.78 (d, 1H), 4.90 (d, 2H), 5.15 (d, 2H), 6.01 (s, 1H), 6.96 (m, 2H), 7.06 (d, 1H), 7.37 (s, 1H) |
| 2-28 | 1.56-1.81 (m, 2H), 2.14 (d, 2H), 2.24 (s, 3H), 2.29 (s, 3H), 2.80 (t, 1H), 3.19 (s, 3H), 3.12-3.37 (m, 2H), 3.67 (s, 2H), 3.81-3.88 (m, 4H), 4.77 (d, 1H), 4.92 (dd, 2H), 5.17 (dd, 2H), 6.01 (s, 1H), 6.77 (d, 1H), 6.96 (m, 2H), 7.06 (d, 1H), 7.16 (d, 1H), 7.37 (s, 1H) |
| 2-29 | 1.66-1.84 (m, 2H), 2.20 (d, 2H), 2.82 (t, 1H), 3.19-3.34 (m, 2H), 3.80 (s, 2H), 3.96 (d, 1H), 4.72 (d, 1H), 4.90 (d, 2H), 5.15 (d, 2H), 6.01 (s, 1H), 7.19 (d, 1H), 7.28-7.34 (m, 2H), 7.38 (s, 1H) |
| 2-30 | 1.70-1.81 (m, 2H), 2.20 (m, 2H), 2.84 (t, 1H), 3.20-3.37 (m, 5H), 3.90-4.01 (m, 3H), 4.70 (d, 1H), 4.95-5.28 (m, 3H), 5.26 (d, 1H), 6.03 (s, 1H), 7.12 (d, 1H), 7.21-7.28 (m, 2H), 7.39 (s, 1H), 7.65 (m, 2H), 7.80 (d, 1H) |

TABLE 182-continued

| No. | CDCl$_3$/TMS δ (ppm) |
|---|---|
| 2-31 | 1.55-1.80 (m, 2H), 2.09-2.37 (m, 14H), 2.80 (t, 1H), 3.10-3.32 (m, 5H), 3.67 (s, 2H), 3.88 (d, 1H), 4.78 (d, 1H), 4.91 (dd, 2H), 5.16 (d, 2H), 6.01 (s, 1H), 6.97 (d, 2H), 7.02 (s, 1H), 7.06 (d, 1H), 7.36 (s, 1H) |
| 2-32 | 1.63-1.84 (m, 2H), 2.09-2.24 (m, 5H), 2.29 (s, 3H), 2.83 (t, 1H), 3.15-3.37 (m, 5H), 3.80 (s, 2H), 3.96 (d, 1H), 4.71 (d, 1H), 4.94 (dd, 2H), 5.17 (d, 2H), 6.02 (s, 1H), 7.02 (s, 1H), 7.19 (d, 1H), 7.30-7.32 (d, 2H), 7.37 (s, 1H) |

TABLE 183

| No. | CDCl$_3$/TMS δ (ppm) |
|---|---|
| 2-33 | 1.53-1.80 (m, 2H), 2.14 (dd, 2H), 2.24 (s, 3H), 2.29 (s, 3H), 2.80 (t, 1H), 3.14-3.32 (m, 5H), 3.89 (s, 2H), 3.87 (d, 1H), 4.78 (d, 1H), 4.98 (d, 2H), 5.19 (dd, 2H), 6.02 (s, 1H), 6.97 (d, 2H), 7.08 (m, 2H), 7.38 (s, 1H), 7.49 (d, 1H) |
| 2-34 | 1.65-1.83 (m, 2H), 2.21 (d, 2H), 2.84 (t, 1H), 3.20-3.37 (m, 5H), 3.81 (s, 2H), 3.97 (d, 1H), 4.72 (d, 1H), 5.10 (dd, 2H), 5.25 (dd, 2H), 6.05 (s, 1H), 7.19 (d, 1H), 7.31 (m, 2H), 7.40 (s, 2H), 7.93 (d, 1H) |
| 2-35 | 1.67-1.84 (m, 2H), 2.20 (d, 2H), 2.83 (t, 1H), 3.21-3.38 (m, 5H), 3.80 (s, 2H), 3.97 (d, 1H), 4.71 (d, 1H), 4.98 (d, 2H), 5.19 (dd, 2H), 6.03 (s, 1H), 7.09 (d, 1H), 7.18 (d, 1H), 7.31 (m, 2H), 7.40 (s, 1H), 7.49 (d, 1H) |
| 2-36 | 1.68-1.84 (m, 2H), 2.20 (d, 2H), 2.83 (t, 1H), 3.19-3.37 (m, 2H), 3.81 (s, 2H), 3.97 (d, 1H), 4.72 (d, 1H), 4.94 (d, 1H), 5.14 (dd, 2H), 5.29 (d, 1H), 6.05 (s, 1H), 7.19 (d, 1H), 7.30-7.37 (m, 4H), 7.40 (s, 1H), 7.85 (d, 1H) |
| 2-37 | 1.58-1.81 (m, 2H), 2.16 (dd, 2H), 2.24 (s, 3H), 2.29 (s, 3H), 2.81 (t, 1H), 3.15 (t, 1H), 3.67 (s, 2H), 3.88 (d, 1H), 4.77 (d, 1H), 5.10 (dd, 2H), 5.25 (dd, 2H), 6.04 (s, 1H), 6.97 (d, 2H), 7.07 (d, 1H), 7.39 (m, 2H), 7.93 (d, 1H) |
| 2-38 | 1.55-1.80 (m, 2H), 2.15 (dd, 2H), 2.24 (s, 3H), 2.29 (s, 3H), 2.80 (t, 1H), 3.11-3.31 (m, 5H), 3.67 (s, 2H), 3.68 (d, 1H), 4.97 (d, 1H), 4.99 (dd, 2H), 5.20 (dd, 2H), 6.02 (s, 1H), 6.97 (d, 2H), 7.07 (d, 1H), 7.15-7.18 (m, 2H), 7.30 (d, 1H), 7.38 (s, 1H) |
| 2-39 | 1.55-1.81 (m, 2H), 2.14 (dd, 2H), 2.24 (s, 3H), 2.29 (s, 3H), 2.81 (t, 1H), 3.14 (t, 1H), 3.24-3.32 (m, 1H), 3.67 (s, 2H), 3.88 (d, 1H), 4.78 (d, 1H), 4.90 (d, 1H), 5.12 (dd, 2H), 5.30 (d, 1H), 6.05 (s, 1H), 6.97 (d, 2H), 7.06 (d, 1H), 7.35-7.40 (m, 3H), 7.85 (d, 1H) |
| 2-40 | 1.53-1.80 (m, 2H), 2.14 (dd, 2H), 2.24 (s, 3H), 2.29 (s, 3H), 2.80 (t, 1H), 3.14-3.34 (m, 5H), 3.67 (s, 2H), 3.87 (d, 1H), 4.78 (d, 1H), 4.97 (dd, 2H), 5.14 (dd, 2H), 6.02 (s, 1H), 6.93-7.00 (m, 3H), 7.06 (d, 1H), 7.38 (s, 1H), 7.78 (d, 1H) |
| 2-41 | 1.64-1.82 (m, 2H), 2.21 (dd, 2H), 2.83 (t, 1H), 3.17-3.36 (m, 5H), 3.81 (s, 2H), 3.96 (d, 1H), 4.72 (d, 1H), 5.00 (dd, 2H), 5.21 (dd, 2H), 6.03 (s, 1H), 7.16-7.21 (m, 2H), 7.30-7.33 (m, 3H), 7.39 (s, 1H) |
| 2-42 | 1.54-1.80 (m, 2H), 2.14 (dd, 2H), 2.24 (s, 3H), 2.29 (s, 3H), 2.80 (t, 1H), 3.13 (t, 1H), 3.24-3.33 (m, 4H), 3.67 (s, 2H), 3.86 (d, 1H), 4.77 (d, 1H), 4.91 (d, 1H), 5.02 (d, 2H), 5.27 (d, 1H), 6.01 (s, 1H), 6.97 (d, 2H), 7.07 (m, 3H), 7.37 (s, 1H) |
| 2-43 | 1.67-1.83 (m, 2H), 2.20 (d, 2H), 2.83 (t, 1H), 3.19-3.35 (m, 5H), 3.80 (s, 2H), 3.96 (d, 1H), 4.71 (d, 1H), 4.92 (d, 1H), 5.02 (d, 2H), 5.27 (d, 1H), 6.02 (s, 1H), 7.07 (d, 2H), 7.18 (d, 1H), 7.30-7.33 (m, 2H), 7.38 (s, 1H) |
| 2-44 | 1.65-1.83 (m, 2H), 2.20 (d, 2H), 2.83 (t, 1H), 3.20-3.38 (m, 5H), 3.81 (s, 2H), 3.97 (d, 1H), 4.72 (d, 1H), 4.94 (dd, 2H), 5.15 (dd, 2H), 6.03 (s, 1H), 6.94 (d, 1H), 7.20 (d, 1H), 7.30-7.33 (m, 2H), 7.40 (s, 1H), 7.78 (d, 1H) |
| 2-45 | 1.55-1.83 (m, 2H), 2.14 (dd, 2H), 2.24-2.29 (m, 9H), 2.80 (t, 1H), 3.10-3.17 (m, 4H), 3.24-3.31 (m, 1H), 3.67 (s, 2H), 3.87 (d, 1H), 4.77 (d, 1H), 4.97 (dd, 2H), 5.15 (dd, 2H), 6.02 (s, 1H), 6.96 (d, 2H), 7.05-7.09 (m, 3H), 7.37 (s, 1H) |
| 2-46 | 1.58-1.82 (m, 2H), 2.19 (dd, 2H), 2.27 (s, 3H), 2.83 (t, 1H), 3.21-3.37 (m, 5H), 3.80 (s, 2H), 3.96 (d, 1H), 4.71 (d, 1H), 4.94 (dd, 2H), 5.15 (dd, 2H), 6.03 (s, 1H), 7.09 (s, 2H), 7.19 (d, 1H), 7.29-7.31 (m, 2H), 7.39 (s, 1H) |
| 2-47 | 1.54-1.80 (m, 2H), 2.14 (dd, 2H), 2.24 (s, 3H), 2.29 (s, 3H), 2.79 (t, 1H), 3.13 (t, 1H), 3.25-3.32 (m, 1H), 3.67 (s, 2H), 3.86 (d, 1H), 4.77 (d, 1H), 4.94 (dd, 2H), 5.04 (d, 1H), 5.24 (d, 1H), 6.02 (s, 1H), 6.49 (t, 1H), 6.96-7.07 (m, 5H), 7.20 (d, 1H), 7.37 (s, 1H) |
| 2-48 | 1.65-1.80 (m, 2H), 2.20 (d, 2H), 2.82 (t, 1H), 3.22-3.35 (m, 2H), 3.80 (s, 2H), 3.96 (d, 1H), 4.72 (d, 1H), 4.91-5.06 (m, 3H), 5.25 (d, 1H), 6.03 (s, 1H), 6.49 (t, 1H), 7.01 (d, 2H), 7.18-7.23 (m, 2H), 7.32 (d, 2H), 7.38 (s, 1H) |

TABLE 184

| No. | CDCl$_3$/TMS δ (ppm) |
|---|---|
| 2-49 | 1.67-1.80 (m, 2H), 2.19 (d, 2H), 2.82 (t, 1H), 3.14 (s, 3H), 3.19-3.34 (m, 2H), 3.80 (s, 2H), 3.95 (d, 1H), 4.72 (d, 1H), 4.99 (dd, 4H), 6.03 (s, 1H), 7.11-7.18 (m, 2H), 7.20 (d, 2H), 7.32 (d, 2H), 7.38 (s, 1H) |
| 2-50 | 1.55-1.80 (m, 2H), 2.14 (d, 2H), 2.24 (s, 3H), 2.29 (s, 3H), 2.79 (t, 1H), 3.13 (t, 1H), 3.26-3.31 (m, 1H), 3.67 (s, 2H), 3.81-3.88 (m, 4H), 4.76 (d, 1H), 4.90 (d, 2H), 5.00 (d, 1H), 5.26 (d, 1H), 6.02 (s, 1H), 6.76 (dd, 2H), 6.97 (d, 2H), 7.06 (d, 1H), 7.16 (t, 1H), 7.36 (s, 1H) |

TABLE 184-continued

| No. | CDCl$_3$/TMS δ (ppm) |
|---|---|
| 2-51 | 1.65-1.81 (m, 2H), 2.19 (d, 2H), 2.82 (t, 1H), 3.21-3.34 (m, 2H), 3.81 (s, 2 + 3H), 3.95 (d, 1H), 4.71 (d, 1H), 4.92 (d, 2H), 5.01 (d, 1H), 5.27 (d, 1H), 6.03 (s, 1H), 6.77 (dd, 2H), 7.15-7.21 (m, 2H), 7.30-7.32 (m, 2H), 7.38 (s, 1H) |
| 2-52 | 1.54-1.81 (m, 2H), 2.14 (d, 2H), 2.24 (s, 3H), 2.29 (s, 3H), 2.80 (t, 1H), 3.13 (t, 1H), 3.26-3.32 (m, 1H), 3.67 (s, 2H), 3.78 (s, 3H), 3.86 (d, 1H), 4.77 (d, 1H), 4.88 (dd, 2H), 5.16 (dd, 2H), 6.02 (s, 1H), 6.70 (dd, 1H), 6.87 (d, 1H), 6.96 (d, 2H), 7.06 (s, 1H), 7.37 (s, 1H) |
| 2-53 | 1.55-1.80 (m, 2H), 2.14 (d, 2H), 2.24 (s, 3H), 2.29 (s, 3H), 2.80 (t, 1H), 3.14 (t, 1H), 3.21-3.32 (m, 7H), 3.67 (s, 2H), 3.87 (d, 1H), 4.76 (d, 1H), 4.98 (d, 2H), 5.21 (d, 2H), 6.01 (s, 1H), 6.97 (d, 2H), 7.06 (s, 1H), 7.27 (m, 2H), 7.38 (s, 1H) |
| 2-54 | 2.24 (s, 3H), 2.28 (s, 3H), 3.19 (s, 3H), 3.40-3.53 (m, 6H), 3.69 (s, 2H), 3.82 (m, 2H), 4.93 (dd, 2H), 5.07 (d, 1H), 5.25 (d, 1H), 5.83 (s, 1H), 6.76 (s, 1H), 6.95-6.99 (m, 2H), 7.06-7.11 (m, 2H), 7.19-7.28 (m, 2H) |
| 2-55 | 1.38-1.45 (m, 2H), 1.90 (d, 2H), 2.22 (s, 3H), 2.30 (s, 3H), 2.67 (t, 2H), 3.06-3.09 (m, 4H), 3.20 (s, 3H), 3.83 (d, 2H), 4.93 (dd, 2H), 5.17 (dd, 2H), 5.99 (s, 1H), 6.89 (s, 1H), 6.95-6.98 (m, 2H), 7.10 (d, 1H), 7.16-7.20 (m, 1H), 7.33 (s, 1H) |
| 2-56 | 1.37-1.41 (m, 2H), 1.89 (d, 2H), 2.22 (s, 3H), 2.30 (s, 3H), 2.67 (t, 2H), 3.06-3.09 (m, 4H), 3.19 (s, 3H), 3.82 (d, 2H), 4.93-5.06 (m, 3H), 5.24 (d, 1H), 5.99 (s, 1H), 6.89 (s, 1H), 6.95 (d, 1H), 7.11 (d, 2H), 7.20-7.28 (m, 2H), 7.32 (s, 1H) |
| 2-57 | 1.54-1.80 (m, 2H), 2.14 (dd, 2H), 2.24 (s, 3H), 2.29 (s, 3H), 2.80 (t, 1H), 3.17 (t, 1H), 3.20 (s, 3H), 3.22-3.31 (m, 1H), 3.67 (s, 2H), 3.87 (d, 1H), 4.78 (d, 1H), 4.95 (dd, 2H), 5.19 (d, 2H), 6.02 (s, 1H), 6.96-6.99 (m, 3H), 7.07 (d, 1H), 7.17-7.20 (m, 1H), 7.38 (s, 1H) |
| 3-1 | 1.74-1.83 (m, 2H), 1.89 (s, 3H), 1.93 (s, 3H), 2.14-2.23 (m, 1H), 2.78 (t, 1H), 3.20 (s, 3H), 3.21-3.38 (m, 2H), 3.99 (d, 1H), 4.66-4.71 (m, 3H), 4.90-5.08 (m, 3H), 5.26 (d, 1H), 6.03 (s, 1H), 7.12 (d, 1H), 7.14-7.28 (m, 2H), 7.38 (s, 1H) |
| 3-2 | 1.72-1.87 (m, 2H), 2.21 (t, 2H), 2.82 (t, 1H), 3.20 (t, 1H), 3.29-3.37 (m, 1H), 3.80 (d, 1H), 4.66 (d, 1H), 4.90-4.96 (m, 4H), 5.03 (d, 1H), 5.24 (d, 1H), 6.03 (s, 1H), 6.93-6.97 (m, 2H), 7.15-7.21 (m, 1H), 7.39 (s, 1H), 7.60 (q, 1H) |
| 3-3 | 1.72-1.87 (m, 2H), 2.25 (t, 2H), 2.86 (t, 1H), 3.20 (m, 4H), 3.28-3.36 (m, 1H), 3.80 (d, 1H), 4.66 (d, 1H), 4.90-4.99 (m, 4H), 5.19 (d, 2H), 6.03 (s, 1H), 7.00 (t, 1H), 7.19 (dd, 1H), 7.39 (s, 1H), 7.60 (q, 1H) |
| 3-4 | 1.71-1.86 (m, 2H), 2.25 (m, 2H), 2.83 (t, 1H), 3.20 (m, 4H), 3.27-3.37 (m, 1H), 3.77-3.82 (m, 4H), 4.65 (d, 1H), 4.89-4.93 (m, 4H), 5.18 (dd, 2H), 6.02 (s, 1H), 6.78 (d, 1H), 7.17 (d, 1H), 7.38 (s, 1H), 7.60 (q, 1H) |
| 3-5 | 1.72-1.85 (m, 2H), 2.25 (t, 2H), 2.83 (t, 1H), 3.20 (m, 4H), 3.26-3.39 (m, 1H), 3.80 (d, 1H), 4.66 (d, 1H), 4.90 (s, 2H), 4.95-5.08 (m, 3H), 5.26 (d, 1H), 6.03 (s, 1H), 7.12 (d, 1H), 7.21-7.29 (m, 2H), 7.38 (s, 1H), 7.60 (q, 1H) |
| 4-1 | 1.31-1.44 (m, 2H), 1.89 (d, 2H), 2.22 (s, 3H), 2.30 (s, 3H), 2.67 (t, 2H), 3.06-3.11 (m, 4H), 3.80-3.85 (m, 5H), 4.86-5.00 (m, 3H), 5.25 (d, 1H), 5.99 (s, 1H), 6.76 (dd, 2H), 6.89 (s, 1H), 6.94 (d, 1H), 7.10-7.16 (m, 2H), 7.32 (s, 1H) |
| 5-2 | 2.42 (brs, 2H), 4.76 (s, 2H), 4.84 (s, 2H), 7.04 (dd, 1H), 7.15 (d, 1H), 7.26-7.31 (m, 1H) |

TABLE 185

| No. | CDCl$_3$/TMS δ (ppm) |
|---|---|
| 5-3 | 2.89 (brs, 2H), 4.84 (s, 4H), 7.31 (dd, 2H) |
| 5-5 | 3.13 (s, 2H), 4.49 (d, 4H), 7.57 (s, 2H) |
| 5-6 | 3.11-3.33 (m, 5H), 4.81 (s, 4H), 7.25-7.28 (m, 1H), 7.37-7.40 (m, 2H) |
| 5-7 | 1.40 (s, 3H), 3.59 (q, 2H), 4.56 (d, 2H), 4.69 (d, 2H), 4.96 (t, 1H), 5.26 (t, 1H), 7.22 (d, 1H), 7.37 (t, 1H), 7.45 (d, 1H) |
| 5-8 | 3.27 (s, 3H), 3.53 (brs, 1H), 3.65 (brs, 1H), 4.80 (s, 2H), 4.84 (s, 2H), 7.11 (dd, 1H), 7.26-7.29 (m, 1H) |
| 5-9 | 2.63 (brs, 2H), 3.16 (s, 3H), 4.76 (s, 4H), 7.21-7.53 (m, 2H), 7.32 (s, 1H), 7.42 (d, 1H) |
| 5-11 | 2.64 (brs, 1H), 2.85 (brs, 1H), 4.72 (s, 4H), 6.97-7.02 (m, 1H), 7.10 (d, 1H), 7.31 (dd, 1H) |
| 5-12 | 2.83 (brs, 1H), 2.98 (brs, 1H), 4.80 (s, 2H), 4.88 (s, 2H), 7.48 (t, 1H), 7.70 (d, 1H), 7.81 (d, 1H) |
| 5-13 | 1.21-1.26 (m, 2H), 1.34-1.37 (m, 2H), 2.72-2.77 (m, 1H), 3.27 (brs, 1H), 3.51 (brs, 1H), 4.78 (s, 2H), 4.95 (s, 2H), 7.29 (d, 1H), 7.35-7.40 (m, 2H) |
| 5-14 | 2.39 (s, 3H), 3.70 (t, 1H), 3.82 (t, 1H), 4.59 (d, 2H), 4.63 (d, 2H), 7.11-7.16 (m, 3H) |
| 5-15 | 3.08 (brs, 1H), 3.15 (brs, 1H), 4.75 (s, 2H), 4.93 (s, 2H), 7.16 (t, 1H), 7.31 (d, 1H), 7.56 (d, 1H) |
| 5-16 | 2.84 (brs, 2H), 4.79 (s, 4H), 7.56 (d, 1H), 7.59 (d, 1H), 7.63 (s, 1H) |
| 5-17 | 2.82 (brs, 2H), 4.84 (s, 4H) |
| 5-19 | 2.46 (s, 3H), 3.40 (s, 3H), 4.62 (dd, 4H), 4.92 (t, 1H), 5.00 (t, 1H), 7.20-7.23 (m, 2H) |
| 5-20 | 2.34 (s, 3H), 3.38 (brs, 1H), 3.46 (brs, 1H), 4.63 (d, 4H), 7.10 (d, 1H), 7.14 (s, 1H), 7.20 (d, 1H) |
| 5-21 | 1.00 (t, 3H), 1.03-1.61 (m, 2H), 1.98-2.06 (m, 2H), 3.12 (t, 1H), 3.37-3.41 (m, 3H), 4.79 (dd, 4H), 7.22 (d, 1H), 7.35-7.40 (m, 2H) |
| 5-22 | 1.17 (t, 3H), 2.04-2.11 (m, 2H), 3.22 (t, 1H), 3.35-3.40 (m, 4H), 4.79 (d, 4H), 7.24 (d, 1H), 7.37-7.45 (m, 2H) |
| 5-23 | 3.30 (brs, 2H), 4.71 (s, 2H), 4.89 (s, 2H), 7.20-7.25 (m, 2H), 7.36 (d, 1H) |
| 5-24 | 2.61 (brs, 2H), 3.85 (s, 3H), 4.89 (s, 2H), 4.95 (s, 2H), 6.78 (d, 1H), 7.51 (d, 1H) |

TABLE 185-continued

| No. | CDCl$_3$/TMS δ (ppm) |
|---|---|
| 5-25 | 0.89 (t, 3H), 1.25-1.40 (m, 6H), 1.48-1.56 (m, 2H), 1.59-1.63 (m, 2H), 2.00-2.07 (m, 2H), 3.19 (brs, 1H), 3.31-3.40 (m, 3H), 4.80 (s, 4H), 7.24 (d, 1H), 7.34-7.39 (m, 2H) |
| 5-26 | 3.39 (s, 3H), 3.81 (s, 3H), 4.63 (dd, 4H), 4.84 (t, 1H), 5.05 (t, 1H), 7.03 (d, 1H), 7.28 (d, 1H) |
| 5-27 | 2.48 (t, 1H), 2.55 (t, 1H), 4.85 (d, 4H), 7.60 (d, 1H), 8.19 (d, 1H), 7.28 (s, 1H) |
| 5-28 | 1.62 (s, 3H), 1.64 (s, 3H), 3.18 (t, 1H), 3.34 (t, 1H), 3.59-3.66 (m, 1H), 4.79 (d, 4H), 7.23 (d, 1H), 7.35-7.40 (m, 2H) |
| 5-29 | 1.53 (t, 3H), 3.28 (q, 2H), 3.39 (brs, 1H), 3.52 (brs, 1H), 4.65 (s, 4H), 7.18 (d, 1H), 7.27 (s, 1H), 7.36 (d, 1H) |
| 5-30 | 2.53 (brs, 2H), 2.83-2.89 (m, 2H), 3.16-3.66 (m, 2H), 4.79 (d, 4H), 7.24-7.27 (m, 1H), 7.39-7.41 (m, 2H) |
| 5-31 | 2.04-2.12 (m, 2H), 2.73 (brs, 2H), 2.91 (t, 4H), 4.72 (s, 4H), 7.23 (s, 2H) |
| 5-32 | 3.05-3.12 (m, 2H), 3.36 (s, 3H), 4.91 (dd, 4H), 7.48 (d, 1H), 7.89 (d, 1H) |
| 5-33 | 4.55 (d, 4H), 4.73 (t, 1H), 5.02 (t, 1H), 6.71 (d, 1H), 6.85 (d, 1H), 7.04 (t, 1H), 9.29 (d, 1H) |
| 5-37 | 3.91 (brs, 1H), 4.00 (brs, 1H), 4.55 (s, 4H), 7.19-7.28 (m, 3H) |
| 5-39 | 3.14 (brs, 1H), 3.33 (m, 4H), 4.75 (s, 2H), 4.83 (s, 2H), 7.18 (dd, 1H), 7.35-7.39 (m, 1H) |
| 5-41 | 3.23 (s, 3H), 3.29 (brs, 1H), 3.68 (brs, 1H), 4.84 (d, 2H), 5.10 (d, 2H), 7.49 (dd, 1H), 7.68 (d, 1H), 8.06 (d, 1H) |
| 5-43 | 4.55 (s, 2H), 4.63 (d, 4H), 4.77 (t, 1H), 5.06 (s, 2H), 7.22 (d, 1H), 7.30-7.32 (m, 2H) |
| 5-44 | 2.91 (brs, 1H), 3.00 (brs, 1H), 4.66 (s, 2H), 4.85 (s, 2H), 7.31-7.43 (m, 8H) |

TABLE 186

| No. | CDCl$_3$/TMS δ (ppm) |
|---|---|
| 5-46 | 2.33 (s, 3H), 2.36 (s, 3H), 3.06 (brs, 1H), 3.17 (brs, 1H), 3.30 (s, 3H), 4.80-4.83 (m, 4H), 7.05 (d, 1H) |
| 5-47 | 2.57 (brs, 2H), 2.85 (s, 3H), 4.88 (s, 2H), 4.94 (s, 2H), 6.84 (d, 1H), 7.35 (d, 1H) |
| 5-48 | 2.10 (s, 2H), 3.29 (s, 3H), 4.86 (s, 2H), 5.01 (s, 2H), 7.17 (d, 1H), 7.64 (d, 1H) |
| 5-53 | 1.32 (s, 9H), 2.87 (brs, 2H), 4.73 (d, 4H), 7.27-7.38 (m, 3H) |
| 5-54 | 2.53 (brs, 1H), 2.76 (brs, 1H), 3.88 (s, 3H), 4.85 (d, 2H), 4.87 (d, 2H), 6.89 (d, 1H), 7.22 (d, 1H) |
| 5-56 | 2.84 (brs, 2H), 4.84 (s, 2H), 4.97 (s, 2H), 6.47 (t, 1H), 6.92-6.96 (m, 2H), 7.16 (dd, 1H) |
| 5-59 | 2.81 (brs, 2H), 4.73 (d, 4H), 7.29-7.38 (m, 3H) |
| 5-60 | 2.66 (brs, 2H), 5.02 (d, 4H), 7.43 (s, 2H) |
| 5-61 | 3.11-3.16 (m, 2H), 3.29 (s, 3H), 4.86 (d, 2H), 5.00 (d, 2H), 7.01 (d, 1H), 7.92 (d, 1H) |
| 5-62 | 3.30-3.38 (m, 8H), 4.86 (d, 4H), 7.39 (s, 2H) |
| 5-64 | 2.86 (brs, 2H), 3.83 (s, 3H), 4.82 (d, 4H), 6.82-6.85 (m, 1H), 6.99 (d, 1H) |
| 5-65 | 2.84 (brs, 2H), 3.16 (s, 3H), 3.81 (s, 3H), 4.93 (s, 4H), 6.73 (d, 1H), 7.12 (d, 1H) |
| 5-66 | 2.53 (brs, 1H), 2.62 (brs, 1H), 3.87 (s, 3H), 4.75 (s, 2H), 4.86 (s, 2H), 6.91 (d, 1H), 6.98 (d, 1H), 7.26-7.28 (m, 1H) |
| 5-67 | 3.27-3.30 (m, 5H), 4.82 (s, 2H), 4.86 (s, 2H), 6.57 (t, 1H), 7.22 (d, 1H), 7.31 (d, 1H) |

The Examples of using the present invention are shown below.

(1) Implementation Procedure of Pharmaceutical Formulation

<Formulation Example 1> Wettable Powder

The compound of formula [1] of the present invention in an amount of 10 parts was mixed with 2 parts of sodium lauryl sulfate, 4 parts of lignin sodium sulfonate, 20 parts of white carbon and 64 parts of clay, then the mixture was pulverized to obtain a 10% wettable powder.

<Formulation Example 2> Suspension Concentrate

The compound of the present invention in an amount of 10 parts, 4 parts of polyoxyethylene arylphenyl ether sulfate, 5 parts of polyoxyethylene alkyl ether, 5 parts of propylene glycol, 0.2 part of silicon antifoaming agent, 0.8 part of sodium montmorillonite, and 50 parts of water were added and mixed, then the mixture was subjected to wet grinding to obtain a ground suspension.

To 75 parts of ground suspension, 10 parts of xanthan gum solution containing xanthan gum, and 2-benzisothiazoline-3-one at respectively 0.2 part and 0.1 part, and 15 parts of water were added, then mixed to obtain a 10% agricultural chemical composition in an aqueous suspension state.

<Formulation Example 3> Emalsifiable Concentrate

The compound of the present invention in an amount of 10 parts, 2 parts of calcium dodecylbenzene sulfonate, 15 parts of castor oil ethoxylate were mixed with 73 parts of aromatic group hydrocarbon mixture to be dissolved into a homogenous 10% emulsifiable oil like liquid.

<Formulation Example 4> Water Dispersible Granule

The compound of the present invention in an amount of 10 parts, 20 parts of sodium lignosulfonate, 10 parts of a sodium salt of naphthalenesulfonic acid condensate, 4 parts of sodium alkylbenzene sulfonate, 0.5 part of silicon antifoaming agent, 5 parts of diatomaceous earth, 10 parts of ammunoium sulfate, 10 parts of tulc, 31.5 parts of clay were added and mixed sufficiently, then the mixture was pulverized to obtain a pulverized substance. To the pulverized substance, a suitable amount of water was added as necessary and granulated with a granulation machine. Then the mixture was sifted after drying to obtain 10% aqueous fine granule.

<Formulation Example 5> Emulsion

The compound of the present invention in an amount of 10 parts, 15 parts of aromatic hydrocarbon mixture, 2 parts of calcium dodecylbenzenesulfonate, 20 parts of polyoxyethylene castor oil, 4 parts of propylene glycol were added and dissolved to obtain a mixture. The mixture was added to 49 parts of water, then mixed with a homogenizer to obtain 10% emulsified liquid.

<Formulation Example 6> Granule

The compound of the present invention in an amount of 10 parts, 3 parts of polycarboxylic acid anionic surfactant, 0.2 part of dioctyl sodium sulfosuccinate, 2 parts of dextrin, 15 parts of sodium bentonite, 69.8 parts of calcium carbonate were added and mixed homogenously, then a suitable amount of water was added and the mixture was kneaded. The mixture was granulated with a basket type granulation machine, and sifted after drying to obtain 10% aqueous fine granule.

<Formulation Example 7> Microemulsion

The compound of the present invention in an amount of 10 parts, 12 parts of dimethyl amide fatty acid, 10 parts of cyclohexanone, 15 parts of aryl phenol ethoxylate were mixed, and 10 parts of alcohol ethoxylate and 43 parts of water were added and stirred under heating for a few minutes to obtain a stable 10% aqueous solution.

(2) Implementation Procedure for Preparation of Test Suspension

A 10% wettable powder created according to the Pharmaceutical Formulation Example 1 was diluted with a Tween20 solution prepared to a concentration of 1/5000, then the compound of formula [1] was prepared to a concentration of 4 ppm. Further, the compound of formula [1] in Test 4 was adjusted to a concentration of 1,000 ppm.

(3) Analysis Test Procedure of the Control Effect Against Plant Diseases

<Test 1 Test of Control Effect Against Tomato Late Blight>

Test suspension was applied to tomato at the 5 leaf stage (species: regina) in an amount of 20 ml per seedling. One day after application, zoospore suspension of *Phytophthora infestans* adjusted to a concentration of $1.0 \times 10^5$ units/ml was misted/inoculated, and the seedlings were incubated in a moist chamber adjusted to 22° C. for 16 hr. Then, the onset of the disease was induced in the chamber, and the lesion area rate on the leaves 4 days after inoculation was investigated to compute the control value using the formula below.

Computational formula of the control value: control value={1−onset area rate of the leaves that were applied the test agent/onset area rate of untreated leaves}×100

<Test 2 Test of Control Effect Against Cucumber Downy Mildew>

Test suspension was applied to cucumber at the 2 leaf stage (species: Sagami hanjiro) in an amount of 20 ml per seedling. One day after application, zoospore suspension of *Pseudoperonospora cubensis* adjusted to a concentration of $1.0 \times 10^4$ units/ml was misted/inoculated, and the seedlings were incubated in a moist chamber adjusted to 22° C. for 16 hr. Then, the onset of the disease was induced in the chamber, and the lesion area rate on the leaves 5 days after inoculation was investigated to compute the control value using the formula below.

Computational formula of the control value: control value={1−onset area rate of the leaves that were applied the test agent/onset area rate of untreated leaves}×100

<Test 3 Test of Control Effect Against Grape Downy Mildew>

Test suspension was applied to grape seedling (species: Neomuscat) in an amount of 20 ml per seedling. One day after application, zoospore suspension of *Plasmopara viticola* adjusted to a concentration of $1.0 \times 10^4$ units/ml was misted/inoculated, and the seedlings were incubated in a moist chamber adjusted to 22° C. for 16 hr. Then, the onset of the disease was induced in the chamber, and the lesion area rate on the leaves 5 days after inoculation was investigated to compute the control value using the formula below.

Computational formula of the control value: control value={1−onset area rate of the leaves that were applied the test agent/onset area rate of untreated leaves}×100

<Test 4 Test of Control Effect Against Rice Damping-Off by the *Pythium* Fungus (Soil Lavage)>

Distilled water was added to the flora of *Pythium graminicola* cultured in bentoglass seed culture and stirred with a mixer, and adjusted the contaminated soil to 5 g of bacteria against 1 kg of soil.

In a cell tray having $31 \times 31$ mm$^2$ per cell, 20 ml of the contaminated soil was filled in each cell, and 3 seeds of rice chaff that has been forced to sprout (Species: koshihikari) were seeded, and 5 ml of soil was added for covering, then 2.5 ml of test suspension was drenched, and the seeds were incubated in a moist chamber adjusted to 28° C. for 72 hr to induce sprouting. Then, in a low temperature room of 5° C., the onset of disease was induced for 2 days, then the disease was nurtured for 14 days in a room of 25° C.

The soil was washed, and the apoptosis strain, growth restrained strain, and a healthy strain were measured and the onset rate was calculated by the following formula.

Onset rate=[Σ(onset strain number by level×onset index)/(investigated strain×3)]×100

[Onset Index]
0: Healthy strain
1: Growth restrained strain
3: Apoptosis strain

Also, the following formula was used to compute the control value from the obtained onset index.

Computational formula of the control value: control value={1−onset area rate at the section applied the test agent/onset area rate of untreated section}×100

(4) Analysis Test Result for the Control Effect Against Plant Diseases <Test 1> to <Test 3>

The test results are shown in [Table 187] to [Table 193]. The numbers show the control value.

TABLE 187

| No. | Test 1 | Test 2 | Test 3 |
|---|---|---|---|
| 1-1 | 100 | 100 | 100 |
| 1-2 | 100 | 100 | 100 |
| 1-3 | 100 | 100 | 100 |
| 1-4 | 100 | 100 | 100 |
| 1-5 | 100 | 100 | 100 |
| 1-6 | 100 | 100 | 100 |
| 1-7 | 100 | 100 | 100 |
| 1-8 | 100 | 100 | 100 |
| 1-9 | 100 | 80 | 100 |
| 1-10 | 100 | 100 | 100 |

TABLE 187-continued

| No. | Test 1 | Test 2 | Test 3 |
|---|---|---|---|
| 1-11 | 100 | 100 | 100 |
| 1-12 | 100 | 100 | 100 |
| 1-13 | 100 | 100 | 100 |
| 1-14 | 100 | 100 | 100 |
| 1-15 | 100 | 100 | 100 |
| 1-16 | 100 | 100 | 100 |
| 1-17 | 100 | 100 | 100 |
| 1-18 | 100 | 100 | 100 |
| 1-19 | 100 | 100 | 100 |
| 1-20 | 100 | 100 | 100 |
| 1-21 | 90 | 100 | 100 |
| 1-22 | 100 | 100 | 100 |
| 1-23 | 100 | 100 | 100 |
| 1-24 | 100 | 100 | 100 |
| 1-25 | 100 | 100 | 100 |
| 1-26 | 100 | 100 | 100 |
| 1-27 | 100 | 100 | 100 |
| 1-28 | 100 | 100 | 100 |
| 1-29 | 100 | 90 | 100 |
| 1-30 | 100 | 100 | 100 |
| 1-31 | 100 | 100 | 100 |
| 1-32 | 100 | 100 | 100 |
| 1-33 | 100 | 100 | 100 |

TABLE 188

| No. | Test 1 | Test 2 | Test 3 |
|---|---|---|---|
| 1-34 | 100 | 100 | 100 |
| 1-35 | 100 | 100 | 100 |
| 1-36 | 100 | 100 | 100 |
| 1-37 | 100 | 100 | 100 |
| 1-38 | 100 | 100 | 100 |
| 1-39 | 100 | 100 | 100 |
| 1-40 | 100 | 100 | 100 |
| 1-41 | 100 | 100 | 100 |
| 1-42 | 100 | 100 | 100 |
| 1-43 | 80 | 100 | 100 |
| 1-44 | 100 | 100 | 100 |
| 1-45 | 100 | 100 | 100 |
| 1-46 | 100 | 100 | 100 |
| 1-47 | 100 | 100 | 100 |
| 1-48 | 100 | 100 | 100 |
| 1-49 | 100 | 100 | 100 |
| 1-50 | 100 | 100 | 100 |
| 1-51 | 100 | 100 | 100 |
| 1-52 | 100 | 100 | 100 |
| 1-53 | 100 | 100 | 100 |
| 1-54 | 100 | 100 | 100 |
| 1-55 | 100 | 100 | 100 |
| 1-56 | 90 | 100 | 100 |
| 1-57 | 100 | 100 | 100 |
| 1-58 | 100 | 100 | 100 |
| 1-59 | 100 | 100 | 100 |
| 1-60 | 100 | 100 | 100 |
| 1-61 | 100 | 100 | 100 |
| 1-62 | 100 | 100 | 100 |
| 1-63 | 100 | 100 | 100 |
| 1-64 | 100 | 100 | 100 |
| 1-65 | 100 | 100 | 100 |
| 1-66 | 100 | 100 | 100 |

TABLE 189

| No. | Test 1 | Test 2 | Test 3 |
|---|---|---|---|
| 1-67 | 100 | 100 | 100 |
| 1-68 | 100 | 100 | 100 |
| 1-69 | 100 | 60 | 100 |
| 1-70 | 100 | 60 | 100 |
| 1-71 | 100 | 100 | 100 |
| 1-72 | 100 | 100 | 100 |
| 1-73 | 90 | 100 | 100 |

TABLE 189-continued

| No. | Test 1 | Test 2 | Test 3 |
|---|---|---|---|
| 1-74 | 100 | 100 | 100 |
| 1-75 | 100 | 100 | 100 |
| 1-76 | 100 | 100 | 100 |
| 1-77 | 100 | 100 | 100 |
| 1-78 | 100 | 100 | 100 |
| 1-79 | 100 | 90 | 90 |
| 1-80 | 100 | 100 | 100 |
| 1-81 | 100 | 100 | 100 |
| 1-82 | 100 | 100 | 100 |
| 1-83 | 100 | 100 | 100 |
| 1-84 | 100 | 100 | 100 |
| 1-85 | 100 | 100 | 100 |
| 1-86 | 100 | 100 | 100 |
| 1-87 | 100 | 100 | 100 |
| 1-88 | 100 | 100 | 100 |
| 1-89 | 80 | 100 | 100 |
| 1-90 | 100 | 100 | 100 |
| 1-91 | 100 | 100 | 100 |
| 1-92 | 100 | 90 | 90 |
| 1-93 | 100 | 100 | 100 |
| 1-94 | 100 | 100 | 100 |
| 1-95 | 100 | 100 | 100 |
| 1-96 | 100 | 100 | 100 |
| 1-97 | 100 | 100 | 100 |
| 1-98 | 100 | 100 | 100 |
| 1-99 | 100 | 100 | 100 |

TABLE 190

| No. | Test 1 | Test 2 | Test 3 |
|---|---|---|---|
| 1-100 | 100 | 100 | 100 |
| 1-101 | 100 | 100 | 100 |
| 1-102 | 100 | 100 | 100 |
| 1-103 | 100 | 100 | 100 |
| 1-104 | 100 | 100 | 100 |
| 1-105 | 100 | 100 | 100 |
| 1-106 | 100 | 100 | 100 |
| 1-107 | 100 | 100 | 100 |
| 1-108 | 100 | 100 | 100 |
| 1-109 | 100 | 100 | 100 |
| 1-110 | 100 | 100 | 100 |
| 1-111 | 100 | 100 | 100 |
| 1-112 | 100 | 100 | 100 |
| 1-113 | 100 | 100 | 100 |
| 1-114 | 100 | 100 | 100 |
| 1-115 | 100 | 100 | 100 |
| 1-116 | 100 | 100 | 100 |
| 1-117 | 100 | 100 | 100 |
| 1-118 | 100 | 100 | 100 |
| 1-119 | 100 | 100 | 100 |
| 1-120 | 100 | 100 | 100 |
| 1-121 | 100 | 100 | 100 |
| 1-122 | 100 | 100 | 100 |
| 1-123 | 100 | 100 | 100 |
| 1-124 | 100 | 100 | 100 |
| 1-125 | 100 | 100 | 100 |
| 1-126 | 100 | 100 | 100 |
| 1-127 | 100 | 100 | 100 |
| 1-128 | 100 | 100 | 100 |
| 1-129 | 100 | 100 | 100 |
| 1-130 | 100 | 100 | 100 |
| 1-131 | 100 | 100 | 100 |
| 1-132 | 100 | 100 | 100 |

TABLE 191

| No. | Test 1 | Test 2 | Test 3 |
|---|---|---|---|
| 1-133 | 100 | 100 | 100 |
| 1-134 | 100 | 100 | 100 |
| 1-135 | 100 | 100 | 100 |
| 1-136 | 100 | 100 | 100 |

TABLE 191-continued

| No. | Test 1 | Test 2 | Test 3 |
|---|---|---|---|
| 1-137 | 100 | 100 | 100 |
| 1-138 | 100 | 100 | 100 |
| 1-139 | 100 | 100 | 100 |
| 1-140 | 100 | 100 | 100 |
| 1-141 | 100 | 100 | 100 |
| 1-142 | 100 | 100 | 100 |
| 1-143 | 100 | 100 | 100 |
| 1-144 | 100 | 100 | 100 |
| 1-145 | 100 | 100 | 100 |
| 1-146 | 100 | 100 | 100 |
| 1-147 | 90 | 90 | 70 |
| 1-148 | 100 | 100 | 100 |
| 1-149 | 100 | 100 | 100 |
| 1-150 | 100 | 100 | 100 |
| 1-151 | 100 | 100 | 100 |
| 1-152 | 100 | 100 | 100 |
| 1-153 | 100 | 100 | 100 |
| 1-154 | 90 | 100 | 100 |
| 1-155 | 100 | 100 | 100 |
| 1-156 | 100 | 100 | 100 |
| 1-157 | 100 | 100 | 100 |
| 1-158 | 100 | 100 | 100 |
| 1-159 | 100 | 100 | 100 |
| 1-160 | 100 | 100 | 100 |
| 1-161 | 100 | 100 | 100 |
| 2-1 | 100 | 100 | 100 |
| 2-2 | 100 | 100 | 100 |
| 2-3 | 100 | 100 | 100 |
| 2-4 | 100 | 100 | 100 |

TABLE 192

| No. | Test 1 | Test 2 | Test 3 |
|---|---|---|---|
| 2-5 | 100 | 100 | 100 |
| 2-6 | 100 | 100 | 100 |
| 2-7 | 100 | 100 | 100 |
| 2-8 | 100 | 100 | 100 |
| 2-9 | 100 | 100 | 100 |
| 2-10 | 80 | 100 | 100 |
| 2-11 | 100 | 100 | 100 |
| 2-12 | 80 | 90 | 80 |
| 2-13 | 50 | 100 | 100 |
| 2-14 | 100 | 100 | 100 |
| 2-15 | 100 | 100 | 100 |
| 2-16 | 100 | 100 | 100 |
| 2-17 | 90 | 100 | 100 |
| 2-18 | 100 | 100 | 100 |
| 2-19 | 100 | 100 | 100 |
| 2-20 | 100 | 100 | 100 |
| 2-21 | 50 | 100 | 100 |
| 2-22 | 100 | 100 | 100 |
| 2-23 | 100 | 100 | 100 |
| 2-24 | 100 | 100 | 100 |
| 2-25 | 40 | 100 | 100 |
| 2-26 | 100 | 100 | 100 |
| 2-27 | 100 | 100 | 100 |
| 2-28 | 90 | 100 | 100 |
| 2-29 | 100 | 100 | 100 |
| 2-30 | 30 | 100 | 100 |
| 2-31 | 0 | 100 | 100 |
| 2-32 | 100 | 100 | 100 |
| 2-33 | 20 | 100 | 100 |
| 2-34 | 90 | 100 | 100 |
| 2-35 | 100 | 100 | 100 |
| 2-36 | 100 | 100 | 100 |
| 2-37 | 90 | 100 | 100 |

TABLE 193

| No. | Test 1 | Test 2 | Test 3 |
|---|---|---|---|
| 2-38 | 100 | 100 | 100 |
| 2-39 | 100 | 100 | 100 |
| 2-40 | 70 | 100 | 100 |

TABLE 193-continued

| No. | Test 1 | Test 2 | Test 3 |
|---|---|---|---|
| 2-41 | 100 | 100 | 100 |
| 2-42 | 90 | 100 | 100 |
| 2-43 | 100 | 100 | 100 |
| 2-44 | 90 | 100 | 100 |
| 2-45 | 90 | 100 | 100 |
| 2-46 | 100 | 100 | 100 |
| 2-47 | 100 | 100 | 100 |
| 2-48 | 100 | 100 | 100 |
| 2-49 | 100 | 0 | 100 |
| 2-50 | 100 | 100 | 100 |
| 2-51 | 100 | 100 | 100 |
| 2-52 | 100 | 100 | 100 |
| 2-53 | 100 | 100 | 100 |
| 2-54 | 90 | 90 | 100 |
| 2-55 | 100 | 100 | 100 |
| 2-56 | 90 | 30 | 70 |
| 2-57 | 100 | 100 | 100 |
| 3-1 | 100 | 100 | 100 |
| 3-2 | 100 | 100 | 100 |
| 3-3 | 100 | 100 | 100 |
| 3-4 | 100 | 100 | 100 |
| 3-5 | 100 | 100 | 100 |
| 3-6 | 100 | 100 | 100 |
| 4-1 | 100 | 100 | 100 |

<Test 5 Test Result of Control Effect Against Plant Disease <Test 4>>

Tests were performed for some compounds, and the result was that all compounds showed a control value of 90 or higher. The Compound Nos. are shown below.

No. 1-3, 1-6, 1-10, 1-11, 1-15, 1-21, 1-22, 1-23, 1-32, 1-33, 1-34, 1-36, 1-40, 1-44, 1-45, 1-47, 1-49, 1-50, 1-51, 1-57, 1-61, 1-62, 1-69, 1-70, 1-72, 1-78, 1-79, 1-84, 1-90, 1-91, 1-95, 1-96, 1-97, 1-100, 1-109, 1-113, 1-115, 1-119, 1-123, 1-129, 1-131, 1-132, 1-133, 1-140, 1-144, 1-147, 1-158, 2-1, 2-2, 2-4, 2-5, 2-7, 2-10, 2-12, 2-13, 2-18, 2-19, 2-20, 2-22, 2-23, 2-29, 2-30, 2-31, 2-39, 2-43, 2-44, 2-45, 2-48, 2-52, 2-55, 2-56, 2-57

INDUSTRIAL APPLICABILITY

The new compound of the present invention shown by formula [1] exhibits particularly good control activity against pathogenic bacteria that infect agricultural/horticultural plants, so they are quite useful as new agricultural chemicals, and have industrial applicability.

The invention claimed is:

1. A compound or a salt thereof according to formula [1]:

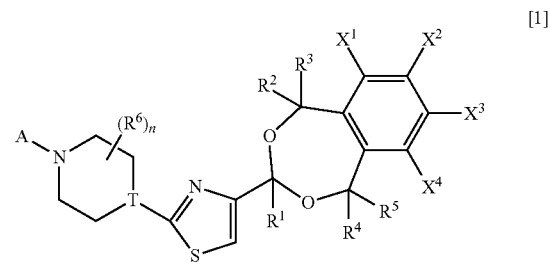

wherein, A is a group selected from

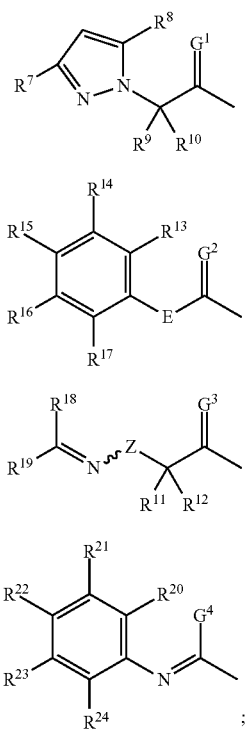

A-1
A-2
A-3
A-4

T is either CH or a nitrogen atom;
$R^1$ is a hydrogen atom, $C_1$-$C_6$ alkyl, $C_2$-$C_6$ alkenyl, $C_1$-$C_6$ haloalkyl, $C_1$-$C_6$ alkoxy, halogen, cyano or hydroxy;
each of $R^2$, $R^3$, $R^4$ and $R^5$ is independently a hydrogen atom, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen, cyano or hydroxyl, or $R^2$ together with $R^3$ and $R^4$ together with $R^5$ are independently taken together with a carbon atom to which they are attached to form a carbonyl group (C=O);
$R^6$ is oxo, $C_1$-$C_6$ alkyl, $C_2$-$C_6$ alkenyl, $C_1$-$C_6$ haloalkyl, $C_1$-$C_6$ alkoxy, halogen, cyano or hydroxy;
n is 0-2;
each of $X^1$, $X^2$, $X^3$ and $X^4$ is independently a hydrogen atom, halogen, cyano, hydroxy, nitro, formyl, mercapto, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, carboxy, carbamoyl, $C_3$-$C_6$ cycloalkyl, $C_3$-$C_8$ halocycloalkyl, $C_3$-$C_6$ cycloalkoxy, $C_3$-$C_8$ halocycloalkoxy, $C_3$-$C_6$ alkynylalkoxy, $C_3$-$C_6$ haloalkynylalkoxy, $C_2$-$C_6$ alkoxyalkyl, $C_4$-$C_{10}$ cycloalkoxyalkyl, $C_2$-$C_6$ haloalkoxyalkyl, $C_4$-$C_{10}$ halocycloalkoxyalkyl, $C_3$-$C_8$ alkoxyalkoxyalkyl, $C_2$-$C_6$ alkoxyalkoxy, $C_4$-$C_{10}$ cycloalkylalkoxy, $C_1$-$C_6$ hydroxyalkyl, $C_4$-$C_{10}$ cycloalkylalkyl, $C_4$-$C_{10}$ alkylcycloalkyl, $C_6$-$C_{14}$ cycloalkylcycloalkyl, $C_4$-$C_{10}$ halocycloalkylalkyl, $C_6$-$C_{14}$ halocycloalkylcycloalkyl, $C_4$-$C_{10}$ haloalkylcycloalkyl, $C_5$-$C_{10}$ alkylcycloalkylalkyl, $C_3$-$C_8$ cycloalkenyl, $C_3$-$C_8$ halocycloalkenyl, —$SR^{25}$, —$S(O)R^{25}$, —$S(O)_2R^{25}$, —$OS(O)_2R^{25}$, —($C_1$-$C_6$ alkyl)$S(O)_2R^{25}$, $C_2$-$C_6$ alkylthioalkyl, $C_2$-$C_6$ alkylsulfinylalkyl, $C_2$-$C_6$ alkylsulfonylalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ haloalkoxycarbonyl, $C_4$-$C_8$ cycloalkoxycarbonyl, $C_5$-$C_{10}$ cycloalkylalkoxycarbonyl, $C_2$-$C_6$ alkylcarbonyloxy, $C_2$-$C_6$ haloalkylcarbonyloxy, $C_4$-$C_8$ cycloalkylcarbonyloxy, $C_2$-$C_6$ alkoxycarbonyloxy, $C_2$-$C_6$ haloalkoxycarbonyloxy, $C_4$-$C_8$ cycloalkoxycarbonyloxy, $C_3$-$C_6$ alkylcarbonylalkoxy, —$NR^{26}R^{27}$, $C_2$-$C_6$ alkylaminoalkyl, $C_3$-$C_8$(dialkylamino)alkyl, $C_2$-$C_6$ haloalkylaminoalkyl, $C_4$-$C_{10}$ cycloalkylaminoalkyl, $C_1$-$C_6$ alkylsulfonylamino, $C_1$-$C_6$ haloalkylsulfonylamino, $C_2$-$C_6$ alkylaminocarbonyl, $C_3$-$C_{10}$(dialkylamino)carbonyl, $C_4$-$C_8$ cycloalkylaminocarbonyl, $C_2$-$C_8$ dialkylhydroxyamino, $C_2$-$C_8$(dialkylamino)hydroxy, $C_3$-$C_{10}$ trialkylhydrazinyl, $C_3$-$C_{10}$ trialkylsilyl, $C_4$-$C_{10}$ trialkylsilylalkyl, $C_5$-$C_{10}$ trialkylsilylalkynyl, $C_3$-$C_{10}$ trialkylsilyloxy, $C_4$-$C_{12}$ trialkylsilylalkyloxy, $C_5$-$C_{12}$ trialkylsilylalkoxyalkyl, $C_5$-$C_{12}$ trialkylsilylalkynyloxy, $C_2$-$C_6$ alkylsulfonyloxyalkyl, $C_2$-$C_6$ haloalkylsulfonyloxyalkyl, —C(=NOR$^{28}$)R$^{29}$, —C(=NR$^{30}$)R$^{29}$, $C_2$-$C_6$ cyanoalkyl, phenyl, phenoxy or benzyl, or $X^1$ together with $X^2$, $X^2$ together with $X^3$ and $X^3$ together with $X^4$ form a $C_2$-$C_6$ alkylene chain that may include an oxygen atom, a sulfur atom, a nitrogen atom, or they are taken together with a carbon atom to which they are attached to form a thiophene ring, a pyridine ring, a pyrrole ring, an imidazole ring, a benzene ring, a naphthalene ring, a pyrimidine ring, a furan ring, a pyrazine ring, a pyrazole ring or an oxazole ring;
$R^{25}$ is $C_1$-$C_8$ alkyl, $C_3$-$C_8$ cycloalkyl, $C_1$-$C_6$ haloalkyl, $C_3$-$C_8$ halocycloalkyl, $C_1$-$C_6$ alkylamino, phenyl or benzyl, and phenyl or benzyl may be substituted with at least one $R^{31}$,
$R^{31}$ is $C_1$-$C_6$ alkyl, $C_3$-$C_8$ cycloalkyl, $C_1$-$C_6$ haloalkyl, $C_1$-$C_6$ alkoxy, $C_1$-$C_6$ haloalkoxy, $C_3$-$C_8$ cycloalkoxy, $C_3$-$C_8$ halocycloalkoxy, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, halogen, cyano or hydroxy;
each of $R^{26}$ and $R^{27}$ is independently a hydrogen atom, $C_1$-$C_6$ alkyl, $C_3$-$C_8$ cycloalkyl, $C_1$-$C_6$ haloalkyl, $C_3$-$C_8$ halocycloalkyl, $C_1$-$C_6$ alkoxy, $C_2$-$C_8$ dialkylamino, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ haloalkoxycarbonyl or $C_3$-$C_{10}$(dialkylamino)carbonyl;
$R^{28}$ is a hydrogen atom, $C_1$-$C_6$ alkyl, $C_1$-$C_6$ haloalkyl or benzyl;
$R^{29}$ is a hydrogen atom, $C_1$-$C_6$ alkyl, $C_3$-$C_8$ cycloalkyl, $C_1$-$C_6$ haloalkyl, $C_3$-$C_8$ halocycloalkyl, $C_4$-$C_{10}$ cycloalkylalkyl, phenyl or benzyl;
$R^{30}$ is $C_1$-$C_6$ alkyl, $C_3$-$C_8$ cycloalkyl, $C_1$-$C_6$ haloalkyl, $C_3$-$C_8$ halocycloalkyl, phenyl or benzyl;
each of $R^7$ and $R^8$ is independently $C_1$-$C_4$ alkyl, $C_3$-$C_6$ cycloalkyl or $C_1$-$C_4$ haloalkyl;
E is —$CR^{32}R^{33}$— or —$NR^{34}$—;
each of $R^9$, $R^{10}$, $R^{11}$, $R^{12}$, $R^{32}$ and $R^{33}$ is independently a hydrogen atom, halogen, cyano, hydroxy, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_1$-$C_6$ haloalkoxy, $C_3$-$C_6$ cycloalkyl, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl or $C_1$-$C_6$ haloalkylsulfonyl;
$R^{34}$ is a hydrogen atom, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_2$-$C_6$ alkoxyalkyl, $C_3$-$C_6$ cycloalkyl, $C_3$-$C_6$ halocycloalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylcarbonyl, $C_2$-$C_6$ haloalkylcarbonyl, $C_2$-$C_6$ alkoxycarbonyl, $C_3$-$C_6$ alkoxycarbonylalkyl, $C_2$-$C_6$ alkylaminocarbonyl, $C_3$-$C_6$ (dialkylamino)carbonyl, $C_1$-$C_6$ alkylsulfonyl or $C_1$-$C_6$ haloalkylsulfonyl;

$G^1$, $G^2$ and $G^3$ is an oxygen atom or a sulfur atom;

each of $R^{13}$, $R^{14}$, $R^{15}$, $R^{16}$, $R^{17}$, $R^{20}$, $R^{21}$, $R^{22}$, $R^{23}$ and $R^{24}$ is independently a hydrogen atom, halogen, cyano, hydroxy, amino, nitro, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_1$-$C_6$ haloalkoxy, $C_3$-$C_6$ cycloalkyl, $C_3$-$C_6$ halocycloalkyl, $C_4$-$C_{10}$ cycloalkylalkyl, $C_4$-$C_{10}$ alkylcycloalkyl, $C_5$-$C_{10}$ alkylcycloalkylalkyl, $C_2$-$C_6$ alkoxyalkyl, $C_1$-$C_6$ hydroxyalkyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_8$ dialkylamino, $C_3$-$C_6$ cycloalkylamino, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl, $C_2$-$C_6$ alkylcarbonyloxy, $C_2$-$C_6$ alkylcarbonylthio, $C_2$-$C_6$ alkylaminocarbonyl, $C_2$-$C_8$ (dialkylamino)carbonyl, or $C_3$-$C_6$ trialkylsilyl;

$R^{18}$ is a hydrogen atom, $C_1$-$C_6$ alkyl, $C_1$-$C_6$ haloalkyl, $C_1$-$C_6$ alkoxy, $C_1$-$C_6$ haloalkoxy, $C_1$-$C_3$ alkylthio, halogen, cyano or hydroxy;

$R^{19}$ is a hydrogen atom, halogen, cyano, hydroxy, formyl, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, carboxy, carbamoyl, $C_3$-$C_6$ cycloalkyl, $C_3$-$C_8$ halocycloalkyl, $C_3$-$C_6$ cycloalkoxy, $C_3$-$C_8$ halocycloalkoxy, $C_2$-$C_6$ alkoxyalkyl, $C_4$-$C_6$ cycloalkylalkyl, $C_4$-$C_6$ alkylcycloalkyl, $C_4$-$C_6$ halocycloalkylalkyl, $C_3$-$C_8$ cycloalkenyl, $C_3$-$C_8$ halocycloalkenyl, $C_1$-$C_6$ alkylthio, $C_1$-$C_6$ haloalkylthio, $C_3$-$C_6$ cycloalkylthio, $C_2$-$C_6$ alkylthioalkyl, $C_2$-$C_6$ alkylsulfinylalkyl, $C_2$-$C_6$ alkylsulfonylalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ haloalkoxycarbonyl, $C_4$-$C_6$ cycloalkoxycarbonyl, $C_5$-$C_{10}$ cycloalkylalkoxycarbonyl, $C_2$-$C_6$ alkylcarbonyloxy, $C_2$-$C_6$ haloalkylcarbonyloxy, $C_1$-$C_6$ alkylamino, $C_1$-$C_6$ dialkylamino, $C_1$-$C_6$ haloalkylamino, $C_1$-$C_6$ halodialkylamino, $C_3$-$C_6$ cycloalkylamino, $C_2$-$C_6$ alkylaminoalkyl, $C_3$-$C_6$ (dialkylamino)alkyl, $C_2$-$C_6$ haloalkylaminoalkyl, $C_1$-$C_6$ alkylsulfonylamino, $C_1$-$C_6$ haloalkylsulfonylamino, $C_2$-$C_6$ alkylcarbonylamino, $C_2$-$C_6$ haloalkylcarbonylamino, $C_2$-$C_6$ alkylaminocarbonyl or $C_3$-$C_{10}$ (dialkylamino)carbonyl; or $R^{18}$ and $R^{19}$ are taken together with a carbon atom to which they are attached to form a 3-7 membered ring containing members selected from carbon atom and at most 4 heteroatoms independently selected from at most 2 oxygen atoms, at most 2 sulfur atoms, at most 2 nitrogen atoms, and at most 2 silicon atoms, wherein at most 3 carbon atom members may be substituted with oxo or thioxo, a sulfur atom member is independently selected from $S(=O)_p(=NR^{35})_q$, a silicon atom member is independently selected from $SiR^{36}R^{37}$, and a ring may be optionally substituted with at most 4 substituents independently selected from halogen, cyano, $C_1$-$C_2$ alkyl, $C_1$-$C_2$ haloalkyl, $C_1$-$C_2$ alkoxy or $C_1$-$C_2$ haloalkoxy on a carbon atom member, and cyano, $C_1$-$C_2$ alkyl or $C_1$-$C_2$ alkoxy on a nitrogen atom member;

$R^{35}$ is independently selected from a hydrogen atom, cyano, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, $C_3$-$C_8$ halocycloalkyl, $C_1$-$C_6$ alkylamino, $C_2$-$C_6$ dialkylamino, $C_1$-$C_6$ haloalkylamino or phenyl;

each of p and q is independently 0, 1 or 2, wherein a sum of p and q is 0, 1 or 2;

each of $R^{36}$ and $R^{37}$ is independently $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ halocycloalkyl, $C_4$-$C_{10}$ cycloalkylalkyl, $C_4$-$C_7$ alkylcycloalkyl or $C_5$-$C_7$ alkylcycloalkylalkyl;

Z is an oxygen atom, a sulfur atom, —N($R^{38}$)—, —C($R^{39}$)$_2$—, —OC($R^{39}$)$_2$—, —SC($R^{39}$)$_2$— or —N($R^{38}$)C($R^{39}$)$_2$—, wherein a left bond is a bond with a nitrogen atom of A-3, and a right bond is a bond with a carbon atom of A-3;

$R^{38}$ is a hydrogen atom, cyano, $C_1$-$C_4$ alkyl, $C_1$-$C_4$ haloalkyl, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_5$ (dialkylamino)carbonyl, $C_1$-$C_4$ alkylsulfonyl or $C_1$-$C_4$ haloalkylsulfonyl;

$R^{18}$ and $R^{38}$ are taken together with a carbon atom and a nitrogen atom to which they are attached to form a 5-7 membered partially unsaturated ring containing members in addition to the linking atoms selected from carbon atom and at most 5 heteroatoms independently selected from at most 1 oxygen atom, at most 1 sulfur atom, at most 3 nitrogen atoms, and a ring may be optionally substituted with at most 3 substituents independently selected from halogen, cyano, nitro, $C_1$-$C_2$ alkyl, $C_1$-$C_2$ haloalkyl, $C_1$-$C_2$ alkoxy or $C_1$-$C_2$ haloalkoxy on a carbon atom member, and cyano, $C_1$-$C_2$ alkyl or $C_1$-$C_2$ alkoxy on a nitrogen atom member;

$R^{39}$ is independently a hydrogen atom, $C_1$-$C_6$ alkyl or $C_1$-$C_6$ haloalkyl, $G^4$ is —O$R^{40}$, —S$R^{41}$, —N$R^{42}R^{43}$ or $R^{44}$;

each of $R^{40}$ and $R^{41}$ is independently $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_2$-$C_6$ alkoxyalkyl, $C_4$-$C_8$ cycloalkoxyalkyl, $C_3$-$C_8$ haloalkoxyalkyl, $C_3$-$C_6$ cycloalkyl, $C_3$-$C_6$ halocycloalkyl, $C_2$-$C_6$ alkylaminoalkyl, $C_3$-$C_6$ (dialkylamino)alkyl, $C_2$-$C_6$ haloalkylaminoalkyl, $C_4$-$C_8$ cycloalkylaminoalkyl, $C_4$-$C_8$ cycloalkylalkyl, $C_4$-$C_8$ alkylcycloalkyl, $C_4$-$C_8$ halocycloalkylalkyl, $C_5$-$C_8$ alkylcycloalkylalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ alkylaminocarbonyl, $C_3$-$C_6$ (dialkylamino)carbonyl or $C_4$-$C_8$ cycloalkylaminocarbonyl;

$R^{42}$ is a hydrogen atom, cyano, amino, hydroxy, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_2$-$C_6$ alkoxyalkyl, $C_1$-$C_6$ alkylamino, $C_2$-$C_8$ dialkylamino, $C_1$-$C_6$ haloalkylamino, $C_2$-$C_8$ halodialkylamino, $C_4$-$C_8$ cycloalkylalkyl, $C_1$-$C_6$ alkylsulfonyl, $C_1$-$C_6$ haloalkylsulfonyl, $C_2$-$C_6$ alkylcarbonyl or $C_2$-$C_6$ haloalkylcarbonyl;

$R^{43}$ is a hydrogen atom, $C_1$-$C_6$ alkyl, $C_2$-$C_6$ alkenyl, $C_2$-$C_6$ alkynyl, $C_1$-$C_6$ haloalkyl or $C_3$-$C_6$ cycloalkyl; or

283

R$^{42}$ and R$^{43}$ are taken together with a nitrogen atom to which they are attached to may form a pyrrolidine ring, a piperidine ring or a morpholine ring;

R$^{44}$ is a hydrogen atom, cyano, C$_1$-C$_4$ alkyl, C$_1$-C$_4$ haloalkyl, C$_2$-C$_4$ alkoxyalkyl, C$_2$-C$_4$ alkylcarbonyl, C$_2$-C$_4$ alkoxycarbonyl, C$_2$-C$_3$ alkylaminocarbonyl, C$_3$-C$_6$ (dialkylamino)carbonyl, C$_1$-C$_6$ haloalkylamino or C$_2$-C$_8$ halodialkylamino}.

2. The compound or a salt thereof according to claim 1, wherein

R$^1$, R$^2$ and R$^4$ are hydrogen atoms;

each of R$^3$ and R$^5$ is independently a hydrogen atom or methyl;

n is 0;

each of X$^1$, X$^2$, X$^3$ and X$^4$ is independently a hydrogen atom, halogen, cyano, hydroxy, nitro, formyl, mercapto, C$_1$-C$_6$ alkyl, C$_2$-C$_6$ alkenyl, C$_2$-C$_6$ alkynyl, C$_3$-C$_6$ cycloalkyl, C$_1$-C$_6$ haloalkyl, C$_1$-C$_6$ hydroxyalkyl, C$_1$-C$_6$ alkoxy, C$_1$-C$_6$ haloalkoxy, carboxy, C$_3$-C$_6$ alkynylalkoxy, C$_2$-C$_6$ alkoxyalkyl, —SR$^{25}$, —S(O)R$^{25}$, —S(O)$_2$R$^{25}$, —OS(O)$_2$R$^{25}$, C$_2$-C$_6$ alkylthioalkyl, C$_2$-C$_6$ alkylcarbonyl, C$_2$-C$_6$ alkoxycarbonyl, C$_2$-C$_6$ alkylcarbonyloxy, C$_2$-C$_6$ alkoxycarbonyloxy, —NR$^{26}$R$^{27}$, C$_1$-C$_6$ alkylsulfonylamino, C$_2$-C$_6$ alkylaminoalkyl, —C(=NOR$^{28}$)R$^{29}$, C$_2$-C$_6$ cyanoalkyl, phenyl, phenoxy or benzyl, or X$^1$ together with X$^2$, X$^2$ together with X$^3$ and X$^3$ together with X$^4$ form a C$_2$-C$_6$ alkylene chain that may contain an oxygen atom, or they are taken together with a carbon atom to which they are attached to form a benzene ring;

R$^{25}$ is C$_1$-C$_8$ alkyl, C$_3$-C$_6$ cycloalkyl, C$_1$-C$_6$ haloalkyl, or C$_1$-C$_6$ alkylamino;

each of R$^{26}$ and R$^{27}$ is independently a hydrogen atom, C$_1$-C$_6$ alkyl, C$_2$-C$_6$ alkylcarbonyl or C$_2$-C$_6$ alkoxycarbonyl;

each of R$^{28}$ and R$^{29}$ is independently a hydrogen atom or C$_1$-C$_6$ alkyl;

each of R$^7$ and R$^8$ is independently C$_1$-C$_6$ alkyl or C$_1$-C$_6$ haloalkyl;

E is —CR$^{32}$R$^{33}$—;

R$^9$, R$^{10}$, R$^{11}$, R$^{12}$, R$^{32}$ and R$^{33}$ are hydrogen atoms;

each of R$^{13}$, R$^{16}$, R$^{20}$ and R$^{23}$ is independently a hydrogen atom, halogen, C$_1$-C$_6$ alkyl or C$_1$-C$_6$ haloalkyl;

R$^{14}$, R$^{15}$, R$^{17}$, R$^{21}$, R$^{22}$ and R$^{24}$ are hydrogen atoms;

each of R$^{18}$ and R$^{19}$ is independently a hydrogen atom, C$_1$-C$_6$ alkyl or C$_1$-C$_6$ haloalkyl;

Z is an oxygen atom;

G$^4$ is —OR$^{40}$;

R$^{40}$ is C$_1$-C$_6$ alkyl.

3. The compound or a salt thereof according to claim 2, wherein

T is CH;

R$^3$ and R$^5$ are hydrogen atoms;

each of X$^1$, X$^2$, X$^3$ and X$^4$ is independently a hydrogen atom, halogen, cyano, hydroxy, nitro, formyl, C$_1$-C$_4$ alkyl, C$_1$-C$_4$ haloalkyl, C$_1$-C$_4$ hydroxyalkyl, C$_1$-C$_4$ alkoxy, C$_1$-C$_4$ haloalkoxy, —SR$^{25}$, —S(O)$_2$R$^{25}$, —OS(O)$_2$R$^{25}$, C$_2$-C$_4$ alkylcarbonyloxy, C$_2$-C$_4$ alkoxycarbonyloxy, or —C(=NOR$^{28}$)R$^{29}$;

R$^{25}$ is C$_1$-C$_4$ alkyl, cyclopropyl or C$_1$-C$_4$ haloalkyl;

each of R$^{28}$ and R$^{29}$ is independently a hydrogen atom or methyl;

each of R$^7$ and R$^8$ is independently C$_1$-C$_4$ alkyl or C$_1$-C$_4$ halo alkyl;

G$^1$, G$^2$ and G$^3$ are oxygen atoms;

each of R$^{13}$, R$^{16}$, R$^{20}$ and R$^{23}$ is independently a hydrogen atom, a chlorine atom, methyl or trifluoromethyl;

284 each of R$^{18}$ and R$^{19}$ is independently a hydrogen atom, C$_1$-C$_4$ alkyl or C$_1$-C$_4$ haloalkyl;

R$^{40}$ is methyl.

4. The compound or a salt thereof according to claim 3, wherein each of X$^1$, X$^2$, X$^3$ and X$^4$ is independently a hydrogen atom, nitro, a fluorine atom, methyl, trifluoromethyl, methoxy, difluoromethoxy, trifluoromethoxy or —OS(O)$_2$R$^{25}$;

R$^{25}$ is methyl;

R$^7$ is trifluoromethyl or difluoromethyl;

R$^8$ is methyl, trifluoromethyl or difluoromethyl;

each of R$^{13}$, R$^{16}$, R$^{20}$ and R$^{23}$ is independently a hydrogen atom or methyl;

each of R$^{18}$ and R$^{19}$ is independently a hydrogen atom, methyl or trifluoromethyl.

5. The compound or a salt thereof according to claim 1, wherein at least one of X$^1$, X$^2$, X$^3$, X$^4$ is —OS(O)$_2$R$^{25}$.

6. The compound or a salt thereof according to claim 5, wherein X$^1$ is —OS(O)$_2$R$^{25}$.

7. The compound or a salt thereof according to claim 6, wherein X$^2$ and X$^3$ are hydrogen atoms.

8. The compound or a salt thereof according to claim 1, wherein A is A-1.

9. The compound or a salt thereof according to claim 1, selected from

4-[4-(1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-fluoro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6,9-difluoro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7,8-dimethyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7,8-dichloro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-ethylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(1,5-dihydro-3H-2,4-naphthodioxepin-3-yl)-2-thiazolyl]-1-[2-[5-methyl-3-(trifluoromethyl)-1H-pyrazole-1-yl]acetyl]piperidine, 4-[4-(7-fluoro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-nitro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-cyclopropylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-bromo-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-[7-(trifluoromethyl)-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-(6,7,8,9-tetrafluoro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(1-methyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methyl-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7-methyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-butylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-propylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-chloro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-bromo-9-methoxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-octylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methoxy-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7-nitro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-isopropylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7-ethylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-[6-(1,1,1-trifluoropropane-3-yl)sulfonyloxy-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-(1,5,7,8,9-pentahydro-3H-2,4-indenodioxepin-3-yl)-2-thiazolyl]-1-[2-[5-methyl-3-(trifluoromethyl)-1H-pyrazole-1-yl]acetyl]piperidine, 4-[4-(6-methylsulfonyloxy-9-nitro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-hydroxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-cyclopropylcarbonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-fluoro-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-[6-(trifluoromethyl)sulfonyloxy-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-(6-methoxycarbonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-methoxy-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(7-chloro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-fluoro-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methylsulfonylamino-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methyl-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(7-fluoro-6-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methoxy-9-nitro-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methylsulfonyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-phenylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7-nitro-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6,9-difluoro-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6,9-difluoro-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-hydroxymethyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-isopropylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-butylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6,7,8,9-tetrafluoro-1,5-dihydro-3H-2,4-benzodioxepin-3-yl)-2-thiazolyl]-1-[2-[3,5-bis(difluoromethyl)-1H-pyrazole-1-yl]acetyl]piperidine,
4-[4-(6-phenyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
4-[4-(6-bromo-9-methoxy-1,5-dihydro-3H-2,4-benzodioxepin-3-yl)-2-thiazolyl]-1-[2-[3,5-bis(difluoromethyl)-1H-pyrazole-1-yl]acetyl]piperidine,
4-[4-(6-chloro-1,5-dihydro-3H-2,4-benzodioxepin-3-yl)-2-thiazolyl]-1-[2-[3,5-bis(difluoromethyl)-1H-pyrazole-1-yl]acetyl]piperidine,
4-[4-(6-octylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine,
4-[4-[7-(trifluoromethyl)-1,5-dihydro-3H-2,4-benzodioxepin-3-yl]-2-thiazolyl]-1-[2-[3,5-bis(difluoromethyl)-1H-pyrazole-1-yl]acetyl]piperidine,
4-[4-(1,5,7,8,9-pentahydro-3H-2,4-indenodioxepin-3-yl)-2-thiazolyl]-1-[2-[3,5-bis(difluoromethyl)-1H-pyrazole-1-yl]acetyl]piperidine,
4-[4-[6-(methoxyimino)methyl-1,5-dihydro-3H-2,4-benzodioxepin-3-yl]-2-thiazolyl]-1-[2-[5-methyl-3-(trifluoromethyl)-1H-pyrazole-1-yl]acetyl]piperidine,
4-[4-(6-methylsulfonyloxy-1,5-dihydro-3H-2,4-benzodioxepin-3-yl)-2-thiazolyl]-1-[2-(2,5-dichlorophenyl)acetyl]piperidine,
4-[4-(6-fluoro-1,5-dihydro-3H-2,4-benzodioxepin-3-yl)-2-thiazolyl]-1-[2-(2,5-dichlorophenyl)acetyl]piperidine,
4-[4-(6,9-difluoro-1,5-dihydro-3H-2,4-benzodioxepin-3-yl)-2-thiazolyl]-1-[2-(2,5-dichlorophenyl)acetyl]piperidine,
4-[4-(6-methylsulfonyloxy-1,5-dihydro-3H-2,4-benzodioxepin-3-yl)-2-thiazolyl]-1-[N-(2,5-dimethylphenyl)carbamoyl]piperidine,
4-[4-(6-methylsulfonyloxy-1,5-dihydro-3H-2,4-benzodioxepin-3-yl)-2-thiazolyl]-1-[2-[(propane-2-ylideneamino)oxy]acetyl]piperidine, and
4-[4-(6-methylsulfonyloxy-1,5-dihydro-3H-2,4-benzodioxepin-3-yl)-2-thiazolyl]-1-[(Z)-[(2, 5-dimethylphenyl)imino](methoxy)methyl]piperidine.

10. A compound or a salt thereof selected from
4-[4-(6,7-dimethyl-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
4-[4-(6-chloro-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
4-[4-(6-bromo-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
4-[4-(6-isopropylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine,
4-[4-(6-butylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine,
4-[4-(6-(chloromethyl)-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
4-[4-(6-formyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
4-[4-[6-(2,2-dimethylhydrazono)methyl-1,5-dihydro-3H-2,4-benzodioxepin-3-yl]-2-thiazolyl]-1-[2-[5-methyl-3-(trifluoromethyl)-1H-pyrazole-1-yl]acetyl]piperidine,
4-[4-[6-(cyanomethyl)-1,5-dihydro-3H-2,4-benzodioxepin-3-yl]-2-thiazolyl]-1-[2-[5-methyl-3-(trifluoromethyl)-1H-pyrazole-1-yl]acetyl]piperidine,
4-[4-(6-phenyl-1,5-dihydro-3H-2,4-benzodioxepin-3-yl)-2-thiazolyl]-1-[2-[3,5-bis(difluoromethyl)-1H-pyrazole-1-yl]acetyl]piperidine,
4-[4-(6-methoxy-9-nitro-1,5-dihydro-3H-2,4-benzodioxepin-3-yl)-2-thiazolyl]-1-[2-[3,5-bis(difluoromethyl)-1H-pyrazole-1-yl]acetyl]piperidine,
4-[4-(1-methyl-1,5-dihydro-3H-2,4-benzodioxepin-3-yl)-2-thiazolyl]-1-[2-[3,5-bis(difluoromethyl)-1H-pyrazole-1-yl]acetyl]piperidine,
4-[4-(1,5-dihydro-3H-2,4-benzodioxepin-3-yl)-2-thiazolyl]-1-[2-[3,5-bis(difluoromethyl)-1H-pyrazole-1-yl]acetyl]piperidine,
4-[4-(1,5-dihydro-3H-2,4-naphthodioxepin-3-yl)-2-thiazolyl]-1-[2-[3,5-bis(difluoromethyl)-1H-pyrazole-1-yl]acetyl]piperidine,
4-[4-(7-tert-butyl-1,5-dihydro-3H-2,4-benzodioxepin-3-yl)-2-thiazolyl]-1-[2-[3,5-bis(difluoromethyl)-1H-pyrazole-1-yl]acetyl]piperidine,
4-[4-(7-tert-butyl-1,5-dihydro-3H-2,4-benzodioxepin-3-yl)-2-thiazolyl]-1-[2-[5-methyl-3-(trifluoromethyl)-1H-pyrazole-1-yl]acetyl]piperidine,
4-[4-(7-fluoro-1,5-dihydro-3H-2,4-benzodioxepin-3-yl)-2-thiazolyl]-1-[2-[3,5-bis(difluoromethyl)-1H-pyrazole-1-yl]acetyl]piperidine,
4-[4-[7-(trifluoromethyl)-1,5-dihydro-3H-2,4-benzodioxepin-3-yl]-2-thiazolyl]-1-[2-[3,5-bis(difluoromethyl)-1H-pyrazole-1-yl]acetyl]piperidine,
4-[4-(6-bromo-9-methoxy-1,5-dihydro-3H-2,4-benzodioxepin-3-yl)-2-thiazolyl]-1-[2-[3,5-bis(trifluoromethyl)-1H-pyrazole-1-yl]acetyl]piperidine,
4-[4-(6-methoxy-9-nitro-1,5-dihydro-3H-2,4-benzodioxepin-3-yl)-2-thiazolyl]-1-[2-[3,5-bis(trifluoromethyl)-1H-pyrazole-1-yl]acetyl]piperidine,
4-[4-(6,7,8,9-tetrafluoro-1,5-dihydro-3H-2,4-benzodioxepin-3-yl)-2-thiazolyl]-1-[2-[3,5-bis(trifluoromethyl)-1H-pyrazole-1-yl]acetyl]piperidine,
4-[4-(1,5-dihydro-3H-2,4-benzodioxepin-3-yl)-2-thiazolyl]-1-[2-[3,5-bis(trifluoromethyl)-1H-pyrazole-1-yl]acetyl]piperidine,
4-[4-[6-(trifluoromethoxy)-9-methoxy-1,5-dihydro-3H-2,4-benzodioxepin-3-yl]-2-thiazolyl]-1-[2-[5-methyl-3-(trifluoromethyl)-1H-pyrazole-1-yl]acetyl]piperidine,
4-[4-(6-fluoro-9-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine,
4-[4-(1-methyl-1,5-dihydro-3H-2,4-benzodioxepin-3-yl)-2-thiazolyl]-1-[2-[3,5-bis(trifluoromethyl)-1H-pyrazole-1-yl]acetyl]piperidine,
4-[4-(1,5-dihydro-3H-2,4-naphthodioxepin-3-yl)-2-thiazolyl]-1-[2-[3,5-bis(trifluoromethyl)-1H-pyrazole-1-yl]acetyl]piperidine,
4-[4-[6-(dimethylaminosulfonyloxy)-1,5-dihydro-3H-2,4-benzodioxepin-3-yl]-2-thiazolyl]-1-[2-[5-methyl-3-(trifluoromethyl)-1H-pyrazole-1-yl]acetyl]piperidine,
4-[4-(7-fluoro-1,5-dihydro-3H-2,4-benzodioxepin-3-yl)-2-thiazolyl]-1-[2-[3,5-bis(trifluoromethyl)-1H-pyrazole-1-yl]acetyl]piperidine,
4-[4-(7-tert-butyl-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-chloro-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-[6-(difluoromethoxy)-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-(7-nitro-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-[6-(hydroxyimino)methyl-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-[6-(difluoromethyl)-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-(7-bromo-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(7-bromo-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6,9-dibromo-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-iodo-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-chloro-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-[6,9-bis(methylsulfonyloxy)-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-(6-cyano-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[3,5-dimethyl-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]thioacetyl]piperidine, 4-[4-(6-fluoro-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]thioacetyl]piperidine, 4-[4-(6-methoxy-9-methylsulfonyloxy-1,5-dihydro-3H-2,4-benzodioxepin-3-yl)-2-thiazolyl]-1-[2-[5-chloro-3-(trifluoromethyl)-1H-pyrazole-1-yl]acetyl]piperidine, 4-[4-(6-methoxy-9-methylsulfonyloxy-1,5-dihydro-3H-2,4-benzodioxepin-3-yl)-2-thiazolyl]-1-[2-(3,5-dichloro-1H-pyrazole-1-yl)acetyl]piperidine, 4-[4-(6-chloro-9-methoxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-bromo-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-chloro-9-methoxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-bromo-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-nitro-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methoxy-9-methylsulfonyloxy-1,5-dihydro-3H-2,4-benzodioxepin-3-yl)-2-thiazolyl]-1-[2-[3,5-dimethyl-1H-pyrazole-1-yl]acetyl]piperidine, 4-[4-(6-chloro-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-methoxy-9-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-chloro-9-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[3,5-bis(dichloromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[3,5-dimethyl-1H-pyrazole-1-yl]acetyl]piperidine, 4-[4-(6,7-dimethyl-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6,7-dimethyl-9-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-bromo-9-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methylsulfonyloxy-9-nitro-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-bromo-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-nitro-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]acetyl]piperazine, 4-[4-(6-methylsulfonyloxy-9-nitro-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-iodo-9-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-iodo-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(7-fluoro-6-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(7-fluoro-6-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-fluoro-9-methoxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6-methoxy-9-methyl-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methoxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-[6-(difluoromethoxy)-1,5-dihydro-3H-2,4-benzodioxepin-3-yl]-2-thiazolyl]-1-[2-[3,5-bis(difluoromethyl)-1H-pyrazole-1-yl]acetyl]piperidine, 4-[4-[6-(difluoromethoxy)-1,5-dihydro-3H-2,4-benzodioxepin-3-yl]-2-thiazolyl]-1-[2-[3,5-bis(trifluoromethyl)-1H-pyrazole-1-yl]acetyl]piperidine, 4-[4-(7-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(7-methylsulfonyloxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methoxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methoxy-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-(6-fluoro-9-methoxy-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-[6-(difluoromethoxy)-9-methylsulfonyloxy-1,5-dihydro-3H-2,4-benzodioxepin-3-yl]-2-thiazolyl]-1-[2-[5-methyl-3-(trifluoromethyl)-1H-pyrazole-1-yl]acetyl]piperidine, 4-[4-(6-acetoxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-[6-(hydroxyimino)methyl-1,5-dihydro-3H-2,4-benzodioxepin-3-yl]-2-thiazolyl]-1-[2-[3,5-bis(difluoromethyl)-1H-pyrazole-1-yl]acetyl]piperidine, 4-[4-[6,9-bis(methylsulfonyloxy)-1,5-dihydro-3H-2,4-benzodioxepin-3-yl]-2-thiazolyl]-1-[2-[3,5-bis(difluoromethyl)-1H-pyrazole-1-yl]acetyl]piperidine, 4-[4-[6,9-bis(methylsulfonyloxy)-1,5-dihydro-3H-2,4-benzodioxepin-3-yl]-2-thiazolyl]-1-[2-[3,5-bis(trifluoromethyl)-1H-pyrazole-1-yl]acetyl]piperidine, 4-[4-(6-cyano-1,5-dihydro-3H-2,4-benzodioxepin-3-yl)-2-thiazolyl]-1-[2-[3,5-bis(difluoromethyl)-1H-pyrazole-1-yl]acetyl]piperidine, 4-[4-[6-(hydroxyimino)methyl-1,5-dihydro-3H-2,4-benzodioxepin-3-yl]-2-thiazolyl]-1-[2-[3,5-bis(trifluoromethyl)-1H-pyrazole-1-yl]acetyl]piperidine, 4-[4-(6-cyano-1,5-dihydro-3H-2,4-benzodioxepin-3-yl)-2-thiazolyl]-1-[2-[3,5-bis(trifluoromethyl)-1H-pyrazole-1-yl]acetyl]piperidine, 4-[4-(6-methylsulfonyloxy-1,5-dihydro-3H-2,4-benzodioxepin-3-yl)-2-thiazolyl]-1-[2-[3,5-bis(difluoromethyl)-1H-pyrazole-1-yl]acetyl]piperazine, 4-[4-(6-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]propanoyl]piperidine, 4-[4-(6-fluoro-9-methylsulfonyloxy-1,5-dihydro-3H-2,4-benzodioxepin-3-yl)-2-thiazolyl]-1-[2-[5-methyl-3-(difluoromethyl)-1H-pyrazole-1-yl]acetyl]piperidine, 4-[4-(6-fluoro-9-methylsulfonyloxy-1,5-dihydro-3-methyl-2,4-benzodioxepin-3-yl)-2-thiazolyl]-1-[2-[5-methyl-3-(trifluoromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2,2-difluoro-2-[5-methyl-3-(trifluoromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[5-methyl-3-(trifluoromethyl)-1H-pyrazole-1-yl]propanoyl]piperidine, 4-[4-(6-fluoro-9-methylsulfonyloxy-1,5-dihydro-3H-2,4-benzodioxepin-3-yl)-2-thiazolyl]-3-methyl-1-[2-[5-methyl-3-(trifluoromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]thioacetyl]piperidine, 4-[4-(6-fluoro-9-methylsulfonyloxy-1,5-dihydro-3H-2,4-benzodioxepin-3-yl)-2-thiazolyl]-2-methyl-1-[2-[5-methyl-3-(trifluoromethyl)-1H-pyrazole-1-yl]acetyl]piperidine, 4-[4-(6-fluoro-9-methylsulfonyloxy-1,5-dihydro-3H-2,4-benzodioxepin-3-yl)-2-thiazolyl]-1-[2-[3,5-bis(difluoromethyl)-1H-pyrazole-1-yl]propanoyl]piperidine, 4-[4-(6-fluoro-9-hydroxy-1,5-dihydro-3H-2,4-benzodioxepin-3-yl)-2-thiazolyl]-1-[2-[5-methyl-3-(trifluoromethyl)-1H-pyrazole-1-yl]acetyl]piperidine, 4-[4-(6,9-difluoro-1,5-dihydro-3H-2,4-benzodioxepin-3-yl)-2-thiazolyl]-1-[2-(2,5-dimethylphenyl)acetyl]piperidine, 4-[4-(6-fluoro-1,5-dihydro-3H-2,4-benzodioxepin-3-yl)-2-thiazolyl]-1-[2-(2,5-dimethylphenyl)acetyl]piperidine, 4-[4-(6-fluoro-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-methoxy-9-nitro-1,5-dihydro-3H-2,4-benzodioxepin-3-yl)-2-thiazolyl]-1-[2-(2,5-dimethylphenyl)acetyl]piperidine, 4-[4-(7-fluoro-1,5-dihydro-3H-2,4-benzodioxepin-3-yl)-2-thiazolyl]-1-[2-(2,5-dimethylphenyl)acetyl]piperidine, 4-[4-(1,5-dihydro-3H-2,4-benzodioxepin-3-yl)-2-thiazolyl]-1-[2-(2,5-dimethylphenyl)acetyl]piperidine, 4-[4-(6-butylsulfonyloxy-1,5-dihydro-3H-2,4-benzodioxepin-3-yl)-2-thiazolyl]-1-[2-(2,5-dimethylphenyl)acetyl]piperidine, 4-[4-(1-methyl-1,5-dihydro-3H-2,4-benzodioxepin-3-yl)-2-thiazolyl]-1-[2-(2,5-dimethylphenyl)acetyl]piperidine, 4-[4-(6-fluoro-9-methylsulfonyloxy-1,5-dihydro-3H-2,4-benzodioxepin-3-yl)-2-thiazolyl]-1-[N-(2,5-dimethylphenyl)carbamoyl]piperidine, 4-[4-(6,9-difluoro-1,5-dihydro-3H-2,4-benzodioxepin-3-yl)-2-thiazolyl]-1-[N-(2,5-dimethylphenyl) carbamoyl]piperidine, 4-[4-(6-fluoro-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-bromo-1,5-dihydro-3H-2,4-benzodioxepin-3-yl)-2-thiazolyl]-1-[2-(2,5-dimethylphenyl)acetyl]piperidine, 4-[4-(7-nitro-1,5-dihydro-3H-2,4-benzodioxepin-3-yl)-2-thiazolyl]-1-[2-(2,5-dimethylphenyl)acetyl]piperidine, 4-[4-(6-bromo-1,5-dihydro-3H-2,4-benzodioxepin-3-yl)-2-thiazolyl]-1-[2-(2,5-dichlorophenyl)acetyl]piperidine, 4-[4-(6-chloro-9-methoxy-1,5-dihydro-3H-2,4-benzodioxepin-3-yl)-2-thiazolyl]-1-[2-(2,5-dimethylphenyl)acetyl]piperidine, 4-[4-(7-nitro-1,5-dihydro-3H-2,4-benzodioxepin-3-yl)-2-thiazolyl]-1-[2-(2,5-dichlorophenyl)acetyl]piperidine, 4-[4-(6-chloro-1,5-dihydro-3H-2,4-benzodioxepin-3-yl)-2-thiazolyl]-1-[2-(2,5-dichlorophenyl)acetyl]piperidine, 4-[4-(6-chloro-9-methoxy-1,5-dihydro-3H-2,4-benzodioxepin-3-yl)-2-thiazolyl]-1-[2-(2,5-dichlorophenyl)acetyl]piperidine, 4-[4-(6-bromo-9-methoxy-1,5-dihydro-3H-2,4-benzodioxepin-3-yl)-2-thiazolyl]-1-[2-(2,5-dimethylphenyl)acetyl]piperidine, 4-[4-(6-bromo-9-methoxy-1,5-dihydro-3H-2,4-benzodioxepin-3-yl)-2-thiazolyl]-1-[2-(2,5-dichlorophenyl)acetyl]piperidine, 4-[4-(6-methoxy-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(6,7,8,9-tetrafluoro-1,5-dihydro-3H-2,4-benzodioxepin-3-yl)-2-thiazolyl]-1-[2-(2,5-dimethylphenyl)acetyl]piperidine, 4-[4-(6-methoxy-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6,7,8,9-tetrafluoro-1,5-dihydro-3H-2,4-benzodioxepin-3-yl)-2-thiazolyl]-1-[2-(2,5-dichlorophenyl)acetyl]piperidine, 4-[4-(6-methylsulfonyloxy-1,5-dihydro-3H-2,4-benzodioxepin-3-yl)-2-thiazolyl]-1-[2-[2,5-bis(trifluoromethyl)phenyl]acetyl]piperidine, 4-[4-(6,7-dimethyl-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6,7-dimethyl-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-bromo-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-methylsulfonyloxy-9-nitro-1,5-dihydro-3H-2,4-benzodioxepin-3-yl)-2-thiazolyl]-1-[2-(2,5-dichlorophenyl)acetyl]piperidine, 4-[4-(6-bromo-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-nitro-1,5-dihydro-3H-2,4-benzodioxepin-3-yl)-2-thiazolyl]-1-[2-(2,5-dichlorophenyl)acetyl]piperidine, 4-[4-(6-methylsulfonyloxy-9-nitro-1,5-dihydro-3H-2,4-benzodioxepin-3-yl)-2-thiazolyl]-1-[2-(2,5-dimethylphenyl)acetyl]piperidine, 4-[4-(6-chloro-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-nitro-1,5-dihydro-3H-2,4-benzodioxepin-3-yl)-2-thiazolyl]-1-[2-(2,5-dimethylphenyl)acetyl]piperidine, 4-[4-(6-iodo-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-chloro-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(7-fluoro-6-methylsulfonyloxy-1,5-dihydro-3H-2,4-benzodioxepin-3-yl)-2-thiazolyl]-1-[2-(2,5-dimethylphenyl)acetyl]piperidine, 4-[4-(7-fluoro-6-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-iodo-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-methoxy-9-methyl-1,5-dihydro-3H-2,4-benzodioxepin-3-yl)-2-thiazolyl]-1-[2-(2,5-dimethylphenyl)acetyl]piperidine, 4-[4-(6-methoxy-9-methyl-1,5-dihydro-3H-2,4-benzodioxepin-3-yl)-2-thiazolyl]-1-[2-(2,5-dichlorophenyl)acetyl]piperidine, 4-[4-[6-(difluoromethoxy)-1,5-dihydro-3H-2,4-benzodioxepin-3-yl]-2-thiazolyl]-1-[2-(2,5-dimethylphenyl)acetyl]piperidine, 4-[4-[6-(difluoromethoxy)-1,5-dihydro-3H-2,4-benzodioxepin-3-yl]-2-thiazolyl]-1-[2-(2,5-dichlorophenyl)acetyl]piperidine, 4-[4-(7-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-methoxy-1,5-dihydro-3H-2,4-benzodioxepin-3-yl)-2-thiazolyl]-1-[2-(2,5-dimethylphenyl)acetyl]piperidine, 4-[4-(6-methoxy-1,5-dihydro-3H-2,4-benzodioxepin-3-yl)-2-thiazolyl]-1-[2-(2,5-dichlorophenyl)acetyl]piperidine, 4-[4-(6-fluoro-9-methoxy-1,5-dihydro-3H-2,4-benzodioxepin-3-yl)-2-thiazolyl]-1-[2-(2,5-dimethylphenyl)acetyl]piperidine, 4-[4-[6,9-bis(methylsulfonyloxy)-1,5-dihydro-3H-2,4-benzodioxepin-3-yl]-2-thiazolyl]-1-[2-(2,5-dimethylphenyl)acetyl]piperidine, 4-[4-(6-methylsulfonyloxy-1,5-dihydro-3H-2,4-benzodioxepin-3-yl)-2-thiazolyl]-1-[2-(2,5-dimethylphenyl)acetyl]piperazine, 4-[4-(6-fluoro-9-methylsulfonyloxy-1,5-dihydro-3H-2,4-benzodioxepin-3-yl)-2-thiazolyl]-1-[N-(2,5-dimethylphenyl)-N-methylcarbamoyl]piperidine, 4-[4-(6-methylsulfonyloxy-1,5-dihydro-3H-2,4-benzodioxepin-3-yl)-2-thiazolyl]-1-[N-(2,5-dimethylphenyl)-N-methylcarbamoyl]piperidine, 4-[4-(6-fluoro-9-methylsulfonyloxy-1,5-dihydro-3H-2,4-benzodioxepin-3-yl)-2-thiazolyl]-1-[2-(2,5-dimethylphenyl)thioacetyl]piperidine, 4-[4-(6-fluoro-1,5-dihydro-3H-2,4-benzodioxepin-3-yl)-2-thiazolyl]-1-[2-[(1,1,1-trifluoroethane-2-ylideneamino)oxy]acetyl]piperidine, 4-[4-(6-fluoro-9-methylsulfonyloxy-1,5-dihydro-3H-2,4-benzodioxepin-3-yl)-2-thiazolyl]-1-[2-[(1,1,1-trifluoroethane-2-ylideneamino)oxy]acetyl]piperidine, 4-[4-(6,9-difluoro-1,5-dihydro-3H-2,4-benzodioxepin-3-yl)-2-thiazolyl]-1-[2-[(1,1,1-trifluoroethane-2-ylideneamino)oxy]acetyl]piperidine, 4-[4-(6-methoxy-9-methylsulfonyloxy-1,5-dihydro-3H-2,4-benzodioxepin-3-yl)-2-thiazolyl]-1-[2-[(1,1,1-trifluoroethane-2-ylideneamino)oxy]acetyl]piperidine, and 4-[4-(6-methylsulfonyloxy-1,5-dihydro-3H-2,4-benzodioxepin-3-yl)-2-thiazolyl]-1-[2-[(1,1,1-trifluoroethane-2-ylideneamino)oxy]acetyl]piperidine.

11. A fungicidal composition comprising a compound or a salt thereof according to claim 1.

12. A method of controlling plant disease generated from phytopathogenic microorganism comprising steps of applying the fungicidal composition of claim 11 to an entire plant or a part thereof or seeds of a plant.

13. A method of producing a compound of formula [1a] comprising a step of reacting a thiazole derivative of formula [2] and a benzene derivative of formula [3] under a presence of an acid or Lewis acid and a solvent:

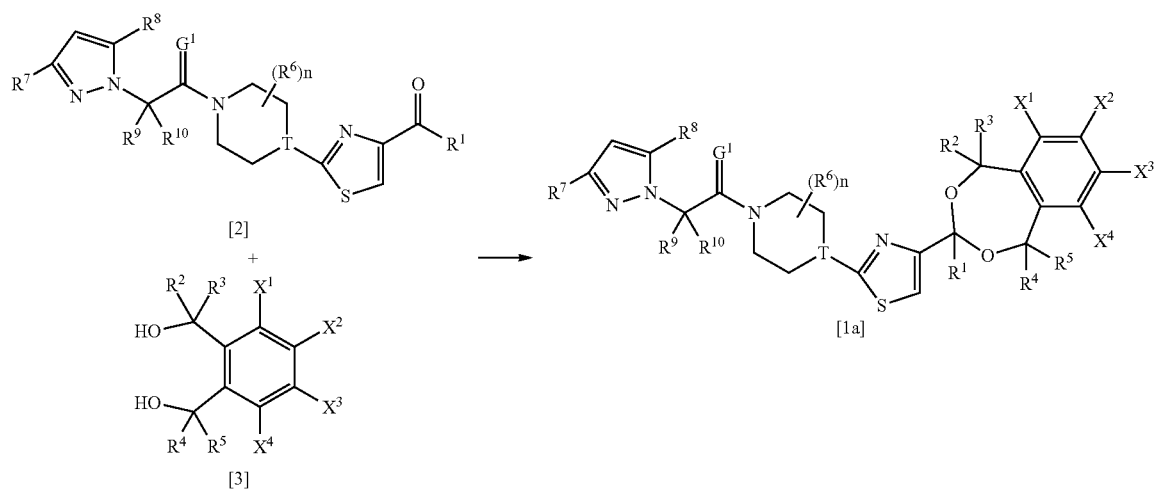

wherein $R^1$, $R^2$, $R^3$, $R^4$, $R^5$, $R^6$, $R^7$, $R^8$, $R^9$, $R^{10}$, $G^1$, $X^1$, $X^2$, $X^3$, $X^4$, T and n are as defined in claim 1.

14. A method of producing a compound of formula [1b] comprising a step of reacting a thiazole derivative of formula [4] and a benzene derivative of formula [3] under a presence of an acid or Lewis acid and a solvent:

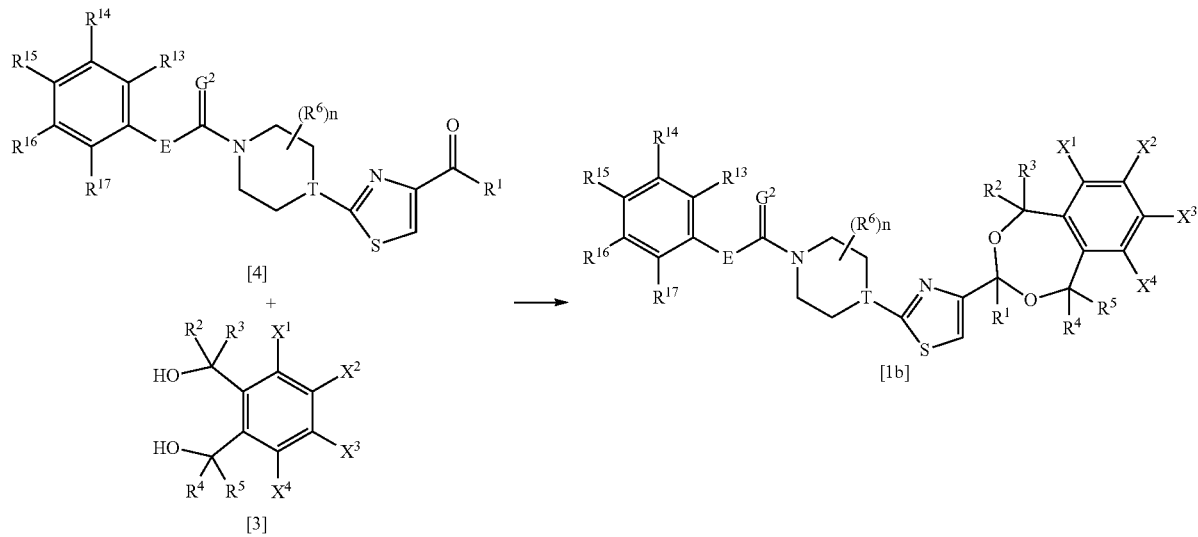

wherein, $R^1$, $R^2$, $R^3$, $R^4$, $R^5$, $R^6$, $R^{13}$, $R^{14}$, $R^{15}$, $R^{16}$, $R^{17}$, E, $G^2$, $X^1$, $X^2$, $X^3$, $X^4$, T and n are as defined in claim 1.

15. A method of producing a compound of formula [1c] comprising a step of reacting a thiazole derivative of formula [5] and a benzene derivative of formula [3] under a presence of an acid or Lewis acid and a solvent:

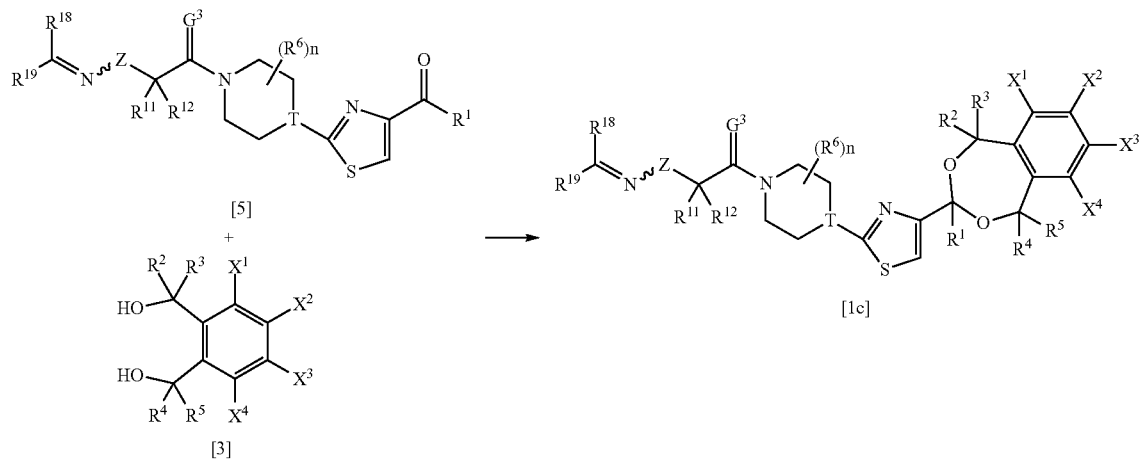

wherein $R^1$, $R^2$, $R^3$, $R^4$, $R^5$, $R^6$, $R^{11}$, $R^{12}$, $R^{18}$, $R^{19}$, $G^3$, $X^1$, $X^2$, $X^3$, $X^4$, Z, T and n are as defined in claim 1.

16. A method of producing a compound of formula [1d] comprising a step of reacting a thiazole derivative of formula [6] and a benzene derivative of formula [3] under a presence of an acid or Lewis acid and a solvent:

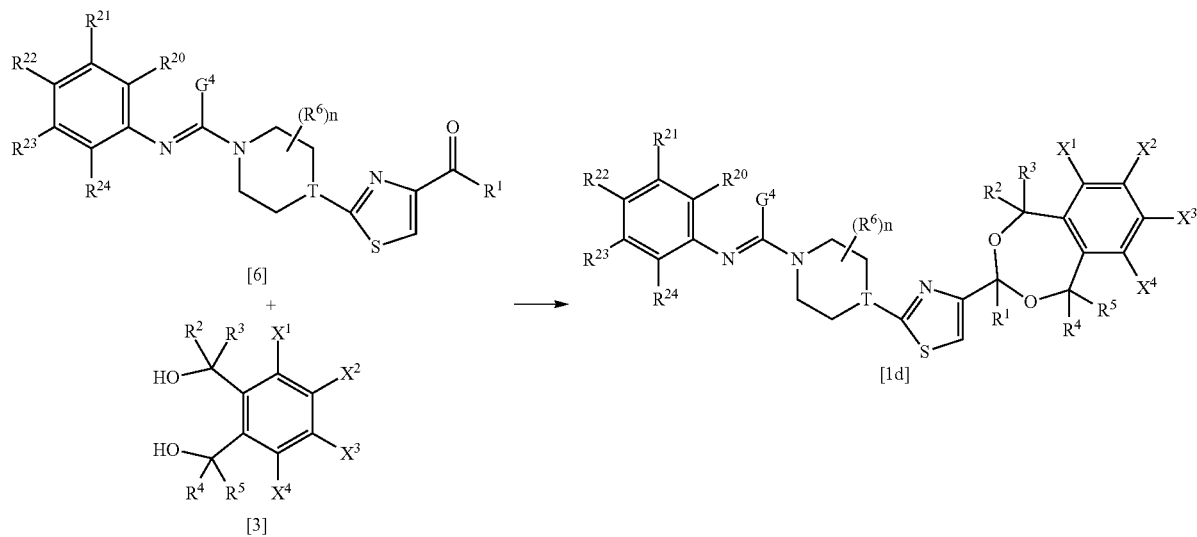

wherein $R^1$, $R^2$, $R^3$, $R^4$, $R^5$, $R^6$, $R^{20}$, $R^{21}$, $R^{22}$, $R^{23}$, $R^{24}$, $G^4$, $X^1$, $X^2$, $X^3$, $X^4$, T and n are as defined in claim 1.

17. A method of producing a compound of formula [1a] comprising a step of reacting a piperidine derivative of formula [7] and a carboxylic acid derivative of formula [8] under a presence of a dehydration/condensation agent and a solvent (step 1) or a step of reacting a piperidine derivative of formula [7] and a carboxylic acid derivative of formula [9] under a presence of a base and a solvent (step 2):

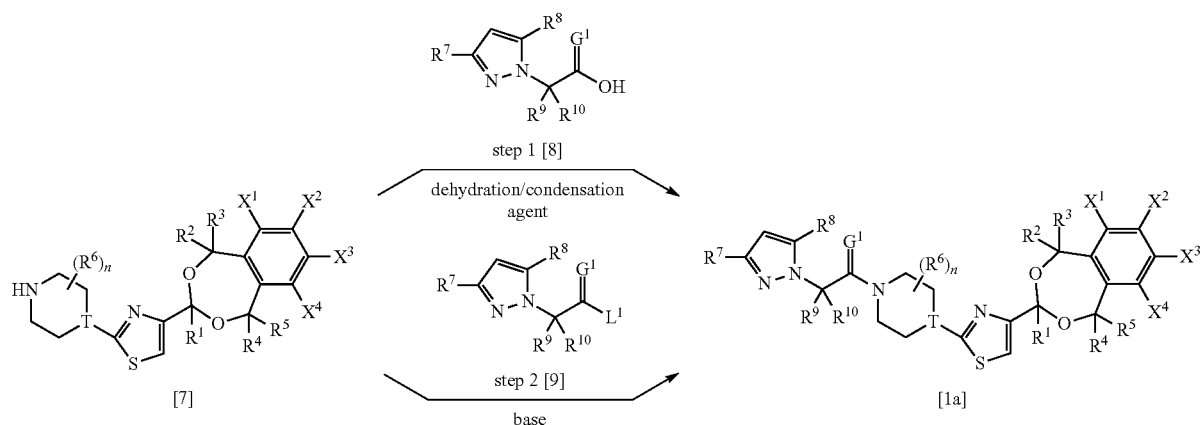

wherein $R^1$, $R^2$, $R^3$, $R^4$, $R^5$, $R^6$, $R^7$, $R^8$, $R^9$, $R^{10}$, $G^1$, $X^1$, $X^2$, $X^3$, $X^4$, T and n are as defined in claim 1, and $L^1$ is a halogen such as a chlorine atom, or a bromine atom.

18. A method of producing a compound of formula [1b] comprising a step of reacting a piperidine derivative of formula [7] and a carboxylic acid derivative of formula [10] under a presence of a dehydration/condensation agent and a solvent (step 1), or a step of reacting a piperidine derivative of formula [7] and a carboxylic acid derivative of formula [11] under a presence of a base and a solvent (step 2):

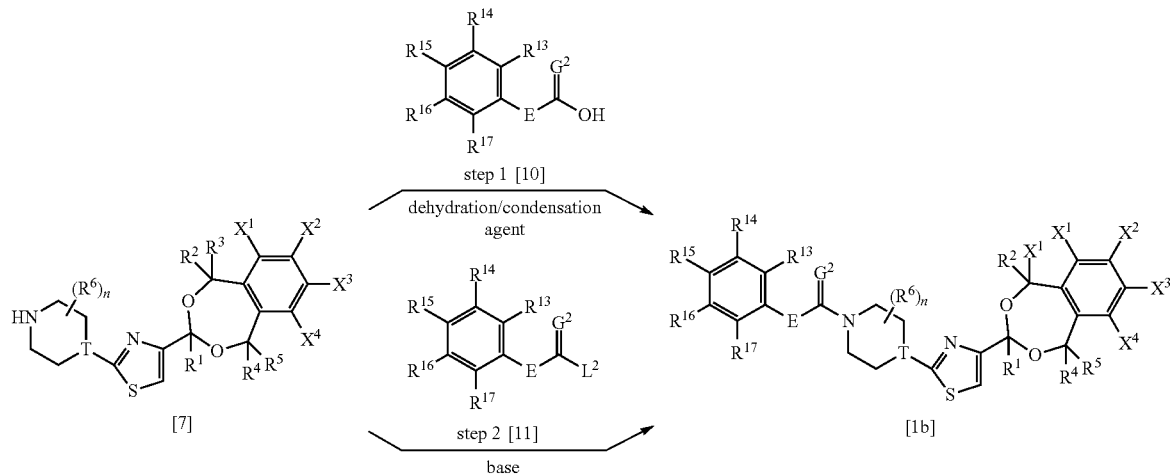

wherein $R^1$, $R^2$, $R^3$, $R^4$, $R^5$, $R^6$, $R^{13}$, $R^{14}$, $R^{15}$, $R^{16}$, $R^{17}$, E, $G^2$, $X^1$, $X^2$, $X^3$, $X^4$, T and n are as defined in claim 1, and $L^2$ is a halogen such as a chlorine atom, or a bromine atom.

19. A method of producing a compound of formula [1c] comprising a step of reacting a piperidine derivative of formula [7] and a carboxylic acid derivative of formula [12] under a presence of a dehydration/condensation agent and a solvent (step 1), or a step of reacting a piperidine derivative of formula [7] and a carboxylic acid derivative of formula [13] under a presence of a base and a solvent (step 2):

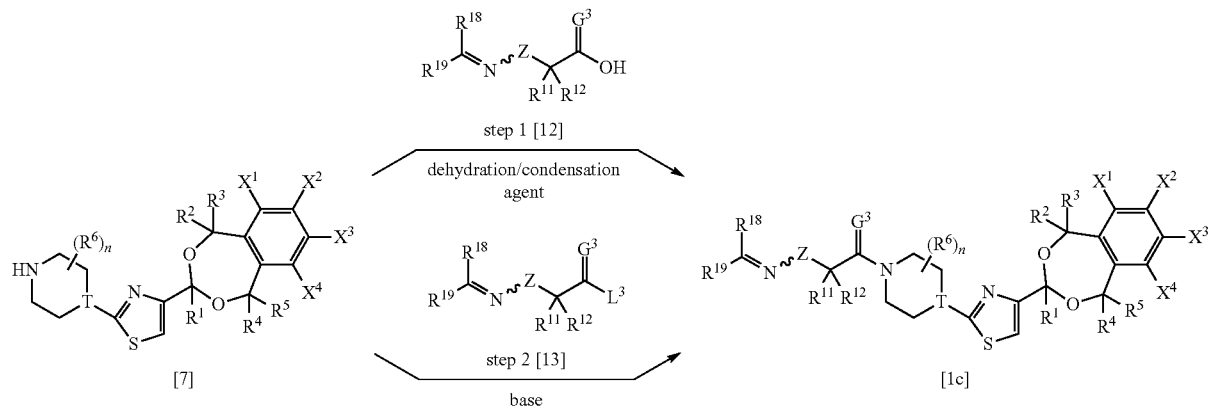

wherein $R^1$, $R^2$, $R^3$, $R^4$, $R^5$, $R^6$, $R^{11}$, $R^{12}$, $R^{18}$, $R^{19}$, $G^3$, $X^1$, $X^2$, $X^3$, $X^4$, Z, T and n are as defined in claim 1, and $L^3$ is a halogen such as a chlorine atom, or a bromine atom.

20. A method of producing a compound of formula [1d] comprising a step of reacting a substituted 11 membered compound of formula [14] and formula [15] under a presence of a base and a solvent:

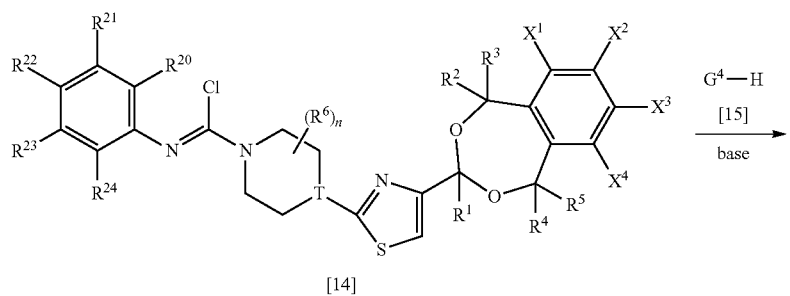

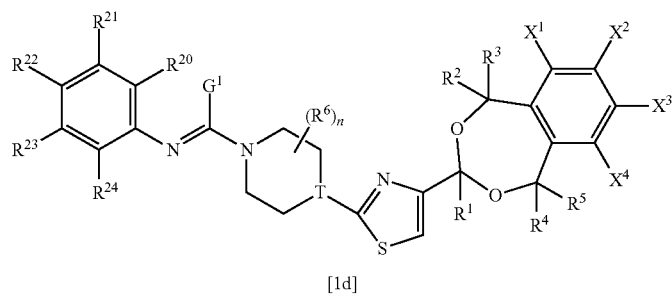

wherein $R^1$, $R^2$, $R^3$, $R^4$, $R^5$, $R^6$, $R^{20}$, $R^{21}$, $R^{22}$, $R^{23}$, $R^{24}$, $G^4$, $X^1$, $X^2$, $X^3$, $X^4$, T and n are as defined in claim 1.

21. A method of producing a compound of formula [1d] comprising a step of reacting a substituted 11 membered compound of formula [16] and formula [17] or formula [18] under a presence of a base and a solvent:

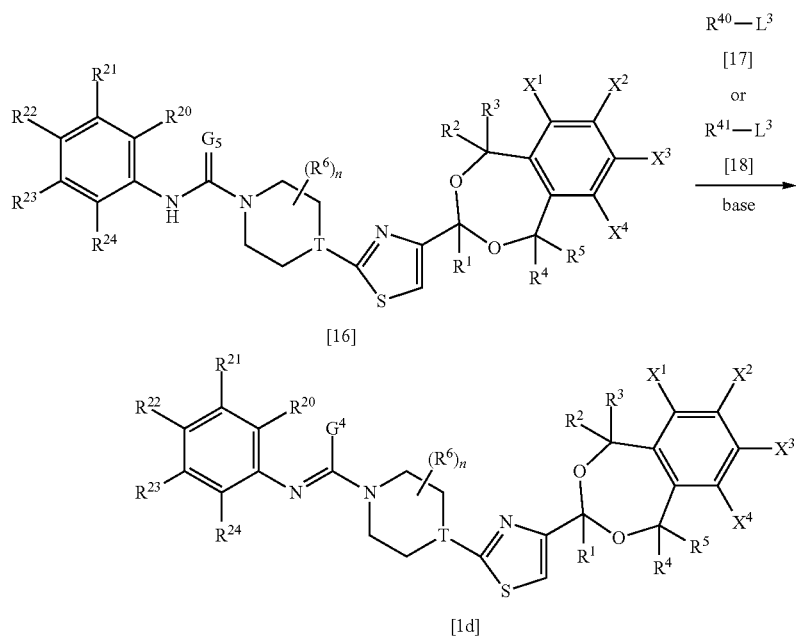
wherein $R^1$, $R^2$, $R^3$, $R^4$, $R^5$, $R^6$, $R^{20}$, $R^{21}$, $R^{22}$, $R^{23}$, $R^{24}$, $R^{40}$, $R^{41}$, $G^4$, $X^1$, $X^2$, $X^3$, $X^4$, T and n are as defined in claim 1, and $G^5$ is an oxygen atom or a sulfur atom, and $L^3$ is a leaving group.
* * * * *

UNITED STATES PATENT AND TRADEMARK OFFICE
CERTIFICATE OF CORRECTION

PATENT NO. : 9,980,487 B2  
APPLICATION NO. : 15/503069  
DATED : March 29, 2018  
INVENTOR(S) : Hiroshi Wada et al.

Page 1 of 2

It is certified that error appears in the above-identified patent and that said Letters Patent is hereby corrected as shown below:

In the Claims

At Column 283, Claim number 1, Line number 8, delete "}".

At Column 300, Claim number 18, Line numbers 33-57, replace formula [1b]

"  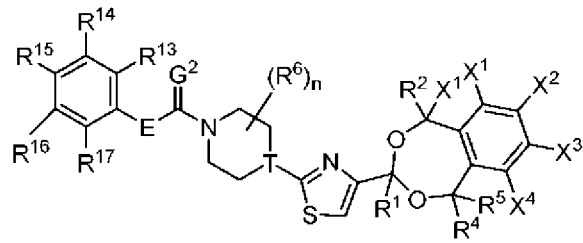  [1b]  "

with --  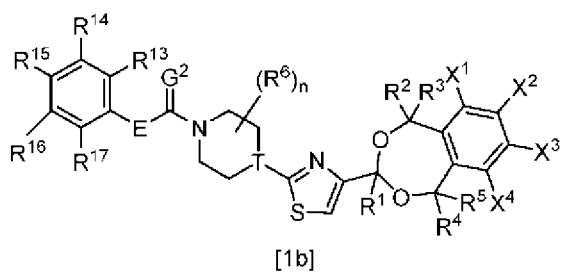  [1b]  --.

Signed and Sealed this  
Tenth Day of July, 2018

Andrei Iancu  
*Director of the United States Patent and Trademark Office*

CERTIFICATE OF CORRECTION (continued)
U.S. Pat. No. 9,980,487 B2

At Column 301, Claim number 20, Line numbers 30-60, replace formula [1d]

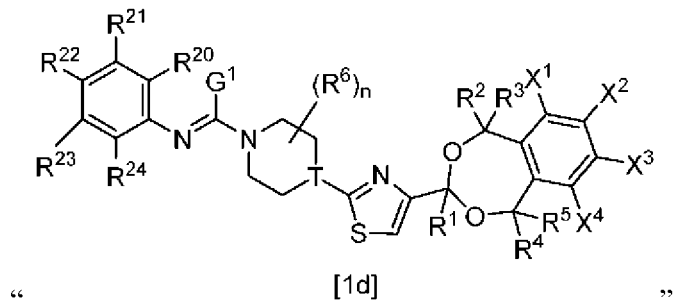

"           [1d]                           "

with --

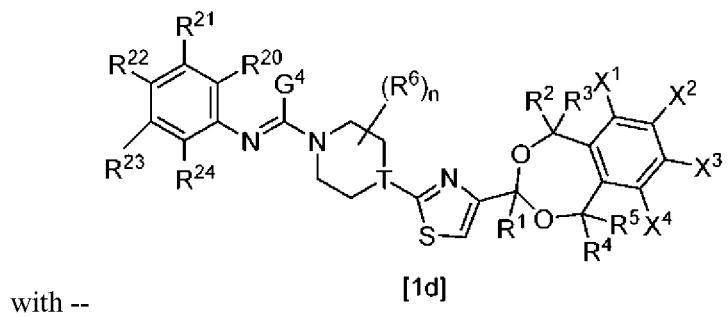

[1d]                           --.